US011266616B2

(12) United States Patent
Kern et al.

(10) Patent No.: US 11,266,616 B2
(45) **Date of Patent: *Mar. 8, 2022**

(54) COMPOSITIONS AND METHODS FOR INHIBITING KINASE ACTIVITY

(71) Applicant: BRANDEIS UNIVERSITY, Waltham, MA (US)

(72) Inventors: Dorothee Kern, Waltham, MA (US); Adelajda Zorba, Waltham, MA (US)

(73) Assignee: BRANDEIS UNIVERSITY, Waltham, MA (US)

( * ) Notice: Subject to any disclaimer, the term of this patent is extended or adjusted under 35 U.S.C. 154(b) by 849 days.

This patent is subject to a terminal disclaimer.

(21) Appl. No.: 16/075,550

(22) PCT Filed: Feb. 8, 2017

(86) PCT No.: PCT/US2017/016923

§ 371 (c)(1),
(2) Date: Aug. 3, 2018

(87) PCT Pub. No.: WO2017/139321

PCT Pub. Date: Aug. 17, 2017

(65) Prior Publication Data

US 2019/0038582 A1 Feb. 7, 2019

Related U.S. Application Data

(60) Provisional application No. 62/292,587, filed on Feb. 8, 2016.

(51) Int. Cl.

| | |
|---|---|
| ***C07K 16/00*** | (2006.01) |
| ***A61K 39/395*** | (2006.01) |
| ***A61K 31/192*** | (2006.01) |
| ***A61K 45/06*** | (2006.01) |
| ***A61K 31/496*** | (2006.01) |
| ***A61K 31/517*** | (2006.01) |
| ***C07K 16/40*** | (2006.01) |
| ***C12Q 1/48*** | (2006.01) |
| ***G16B 15/30*** | (2019.01) |
| ***A61P 35/00*** | (2006.01) |
| ***G16B 15/00*** | (2019.01) |
| ***A61K 9/00*** | (2006.01) |
| *G16C 20/50* | (2019.01) |

(52) U.S. Cl.

CPC .......... *A61K 31/192* (2013.01); *A61K 9/0019* (2013.01); *A61K 31/496* (2013.01); *A61K 31/517* (2013.01); *A61K 45/06* (2013.01); *A61P 35/00* (2018.01); *C07K 16/40* (2013.01); *C12Q 1/485* (2013.01); *G16B 15/00* (2019.02); *G16B 15/30* (2019.02); *G01N 2500/04* (2013.01); *G16C 20/50* (2019.02)

(58) Field of Classification Search

None

See application file for complete search history.

(56) References Cited

U.S. PATENT DOCUMENTS

| | | | | |
|---|---|---|---|---|
| 2006/0078975 | A1 | 4/2006 | Anderson et al. | |
| 2008/0051327 | A1 | 2/2008 | Conti et al. | |
| 2011/0104782 | A1 | 5/2011 | Cheetham et al. | |
| 2011/0143963 | A1 | 6/2011 | Koide et al. | |
| 2012/0046307 | A1 * | 2/2012 | Engel ...................... | C07C 59/88 514/266.3 |

OTHER PUBLICATIONS

Almagro & Fransson, Frontiers in Bioscience 2008; 13:1619-33 (Year: 2008).*

Padlan (Advances in Protein Chemistry, 1996, 49:57-133) (Year: 1996).*

Berglund et al, Protein Science, 2008, 17:606-613 (Year: 2008).*

Corada (Blood, 2001; 97:1679-84) (Year: 2001).*

Kulkarni-Kale et al. Nucleic Acid Research, 2005, 33:W168-W171 (Year: 2005).*

Meulenbeld et al. (Expert Opinion on Investigational Drugs, vol. 21, 2012, Issue 3). (Year: 2012).*

Burgess, et al., "Alloseteric inhibition of Aurora-A kinase by a synthetic vNAR domain," Open Biology, Jul. 13, 2016 (13.07.206) vol. 6, No. 7, pp. 1-10.

Janecek, et al., "Allosteric modulation of AURKA kinase activity by a small-molecule inhibitor of its protein-protein interaction with TPX2," Scientific Reports, Jun. 24, 2016 (Jun. 24, 2016), vol. 6, No. 28528, pp. 1-12.

International Search Report and Written Opinion for corresponding PCT patent application PCT/US2017/016923, dated Apr. 21, 2017 (15 pages).

Oelschlaeger, et al.; "Fluorophor-linked immunosorbent assay: a time- and cost-saving method for the characterization of antibody fragments using a fusion protein of a single-chain antibody fragment and enhanced green fluorescent protein"; Analytical Biochemistry, vol. 309, Issue No. 1; 2002; pp. 27-34.

(Continued)

*Primary Examiner* — Meera Natarajan

(74) *Attorney, Agent, or Firm* — Cantor Colburn LLP

(57) ABSTRACT

The present invention features therapeutic compositions comprising an agent that specifically binds to a PIF pocket of Aurora A kinase and an agent that specifically binds to an ATP-binding site of Aurora A kinase, and the use of the therapeutic compositions to modulate Aurora A kinase for the treatment of cancer.

5 Claims, 50 Drawing Sheets

Specification includes a Sequence Listing.

(56) References Cited

OTHER PUBLICATIONS

Ohashi, et al.; "Phospho-regulation of human protein kinase Aurora-A: analysis using anti-phospho-Thr288 monoclonal antibodies"; Oncogene, vol. 25, Issue No. 59; 2006; pp. 7691-7702.
Wojcik, et al.; "A potent and highly specific FN3 monobody inhibitor of the Abl SH2 domain"; Nature Structual and Molecular Biology, vol. 17, Issue No. 4; 2010; pp. 519-527.
Woldring, et al.; "High-Throughput Ligand Discovery Reveals a Sitewise Gradient of Diversity in Broadly Evolved Hydrophilic Fibronectin Domains" PLoS One, vol. 10, Issue No. 9; 2015; DOI: https://doi.org/10.1371/journal.pone.0138956.

* cited by examiner

FIG. 4
Monobody 10kDa
Antibody 150kDa
Antigen Binding Sites

FIG. 7

Monobody Mb2
MKHHHHHHSS GLNDIFEAQK IEWHEENLYF Q/GSVSSVPTK LEVVAATPTS
LLISWDAFGHQYEPVYYYRI TYGETGGNSP VQEFTVPGYY STATISGLKP GVDYTITVYA
WYVDGSYSSPISINYRT
(SEQ ID NO: 14)
Molecular weight:14385.8Da, Ext. coefficient: 35870 $M^{-1}$ $cm^{-1}$, Abs 0.1%: 2.493 g/l

High-resolution X-ray structure of deP Aurora A kinase bound to TPX2, activating monobody Mb54 or inhibitory monobody Mb60

| FIG. 16A |
| --- |
| FIG. 16B |

Highlighting residues of the PIF pocket that contact TPX2, activating monobody Mb54 or inhibitory monobody Mb60 as well as hallmarks of active (DFGin/complete R -spine) vs. inactive (DFG out/incomplete R-spine) Aurora A kinase

TNP-ATP
ex.479nm, em.500-600

$K_I = 138.23 \pm 20.2\ \mu M$ $v_{obs} = (k_{TPX2}{}^{*}[TPX2]^{*}[T288V]^{*}\mathbf{K_I})/(K_d{}^{TPX2}{}^{*}[PS48]+\mathbf{K_I}{}^{*}[TPX2])$ Li et al., *Cell Research,* 2005

1.TPX2(1-45*)-mCherry

Single cell quantification of H3_P in TPX2(1-45*)mCherry transfected cells

Transfection efficiency

H3_P and DNA staining

Control = 0hr after nocodazole release

H3_P and DNA staining

**TPX2(1-45*)-mCherry = 0hr after nocodazole release**

COMPOSITIONS AND METHODS FOR INHIBITING KINASE ACTIVITY

CROSS-REFERENCE TO RELATED APPLICATION

This application is the U.S. national phase application, pursuant to 35 U.S.C. § 371, of PCT International Application Ser. No.: PCT/US2017/016923, filed Feb. 8, 2017, designating the United States and published in English, which claims the benefit of the following U.S. Provisional Application No. 62/292,587, filed Feb. 8, 2016, the entire contents of each of which are incorporated herein by reference.

STATEMENT OF RIGHTS TO INVENTIONS MADE UNDER FEDERALLY SPONSORED RESEARCH

This invention was made with government support under Grant No. DE-FG02-05ER15699 awarded by the U.S. Department of Energy and Grant Nos. GM100966-01 and GM096053 awarded by the National Institutes of Health. The government has certain rights in the invention.

SEQUENCE LISTING

The instant application contains a Sequence Listing which has been submitted electronically in ASCII format and is hereby incorporated by reference in its entirety herein. The ASCII copy, created on Feb. 2, 2017, is named 167703.010801-Sequence Listing_ST25 and is 25,189 bytes in size.

BACKGROUND OF THE INVENTION

Deregulation of protein kinases can lead to aberrant signaling and abnormal events in cells that may contribute to the formation or growth of a cancer. An example of such a protein kinase is Aurora A kinase, an oncoprotein that is overexpressed in a multitude of cancers. A number of small molecule kinase inhibitors that target the ATP binding pocket of the kinase have been developed. However, over time, a patient can develop resistance to the kinase inhibitor. For example, if the kinase acquires a mutation in the ATP binding pocket that weakens or abolishes binding of the kinase inhibitor to the pocket, the kinase inhibitor is no longer effective. Accordingly, new methods of inhibiting kinase activity, particularly methods for inhibiting kinase activity that also inhibit development of resistance to kinase inhibition in a cancer patient, are urgently required.

SUMMARY OF THE INVENTION

The present invention features therapeutic compositions comprising an agent that specifically binds a PIF pocket of a kinase and an agent that binds an ATP-binding site of a kinase, methods of decreasing kinase activity using the therapeutic compositions, and the use of the therapeutic compositions to inhibit the Aurora A kinase for the treatment of cancer.

In one aspect, the invention provides a pharmaceutical composition containing an effective amount of an agent that specifically binds a PIF pocket on a kinase, an effective amount of an agent that specifically binds an ATP-binding site on the kinase, and a pharmaceutically acceptable carrier. In various embodiments of any one of the aspects delineated herein, the agent that specifically binds a PIF pocket and/or the agent that specifically binds an ATP-binding site is an antibody or antigen binding fragment thereof, antibody mimetic, peptide, polynucleotide, or small molecule compound. In various embodiments, the kinase is Aurora A kinase.

In some embodiments, the agent that specifically binds the PIF pocket site competes with TPX2 for binding to Aurora A kinase. In some other embodiments, binding of the agent that specifically binds the PIF pocket increases affinity of binding of the agent that specifically binds the ATP-binding site. In some embodiments, the increase in affinity is at least about 2-fold, at least about 4-fold, at least about 6-fold, at least about 8-fold, or at least about 10-fold. In various embodiments, binding of the agent that specifically binds the ATP-binding site decreases kinase activity. In some embodiments, binding of the agent that specifically binds the PIF pocket decreases kinase activity. In some other embodiments, binding of the agent that specifically binds the PIF pocket decreases kinase activity by increasing affinity of binding of the agent that specifically binds the ATP-binding site, shifting equilibrium to an inactive kinase conformation, and/or competing with TPX2 for binding to the PIF pocket.

In various embodiments of any one of the aspects delineated herein, the agent that specifically binds the PIF pocket contacts a residue in the PIF pocket of Aurora A kinase, where the residue is any one of the following Aurora A kinase residues: E175, H176, R179, Y199, and H201. In various embodiments, the agent that specifically binds the PIF pocket is a monobody containing any one of the following sequences:

```
AuroraA_44 (Mb44), also named (Mb4) herein.
                                             (SEQ ID NO: 1)
GSVSSVPTKL EVVAATPTSL LISWDAPAVT VDFYVITYGE

TGGYSYPWQE FEVPGSKSTA TISGLKPGVD YTITVYADYG

QYFYSPISIN YRT

AuroraA_51 (Mb51), also named (Mb5) herein.
                                             (SEQ ID NO: 2)
GSVSSVPTKL EVVAATPTSL LISWDAKPMS YEPVYYYRIT

YGETGGNSPV QEFTVPGYYS TATISGLKPG VDYTITVYAD

SMSSYYYSPI SINYRT

AuroraA_56 (Mb56), also named (Mb3) herein.
                                             (SEQ ID NO: 3)
GSVSSVPTKL EVVAATPTSL LISWDAMSDW YYWVDYYRIT

YGETGGNSPV QEFTVPGSYS TATISGLKPG VDYTITVYAS

DDVWGDYSPI SINYRT

AuroraA_60 (Mb60), also named (Mb2) herein.
                                             (SEQ ID NO: 4)
GSVSSVPTKL EVVAATPTSL LISWDAPAVT VVHYVITYGE

TGGNSPVQEF TVPGSKSTAT ISGLKPGVDY TITVYAIDFY

WGSYSPISIN YRT
```

In some embodiments, the agent that specifically binds the PIF pocket is PS48. In some other embodiments, the agent that specifically binds the ATP-binding site is Danusertib.

In various embodiments, the pharmaceutical composition further contains a vehicle for intracellular delivery. In some embodiments, the composition is formulated for intravenous delivery.

In another aspect, the invention provides a method of decreasing activity of a kinase. The method contains the step of contacting a kinase with an effective amount of an agent that specifically binds a PIF pocket on the kinase and an effective amount of an agent that specifically binds an ATP-binding site of the kinase, thereby decreasing activity of the kinase.

In yet another aspect, the invention provides a method of inhibiting development of resistance to kinase inhibition in a subject. The method contains the step of administering to the subject an effective amount of an agent that specifically binds a PIF pocket on the kinase and an effective amount of an agent that specifically binds an ATP-binding site of the kinase, thereby preventing or inhibiting development of resistance to kinase inhibition in the subject.

In still another aspect, the invention provides a method of inhibiting growth and/or proliferation of a cancer cell, the method containing the step of administering to the subject an effective amount of an agent that specifically binds a PIF pocket on the kinase and an effective amount of an agent that specifically binds an ATP-binding site of the kinase, thereby inhibiting growth and/or proliferation of a cancer cell.

In another aspect, the invention provides a method of treating a cancer associated with kinase activity in a subject. The method contains the step of administering to the subject an effective amount of an agent that specifically binds a PIF pocket on the kinase and an effective amount of an agent that specifically binds an ATP-binding site of the kinase, thereby treating a cancer associated with kinase activity in the subject.

In yet another aspect, the invention provides a method of increasing affinity of binding of a kinase inhibitor to an ATP-binding site of a kinase. The method contains the step of contacting the kinase with an effective amount of an agent that specifically binds a PIF pocket on the kinase, thereby increasing affinity of binding of the kinase inhibitor to the ATP-binding site of the kinase.

In another aspect, the invention provides a method of increasing efficacy of a kinase inhibitor that binds to an ATP-binding site on the kinase, the method containing the step of contacting the kinase with an effective amount of an agent that specifically binds a PIF pocket on the kinase, thereby increasing efficacy of the kinase inhibitor.

In various embodiments of any one of the aspects delineated herein, the agent that specifically binds the PIF pocket and/or the agent that specifically binds the ATP-binding site is administered intravenously. In various embodiments, the kinase is in vivo or in vitro. In some embodiments, the subject is human. In some other embodiments, an effective amount of the agent that specifically binds the PIF pocket is an amount of the agent that decreases the amount of the agent that specifically binds the ATP-binding site required to achieve a selected level of decrease in kinase activity.

In another aspect, the invention provides a method of decreasing activity of a kinase, the method containing the step of contacting the kinase with the composition of any one of the aspects delineated herein, thereby decreasing activity of the kinase.

In yet another aspect, the invention provides a method of preventing or inhibiting development of resistance to kinase inhibition in a subject, the method containing the step of administering to the subject the composition of any one of the aspects delineated herein, thereby preventing or inhibiting development of resistance to kinase inhibition in the subject.

In still another aspect, the invention provides a method of treating a cancer associated with kinase activity in a subject, the method comprising administering to the subject, the method containing the step of administering to the subject the composition of any one of the aspects delineated herein, thereby treating a cancer associated with kinase activity in the subject.

In another aspect, the invention provides a method for identifying an inhibitor or activator of Aurora A kinase. The method contains the steps of: (a) providing a three-dimensional structure of a Aurora A kinase polypeptide having at least one atomic coordinate, or surrogate thereof, from Appendix A for each of the amino acid residues 165-210 of a binding site of the Aurora A kinase polypeptide or atomic coordinates that have a root mean square deviation of the coordinates of less than 3 angstroms; and (b) producing a structure for a candidate compound wherein the structure defines a molecule having sufficient surface complementary to the Aurora A kinase polypeptide to bind the site in an aqueous solution.

In various embodiments of any one of the aspects delineated herein, the candidate compound is identified as an inhibitor of Aurora A kinase if an interaction between the candidate compound and the binding site mimics an interaction between monobody Mb60 and one or more of the following residues of Aurora A kinase: E175, H176, R179, Y199, and H201. In some embodiments, the candidate compound is identified as an activator of Aurora A kinase if an interaction between the candidate compound and the binding site mimics an interaction between monobody Mb54 and one or more of the following residues of Aurora A kinase: E170, K166, E175, H176, H201, L178, R179, Y199, and V182.

In various embodiments of any one of the aspects delineated herein, the method further contains the step of (c) evaluating the ability of the compound to bind an Aurora A kinase polypeptide in an in vitro, in vivo, or ex vivo assay. In some embodiments, the method further contains the step of (d) evaluating the ability of the compound to inhibit or activate kinase activity of Aurora A kinase polypeptide in an in vitro or in vivo assay. In some other embodiments, the method further contains the step of (e) evaluating ability of the compound to shift equilibrium to an inactive or active conformation of Aurora A kinase.

In various embodiments, the structure of the candidate compound is designed de novo. In some other embodiments, the method further contains the step of modifying the candidate compound based upon the positioning, alignment, and interactions between the candidate compound and one or more amino acids comprising the binding site.

In some embodiments, the interactions comprise an interaction between monobody Mb60 and one or more of the following residues of Aurora A kinase: E175, H176, R179, Y199, and H201, and/or an interaction between monobody Mb54 and one or more of the following residues of Aurora A kinase: E170, K166, E175, H176, H201, L178, R179, Y199, and V182. In some other embodiments, the candidate compound is modified such that an interaction between the candidate compound and the binding site better mimics an interaction between monobody Mb60 and one or more of the following residues of Aurora A kinase: E175, H176, R179, Y199, and H201. In still other embodiments, the candidate compound is modified such that an interaction between the candidate compound and the binding site does not mimic an interaction between monobody Mb54 and one or more of the following residues of Aurora A kinase: E170, K166, E175, H176, H201, L178, R179, Y199, and V182.

In various embodiments, the results of the evaluation in the step of evaluating the ability of the compound to bind an Aurora A kinase polypeptide in an in vitro, in vivo, or ex vivo assay, the step of evaluating the ability of the compound to inhibit or activate kinase activity of Aurora A kinase polypeptide in an in vitro or in vivo assay, or the step of evaluating ability of the compound to shift equilibrium to an inactive or active conformation of Aurora A kinase provide further structure related binding information such that other candidate compounds are selected for evaluation in any one of the steps.

In another aspect, the invention provides a method of identifying a modulator of a kinase having a PIF pocket. The method contains the steps of: (a) obtaining a three-dimensional structure of the PIF pocket bound to a natural modulator of the kinase; (b) producing a structure for a candidate compound, wherein the structure defines a molecule having sufficient surface complementary to the kinase to bind the PIF pocket in an aqueous solution; and (c) identifying the candidate compound as a modulator of the kinase if an interaction between the candidate compound and the PIF pocket mimics an interaction between the natural modulator and the PIF pocket.

In various embodiments, the method further contains the step of evaluating the ability of the compound to bind the kinase in an in vitro, in vivo, or ex vivo assay. In some embodiments, the method further contains the step of evaluating the ability of the compound to inhibit or activate kinase activity of the kinase in an in vitro or in vivo assay. In still other embodiments, the method contains the step of evaluating ability of the compound to shift equilibrium to an inactive or active conformation of the kinase. In some embodiments, the structure of the candidate compound is designed de novo. In some other embodiments, the method further contains the step of modifying the candidate compound based upon the positioning, alignment, and interactions between the candidate compound and one or more amino acids comprising the PIF pocket. In some embodiments, the candidate compound is modified such that an interaction between the candidate compound and the PIF pocket better mimics an interaction between the natural modulator and the PIF pocket.

In various embodiments, the results of the evaluation in the step of evaluating the ability of the compound to bind the kinase in an in vitro, in vivo, or ex vivo assay, the step of evaluating the ability of the compound to inhibit or activate kinase activity of the kinase in an in vitro or in vivo assay, or the step of evaluating ability of the compound to shift equilibrium to an inactive or active conformation of the kinase provide further structure related binding information such that other candidate compounds are selected for evaluation in any one of the steps. In some embodiments, the kinase is any one of the following AGC kinases: PKA, Akt1, Akt2, PKCβ, $PKC_1$, PKCθ, Rock1, Rock2, DMPK, Grk1, and Grk2.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, "activity" or "biological activity" of a polypeptide refers to any biological function of the polypeptide. Activity of a polypeptide may refer to the polypeptide's enzymatic or catalytic activity, such as kinase activity. For example, "kinase activity" of Aurora A kinase refers to Aurora A kinase's phosphorylation of a serine or threonine residue on a substrate polypeptide. Exemplary biological activities of Aurora A kinase include regulation of mitotic entry and progression, spindle assembly, and spindle stability.

In some embodiments, kinase activity of Aurora A kinase is measured by measuring rate of phosphorylation of a substrate by Aurora A kinase. By "phosphorylation rate" or "rate of phosphorylation" is meant the kinetic rate of a phosphorylation reaction catalyzed by a kinase. An increase in the rate of phosphorylation indicates increased kinase activity. Conversely, a decrease in the rate of phosphorylation indicates decreased kinase activity.

An exemplary measure of the rate is the value of a rate constant, k. The rate constant may be determined by plotting the concentrations of phosphorylated substrate against time, and fitting a curve or line to the concentration vs. time data. In some embodiments, the rate constant is determined by determining the slope of a line fit to concentrations of phosphorylated substrate of Aurora A kinase over time. Exemplary peptide substrates of Aurora A kinase include, but are not limited to, AP (APSSRRTTLCGTL) (SEQ ID NO: 5), Kemptide (LRRASLG) (SEQ ID NO: 6), or Lats2 (ATLARRDSLQKPGLE) (SEQ ID NO: 7). The rate of phosphorylation may be dependent on assay conditions, such as temperature. Thus, an exemplary method of comparing effects of a modulator of Aurora A kinase on Aurora A's phosphorylation rate is to compare the rates of phosphorylation of Aurora A kinase contacted and not contacted with the modulator under identical or nearly identical assay conditions.

The term "antibody," as used herein, refers to an immunoglobulin molecule which specifically binds with an antigen. Methods of preparing antibodies are well known to those of ordinary skill in the science of immunology. Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. Antibodies also include dimers that may be naturally occurring or constructed from single chain antibodies or antibody fragments. The antibodies in the present invention may exist in a variety of forms including, for example, polyclonal antibodies, monoclonal antibodies, Fv, Fab and F(ab') 2, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab') 2, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments. The antibody fragment also includes a human antibody or a humanized antibody or a portion of a human antibody or a humanized antibody.

Antibodies can be made by any of the methods known in the art utilizing a polypeptide of the invention (e.g., Aurora A kinase), or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding a polypeptide of the invention or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding the polypeptide, or immunogenic fragments thereof, can be expressed in cells in vitro, followed by isolation of the polypeptide and administration of the polypeptide to a suitable host in which antibodies are raised.

Alternatively, antibodies against the polypeptide may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

By "antibody mimetic" or "antibody mimic" is meant a molecule which specifically binds an antigen, but is not structurally related to antibodies. Typically, antibody mimetics specifically binding to a target are produced by screening libraries of mutagenized molecular scaffolds. Examples of molecular scaffolds include, without limitation, a fibronectin III (FN3) domain. The molecular scaffold is typically a smaller molecule than an antibody (e.g., about 50-200 residues). Examples of antibody mimetics include, without limitation, affibodies, affilins, affitins, anticalins, avimers, DARPins, Kunitz domain derived peptides, knottins and monobodies. In particular embodiments, an antibody mimetic of the invention is a monobody specifically binding to the PIF pocket of Aurora A kinase.

As used herein, "affinity" or "binding affinity" refers to the strength of binding of an agent to another agent (in particular, binding of a small molecule compound or a polypeptide to another polypeptide). An exemplary quantitative measure of affinity is the dissociation constant, $K_d$. The $K_d$ is a measure relating concentrations of unbound agents with concentrations of bound agents at equilibrium. For example, in an exemplary binding reaction, an agent (A) binds to another agent (B) to form a complex (AB). The dissociation constant, $K_d$, for the binding between A and B is $K_d$=[A][B]/[AB], where [A] is the concentration of unbound A at equilibrium, [B] is the concentration of unbound B at equilibrium, and [AB] is the concentration of A and B bound together (i.e., concentration of bound A or bound B) at equilibrium. A high affinity of A to B is reflected in low concentrations of unbound A and unbound B and high concentrations of A bound to B at equilibrium. Low concentrations of unbound A and unbound B and high concentrations of A bound to B at equilibrium yield a low $K_d$ value. Thus, the $K_d$ is inversely related to affinity; a lower value of $K_d$ indicates a higher affinity.

By "AGC kinase" or "AGC protein kinase" is meant a protein kinase belonging to a group of protein kinases that includes at least about 60 protein kinases in the human genome, which are classified into at least the following kinase families: PDK1, AKT/PKB, SGK, PKA, PKG, PKC, PKN/PRK, RSK, NDR, MAST, YANK, DMPK, GRK, and SGK494. AGC kinases are involved in diverse cellular functions. Fundamental in the regulation of many AGC kinases is a regulatory site known as the "PIF pocket" of the AGC kinase (Arencibia et al., *Biochim Biophys Acta* (2013); 1834(7):1302-21). In some embodiments, the AGC kinase is PKA, Akt1, Akt2, PKCβ, $PKC_\iota$, PKCθ, Rock1, Rock2, DMPK, Grk1, or Grk2.

By "agent" is meant any small molecule chemical compound, antibody, antibody mimetic, nucleic acid molecule, or polypeptide, or fragments thereof. In certain embodiments, an agent that specifically binds to an allosteric site, such as the PIF pocket, of Aurora A kinase is a monobody or a small molecule compound. In particular embodiments, an agent that specifically binds to an ATP-binding site of Aurora A kinase is a small molecule compound.

By "allosteric regulation," "allosteric control," or "allosteric modulation" of polypeptide activity is meant modulation of activity of the polypeptide via binding of an effector molecule to a site other than the polypeptide's active site. Binding of the effector molecule to this site, referred to herein as the "allosteric site," can induce conformational changes in the polypeptide that alters the active site, thereby altering the polypeptide's activity. The TPX2 polypeptide is an exemplary allosteric regulator of kinase activity of a polypeptide. TPX2 polypeptide binds to the PIF pocket of Aurora A kinase, an allosteric site on Aurora A kinase. TPX2 polypeptide does not bind to the Aurora A kinase ATP-binding site, the active site of Aurora A kinase. The binding of the TPX2 polypeptide to the PIF pocket of Aurora A kinase increases kinase activity of Aurora A kinase. In some embodiments, a monobody of the invention is an allosteric regulator of kinase activity of Aurora A kinase. In particular embodiments, a monobody binds to the allosteric site, such as the PIF pocket, of Aurora A kinase. In some embodiments, a small molecular compound binds to the allosteric site of Aurora A kinase. In particular embodiments, the binding of a monobody or small molecule compound to the allosteric site inhibits kinase activity of Aurora A kinase. In some embodiments, binding at the allosteric site inhibits kinase activity of Aurora A kinase by competing for binding to the site with TPX2 polypeptide, shifting equilibrium to the inactive kinase conformation, and/or increasing affinity of binding of an agent to the ATP-binding site.

By "ameliorate" is meant decrease, suppress, attenuate, diminish, arrest, or destabilize the development or progression of a disease. Diseases include cancers characterized by an increase in Aurora A kinase activity.

By "alteration" is meant an increase or decrease in the expression levels or activity of a gene or polypeptide as detected by standard art known methods such as those described herein. As used herein, an alteration includes a 10% change in expression levels or activity, a 25% change, a 40% change, and a 50% or greater change in expression levels or activity. In some embodiments, the activity is kinase activity. In one embodiment, a monobody of the invention alters Aurora A kinase activity by at least about 5%, 10%, 15%, 20%, 25% or more.

By "analog" is meant a molecule that is not identical, but has analogous functional or structural features. In some embodiments, an analog of ATP is AMPPCP (i.e., Beta, gamma-Methylene ATP, also called phosphomethylphosphonic acid adenylate ester). In some other embodiments, a fluorescent analog of ATP is TNP-ATP.

By "Aurora A," "Aurora A kinase," or "Aurora A polypeptide" is meant a polypeptide or fragment thereof having at least about 85% or greater amino acid identity to the amino acid sequence provided at NCBI Accession No. NP_940839 and having serine/threonine kinase activity. An exemplary polypeptide sequence of Aurora A kinase is provided below:

(SEQ ID NO: 8)

```
1   mdrskencis gpvkatapvg gpkrvlvtqq fpcqnplpvn sgqaqrvlcp snssqriplq
61  aqklvsshkp vqnqkqklq atsvphpvsr plnntqkskq plpsapennp eeelaskqkn
121 eeskkrqwal edfeigrplg kgkfgnvyla rekqskfila lkvlfkaqle kagvehqlrr
181 eveiqshlrh pnilrlygyf hdatrvylil eyaplgtvyr elqklskfde qrtatyitel
241 analsychsk rvihrdikpe nlllgsagel kiadfgwsvh apssrrttlc gtldylppem
301 iegrmhdekv dlwslgvlcy eflvgkppfe antyqetykr isrveftfpd fvtegardli
361 srllkhnpsq rpmlrevleh pwitansskp sncqnkesas kqs
```

By "Aurora A polynucleotide" is meant a polynucleotide encoding an Aurora A polypeptide. An exemplary Aurora A polynucleotide sequence is provided at NCBI Accession No. NM_198437.1. The sequence is provided below:

(SEQ ID NO: 9)

```
1   acaaggcagc ctcgctcgag cgcaggccaa tcggctttct agctagaggg tttaactcct
61  atttaaaaag aagaaccttt gaattctaac ggctgagctc ttggaagact tgggtccttg
121 ggtcgcaggc atcatggacc gatctaaaga aaactgcatt tcaggacctg ttaaggctac
181 agctccagtt ggaggtccaa aacgtgttct cgtgactcag caatttcctt gtcagaatcc
241 attacctgta aatagtggcc aggctcagcg ggtcttgtgt ccttcaaatt cttcccagcg
301 cattcctttg caagcacaaa agcttgtctc cagtcacaag ccggttcaga atcagaagca
361 gaagcaattg caggcaacca gtgtacctca tcctgtctcc aggccactga ataacaccca
421 aaagagcaag cagcccctgc catcggcacc tgaaaataat cctgaggagg aactggcatc
481 aaaacagaaa aatgaagaat caaaaaagag gcagtgggct ttggaagact ttgaaattgg
541 tcgccctctg ggtaaaggaa agtttggtaa tgtttatttg gcaagagaaa agcaaagcaa
601 gtttattctg gctcttaaag tgttatttaa agctcagctg gagaaagccg gagtggagca
661 tcagctcaga agagaagtag aaatacagtc ccaccttcgg catcctaata ttcttagact
721 gtatggttat ttccatgatg ctaccagagt ctacctaatt ctggaatatg caccacttgg
781 aacagtttat agagaacttc agaaactttc aaagtttgat gagcagagaa ctgctactta
841 tataacagaa ttggcaaatg ccctgtctta ctgtcattcg aagagagtta ttcatagaga
901 cattaagcca gagaacttac ttcttggatc agctggagag cttaaaattg cagattttgg
```

-continued 961 gtggtcagta catgctccat cttccaggag gaccactctc tgtggcaccc tggactacct 1021 gccccctgaa atgattgaag gtcggatgca tgatgagaag gtggatctct ggagccttgg 1081 agttctttgc tatgaatttt tagttgggaa gcctcctttt gaggcaaaca cataccaaga 1141 gacctacaaa agaatatcac gggttgaatt cacattccct gactttgtaa cagagggagc 1201 cagggacctc atttcaagac tgttgaagca taatcccagc cagaggccaa tgctcagaga 1261 agtacttgaa caccccctgga tcacagcaaa ttcatcaaaa ccatcaaatt gccaaaacaa 1321 agaatcagct agcaaacagt cttaggaatc gtgcaggggg agaaatcctt gagccagggc 1381 tgccatataa cctgacagga acatgctact gaagtttatt ttaccattga ctgctgccct 1441 caatctagaa cgctacacaa gaaatatttg ttttactcag caggtgtgcc ttaacctccc 1501 tattcagaaa gctccacatc aataaacatg acactctgaa gtgaaagtag ccacgagaat 1561 tgtgctactt atactggttc ataatctgga ggcaaggttc gactgcagcc gccccgtcag 1621 cctgtgctag gcatggtgtc ttcacaggag gcaaatccag agcctggctg tggggaaagt 1681 gaccactctg ccctgacccc gatcagttaa ggagctgtgc aataaccttc ctagtacctg 1741 agtgagtgtg taacttattg ggttggcgaa gcctggtaaa gctgttggaa tgagtatgtg 1801 attcttttta agtatgaaaa taaagatata tgtacagact tgtatttttt ctctggtggc 1861 attcctttag gaatgctgtg tgtctgtccg gcaccccggt aggcctgatt gggtttctag 1921 tcctccttaa ccacttatct cccatatgag agtgtgaaaa ataggaacac gtgctctacc 1981 tccatttagg gatttgcttg ggatacagaa gaggccatgt gtctcagagc tgttaagggc 2041 ttattttttt aaaacattgg agtcatagca tgtgtgtaaa ctttaaatat gcaaataaat 2101 aagtatctat gtctaaaaaa a In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The terms "binding," "bind," "bound" refer to an interaction between two molecules. The interaction may include a covalent or non-covalent bond. The interaction may also be reversible or irreversible depending on the type of interaction, such as covalent bond formation.

By "danusertib" is meant an inhibitor of Aurora A kinase having the structure as shown below. Danusertib binds to the ATP-binding site of Aurora A kinase.

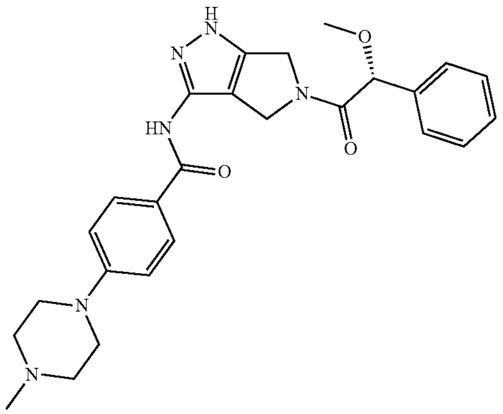 [SMILES: CO[C@@H](C(=O)N1Cc2[nH]nc(NC(=O)c3ccc(N4CCN(C)CC4)cc3)c2C1)c1ccccc1]

"Detect" refers to identifying the presence, absence or amount of the analyte to be detected.

By "detectable label," "detectable moiety," or "detectable tag" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include cancers characterized by an increase in an Aurora A kinase activity or misregulation of Aurora A kinase.

By "dephosphorylated Aurora A kinase" is meant lack of phosphorylation of T288 in the activation loop of Aurora A. Dephosphorylated Aurora A kinase favors the inactive conformation whereas phosphorylated Aurora A kinase is primarily in the active conformation.

By "effective amount" is meant the amount of an agent required to ameliorate the symptoms of a disease relative to an untreated patient. The effective amount of active agent(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "epitope tag" is meant a peptide sequence having immunoreactivity. Exemplary epitope tags include, but are not limited to V5-tag, Myc-tag, a 6×-His tag, and HA-tag.

The invention provides a number of targets that are useful for the development of highly specific drugs to treat or ameliorate a disorder characterized by the methods delineated herein. In addition, the methods of the invention provide a facile means to identify therapies that are safe for use in subjects.

By "fragment" is meant a portion of a polypeptide or nucleic acid molecule. This portion contains at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "fusion protein" or "fusion polypeptide" is meant a polypeptide or fragment thereof that combines at least two amino acid sequences that are not naturally contiguous. In some embodiments, a fusion polypeptide comprises an amino acid sequence encoding a monobody of the invention fused to an amino acid sequence encoding a supercharged polypeptide (e.g., a supercharged green fluorescent protein (GFP)). In other embodiments, the fusion polypeptide comprises an amino acid sequence encoding a monobody of the invention fused to an amino acid sequence encoding an epitope tag or a detectable tag.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence. "Polynucleotide" and "nucleic acid molecule" are used interchangeably herein.

Unless otherwise specified, a "polynucleotide encoding an amino acid sequence," a "polynucleotide encoding a polypeptide," or a "nucleotide sequence encoding an amino acid sequence," includes all nucleotide sequences that are degenerate versions of each other and that encode the same amino acid sequence. The phrase nucleotide sequence that encodes a polypeptide or an RNA may also include introns to the extent that the nucleotide sequence encoding the polypeptide may in some version contain an intron(s).

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. In some embodiments, the preparation is at least 75%, at least 90%, or at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "monobody" is meant an antibody mimetic comprising a fibronectin type III domain (FN3) as a molecular scaffold. Monobodies are produced from combinatorial libraries in which portions of the FN3 scaffold are diversified using highly tailored mixtures of amino acids by utilizing phage display and yeast surface display techniques. These techniques have successfully generated a large number of monobodies that have high affinity and high specificity to their respective targets. Monobodies and methods of generating monobodies are further described in, for example, PCT/US2007/078039, U.S. Pat. No. 6,673,901, and PCT/US2011/046160, which are incorporated herein in its entirety.

As used herein, an "inhibitory monobody" or "inhibitor monobody" is meant a monobody that binds a kinase and decreases kinase activity. As used herein, an "activating monobody" or "activator monobody" is meant a monobody that binds a kinase and increases kinase activity. In some embodiments, an inhibitory monobody binds an allosteric site of Aurora A kinase and shifts equilibrium to the inactive conformation. In some embodiments, an activating monobody binds an allosteric site of Aurora A kinase and shifts equilibrium to the active conformation.

By "monobody Mb2" (also known as (aka) "monobody Mb6" herein) is meant a monobody or fragment thereof that binds an allosteric site on Aurora A kinase, increases Aurora A kinase activity, and has at least about 85% amino acid sequence identity to the following amino acid sequence:

```
AuroraA_2(Mb2)(aka Mb6)
                                         (SEQ ID NO: 10)
GSVSSVPTKL EVVAATPTSL LISWDAFGHQ YEPVYYYRIT

YGETGGNSPV QEFTVPGYYS TATISGLKPG VDYTITVYAW

YVDGSYSSPI SINYRT
```

Monobody Mb2 of the priority document (aka Mb6 herein) has neutral activity on Aurora A kinase as shown in the chart below and as described infra.

By "monobody Mb44" (also known as "monobody Mb4" herein) is meant a monobody or fragment thereof that binds an allosteric site on Aurora A kinase, reduces Aurora A kinase activity, and that has at least about 85% amino acid sequence identity to the following amino acid sequence:

```
AuroraA_44(Mb44)(aka Mb4)
                                         (SEQ ID NO: 1)
GSVSSVPTKL EVVAATPTSL LISWDAPAVT VDFYVITYGE

TGGYSYPWQE FEVPGSKSTA TISGLKPGVD YTITVYADYG

QYFYSPISIN YRT
```

By "monobody Mb51" (also known as "monobody Mb5" herein) is meant a monobody or fragment thereof that binds an allosteric site on Aurora A kinase and has at least about 85% amino acid sequence identity to the following amino acid sequence:

```
AuroraA_51(Mb51)(aka Mb5)
                                         (SEQ ID NO: 2)
GSVSSVPTKL EVVAATPTSL LISWDAKPMS YEPVYYYRIT

YGETGGNSPV QEFTVPGYYS TATISGLKPG VDYTITVYAD

SMSSYYYSPI SINYRT
```

By "monobody Mb54" (also known as "monobody Mb1" herein) is meant a monobody that binds an allosteric site on Aurora A kinase, increases Aurora A kinase activity, and has at least about 85% amino acid sequence identity to the following amino acid sequence:

```
AuroraA_54(Mb54)(aka Mb1)
                                        (SEQ ID NO: 11)
GSVSSVPTKL EVVAATPTSL LISWDAQTYQ MYDYVSYYRI

TYGETGGNSP VQEFTVPGYY STATISGLKP GVDYTITVYA

EGYYSSYSPI SINYRT
```

By "monobody Mb56" (also known as "monobody Mb3" herein) is meant a monobody that binds an allosteric site on Aurora A kinase, decreases Aurora A kinase activity, and has at least 85% amino acid sequence identity to the following amino acid sequence:

```
AuroraA_56(Mb56)(aka Mb3)
                                         (SEQ ID NO: 3)
GSVSSVPTKL EVVAATPTSL LISWDAMSDW YYWVDYYRIT

YGETGGNSPV QEFTVPGSYS TATISGLKPG VDYTITVYAS

DDVWGDYSPI SINYRT
```

By "monobody Mb60" (also known as "monobody Mb2" herein) is meant a monobody that binds an allosteric site on Aurora A kinase, decreases Aurora A kinase activity, and has at least 85% amino acid sequence identity to the following amino acid sequence:

```
AuroraA_60(Mb60)(aka Mb2)
                                         (SEQ ID NO: 4)
GSVSSVPTKL EVVAATPTSL LISWDAPAVT VVHYVITYGE

TGGNSPVQEF TVPGSKSTAT ISGLKPGVDY TITVYAIDFY

WGSYSPISIN YRT
```

It will be understood that the monobodies (Mbs) described supra and infra (e.g., in the Brief Description of the Drawings, Figures and Examples) may be denoted by alternative names, but are otherwise wholly identical in all of their aspects. The equivalency in the nomenclature that identifies each of the described monobodies, as well as their activity as an activator or inhibitor of Aurora A kinase, are set forth below:

| Provisional Application No. 62/292,587 Name of Monobody (Mb) | Alternative/ Equivalent Name of Monobody (Mb) | Activity of Monobody on Aurora A kinase |
|---|---|---|
| Mb54 | =Mb1 | activator |
| Mb60 | =Mb2 | inhibitor |
| Mb56 | =Mb3 | inhibitor |
| Mb44 | =Mb4 | inhibitor |
| Mb51 | =Mb5 | inhibitor |
| Mb2 | =Mb6 | neutral |

By "marker" is meant any protein or polynucleotide having an alteration in expression level or activity that is associated with a disease or disorder.

By "mutation" is meant a change in a polypeptide or polynucleotide sequence relative to a wild-type reference sequence. Exemplary mutations include point mutations, missense mutations, amino acid substitutions, and frame-shift mutations.

By "natural modulator" of a kinase is meant an agent, such as a polypeptide, that binds to a site on the kinase and modulates activity of the kinase in a natural or endogenous setting in a cell. In some embodiments, a natural modulator of Aurora A kinase is TPX2. In some other embodiments, the site on the kinase bound by the natural modulator is a PIF pocket.

As used herein, "obtaining" as in "obtaining an agent" includes synthesizing, purchasing, or otherwise acquiring the agent.

By "PS48" is meant an inhibitor of Aurora A kinase having the structure shown below:

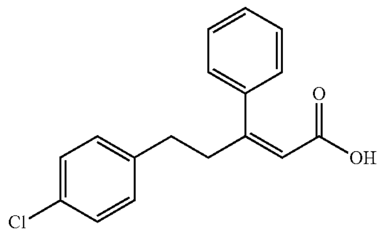 [SMILES: O=C(O)/C=C(/CCc1ccc(Cl)cc1)c1ccccc1]

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, at least about 20 amino acids, at least about 25 amino acids, and at least about 35 amino acids, at least about 50 amino acids, or at least about 100 amino acids. For nucleic acids, the length of the reference nucleic acid sequence will generally be at least about 50 nucleotides, at least about 60 nucleotides, at least about 75 nucleotides, and at least about 100 nucleotides or at least about 300 nucleotides or any integer thereabout or therebetween.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) *Methods Enzymol.* 152:399; Kimmel, A. R. (1987) *Methods Enzymol.* 152:507).

For example, stringent salt concentration will ordinarily be less than about 750 mM NaCl and 75 mM trisodium citrate, less than about 500 mM NaCl and 50 mM trisodium citrate, and less than about 250 mM NaCl and 25 mM trisodium citrate. Low stringency hybridization can be obtained in the absence of organic solvent, e.g., formamide, while high stringency hybridization can be obtained in the presence of at least about 35% formamide, at least about 50% formamide. Stringent temperature conditions will ordinarily include temperatures of at least about 30° C., at least about 37° C., and at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In one embodiment, hybridization will occur at 37° C. in 500 mM NaCl, 50 mM trisodium citrate, 1% SDS, 35% formamide, and 100 μg/ml denatured salmon sperm DNA (ssDNA). In another embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps can be less than about 30 mM NaCl and 3 mM trisodium citrate or less than about 15 mM NaCl and 1.5 mM trisodium citrate. Stringent temperature conditions for the wash steps will ordinarily include a temperature of at least about 25° C., at least about 42° C., and at least about 68° C. In one embodiment, wash steps will occur at 25° C. in 30 mM NaCl, 3 mM trisodium citrate, and 0.1% SDS. In another embodiment, wash steps will occur at 42° C. in 15 mM NaCl, 1.5 mM trisodium citrate, and 0.1% SDS. In still another embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (*Science* 196:180, 1977); Grunstein and Hogness (*Proc. Natl. Acad. Sci., USA* 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

As used herein, an agent that "shifts equilibrium" to an inactive conformation of a kinase is meant that in the presence of the agent, the fraction of the kinase population in the inactive conformation at equilibrium is increased relative to the fraction of the kinase population in the inactive conformation at equilibrium in the absence of the agent. Conversely, an agent that shifts equilibrium to the active conformation of a kinase is meant that in the presence of the agent, the fraction of the kinase population in the active conformation at equilibrium is increased relative to the fraction of the kinase population in the active conformation at equilibrium in the absence of the agent.

As used herein, an "inactive" conformation of a kinase is a conformation of the kinase where although access of ATP and binding of ATP to the ATP binding pocket can be achieved, as in the "active" Aurora A kinase conformation, the rest of the Aurora A kinase residues are not properly positioned for catalysis. In some embodiments, ATP or an analog of ATP binds Aurora A kinase in the inactive conformation. In some other embodiments, ATP or an analog of ATP binds Aurora A kinase in the active conformation. In still other embodiments, danusertib binds Aurora A kinase in the inactive conformation.

In some embodiments, the kinase is Aurora A kinase. In particular embodiments, an inactive conformation of Aurora A kinase is the DFG out ($DFG_{out}$) conformation. In some other embodiments, an active conformation of Aurora A kinase is the DFG in ($DFG_{in}$) conformation. In particular embodiments, ATP or an analog of ATP binds the ATP-binding site of Aurora A kinase and does not bind to the PIF pocket.

By "specifically binds" is meant an agent that recognizes and binds a polypeptide, or fragment thereof, of the invention, but which does not substantially recognize and bind other molecules in a sample, for example, a biological sample, which naturally includes a polypeptide of the invention. An agent may also "specifically bind" to a particular site on a polypeptide, and not bind to other sites of the polypeptide. In some embodiments, an agent specifically binds to an allosteric site, such as the PIF pocket, of Aurora A kinase. In some embodiments, an agent specifically binds to the ATP binding site of Aurora A kinase.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Such a sequence can be at least 60%, at least 80%, at least 85%, at least 90%, at least 95% or even at least 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

By "supercharged polypeptide" or "supercharged fragment" is meant a polypeptide or fragment thereof, either engineered or naturally existing, with unusually high positive or negative net theoretical charge (typically >1 net charge unit per kD of molecular weight). A polypeptide may be engineered to be "supercharged" by substituting residues on the polypeptide for residues having a charge. A polypeptide may also be "supercharged" by fusion to a supercharged polypeptide. In some embodiments, a monobody of the invention is supercharged by fusing the monobody to a supercharged green fluorescent protein (GFP).

Supercharged polypeptides having a negative net theoretical charge are "supernegatively" charged; conversely, supercharged polypeptides having a positive net theoretical charge are "superpositively" charged. Supercharged polypeptides typically exhibit resistance to thermally or chemically induced aggregation. Supercharged polypeptides may also be able to bind and penetrate cells (particularly, mammalian cells), and can therefore deliver nucleic acid or protein cargoes into cells. In some embodiments, a supercharged monobody of the invention (e.g., a monobody fused to a supercharged polypeptide such as supercharged GFP) is delivered to a cell. In some other embodiments, the supercharged monobody is delivered to a cell by cationic liposome mediated delivery. Methods for engineering supercharged polypeptides for intracellular delivery of proteins into cells and for delivering supercharged polypeptides into a cell are described in, for example, Zuris et al. (2015), *Nat. Biotechnol.* 33, 73-80 and Liu et al. (2012), *Methods Enzymol.* 503: 293-319.

By "TPX2 polypeptide" is meant a polypeptide or fragment thereof having at least about 85% or greater amino acid identity to the amino acid sequence provided at GenBank Accession Nos. EAW76422.1, EAW76421.1, and EAW76420.1 (various isoforms) and having TPX2 biological activity. Exemplary biological activities of TPX2 include, without limitation, binding to Aurora A kinase and mediating localization of Aurora A kinase to the spindles. The exemplary TPX2 polypeptide sequence at GenBank Accession No. EAW76422.1 is provided below:

```
                                                               (SEQ ID NO: 12)
  1  msqvkssysy dapsdfinfs slddegdtqn idswfeekan lenkllgkng tgglfqgktp
 61  lrkanlqqai vtplkpvdnt yykeaekenl veqsipsnac ssleveaais rktpaqpqrr
121  slrlsaqkdl eqkekhhvkm kakrcatpvi ideilpskkm kvsnnkkkpe eegsahqdta
181  eknasspeka kgrhtvpcmp pakqkflkst eegeleksmk mqqevvemrk kneefkklal
241  agigqpvkks vsqvtksvdf hfrtderikq hpknqeeyke vnftselrkh pssparvtkg
301  ctivkpfnls qgkkrtfdet vstyvplaqq vedfhkrtpn ryhlrskkdd iktgscsvtq
361  agvqwrdhgs lqcptpglkq ssclslpnll pskssvtkic rdpqtpvlqt khraravtck
421  staeleaeel eklqqykfka reldprileg gpilpkkppv kpptepigfd leiekriger
481  eskkktedeh fefhsrpcpt kiledvvgvp ekkvlpitvp kspafalknr irmptkedee
541  edepvvikaq pvphygvpfk pqipeartve icpfsfdsrd kerqlqkekk ikelqkgevp
601  kfkalplphf dtinlpekkv knvtqiepfc letdrrgalk aqtwkhqlee elrqqkeaac
661  fkarpntvis qepfvpkkek ksvaeglsgs lvqepfqlat ekrakergel ekrmaeveaq
721  kaqqleearl qeeeqkkeel arlrrelvhk anpirkyqgl eikssdqplt vpvspkfstr
781  fhc
```

By "TPX2 polynucleotide" is meant a polynucleotide encoding a TPX2 polypeptide. An exemplary TPX2 polynucleotide sequence is provided at NCB1 Accession No. NM_012112. The sequence is provided below:

```
                                                               (SEQ ID NO: 13)
  1  agtggactca cgcaggcgca ggagactaca cttcccagga actccgggcc gcgttgttcg
 61  ctggtacctc cttctgactt ccggtattgc tgcggtctgt agggccaatc gggagcctgg
121  aattgctttc ccggcgctct gattggtgca ttcgactagg ctgcctgggt tcaaaatttc
181  aacgatactg aatgagtccc gcggcgggtt ggctcgcgct tcgttgtcag atctgaggcg
241  aggctaggtg agccgtggga agaaaagagg gagcagctag ggcgcgggtc tccctcctcc
301  cggagtttgg aacggctgaa gttcaccttc cagcccctag cgccgttcgc gccgctaggc
```

-continued 361 ctggcttctg aggcggttgc ggtgctcggt cgccgcctag gcggggcagg gtgcgagcag 421 gggcttcggg ccacgcttct cttggcgaca ggattttgct gtgaagtccg tccgggaaac 481 ggaggaaaaa aagagttgcg ggaggctgtc ggctaataac ggttcttgat acatatttgc 541 cagacttcaa gatttcagaa aaggggtgaa agagaagatt gcaactttga gtcagacctg 601 taggcctgat agactgatta aaccacagaa ggtgacctgc tgagaaaagt ggtacaaata 661 ctgggaaaaa cctgctcttc tgcgttaagt gggagacaat gtcacaagtt aaaagctctt 721 attcctatga tgccccctcg gatttcatca atttttcatc cttggatgat gaaggagata 781 ctcaaaacat agattcatgg tttgaggaga aggccaattt ggagaataag ttactgggga 841 agaatggaac tggagggctt tttcagggca aaactccttt gagaaaggct aatcttcagc 901 aagctattgt cacacctttg aaaccagttg acaacactta ctacaaagag gcagaaaaag 961 aaaatcttgt ygaacaatcc attcuytcaa atgcttgttc ttccctggaa gttgaggcag 1021 ccatatcaag aaaaactcca gcccagcctc agagaagatc tcttaggctt tctgctcaga 1081 aggatttgga acagaaagaa aagcatcatg taaaaatgaa agccaagaga tgtgccactc 1141 ctgtaatcat cgatgaaatt ctaccctcta agaaaatgaa agtttctaac aacaaaaaga 1201 agccagagga agaaggcagt gctcatcaag atactgctga aaagaatgca tcttccccag 1261 agaaagccaa gggtagacat actgtgcctt gtatgccacc tgcaaagcag aagtttctaa 1321 aaagtactga ggagcaagag ctggagaaga gtatgaaaat gcagcaagag gtggtggaga 1381 tgcggaaaaa gaatgaagaa ttcaagaaac ttgctctggc tggaataggg caacctgtga 1441 agaaatcagt gagccaggtc accaaatcag ttgacttcca cttccgcaca gatgagcgaa 1501 tcaaacaaca tcctaagaac caggaggaat ataaggaagt gaactttaca tctgaactac 1561 gaaagcatcc ttcatctcct gcccgagtga ctaagggatg taccattgtt aagcctttca 1621 acctgtccca aggaaagaaa agaacatttg atgaaacagt ttctacatat gtgccccttg 1681 cacagcaagt tgaagacttc cataaacgaa cccctaacag atatcatttg aggagcaaga 1741 aggatgatat taacctgtta ccctccaaat cttctgtgac caagatttgc agagacccac 1801 agactcctgt actgcaaacc aaacaccgtg cacgggctgt gacctgcaaa agtacagcag 1861 agctggaggc tgaggagctc gagaaattgc aacaatacaa attcaaagca cgtgaacttg 1921 atcccagaat acttgaaggt gggcccatct tgcccaagaa accacctgtg aaaccaccca 1981 ccgagcctat tggctttgat ttggaaattg agaaaagaat ccaggagcga gaatcaaaga 2041 agaaaacaga ggatgaacac tttgaatttc attccagacc ttgccctact aagattttgg 2101 aagatgttgt gggtgttcct gaaaagaagg tacttccaat caccgtcccc aagtcaccag 2161 cctttgcatt gaagaacaga attcgaatgc ccaccaaaga agatgaggaa gaggacgaac 2221 cggtagtgaL aaaagctcaa cctgtgccac attatggggt gccttttaag ccccaaatcc 2281 cagaggcaag aactgtggaa atatgccctt tctcgtttga ttctcgagac aaagaacgtc 2341 agttacagaa ggagaagaaa ataaaagaac tgcagaaagg ggaggtgccc aagttcaagg 2401 cacttccctt gcctcatttt gacaccatta acctgccaga gaagaaggta aagaatgtga 2461 cccagattga acctttctgc ttggagactg acagaagagg tgctctgaag gcacagactt 2521 ggaagcacca gctggaagaa gaactgagac agcagaaaga agcagcttgt ttcaaggctc 2581 gtccaaacac cgtcatctct caggagccct ttgttcccaa gaaagagaag aaatcagttg 2641 ctgagggcct ttctggttct ctagttcagg aaccttttca gctggctact gagaagagag 2701 ccaaagagcg gcaggagctg gagaagagaa tggctgaggt agaagcccag aaagcccagc -continued

```
2761  agttggagga ggccagacta caggaggaag agcagaaaaa agaggagctg gccaggctac
2821  ggagagaact ggtgcataag gcaaatccaa tacgcaagta ccagggtctg gagataaagt
2881  caagtgacca gcctctgact gtgcctgtat ctcccaaatt ctccactcga ttccactgct
2941  aaactcagct gtgagctgcg gataccgccc ggcaatggga cctgctctta acctcaaacc
3001  taggaccgtc ttgctttgtc attgggcatg gagagaaccc atttctccag acttttacct
3061  acccgtgcct gagaaagcat acttgacaac tgtggactcc agttttgttg agaattgttt
3121  tcttacatta ctaaggctaa taatgagatg taactcatga atgtctcgat tagactccat
3181  gtagttactt cctttaaacc atcagccggc cttttatatg ggtcttcact ctgactagaa
3241  tttagtctct gtgtcagcac agtgtaatct ctattgctat tgccccttac gactctcacc
3301  ctctccccac ttttttaaa aattttaacc agaaaataaa gatagttaaa tcctaagata
3361  gagattaagt catggtttaa atgaggaaca atcagtaaat cagattctgt cctcttctct
3421  gcataccgtg aatttatagt taaggatccc tttgctgtga gggtagaaaa cctcaccaac
3481  tgcaccagtg aggaagaaga ctgcgtggat tcatggggag cctcacagca gccacgcagc
3541  aggctctggg tggggctgcc gttaaggcac gttctttcct tactggtgct gataacaaca
3601  gggaaccgtg cagtgtgcat tttaagacct ggcctggaat aaatacgttt tgtctttccc
3661  tcaaaaaaaa aaaaaaaaaa aaaaa
```

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a plot showing raw data collected (amount of heat released or absorbed during the course of the titration) in an isothermal titration calorimetry assay measuring the thermodynamics of binding of dephosphorylated Aurora A kinase and danusertib. FIG. 1B is an isotherm derived from the results as shown in FIG. 1A. FIG. 1C is a plot showing raw data collected (amount of heat released or absorbed during the course of the titration) in an isothermal titration calorimetry assay measuring the thermodynamics of binding of dephosphorylated Aurora A kinase-TPX2 chimera and danusertib. FIG. 1D is an isotherm derived from the results shown in FIG. 1C. The dissociation constant ($K_d$), heat of enthalpy (ΔH), and heat of entropy (ΔS) of each of the binding reactions are indicated in the respective plots (FIG. 1B and FIG. 1D).

FIG. 2A is a plot showing raw data collected (amount of heat released or absorbed during the course of the titration) in an isothermal titration calorimetry assay measuring the thermodynamics of binding of Aurora A kinase (saturated with PS48) and danusertib. FIG. 2B is an isotherm derived from the results shown in FIG. 2A. The dissociation constant ($K_d$), heat of enthalpy (ΔH), and heat of entropy (ΔS) of the binding reaction is indicated in FIG. 2B.

FIG. 3A is a plot showing raw data collected (amount of heat released or absorbed during the course of the titration) in an isothermal titration calorimetry assay measuring the thermodynamics of binding of dephosphorylated Aurora A kinase and PS48. FIG. 3B is a plot showing an isotherm derived from the results shown in FIG. 3A. FIG. 3C is a plot showing raw data collected (amount of heat released or absorbed during the course of the titration) in an isothermal titration calorimetry assay measuring the thermodynamics of binding of dephosphorylated Aurora A kinase (saturated with danusertib) and PS48. FIG. 3D is a plot showing an isotherm derived from the results shown in FIG. 3C. The dissociation constant ($K_d$), heat of enthalpy ($\Delta H$), and heat of entropy ($\Delta S$) of each of the binding reactions is indicated in the respective plots (FIG. 3B and FIG. 3D).

FIG. 7 shows a sequence of monobody Mb2 (aka Mb6) containing a Histidine ($His_6$) tag (SEQ ID NO: 14). The slash shows where TEV protease cuts the polypeptide to give rise to the un-$His_6$-tagged version of monobody Mb2 (aka Mb6) that is used in subsequent experiments.

FIGS. 10A and 10B present plots showing the results of isothermal titration calorimetry assays to characterize the thermodynamics of binding of dephosphorylated Aurora A kinase and danusertib (Left plot), binding of dephosphorylated Aurora A kinase+monobody Mb54 (AurA complexed with Mb54) and danusertib (Middle plot) and binding of dephosphorylated Aurora A kinase+monobody Mb60 (AurA complexed with Mb60) and danusertib (Right plot). FIG. 10A shows plots depicting the raw data collected (amount of heat released or absorbed during the course of the titration) in an isothermal titration calorimetry assay measuring the thermodynamics of binding of dephosphorylated Aurora A kinase and danusertib without monobody (Left panel), with monobody Mb54, (Middle panel), or with monobody Mb60, (Right panel) and danusertib. FIG. 10B shows plots depicting the isotherms derived from the results shown in FIG. 10A. FIG. 10C presents bar graphs showing the dissociation constant ($K_d$) of danusertib (in nM) in the binding reactions of FIGS. 10A and 10B. In FIG. 10C, the monobody "Mb54" of FIGS. 10A and 10B is called "Mb1," and the monobody "Mb60" of FIGS. 10A and 10B is called "Mb2." It is to be understood that in FIGS. 10A-10C, Mb54 is the same monobody as Mb1, and Mb60 is the same monobody as Mb2. Accordingly, "Mb54" and "Mb1" denote alternative names for the same monobody, and "Mb60" and "Mb2" denote alternative names for the same monobody. The results show that pre-saturating dephosphorylated Aurora A kinase with the activating monobody Mb54 (aka Mb1), a $DFG_{in}$ binder, weakens the binding affinity of danusertib, which is a $DFG_{out}$ binder, by 19-fold, while pre-saturating dephosphorylated Aurora A kinase with the inhibiting monobody Mb60 (aka Mb2), a $DFG_{out}$ binder, tightens the binding affinity of danusertib by 4.7-fold (FIG. 10C). The binding of danusertib to dephosphorylated Aurora A kinase was measured in the presence of AMPPCP and fit with a competitive model due to the tight binding of danusertib to dephosphorylated Aurora A kinase.

FIG. 11B shows plots and graphs similar to those described for FIG. 11A, except that a different monobody, i.e., Mb60 (aka Mb2), was used. Also, similar to FIG. 11A, in the bar graph and results shown on the right side of FIG. 11B, the monobody "Mb60" is called "Mb2." It is to be understood that the monobody designated "Mb2" in FIG. 11B is the same monobody as "Mb60" in the figure. Accordingly, "Mb60" and "Mb2" denote alternative names for the same monobody. The results of FIGS. 11A and 11B show that pre-saturating dephosphorylated Aurora A kinase with danusertib, a $DFG_{out}$ ATP-competitive inhibitor, weakens the binding of the activating monobody Mb54 (aka Mb1) to dephosphorylated Aurora A kinase (FIG. 11A) and tightens the binding affinity of the monobody Mb60 (aka Mb2) to dephosphorylated Aurora A kinase (FIG. 11B).

FIG. 12B presents bar graphs showing the dissociation constant ($K_d$) of barasertib (in nM) in the binding reactions of FIG. 12A. In FIG. 12B, the monobody "Mb44" of FIG. 12A is called "Mb4" and the monobody "Mb51" of FIG. 12A is called "Mb5." It is to be understood that in FIG. 12A, Mb44 is the same monobody as Mb4 in FIG. 12B, and Mb51 in FIG. 12A is the same monobody as Mb5 in FIG. 12B. Accordingly, "Mb44" and "Mb4" denote alternative names for the same monobody, and "Mb51" and "Mb5" denote alternative names for the same monobody. The results show that pre-saturating dephosphorylated Aurora A kinase with the inhibiting monobodies Mb44 (aka Mb4) and Mb51 (aka Mb5), which are $DFG_{out}$ binders, weakens the binding affinity of the ATP-competitive inhibitor barasertib, which is a $DFG_{in}$ binder, by about 4-fold (FIG. 12B).

FIG. 13B shows plots and graphs similar to those described for FIG. 13A, except that a different monobody, i.e., Mb51, was used in the assays. Also, in the bar graph and results shown at the right side of FIG. 13B, the monobody "Mb51" is called "Mb5." It is to be understood that the monobody designated "Mb5" in FIG. 13B is the same monobody as "Mb51" denoted in this figure. Accordingly, "Mb51" and "Mb5" are alternative names for the same monobody. The results of FIGS. 13A and 13B show that pre-saturating dephosphorylated Aurora A kinase with barasertib, a $DFG_{in}$ ATP-competitive inhibitor, weakens the binding affinity of the inhibiting monobodies Mb44 (aka Mb4) and Mb51 (aka Mb5) to dephosphorylated Aurora A kinase by about 5-fold (FIG. 13A) and 2.8-fold (FIG. 13B), respectively.

FIG. 16 also compares hallmarks of active (DFGin/complete R-spine) vs. inactive (DFG out/incomplete R-spine) Aurora A kinase in the crystal structures of dephosphorylated Aurora A kinase bound to TPX2, activating monobody Mb54 or inhibitory monobody Mb60.

In FIGS. 17A-17F, alternative names of the monobodies described herein are used. In particular, monobody "Mb2" (in FIGS. 17A and 17C-17F) is the same monobody as "Mb60" herein; monobody "Mb0" (in FIGS. 17E and 17F) is a nonbinding control monobody; monobody "Mb1" (in FIGS. 17E and 17F) is the same monobody as "Mb54" herein; neutral monobody "Mb6" (in FIGS. 17E and 17F) is the alternative name for neutral monobody "Mb2" (of Application No. 62/292,587). FIG. 17A shows a sGFP-Mb60 (aka Mb2) construct that was built for the purposes of mammalian-cell-based-protein delivery. The polypeptide encoded by this sGFP-Mb60 fusion construct was first tested for Aurora A binding affinity and ability to inhibit Aurora A kinase. sGFP-Mb60 (aka Mb2) has a binding affinity to Aurora A kinase comparable to that of Mb60 (aka Mb2). The sGFP-Mb60 polypeptide also inhibits Aurora A to the same extent as Mb60. FIG. 17B shows the affinity of the fusion polypeptide sGFP-Mb60 to Aurora A kinase as measured by isothermal titration calorimetry (ITC). The error bars represent the standard error for the estimate of $K_d$ and are a measure of the goodness of fit of the data. FIG. 17C is a plot showing inhibition of Aurora A kinase activity by the sGFP-Mb60 (aka Mb2) fusion polypeptide and by the monobody Mb60 alone. FIG. 17D presents microscopy photographs of the delivery of the fusion polypeptide sGFP-Mb60 into cultured HEK293 cells over time, i.e., at 0 hr, 1 hr, 7 hr and 24 hr. As observed in FIG. 17D, sGFP-Mb60's optimal cell delivery occurs after 7 hrs of exposure. FIG. 17E presents a bar graph of luminescence (mean±SEM, n=4 measurements/dataset) as a measure of HEK293 viability after cells were treated for 7 hours under the conditions indicated below the x-axis. Asterisks indicate significance levels of between-conditions t-test comparisons of the different conditions with liposome-treated control; ns=p>0.5; =p≤0.01; *=p≤0.001. FIG. 17F depicts a set of immunofluorescent images of cells at 7 hours after delivery of the sGFP-Mb60 or control sGFP to follow co-localization of sGFP, sGFP-Mb0 (non-binding monobody control), an sGFP-Mb1 (aka Mb54), activating fusion polypeptide, an sGFP-Mb2 (aka Mb60) inhibiting fusion polypeptide, and sGFP-Mb6 neutral fusion polypeptide in HEK293 cells at different stages of mitosis. Cells were quadruple stained to visualize DNA/sGFP(−Mbs)/Aurora A kinase/TPX2. Strong co-localization was observed for the monobodies that bound to Aurora A kinase compared with a granular and uniformly dispersed signal observed in the controls. In the images, DNA stained blue; GFP stained green; Aurora A kinase stained red; and TXPX2 stained green.

FIGS. 18A and 18B show ITC measurement plots at 25° C. in which different Aurora A kinase to monobody (AurA:monobody) ratios were used. The concentrations used were 40 μM AurA+280 μM Mb0 (1:7 ratio, FIG. 18A, left); 40 μM AurA+600 μM Mb0 (1:15 ratio, FIG. 18A, right); and 40 μM AurA+600 μM sGFP-Mb0 (1:15 ratio, FIG. 18B). FIG. 18C shows a bar graph presenting Aurora A kinase activity in the absence and presence of nonbinding monobody Mb0 or sGFP-Mb0 and 1 μM AurA at 3 mM Lats2. FIG. 18D shows a plot and graph in which the binding affinity of sGFP-Mb54 (aka Mb1) (280 μM) to AurA (40 μM) was measured by ITC. FIG. 18E shows a graph depicting Aurora A kinase activity in the absence and presence of monobody Mb54 (aka Mb1) and the fusion product sGFP-Mb54 (aka Mb1). FIG. 18F shows a plot and graph in which the binding affinity of activity neutral sGFP-Mb6 (280 μM) to AurA (40 μM) was measured by ITC. FIG. 18G shows a graph depicting AurA kinase activity in the absence and presence of neutral monobody Mb6 and the sGFP-Mb6 fusion product. Error bars in FIGS. 18D and 18F represent the standard error for the estimate of $K_d$ and are a measure of the goodness of fit of the data. Error bars in FIG. 18C were calculated through jackknifing. The results demonstrate that Mb0, a nonbinding control monobody, and the sGFP-Mb0 fusion product did not bind to Aurora A kinase, whereas the sGFP-Mb54 (aka Mb1) and sGFP-Mb60 (aka Mb2) fusion products closely mimicked the binding of monobodies Mb54 (aka Mb1) and Mb60 (aka Mb2), respectively. As noted above, monobody "Mb1" in FIGS. 18D and 18E is also called "Mb54" herein; activity neutral monobody "Mb6" in FIGS. 18F and 18G is the same monobody as activity neutral monobody "Mb2" (as described in the Definitions, supra).

FIG. 22 shows interaction between residues of TPX2 and the PIF pocket of Aurora A.

FIG. 24A is a plot showing raw data collected (amount of heat released or absorbed during the course of the titration) in an isothermal titration calorimetry assay measuring the thermodynamics of binding of dephosphorylated Aurora A kinase and PS48. FIG. 24B is an isotherm derived from the results shown in FIG. 24A. FIG. 24C is a plot showing raw data collected (amount of heat released or absorbed during the course of the titration) in an isothermal titration calorimetry assay measuring binding in a control reaction (PS48 and buffer). FIG. 24D is a plot showing an isotherm derived from the results shown in FIG. 24C. As expected, no binding was observed in the control reaction. The dissociation constant ($K_d$), heat of enthalpy (ΔH), and heat of entropy (ΔS) of the binding reaction between Aurora A kinase and PS48 are shown in FIG. 24B.

FIG. 25A is a plot showing raw data collected (amount of heat released or absorbed during the course of the titration) in an isothermal titration calorimetry assay measuring the thermodynamics of binding of PS48 to dephosphorylated Aurora A kinase (pre-saturated with AMPPCP). FIG. 25B is a plot showing an isotherm derived from the results shown in FIG. 25A. FIG. 25C is a plot showing raw data collected (amount of heat released or absorbed during the course of the titration) in an isothermal titration calorimetry assay measuring binding of PS48 and AMPPCP and buffer. FIG. 25D is a plot showing an isotherm derived from the results shown in FIG. 25C. No binding was observed in the reaction between PS48, AMPPCP, and buffer, as expected. The dissociation constant ($K_d$), heat of enthalpy (ΔH), and heat of entropy (ΔS) of the binding of PS48 and Aurora A kinase and AMPPCP are shown in FIG. 25B.

FIG. 26A shows the structure of TNP-ATP, a fluorescent analog of ATP. TNP-ATP is excited at a wavelength of 479 nm and fluoresces at 500-600 nm. FIG. 26B is a plot showing an emission spectrum of TNP-ATP. FIG. 26C is a plot showing fluorescence spectroscopy of dephosphorylated Aurora A kinase incubated with varying amounts of TNP-ATP. FIG. 26D is a plot showing fluorescence spectroscopy of dephosphorylated Aurora A kinase and PS48 incubated with varying amounts of TNP-ATP. FIG. 26E is a plot showing fluorescence intensities measured during titration of TNP-ATP in the Aurora A kinase and PS48 sample and Aurora A kinase only sample. The dissociation constant of TNP-ATP binding to Aurora A kinase in the absence and presence of PS48 is shown at the bottom of FIG. 26E. PS48 does not affect binding of TNP-ATP, an ATP-binding site small molecule, suggesting that PS48 does not bind to the ATP-binding site of Aurora A kinase.

FIG. 27A is a plot showing $^{1}H$-$^{15}N$ heteronuclear single quantum coherence (HSQC) spectra of selected titration points (250 μM TPX2, 250 μM TPX2+100 μM Aurora A, and 250 μM TPX2+100 μM Aurora A+1.5 mM PS48). A magnified view showing separation of peaks is indicated by an arrow. FIG. 27B is a plot showing changes in chemical shift (Δδ) at 200 μM TPX2 and varying concentrations of Aurora A. FIG. 27C is a plot showing changes in chemical shift (Δδ) at 200 μM TPX2 and 100 μM Aurora A and varying concentrations of PS48.

FIG. 28A is a plot showing measurements of phosphorylation of kemptide (a peptide substrate for Aurora A kinase) when incubated with dephosphorylated Aurora A kinase and TPX2 and various increasing amounts of PS48. FIG. 28B is a plot showing an analysis of the phosphorylation rate measurements indicating PS48 inhibits kinase activity by competing off TPX2 binding. In the assays shown, 1 μM $A^{122-403}$ T288V, 100 μM $TPX2^{1-45}$ and 1 mM kemptide was used.

Figures 1A, 1B, 1C, 1D:
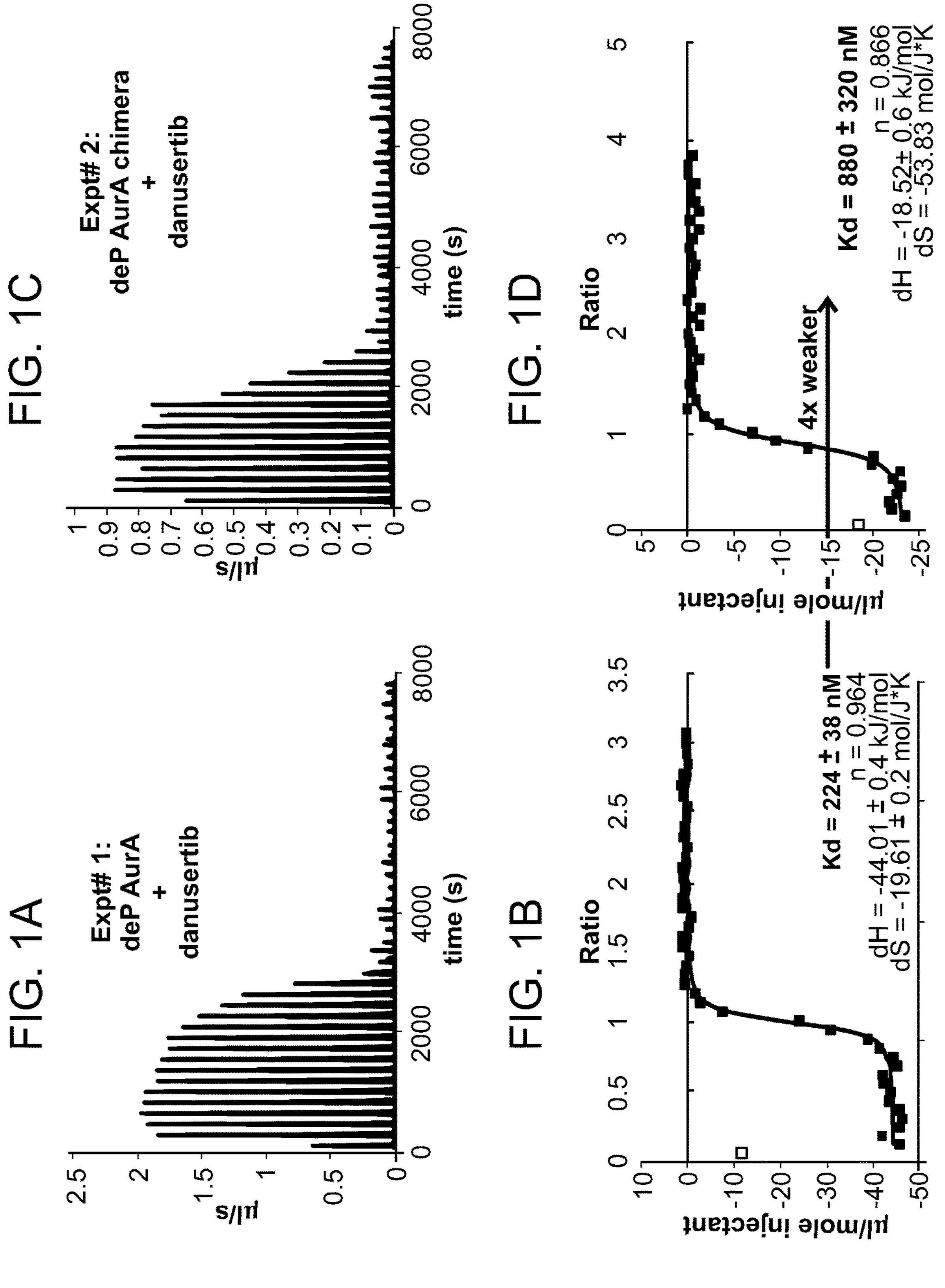
FIGS. 1A-1D are plots showing results of isothermal titration calorimetry (ITC) assays to characterize the thermodynamics of binding of dephosphorylated Aurora A kinase and danusertib (FIGS. 1A-1B) and binding of dephosphorylated Aurora A kinase—TPX2 chimera to danusertib (FIGS. 1C-1D).

Appendix A provides a file listing atomic coordinates of Aurora A kinase bound with inhibitory monobody Mb60 and danusertib.

Appendix B provides a file listing atomic coordinates of Aurora A kinase bound with activating monobody Mb54 and AMPPCP.

DETAILED DESCRIPTION OF THE INVENTION

The invention features compositions and methods that are useful for modulating kinase activity, particularly compositions and methods for enhancing kinase inhibition in a subject. The invention is based, at least in part, on the discovery of cooperative binding at the PIF pocket of Aurora A kinase and the ATP-binding site of Aurora A kinase: an agent binding at the PIF pocket of Aurora A kinase could increase affinity of binding of another agent at Aurora A kinase's ATP-binding site. Without being bound by theory, it is believed that the increased affinity of binding results from the particular residue contacts made by the agent bound to the PIF pocket, which could change the conformation of the kinase, thereby shifting equilibrium to either active or inactive conformation.

In some embodiments, the agent binding to an allosteric site (PIF pocket) on Aurora A kinase is a monobody as described herein and further described in U.S. Patent Application Ser. No. 62/254,974, which is herewith incorporated in its entirety. In some other embodiments, the agent binding the PIF pocket of Aurora A kinase is PS48. Treatment of cells with monobodies inhibiting Aurora A activity or PS48 was found to disrupt TPX2 binding to Aurora A, disrupt Aurora A localization to the spindles, and trigger cell death.

Cooperativity Between Binding at PIF Pocket and ATP-Binding Site Aurora A Kinase Aurora A is an oncoprotein that is overexpressed in a multitude of cancers. Aurora A kinase is implicated in the regulation of mitotic entry and progression, spindle assembly, and spindle stability. Deregulation of Aurora A's kinase activity can result in defects in spindle assembly, chromosome alignment, and cytokinesis. Without intending to be bound by theory, overexpression of Aurora A kinase is believed to contribute to tumor formation, growth, and proliferation.

Thus, ways to inhibit Aurora A via small molecules have been actively pursued by researchers in both academia and industry. In particular, efforts to develop small molecule inhibitors of Aurora A's kinase activity have focused primarily on targeting Aurora A's ATP-binding site. A number of small molecule inhibitors of Aurora A kinase which bind Aurora A's ATP-binding site, such as danusertib, have been developed.

However, efforts to develop inhibitors of kinases have not focused on targeting sites other than the ATP binding site (e.g., the PIF pocket). Neither have efforts to develop inhibitors focused on targeting multiple different sites on the kinase (e.g., the ATP binding site and the PIF pocket). Aurora A kinase is allosterically activated by TPX2, which binds to the PIF pocket of Aurora A. In order to localize to the spindle microtubules and allow for proper progression of mitosis, Aurora A must bind to TPX2, and must be allosterically activated by TPX2.

Targeting both the allosteric site (i.e., PIF pocket) and ATP binding site of kinases such as Aurora A kinase offers a more attractive strategy for inhibiting kinase activity. Unlike the ATP-binding pocket (the major target to date for kinase inhibitors as cancer drugs), which is highly conserved across kinases, the allosteric PIF pocket of human protein kinases is variable among different kinases, thereby offering the potential of developing much more specific kinase inhibitors. A specific kinase inhibitor would have the advantage of potentially having less toxic or negative side effects on a patient.

Studies described herein reveal that using a combination of an inhibitor targeting the allosteric PIF pocket and an inhibitor targeting the ATP-binding pocket can have a synergistic effect on inhibition of the kinase due to positive cooperativity of binding at the PIF pocket and ATP-binding pocket. As further described herein, targeting the allosteric PIF pocket with a kinase inhibitor that specifically binds to the ATP-binding pocket, an ATP-competitive inhibitor, (e.g., danusertib) can increase affinity of binding of the inhibitor binding to the ATP-binding site. Thus, in the presence of a kinase inhibitor that bound the allosteric PIF pocket (which would be a specific kinase inhibitor), a lower amount of a kinase inhibitor that specifically bound to the ATP-binding pocket would be required to achieve effective inhibition of kinase activity. In some embodiments, effective inhibition of a kinase is achieved with a lower amount of an agent specifically binding the allosteric site and/or a lower amount of the agent specifically binding ATP-binding site when the agents are used in combination with each other than the respective amount of each agent that would have been required to achieve the same degree of inhibition if each agent was used individually.

Additionally, the use of the combination of agents of the invention reduces the chance of occurrence of mutation(s) in the kinase targeted by the agents that would reduce or abolish binding of both agents to the kinase. A mutation that may arise in one of the binding sites (e.g., the ATP binding site or PIF pocket) could abolish or reduce binding at the particular site. If only a single agent was used, a mutation at the site where the agent bound could abolish or reduce binding at that site, thereby reducing or abolishing the ability of the agent to inhibit kinase activity. Thus, resistance to kinase inhibition by a single kinase inhibitor agent can be developed in a patient fairly easily. By using at least two agents, each of which binds a different site on the kinase, mutation(s) in each of the binding sites that reduces or abolished binding at each site would have to occur in order for a patient to develop resistance to kinase inhibition. The probability of such a combination of mutations arising is extremely low. Thus, resistance to kinase inhibition by the combination of both agents would be difficult to develop.

In some embodiments, the agent that specifically binds to an allosteric site of Aurora A kinase is an antibody mimetic, such as a monobody. Monobodies are not routinely explored in the kinase field. Not many monobodies are known to bind kinases, although few examples are known (e.g., monobodies that bind to Abl).

In some embodiments, the antibody mimetic or monobody specifically binds to the PIF pocket of Aurora A kinase. In some other embodiments, binding of the antibody mimetic or monobody disrupts binding of TPX2 to Aurora A kinase. The PIF pocket is a highly malleable interface that is ideal for drug discovery. In some embodiments, an antibody mimetic such as a monobody could mimic the TPX2 interaction and thus displace this protein. In still other embodiments, a small molecule compound (e.g., PS48) can displace or disrupt TPX2 binding to the PIF pocket.

In some embodiments, the invention features use of the antibody mimetics or monobodies specifically binding to the PIF pocket of Aurora A kinase in combination with an agent such as a small molecule specifically binding to the ATP binding site of Aurora A kinase (e.g., danusertib) to treat a cancer or an Aurora A-associated disease.

Recombinant Polypeptide Expression

The invention provides recombinant antibody mimetics (in particular, monobodies), which are useful alone or in combination with agents that specifically bind an ATP-binding site of a kinase for treating a cancer or inhibiting growth and/or proliferation of a cancer in a subject. When delivered to a cell (particularly a cancer cell), the polypeptides of the invention modulate or inhibit Aurora A's kinase activity in a cell, disrupt TPX2 binding to Aurora A kinase, and/or disrupt Aurora A's localization to the spindles. Inhibition of Aurora A's kinase activity and/or disruption of any of Aurora A's other activities (e.g., binding with TPX2 or localization to the spindles) causes cell death. Accordingly, the invention provides allosteric activation and inactivation of Aurora A kinase by monobodies that modulate a kinase by binding to the kinase domain (catalytic domain) itself, specifically, the hydrophobic domain away from the ATP-binding site, so as to prevent cell growth and/or proliferation.

Recombinant polypeptides of the invention are produced using virtually any method known to the skilled artisan. Typically, recombinant polypeptides are produced by transformation of a suitable host cell with all or part of a polypeptide-encoding nucleic acid molecule or fragment thereof in a suitable expression vehicle. Accordingly, the invention provides methods of producing a polypeptide of the invention, the method comprising (a) heterologously expressing an expression vector comprising a polynucleotide encoding the polypeptide in a host cell; and (b) isolating the polypeptide from the host cell.

Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, COS cells). Such cells are available from a wide range of sources (e.g., the American Type Culture Collection, Rockland, Md.; also, see, e.g., Ausubel et al., Current Protocol in Molecular Biology, New York: John Wiley and Sons, 1997). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

In some embodiments, the polypeptides of the invention are produced in a bacterial expression system with yields of up to 50-100 mg per liter of culture. One particular bacterial expression system for polypeptide production is the *E. coli* pET expression system (e.g., pET-28) (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Alternatively, recombinant polypeptides of the invention are expressed in *Pichia pastoris*, a methylotrophic yeast. *Pichia* is capable of metabolizing methanol as the sole carbon source. The first step in the metabolism of methanol is the oxidation of methanol to formaldehyde by the enzyme, alcohol oxidase. Expression of this enzyme, which is coded for by the AOX1 gene is induced by methanol. The AOX1 promoter can be used for inducible polypeptide expression or the GAP promoter for constitutive expression of a gene of interest.

Once the recombinant polypeptide of the invention is expressed, it is isolated, for example, using affinity chromatography. In one example, an antibody (e.g., produced as described herein) raised against a polypeptide of the invention may be attached to a column and used to isolate the recombinant polypeptide. In some embodiments, to facilitate purification of the recombinant polypeptide, the polypeptide comprises an epitope tag fused to antibody mimetic or monobody. The polypeptide is then isolated using an antibody against the epitope tag. Lysis and fractionation of polypeptide-harboring cells prior to affinity chromatography may be performed by standard methods (see, e.g., Ausubel et al., supra). Alternatively, the polypeptide is isolated using a sequence tag, such as a hexahistidine tag, that binds to nickel column. Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980). Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, Ill.). These general techniques of polypeptide expression and purification can also be used to produce and isolate useful peptide fragments or analogs (described herein).

In addition, or in the alternative, the polypeptides or fusion polypeptides of the invention may be produced using chemical methods to synthesize the desired amino acid sequence, in whole or in part. For example, polypeptides can be synthesized by solid phase techniques, cleaved from the resin, and purified by preparative high performance liquid chromatography (e.g., Creighton (1983) Proteins: Structures And Molecular Principles, WH Freeman and Co, New York N.Y.). The composition of the synthetic polypeptides may be confirmed by amino acid analysis or sequencing (e.g., the Edman degradation procedure). Additionally, the amino acid sequence of a fusion polypeptide of the invention, or any part thereof, may be altered during direct synthesis and/or combined using chemical methods with a sequence from other subunits, or any part thereof, to produce a variant polypeptide.

Methods of Treatment

The combination of an agent specifically binding to an allosteric site of a kinase, such as the PIF pocket of Aurora A, and an agent specifically binding to the ATP-binding site of a kinase was identified as useful for preventing or ameliorating a disease associated with kinase misregulation (particularly misregulation of Aurora A kinase), such as cancer. Diseases and disorders associated with misregulated kinase activity (e.g., increased kinase activity of Aurora A) may be treated using the methods and compositions of the invention.

Accordingly, the present invention provides methods using the combination of agents comprising (1) an agent specifically binding to an allosteric site of a kinase, such as the PIF pocket of Aurora A, and (2) an agent specifically binding to the ATP-binding site of a kinase. Such agents can be, for example, an antibody, antibody mimetic (e.g., monobody), peptides, nucleic acid molecules, or small molecule compounds. Examples of an agent specifically binding to an allosteric site of a kinase include, without limitation, PS48 and monobodies Mb2 (aka Mb6), Mb54, and Mb56. In some embodiments, the agent that specifically binds an allosteric site on a kinase is PS48 or any other agents structurally and functionally similar to PS48 and capable of binding to the PIF pocket of Aurora A kinase. An example of an agent specifically binding to an ATP-binding site of a kinase includes, without limitation, danusertib.

As described herein, Aurora A kinase is overexpressed in many cancer types and is believed to contribute to cancer formation and growth. The combination of agents described herein is able to (1) inhibit activity of Aurora A, and (2) disrupt Aurora A localization to the spindles. Further, use of the combination of agents, rather than a single agent, to inhibit Aurora A kinase may have the additional benefit of increasing affinity of binding of one of the agents to Aurora A, thus decreasing the amount of the agent required to achieve a desired level of kinase inhibition. This can be important in cases, for example, where a particular kinase inhibitor has negative or toxic effects when used at high amounts.

Additionally, the use of the combination of agents of the invention reduces the chance of occurrence of mutation(s) in the kinase targeted by the agents that would reduce or abolish binding of both agents to the kinase. A mutation that may arise in one of the binding sites (e.g., the ATP binding site or PIF pocket) could abolish or reduce binding at the particular site. If only a single agent was used, a mutation at the site where the agent bound could abolish or reduce binding at that site, thereby reducing or abolishing the ability of the agent to inhibit kinase activity. Thus, resistance to kinase inhibition by a single kinase inhibitor agent can be developed in a patient fairly easily. By using at least two agents, each of which binds a different site on the kinase, mutation(s) in each of the binding sites that reduces or abolished binding at each site would have to occur in order for a patient to develop resistance to kinase inhibition. Thus, the present invention also provides a method of inhibiting development of resistance to kinase inhibition in a subject.

The method contains the step of administering to the subject an effective amount of an agent that specifically binds an allosteric site on the kinase and an effective amount of an agent that specifically binds an ATP-binding site of the kinase.

As described herein, inhibition of Aurora A's kinase activity and disruption of localization of Aurora A to the spindles in a cell (in particular, a cancer cell) triggers cell death. Thus, the present invention provides methods of inhibiting proliferation and/or reducing survival of a cancer cell and methods of treating a cancer or symptoms thereof, which comprise administering a therapeutically effective amount of a pharmaceutical composition comprising the combination of agents as described herein to a subject (e.g., a mammal such as a human). One embodiment is a method of treating a subject suffering from or susceptible to a cancer or disorder or symptom thereof, particularly a cancer associated with overexpressed Aurora A kinase or deregulated Aurora A kinase activity. The method includes the step of administering to the mammal a therapeutic amount of the combination of agents herein sufficient to treat the disease or disorder or symptom thereof, under conditions such that the disease or disorder is treated.

The methods herein include administering to the subject (including a subject identified as in need of such treatment) an effective amount of an antibody mimetic, monobody, or polynucleotide described herein, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of the combination of agents described herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, activity or expression of Aurora A kinase, family history, and the like). The therapeutic agents herein may be also used in the treatment of any other disorders in which Aurora A kinase may be implicated.

For therapeutic uses, compositions comprising the therapeutic combination of agents disclosed herein (e.g., an agent binding to an ATP-binding site of a kinase and an agent binding to an allosteric site of the kinase) may be administered systemically, for example, formulated in a pharmaceutically-acceptable buffer such as physiological saline. Routes of administration include, for example, subcutaneous, intravenous, intraperitoneally, intramuscular, intradermal injections that provide continuous, sustained levels of the drug in the patient, or any appropriate method of providing the antibiotic composition to the patient. Treatment of human patients or other animals is carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the kinase associated disease (e.g., cancer). Generally, amounts will be in the range of those used for other agents used in the treatment of other diseases associated with kinase misregulation, although in certain instances lower amounts will be needed because of the increased specificity of the agent.

In some embodiments, an agent is administered at a dosage that reduces proliferation, survival, activity of, or kills cancer cells as determined by a method known to one skilled in the art, or using any that assay that measures inhibition of target kinase activity by the combination of agents. In one embodiment, an agent specifically binding to an allosteric site of a kinase (e.g., a monobody disclosed herein or PS48) is administered at a dosage that increases binding affinity of a kinase inhibitor (e.g., danusertib) that specifically binds to the ATP-binding site of the kinase. In one embodiment, an agent specifically binding to an allosteric site of a kinase is administered at a dosage that reduces by at least 2- or 4-fold (e.g., 2-, 3-, 4-, 5-, 6-, 7-, 8-, 9-, 10-fold or more) the amount of an agent specifically binding to the ATP-binding site of the kinase required to achieve a particular level of kinase inhibition. In particular embodiments, the agent specifically binding to an allosteric site of a kinase is administered prior to administration of the agent binding to the ATP-binding site, concurrently with the agent binding to the ATP-binding site, or following administration of the agent binding to the ATP-binding site. In one embodiment, the combination of an agent specifically binding to an allosteric site of a kinase and an agent specifically binding to an ATP-binding site of the kinase is administered with one or more therapeutic agents.

In one embodiment, the invention provides a method of monitoring treatment progress. The method includes the step of determining a level of activity of a kinase (e.g., any target kinase delineated herein, such as Aurora A kinase, whose activity is modulated by an agent herein) or diagnostic measurement (e.g., screen, assay) in a subject suffering from or susceptible to a disorder or symptoms thereof associated with Aurora A kinase, in which the subject has been administered a therapeutic amount of an antibody mimetic, monobody, or polynucleotide herein sufficient to treat the disease or symptoms thereof. An activity of Aurora A may include, for example, Aurora A's kinase activity, localization to the spindles, or functions during mitotic progress. The activity level of Aurora A determined in the method can be compared to known activity levels of Aurora A in either healthy normal controls or in other afflicted patients to establish the subject's disease status. In some embodiments, a second activity level of Aurora A in the subject is determined at a time point later than the determination of the first level, and the two levels are compared to monitor the course of disease or the efficacy of the therapy. In certain embodiments, a pre-treatment level of Aurora A activity in the subject is determined prior to beginning treatment according to this invention; this pre-treatment level of Aurora A activity can then be compared to the level of activity of Aurora A in the subject after the treatment commences, to determine the efficacy of the treatment.

Methods of Delivery

In some embodiments, the agent specifically binding to an allosteric site (e.g., PIF pocket) of a kinase is an antibody mimetic or a monobody. Antibody mimetics or monobodies of the invention, which are useful for specifically modulating or inhibiting Aurora A kinase in a cell, may be delivered to a cell (particularly a cancer cell) in any manner such that the antibody mimetic or monobody is in functional form in the cell. The antibody mimetic or monobody may be delivered to cells as polypeptides. Alternatively, a polynucleotide encoding an amino acid sequence of the antibody mimetic or monobody may be delivered to cells for heterologous expression of the antibody mimetic or monobody in the cells. Thus, the present invention features monobodies or polypeptides delivered to a cell by contacting the cell with a composition comprising the monobody or polypeptide or by heterologously expressing the monobody or polypeptide in the cell.

Intracellular Delivery of Polypeptides

Polypeptides of the invention, such as antibody mimetics or monobodies, may be delivered intracellularly to cells. The polypeptide must be delivered to the cells of a subject in a form in which they can be taken up so that therapeutically effective levels of the antibody mimetic or monobody, or fragment thereof, is in functional form in the cells.

Methods of intracellular delivery of polypeptides are known to one of skill in the art. Exemplary methods of intracellular delivery of polypeptides include, without limitation, incorporation of the polypeptide into a liposome. Liposomes are phospholipid vesicles with sizes varying from 50 to 1000 nm, which can be loaded with polypeptides or other agents. Liposomal intracellular delivery of polypeptides into cells typically relies on endocytosis of the liposome-encapsulated polypeptide into the cell. Examples of suitable liposomes for intracellular delivery of polypeptides may be pH-sensitive liposomes. Such liposomes are made of pH-sensitive components; after being endocytosed in intact form, the liposome fuses with the endovacuolar membrane under lowered pH inside the endosome and destabilizes it, thereby releasing the contents (including the polypeptides encapsulated in the liposome) into the cytoplasm. The liposomes may also be further modified to enhance their stability or lifetime during circulation (e.g., by PEGylated liposomes). Liposomes may also be modified to specifically target antigens (e.g., "immunoliposomes" or liposomes embedded with antibodies an antigen). Antibody-bearing liposomes may have the advantages of targetability and facilitated uptake via receptor-mediated endocytosis.

Other methods of intracellular delivery of polypeptides include, without limitation, use of cell penetrating peptides (CPPs). A cell penetrating peptide or "CPP" is a protein or peptide that can translocate through cellular membranes. A polypeptide for delivery into a cell is fused with a CPP, thereby enabling or enhancing delivery of the polypeptide fusion into the cell. Cell penetrating peptides include, for example, a trans-activating transcriptional activator (TAT) from HIV-1, Antenapedie (Antp, a transcription factor in *Drosophila*), and VP22 (a herpes virus protein).

Another exemplary method for intracellular delivery of polypeptides of the invention is the use of supercharged proteins. Supercharged proteins or supercharged polypeptides are a class of engineered or naturally existing polypeptides having an unusually high positive or negative net theoretical charge. Membranes of cells are typically negatively charged. Superpositively charged polypeptides are able to penetrate cells (particularly mammalian cells), and associating cargo with superpositively charged polypeptides (e.g., polypeptides or polynucleotides) can enable functional delivery of these macromolecules into cells, in vitro or in vivo. Methods of generating supercharged polypeptides and using supercharged polypeptides for intracellular polypeptide delivery are described in further detail in, for example, Zuris et al. *Nat. Biotechnol.* (2015) 33:73-80 and Liu et al. *Methods Enzymol.* (2012), 503: 293-319.

The present invention features a monobody fused to a supercharged fragment sufficient to mediate intracellular delivery of the polypeptide. Supercharged polypeptides (or fusion polypeptides) may also be used in combination with charged liposomes to enable efficient delivery of polypeptides in a cell. In some embodiments, the polypeptides (antibody mimetics or monobodies) of the invention are delivered intracellularly by fusion of the polypeptide with a supercharged polypeptide (e.g., supercharged green fluorescent protein (GFP)). The supercharged polypeptide may be supernegatively charged. In some other embodiments, the polypeptide fusions (e.g. antibody mimetic or monobody fused to a supercharged polypeptide) are incorporated into a liposome. In particular embodiments, the liposome is a cationic liposome. The cationic liposomes bearing supercharged antibody mimetic or monody fusion are contacted with cells and efficiently delivered into the cells in functional form.

Polynucleotide Therapy

Another therapeutic approach for treating a cancer or a disease associated with Aurora A is polynucleotide therapy using a polynucleotide encoding an antibody mimetic or monobody of the invention, or an antigen binding fragment thereof. Thus, provided herein are isolated polynucleotides encoding an antibody mimetic or monobody of the invention, or an antigen binding fragment thereof. Expression of such polynucleotides or nucleic acid molecules in a cancer cell is expected to reduce survival of the cell and/or increase cell death. Such nucleic acid molecules can be delivered to cells of a subject having a cancer. The nucleic acid molecules must be delivered to the cells of a subject in a form in which they can be taken up so that therapeutically effective levels of the antibody mimetic or monobody, or fragment thereof, can be produced.

Transducing viral (e.g., retroviral, adenoviral, and adeno-associated viral) vectors can be used for somatic cell gene therapy, especially because of their high efficiency of infection and stable integration and expression (see, e.g., Cayouette et al., *Human Gene Therapy* 8:423-430, 1997; Kido et al., *Current Eye Research* 15:833-844, 1996; Bloomer et al., *Journal of Virology* 71:6641-6649, 1997; Naldini et al., Science 272:263-267, 1996; and Miyoshi et al., Proc. Natl. Acad. Sci. U.S.A. 94:10319, 1997). For example, a polynucleotide encoding an antibody mimetic or monobody, or a fragment thereof, can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, *Human Gene Therapy* 15-14, 1990; Friedman, *Science* 244:1275-1281, 1989; Eglitis et al., *BioTechniques* 6:608-614, 1988; Tolstoshev et al., *Current Opinion in Biotechnology* 1:55-61, 1990; Sharp, *The Lancet* 337:1277-1278, 1991; Cornetta et al., *Nucleic Acid Research and Molecular Biology* 36:311-322, 1987; Anderson, *Science* 226:401-409, 1984; Moen, *Blood Cells* 17:407-416, 1991; Miller et al., *Biotechnology* 7:980-990, 1989; Le Gal La Salle et al., *Science* 259:988-990, 1993; and Johnson, Chest 107:77S-

83S, 1995). Retroviral vectors are particularly well developed and have been used in clinical settings (Rosenberg et al., *N. Engl. J. Med* 323:370, 1990; Anderson et al., U.S. Pat. No. 5,399,346). In some embodiments, a viral vector is used to administer a polynucleotide encoding an antibody mimetic or monobody (or fragment thereof) systemically.

Non-viral approaches can also be employed for the introduction of therapeutic to a cell of a patient requiring inhibition of a cancer or induction of cell death in a cancer. For example, a nucleic acid molecule can be introduced into a cell by administering the nucleic acid in the presence of lipofection (Feigner et al., *Proc. Natl. Acad. Sci. U.S.A.* 84:7413, 1987; Ono et al., *Neuroscience Letters* 17:259, 1990; Brigham et al., *Am. J. Med. Sci.* 298:278, 1989; Staubinger et al., *Methods in Enzymology* 101:512, 1983), asialoorosomucoid-polylysine conjugation (Wu et al., *Journal of Biological Chemistry* 263:14621, 1988; Wu et al., *Journal of Biological Chemistry* 264:16985, 1989), or by micro-injection under surgical conditions (Wolff et al., *Science* 247:1465, 1990). The nucleic acids can be administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of normal genes into the affected tissues of a patient can also be accomplished by transferring a normal nucleic acid into a cultivatable cell type ex vivo (e.g., an autologous or heterologous primary cell or progeny thereof), after which the cell (or its descendants) are injected into a targeted tissue.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Pharmaceutical Compositions

The present invention features compositions useful for treating a cancer in a subject. In some embodiments, the composition comprises an agent that specifically binds to an allosteric site (PIF pocket) of Aurora A kinase and an agent that specifically binds to an ATP binding site of Aurora A kinase. In some embodiments, the agent is a monobody. In some other embodiments, the agent is a small molecule compound. In some other embodiments, the composition comprises a polynucleotide encoding an amino acid sequence of an antibody mimetic, monobody, or fragment thereof. In particular embodiments, the composition further comprises a liposome.

The administration of a composition comprising a combination of agents herein for the treatment of a cancer may be by any suitable means that results in a concentration of the therapeutic that, combined with other components, is effective in ameliorating, reducing, or stabilizing a cancer in a subject. The composition may be administered systemically, for example, formulated in a pharmaceutically-acceptable buffer such as physiological saline. Routes of administration include, for example, subcutaneous, intravenous, intraperitoneally, intramuscular, or intradermal injections that provide continuous, sustained levels of the agent in the patient. The amount of the therapeutic agent to be administered varies depending upon the manner of administration, the age and body weight of the patient, and with the clinical symptoms of the cancer. Generally, amounts will be in the range of those used for other agents used in the treatment of cancer or other diseases associated with Aurora A kinase, although in certain instances lower amounts will be needed because of the increased specificity of the agent. A composition is administered at a dosage that inhibits Aurora A activity or that decreases cancer cell proliferation as determined by a method known to one skilled in the art.

The therapeutic agent(s) may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active agent substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with a tumor; (v) formulations that allow for convenient dosing, such that doses are administered, for example, once every one or two weeks; and (vi) formulations that target a cancer using carriers or chemical derivatives to deliver the therapeutic agent to a particular cell type (e.g., cancer cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the agent in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a cancer, the composition may include suitable parenterally acceptable carriers and/or excipients. The active therapeutic agent(s) (e.g., an antibody mimic, monobody, or polynucleotide described herein) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

In some embodiments, the composition comprising the active therapeutic(s) (i.e., a monobody, antibody mimetic, small molecule compound, or polynucleotide herein) is formulated for intravenous delivery. As indicated above, the pharmaceutical compositions according to the invention may be in the form suitable for sterile injection. To prepare such a composition, the suitable therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the agents is only sparingly or slightly soluble in water, a dissolution enhancing or solubilizing agent can be added, or the solvent may include 10-60% w/w of propylene glycol or the like.

Methods of Identifying Agents that Bind to PIF Pocket and Inhibit or Activate Kinase Activity In some aspects, the present invention features methods of identifying or designing agents (e.g., small molecule compounds or peptides) useful for modulating kinase activity, particularly, inhibiting Aurora A kinase activity. The crystal structure information presented herein may be useful in designing agents and modeling them or their potential interactions with binding site(s), particularly the PIF pocket, of Aurora A kinase. Agents may be identified from following design and model work performed in silico. An agent identified using the present invention may be effective for the treatment of disorders associated with kinase misregulation, such as cancer.

Interactions Between PIF Pocket and Natural Modulator of a Kinase

In some aspects, the present invention features methods of identifying or designing an agent that modulates activity of a kinase having a PIF pocket. As described herein, without wishing to be bound by theory, binding at a PIF pocket of a kinase is believed to be a general mechanism of regulation of AGC kinases. AGC kinases belong to a family of more than 60 human kinases, which are known to have a PIF pocket as a regulatory site.

By obtaining an X-ray crystal structure of the AGC kinase bound to a natural modulator (e.g., a polypeptide or other agent known to bind to the PIF pocket of the AGC kinase in a natural setting and thereby modulate activity of the kinase), particular residue contact(s) made between the natural modulator and the PIF pocket can be identified. Such information can be useful in designing agents (e.g., small molecule compounds) that similarly bind the PIF pocket and modulate kinase activity. Accordingly, in some embodiments, the method of identifying or designing an agent that modulates activity of a kinase having a PIF pocket contains the steps of: (a) obtaining a three-dimensional structure of the PIF pocket bound to a natural modulator of the kinase; (b) producing a structure for a candidate compound, wherein the structure defines a molecule having sufficient surface complementary to the kinase to bind the PIF pocket in an aqueous solution; and (c) identifying the candidate compound as a modulator of the kinase if an interaction between the candidate compound and the PIF pocket mimics an interaction between the natural modulator and the PIF pocket. In some embodiments, the method further comprises further modifying the structure of the candidate compound such that the interaction between the candidate compound and PIF pocket better mimics the interaction between the natural modulator and the PIF pocket.

In Silico Drug Design

The present invention permits the use of virtual design techniques (i.e., computer modeling or "in silico") to design, select, and synthesize compounds or other agents (e.g., peptides) capable of regulating kinase activity, in particular, Aurora A kinase activity. In turn, these compounds may be effective in the treatment of a disorder associated with misregulated kinase activity, such as cancer.

In addition to the more traditional sources of test agents, computer modeling and searching technologies permit the rational selection of test compounds by utilizing structural information from the functional binding sites (e.g., PIF pocket) on proteins of the present invention (e.g., kinases such as Aurora A kinase). Such rational selection of agents may decrease the number of agents that may need to be screened to identify therapeutic candidate agents. In some embodiments, the PIF pocket of Aurora A kinase comprises any one or more of amino acid residues 165-210 of Aurora A kinase. In other embodiments, in addition to the PIF pocket, monobodies are found to interact with the activation loop (residues 275-290 of Aurora A kinase) and some of the beta sheets comprising the N-lobe of Aurora A kinase. Without being bound by theory, it is believed that although PIF pocket binding is responsible for allosteric activation/inhibition of Aurora A kinase, anchoring of monobodies to sites proximal to the PIF pocket, could help in increase interaction and thus tighter binding between Aurora A kinase and the monobodies.

Knowledge of the protein sequences of the present invention may allow for generation of models of their binding sites that may be used to screen for potential agent(s) that bind to the binding sites. This process may be accomplished with the skills known in the art. One approach involves generating a sequence alignment of the protein sequence to a template (derived from the crystal structures or NMR-based model of a similar protein(s)), conversion of the amino acid structures and refining the model by molecular mechanics and visual examination. If a strong sequence alignment may not be obtained, then a model may also be generated by building models of the hydrophobic helices. Mutational data that point towards contact residues may also be used to position the helices relative to each other so that these contacts are achieved. During this process, docking of the known ligands into the binding site cavity within the helices may also be used to help position the helices by developing interactions that may stabilize the binding of the ligand. The model may be completed by refinement using molecular mechanics and loop building using standard homology modeling techniques. General information regarding modeling may be found in Schoneberg, T. et. al., *Molecular and Cellular Endocrinology,* 151:181-193 (1999), Flower, D., *Biochim Biophys Acta,* 1422, 207-234 (1999), and Sexton, P. M., *Curr. Opin. Drug Discovery and Development,* 2, 440-448 (1999).

Once the model is completed, it may be used in conjunction with one of several computer programs to narrow the number of compounds to be screened, e.g., the DOCK program (UCSF Molecular Design Institute, San Francisco, Calif. 94143) or FLEXX (Tripos Inc., MO). One may also screen databases of commercial and/or proprietary compounds for steric fit and rough electrostatic complementarity to the binding site. In one embodiment, the docking program is ZDOCK (Pierce et al., *Bioinformatics.* 2014 Jun. 15; 30(12):1771-3). In another embodiment, the docking program is AutoDock Vina (Trott et al., *Journal of Computational Chemistry* 31 (2010) 455-461).

In Silico Screening of Agents

In one aspect, the invention provides means to carry out virtual screening of agents using the disclosed atomic coordinates or coordinates derived therefrom. The atomic coordinates of the three-dimensional structure elucidated by the invention are input into a computer so that images of the structure and various parameters are shown on the display. The resultant data are input into a virtual agent library. Since a virtual agent library is contained in a virtual screening software, the above-described data may be input into such a software. Agents may be searched for, using a three-dimensional structure database of virtual or non-virtual agents, such as MDDR (Prous Science, Spain).

The potential interactions of an agent may be analyzed prior to its actual synthesis and testing by the use of computer modeling techniques. If the theoretical structure of the given agent suggests insufficient interactions with Aurora A kinase, or suggests undesired interactions (e.g., interactions that mimic interactions of the activating monobody with the PIF pocket of Aurora A) synthesis and testing of the agent may be obviated. However, if computer modeling indicates sufficient interactions, the molecule may then be synthesized and tested for its ability to modulate kinase activity, using various methods described herein and/or that are known to a person skilled in the art. In one embodiment, the molecule is tested for its ability to modulate (particularly, inhibit) kinase activity using the assays described herein (e.g., an HPLC-based or an ATP/NADH-coupled-assay-based measurement of the phosphorylation of a Aurora A kinase substrate as described herein).

Agents may be computationally evaluated and designed by means of a series of steps in which chemical entities or fragments are screened and selected for their ability to bind with individual binding sites or combinations thereof (e.g., P0, P+1, P−1) or other areas of Aurora A kinase.

One skilled in the art may use any of several methods to screen chemical entities or fragments for their ability to bind to Aurora A and more particularly with the specific binding sites or functional sites described herein (e.g., PIF pocket of Aurora A). Sequences of other kinases may also be threaded onto the protein backbone of an Aurora A kinase domain (e.g., PIF pocket of Aurora A) derived from the crystal structure, with side chain positions optimized using methods known in the art. The resulting structural models may then be used to discover chemical entities or fragments that modulate kinase activity via in silico docking. The process may begin by visual inspection of, for example, the functional site on the computer screen based on the Aurora A coordinates presented in Appendix A or Appendix B. Selected fragments or chemical entities may then be positioned in a variety of orientations, or docked, within a binding site of Aurora A (e.g., PIF pocket). In some embodiments, the candidate agent is docked to the PIF pocket of Aurora A kinase. In some other embodiments, candidate agent(s) that have interaction(s) mimicking the interaction of an inhibitory monobody with the PIF pocket of Aurora A as described herein is selected for testing or further optimization. In still other embodiments, candidate agent(s) that have interaction(s) mimicking the interaction of an activating monobody with the PIF pocket of Aurora A as described herein is not selected for testing or further optimization. Docking may be accomplished using software such as QUANTA™, SYBYL™, followed by energy minimization and molecular dynamics with molecular mechanics forcefields softwares, such as CHARMM™ and AMBER™.

Specialized computer programs may also assist in the process of selecting fragments or chemical entities. These include, but are not limited to, GRID™ (Goodford, P. J., J. Med. Chem., 28, 849-857 (1985)); MCSS™ (Miranker, A. and M. Karplus, "Proteins: Structure, Function and Genetics, 11, 29-34 (1991)); (3) AUTODOCK™ (Goodsell, D. S. and A. J. Olsen, Proteins: Structure, Function, and Genetics, 8, 195-202 (1990; DOCK™ (Kuntz, I. D. et al., J. Mol. Biol., 161, pp. 269-288 (1982)); GLIDE™ (Schrodinger Inc.); FLEXX™ (Tripos Inc); (7) GOLD™ (Jones et al., J. Mol. Biol., 245, 43-53, 1995).

Once suitable chemical entities or fragments have been selected, they may be assembled in silico or synthesized into a single compound. Chemical syntheses may be carried out by methods known in the art. In silico assembly may proceed by visual inspection of the relationship of the fragments to each other on the three-dimensional image displayed on a computer screen in relation to the structure coordinates of RAGE. This may be followed by manual model building using softwares such as QUANTA™ or SYBYL™.

Useful programs for connecting the individual chemical entities or fragments include the following: CAVEAT™ (Bartlett, P. A. et al, Royal Chem. Soc., 78, 182-196 (1989)); 3D Database systems such as MACCS-3D™ (MDL Information Systems, San Leandro, Calif.); and HOOK™ (Molecular Simulations, Burlington, Mass.). In addition to building an agent in a step-wise fashion as described above, agents may be designed as a whole or "de novo" using an empty active site or optionally including some portion(s) of a known agent. Such methods include, but are not limited to, LUDI™ (Bohm, H.-J., J. Corn R. *Aid. Molec. Design,* 6, pp. 61-78 (1992)); LEGEND™ (Nishibata, Y. and A. Itai, *Tetrahedron,* 47, p. 8985 (1991)), and LEAPFROG™ (Tripos Inc., St. Louis, Mo.).

Once an agent has been designed or selected, the efficiency with which that agent may modulate kinase activity (e.g., kinase activity of Aurora A) may be tested and optimized by computational evaluation. For example, an agent may demonstrate a relatively small difference in energy between its bound and unbound states (i.e., a small deformation energy of binding). In some embodiments, an agent may interact with Aurora A kinase in more than one conformation that is similar in overall binding energy. In such case, the deformation energy of binding can be taken to be the difference between the energy of the unbound agent and the average energy of the conformations observed.

An agent that is designed or selected may be further computationally optimized so that in its bound state it may lack repulsive electrostatic interactions. Such interactions include repulsive charge-charge, dipole-dipole, and charge-dipole interactions. The sum of all electrostatic interactions between the agent and Aurora A, may make a neutral or favorable contribution to the enthalpy of binding. Software programs to evaluate agent deformation energy and electrostatic interaction include, e.g., Gaussian 92™ (M. J. Frisch, Gaussian, Inc., Pittsburgh, Pa.); AMBER™ (P. A. Kollman, University of California at San Francisco, Calif.); QUANTA/CHARMM™ (Molecular Simulations, Inc., Burlington, Mass.); and Insight II/Discover™ (Biosysm Technologies Inc., San Diego, Calif.).

In some embodiments, an agent that is designed or selected is also be further computationally optimized so that in its bound state, the interactions of the agent with the PIF pocket mimic interactions made by the inhibitory monobody with the PIF pocket and/or does not mimic interactions made by the activating monobody with the PIF pocket.

Once an agent has been optimally selected or designed, substitutions may be made in some of its atoms or side groups in order to improve or modify its binding properties. Initial substitutions may be conservative, i.e., the replacement group will have approximately the same size, shape, hydrophobicity and charge as the original group. Such substituted agents may then be analyzed for efficiency of fit to Aurora A kinase by software programs similar to those described.

Crystallographic Evaluation of Chemical Entities for Binding to Aurora a Kinase

The invention allows one skilled in the art to study the binding of agents to Aurora A kinase by exposing either individual agents or mixtures of agents (such as may be obtained from combinatorial libraries) into Aurora A crystals or, alternatively, by co-crystallization of the compounds of interest with Aurora A, using methods known in the art, and those described in the Examples herein. Acquisition and analysis of X-ray diffraction data from these crystals may then be performed using standard methods. If an agent binds to Aurora A then positive difference electron density will be observed in the Fourier maps calculated using the X-ray diffraction intensities and phases obtained from the Aurora A model presented herein. Models of the chemical entities may then be built into the electron density using standard methods, and the resulting structures may be refined against the X-ray diffraction data, providing experimental data describing the interaction of the agents of interest. Those skilled in the art may use these models to design compounds based either on purely structural data; or on combination of structural data, biological/chemical activity based structure-activity relationship, and in silico drug design.

The agents that are thus designed or selected may further be tested in an in vitro, in vivo, or ex vivo assays to determine if they modulate kinase activity. Such assays are known to one skilled in the art. In some embodiments, the assay is a HPLC-based assay as described herein.

Kits

The invention provides kits for the treatment or prevention of cancer, particularly cancers associated with overexpression of a kinase, such as Aurora A kinase. In one embodiment, the kit includes a therapeutic or prophylactic composition containing an effective amount of an agent that specifically binds an allosteric site on a kinase and an effective amount of an agent that specifically binds an ATP-binding site on the kinase. In some embodiments, the kit comprises a sterile container which contains a therapeutic or prophylactic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, a composition comprising the combination of agents the invention is provided together with instructions for administering the agent to a subject having or at risk of developing cancer. The instructions will generally include information about the use of the composition for the treatment or prevention of cancer. In other embodiments, the instructions include at least one of the following: description of the therapeutic agent; dosage schedule and administration for treatment or prevention of ischemia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Biochemical Characterization of Binding of PS48 and Danusertib to Aurora A Kinase A combinatorial drug study using isothermal titration calorimetry (ITC) was performed to characterize binding of a combination of danusertib and PS48 to Aurora A kinase. Danusertib is a small molecule inhibitor of Aurora A kinase and binds to the ATP-binding site of Aurora A. PS48 is another small molecule inhibitor of Aurora A kinase. As described elsewhere herein, PS48 does not bind to the ATP-binding site of Aurora A, but competes with TPX2 to bind to the PIF pocket of Aurora A.

FIGS. 1A-1B show results of an ITC assay measuring binding of dephosphorylated Aurora A kinase and danusertib. Danusertib bound Aurora A kinase with nanomolar affinity (a $K_d$ of about 224 nM). FIGS. 1C-1D show ITC assay results for a dephosphorylated Aurora A kinase chimera (a dephosphorylated Aurora A kinase with a PIF pocket occupied by TPX2) and danusertib. Results showed binding of danusertib to the Aurora A kinase chimera, indicating that danusertib does not bind to the PIF pocket of Aurora A. However, binding of danusertib to the Aurora A kinase chimera was about 4 times weaker than binding to Aurora A kinase. This indicated that binding of the allosteric activator TPX2 at the PIF pocket of Aurora A could modulate affinity of binding of danusertib to the ATP binding site of Aurora A kinase. This modular binding affinity could be due to TPX2 inducing a DFGin conformation of the kinase which is not the preferred binding state of the DFGout binder, danusertib.

Figure 3C:
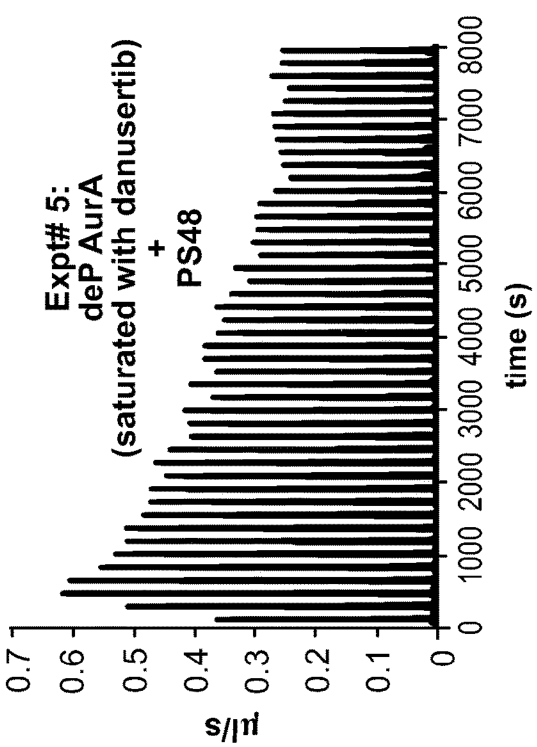
FIGS. 3A-3D are plots showing results of isothermal titration calorimetry (ITC) assays to characterize the thermodynamics of binding of dephosphorylated Aurora A kinase and PS48 (FIGS. 3A-3B) and binding of dephosphorylated Aurora A kinase (saturated with danusertib) and PS48 (FIGS. 3C-3D).
Figure 3A:
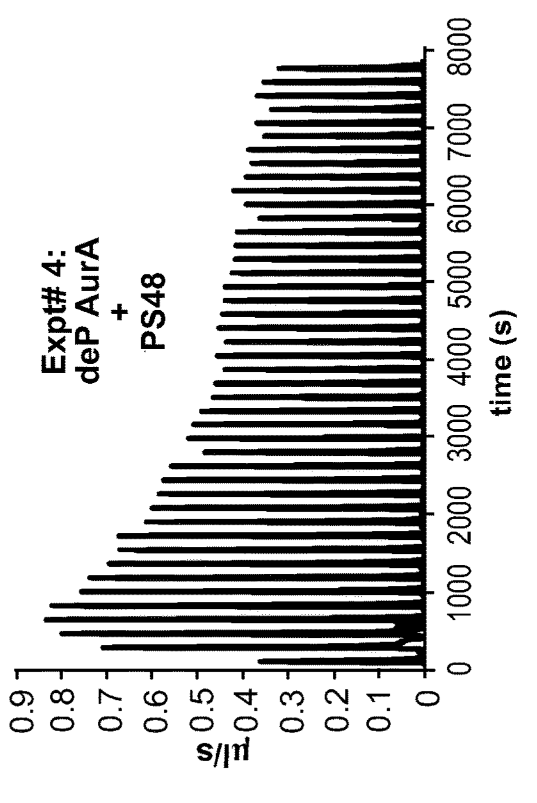
Figure 3D:
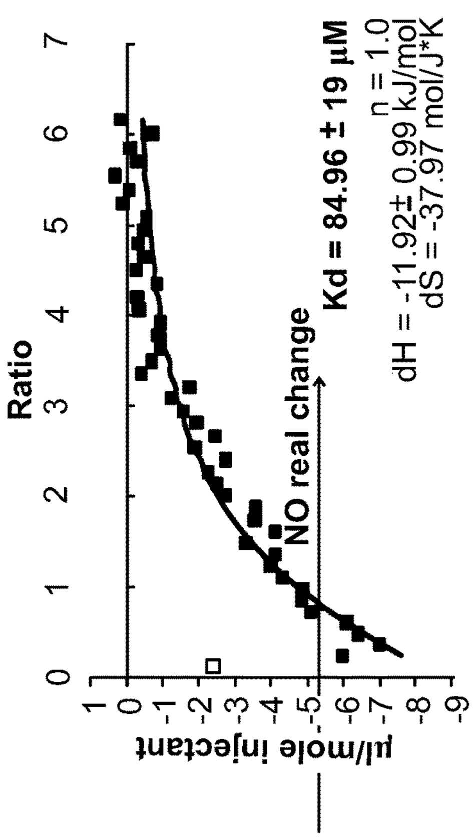
Figure 3B:
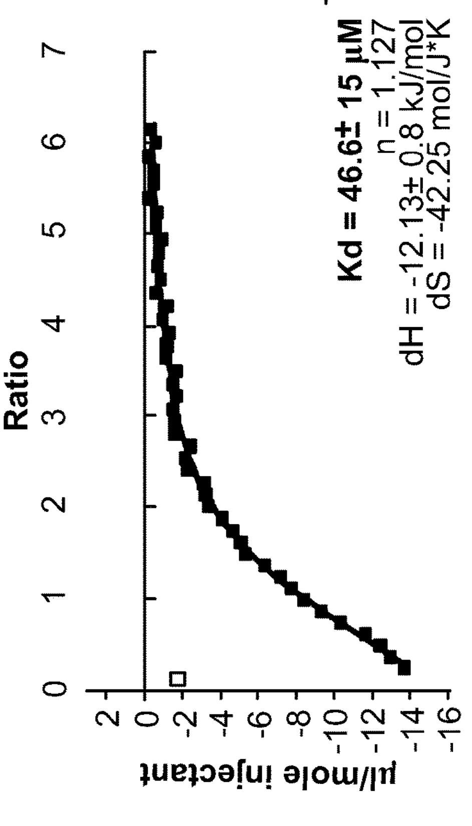

FIGS. 3A-3B show results of an ITC assay measuring binding of PS48 to dephosphorylated Aurora A kinase. As shown in FIG. 3B, PS48 binds Aurora A kinase with micromolar affinity ($K_d$ of binding of PS48 to Aurora A kinase was measure to be about 46. μM). PS48 binds Aurora A kinase much more weakly than danusertib, as danusertib bound Aurora A kinase with nanomolar affinity.

FIGS. 3C-3D depict ITC assay results measuring binding of PS48 to dephosphorylated Aurora A kinase saturated with danusertib. In the presence of saturating amounts of danusertib, PS48 bound to dephosphorylated Aurora A kinase with a $K_d$ of about 84.96 μM. This indicated that binding of danusertib to the ATP binding site of Aurora A did not significantly affect affinity of binding of PS48 to Aurora A at the PIF pocket.

Figure 2A:
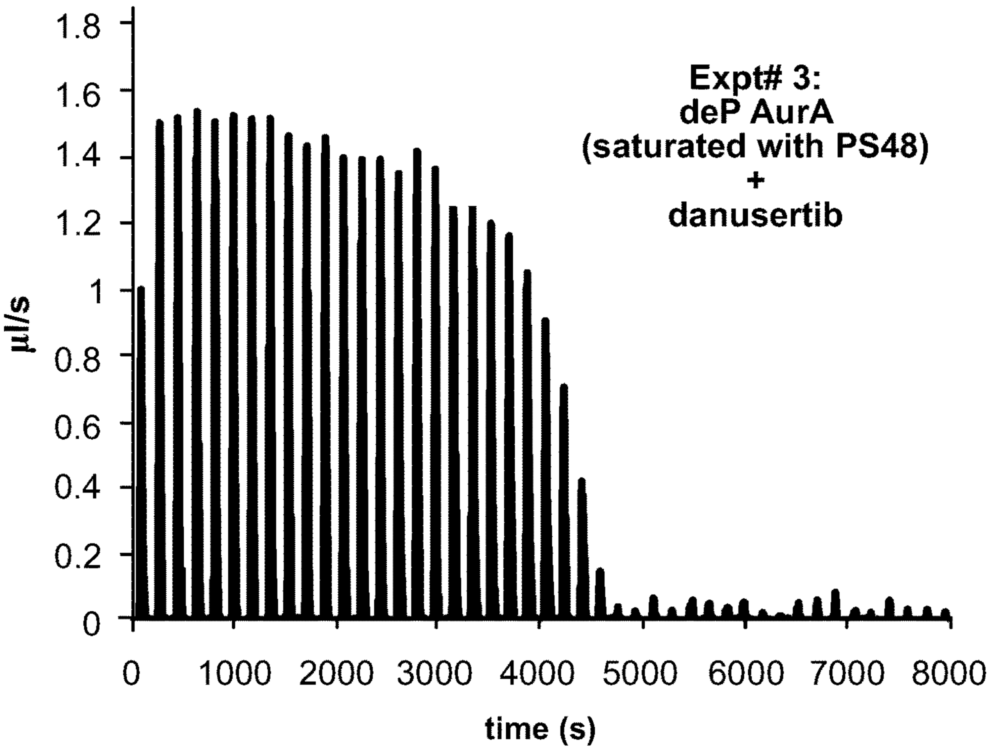
FIGS. 2A and 2B are plots showing results of isothermal titration calorimetry (ITC) assays to characterize the thermodynamics of binding of danusertib to Aurora A kinase (saturated with PS48).
Figure 2B:
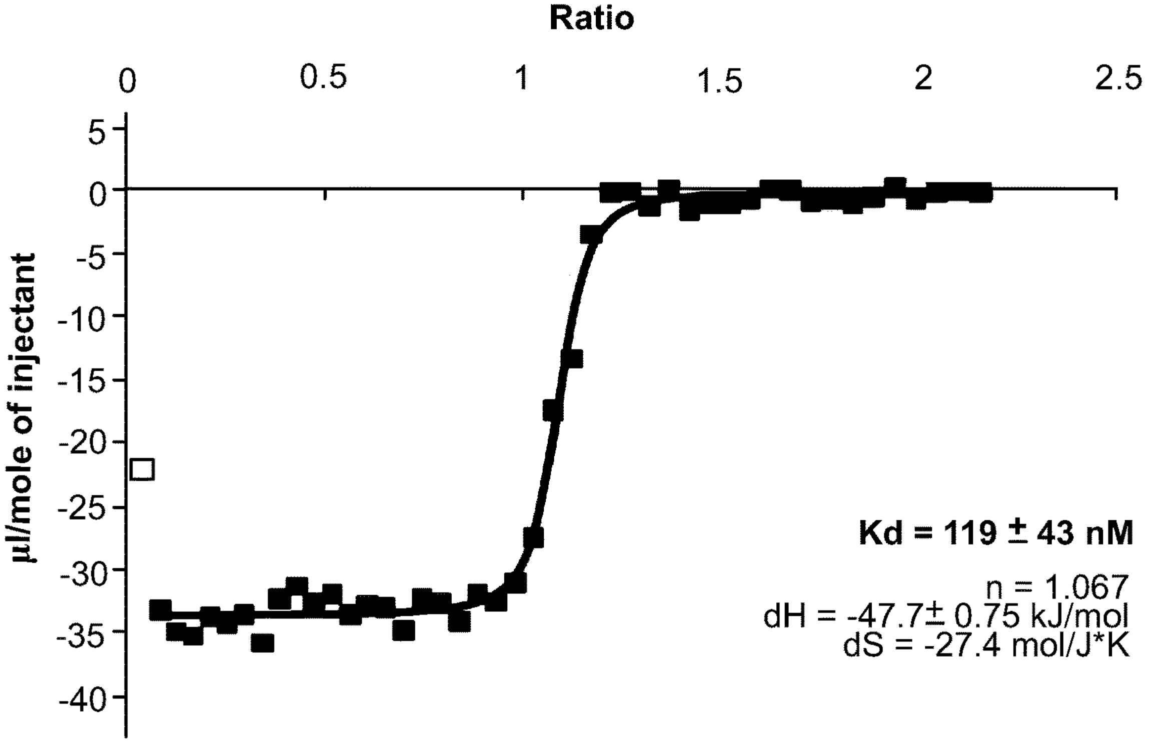

To determine whether binding of PS48 to the PIF pocket of Aurora A kinase could alter affinity of binding of danusertib at the ATP-binding site, an ITC assay was performed to measure binding of danusertib to dephosphorylated Aurora A kinase at saturating levels of PS48. Results of the assay are shown in FIGS. 2A-2B. Danusertib bound to Aurora A kinase with a $K_d$ of about 119 nM, indicating that binding of Danusertib to Aurora A was about 2 times tighter in the presence of saturating levels of PS48. Without being bound by theory, it is believed that increased binding of PS48 (or a similar molecule) at the PIF pocket could more strongly increase binding affinity of danusertib to the ATP binding site. However, as measured herein, PS48 bound the PIF pocket with only micromolar affinity (FIG. 3B). While increasing binding of PS48 to the PIF pocket could be achieved by increasing levels of PS48, it was found that at very high concentrations, PS48 was not stable.

Example 2: Binding of Activating or Inhibitory Monobodies to Allosteric Site Shifts Equilibrium to Inactive or Active Kinase Conformation and Modulates Affinity of Binding of Danusertib to ATP-Binding Site To further determine how binding at the PIF pocket could alter binding of danusertib to the ATP-binding site, other molecules that specifically bound the PIF pocket were investigated. Specifically, binding of danusertib to Aurora A kinase in the presence of monobodies that specifically bound the PIF pocket of Aurora A kinase was investigated.

Figure 4:
FIG. 4 is a schematic representation of three dimensional structures of an exemplary antibody (left) having a size of about 150 kDa and an exemplary monobody having a size of about 10 kDa (right). Antigen binding sites on the exemplary antibody and exemplary monobody are encircled.
Figure 14:
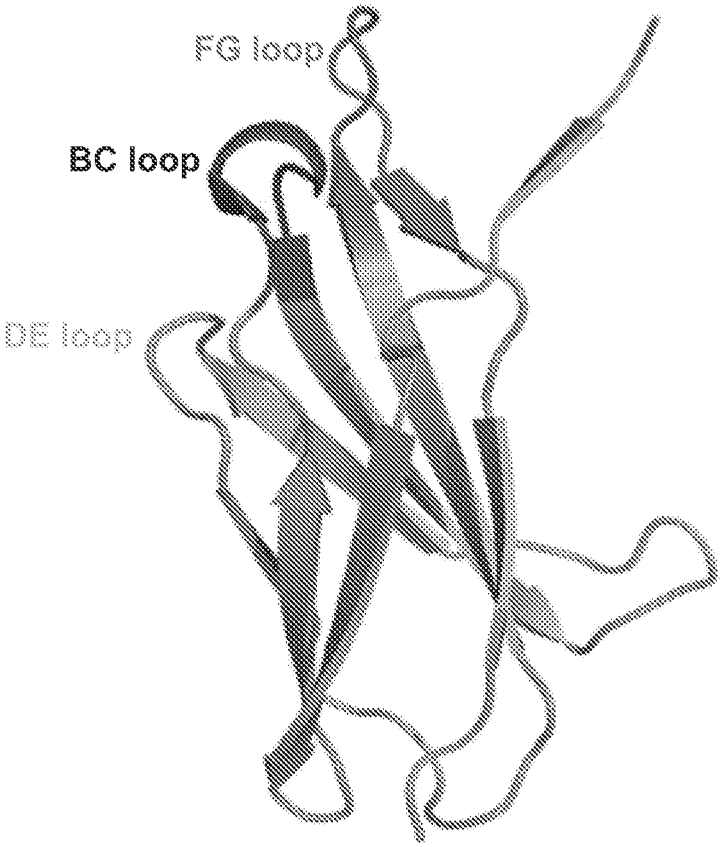
FIG. 14 is a schematic representation of an exemplary monobody showing variable loops (FG loops, BC loop, DE loop) on the monobody. The variable loops comprise the complementarity determining region ("CDR") of the monobody.

Briefly, a monobody is an antibody mimetic. Like an antibody, a monobody can specifically bind an antigen through variable region(s) on the monobody (FIG. 14). Structurally, however, a monobody is generally different from an antibody (FIG. 4). Monobodies specifically binding to a target are produced by screening libraries of mutagenized molecular scaffolds, such as a fibronectin III (FN3) domain. The molecular scaffold is typically a smaller molecule than an antibody; thus, a monobody is typically much smaller than an antibody (FIG. 4).

Figures 9, 9A:
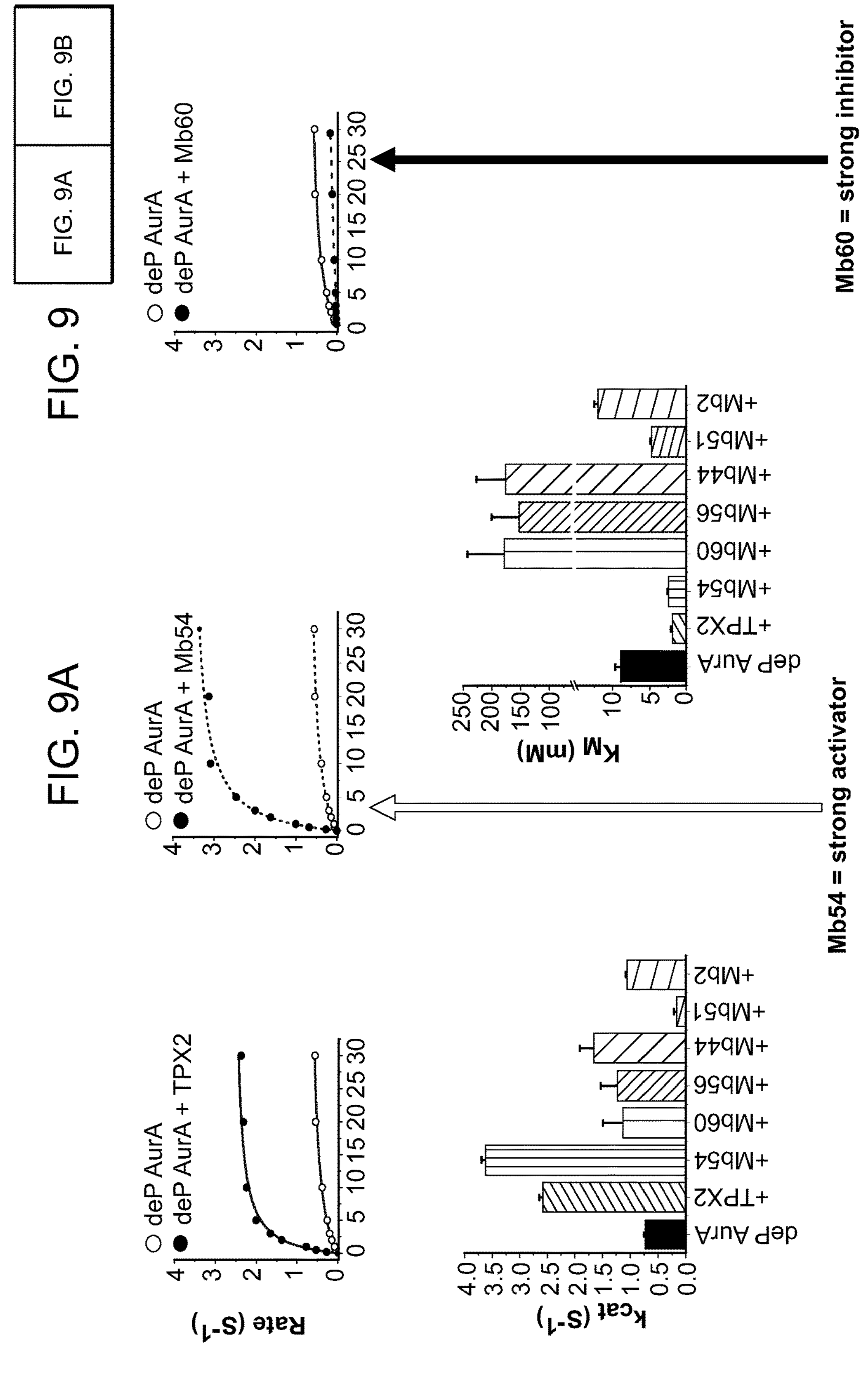
FIG. 9 is a set of plots showing that monobodies in a study described herein (Mb54, Mb60, Mb56, Mb44, Mb51 and Mb2) activate or inhibit Aurora A kinase activity to varying degrees, with monobody Mb2 (aka Mb6) being the weakest regulator and monobodies Mb54 and Mb60 being the strongest activator and inhibitor monobodies, respectively. The open circles, show measurement of phosphorylation of Lats2 (a peptide substrate for Aurora A kinase) when incubated with Aurora A kinase and TPX2, Mb54, Mb60, Mb56, Mb44, Mb51 and Mb2 (aka Mb6) (filled circles and red, green, orange, brown, magenta, purple and light blue datasets, respectively). The bottom plot shows a (moving from left to right), analysis of $k_{cat}$, $K_M$, $k_{cat}/K_M$ and fold increase in $k_{cat}/K_M$ which, in turn is a measure of the enzyme's catalytic efficiency. The measurements indicate that the monobodies Mb2 (aka Mb6), Mb51, Mb54, and Mb56 modulate Aurora A kinase activity by activating or inhibiting Aurora A kinase activity, with various degrees of activation or inhibition. Monobody Mb54 was identified herein as a monobody that shifts Aurora A kinase equilibrium to the DFG-in (active) state. Monobody Mb60 was identified herein as a monobody that shifts Aurora A kinase equilibrium to the DFG-out (inactive) state.
Figure 9B:
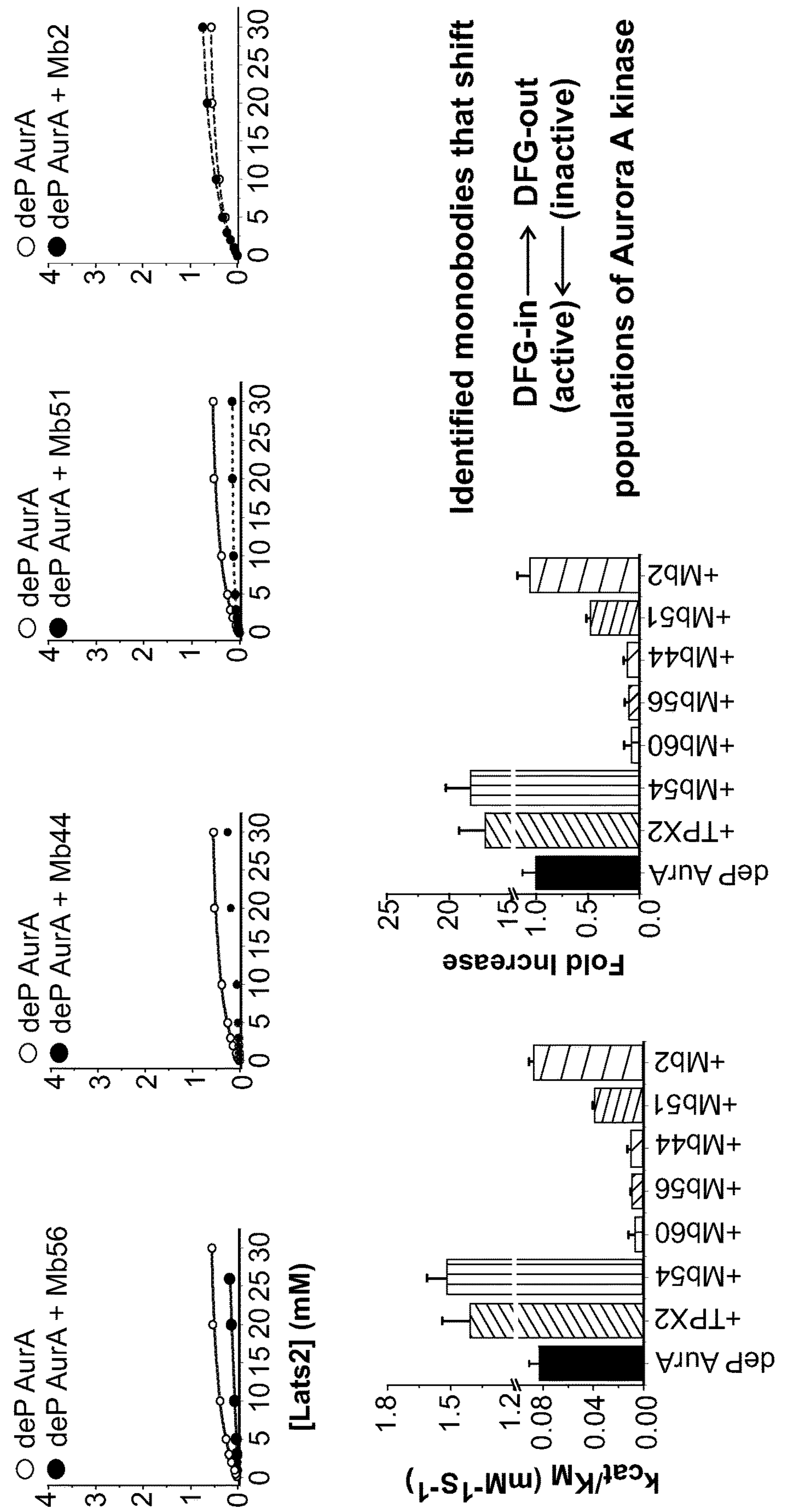

As described elsewhere herein, monobodies that specifically bound tightly to the PIF pocket of human Aurora A kinase were generated and biochemically characterized. Using a quantitative High Performance Liquid Chromatography (HPLC)-based assay, kinetics of Aurora A activation by the monobodies was determined. Monobody Mb54 was found to activate Aurora A kinase activity (FIG. 9). Monobodies Mb56, Mb51 and Mb44 were found to strongly inhibit Aurora A kinase activity, whereas monobody Mb2 (aka Mb6) did not significantly modulate Aurora A kinase activity, although it bound to Aurora A kinase with low nM affinity (FIG. 9).

Figure 5:
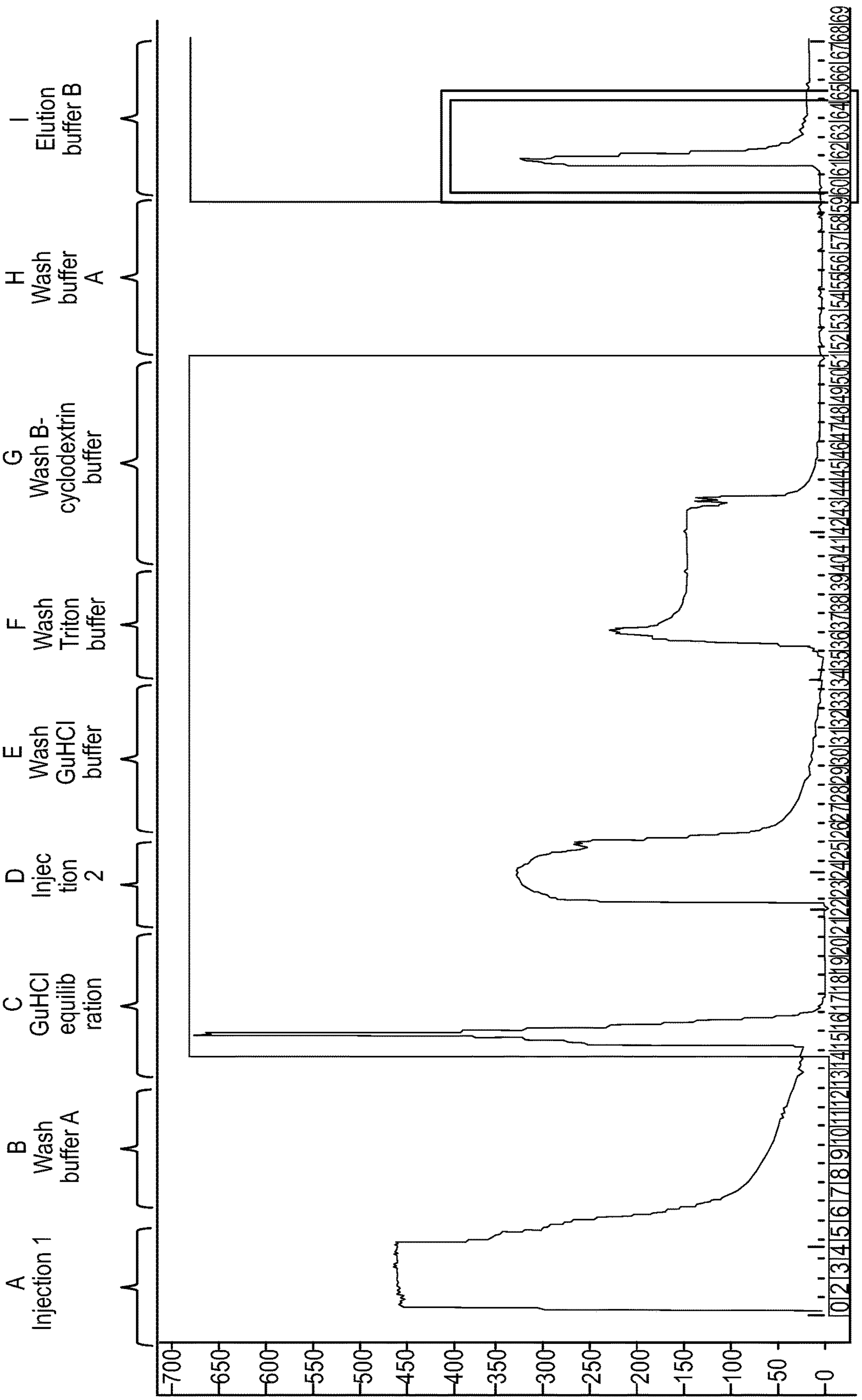
FIG. 5 is a plot showing purification of monobody Mb2 (aka Mb6) from cell lysate by affinity chromatography. Monobody Mb2 (aka Mb6) contains a histidine tag. The peak corresponding to monobody Mb2 (aka Mb6) is indicated by a box. As noted herein, "Mb2" is also designated by its alternative name "Mb6" infra.
Figure 6:
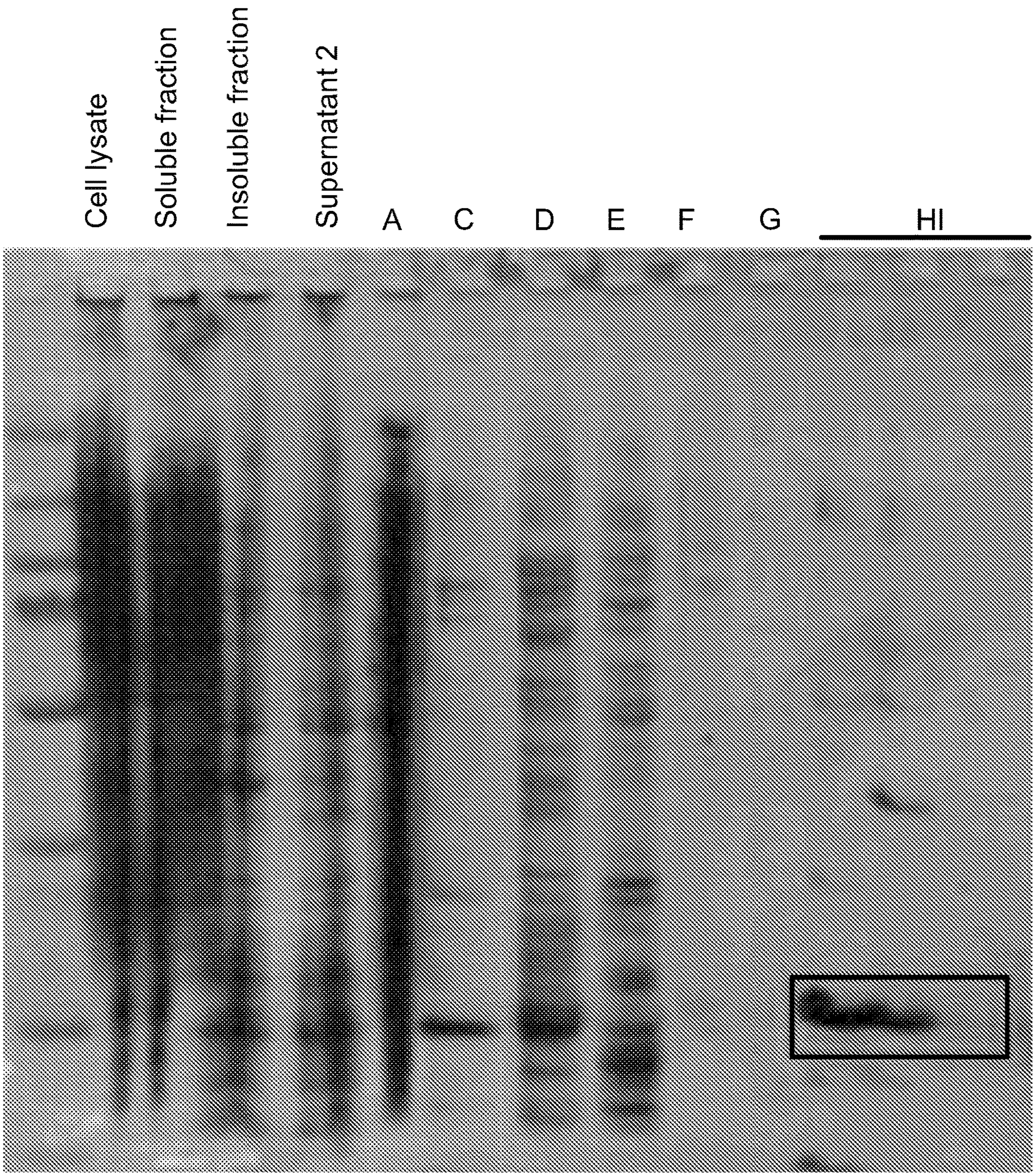
FIG. 6 is a protein gel image of proteins in the flow-through from the affinity chromatography purification of monobody Mb2 (aka Mb6). The samples labeled A, C, D, E, F, and G correspond to samples from the flow-through from various steps (labeled correspondingly) of the purification as shown in FIG. 5. The band corresponding to monobody Mb2 (aka Mb6) is indicated by the box. As noted herein, "Mb2" is also designated by its alternative name "Mb6" infra.

To investigate binding of danusertib to Aurora A kinase in the presence of monobodies, monobodies were recombinantly expressed and purified from cell lysates. FIGS. 5-6 show purification of a histidine tagged monobody Mb2 (aka Mb6) used in the in vitro binding studies described herein. The sequence of histidine tagged monobody Mb2 (aka Mb6) (SEQ ID NO: 14) is provided in FIG. 7.

Figures 8, 8A:
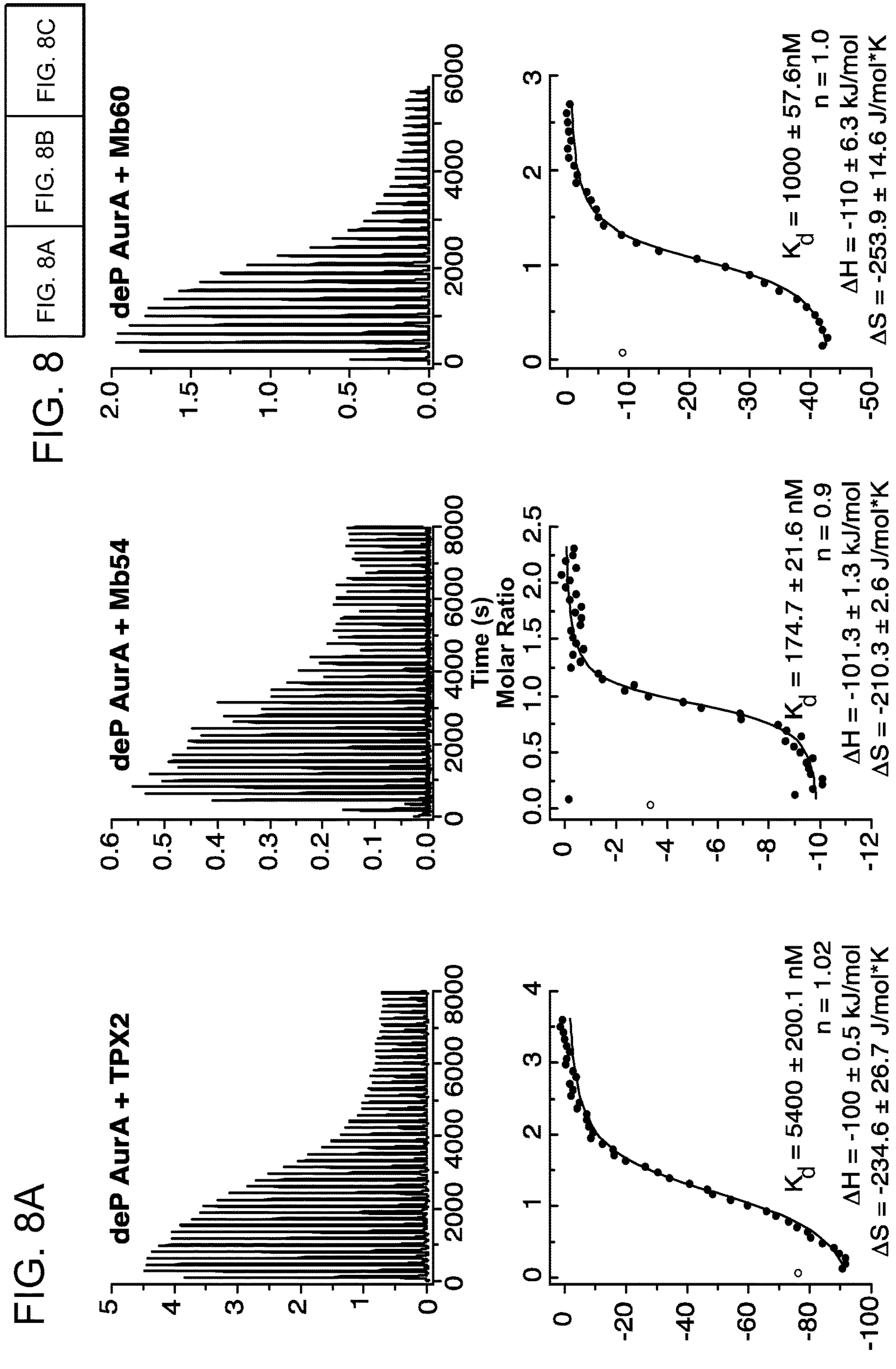
FIG. 8 shows a summary of results of isothermal titration calorimetry (ITC) assays characterizing binding of dephosphorylated Aurora A kinase to TPX2 (for reference, given that this is the naturally occurring allosteric activator of Aurora A kinase and monobodies Mb54, Mb60, Mb56, Mb44, Mb51 and Mb2, which are designated infra by their alternative names Mb1, Mb2, Mb3, Mb4, Mb5 and Mb6, respectively, as described herein. The dissociation constant ($K_d$) for each of the binding reactions of dephosphorylated Aurora A kinase to monobodies Mb54 (aka Mb1), Mb60 (aka Mb2), Mb56 (aka Mb3), Mb44 (aka Mb4), Mb51 (aka Mb5) and Mb2 (aka Mb6), is shown the raw isothermal titration calorimetry data, in the respective isotherms.
Figure 8B:
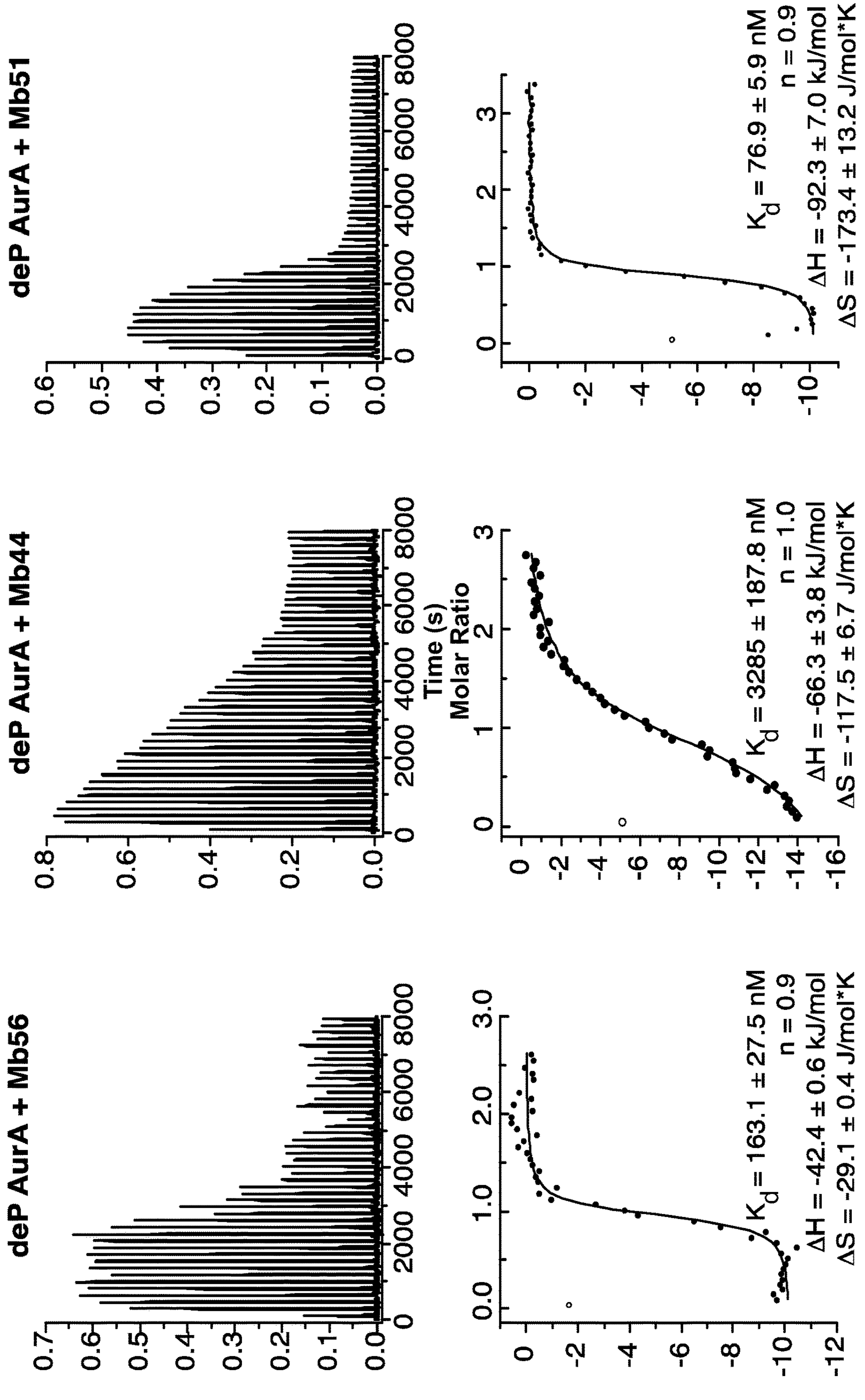
Figure 8C:
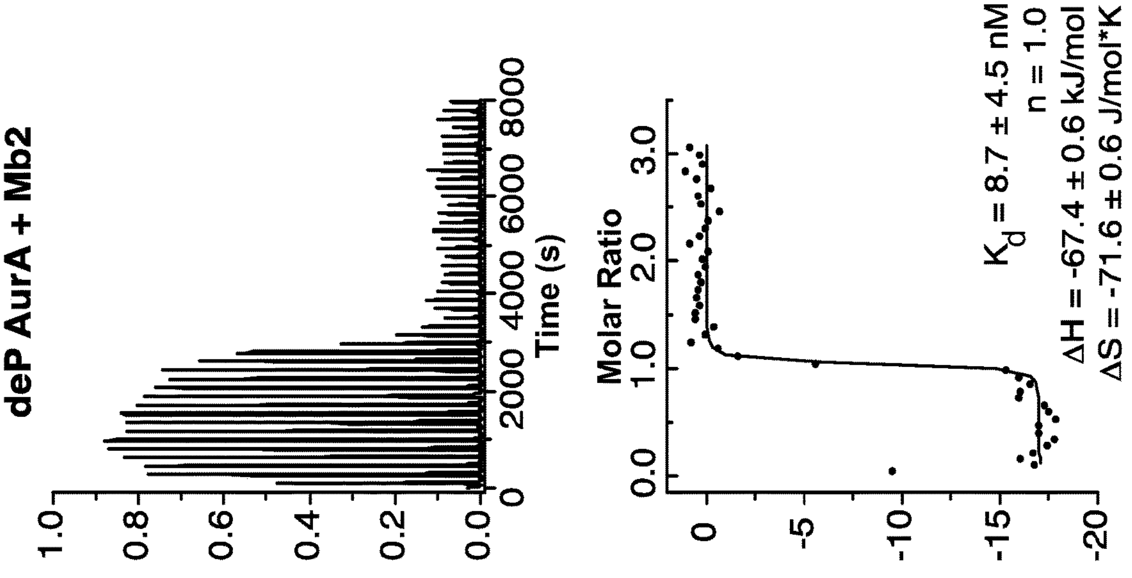

FIG. 8 shows results of ITC assays characterizing binding of all six monobodies (Mb54, Mb60, Mb56, Mb44, Mb51 and Mb2 (aka Mb6)) to dephosphorylated Aurora A kinase. As shown in FIG. 8, monobodies Mb2 (aka Mb6), Mb51, Mb54, and Mb56 all bound dephosphorylated Aurora A kinase with generally low nanomolar affinities, indicating tight binding of these monobodies to dephosphorylated Aurora A kinase. On the other hand, monobodies Mb44 and Mb60 bound Aurora A kinase with slightly lower affinity, at low μM levels.

Figure 10A:
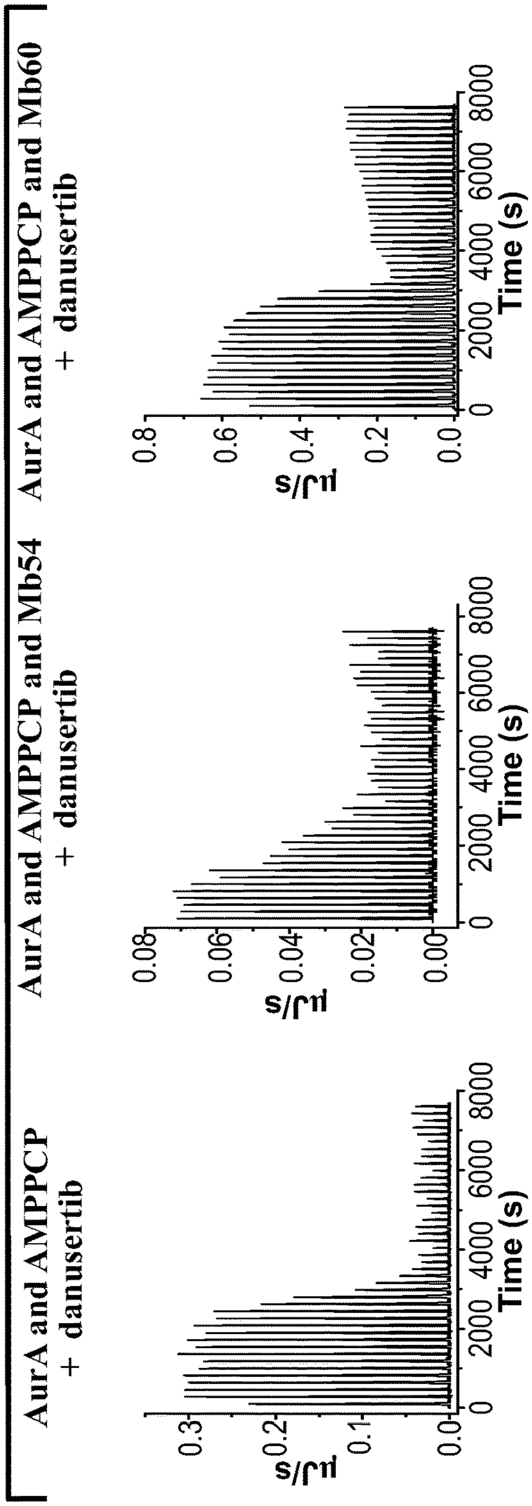
FIGS. 10A-10C.
Figure 10B:
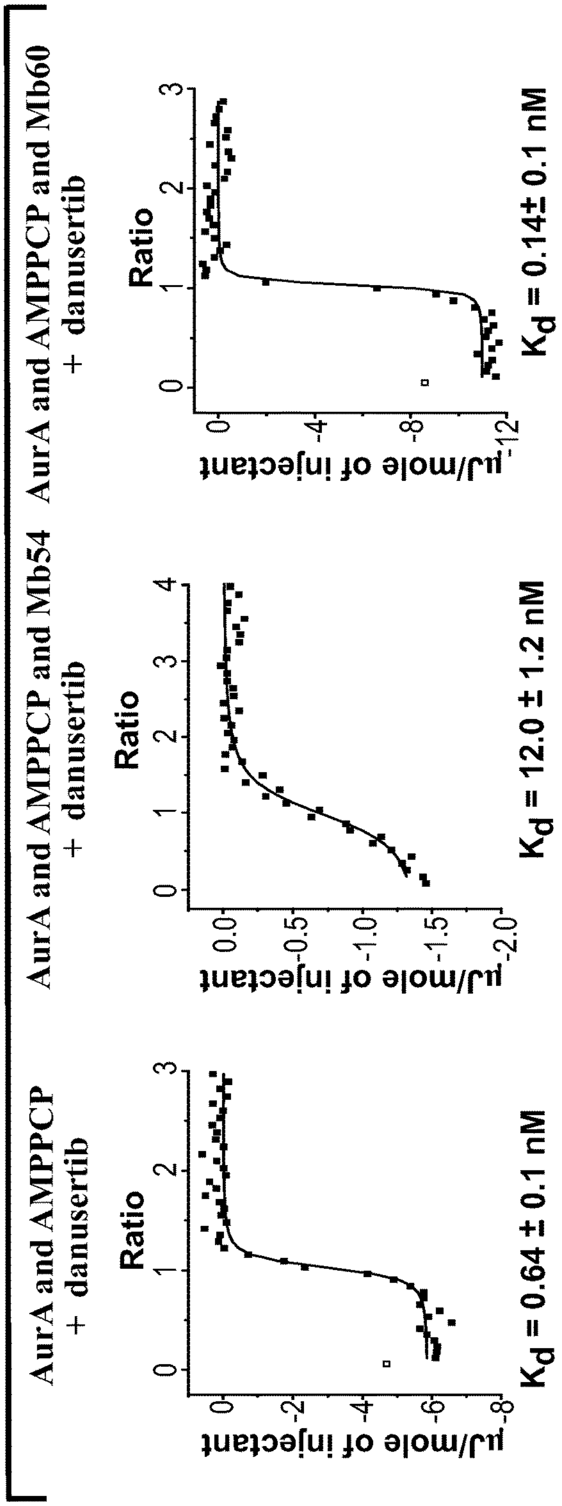
Figure 10C:
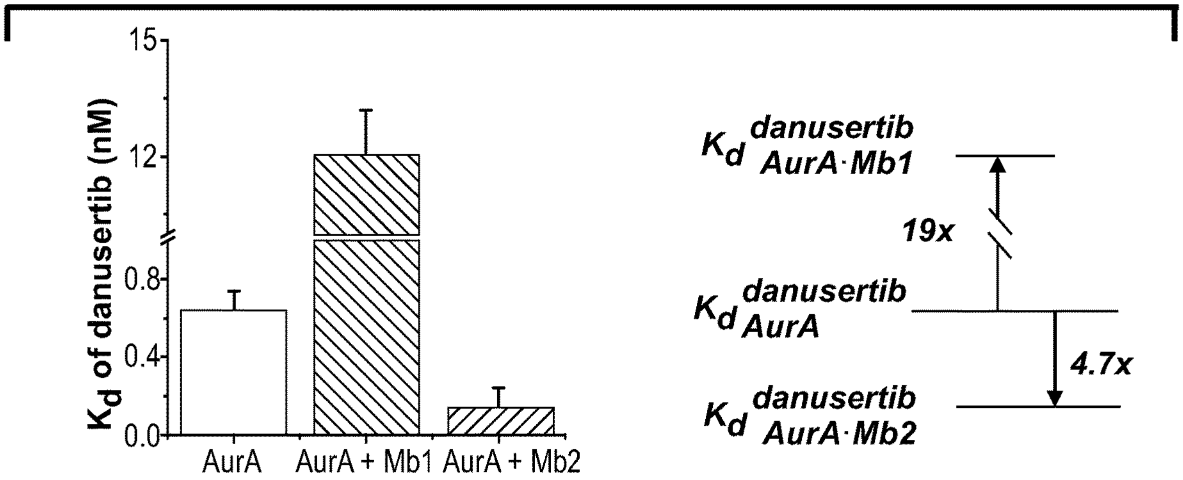

Next, ITC assays to measure binding of danusertib to dephosphorylated Aurora A kinase in the presence of each of the monobodies were performed. FIGS. 10A-10C show that pre-saturating Aurora A kinase with the monobody Mb54 (aka Mb1), an activating monobody, to form a complex between the kinase and the Mb54 monobody, weakened the binding affinity of danusertib by 19-fold (FIG. 10C), while pre-saturating Aurora A kinase with the monobody Mb60 (aka Mb2), an inhibiting monobody, forming a complex between the kinase and the Mb60 monobody, tightened the binding affinity of danusertib by 4.7-fold (FIG. 10C). Binding of Mb60 to the PIF pocket (allosteric site of Aurora A kinase) significantly increased affinity of danusertib to the ATP-binding site. As described elsewhere herein, monobody Mb60 was found to be an inhibitory monobody (i.e., binding of monobody Mb60 to Aurora A kinase alone inhibited Aurora A kinase activity). As described herein, Mb60 inhibited Aurora A kinase activity by shifting equilibrium to an inactive conformation ("DFG out" conformation) and is thus a "$DFG_{out}$" binder of Aurora A kinase. Without being bound by theory, it is believed that monobody Mb60 makes specific "inhibitory contacts" when it binds the PIF pocket, which shifts Aurora A kinase equilibrium to the inactive DFG out conformation. Danusertib binds to the inactive Aurora A kinase conformation, and does not bind to Aurora A kinase in the active "DFG in" conformation. Thus, in the presence of a monobody such as Mb60, a greater population of Aurora A kinase is in the inactive conformation at equilibrium, enabling danusertib to bind more easily to Aurora A kinase. Further, the converse is true. When bound to the inactive conformation, danusertib can stabilize the inactive state of Aurora A kinase, allowing tighter binding of inhibitory monobody to Aurora A kinase that is now primarily sampling the inactive conformation thanks to danusertib (data not shown).

Figure 11A:
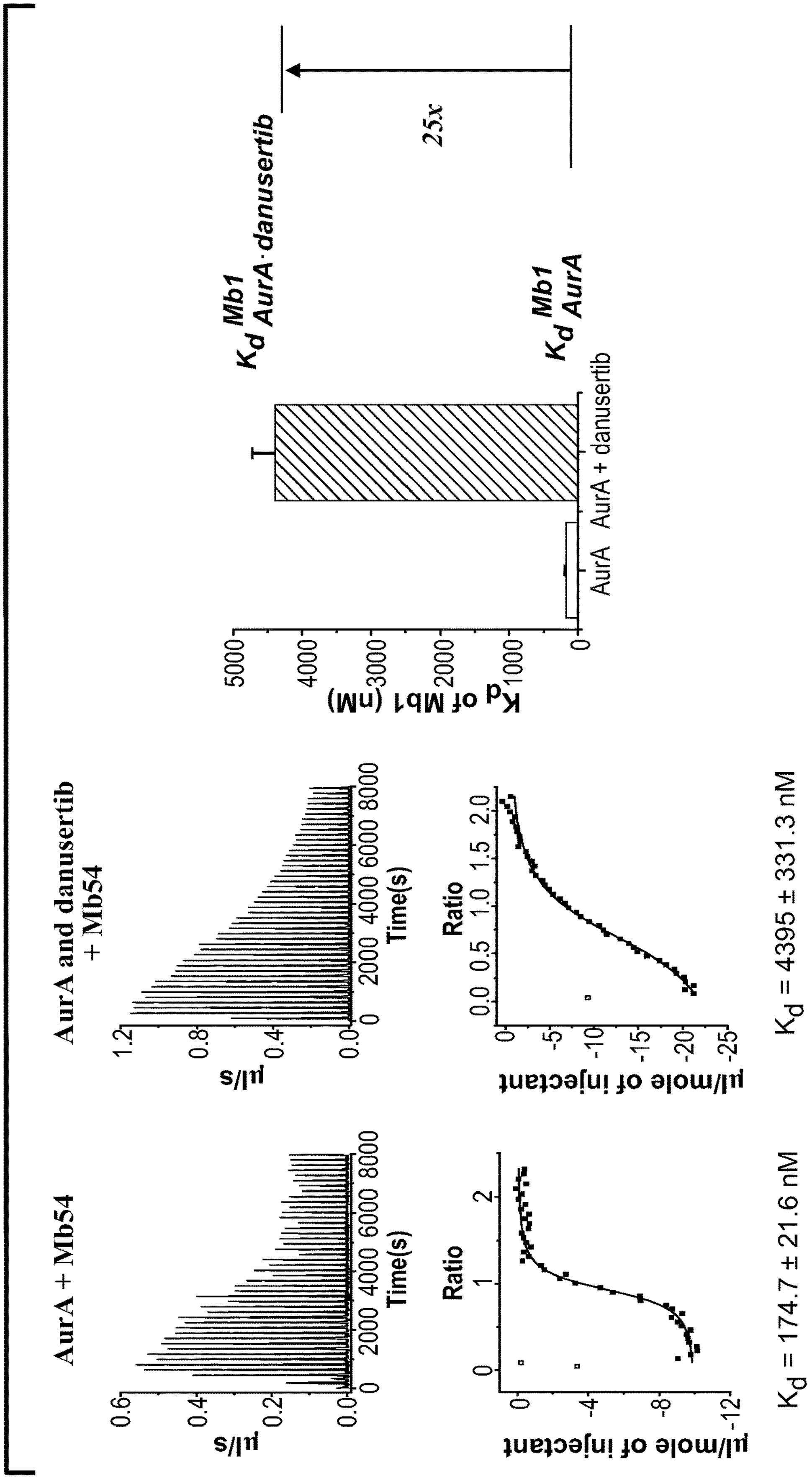
FIGS. 11A and 11B present plots and graphs showing the results of isothermal titration calorimetry assays to characterize the thermodynamics of binding of dephosphorylated Aurora A kinase+monobody Mb54 ("AurA+Mb54," left) and binding of dephosphorylated Aurora A kinase complexed with danusertib+monobody Mb54 ("AurA and danusertib+Mb54," right). The plots on the left side of FIG. 11A show the results of isothermal titration calorimetry assays to characterize the thermodynamics of binding of dephosphorylated Aurora A kinase and monobody Mb54 ("AurA+Mb54"), (left), and the binding of dephosphorylated Aurora A kinase and danusertib complex and monobody Mb54 ("AurA and danusertib+Mb54"), (right), as indicated in the figure. As in FIGS. 10A and 10B, the top plots on the left side of FIG. 11A show the raw data collected (amount of heat released or absorbed during the course of the titration) in an isothermal titration calorimetry assay measuring the thermodynamics of binding as described above, and the bottom plots on the left side of FIG. 11A show the isotherms derived from the results shown in the plots directly above. The bar graph on the right side of FIG. 1A show the dissociation constant (K) of the monobody (in nM) in the binding reactions shown on the left side of FIG. 11A. In the bar graph and results shown on the right side of FIG. 11A, the monobody "Mb54" is called "Mb1." It is to be understood that the monobody designated "Mb1" in FIG. 11A is the same monobody as "Mb54" in this figure. Accordingly, "Mb54" and "Mb1" denote alternative names for the same monobody.
Figure 11B:
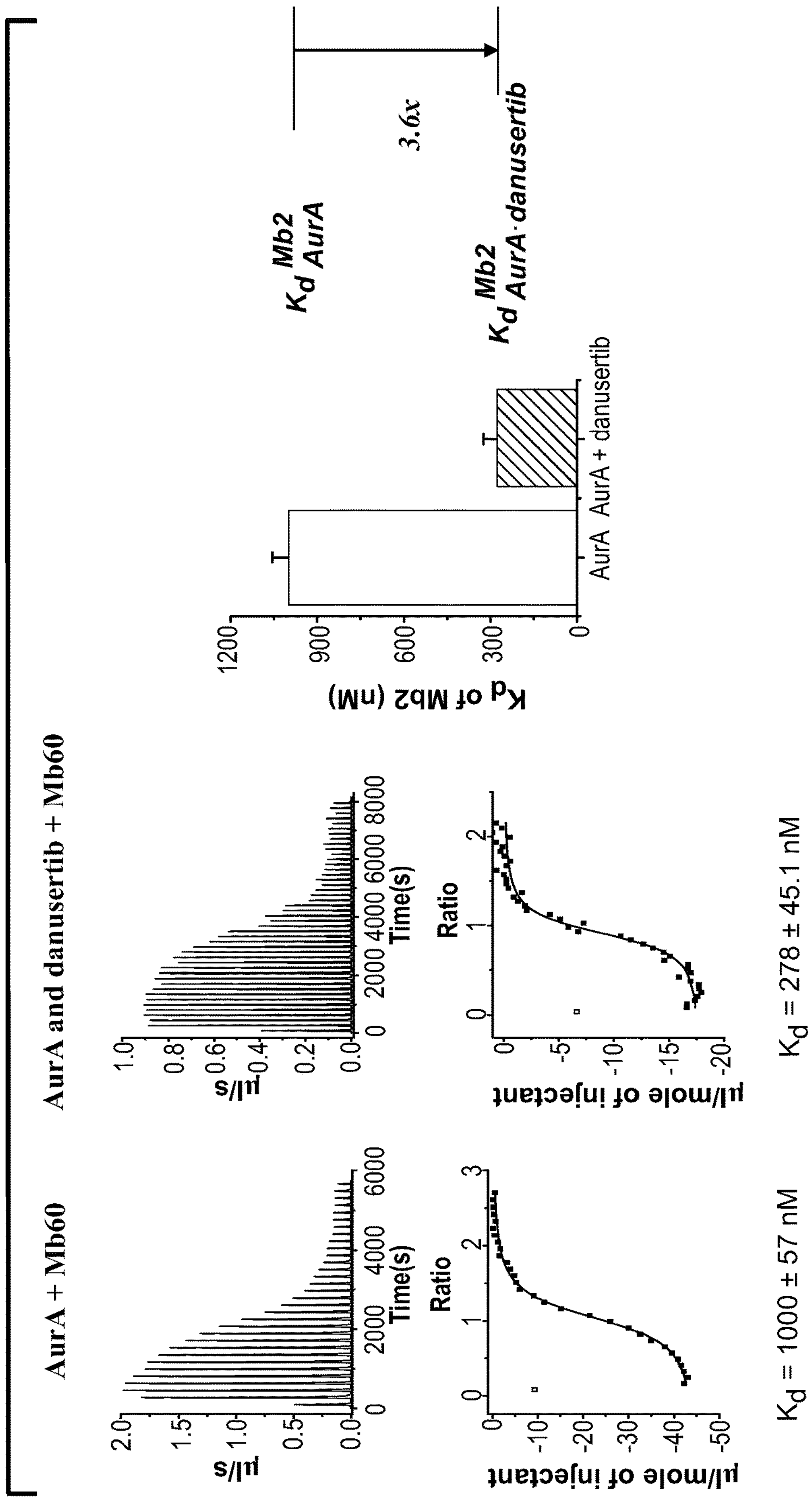
Figure 12A:
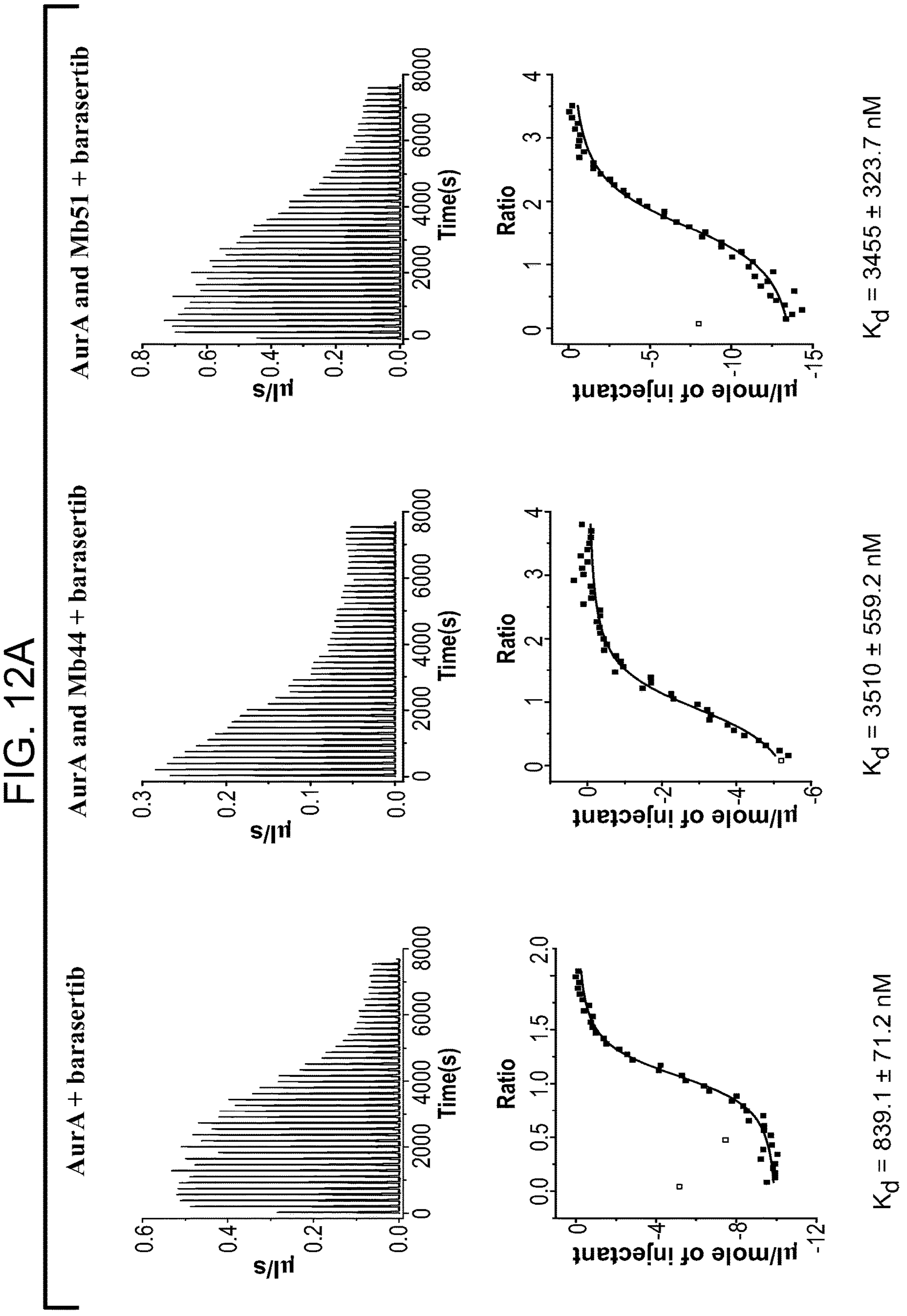
FIGS. 12A and 12B present plots and graphs showing the results of isothermal titration calorimetry assays and binding cooperativity between Aurora A kinase complexed with different monobodies in the presence of the ATP-competitive inhibitor barasertib. The upper portion of FIG. 12A presents plots showing raw data collected (amount of heat released or absorbed during the course of the titration) in an isothermal titration calorimetry assay measuring the thermodynamics of binding of dephosphorylated Aurora A kinase and barasertib ("Aura+barasertib," Left plots), binding of dephosphorylated Aurora A kinase complexed with monobody Mb44 in the presence of barasertib ("AurA and Mb44+barasertib," Middle plots) and binding of dephosphorylated Aurora A kinase complexed with monobody Mb51 in the presence of barasertib ("AurA and Mb51+barasertib," Right plots). The lower portion of FIG. 12A shows graphs depicting the isotherms derived from the results shown in the upper plots of this figure.
Figure 12B:
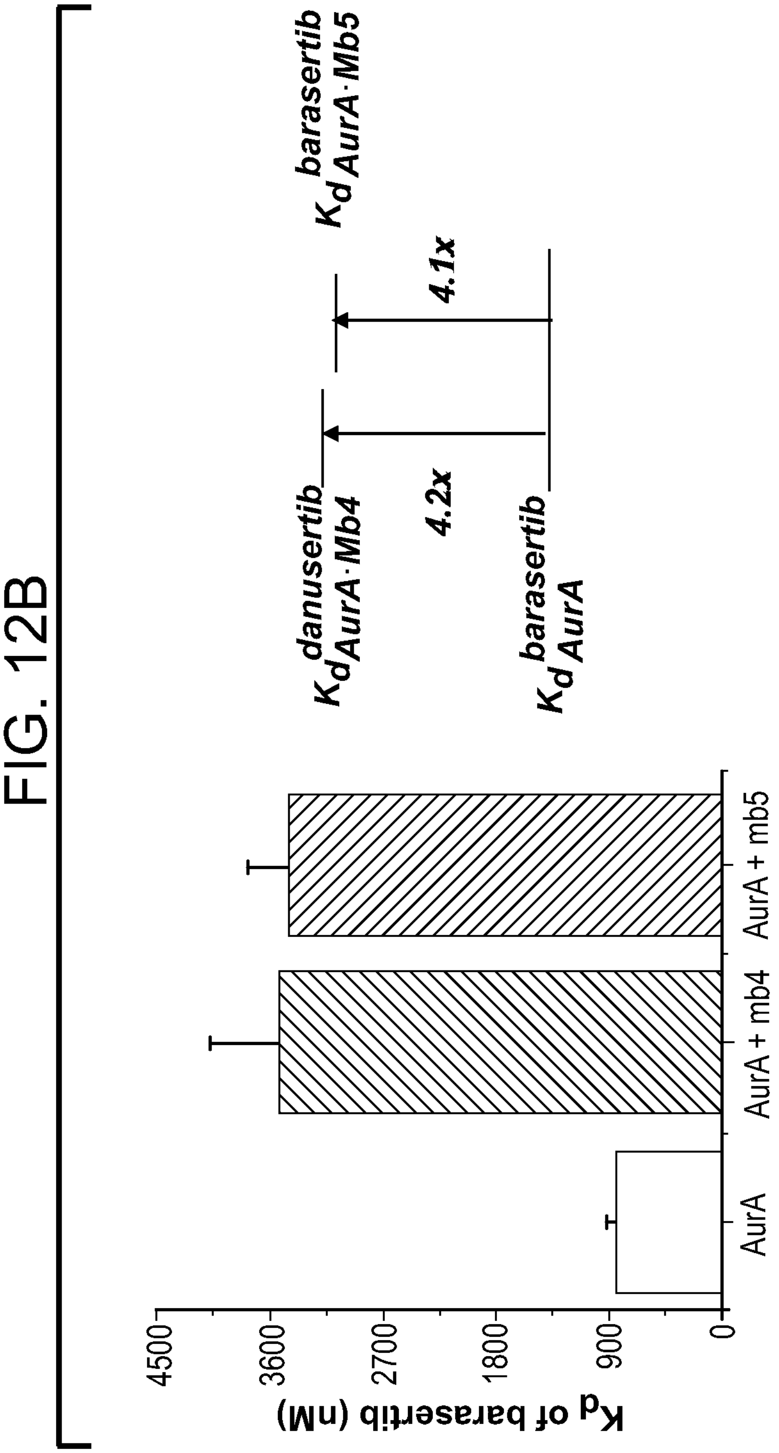
Figure 13A:
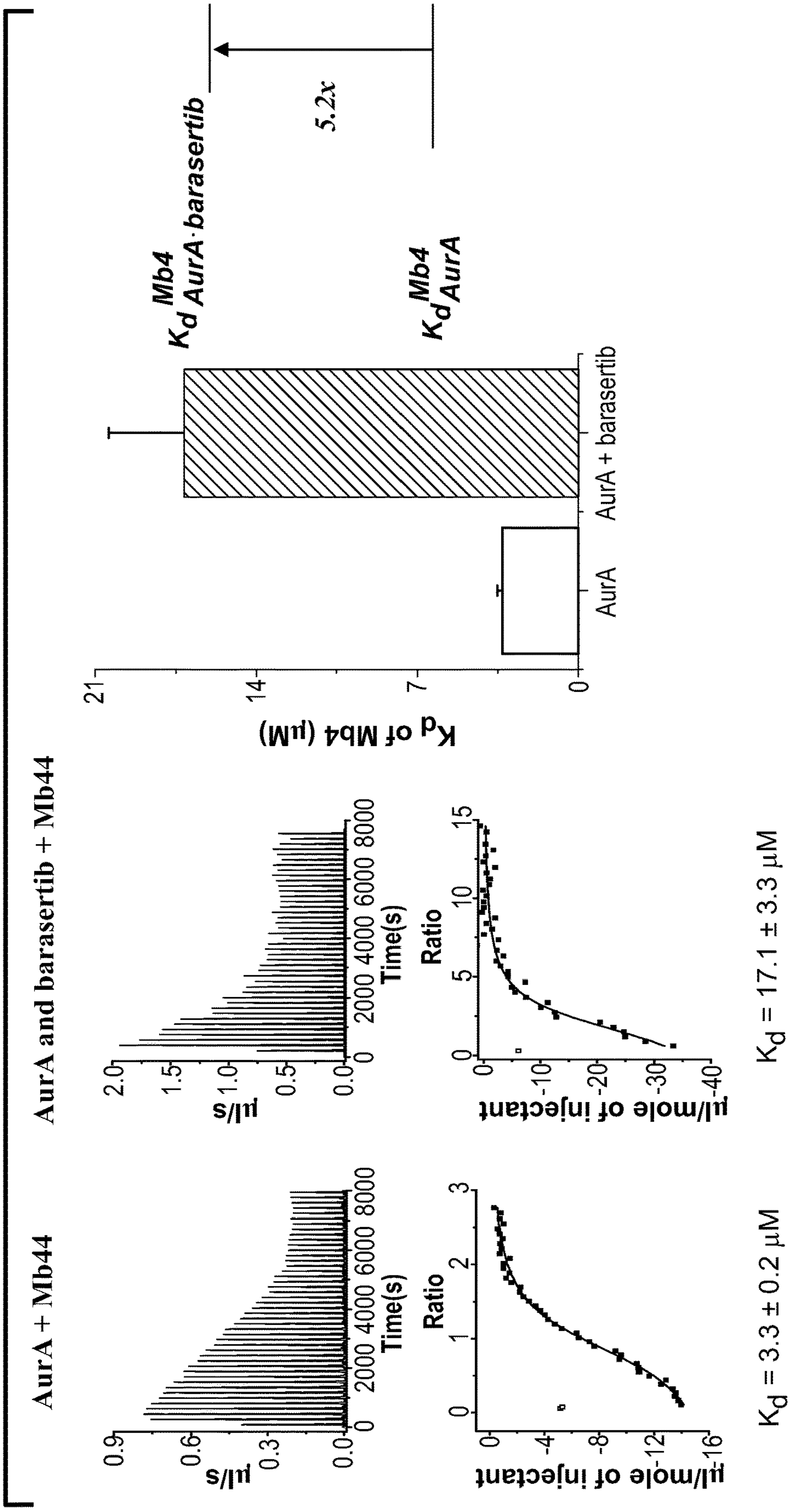
FIGS. 13A and 13B present plots and graphs showing the results of isothermal titration calorimetry assays to characterize the thermodynamics of binding of dephosphorylated Aurora A kinase and monobody M44 ("AurA+Mb44") and Aurora A kinase pre-saturated with the ATP-competitive inhibitor barasertib in the presence of monobody Mb44 ("AurA and barasertib+Mb44"), as indicated on the left side of FIG. 13A. As in FIG. 11A, the top plots on the left side of FIG. 13A show the raw data collected (amount of heat released or absorbed during the course of the titration) in an isothermal titration calorimetry assay measuring the thermodynamics of binding as described above, and the bottom plots on the left side of FIG. 13A show the isotherms derived from the results shown in the plots directly above. The bar graph on the right side of FIG. 13A show the dissociation constant ($K_d$) of the monobody (in nM) in the binding reactions shown on the left side of FIG. 13A. In the bar graphs and results shown on the right side of FIG. 13A, the monobody "Mb44" is called "Mb4." It is to be understood that the monobody designated "Mb4" in FIG. 13A is the same monobody as "Mb44" in this figure. Accordingly, "Mb44" and "Mb4" denote alternative names for the same monobody.
Figure 13B:
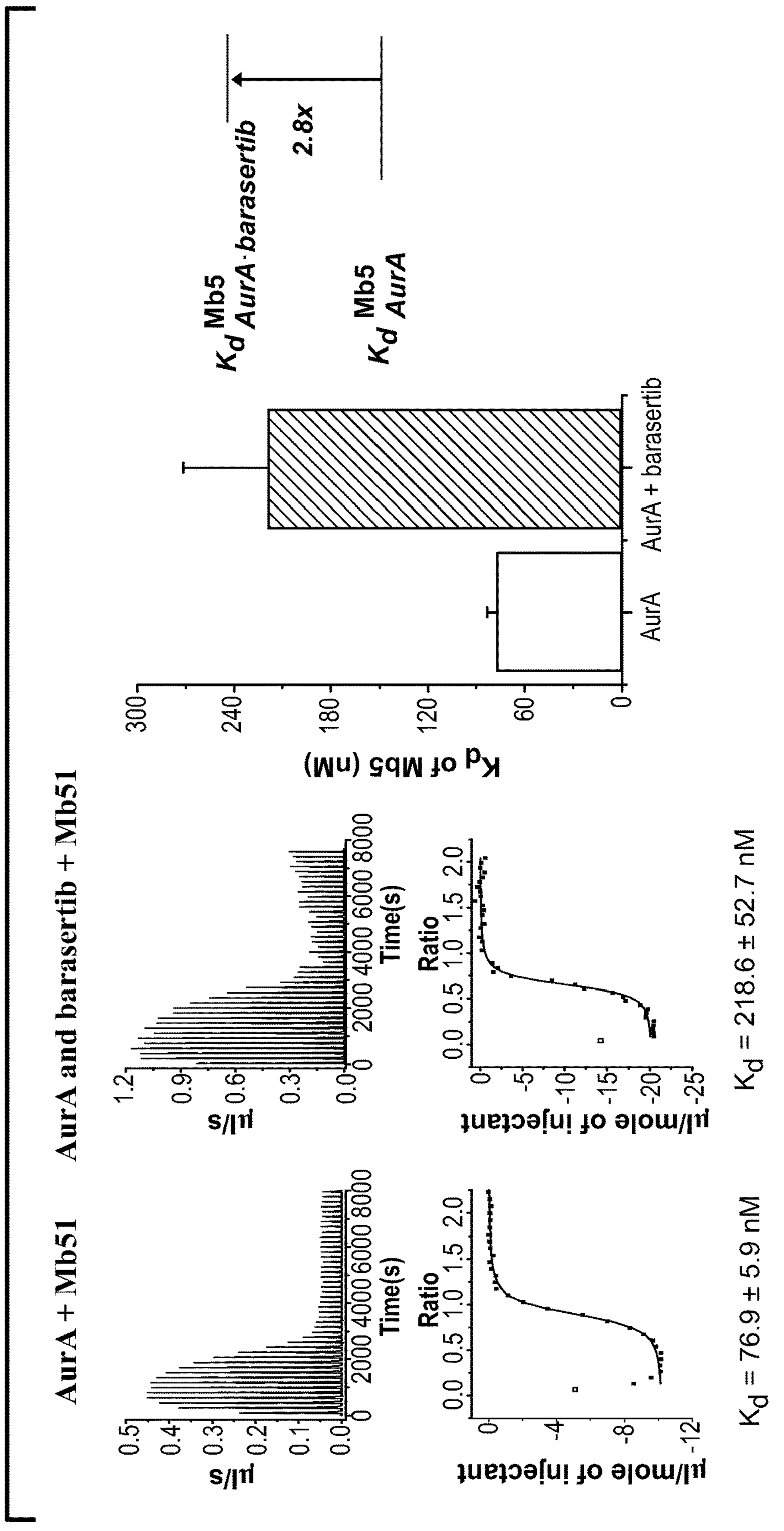

FIGS. 11A and 11B show ITC results of negative cooperativity of the activating Mb54 (aka Mb1) monobody and positive cooperativity of the inhibiting monobody Mb60 (aka Mb2) on Aurora A kinase in complex with danusertib. As shown in FIG. 11A, pre-saturating dephosphorylated Aurora A kinase with danusertib, a $DFG_{out}$ ATP-competitive inhibitor, weakened the binding affinity of the activating monobody Mb54 (aka Mb1), and tightened the binding affinity of the inhibiting monobody Mb60 (aka Mb2) to Aurora A kinase (FIG. 11B). FIGS. 12A and 12B show ITC results measuring binding of the ATP-competitive inhibitor barasertib, a $DFG_{in}$ binder of Aurora A kinase (Left plots), and Aurora A kinase in complex with monobodies. Shown in FIG. 12A are the results of the binding of barasertib to dephosphorylated Aurora A kinase and the negative cooperativity of the barasertib on a complex of Aurora A kinase and monobody Mb44 (aka Mb4), (Middle plots), or a complex of Aurora A kinase and monobody Mb51 (aka Mb5), (Right plots). Pre-saturating Aurora A with the inhibiting monobodies Mb44 and Mb51, which are both $DFG_{out}$ binders of the kinase, weakens the binding affinity of barasertib, which is a $DFG_{in}$ ATP-competitive inhibitor, by 4-fold (FIG. 12B). FIGS. 13A and 13B show ITC results of the negative cooperativity between the inhibiting monobodies Mb44 (aka Mb4) and Mb51 (aka Mb5) on a complex of Aurora A kinase and the ATP-competitive inhibitor barasertib, a $DFG_{in}$ binder of Aurora A kinase. Pre-saturating Aurora A kinase with barasertib weakened the binding affinities of the inhibiting monobodies Mb44 (aka Mb4), (FIG. 13A), and Mb51 (aka Mb5), (FIG. 13B), by 5-fold (FIG. 13A) and 2.8-fold (FIG. 13B), respectively.

Figure 29:
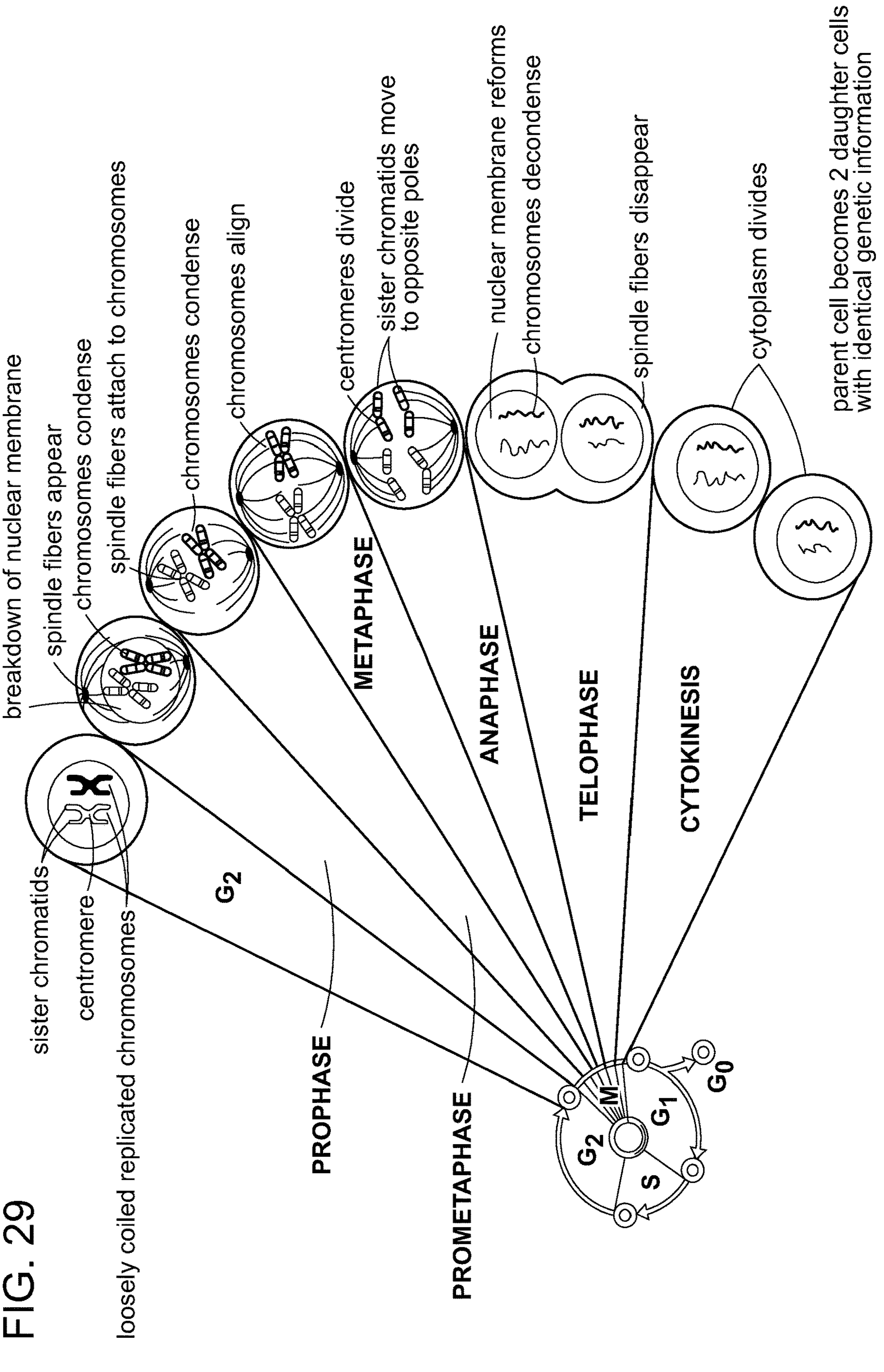
FIG. 29 is a schematic showing a summary of events during different stages of the cell cycle.

Example 3: Small Molecule Compound PS48 Competes with TPX2 for Binding to Allosteric Site and Inhibits Kinase Activity of Aurora A In Vitro The in vivo and in vitro effects of PS48 binding to Aurora A kinase was investigated. Aurora A kinase is implicated in regulation of mitotic progression, particularly spindle assembly and maintenance of the mitotic spindle. During the transition to mitosis, Aurora A kinase is known to localize to the centrosomes and the spindle, with levels and activity of Aurora A kinase peaking during this point. TPX2 activates Aurora A kinase and targets Aurora A kinase to the spindle during mitosis. A summary of the cell cycle is provided in FIG. 29.

Figure 19:
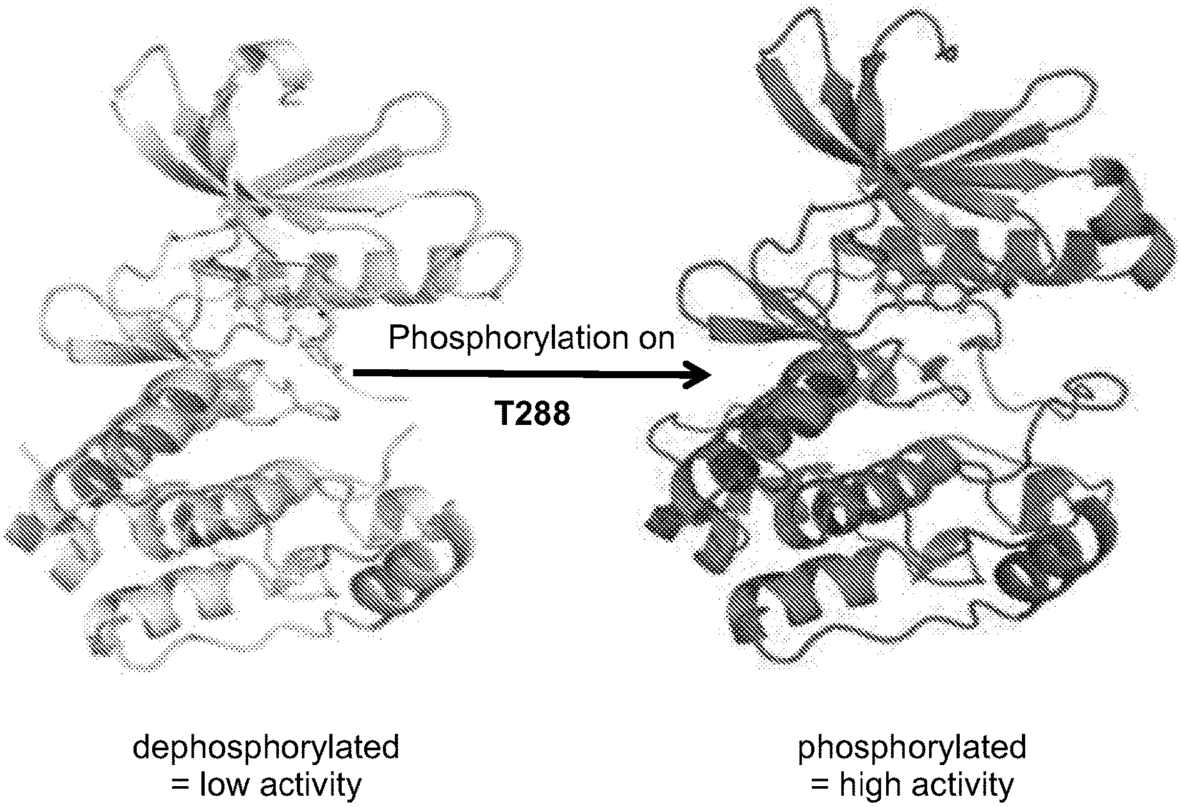
FIG. 19 is a schematic representation showing three-dimensional structure of dephosphorylated Aurora A kinase and phosphorylated Aurora A kinase. Aurora A kinase is phosphorylated on residue T288. Dephosphorylated Aurora A kinase has low kinase activity, and phosphorylated Aurora A kinase has high kinase activity.
Figure 20:
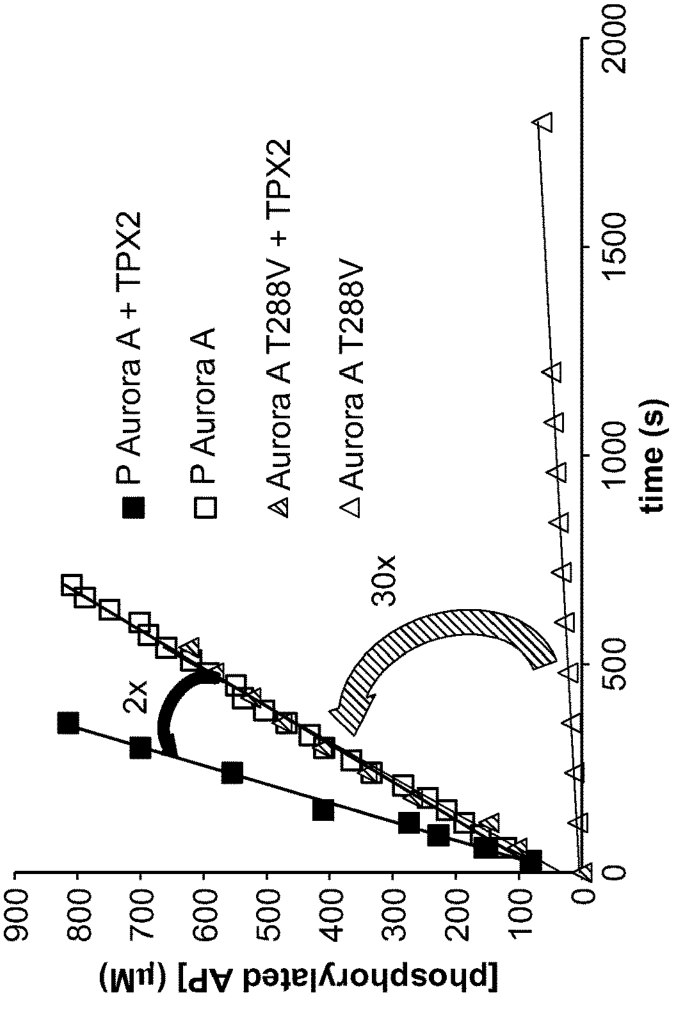
FIG. 20 is a plot showing measurements of phosphorylation of AP (a peptide substrate for Aurora A kinase) when incubated with phosphorylated Aurora A kinase and TPX2, phosphorylated Aurora A kinase only, Aurora A T288V mutant (a dephosphorylated Aurora A kinase) and TPX2, and Aurora A T288V mutant only.

Aurora A kinase is known to be phosphorylated on residue T288 (FIG. 19) and Aurora A kinase can autophosphorylate itself. Phosphorylation of Aurora A increases its kinase activity; dephosphorylated Aurora A kinase has low kinase activity (FIG. 19). An Aurora A kinase T288V mutant is a constitutively dephosphorylated. FIG. 20 shows that binding of TPX2 to dephosphorylated Aurora A (Aurora A T288V mutant) greatly increased its kinase activity, whereas binding of TPX2 to phosphorylated Aurora A (which already has high kinase activity) only slightly increased kinase activity.

Figure 21:
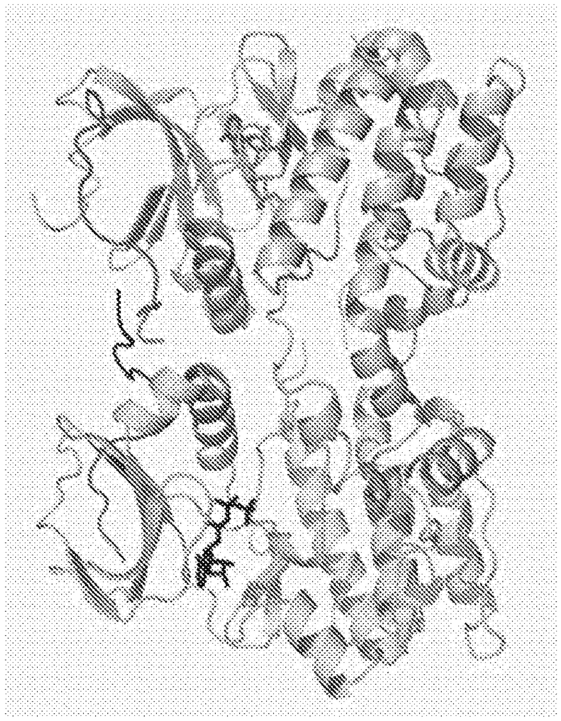
FIG. 21 is a schematic representation of a three-dimensional structure of dephosphorylated Aurora A kinase in the presence of TPX2. Dephosphorylated Aurora A adopts an active conformation in the presence of TPX2 (also shown in FIG. 15 (top)).
Figure 22:
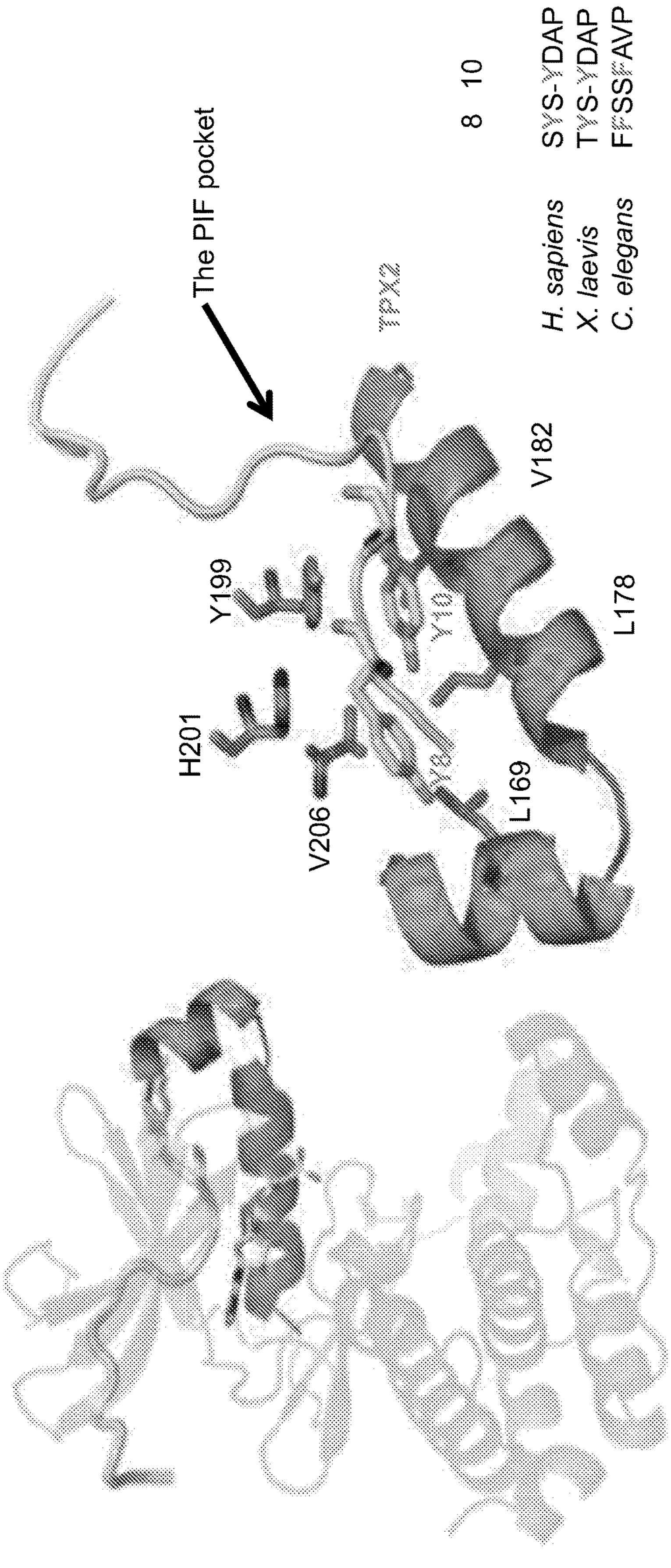
FIG. 22 is a schematic representation a three-dimensional structure of the PIF pocket of Aurora A kinase bound to TPX2.
Figure 23:
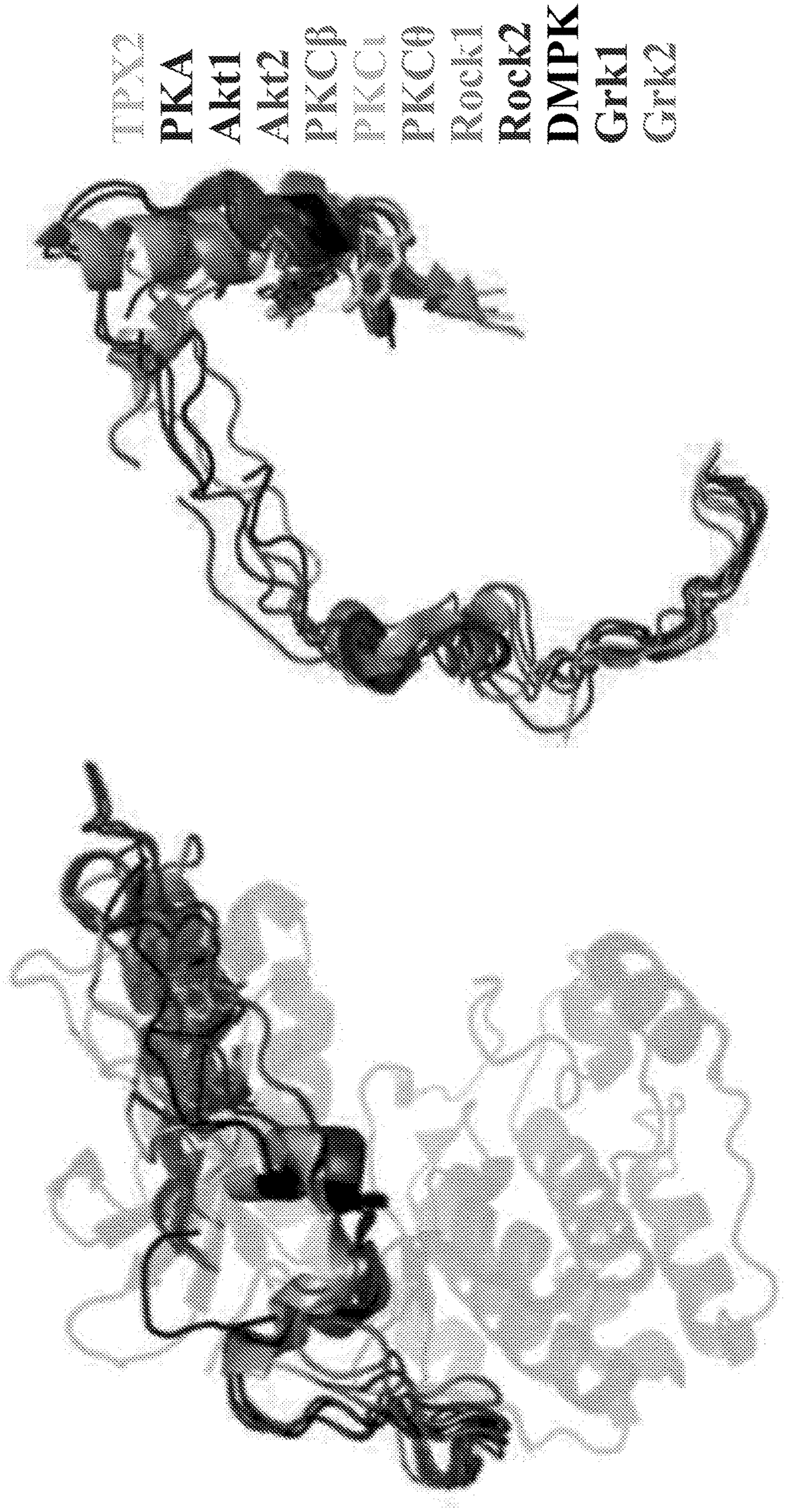
FIG. 23 is a schematic representation showing superposition of three-dimensional structures of exemplary AGC-like proteins.
Figure 24A:
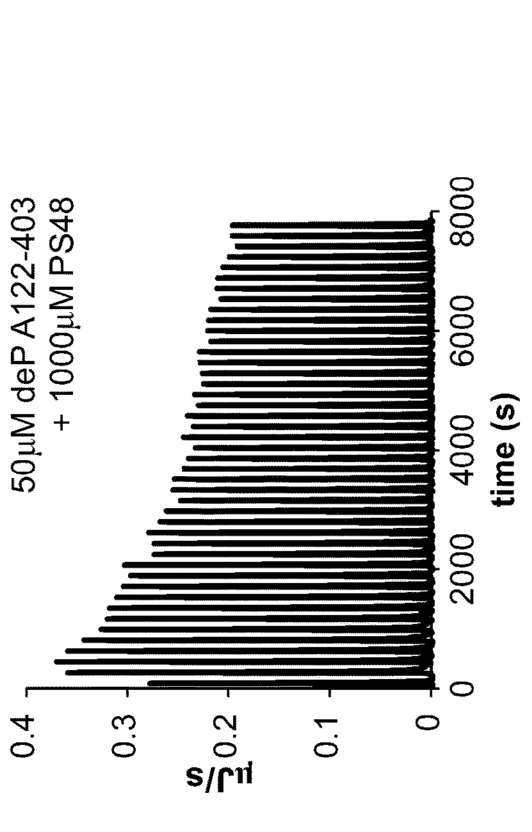
FIGS. 24A-24D are plots showing results of isothermal titration calorimetry assays to characterize the thermodynamics of binding of dephosphorylated Aurora A kinase and PS48.
Figure 24B:
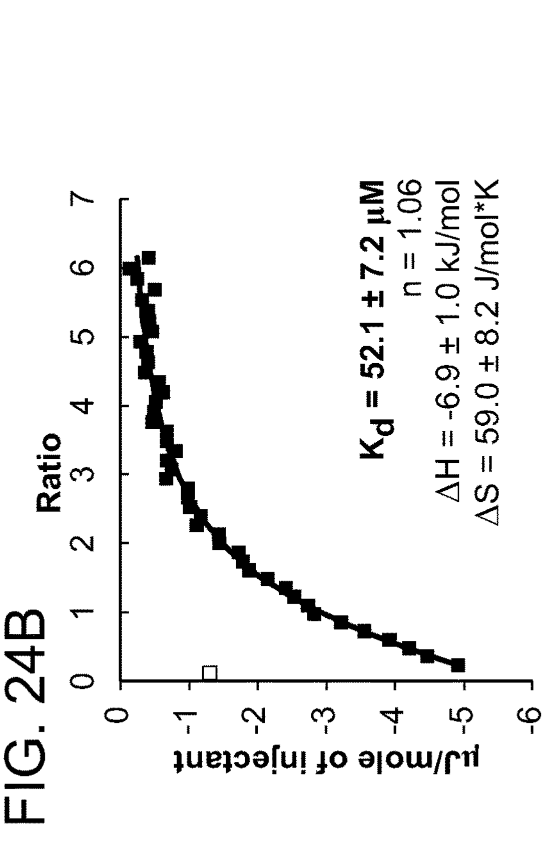
Figure 24C:
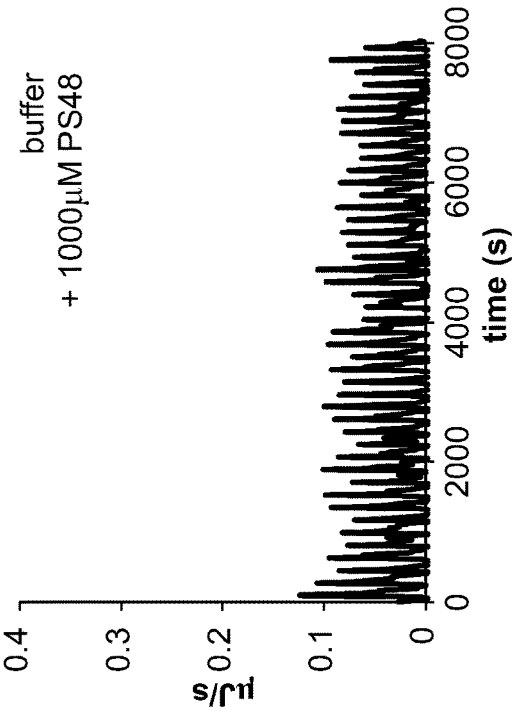
Figure 24D:
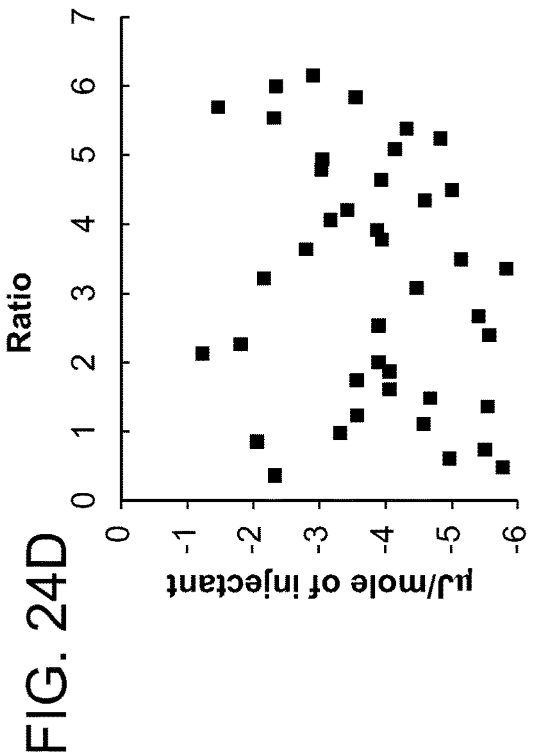
Figure 25A:
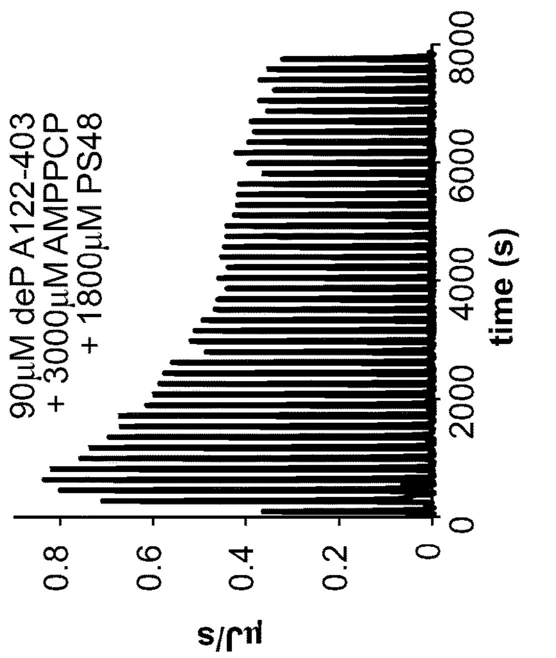
FIGS. 25A-25D are plots showing results of isothermal titration calorimetry assays to characterize the thermodynamics of binding of dephosphorylated Aurora A kinase and PS48 in the presence of an AMPPCP (an ATP mimic that, at the concentrations used for the experiment, it would have fully occupied that ATP binding site of Aurora A kinase).
Figure 25B:
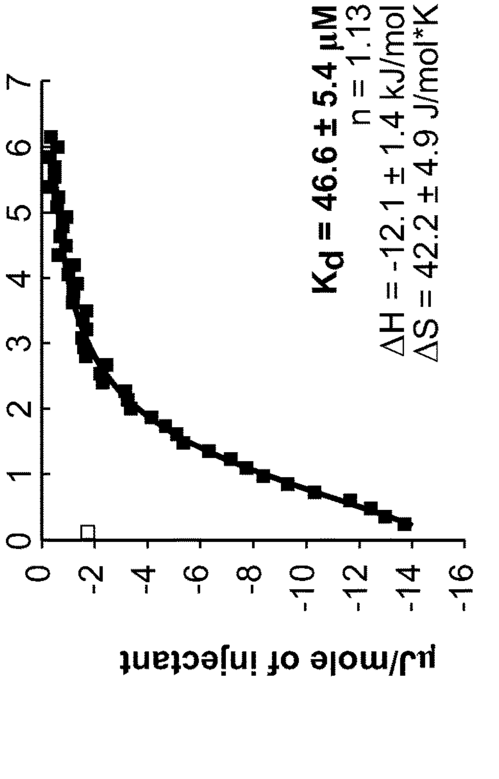
Figure 25C:
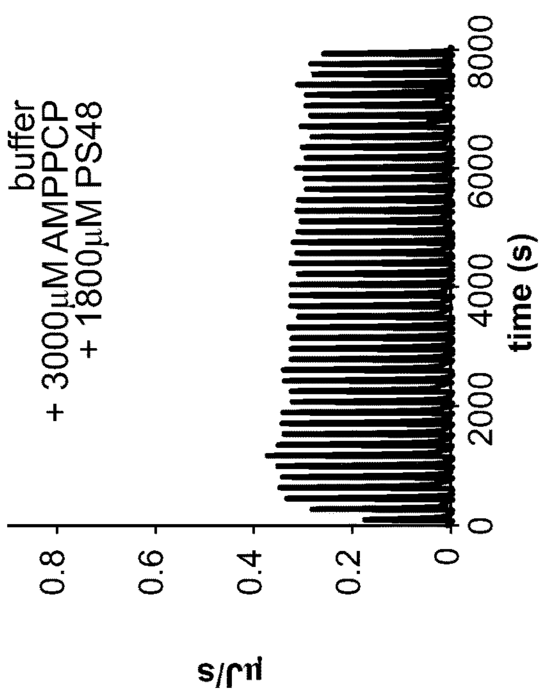
Figure 25D:
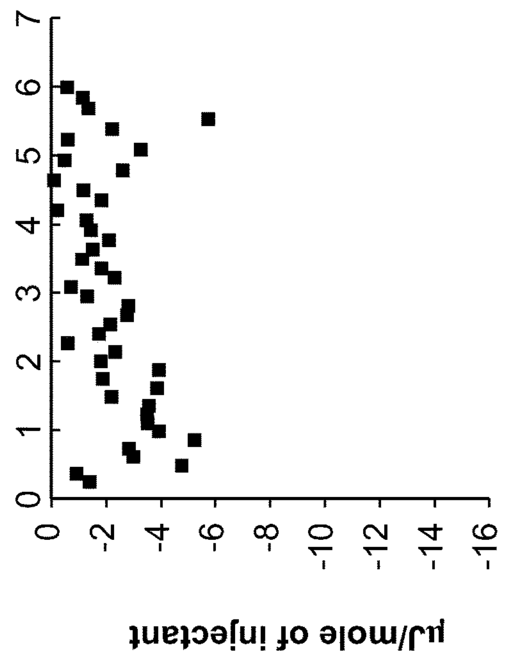
Figure 26A:
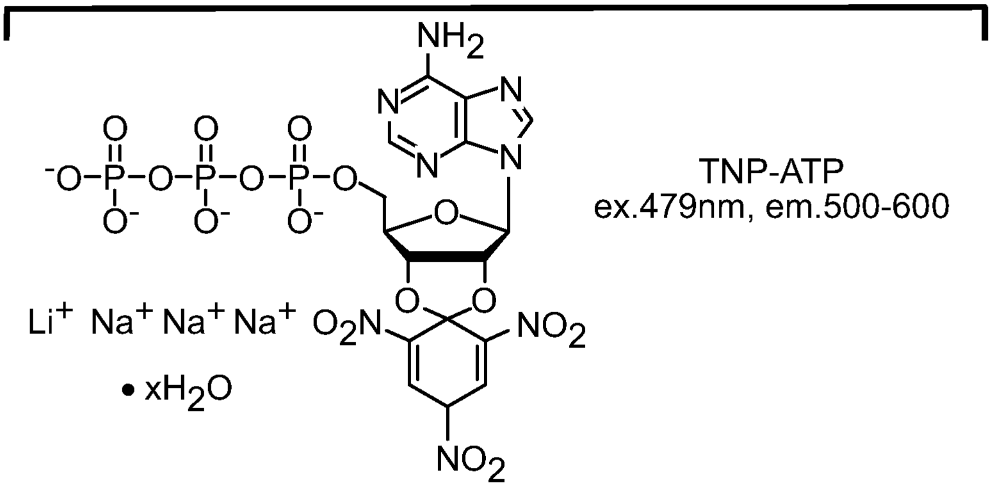
FIGS. 26A-26E are a set of plots and schematics showing the PS48 does not bind to the ATP binding site of Aurora A kinase.
Figure 26B:
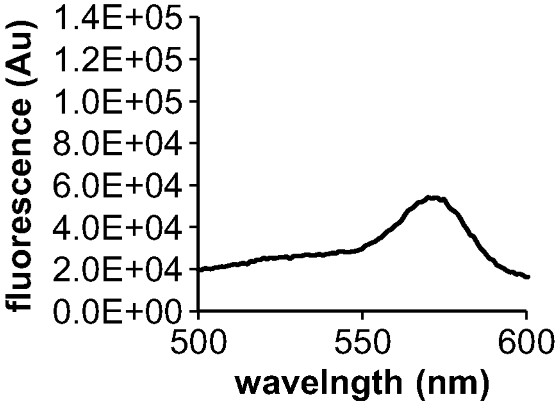
Figure 26C:
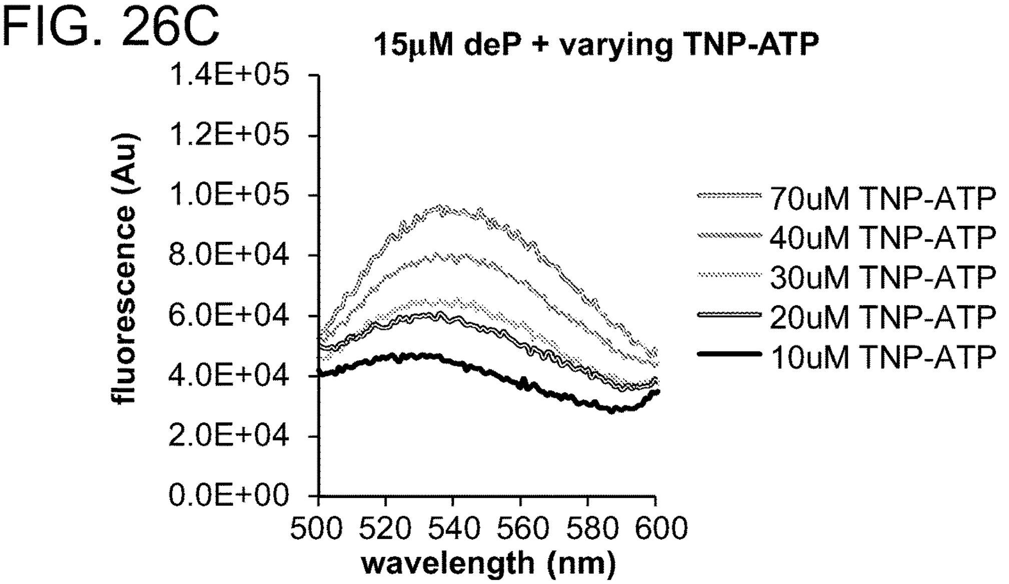
Figure 26D:
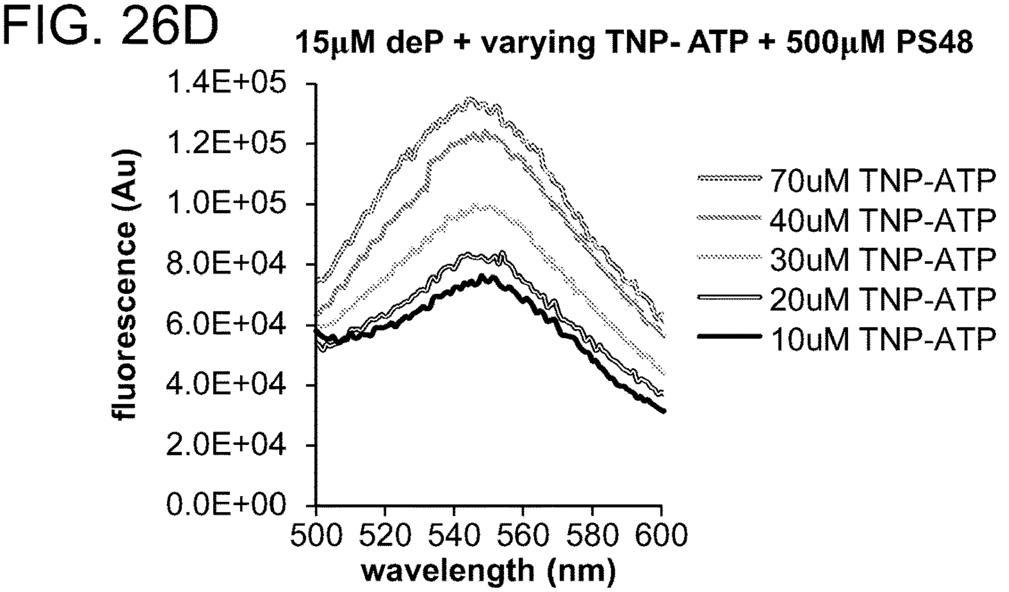
Figure 26E:
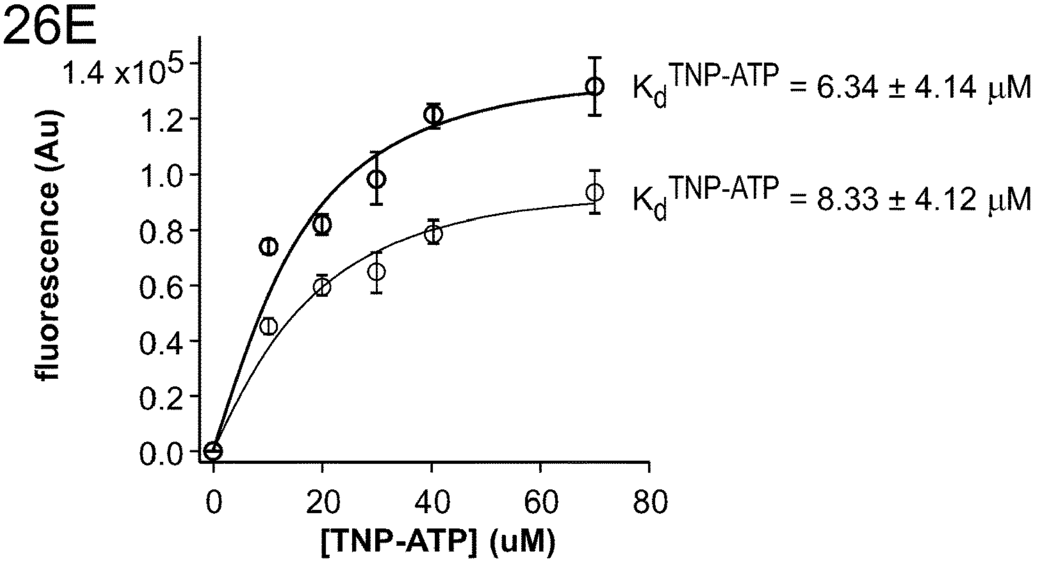

X-ray crystallography experiments showed that binding of TPX2 activates Aurora A kinase allosterically (FIG. 21). TPX2 binds to the PIF pocket of Aurora A. FIG. 22 shows residue contacts made when TPX2 is bound to the PIF pocket. FIG. 23 shows a superposition of the PIF pocket of various AGC-like proteins. The AGC kinases are a family of more than 60 human kinases, which are known to have a PIF pocket as a regulatory site. Without intending to be bound by theory, it is believed allosteric regulation of kinase activity by binding of TPX2 or another molecule making particular contacts at the PIF pocket that shift kinase equilibrium to an inactive or active conformation can be a general mechanism of regulation of AGC kinases.

Figure 27A:
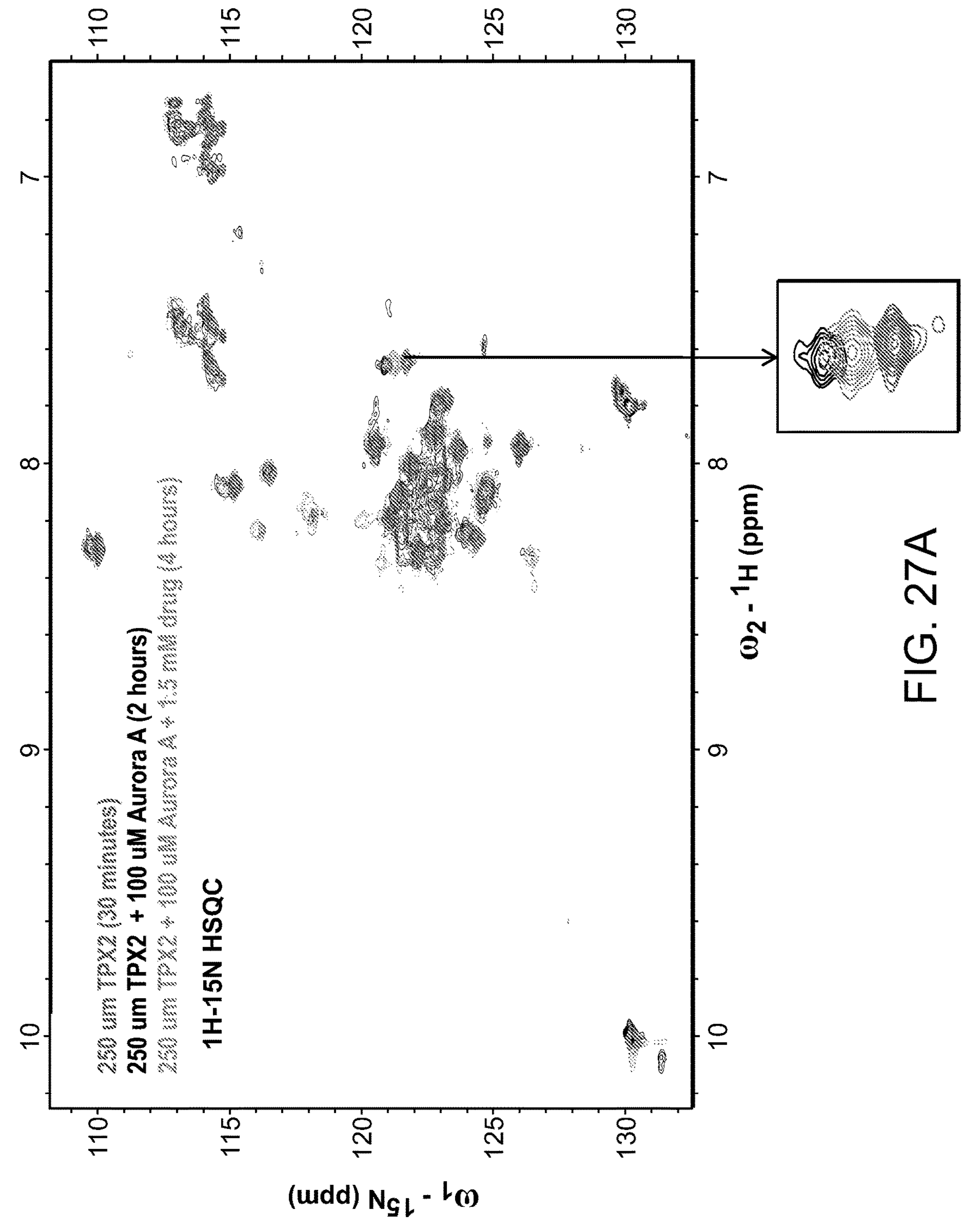
FIGS. 27A-27C is a set of plots showing results of NMR titration showing that PS48 binds to the TPX2 binding site of Aurora A kinase.
Figure 27B:
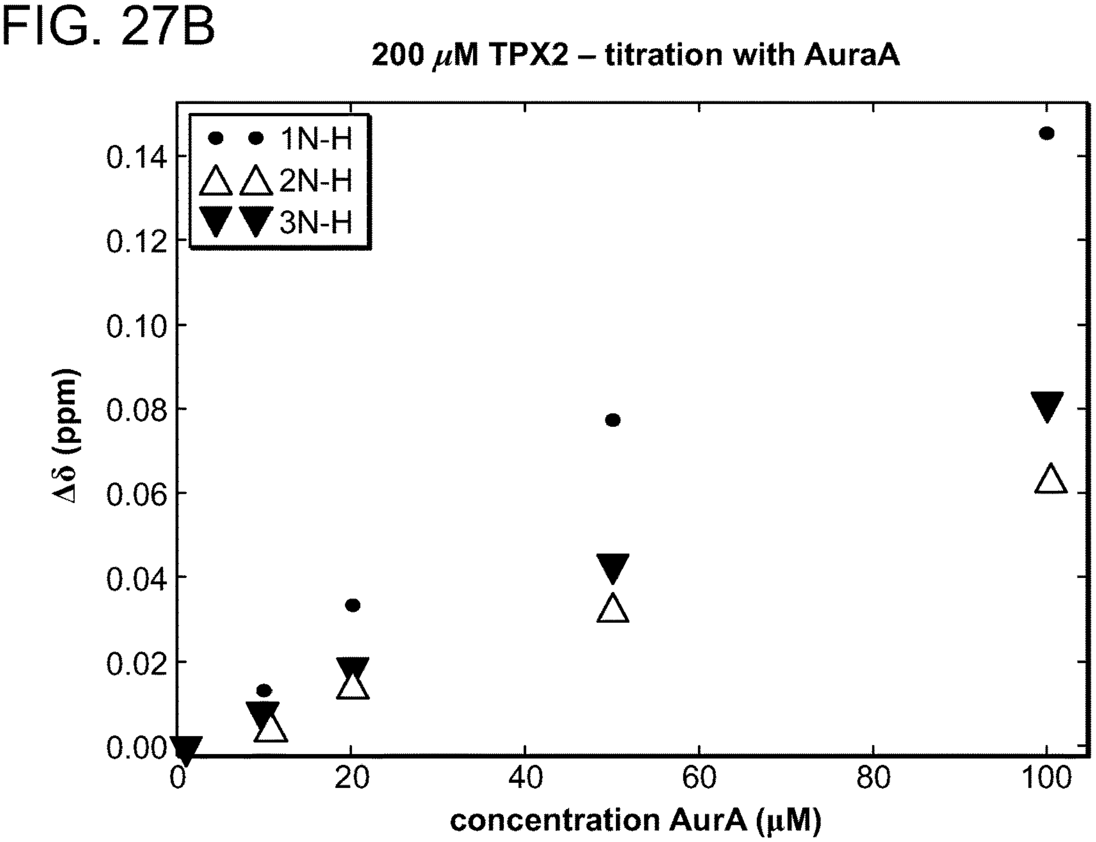
Figure 27C:
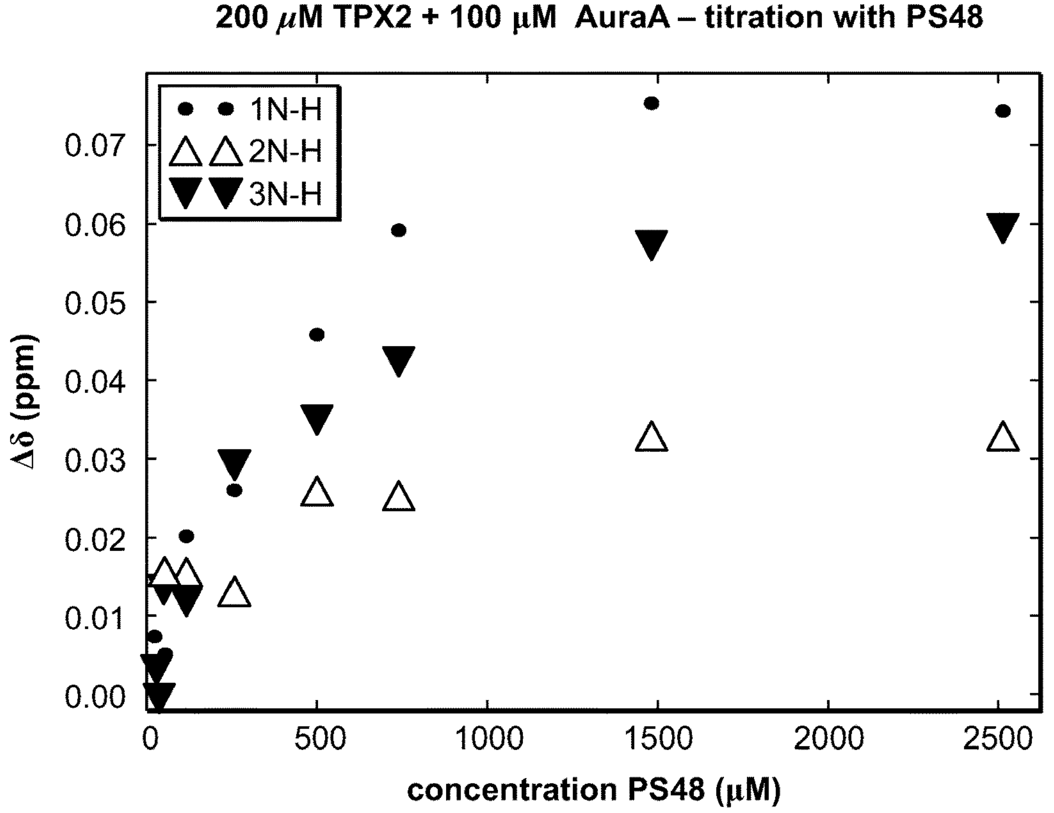
Figures 28A, 28B:
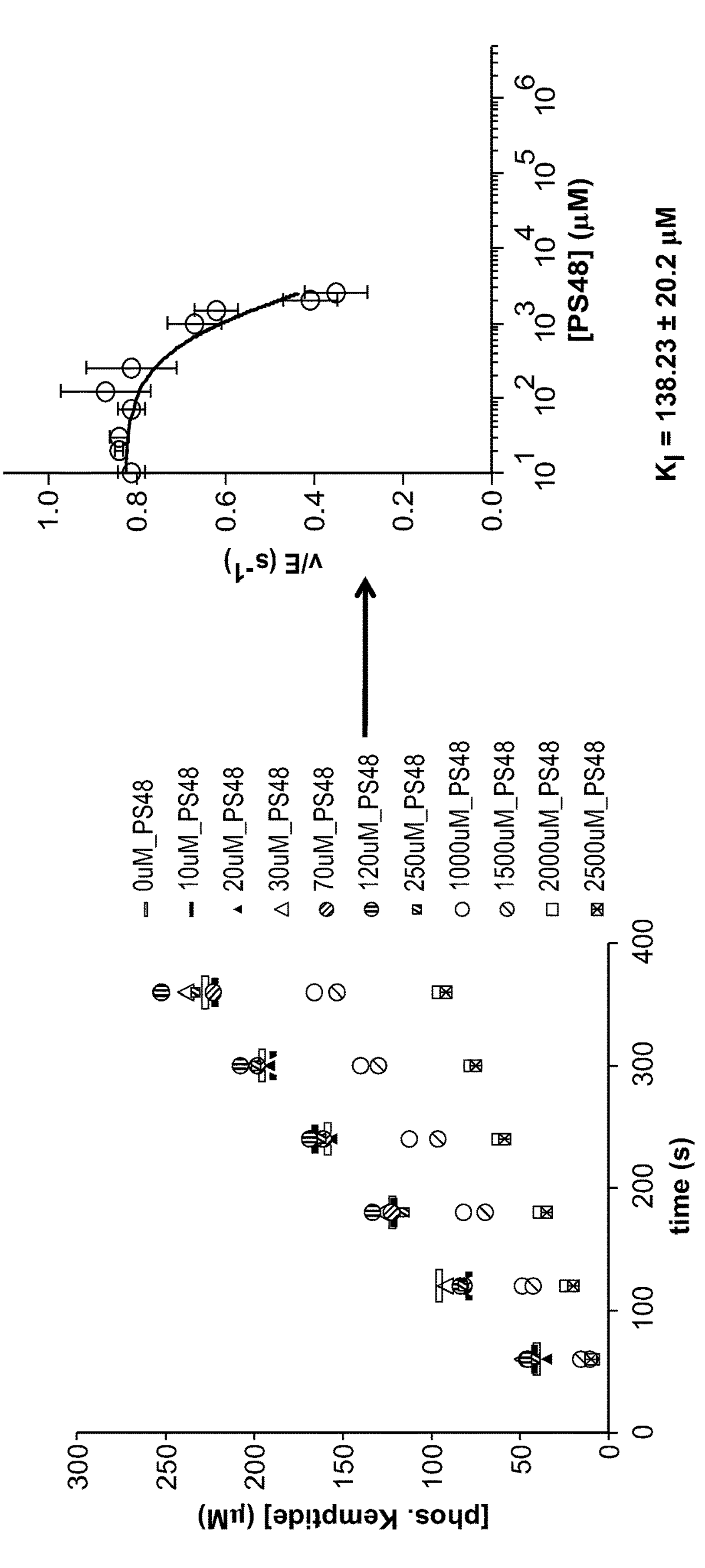
FIGS. 28A-28B is a set of plots showing PS48 binds to the TPX2 binding site of Aurora A kinase and PS48 competes with TPX2 for binding to Aurora A kinase in vitro.

Next, whether the interaction of TPX2 with the PIF pocket of Aurora A kinase can be disrupted by the small molecule PS48 was investigated. As shown in FIGS. 24A-24D, FIGS. 25A-25D, and FIGS. 26A-26E, PS48 does not bind to the ATP binding site of Aurora A kinase. NMR titration experiments showed PS48 bound to the TPX2 binding site of Aurora A kinase (FIGS. 27A-27C). Measurements of kinase activity of Aurora A incubated with TPX2 and varying amounts of PS48 showed PS48 competed for binding to the same site of Aurora A kinase, thus disrupting binding of TPX2 to Aurora A kinase (FIGS. 28A and 28B).

Figure 30:
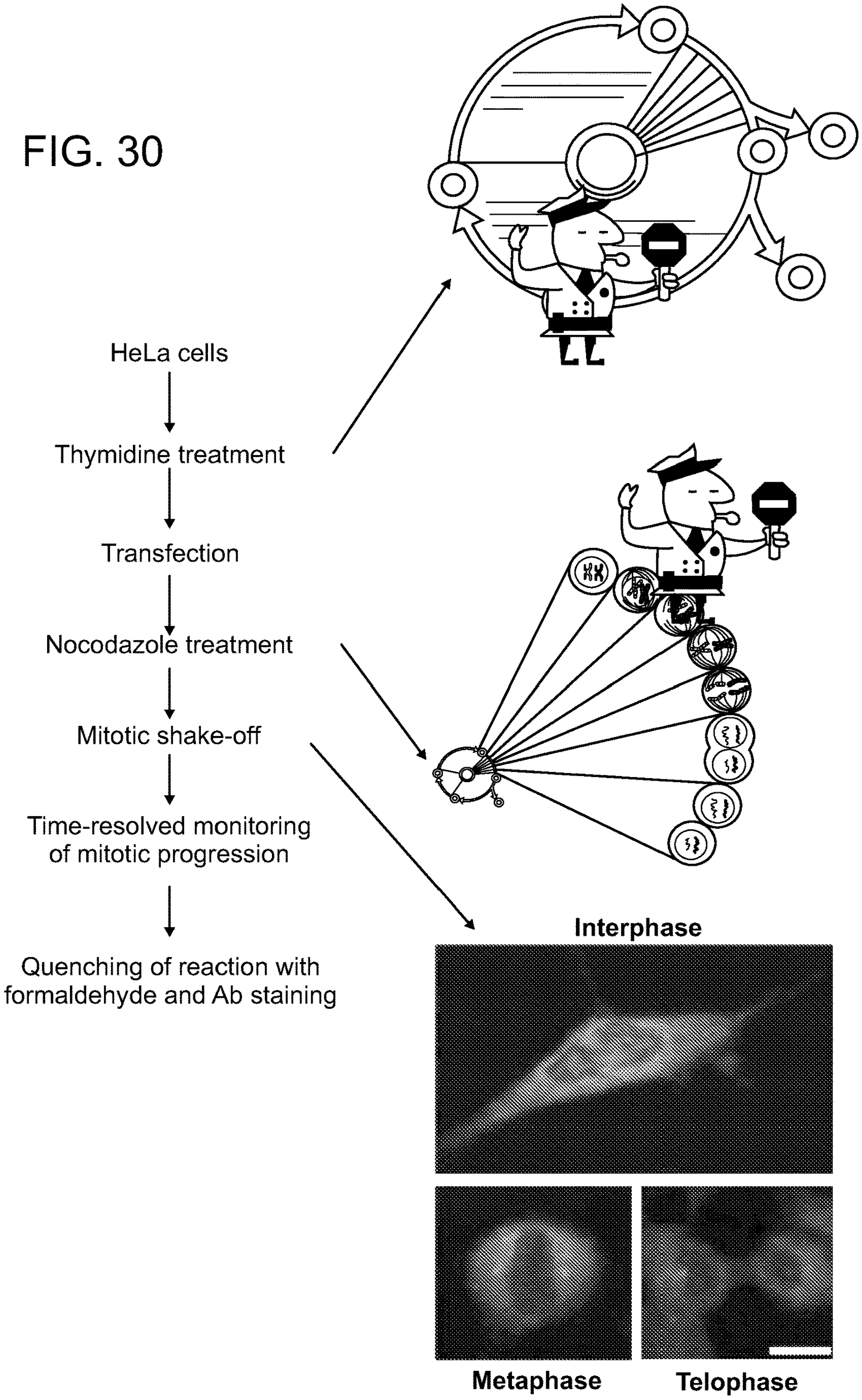
FIG. 30 is a schematic showing a summary of a protocol used for cell synchronization experiments described herein to visualize effects of PS48 on TPX2 and Aurora A interaction in vivo.
Figure 33:
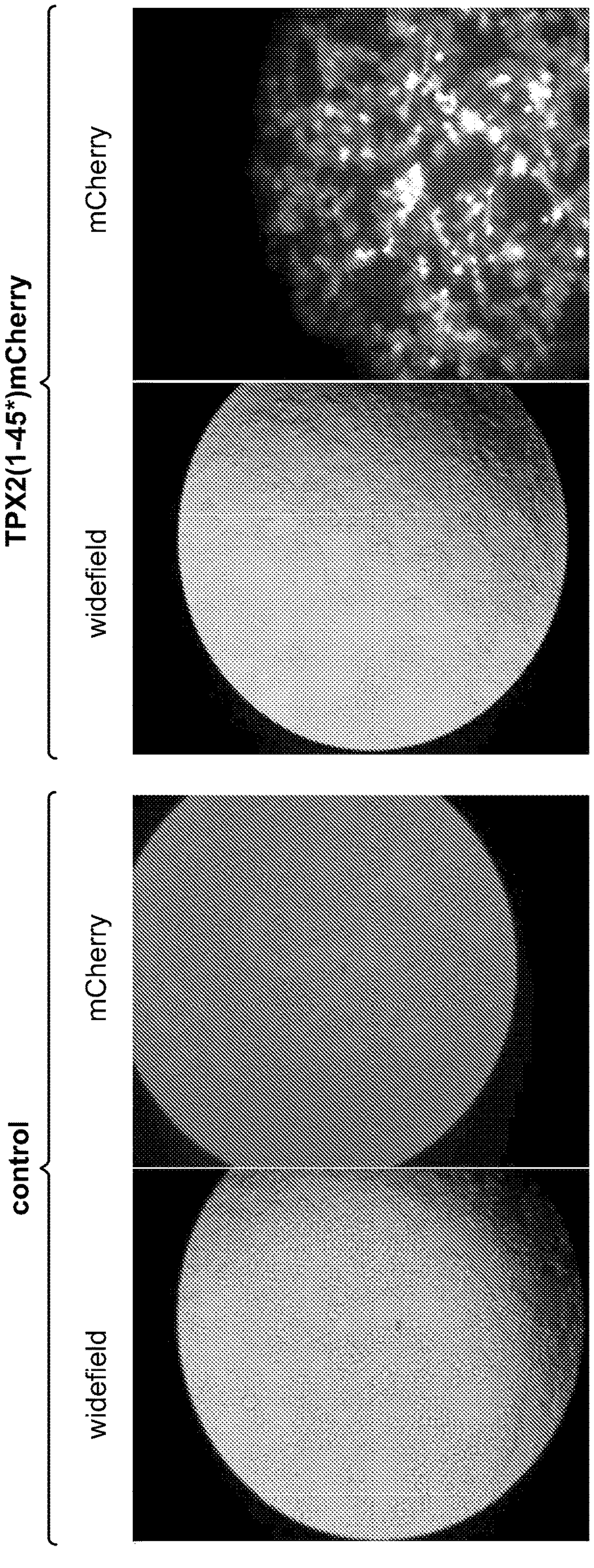
FIG. 33 is a set of micrographs showing HEK293 cells transfected with TPX2(1-45*)-mCherry. The transfection efficiency observed indicates the cell imaging experiments described herein (which were performed in HeLa cells) can also be performed in HEK293 cells.
Figure 34:
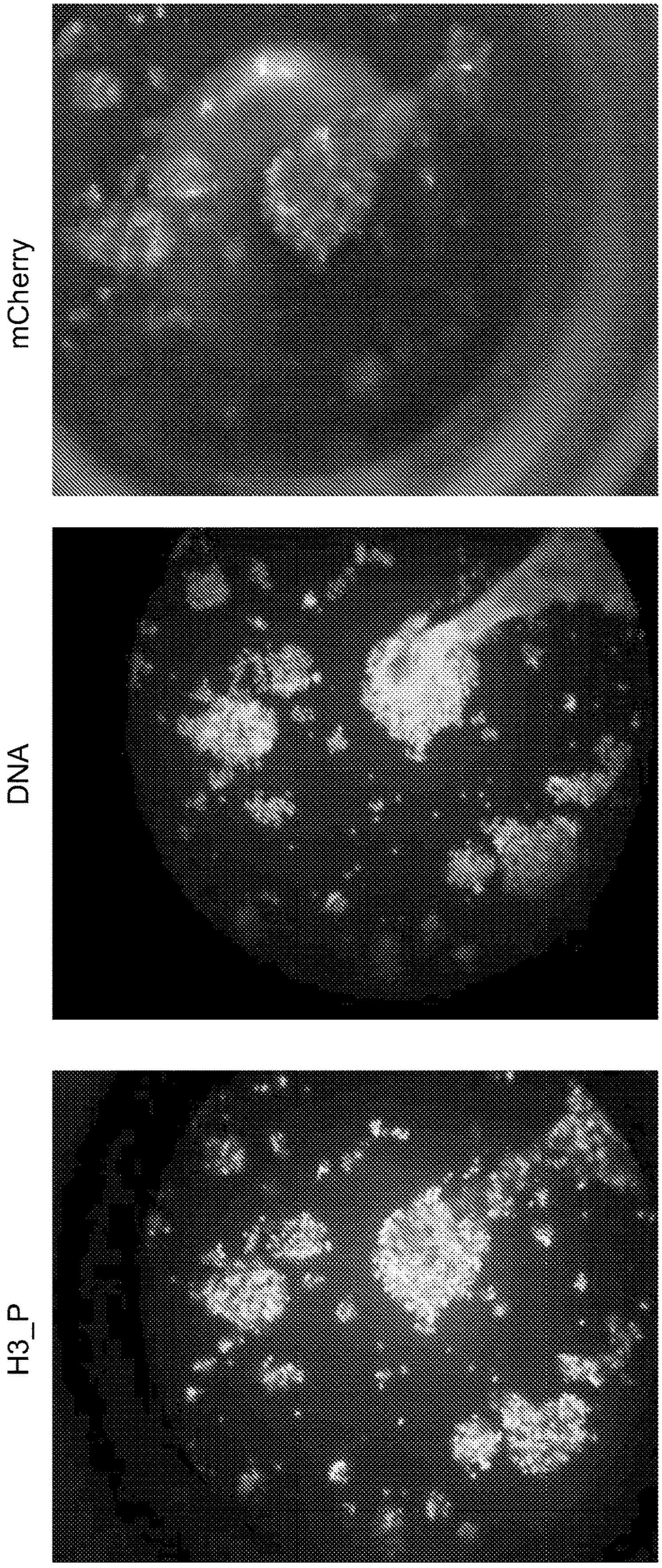
FIG. 34 is a set of micrographs showing staining of H3_P (phosphorylated histone H3) and DNA in control HEK293 cells at 0 hr after nocodazole release.
Figure 35:
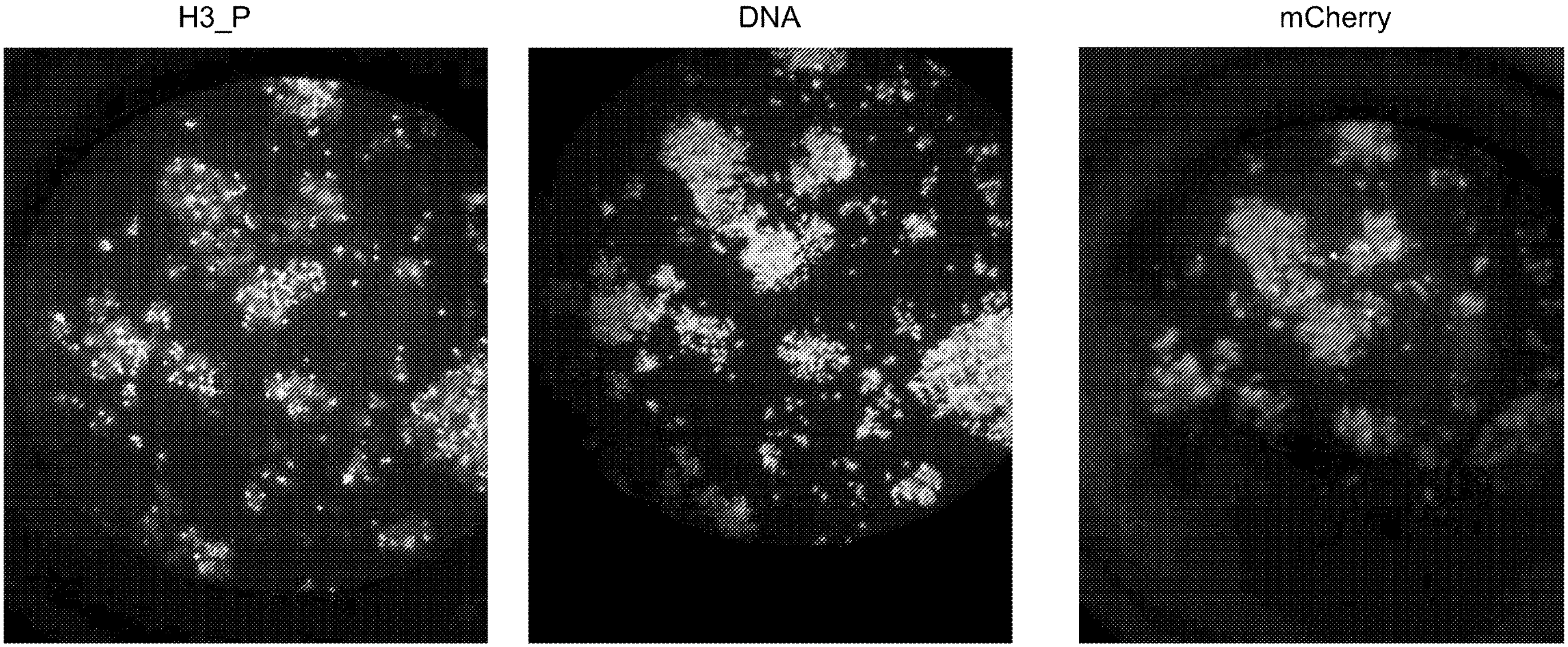
FIG. 35 is a set of micrographs showing staining of H3_P (phosphorylated histone H3) and DNA HEK293 cells transfected with TPX2(1-45*)-mCherry at 0 hr after nocodazole release.

Example 4: Small Molecule Compound PS48 Competes with TPX2 for Binding to Allosteric Site and Inhibits Activities of Aurora A Kinase In Vivo The physiological importance of the Aurora A-TPX2 interaction was then investigated through experiments using PS48 to disrupt the Aurora A-TPX2 interaction in vivo. As described herein, during the transition to mitosis, Aurora A kinase is known to localize to the centrosomes and the spindle, with levels and activity of Aurora A kinase peaking during this point. TPX2 activates Aurora A kinase and targets Aurora A kinase to the spindle during mitosis. Thus, to observe effects of disruption of the Aurora A-TPX2 interaction on the biological in vivo activities of Aurora A kinase, cells in the experiment needed to be synchronized. A summary of the procedure used to synchronize cells is shown in FIG. 30. The live cell imaging experiments to monitor Aurora A kinase and TPX2 in vivo interaction herein were performed using HeLa cells; however, HEK293 cells may also be used (FIGS. 33-35).

Figure 17A:
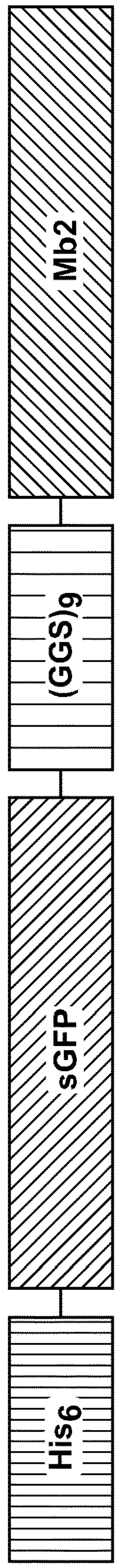
FIGS. 17A-17F present a set of plots, images and graphs showing data gathered using cultured HEK293 cells.
Figure 17B:
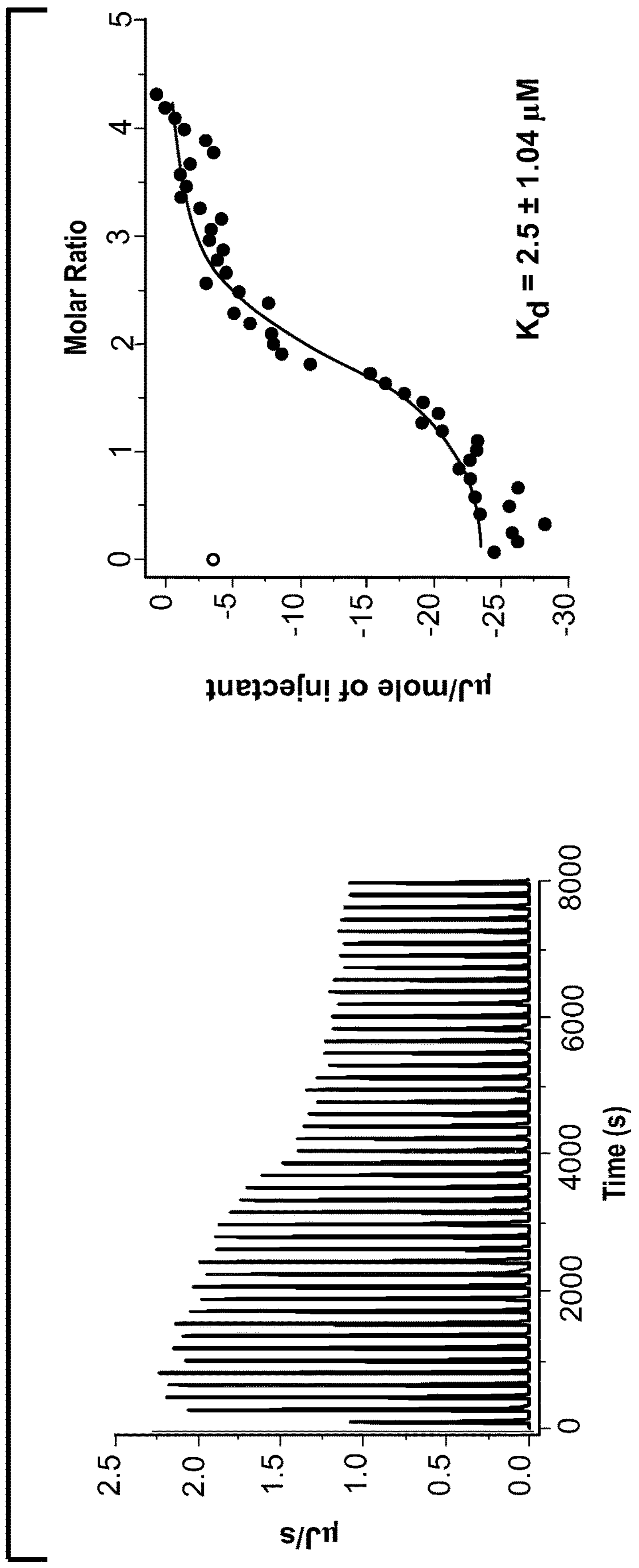
Figure 17C:
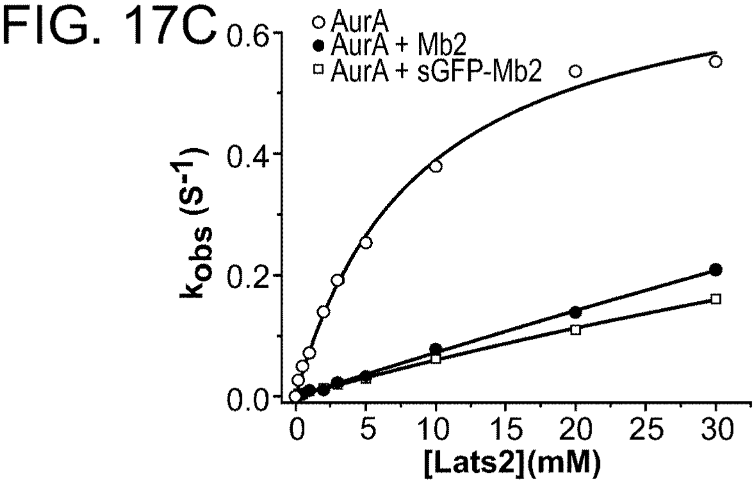
Figure 17D:
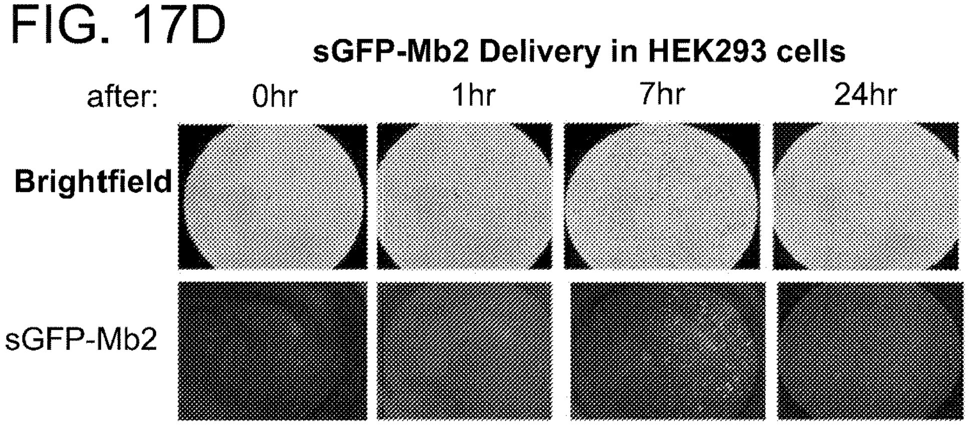
Figure 17E:
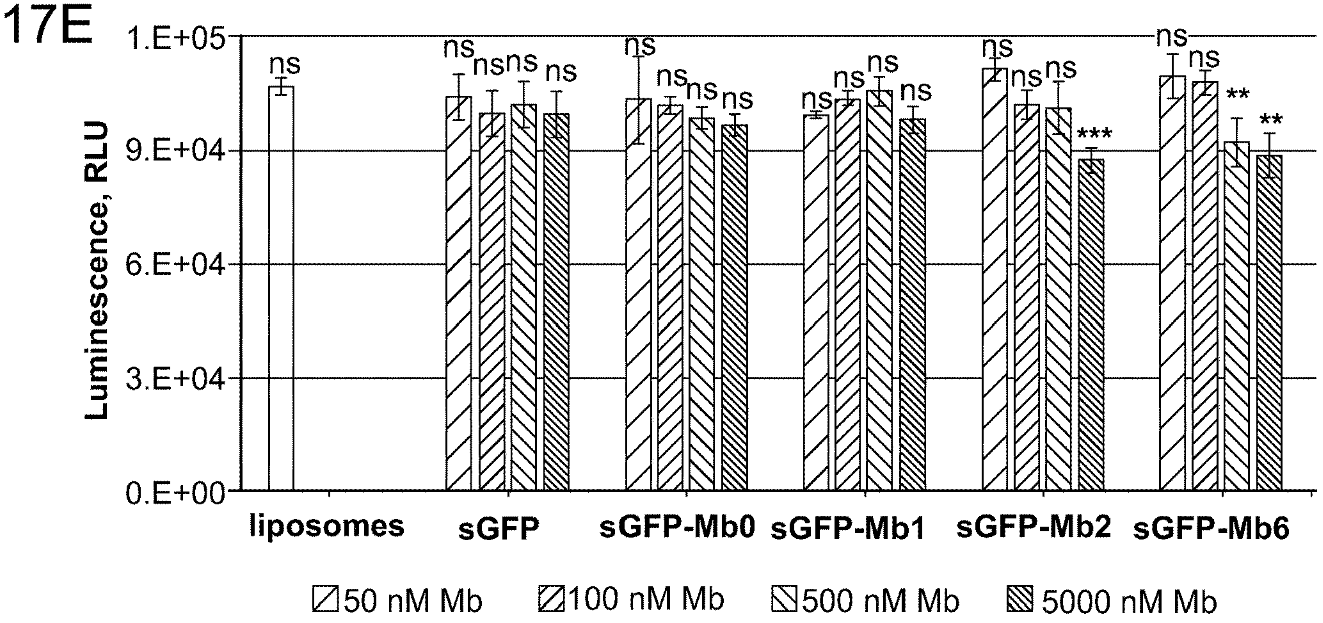
Figure 17F:
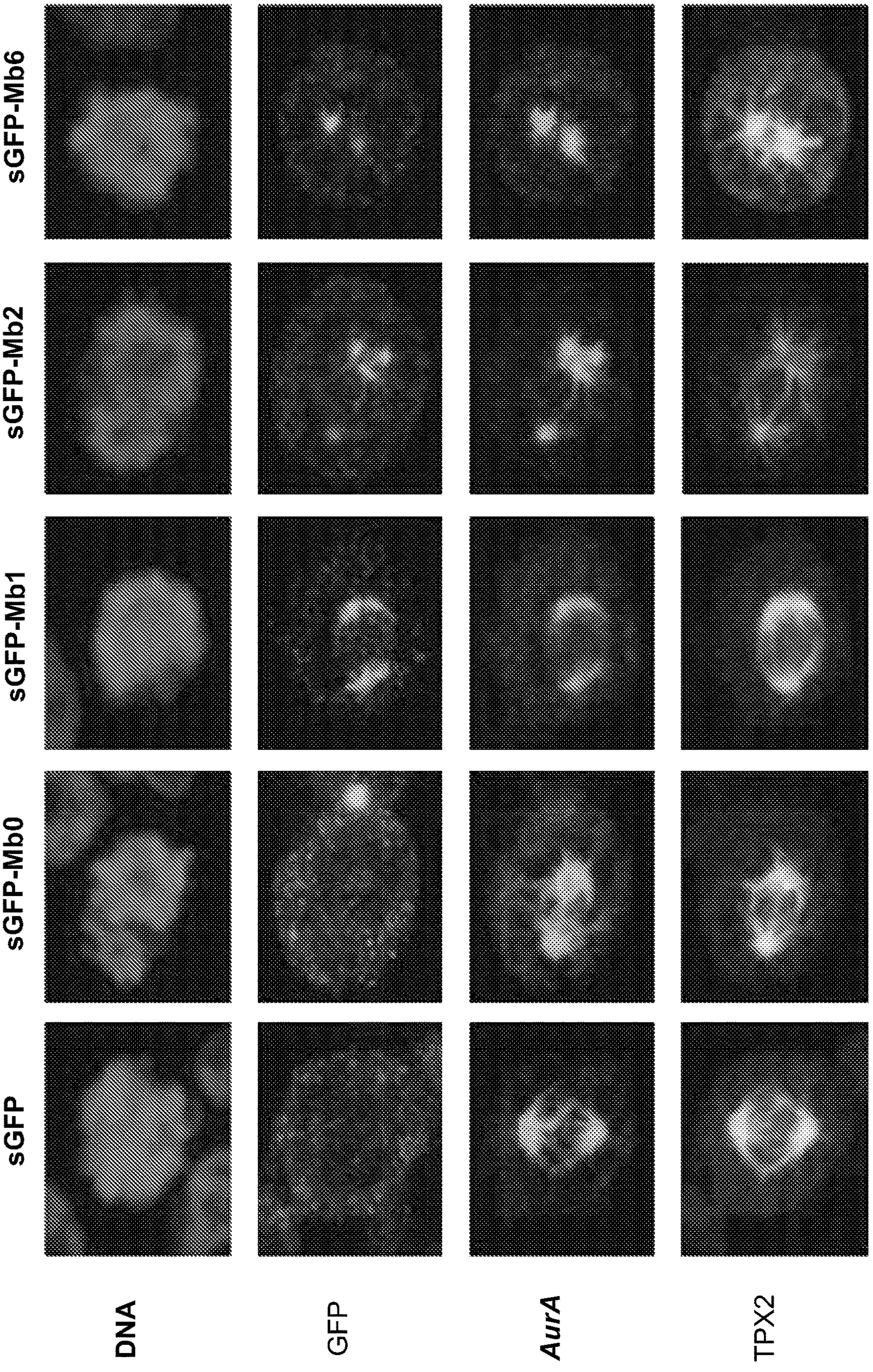
Figures 18A, 18B, 18C:
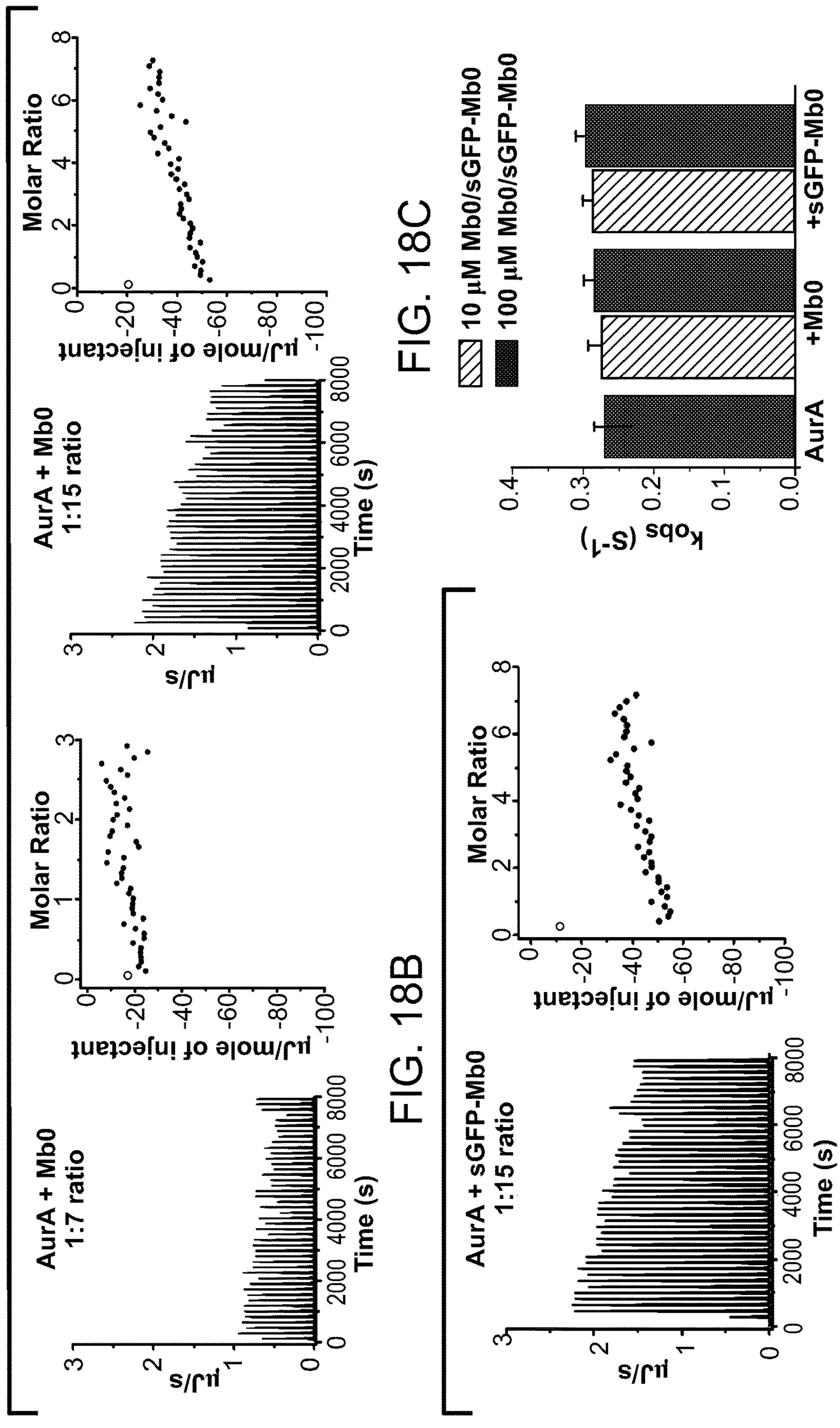
FIGS. 18A-18G are a set of plots and graphs showing the results of isothermal titration calorimetry (ITC) assays to characterize the thermodynamics of binding of Aurora A kinase ("AurA") and monobodies as described herein, or monobody fusion polypeptides as described above.
Figure 18E:
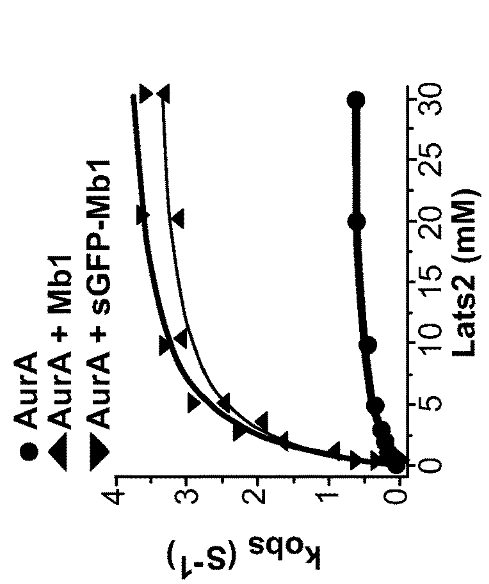
Figure 18G:
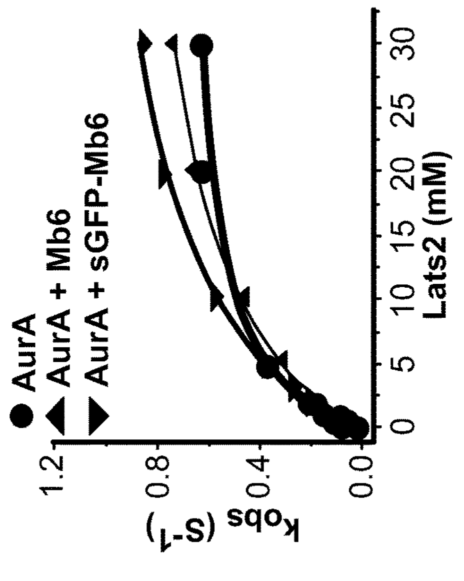
Figure 18D:
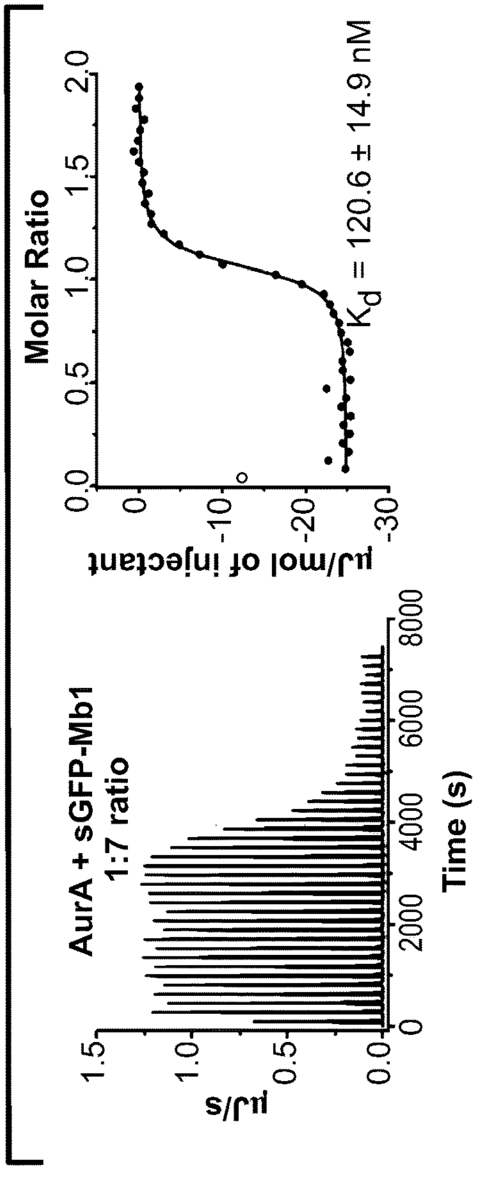
Figure 18F:
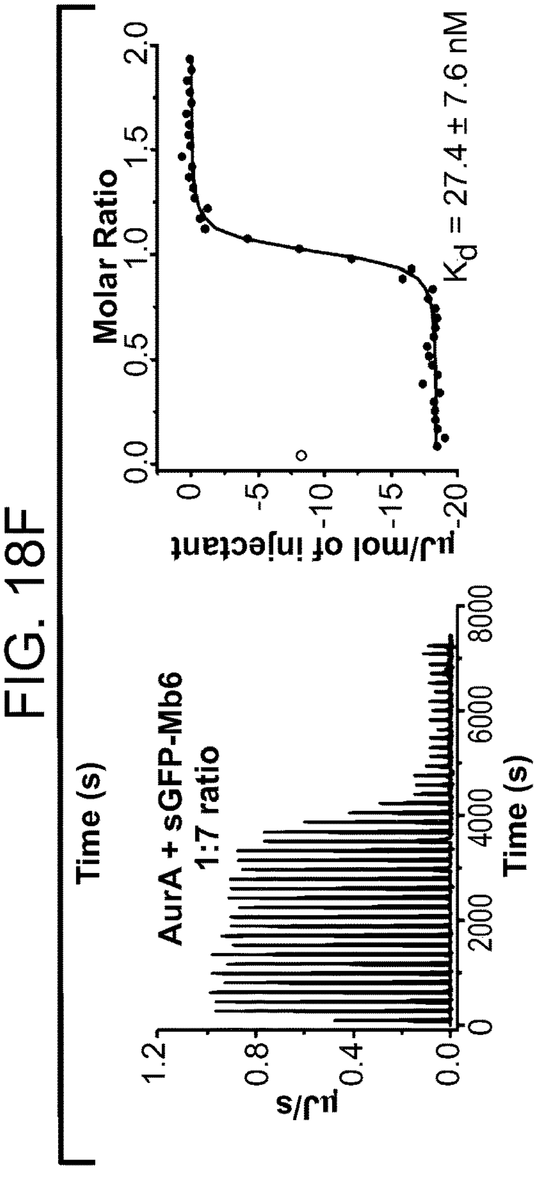

FIGS. 17A-17F present a set of plots and images showing in vivo data gathered using cultured mammalian HEK293 cells. FIG. 17A shows a schematic depiction of a sGFP-Mb60 fusion construct that was built for the purposes of mammalian-cell-based-protein delivery and to deliver the monobody Mb60 (aka Mb2) into HEK293 cells. The polypeptide encoded by this fusion sGFP-Mb60 construct was first tested for Aurora A binding affinity and ability to inhibit Aurora A kinase. It was confirmed that the sGFP tag of the sGFP-Mb60 fusion protein did not affect the binding affinity of the monobody Mb60 (Mb2) to Aurora A kinase or its inhibition of Aurora A kinase activity (FIGS. 17B and 17C). The sGFP-Mb60 fusion polypeptide has a binding affinity to Aurora A kinase comparable to that of monobody Mb60. The sGFP-Mb60 polypeptide also inhibits Aurora A to the same extent as Mb60. As observed in FIG. 17D, optimal cell delivery of sGFP-Mb60 occurred after 7 hrs of exposure. FIG. 17F shows images assessing the delivery of various sGFP-monobody fusion products into HEK293 cells. The control, sGFP alone, sGFP-Mb0 (a monobody incapable of binding Aurora A kinase), as well as sGFP-Mb1 (aka Mb54 herein, an activating monobody), sGFP-Mb2 (aka Mb60 herein, an inhibiting monobody) and sGFP-Mb6 (an activity-neutral monobody) were shown to be delivered into cells (FIG. 18F and FIGS. 18A-18G). Dosing of HEK293 cells at various monobody concentrations caused statistically significant cell death by the inhibitory monobody sGFP-Mb2 (aka Mb60) and the activity-neutral Mb (sGFP-Mb6), but not by the controls (FIG. 17E). Surprisingly, the activating sGFP-Mb1 (aka Mb54) did not cause cell death, perhaps due to compensation of disruption of localization by Aurora A kinase activation (FIG. 17E).

Immunofluorescence experiments showed that all monobodies that bound Aurora A kinase in vitro co-localized with Aurora A kinase in HEK293 cells (FIG. 17F), demonstrating the high specificity of the monobodies in a cellular context. To further test the specificity of the interaction, the co-localization of Aurora A kinase with sGFP alone, sGFP-Mb0, sGFP Mb1 (aka Mb54) or neutral monobody sGFP-Mb6 was assessed (FIG. 17F). The controls (sGFP, sGFP-Mb0) did not co-localize with Aurora A kinase and showed a granular and uniformly dispersed signal, whereas the Aurora A kinase-binding monobodies (sGFP-Mb1 (aka Mb54), sGFP-Mb2 (aka Mb60) and neutral sGFP-Mb6) showed strong co-localization in cells (FIG. 17F). This analysis suggests that the non-control monobodies bind specifically to Aurora A kinase in HEK293 cells, and that the replacement of TPX2 from Aurora A kinase's hydrophobic binding pocket and inhibition of Aurora A kinase by Mb2 (aka Mb60) results in untimely cell death.

Figure 31:
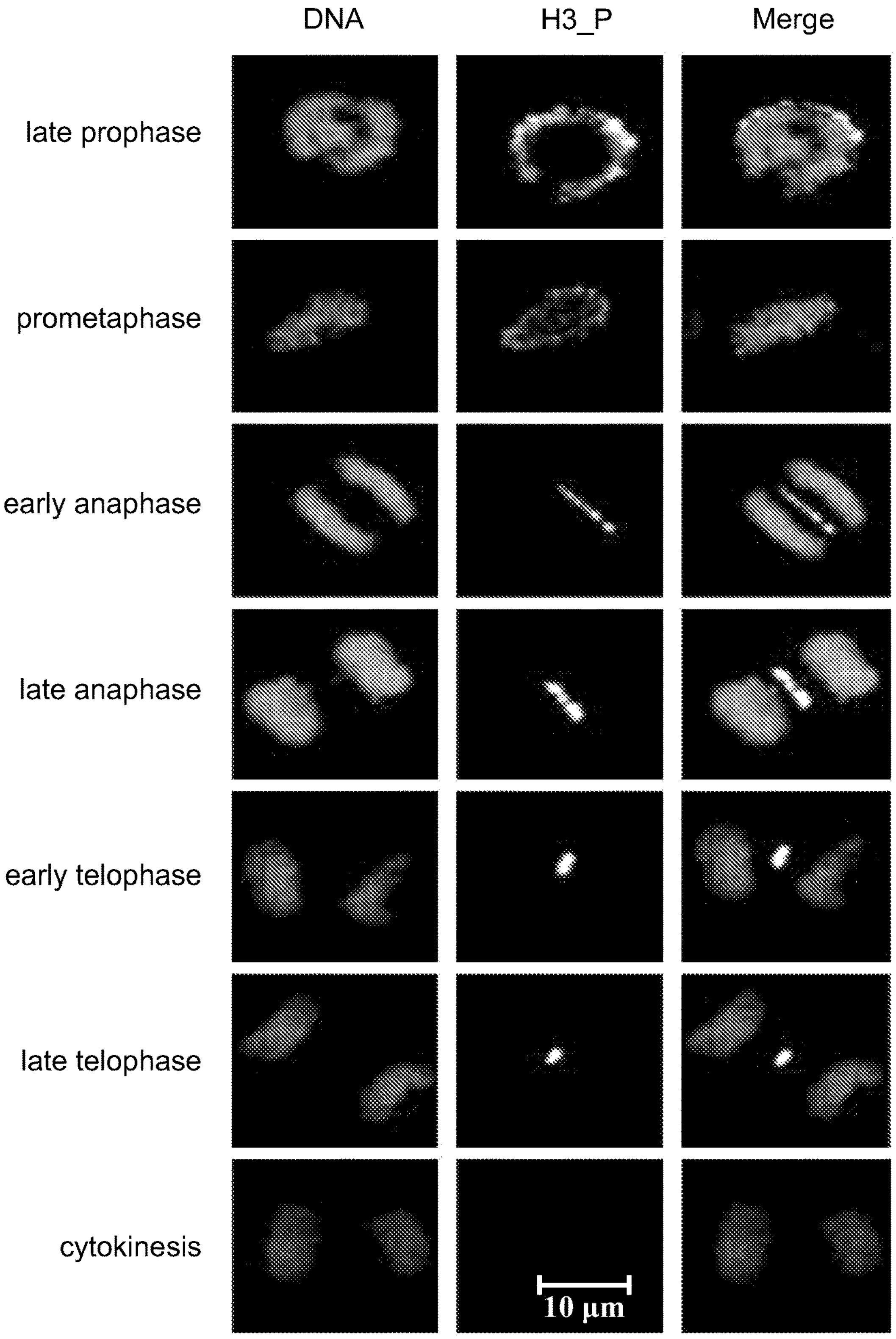
FIG. 31 is an exemplary set of micrographs showing localization of DNA and H3_P (phosphorylated histone H3) during different stages of the cell cycle.

To monitor mitotic progression over time with fine resolution, in addition to staining DNA, phosphorylated histone H3 ("H3_P") was also stained to monitor levels of H3_P in cells during live cell imaging (FIG. 31). Phosphorylation of Ser10 of histone H3 is considered to be a temporal marker of mitotic progression. FIG. 30 shows exemplary H3_P levels and localization in a cell during mitotic progression. In a normally dividing cell, H3_P peaks at metaphase where it is thought that H3 decorated with a negative charge could then electrostatically repulse interactions with DNA, thereby causing unraveling of histone from DNA and allowing for chromosome condensation. H3_P decreases upon mitotic exit.

Figure 32:
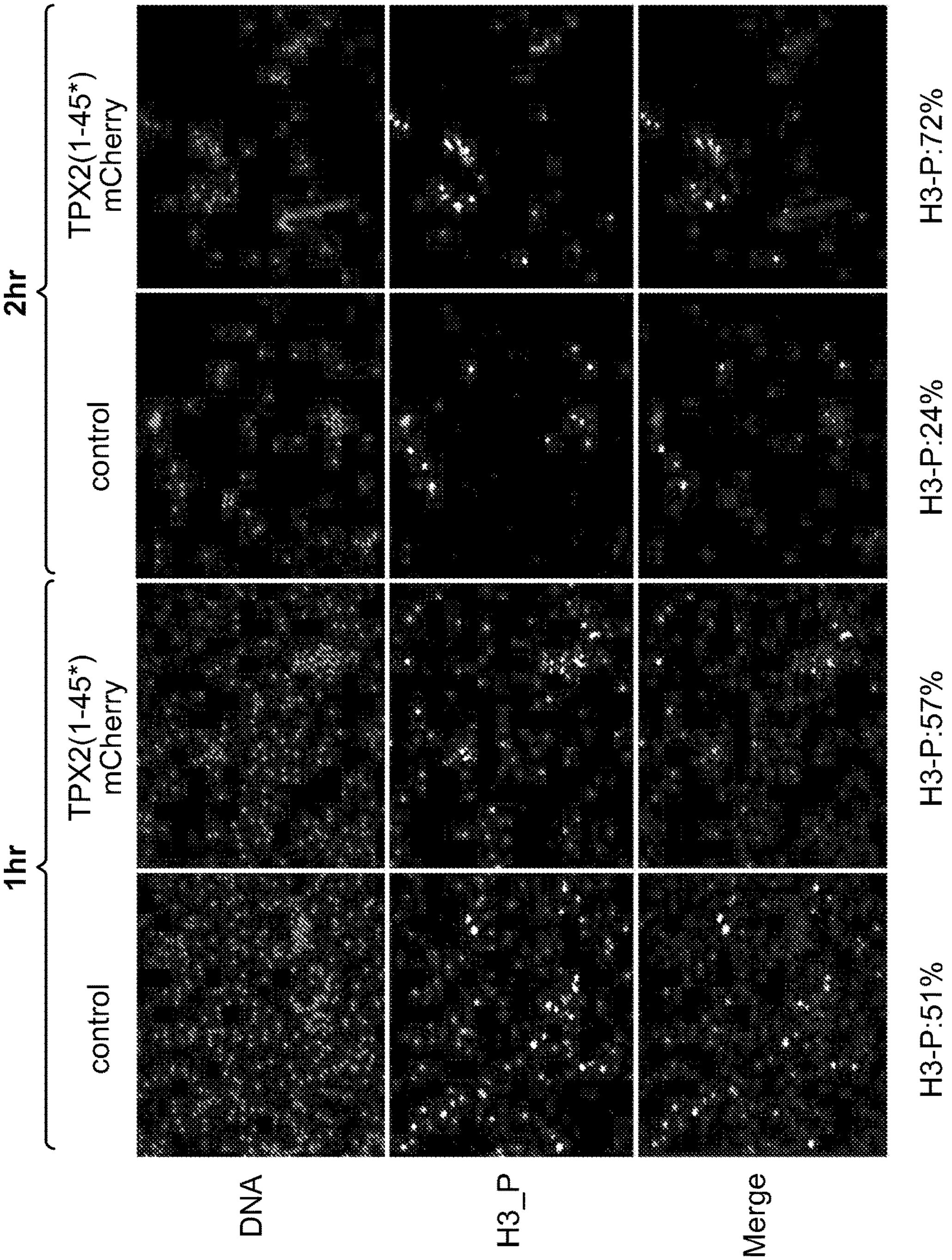
FIG. 32 is a set of micrographs showing single cell quantification of H3_P (phosphorylated histone H3) in HeLa cells transfected with TPX2(1-45*)-mCherry.

As shown in FIGS. 32 and 33, cells transfected with TPX2(1-45*)mCherry exhibited a phenotype where cells were stuck in the metaphase/anaphase transition point longer, as indicated by H3_P levels in the cell population, indicating abnormal mitotic progression. Human TPX2 is 747 amino acids residues long. Out of those, the first 45 residues are necessary and sufficient not only to bind to Aurora A kinase, but also to impart the full TPX2 effect; i.e. shift Aurora A kinase to an active conformation. The rest of the TPX2 residues become important in nuclear envelope rupture (the middle part of TPX2) and in localization to microtubules (the end, C-terminal domain of TPX2). The importin binding domain is crucial in TPX2-importin interactions that keep TPX2 inside the nucleus. In response to a RanGTP gradient, the nuclear envelope rupture and the TPX2-importin domain interaction is disrupted. TPX2 can now on one hand, bind to Aurora A kinase through TPX2's N-terminal domain and, on the other hand, TPX2 can bind to kinesin that localizes this Aurora A kinase—TPX2—kinesin ternary complex to microtubules. This step is crucial in spindle formation and normal mitotic progression. TPX2 (1-45*)mCherry mimics endogenous TPX2 in that it has the Aurora A binding domain (residues 1-45) intact (the * denotes truncation of the wild type TPX2 sequence after residue 45 and mCherry denotes a fluorescent, fusion protein that was added to the TPX2 construct to allow for our construct's detection). However, it does not contain the microtubule binding domain, thus rendering TPX2(1-45*) mCherry incapable of locating Aurora A kinase to the spindle microtubules of a dividing cell. This, in turn, leads to delayed mitosis that is recorded through prolongation of Histone H3 phosphorylation at Ser 10. (FIGS. 34 and 35).

Figure 36:
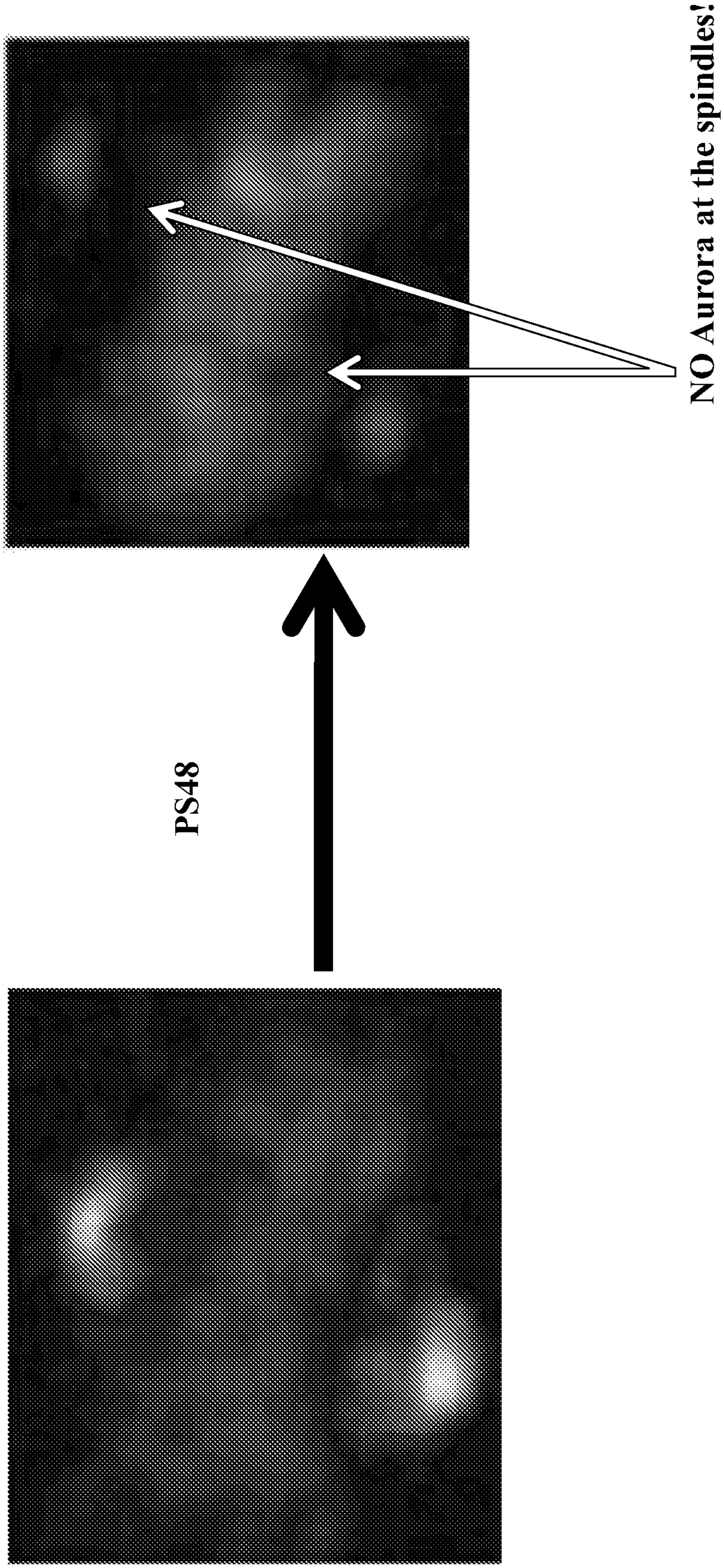
FIG. 36 is a set of micrographs showing that PS48 competes off TPX2 in vivo. In HeLa cells treated with PS48, Aurora A kinase was not observed at the spindles.
Figure 37:
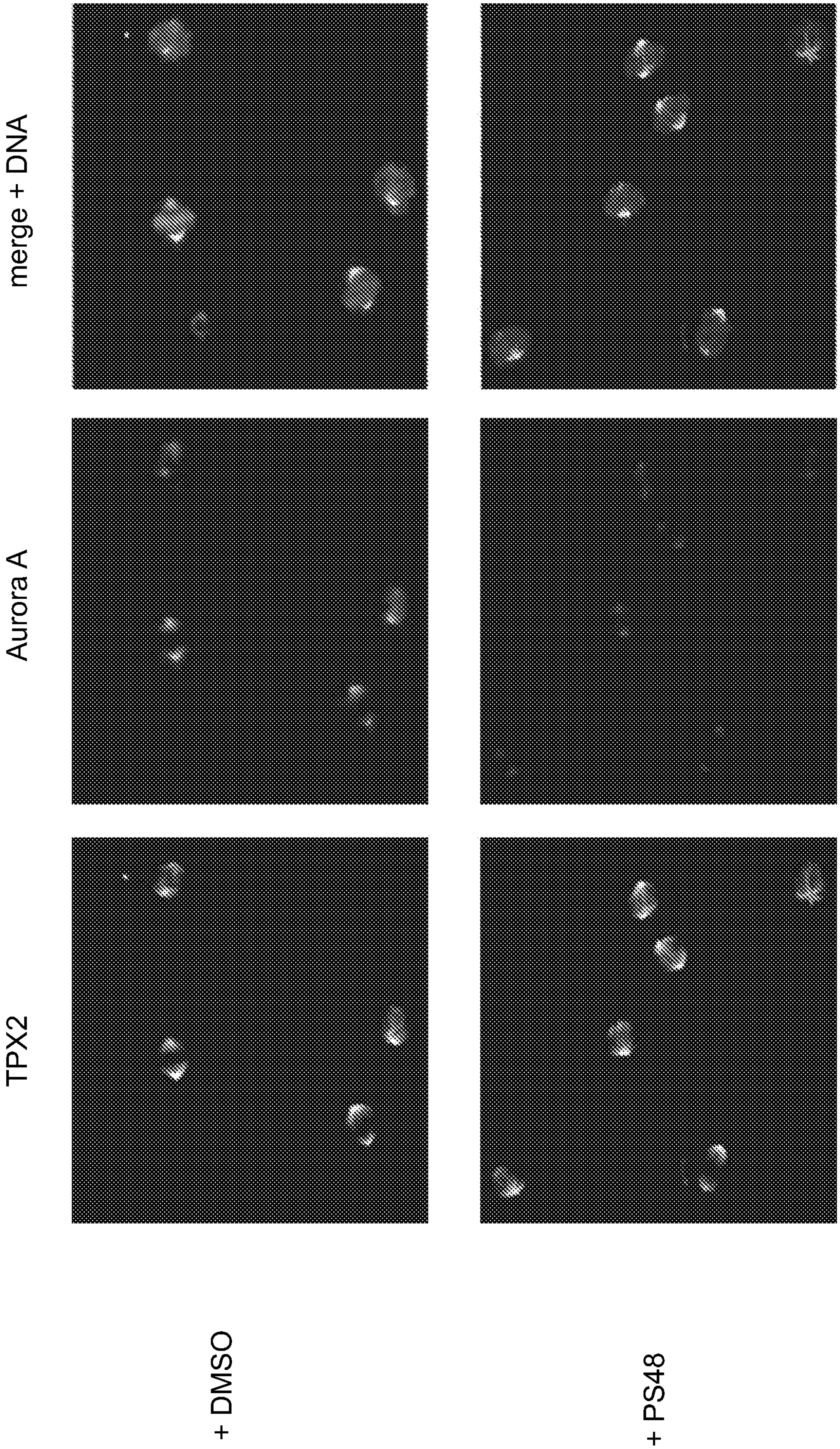
FIG. 37 is a set of micrographs showing localization of TPX2, Aurora A, and DNA during metaphase in cells treated with PS48 (bottom row) and DMSO (control) (top row).
Figure 39:
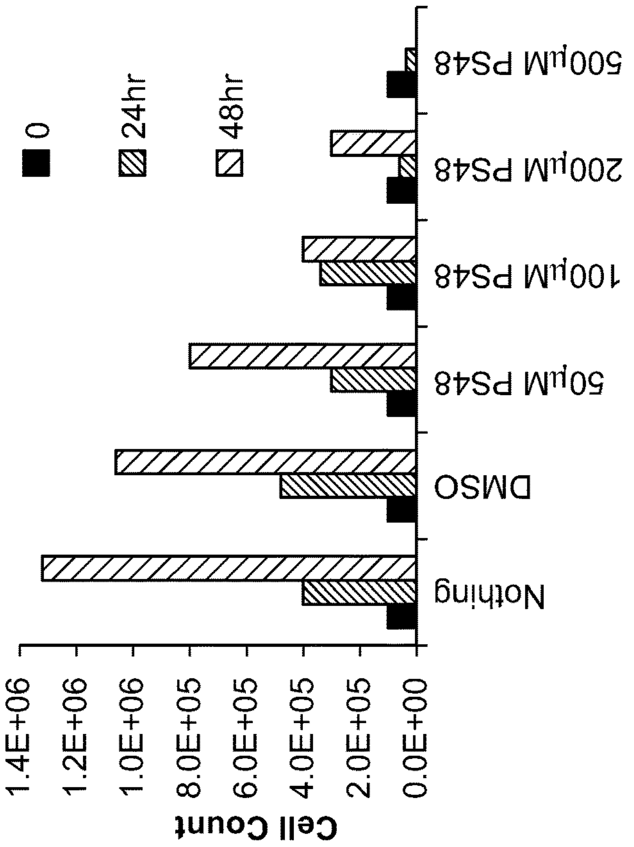
FIG. 39 is a plot showing that HeLa cell viability is PS48-dose dependent.
Figure 38:
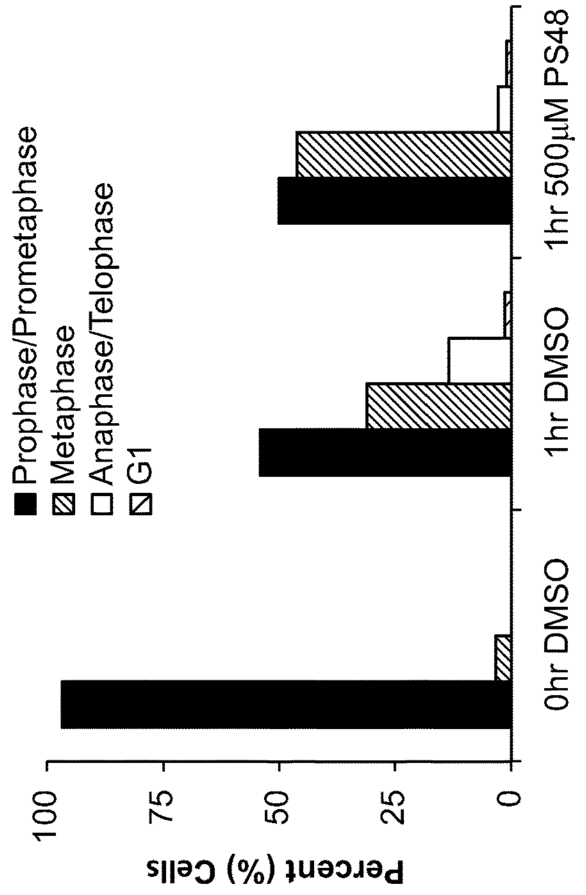
FIG. 38 is a plot showing that progression of HeLa cells through mitosis is prolonged in the presence of PS48.

FIGS. 36 and 37 show that in cells treated with PS48, localization of Aurora A to the spindle during mitosis was not observed. Single cell quantification of cells treated with PS48 and a control agent (DMSO) showed progression of HeLa cells through mitosis was prolonged in the presence of PS48 (FIG. 38). The phenotype observed was similar to the phenotype observed in TPX2(1-45*)mCherry transfected cells, where cells were stuck in the metaphase/anaphase transition point for a longer period, indicating abnormal mitotic progression. Finally, PS48 decreased cell viability, as shown in FIG. 39.

Figure 15:
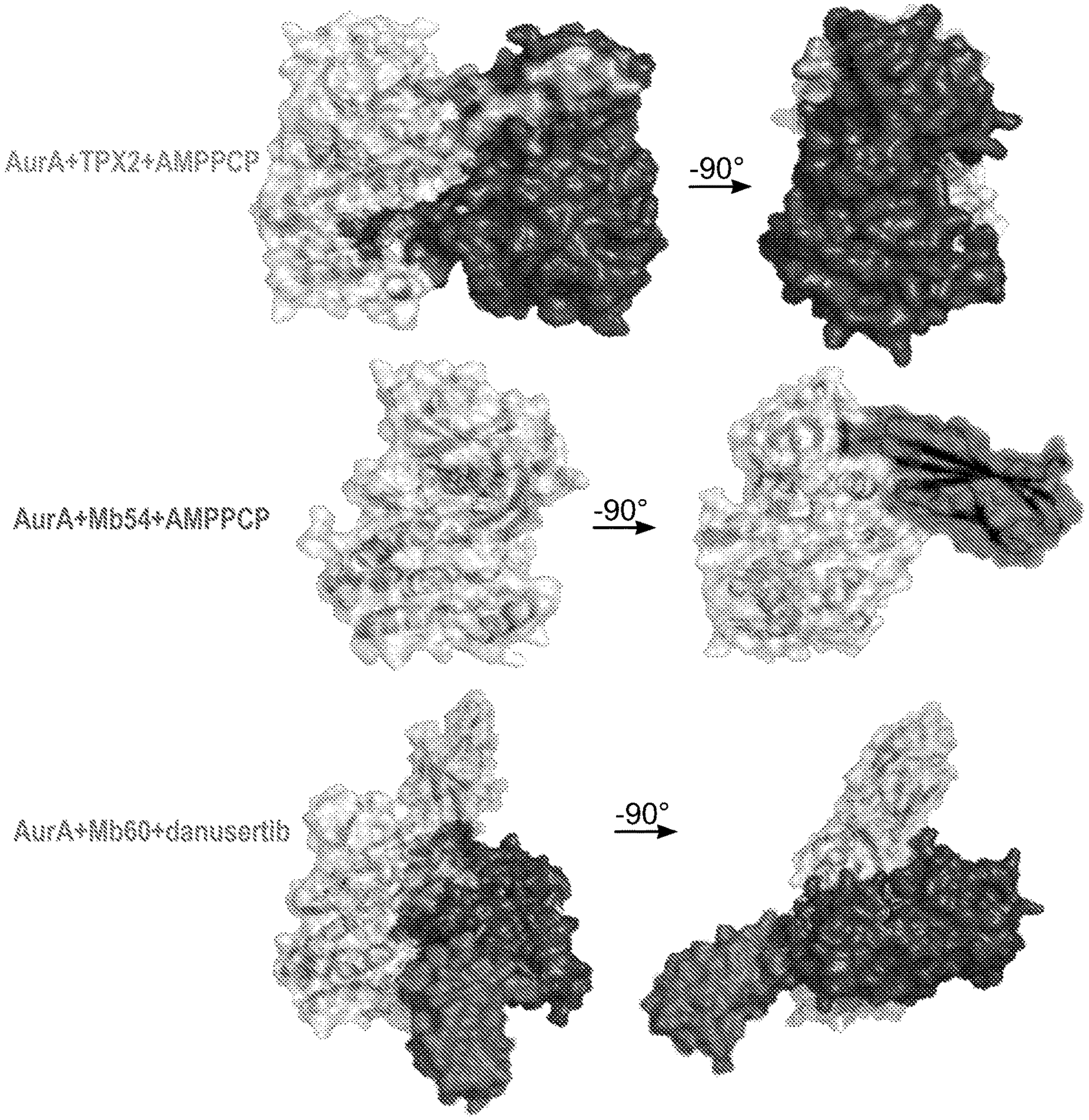
FIG. 15 is a set of several high-resolution X-ray structures of dephosphorylated Aurora A kinase bound to TPX2, activating monobody Mb54 or inhibitory monobody Mb60.

Example 5: High Resolution X-Ray Crystallography of Inhibitor (Mb60) and Activating (Mb54) Monobody Bound to Aurora A Kinase and Danusertib or AMPPCP High-resolution X-ray crystallography structures of Aurora A in the presence of an activating Mb54 bound to the PIF pocket, an inhibitory monobody Mb60 bound to the PIF pocket, and ATP-competitive drugs bound to the ATP-binding site such as AMPPCP or danusertib were solved (FIG. 15). The atomic coordinates of the X-ray structures are provided Appendix A and Appendix B.

Figures 16, 16A:
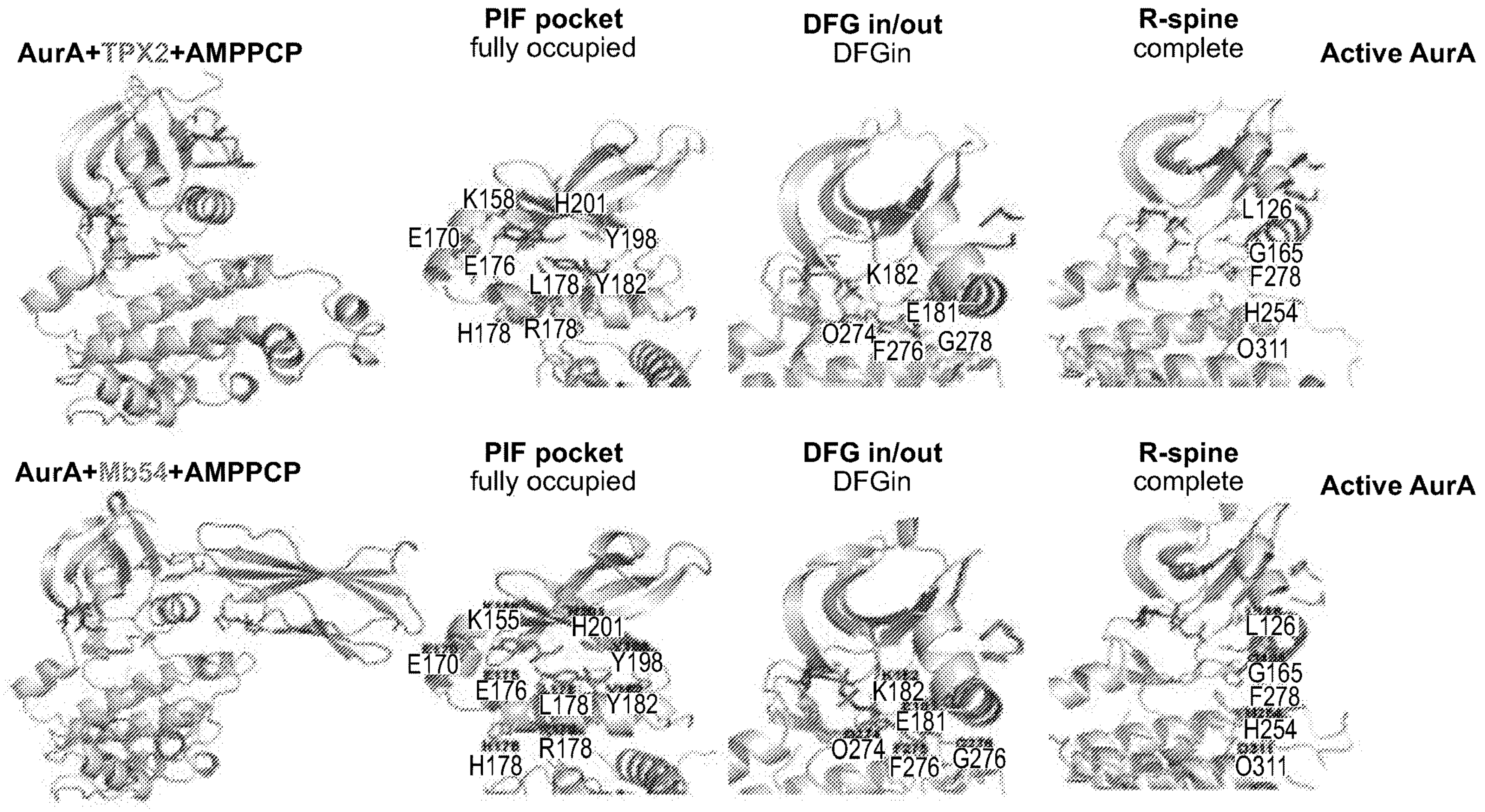
FIG. 16 is a set of high-resolution X-ray structures highlighting residues of the PIF pocket that contact TPX2, activating monobody Mb54 or inhibitory monobody Mb60.
Figure 16B:
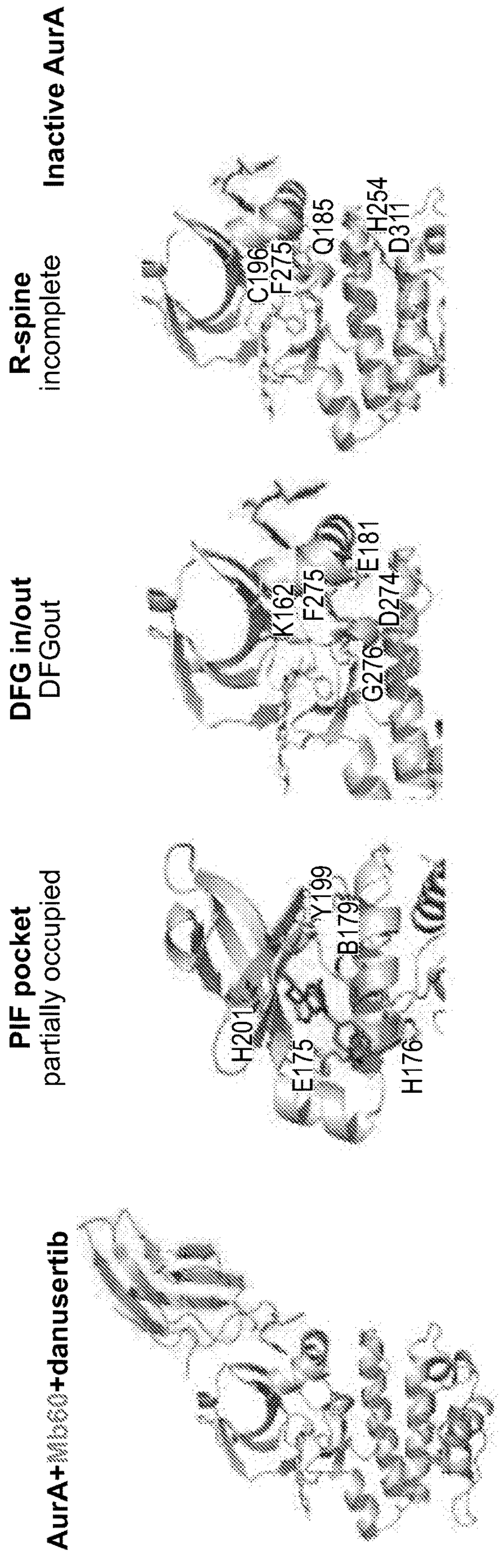

The high-resolution x-ray structures of complexes with activating and inhibiting monobodies with Aurora A revealed particular residue contacts make by the inhibitory and activating monobody with the PIF pocket (FIG. 16). In general, the activating monobody made much more extensive hydrophobic contacts with the PIF pocket of Aurora A kinase by primarily anchoring two tyrosine residues (Y32 and Y34) into the PIF pocket socket. By contrast, inhibitory monobody Mb60 only tangentially interacted with the PIF pocket (FIG. 16). Without being bound by theory, it is believed that molecules which bind the PIF pocket and make similar residue contacts as the activating or inhibitory monobody would similarly shift equilibrium to the active or inactive kinase conformation. A molecule specifically binding the PIF pocket and making similar residue contacts as the inhibitory monobody, for example, would shift equilibrium to the inactive kinase conformation, thus increasing affinity of kinase inhibitors, such as danusertib, that bind to the ATP-binding site of Aurora A kinase in the inactive conformation. Thus, the residue contacts made by the inhibitory and activating monobody with the PIF pocket would inform rational drug design, as molecules that make residue contacts to the PIF pocket that are similar to the contacts made the inhibitory monobody can be designed or selected. Further, molecules that specifically bind the PIF pocket can be designed or selected based on the criterion that the molecule does not make residue contacts similar to the residue contacts made by the activating monobody.

Results described herein were obtained using the following materials and methods.

Cloning and Purification of Aurora A Kinase

Aurora A kinase was obtained through a lambda protein phosphatase (λPP) co-expression system. Codon-optimized Aurora $A^{122-403}$ in pET28a and untagged λPP in T7-7 plasmid were co-transformed in BL21(DE3) cells and spread on Kan/Amp 2×YT plates. The most robust colony was used for a 2×YT pre-culture and later on to inoculate a 1 L culture to an OD of 0.2. Cells were induced with 0.6 mM IPTG for 5 h at 37° C. It was noticed that although Aurora A could grow reasonably well in LB media, λPP could not; hence, the choice of 2×YT media for all co-expression needs. Purification involved a Nickel-Nitriloacetic acid (NiNTA) column, followed by overnight TEV (tobacco etch virus protease) cleavage and GST-λPP (glutathione S-transferase tagged λPP) treatment, in tandem NiNTA-GST columns and finally a 26/60 S200 size exclusion column. Mass spectrometry (MS) was used to confirm that Aurora A kinase was completely dephosphorylated. At the end of the purification, Aurora A was dialyzed against buffer C (20 mM TrisHCl (pH 7.0), 200 mM NaCl, 20 mM $MgCl_2$, 5 mM TCEP, 10% (vol/vol) glycerol), flash-frozen with liquid nitrogen into 1 mL aliquots and stored at −80° C. Typical yields were 8-10 mg of phosphorylated Aurora A and 45-50 mg of dephosphorylated Aurora A (expressed in the presence of λPP) per liter of *E. coli* culture. PS48 and AMPPCP were obtained from Sigma.

In Vitro Kinase Assays

Aurora A, either phosphorylated/dephosphorylated wild type or mutant protein, was mixed with either AP (APSSRRTTLCGTL) (SEQ ID NO: 5), Kemptide (LRRASLG) (SEQ ID NO: 6), or Lats2 (ATLARRDSLQKPGLE) (SEQ ID NO: 7), in the absence or presence of 50 μM TPX2 in kinase buffer (20 mM TrisHCl, 200 mM NaCl, 3% [vol/vol] glycerol, 20 mM $MgCl_2$, 1 mM TCEP, pH 7.50). These substrates comprise the consensus sequence for Aurora A ([R/K/N]—R—X—[S/T]-B where B is any hydrophobic residue with the exception of Pro) (Ferrari et al., 2005, *Biochem. J.,* 390(Pt 1):293-302; Ohashi et al., 2006, *Oncogene,* 25:7691-7702; Sardon et al., 2010, *EMBO Reports,* 11:977-984). Peptides were ordered through Genscript. For HPLC-based activity assays the following protocol was used. The reaction was initiated with the addition of 5 mM ATP. Then 5 μl time points were collected, resuspended in 10 μl 6% (vol/vol) trichloroacetic acid (in water) to quench the reaction, and neutralized with 50 μl 100 mM $KH_2PO_4$, pH 8.0 to provide the appropriate pH for nucleotide separation. The mixture was then passed through a 0.22 μm SpinX column to remove any protein precipitation. Reverse phase-high performance liquid chromatography (RP-HPLC) and an ACE 5 C18-AR, 100 Å pore size column, were used to separate nucleotides as well as peptides. For nucleotide runs, 2 μl of the aforementioned mixture was sufficient for analysis, whereas for the peptide runs the optimal injection volume was 20 μl. Nucleotide runs were routinely performed to ensure no unproductive hydrolysis was occurring during the experiment. An isocratic elution run in 100 mM $KH_2PO_4$, pH 6.0 was performed for this purpose. For the peptide runs, a gradient of 0-30% of elution buffer lasting 10 min at 0.4 mL/min was sufficient to separate phosphorylated from non-phosphorylated species. The running buffer was 0.1% TFA (vol/vol) in water, while the elution buffer was 100% acetonitrile. Lastly, to ensure full saturation of Aurora A by TPX2 and test these proteins were well behaved, a dose-dependence curve of the effect of TPX2 on Aurora A was obtained.

For ATP/NADH-coupled assay-based reaction, the following protocol was used. Phosphorylation of different concentrations of Lats2 peptide was monitored using the ATP/NADH coupled assay in a 96-well plate format. Reactions were carried in the presence of 1 μM dephosphorylated or 0.05 μM phosphorylated Aurora and 5 mM ATP in assay buffer (20 mM TrisHCl, 200 mM NaCl, 20 mM $MgCl_2$, 10% (v/v) glycerol, 1 mM TCEP, pH 7.50) at 25° C. When reactions were carried in the presence of monobodies, the following concentrations were used: 10 μM Mb54, 70 μM Mb60, 50 μM Mb56, 10 μM Mb44, 2 μM Mb51 and 50 μM Mb2 (aka Mb6).

Isothermal Titration Calorimetry

Titrations were carried out using Nano ITC isothermal titration calorimeter (TA Instruments) and analyzed via the NanoAnalyze software using the independent fit model. Injectant was added in 1 μl volume, every 180 s, with a constant stirring speed at 350 rpm and at 25° C. Prior to ITC titration, both protein and TPX2 or monobody were dialyzed/resuspended in ITC buffer (20 mM TrisHCl, 200 mM NaCl, 3% (vol/vol) glycerol, 1 mM TCEP, pH 7.50). PS48, AMPPCP or danusertib powder was resuspended in filtered ITC buffer. In cases where powder was not available, Danusertib 100% DMSO was used and eventually diluted to a working concentration in ITC buffer. The DMSO percentage of the titrated Aurora A kinase in the ITC sample cell was carefully matched to that of the titrant danusertib, so that no false positive heats of interactions would occur as a result of DMSO dilution.

Crystallographic Methods

Crystals of dephosphorylated Aurora $A^{122-403}$ in complex with danusertib and inhibitory monobody, Mb60, were grown at 18° C. by vapor diffusion and the hanging drop method. A 1:1 ratio of protein mixture:mother liquor was obtained by combining 0.5 μl of (30 μM (10 mg/ml) deP Aurora $A^{122-403}$+5 mM danusertib+300 μM Mb60) with 0.5 μl of mother liquor (0.1M BisTris pH 5.50, 0.2M Ammonium Acetate, 25% PEG3350). Similarly, crystals of dephosphorylated Aurora $A^{122}$-403 in complex with AMPPCP and activating monobody, Mb54, were obtained by combining 0.5 μl of 30 μM (10 mg/ml) deP Aurora $A^{122-403}$+5 mM AMPPCP+30 μM Mb54) with 0.5 μl of mother liquor (0.1M MES Sodium Salt pH 6.50, 0.2M Ammonium Sulfate, 4% (v/v) 1,3-propanediol, 30% (w/v) PEG8000). These latter crystals were also grown at 18° C. by vapor diffusion and the hanging drop method. Prior to crystallization, Aurora A and monobodies were kept in storage buffer (20 mM TrisHCl, 200 mM NaCl, 10% (v/v) glycerol, 20 mM $MgCl_2$, 5 mM TCEP, pH 7.50). AMPPCP was prepared fresh from powder the day of crystallization in concentrations of 100-120 mM in storage buffer whereas stocks of danusertib in 100% DMSO were used for co-crystallization.

Diffraction data were collected at 100K at Advanced Light Source (Lawrence Berkeley National Laboratory) beamlines 8.2.1 and 8.2.2. Data were processed with the automated data reduction program $X_{1A}2$ (Winter, *J Appl Cryst,* 2010(43): p. 186-190) that is part of the CCP4-suite (Winn et al., *Acta Crystallogr D Biol Crystallogr,* 2011. 67(Pt 4): p. 235-42) and uses iMOSFLM (Battye et al., *Acta Crystallogr D Biol Crystallogr,* 2011. 67(Pt 4): p. 271-81) for integration and Scala (Evans, *Acta Crystallogr D Biol Crystallogr,* 2006. 62(Pt 1): p. 72-82) for scaling. Initial phases were obtained by molecular replacement (CCP4 program MOLREP (Vagin, *J Appl Cryst,* 1997(30): p. 1022-1025) by using an Aurora A kinase structure (PDB ID 1MQ4) as a search model. The refinement was carried out with the programs REFMAC5 (Murshudov et al., *Acta Crystallogr D Biol Crystallogr,* 2011. 67(Pt 4): p. 355-67) and PHENIX.REFINE (Adams et al., *Acta Crystallogr D Biol Crystallogr,* 2010. 66(Pt 2): p. 213-21), followed by manual rebuilding in the program COOT (Emsley et al., *Acta Crystallogr D Biol Crystallogr,* 2004. 60(Pt 12 Pt 1): p. 2126-32; Emsley et al., *Acta Crystallogr D Biol Crystallogr,* 2010. 66(Pt 4): p. 486-501.).

Generation and Characterization of Monobodies Specifically Binding to the PIF Pocket of Aurora A Kinase A high-throughput yeast-display library screening of more than a million monobody clones to identify activating and inhibitory monobodies towards Aurora A kinase was performed. Using phage display and Aurora A constructs, monobody libraries were screened for monobodies that bound tightly to the PIF pocket of human Aurora A kinase.

The selection scheme relied on (1) a round of positive selection that selected for monobodies binding more strongly to Aurora A than Aurora A-TPX2 chimera and (2) further refinement of selection by using Y199H and Y199K Aurora A hotspot mutants in negative selection rounds of current monobody pools. From the screen, a number of monobodies specifically binding to and having a high affinity for the PIF pocket of Aurora A were identified.

Monobodies Mb2 (aka Mb6), Mb44, Mb51, Mb56, Mb54, and Mb60 were selected for further biochemical characterization of the Aurora A-monobody interaction. Specifically, the affinity to Aurora A kinase and the ability of these monobodies to activate or inhibit the kinase activity of Aurora A kinase were measured.

Isothermal titration calorimetry (ITC) experiments using the monobodies were performed to determine the thermodynamics of the Aurora A—monobody interaction. Results showed that the monobodies bound to Aurora A kinase with affinities ranging in the nanomolar (nM) to low micromolar (μM) range. The monobodies bound to Aurora A with higher affinity than TPX2's affinity to Aurora A (affinity of TPX2 for Aurora A was measured to be about 5 μM).

A quantitative High Performance Liquid Chromatography (HPLC)-based assay and an ATP/NADH-coupled assay were established and used to determine the kinetics of Aurora A activation by the monobodies. Assay results showed that the monobodies had a differential effect on the kinase activity of Aurora A. At least one monobody (Mb54) showed activation of kinase activity of Aurora A. Several showed strong inhibition of Aurora A's kinase activity (e.g., Mb60).

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

APPENDIX A

Atomic coordinates of Aurora A + Inhibitory Monobody Mb60 + Danusertib

| | | | | |
|---|---|---|---|---|
| HEADER | dePAurA+inhibitoryMonobody+danusertib | | 22 Dec. 2015 | XXXX |
| COMPND | dePAurA+inhibitoryMonobody+danusertib | | | |
| REMARK | 3 | | | |
| REMARK | 3 | REFINEMENT. | | |
| REMARK | 3 | PROGRAM: | REFMAC 5.8.0135 | |
| REMARK | 3 | AUTHORS: | MURSHUDOV, SKUBAK, LEBEDEV, PANNU, | |
| REMARK | 3 | | STEINER, NICHOLLS, WINN, LONG, VAGIN | |
| REMARK | 3 | | | |
| REMARK | 3 | REFINEMENT TARGET: MAXIMUM LIKELIHOOD | | |
| REMARK | 3 | | | |
| REMARK | 3 | DATA USED IN REFINEMENT. | | |
| REMARK | 3 | RESOLUTION RANGE HIGH (ANGSTROMS): | 1.97 | |
| REMARK | 3 | RESOLUTION RANGE LOW (ANGSTROMS): | 44.19 | |
| REMARK | 3 | DATA CUTOFF (SIGMA(F)): | NONE | |
| REMARK | 3 | COMPLETENESS FOR RANGE (%): | 95.22 | |
| REMARK | 3 | NUMBER OF REFLECTIONS: | 57690 | |
| REMARK | 3 | | | |
| REMARK | 3 | FIT TO DATA USED IN REFINEMENT. | | |
| REMARK | 3 | CROSS-VALIDATION METHOD: | THROUGHOUT | |
| REMARK | 3 | FREE R VALUE TEST SET SELECTION: | RANDOM | |
| REMARK | 3 | R VALUE (WORKING + TEST SET): | 0.23372 | |
| REMARK | 3 | R VALUE (WORKING SET): | 0.23287 | |
| REMARK | 3 | FREE R VALUE: | 0.28359 | |
| REMARK | 3 | FREE R VALUE TEST SET SIZE (%): | 1.6 | |
| REMARK | 3 | FREE R VALUE TEST SET COUNT: | 966 | |
| REMARK | 3 | | | |
| REMARK | 3 | FIT IN THE HIGHEST RESOLUTION BIN. | | |
| REMARK | 3 | TOTAL NUMBER OF BINS USED: | 20 | |
| REMARK | 3 | BIN RESOLUTION RANGE HIGH: | 1.974 | |
| REMARK | 3 | BIN RESOLUTION RANGE LOW: | 2.025 | |
| REMARK | 3 | REFLECTION IN BIN (WORKING SET): | 4096 | |
| REMARK | 3 | BIN COMPLETENESS (WORKING+TEST) (%): | 93.63 | |
| REMARK | 3 | RIN R VALUE (WORKING SET): | 0.324 | |
| REMARK | 3 | BIN FREE R VALUE SET COUNT: | 75 | |
| REMARK | 3 | BIN FREE R VALUE: | 0.337 | |
| REMARK | 3 | | | |
| REMARK | 3 | NUMBER OF NON-HYDROGEN ATOMS USED IN REFINEMENT. | | |
| REMARK | 3 | ALL ATOMS: | 5509 | |
| REMARK | 3 | | | |
| REMARK | 3 | B VALUES. | | |
| REMARK | 3 | FROM WILSON PLOT (A**2): | NULL | |
| REMARK | 3 | MEAN B VALUE (OVERALL, A**2): | 45.163 | |
| REMARK | 3 | OVERALL ANISOTROPIC B VALUE. | | |
| REMARK | 3 | B11 (A**2): | 0.02 | |
| REMARK | 3 | B22 (A**2): | −0.02 | |
| REMARK | 3 | B33 (A**2): | 0.01 | |

APPENDIX A-continued

Atomic coordinates of Aurora A + Inhibitory Monobody Mb60 + Danusertib

```
REMARK   3      B12 (A**2):                 0.00
REMARK   3      B13 (A**2):                 0.00
REMARK   3      B23 (A**2):                 0.00
REMARK   3
REMARK   3      ESTIMATED OVERALL COORDINATE ERROR.
REMARK   3      ESU BASED ON R VALUE (A):                                    0.185
REMARK   3      ESU BASED ON FREE R VALUE (A):                               0.177
REMARK   3      ESU BASED ON MAXIMUM LIKELIHOOD (A):                         0.163
REMARK   3      ESU FOR B VALUES BASED ON MAXIMUM LIKELIHOOD (A**2):         6.190
REMARK   3
REMARK   3      CORRELATION COEFFICIENTS.
REMARK   3      CORRELATION COEFFICIENT FO-FC:                   0.940
REMARK   3      CORRELATION COEFFICIENT FO-FC FREE:              0.907
REMARK   3
REMARK   3      RMS DEVIATIONS FROM IDEAL VALUES                   COUNT       RMS     WEIGHT
REMARK   3      BOND LENGTHS REFINED ATOMS (A):                     5565;      0.017;    0.019
REMARK   3      BOND LENGTHS OTHERS (A):                            5297;      0.002;    0.020
REMARK   3      BOND ANGLES REFINED ATOMS (DEGREES):                7559;      2.088;    1.975
REMARK   3      BOND ANGLES OTHERS (DEGREES):                      12181;      1.084;    3.000
REMARK   3      TORSION ANGLES, PERIOD 1 (DEGREES):                  654;      7.069;    5.000
REMARK   3      TORSION ANGLES, PERIOD 2 (DEGREES):                  246;     35.149;   23.008
REMARK   3      TORSION ANGLES, PERIOD 3 (DEGREES):                  926;     15.942;   15.000
REMARK   3      TORSION ANGLES, PERIOD 4 (DEGREES):                   37,    -20.981;   15.000
REMARK   3      CHIRAL-CENTER RESTRAINTS (A**3):                     836;      0.110;    0.200
REMARK   3      GENERAL PLANES REFINED ATOMS (A):                   6109;      0.009;    0.021
REMARK   3      GENERAL PLANES OTHERS (A):                          1302;      0.002;    0.020
REMARK   3
REMARK   3      ISOTROPIC THERMAL FACTOR RESTRAINTS.               COUNT       RMS     WEIGHT
REMARK   3      MAIN-CHAIN BOND REFINED ATOMS (A**2):               2640;      3.815;    4.288
REMARK   3      MAIN-CHAIN BOND OTHER ATOMS (A**2):                 2639;      3.813;    4.288
REMARK   3      MAIN-CHAIN ANGLE REFINED ATOMS (A**2):              3286;      5.292;    6.405
REMARK   3      MAIN-CHAIN ANGLE OTHER ATOMS (A**2):                3287;      5.292;    6.405
REMARK   3      SIDE-CHAIN BOND REFINED ATOMS (A**2):               2925;      4.386;    4.688
REMARK   3      SIDE-CHAIN BOND OTHER ATOMS (A**2):                 2926;      4.386;    4.688
REMARK   3      SIDE-CHAIN ANGLE OTHER ATOMS (A**2):                4274;      6.527;    6.870
REMARK   3      LONG RANGE B REFINED ATOMS (A**2):                  6327;      8.364;   34.746
REMARK   3      LONG RANGE B OTHER ATOMS (A**2):                    6307;      8.369;   34.746
REMARK   3
REMARK   3      NCS RESTRAINTS STATISTICS
REMARK   3      NUMBER OF NCS GROUPS:       NULL
REMARK   3
REMARK   3      TWIN DETAILS
REMARK   3      NUMBER OF TWIN DOMAINS:                NULL
REMARK   3
REMARK   3
REMARK   3      TLS DETAILS
REMARK   3      NUMBER OF TLS GROUPS:       NULL
REMARK   3
REMARK   3
REMARK   3      BULK SOLVENT MODELLING.
REMARK   3      METHOD USED: MASK
REMARK   3      PARAMETERS FOR MASK CALCULATION
REMARK   3      VDW PROBE RADIUS:           1.20
REMARK   3      ION PROBE RADIUS:           0.80
REMARK   3      SHRINKAGE RADIUS:           0.80
REMARK   3
REMARK   3      OTHER REFINEMENT REMARKS:
REMARK   3      HYDROGENS HAVE BEEN ADDED IN THE RIDING POSITIONS
REMARK   3      U VALUES:          REFINED INDIVIDUALLY
REMARK   3
LINKR                   HIS A 280                        LEU A 293                 gap
LINKR                   TYR B 38                         GLN B 48                  gap
LINKR                   LEU B 64                         THR B 71                  gap
LINKR                   HIS D 280                        THR D 292                 gap
CISPEP   1      VAL B       6       PRO B     7                     0.00
CISPEP   2      VAL E       6       PRO E     7                     0.00
CRYST1     65.619      73.225   179.315   90.00      90.00      90.00       P 21 21 21
SCALE1        0.015239          0.000000  0.000000              0.00000
SCALE2        0.000000          0.013657  0.000000              0.00000
SCALE3        0.000000          0.000000  0.005577              0.00000
ATOM     1      N      TRP   A   128   33.804    -15.081     7.036     1.00   74.36   A    N
ATOM     2      CA     TRP   A   128   33.600    -16.280     7.905     1.00   71.89   A    C
ATOM     3      CB     TRP   A   128   34.038    -16.043     9.356     1.00   76.21   A    C
ATOM     4      CG     TRP   A   128   35.211    -15.159     9.658     1.00   72.69   A    C
ATOM     5      CD1    TRP   A   128   35.238    -13.795     9.633     1.00   71.98   A    C
ATOM     6      NE1    TRP   A   128   36.471    -13.336    10.046     1.00   66.97   A    N
ATOM     7      CE2    TRP   A   128   37.250    -14.409    10.387     1.00   66.06   A    C
ATOM     8      CD2    TRP   A   128   36.476    -15.577    10.177     1.00   68.00   A    C
```

APPENDIX A-continued

| Atomic coordinates of Aurora A + Inhibitory Monobody Mb60 + Danusertib | | | | | | | | | | | |
|---|---|---|---|---|---|---|---|---|---|---|---|
| ATOM | 9 | CE3 | TRP | A | 128 | 37.047 | −16.827 | 10.456 | 1.00 | 76.55 | A | C |
| ATOM | 10 | CZ3 | TRP | A | 128 | 38.367 | −16.871 | 10.937 | 1.00 | 78.99 | A | C |
| ATOM | 11 | CH2 | TRP | A | 128 | 39.109 | −15.681 | 11.138 | 1.00 | 75.58 | A | C |
| ATOM | 12 | CZ2 | TRP | A | 128 | 38.570 | −14.450 | 10.863 | 1.00 | 70.08 | A | C |
| ATOM | 13 | C | TRP | A | 128 | 32.138 | −16.729 | 8.000 | 1.00 | 72.27 | A | C |
| ATOM | 14 | O | TRP | A | 128 | 31.195 | −16.073 | 7.510 | 1.00 | 54.31 | A | O |
| ATOM | 15 | N | ALA | A | 129 | 31.959 | −17.861 | 8.674 | 1.00 | 71.72 | A | N |
| ATOM | 16 | CA | ALA | A | 129 | 30.634 | −18.268 | 9.139 | 1.00 | 71.77 | A | C |
| ATOM | 17 | CB | ALA | A | 129 | 29.861 | −18.989 | 8.039 | 1.00 | 72.19 | A | C |
| ATOM | 18 | C | ALA | A | 129 | 30.820 | −19.156 | 10.343 | 1.00 | 64.69 | A | C |
| ATOM | 19 | O | ALA | A | 129 | 31.944 | −19.490 | 10.681 | 1.00 | 59.73 | A | O |
| ATOM | 20 | N | LEU | A | 130 | 29.706 | −19.547 | 10.953 | 1.00 | 66.18 | A | N |
| ATOM | 21 | CA | LEU | A | 130 | 29.681 | −20.454 | 12.111 | 1.00 | 78.12 | A | C |
| ATOM | 22 | CB | LEU | A | 130 | 28.221 | −20.876 | 12.366 | 1.00 | 78.50 | A | C |
| ATOM | 23 | CG | LEU | A | 130 | 27.759 | −21.380 | 13.737 | 1.00 | 82.17 | A | C |
| ATOM | 24 | CD1 | LEU | A | 130 | 26.331 | −20.911 | 14.033 | 1.00 | 80.81 | A | C |
| ATOM | 25 | CD2 | LEU | A | 130 | 27.856 | −22.907 | 13.834 | 1.00 | 88.22 | A | C |
| ATOM | 26 | C | LEU | A | 130 | 30.625 | −21.680 | 11.931 | 1.00 | 87.46 | A | C |
| ATOM | 27 | O | LEU | A | 130 | 31.159 | −22.218 | 12.919 | 1.00 | 90.60 | A | O |
| ATOM | 28 | N | GLU | A | 131 | 30.884 | −22.044 | 10.665 | 1.00 | 83.54 | A | N |
| ATOM | 29 | CA | GLU | A | 131 | 31.571 | −23.280 | 10.301 | 1.00 | 83.08 | A | C |
| ATOM | 30 | CB | GLU | A | 131 | 31.342 | −23.653 | 8.821 | 1.00 | 84.41 | A | C |
| ATOM | 31 | CG | GLU | A | 131 | 29.935 | −23.396 | 8.252 | 1.00 | 87.85 | A | C |
| ATOM | 32 | CD | GLU | A | 131 | 28.774 | −23.592 | 9.241 | 1.00 | 91.86 | A | C |
| ATOM | 33 | OE1 | GLU | A | 131 | 27.759 | −22.887 | 9.058 | 1.00 | 77.49 | A | O |
| ATOM | 34 | OE2 | GLU | A | 131 | 28.853 | −24.430 | 10.186 | 1.00 | 84.49 | A | O |
| ATOM | 35 | C | GLU | A | 131 | 33.052 | −23.270 | 10.569 | 1.00 | 76.66 | A | C |
| ATOM | 36 | O | GLU | A | 131 | 33.606 | −24.320 | 10.806 | 1.00 | 84.19 | A | O |
| ATOM | 37 | N | ASP | A | 132 | 33.691 | −22.107 | 10.544 | 1.00 | 68.75 | A | N |
| ATOM | 38 | CA | ASP | A | 132 | 35.117 | −22.016 | 10.877 | 1.00 | 63.30 | A | C |
| ATOM | 39 | CB | ASP | A | 132 | 35.664 | −20.633 | 10.521 | 1.00 | 71.05 | A | C |
| ATOM | 40 | CG | ASP | A | 132 | 35.511 | −20.272 | 9.050 | 1.00 | 72.62 | A | C |
| ATOM | 41 | OD1 | ASP | A | 132 | 34.532 | −19.560 | 8.709 | 1.00 | 77.13 | A | O |
| ATOM | 42 | OD2 | ASP | A | 132 | 36.390 | −20.668 | 8.259 | 1.00 | 73.19 | A | O |
| ATOM | 43 | C | ASP | A | 132 | 35.434 | −22.278 | 12.374 | 1.00 | 57.95 | A | C |
| ATOM | 44 | O | ASP | A | 132 | 36.624 | −22.443 | 12.747 | 1.00 | 54.88 | A | O |
| ATOM | 45 | N | PHE | A | 133 | 34.398 | −22.310 | 13.221 | 1.00 | 51.04 | A | N |
| ATOM | 46 | CA | PHE | A | 133 | 34.574 | −22.379 | 14.657 | 1.00 | 56.14 | A | C |
| ATOM | 47 | CB | PHE | A | 133 | 34.022 | −21.100 | 15.325 | 1.00 | 60.69 | A | C |
| ATOM | 48 | CG | PHE | A | 133 | 34.580 | −19.845 | 14.736 | 1.00 | 57.21 | A | C |
| ATOM | 49 | CD1 | PHE | A | 133 | 35.865 | −19.434 | 15.067 | 1.00 | 52.42 | A | C |
| ATOM | 50 | CE1 | PHE | A | 133 | 36.415 | −18.305 | 14.463 | 1.00 | 58.27 | A | C |
| ATOM | 51 | CZ | PHE | A | 133 | 35.670 | −17.580 | 13.528 | 1.00 | 51.21 | A | C |
| ATOM | 52 | CE2 | PHE | A | 133 | 34.385 | −17.982 | 13.187 | 1.00 | 49.83 | A | C |
| ATOM | 53 | CD2 | PHE | A | 133 | 33.845 | −19.110 | 13.776 | 1.00 | 54.12 | A | C |
| ATOM | 54 | C | PHE | A | 133 | 33.882 | −23.579 | 15.264 | 1.00 | 57.61 | A | C |
| ATOM | 55 | O | PHE | A | 133 | 32.777 | −23.914 | 14.868 | 1.00 | 54.17 | A | O |
| ATOM | 56 | N | GLU | A | 134 | 34.550 | −24.180 | 16.251 | 1.00 | 61.14 | A | N |
| ATOM | 57 | CA | GLU | A | 134 | 33.964 | −25.202 | 17.111 | 1.00 | 65.13 | A | C |
| ATOM | 58 | CB | GLU | A | 134 | 35.026 | −26.240 | 17.524 | 1.00 | 71.90 | A | C |
| ATOM | 59 | CG | GLU | A | 134 | 35.764 | −26.755 | 16.281 | 1.00 | 79.69 | A | C |
| ATOM | 60 | CD | GLU | A | 134 | 36.836 | −27.786 | 16.526 | 1.00 | 78.25 | A | C |
| ATOM | 61 | OE1 | GLU | A | 134 | 37.494 | −27.737 | 17.590 | 1.00 | 75.17 | A | O |
| ATOM | 62 | OE2 | GLU | A | 134 | 37.032 | −28.613 | 15.597 | 1.00 | 76.74 | A | O |
| ATOM | 63 | C | GLU | A | 134 | 33.402 | −24.434 | 18.288 | 1.00 | 60.82 | A | C |
| ATOM | 64 | O | GLU | A | 134 | 34.135 | −23.794 | 19.044 | 1.00 | 58.89 | A | O |
| ATOM | 65 | N | ILE | A | 135 | 32.093 | −24.533 | 18.427 | 1.00 | 61.14 | A | N |
| ATOM | 66 | CA | ILE | A | 135 | 31.260 | −23.622 | 19.183 | 1.00 | 64.46 | A | C |
| ATOM | 67 | CB | ILE | A | 135 | 29.869 | −23.470 | 18.481 | 1.00 | 78.24 | A | C |
| ATOM | 68 | CG1 | ILE | A | 135 | 30.053 | −23.086 | 16.988 | 1.00 | 87.57 | A | C |
| ATOM | 69 | CD1 | ILE | A | 135 | 30.025 | −24.268 | 15.997 | 1.00 | 85.50 | A | C |
| ATOM | 70 | CG2 | ILE | A | 135 | 28.916 | −22.530 | 19.257 | 1.00 | 79.86 | A | C |
| ATOM | 71 | C | ILE | A | 135 | 31.098 | −24.252 | 20.545 | 1.00 | 64.96 | A | C |
| ATOM | 72 | O | ILE | A | 135 | 30.252 | −25.117 | 20.740 | 1.00 | 73.37 | A | O |
| ATOM | 73 | N | GLY | A | 136 | 31.924 | −23.832 | 21.489 | 1.00 | 72.80 | A | N |
| ATOM | 74 | CA | GLY | A | 136 | 31.945 | −24.425 | 22.828 | 1.00 | 70.75 | A | C |
| ATOM | 75 | C | GLY | A | 136 | 30.829 | −24.006 | 23.794 | 1.00 | 71.04 | A | C |
| ATOM | 76 | O | GLY | A | 136 | 29.648 | −23.926 | 23.440 | 1.00 | 76.11 | A | O |
| ATOM | 77 | N | ARG | A | 137 | 31.232 | −23.737 | 25.028 | 1.00 | 68.03 | A | N |
| ATOM | 78 | CA | ARG | A | 137 | 30.326 | −23.674 | 26.180 | 1.00 | 74.60 | A | C |
| ATOM | 79 | CB | ARG | A | 137 | 30.941 | −24.430 | 27.367 | 1.00 | 74.58 | A | C |
| ATOM | 80 | CG | ARG | A | 137 | 32.400 | −24.086 | 27.682 | 1.00 | 69.32 | A | C |
| ATOM | 81 | CD | ARG | A | 137 | 32.674 | −24.101 | 29.176 | 1.00 | 64.85 | A | C |
| ATOM | 82 | NE | ARG | A | 137 | 34.092 | −23.854 | 29.420 | 1.00 | 66.38 | A | N |
| ATOM | 83 | CZ | ARG | A | 137 | 34.641 | −22.805 | 30.053 | 1.00 | 60.95 | A | C |
| ATOM | 84 | NH1 | ARG | A | 137 | 33.910 | −21.832 | 30.599 | 1.00 | 58.27 | A | N |
| ATOM | 85 | NH2 | ARG | A | 137 | 35.971 | −22.756 | 30.158 | 1.00 | 56.52 | A | N |
| ATOM | 86 | C | ARG | A | 137 | 30.093 | −22.224 | 26.589 | 1.00 | 74.19 | A | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 87 | O | ARG | A | 137 | 31.028 | −21.422 | 26.500 | 1.00 | 68.74 | A | O |
| ATOM | 88 | N | PRO | A | 138 | 28.878 | −21.884 | 27.074 | 1.00 | 76.19 | A | N |
| ATOM | 89 | CA | PRO | A | 138 | 28.691 | −20.480 | 27.490 | 1.00 | 75.95 | A | C |
| ATOM | 90 | CB | PRO | A | 138 | 27.336 | −20.484 | 28.218 | 1.00 | 70.94 | A | C |
| ATOM | 91 | CG | PRO | A | 138 | 26.619 | −21.666 | 27.675 | 1.00 | 73.42 | A | C |
| ATOM | 92 | CD | PRO | A | 138 | 27.666 | −22.693 | 27.310 | 1.00 | 74.25 | A | C |
| ATOM | 93 | C | PRO | A | 138 | 29.819 | −19.970 | 28.412 | 1.00 | 75.55 | A | C |
| ATOM | 94 | O | PRO | A | 138 | 30.370 | −20.733 | 29.214 | 1.00 | 71.45 | A | O |
| ATOM | 95 | N | LEU | A | 139 | 30.212 | −18.717 | 28.201 | 1.00 | 71.75 | A | N |
| ATOM | 96 | CA | LEU | A | 139 | 31.058 | −17.984 | 29.130 | 1.00 | 66.33 | A | C |
| ATOM | 97 | CB | LEU | A | 139 | 32.083 | −17.156 | 28.367 | 1.00 | 63.74 | A | C |
| ATOM | 98 | CG | LEU | A | 139 | 33.284 | −17.902 | 27.828 | 1.00 | 63.38 | A | C |
| ATOM | 99 | CD1 | LEU | A | 139 | 34.105 | −16.972 | 26.939 | 1.00 | 58.47 | A | C |
| ATOM | 100 | CD2 | LEU | A | 139 | 34.133 | −18.452 | 28.968 | 1.00 | 56.81 | A | C |
| ATOM | 101 | C | LEU | A | 139 | 30.171 | −17.076 | 29.972 | 1.00 | 64.02 | A | C |
| ATOM | 102 | O | LEU | A | 139 | 30.286 | −17.062 | 31.187 | 1.00 | 72.52 | A | O |
| ATOM | 103 | N | GLY | A | 140 | 29.304 | −16.308 | 29.309 | 1.00 | 65.30 | A | N |
| ATOM | 104 | CA | GLY | A | 140 | 28.346 | −15.420 | 29.974 | 1.00 | 61.45 | A | C |
| ATOM | 105 | C | GLY | A | 140 | 27.133 | −15.173 | 29.091 | 1.00 | 64.62 | A | C |
| ATOM | 106 | O | GLY | A | 140 | 27.186 | −15.396 | 27.879 | 1.00 | 74.97 | A | O |
| ATOM | 107 | N | LYS | A | 141 | 26.035 | −14.734 | 29.697 | 1.00 | 64.13 | A | N |
| ATOM | 108 | CA | LYS | A | 141 | 24.913 | −14.166 | 28.945 | 1.00 | 66.53 | A | C |
| ATOM | 109 | CB | LYS | A | 141 | 23.569 | −14.487 | 29.618 | 1.00 | 67.81 | A | C |
| ATOM | 110 | CG | LYS | A | 141 | 22.368 | −14.201 | 28.716 | 1.00 | 76.41 | A | C |
| ATOM | 111 | CD | LYS | A | 141 | 21.069 | −14.927 | 29.086 | 1.00 | 77.68 | A | C |
| ATOM | 112 | CE | LYS | A | 141 | 20.234 | −14.177 | 30.118 | 1.00 | 76.00 | A | C |
| ATOM | 113 | NZ | LYS | A | 141 | 20.751 | −14.374 | 31.503 | 1.00 | 73.84 | A | N |
| ATOM | 114 | C | LYS | A | 141 | 25.108 | −12.635 | 28.753 | 1.00 | 65.52 | A | C |
| ATOM | 115 | O | LYS | A | 141 | 25.308 | −11.875 | 29.720 | 1.00 | 52.75 | A | O |
| ATOM | 116 | N | GLY | A | 142 | 25.097 | −12.197 | 27.495 | 1.00 | 63.80 | A | N |
| ATOM | 117 | CA | GLY | A | 142 | 24.950 | −10.770 | 27.166 | 1.00 | 62.83 | A | C |
| ATOM | 118 | C | GLY | A | 142 | 23.484 | −10.369 | 27.171 | 1.00 | 62.99 | A | C |
| ATOM | 119 | O | GLY | A | 142 | 22.595 | −11.237 | 27.269 | 1.00 | 57.86 | A | O |
| ATOM | 120 | N | LYS | A | 143 | 23.222 | −9.059 | 27.078 | 1.00 | 63.85 | A | N |
| ATOM | 121 | CA | LYS | A | 143 | 21.840 | −8.567 | 26.970 | 1.00 | 67.06 | A | C |
| ATOM | 122 | CB | LYS | A | 143 | 21.762 | −7.032 | 27.004 | 1.00 | 70.34 | A | C |
| ATOM | 123 | CG | LYS | A | 143 | 20.357 | −6.489 | 26.706 | 1.00 | 76.65 | A | C |
| ATOM | 124 | CD | LYS | A | 143 | 20.129 | −5.041 | 27.128 | 1.00 | 78.62 | A | C |
| ATOM | 125 | CE | LYS | A | 143 | 18.762 | −4.559 | 26.646 | 1.00 | 77.98 | A | C |
| ATOM | 126 | NZ | LYS | A | 143 | 18.418 | −3.176 | 27.095 | 1.00 | 76.49 | A | N |
| ATOM | 127 | C | LYS | A | 143 | 21.175 | −9.095 | 25.703 | 1.00 | 65.11 | A | C |
| ATOM | 128 | O | LYS | A | 143 | 19.984 | −9.374 | 25.715 | 1.00 | 54.66 | A | O |
| ATOM | 129 | N | PHE | A | 144 | 21.955 | −9.193 | 24.615 | 1.00 | 65.71 | A | N |
| ATOM | 130 | CA | PHE | A | 144 | 21.431 | −9.495 | 23.270 | 1.00 | 63.82 | A | C |
| ATOM | 131 | CB | PHE | A | 144 | 21.899 | −8.426 | 22.245 | 1.00 | 58.70 | A | C |
| ATOM | 132 | CG | PHE | A | 144 | 21.349 | −7.055 | 22.553 | 1.00 | 63.56 | A | C |
| ATOM | 133 | CD1 | PHE | A | 144 | 20.085 | −6.681 | 22.106 | 1.00 | 59.80 | A | C |
| ATOM | 134 | CE1 | PHE | A | 144 | 19.549 | −5.450 | 22.438 | 1.00 | 64.30 | A | C |
| ATOM | 135 | CZ | PHE | A | 144 | 20.255 | −4.588 | 23.268 | 1.00 | 64.21 | A | C |
| ATOM | 136 | CE2 | PHE | A | 144 | 21.505 | −4.963 | 23.747 | 1.00 | 64.14 | A | C |
| ATOM | 137 | CD2 | PHE | A | 144 | 22.042 | −6.190 | 23.395 | 1.00 | 60.84 | A | C |
| ATOM | 138 | C | PHE | A | 144 | 21.705 | −10.935 | 22.820 | 1.00 | 62.38 | A | C |
| ATOM | 139 | O | PHE | A | 144 | 21.109 | −11.397 | 21.835 | 1.00 | 65.62 | A | O |
| ATOM | 140 | N | GLY | A | 145 | 22.564 | −11.648 | 23.546 | 1.00 | 54.73 | A | N |
| ATOM | 141 | CA | GLY | A | 145 | 22.658 | −13.101 | 23.393 | 1.00 | 60.26 | A | C |
| ATOM | 142 | C | GLY | A | 145 | 23.687 | −13.659 | 24.342 | 1.00 | 59.89 | A | C |
| ATOM | 143 | O | GLY | A | 145 | 23.909 | −13.092 | 25.403 | 1.00 | 69.16 | A | O |
| ATOM | 144 | N | ASN | A | 146 | 24.339 | −14.749 | 23.958 | 1.00 | 56.86 | A | N |
| ATOM | 145 | CA | ASN | A | 146 | 25.426 | −15.302 | 24.762 | 1.00 | 53.85 | A | C |
| ATOM | 146 | CB | ASN | A | 146 | 25.214 | −16.784 | 25.036 | 1.00 | 63.57 | A | C |
| ATOM | 147 | CG | ASN | A | 146 | 23.806 | −17.100 | 25.481 | 1.00 | 66.75 | A | C |
| ATOM | 148 | OD1 | ASN | A | 146 | 23.142 | −16.302 | 26.159 | 1.00 | 69.52 | A | O |
| ATOM | 149 | ND2 | ASN | A | 146 | 23.325 | −18.270 | 25.073 | 1.00 | 67.89 | A | N |
| ATOM | 150 | C | ASN | A | 146 | 26.779 | −15.144 | 24.144 | 1.00 | 49.32 | A | C |
| ATOM | 151 | O | ASN | A | 146 | 26.911 | −14.874 | 22.949 | 1.00 | 49.25 | A | O |
| ATOM | 152 | N | VAL | A | 147 | 27.788 | −15.339 | 24.983 | 1.00 | 46.18 | A | N |
| ATOM | 153 | CA | VAL | A | 147 | 29.171 | −15.413 | 24.561 | 1.00 | 50.23 | A | C |
| ATOM | 154 | CB | VAL | A | 147 | 30.075 | −14.410 | 25.297 | 1.00 | 48.29 | A | C |
| ATOM | 155 | CG1 | VAL | A | 147 | 31.424 | −14.311 | 24.589 | 1.00 | 48.13 | A | C |
| ATOM | 156 | CG2 | VAL | A | 147 | 29.393 | −13.059 | 25.424 | 1.00 | 49.48 | A | C |
| ATOM | 157 | C | VAL | A | 147 | 29.632 | −16.808 | 24.903 | 1.00 | 56.63 | A | C |
| ATOM | 158 | O | VAL | A | 147 | 29.229 | −17.345 | 25.939 | 1.00 | 62.28 | A | O |
| ATOM | 159 | N | TYR | A | 148 | 30.467 | −17.373 | 24.020 | 1.00 | 58.61 | A | N |
| ATOM | 160 | CA | TYR | A | 148 | 30.870 | −18.775 | 24.030 | 1.00 | 54.09 | A | C |
| ATOM | 161 | CB | TYR | A | 148 | 30.229 | −19.526 | 22.834 | 1.00 | 53.40 | A | C |
| ATOM | 162 | CG | TYR | A | 148 | 28.712 | −19.609 | 22.853 | 1.00 | 48.22 | A | C |
| ATOM | 163 | CD1 | TYR | A | 148 | 28.058 | −20.472 | 23.721 | 1.00 | 48.30 | A | C |
| ATOM | 164 | CE1 | TYR | A | 148 | 26.670 | −20.559 | 23.748 | 1.00 | 50.90 | A | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 165 | CZ | TYR | A | 148 | 25.910 | −19.783 | 22.901 | 1.00 | 53.89 | A | C |
| ATOM | 166 | OH | TYR | A | 148 | 24.527 | −19.854 | 22.955 | 1.00 | 50.85 | A | O |
| ATOM | 167 | CE2 | TYR | A | 148 | 26.542 | −18.917 | 22.016 | 1.00 | 53.84 | A | C |
| ATOM | 168 | CD2 | TYR | A | 148 | 27.935 | −18.837 | 22.005 | 1.00 | 52.05 | A | C |
| ATOM | 169 | C | TYR | A | 148 | 32.381 | −18.829 | 23.884 | 1.00 | 55.88 | A | C |
| ATOM | 170 | O | TYR | A | 148 | 32.960 | −18.036 | 23.115 | 1.00 | 54.47 | A | O |
| ATOM | 171 | N | LEU | A | 149 | 33.022 | −19.761 | 24.600 | 1.00 | 55.80 | A | N |
| ATOM | 172 | CA | LEU | A | 149 | 34.396 | −20.205 | 24.255 | 1.00 | 62.00 | A | C |
| ATOM | 173 | CB | LEU | A | 149 | 34.955 | −21.213 | 25.282 | 1.00 | 64.62 | A | C |
| ATOM | 174 | CG | LEU | A | 149 | 36.467 | −21.488 | 25.412 | 1.00 | 66.95 | A | C |
| ATOM | 175 | CD1 | LEU | A | 149 | 37.037 | −22.219 | 24.201 | 1.00 | 74.18 | A | C |
| ATOM | 176 | CD2 | LEU | A | 149 | 37.288 | −20.233 | 25.704 | 1.00 | 67.76 | A | C |
| ATOM | 177 | C | LEU | A | 149 | 34.298 | −20.834 | 22.858 | 1.00 | 57.58 | A | C |
| ATOM | 178 | O | LEU | A | 149 | 33.261 | −21.422 | 22.506 | 1.00 | 61.43 | A | O |
| ATOM | 179 | N | ALA | A | 150 | 35.326 | −20.630 | 22.045 | 1.00 | 54.07 | A | N |
| ATOM | 180 | CA | ALA | A | 150 | 35.332 | −21.124 | 20.689 | 1.00 | 53.27 | A | C |
| ATOM | 181 | CB | ALA | A | 150 | 34.635 | −20.147 | 19.758 | 1.00 | 58.82 | A | C |
| ATOM | 182 | C | ALA | A | 150 | 36.736 | −21.353 | 20.222 | 1.00 | 56.80 | A | C |
| ATOM | 183 | O | ALA | A | 150 | 37.661 | −20.783 | 20.746 | 1.00 | 49.08 | A | O |
| ATOM | 184 | N | ARG | A | 151 | 36.869 | −22.240 | 19.239 | 1.00 | 64.11 | A | N |
| ATOM | 185 | CA | ARG | A | 151 | 38.143 | −22.622 | 18.674 | 1.00 | 64.11 | A | C |
| ATOM | 186 | CB | ARG | A | 151 | 38.431 | −24.102 | 18.971 | 1.00 | 68.72 | A | C |
| ATOM | 187 | CG | ARG | A | 151 | 38.647 | −24.411 | 20.445 | 1.00 | 77.86 | A | C |
| ATOM | 188 | CD | ARG | A | 151 | 38.144 | −25.790 | 20.864 | 1.00 | 87.39 | A | C |
| ATOM | 189 | NE | ARG | A | 151 | 37.472 | −25.753 | 22.171 | 1.00 | 95.09 | A | N |
| ATOM | 190 | CZ | ARG | A | 151 | 36.186 | −25.431 | 22.390 | 1.00 | 94.72 | A | C |
| ATOM | 191 | NH1 | ARG | A | 151 | 35.717 | −25.443 | 23.641 | 1.00 | 94.57 | A | N |
| ATOM | 192 | NH2 | ARG | A | 151 | 35.358 | −25.092 | 21.391 | 1.00 | 87.98 | A | N |
| ATOM | 193 | C | ARG | A | 151 | 37.981 | −22.437 | 17.192 | 1.00 | 63.25 | A | C |
| ATOM | 194 | O | ARG | A | 151 | 36.943 | −22.850 | 16.626 | 1.00 | 57.38 | A | O |
| ATOM | 195 | N | GLU | A | 152 | 38.985 | −21.827 | 16.560 | 1.00 | 59.70 | A | N |
| ATOM | 196 | CA | GLU | A | 152 | 39.063 | −21.834 | 15.100 | 1.00 | 58.99 | A | C |
| ATOM | 197 | CB | GLU | A | 152 | 40.165 | −20.895 | 14.632 | 1.00 | 54.44 | A | C |
| ATOM | 198 | CG | GLU | A | 152 | 40.182 | −20.708 | 13.114 | 1.00 | 63.81 | A | C |
| ATOM | 199 | CD | GLU | A | 152 | 41.071 | −21.696 | 12.375 | 1.00 | 63.64 | A | C |
| ATOM | 200 | OE1 | GLU | A | 152 | 42.239 | −21.893 | 12.790 | 1.00 | 57.40 | A | O |
| ATOM | 201 | OE2 | GLU | A | 152 | 40.589 | −22.266 | 11.372 | 1.00 | 66.74 | A | O |
| ATOM | 202 | C | GLU | A | 152 | 39.379 | −23.286 | 14.674 | 1.00 | 57.70 | A | C |
| ATOM | 203 | O | GLU | A | 152 | 40.347 | −23.843 | 15.180 | 1.00 | 52.72 | A | O |
| ATOM | 204 | N | LYS | A | 153 | 38.576 | −23.866 | 13.768 | 1.00 | 62.40 | A | N |
| ATOM | 205 | CA | LYS | A | 153 | 38.659 | −25.323 | 13.387 | 1.00 | 62.67 | A | C |
| ATOM | 206 | CB | LYS | A | 153 | 37.696 | −25.677 | 12.244 | 1.00 | 60.08 | A | C |
| ATOM | 207 | CG | LYS | A | 153 | 36.247 | −25.986 | 12.636 | 1.00 | 62.08 | A | C |
| ATOM | 208 | CD | LYS | A | 153 | 35.630 | −26.977 | 11.642 | 1.00 | 61.40 | A | C |
| ATOM | 209 | CE | LYS | A | 153 | 34.109 | −27.123 | 11.669 | 1.00 | 64.93 | A | C |
| ATOM | 210 | NZ | LYS | A | 153 | 33.378 | −26.441 | 12.774 | 1.00 | 64.90 | A | N |
| ATOM | 211 | C | LYS | A | 153 | 40.047 | −25.835 | 12.994 | 1.00 | 57.27 | A | C |
| ATOM | 212 | O | LYS | A | 153 | 40.583 | −26.705 | 13.662 | 1.00 | 62.00 | A | O |
| ATOM | 213 | N | GLN | A | 154 | 40.616 | −25.286 | 11.926 | 1.00 | 59.48 | A | N |
| ATOM | 214 | CA | GLN | A | 154 | 41.921 | −25.731 | 11.410 | 1.00 | 64.38 | A | C |
| ATOM | 215 | CB | GLN | A | 154 | 42.248 | −25.057 | 10.074 | 1.00 | 63.08 | A | C |
| ATOM | 216 | CG | GLN | A | 154 | 41.363 | −25.517 | 8.921 | 1.00 | 68.91 | A | C |
| ATOM | 217 | CD | GLN | A | 154 | 41.606 | −24.738 | 7.620 | 1.00 | 72.40 | A | C |
| ATOM | 218 | OE1 | GLN | A | 154 | 42.660 | −24.128 | 7.418 | 1.00 | 60.67 | A | O |
| ATOM | 219 | NE2 | GLN | A | 154 | 40.614 | −24.755 | 6.737 | 1.00 | 71.38 | A | N |
| ATOM | 220 | C | GLN | A | 154 | 43.128 | −25.561 | 12.351 | 1.00 | 74.66 | A | C |
| ATOM | 221 | O | GLN | A | 154 | 44.148 | −26.234 | 12.147 | 1.00 | 78.66 | A | O |
| ATOM | 222 | N | SER | A | 155 | 43.055 | −24.663 | 13.339 | 1.00 | 74.99 | A | N |
| ATOM | 223 | CA | SER | A | 155 | 44.188 | −24.476 | 14.279 | 1.00 | 73.27 | A | C |
| ATOM | 224 | CB | SER | A | 155 | 44.860 | −23.102 | 14.081 | 1.00 | 70.49 | A | C |
| ATOM | 225 | OG | SER | A | 155 | 44.058 | −22.041 | 14.579 | 1.00 | 68.17 | A | O |
| ATOM | 226 | C | SER | A | 155 | 43.847 | −24.700 | 15.755 | 1.00 | 71.14 | A | C |
| ATOM | 227 | O | SER | A | 155 | 44.766 | −24.782 | 16.587 | 1.00 | 65.11 | A | O |
| ATOM | 228 | N | LYS | A | 156 | 42.554 | −24.792 | 16.091 | 1.00 | 64.92 | A | N |
| ATOM | 229 | CA | LYS | A | 156 | 42.123 | −24.939 | 17.490 | 1.00 | 70.57 | A | C |
| ATOM | 230 | CB | LYS | A | 156 | 42.751 | −26.219 | 18.110 | 1.00 | 74.82 | A | C |
| ATOM | 231 | CG | LYS | A | 156 | 41.979 | −26.876 | 19.248 | 1.00 | 83.21 | A | C |
| ATOM | 232 | CD | LYS | A | 156 | 40.602 | −27.358 | 18.799 | 1.00 | 93.26 | A | C |
| ATOM | 233 | CE | LYS | A | 156 | 40.090 | −28.482 | 19.692 | 1.00 | 99.27 | A | C |
| ATOM | 234 | NZ | LYS | A | 156 | 38.693 | −28.877 | 19.353 | 1.00 | 96.41 | A | N |
| ATOM | 235 | C | LYS | A | 156 | 42.417 | −23.690 | 18.384 | 1.00 | 70.16 | A | C |
| ATOM | 236 | O | LYS | A | 156 | 42.182 | −23.743 | 19.608 | 1.00 | 64.52 | A | O |
| ATOM | 237 | N | PHE | A | 157 | 42.895 | −22.583 | 17.784 | 1.00 | 65.63 | A | N |
| ATOM | 238 | CA | PHE | A | 157 | 43.235 | −21.361 | 18.527 | 1.00 | 64.89 | A | C |
| ATOM | 239 | CB | PHE | A | 157 | 43.872 | −20.313 | 17.608 | 1.00 | 67.79 | A | C |
| ATOM | 240 | CG | PHE | A | 157 | 44.323 | −19.056 | 18.311 | 1.00 | 65.08 | A | C |
| ATOM | 241 | CD1 | PHE | A | 157 | 45.575 | −18.993 | 18.923 | 1.00 | 61.83 | A | C |
| ATOM | 242 | CE1 | PHE | A | 157 | 46.007 | −17.828 | 19.546 | 1.00 | 62.39 | A | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 243 | CZ | PHE | A | 157 | 45.187 | −16.701 | 19.553 | 1.00 | 61.10 | A | C |
| ATOM | 244 | CE2 | PHE | A | 157 | 43.937 | −16.750 | 18.957 | 1.00 | 58.94 | A | C |
| ATOM | 245 | CD2 | PHE | A | 157 | 43.515 | −17.906 | 18.320 | 1.00 | 66.24 | A | C |
| ATOM | 246 | C | PHE | A | 157 | 41.976 | −20.795 | 19.175 | 1.00 | 55.17 | A | C |
| ATOM | 247 | O | PHE | A | 157 | 40.891 | −20.777 | 18.568 | 1.00 | 48.55 | A | O |
| ATOM | 248 | N | ILE | A | 158 | 42.153 | −20.363 | 20.421 | 1.00 | 52.63 | A | N |
| ATOM | 249 | CA | ILE | A | 158 | 41.068 | −20.129 | 21.346 | 1.00 | 57.73 | A | C |
| ATOM | 250 | CB | ILE | A | 158 | 41.519 | −20.474 | 22.806 | 1.00 | 68.34 | A | C |
| ATOM | 251 | CG1 | ILE | A | 158 | 42.125 | −21.908 | 22.923 | 1.00 | 68.92 | A | C |
| ATOM | 252 | CD1 | ILE | A | 158 | 41.139 | −23.054 | 22.800 | 1.00 | 72.40 | A | C |
| ATOM | 253 | CG2 | ILE | A | 158 | 40.386 | −20.253 | 23.820 | 1.00 | 68.19 | A | C |
| ATOM | 254 | C | ILE | A | 158 | 40.644 | −18.645 | 21.261 | 1.00 | 51.40 | A | C |
| ATOM | 255 | O | ILE | A | 158 | 41.474 | −17.762 | 21.436 | 1.00 | 51.14 | A | O |
| ATOM | 256 | N | LEU | A | 159 | 39.361 | −18.418 | 21.000 | 1.00 | 46.81 | A | N |
| ATOM | 257 | CA | LEU | A | 159 | 38.736 | −17.090 | 20.866 | 1.00 | 53.46 | A | C |
| ATOM | 258 | CB | LEU | A | 159 | 38.524 | −16.732 | 19.395 | 1.00 | 46.59 | A | C |
| ATOM | 259 | CG | LEU | A | 159 | 39.680 | −16.749 | 18.422 | 1.00 | 45.94 | A | C |
| ATOM | 260 | CD1 | LEU | A | 159 | 39.076 | −16.836 | 17.036 | 1.00 | 47.27 | A | C |
| ATOM | 261 | CD2 | LEU | A | 159 | 40.616 | −15.550 | 18.544 | 1.00 | 50.40 | A | C |
| ATOM | 262 | C | LEU | A | 159 | 37.351 | −17.098 | 21.491 | 1.00 | 52.68 | A | C |
| ATOM | 263 | O | LEU | A | 159 | 36.792 | −18.151 | 21.714 | 1.00 | 60.15 | A | O |
| ATOM | 264 | N | ALA | A | 160 | 36.768 | −15.930 | 21.722 | 1.00 | 48.17 | A | N |
| ATOM | 265 | CA | ALA | A | 160 | 35.404 | −15.886 | 22.228 | 1.00 | 49.44 | A | C |
| ATOM | 266 | CB | ALA | A | 160 | 35.273 | −14.893 | 23.362 | 1.00 | 47.51 | A | C |
| ATOM | 267 | C | ALA | A | 160 | 34.535 | −15.484 | 21.103 | 1.00 | 47.21 | A | C |
| ATOM | 268 | O | ALA | A | 160 | 34.935 | −14.664 | 20.318 | 1.00 | 52.84 | A | O |
| ATOM | 269 | N | LEU | A | 161 | 33.335 | −16.030 | 21.052 | 1.00 | 49.12 | A | N |
| ATOM | 270 | CA | LEU | A | 161 | 32.375 | −15.666 | 20.048 | 1.00 | 46.38 | A | C |
| ATOM | 271 | CB | LEU | A | 161 | 32.051 | −16.853 | 19.182 | 1.00 | 48.65 | A | C |
| ATOM | 272 | CG | LEU | A | 161 | 31.104 | −16.568 | 18.005 | 1.00 | 52.91 | A | C |
| ATOM | 273 | CD1 | LEU | A | 161 | 31.929 | −16.175 | 16.793 | 1.00 | 49.68 | A | C |
| ATOM | 274 | CD2 | LEU | A | 161 | 30.202 | −17.758 | 17.679 | 1.00 | 52.08 | A | C |
| ATOM | 275 | C | LEU | A | 161 | 31.093 | −15.133 | 20.676 | 1.00 | 50.80 | A | C |
| ATOM | 276 | O | LEU | A | 161 | 30.365 | −15.879 | 21.383 | 1.00 | 51.63 | A | O |
| ATOM | 277 | N | LYS | A | 162 | 30.792 | −13.868 | 20.356 | 1.00 | 46.94 | A | N |
| ATOM | 278 | CA | LYS | A | 162 | 29.667 | −13.145 | 20.950 | 1.00 | 48.47 | A | C |
| ATOM | 279 | CB | LYS | A | 162 | 30.042 | −11.697 | 21.228 | 1.00 | 47.24 | A | C |
| ATOM | 280 | CG | LYS | A | 162 | 28.987 | −10.876 | 21.964 | 1.00 | 45.31 | A | C |
| ATOM | 281 | CD | LYS | A | 162 | 29.683 | −9.886 | 22.874 | 1.00 | 49.65 | A | C |
| ATOM | 282 | CE | LYS | A | 162 | 28.743 | −8.820 | 23.403 | 1.00 | 53.66 | A | C |
| ATOM | 283 | NZ | LYS | A | 162 | 29.464 | −7.585 | 23.830 | 1.00 | 51.73 | A | N |
| ATOM | 284 | C | LYS | A | 162 | 28.578 | −13.177 | 19.973 | 1.00 | 44.94 | A | C |
| ATOM | 285 | O | LYS | A | 162 | 28.833 | −12.877 | 18.825 | 1.00 | 51.75 | A | O |
| ATOM | 286 | N | VAL | A | 163 | 27.371 | −13.517 | 20.440 | 1.00 | 43.28 | A | N |
| ATOM | 287 | CA | VAL | A | 163 | 26.156 | −13.556 | 19.652 | 1.00 | 47.71 | A | C |
| ATOM | 288 | CB | VAL | A | 163 | 25.426 | −14.911 | 19.917 | 1.00 | 55.47 | A | C |
| ATOM | 289 | CG1 | VAL | A | 163 | 23.999 | −14.939 | 19.348 | 1.00 | 55.19 | A | C |
| ATOM | 290 | CG2 | VAL | A | 163 | 26.272 | −16.068 | 19.404 | 1.00 | 52.70 | A | C |
| ATOM | 291 | C | VAL | A | 163 | 25.241 | −12.401 | 20.063 | 1.00 | 47.07 | A | C |
| ATOM | 292 | O | VAL | A | 163 | 25.210 | −12.050 | 21.228 | 1.00 | 55.99 | A | O |
| ATOM | 293 | N | LEU | A | 164 | 24.533 | −11.796 | 19.107 | 1.00 | 45.14 | A | N |
| ATOM | 294 | CA | LEU | A | 164 | 23.444 | −10.847 | 19.409 | 1.00 | 45.49 | A | C |
| ATOM | 295 | CB | LEU | A | 164 | 23.913 | −9.380 | 19.266 | 1.00 | 47.08 | A | C |
| ATOM | 296 | CG | LEU | A | 164 | 25.215 | −8.962 | 19.983 | 1.00 | 46.05 | A | C |
| ATOM | 297 | CD1 | LEU | A | 164 | 26.407 | −9.082 | 19.081 | 1.00 | 44.84 | A | C |
| ATOM | 298 | CD2 | LEU | A | 164 | 25.143 | −7.513 | 20.497 | 1.00 | 52.68 | A | C |
| ATOM | 299 | C | LEU | A | 164 | 22.235 | −11.053 | 18.516 | 1.00 | 47.06 | A | C |
| ATOM | 300 | O | LEU | A | 164 | 22.374 | −11.076 | 17.296 | 1.00 | 57.29 | A | O |
| ATOM | 301 | N | PHE | A | 165 | 21.042 | −11.143 | 19.106 | 1.00 | 49.17 | A | N |
| ATOM | 302 | CA | PHE | A | 165 | 19.833 | −11.460 | 18.342 | 1.00 | 56.01 | A | C |
| ATOM | 303 | CB | PHE | A | 165 | 18.724 | −12.147 | 19.195 | 1.00 | 56.17 | A | C |
| ATOM | 304 | CG | PHE | A | 165 | 18.918 | −13.646 | 19.354 | 1.00 | 59.42 | A | C |
| ATOM | 305 | CD1 | PHE | A | 165 | 18.386 | −14.532 | 18.427 | 1.00 | 66.56 | A | C |
| ATOM | 306 | CE1 | PHE | A | 165 | 18.586 | −15.906 | 18.555 | 1.00 | 69.91 | A | C |
| ATOM | 307 | CZ | PHE | A | 165 | 19.339 | −16.409 | 19.610 | 1.00 | 62.55 | A | C |
| ATOM | 308 | CE2 | PHE | A | 165 | 19.876 | −15.539 | 20.542 | 1.00 | 63.79 | A | C |
| ATOM | 309 | CD2 | PHE | A | 165 | 19.672 | −14.166 | 20.408 | 1.00 | 62.38 | A | C |
| ATOM | 310 | C | PHE | A | 165 | 19.296 | −10.209 | 17.649 | 1.00 | 62.39 | A | C |
| ATOM | 311 | O | PHE | A | 165 | 18.937 | −9.191 | 18.285 | 1.00 | 62.53 | A | O |
| ATOM | 312 | N | LYS | A | 166 | 19.221 | −10.321 | 16.332 | 1.00 | 58.18 | A | N |
| ATOM | 313 | CA | LYS | A | 166 | 18.736 | −9.263 | 15.489 | 1.00 | 59.02 | A | C |
| ATOM | 314 | CB | LYS | A | 166 | 18.681 | −9.722 | 14.037 | 1.00 | 56.59 | A | C |
| ATOM | 315 | CG | LYS | A | 166 | 20.057 | −9.880 | 13.386 | 1.00 | 55.81 | A | C |
| ATOM | 316 | CD | LYS | A | 166 | 19.878 | −9.966 | 11.889 | 1.00 | 58.26 | A | C |
| ATOM | 317 | CE | LYS | A | 166 | 21.156 | −10.236 | 11.129 | 1.00 | 61.22 | A | C |
| ATOM | 318 | NZ | LYS | A | 166 | 20.819 | −10.295 | 9.679 | 1.00 | 67.92 | A | N |
| ATOM | 319 | C | LYS | A | 166 | 17.382 | −8.709 | 15.915 | 1.00 | 66.31 | A | C |
| ATOM | 320 | O | LYS | A | 166 | 17.189 | −7.483 | 15.872 | 1.00 | 75.04 | A | O |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 321 | N | ALA | A | 167 | 16.464 | −9.569 | 16.355 | 1.00 | 59.53 | A | N |
| ATOM | 322 | CA | ALA | A | 167 | 15.133 | −9.090 | 16.722 | 1.00 | 64.46 | A | C |
| ATOM | 323 | CB | ALA | A | 167 | 14.172 | −10.233 | 17.025 | 1.00 | 64.14 | A | C |
| ATOM | 324 | C | ALA | A | 167 | 15.210 | −8.134 | 17.887 | 1.00 | 62.61 | A | C |
| ATOM | 325 | O | ALA | A | 167 | 14.516 | −7.113 | 17.900 | 1.00 | 71.35 | A | O |
| ATOM | 326 | N | GLN | A | 168 | 16.077 | −8.441 | 18.843 | 1.00 | 69.67 | A | N |
| ATOM | 327 | CA | GLN | A | 168 | 16.255 | −7.579 | 20.019 | 1.00 | 73.01 | A | C |
| ATOM | 328 | CB | GLN | A | 168 | 17.004 | −8.327 | 21.116 | 1.00 | 77.84 | A | C |
| ATOM | 329 | CG | GLN | A | 168 | 16.302 | −9.594 | 21.596 | 1.00 | 78.31 | A | C |
| ATOM | 330 | CD | GLN | A | 168 | 17.158 | −10.404 | 22.538 | 1.00 | 72.58 | A | C |
| ATOM | 331 | OE1 | GLN | A | 168 | 17.279 | −11.617 | 22.388 | 1.00 | 67.72 | A | O |
| ATOM | 332 | NE2 | GLN | A | 168 | 17.762 | −9.735 | 23.520 | 1.00 | 76.26 | A | N |
| ATOM | 333 | C | GLN | A | 168 | 16.989 | −6.288 | 19.658 | 1.00 | 66.10 | A | C |
| ATOM | 334 | O | GLN | A | 168 | 16.526 | −5.205 | 20.010 | 1.00 | 69.95 | A | O |
| ATOM | 335 | N | LEU | A | 169 | 18.117 | −6.412 | 18.944 | 1.00 | 63.72 | A | N |
| ATOM | 336 | CA | LEU | A | 169 | 18.844 | −5.250 | 18.382 | 1.00 | 57.91 | A | C |
| ATOM | 337 | CB | LEU | A | 169 | 19.904 | −5.696 | 17.354 | 1.00 | 60.55 | A | C |
| ATOM | 338 | CG | LEU | A | 169 | 21.178 | −6.436 | 17.807 | 1.00 | 56.55 | A | C |
| ATOM | 339 | CD1 | LEU | A | 169 | 22.098 | −6.660 | 16.631 | 1.00 | 58.26 | A | C |
| ATOM | 340 | CD2 | LEU | A | 169 | 21.976 | −5.717 | 18.892 | 1.00 | 59.44 | A | C |
| ATOM | 341 | C | LEU | A | 169 | 17.884 | −4.257 | 17.727 | 1.00 | 53.30 | A | C |
| ATOM | 342 | O | LEU | A | 169 | 17.939 | −3.085 | 18.029 | 1.00 | 54.68 | A | O |
| ATOM | 343 | N | GLU | A | 170 | 16.977 | −4.759 | 16.882 | 1.00 | 60.99 | A | N |
| ATOM | 344 | CA | GLU | A | 170 | 15.934 | −3.951 | 16.209 | 1.00 | 67.80 | A | C |
| ATOM | 345 | CB | GLU | A | 170 | 15.041 | −4.805 | 15.273 | 1.00 | 80.26 | A | C |
| ATOM | 346 | CG | GLU | A | 170 | 15.588 | −4.996 | 13.833 | 1.00 | 83.75 | A | C |
| ATOM | 347 | CD | GLU | A | 170 | 15.348 | −6.393 | 13.199 | 1.00 | 85.95 | A | C |
| ATOM | 348 | OE1 | GLU | A | 170 | 14.466 | −7.165 | 13.664 | 1.00 | 89.32 | A | O |
| ATOM | 349 | OE2 | GLU | A | 170 | 16.053 | −6.733 | 12.208 | 1.00 | 67.14 | A | O |
| ATOM | 350 | C | GLU | A | 170 | 15.074 | −3.222 | 17.211 | 1.00 | 71.50 | A | C |
| ATOM | 351 | O | GLU | A | 170 | 14.935 | −2.005 | 17.133 | 1.00 | 70.71 | A | O |
| ATOM | 352 | N | LYS | A | 171 | 14.541 | −3.948 | 18.183 | 1.00 | 75.74 | A | N |
| ATOM | 353 | CA | LYS | A | 171 | 13.631 | −3.328 | 19.164 | 1.00 | 80.42 | A | C |
| ATOM | 354 | CB | LYS | A | 171 | 12.767 | −4.378 | 19.915 | 1.00 | 87.26 | A | C |
| ATOM | 355 | CG | LYS | A | 171 | 11.666 | −5.076 | 19.098 | 1.00 | 91.20 | A | C |
| ATOM | 356 | CD | LYS | A | 171 | 11.055 | −4.283 | 17.928 | 1.00 | 97.91 | A | C |
| ATOM | 357 | CE | LYS | A | 171 | 10.419 | −2.933 | 18.291 | 1.00 | 103.39 | A | C |
| ATOM | 358 | NZ | LYS | A | 171 | 9.692 | −2.905 | 19.592 | 1.00 | 109.94 | A | N |
| ATOM | 359 | C | LYS | A | 171 | 14.294 | −2.374 | 20.153 | 1.00 | 63.55 | A | C |
| ATOM | 360 | O | LYS | A | 171 | 13.662 | −1.386 | 20.559 | 1.00 | 69.29 | A | O |
| ATOM | 361 | N | ALA | A | 172 | 15.539 | −2.639 | 20.538 | 1.00 | 52.04 | A | N |
| ATOM | 362 | CA | ALA | A | 172 | 16.296 | −1.636 | 21.318 | 1.00 | 51.31 | A | C |
| ATOM | 363 | CB | ALA | A | 172 | 17.476 | −2.272 | 22.019 | 1.00 | 55.05 | A | C |
| ATOM | 364 | C | ALA | A | 172 | 16.777 | −0.421 | 20.495 | 1.00 | 52.03 | A | C |
| ATOM | 365 | O | ALA | A | 172 | 17.264 | 0.551 | 21.067 | 1.00 | 56.39 | A | O |
| ATOM | 366 | N | GLY | A | 173 | 16.686 | −0.506 | 19.165 | 1.00 | 55.85 | A | N |
| ATOM | 367 | CA | GLY | A | 173 | 17.026 | 0.575 | 18.272 | 1.00 | 50.88 | A | C |
| ATOM | 368 | C | GLY | A | 173 | 18.497 | 0.928 | 18.262 | 1.00 | 48.51 | A | C |
| ATOM | 369 | O | GLY | A | 173 | 18.865 | 2.120 | 18.171 | 1.00 | 45.22 | A | O |
| ATOM | 370 | N | VAL | A | 174 | 19.317 | −0.115 | 18.307 | 1.00 | 46.77 | A | N |
| ATOM | 371 | CA | VAL | A | 174 | 20.772 | −0.045 | 18.512 | 1.00 | 45.78 | A | C |
| ATOM | 372 | CB | VAL | A | 174 | 21.091 | −0.600 | 19.931 | 1.00 | 54.97 | A | C |
| ATOM | 373 | CG1 | VAL | A | 174 | 20.765 | −2.105 | 20.048 | 1.00 | 59.17 | A | C |
| ATOM | 374 | CG2 | VAL | A | 174 | 22.530 | −0.346 | 20.320 | 1.00 | 61.88 | A | C |
| ATOM | 375 | C | VAL | A | 174 | 21.563 | −0.830 | 17.405 | 1.00 | 44.96 | A | C |
| ATOM | 376 | O | VAL | A | 174 | 22.803 | −0.909 | 17.416 | 1.00 | 40.35 | A | O |
| ATOM | 377 | N | GLU | A | 175 | 20.855 | −1.391 | 16.427 | 1.00 | 47.01 | A | N |
| ATOM | 378 | CA | GLU | A | 175 | 21.512 | −2.163 | 15.370 | 1.00 | 51.33 | A | C |
| ATOM | 379 | CB | GLU | A | 175 | 20.475 | −2.644 | 14.327 | 1.00 | 53.83 | A | C |
| ATOM | 380 | CG | GLU | A | 175 | 21.184 | −3.349 | 13.162 | 1.00 | 52.58 | A | C |
| ATOM | 381 | CD | GLU | A | 175 | 20.354 | −4.382 | 12.438 | 1.00 | 54.98 | A | C |
| ATOM | 382 | OE1 | GLU | A | 175 | 19.115 | −4.128 | 12.301 | 1.00 | 48.01 | A | O |
| ATOM | 383 | OE2 | GLU | A | 175 | 20.982 | −5.413 | 12.009 | 1.00 | 46.34 | A | O |
| ATOM | 384 | C | GLU | A | 175 | 22.584 | −1.318 | 14.659 | 1.00 | 51.12 | A | C |
| ATOM | 385 | O | GLU | A | 175 | 23.727 | −1.740 | 14.457 | 1.00 | 45.49 | A | O |
| ATOM | 386 | N | HIS | A | 176 | 22.148 | −0.132 | 14.260 | 1.00 | 49.59 | A | N |
| ATOM | 387 | CA | HIS | A | 176 | 22.969 | 0.875 | 13.650 | 1.00 | 49.29 | A | C |
| ATOM | 388 | CB | HIS | A | 176 | 22.094 | 2.126 | 13.411 | 1.00 | 55.90 | A | C |
| ATOM | 389 | CG | HIS | A | 176 | 22.833 | 3.300 | 12.829 | 1.00 | 65.07 | A | C |
| ATOM | 390 | ND1 | HIS | A | 176 | 22.283 | 4.562 | 12.778 | 1.00 | 69.33 | A | N |
| ATOM | 391 | CE1 | HIS | A | 176 | 23.152 | 5.396 | 12.231 | 1.00 | 69.63 | A | C |
| ATOM | 392 | NE2 | HIS | A | 176 | 24.241 | 4.718 | 11.914 | 1.00 | 66.79 | A | N |
| ATOM | 393 | CD2 | HIS | A | 176 | 24.077 | 3.410 | 12.292 | 1.00 | 68.92 | A | C |
| ATOM | 394 | C | HIS | A | 176 | 24.170 | 1.178 | 14.503 | 1.00 | 48.02 | A | C |
| ATOM | 395 | O | HIS | A | 176 | 25.319 | 1.166 | 14.009 | 1.00 | 42.26 | A | O |
| ATOM | 396 | N | GLN | A | 177 | 23.924 | 1.428 | 15.784 | 1.00 | 45.14 | A | N |
| ATOM | 397 | CA | GLN | A | 177 | 25.014 | 1.738 | 16.708 | 1.00 | 47.79 | A | C |
| ATOM | 398 | CB | GLN | A | 177 | 24.397 | 2.085 | 18.070 | 1.00 | 54.37 | A | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 399 | CG | GLN | A | 177 | 25.405 | 2.236 | 19.188 | 1.00 | 57.02 | A | C |
| ATOM | 400 | CD | GLN | A | 177 | 24.806 | 2.593 | 20.537 | 1.00 | 53.53 | A | C |
| ATOM | 401 | OE1 | GLN | A | 177 | 23.584 | 2.847 | 20.689 | 1.00 | 43.87 | A | O |
| ATOM | 402 | NE2 | GLN | A | 177 | 25.677 | 2.609 | 21.538 | 1.00 | 45.33 | A | N |
| ATOM | 403 | C | GLN | A | 177 | 26.066 | 0.590 | 16.815 | 1.00 | 42.94 | A | C |
| ATOM | 404 | O | GLN | A | 177 | 27.287 | 0.793 | 16.763 | 1.00 | 38.73 | A | O |
| ATOM | 405 | N | LEU | A | 178 | 25.585 | −0.631 | 16.923 | 1.00 | 41.58 | A | N |
| ATOM | 406 | CA | LEU | A | 178 | 26.484 | −1.767 | 16.911 | 1.00 | 46.32 | A | C |
| ATOM | 407 | CB | LEU | A | 178 | 25.671 | −3.082 | 16.955 | 1.00 | 48.61 | A | C |
| ATOM | 408 | CG | LEU | A | 178 | 26.487 | −4.398 | 16.967 | 1.00 | 52.24 | A | C |
| ATOM | 409 | CD1 | LEU | A | 178 | 27.440 | −4.471 | 18.137 | 1.00 | 51.38 | A | C |
| ATOM | 410 | CD2 | LEU | A | 178 | 25.592 | −5.639 | 16.955 | 1.00 | 56.54 | A | C |
| ATOM | 411 | C | LEU | A | 178 | 27.390 | −1.761 | 15.665 | 1.00 | 42.66 | A | C |
| ATOM | 412 | O | LEU | A | 178 | 28.617 | −1.985 | 15.725 | 1.00 | 40.80 | A | O |
| ATOM | 413 | N | ARG | A | 179 | 26.772 | −1.523 | 14.520 | 1.00 | 44.11 | A | N |
| ATOM | 414 | CA | ARG | A | 179 | 27.527 | −1.677 | 13.295 | 1.00 | 44.07 | A | C |
| ATOM | 415 | CB | ARG | A | 179 | 26.622 | −1.511 | 12.091 | 1.00 | 46.15 | A | C |
| ATOM | 416 | CG | ARG | A | 179 | 27.325 | −1.666 | 10.768 | 1.00 | 44.09 | A | C |
| ATOM | 417 | CD | ARG | A | 179 | 28.144 | −2.947 | 10.664 | 1.00 | 49.60 | A | C |
| ATOM | 418 | NE | ARG | A | 179 | 28.797 | −2.860 | 9.385 | 1.00 | 50.33 | A | N |
| ATOM | 419 | CZ | ARG | A | 179 | 29.952 | −2.261 | 9.161 | 1.00 | 49.88 | A | C |
| ATOM | 420 | NH1 | ARG | A | 179 | 30.675 | −1.724 | 10.146 | 1.00 | 52.51 | A | N |
| ATOM | 421 | NH2 | ARG | A | 179 | 30.369 | −2.181 | 7.919 | 1.00 | 51.34 | A | N |
| ATOM | 422 | C | ARG | A | 179 | 28.656 | −0.680 | 13.293 | 1.00 | 41.90 | A | C |
| ATOM | 423 | O | ARG | A | 179 | 29.784 | −1.000 | 12.907 | 1.00 | 39.90 | A | O |
| ATOM | 424 | N | ARG | A | 180 | 28.369 | 0.532 | 13.772 | 1.00 | 46.99 | A | N |
| ATOM | 425 | CA | ARG | A | 180 | 29.430 | 1.538 | 13.868 | 1.00 | 45.66 | A | C |
| ATOM | 426 | CB | ARG | A | 180 | 28.845 | 2.875 | 14.308 | 1.00 | 49.75 | A | C |
| ATOM | 427 | CG | ARG | A | 180 | 29.856 | 4.029 | 14.348 | 1.00 | 53.81 | A | C |
| ATOM | 428 | CD | ARG | A | 180 | 29.305 | 5.210 | 15.113 | 1.00 | 53.99 | A | C |
| ATOM | 429 | NE | ARG | A | 180 | 27.985 | 5.485 | 14.567 | 1.00 | 50.50 | A | N |
| ATOM | 430 | CZ | ARG | A | 180 | 26.821 | 5.415 | 15.216 | 1.00 | 51.29 | A | C |
| ATOM | 431 | NH1 | ARG | A | 180 | 26.736 | 5.175 | 16.519 | 1.00 | 51.70 | A | N |
| ATOM | 432 | NH2 | ARG | A | 180 | 25.704 | 5.651 | 14.545 | 1.00 | 55.85 | A | N |
| ATOM | 433 | C | ARG | A | 180 | 30.513 | 1.107 | 14.825 | 1.00 | 39.14 | A | C |
| ATOM | 434 | O | ARG | A | 180 | 31.721 | 1.188 | 14.519 | 1.00 | 41.27 | A | O |
| ATOM | 435 | N | GLU | A | 181 | 30.096 | 0.693 | 16.025 | 1.00 | 40.47 | A | N |
| ATOM | 436 | CA | GLU | A | 181 | 31.076 | 0.356 | 17.093 | 1.00 | 43.02 | A | C |
| ATOM | 437 | CB | GLU | A | 181 | 30.348 | 0.067 | 18.417 | 1.00 | 46.94 | A | C |
| ATOM | 438 | CG | GLU | A | 181 | 29.878 | 1.355 | 19.103 | 1.00 | 49.66 | A | C |
| ATOM | 439 | CD | GLU | A | 181 | 28.883 | 1.166 | 20.232 | 1.00 | 47.24 | A | C |
| ATOM | 440 | OE1 | GLU | A | 181 | 28.891 | 0.129 | 20.912 | 1.00 | 55.62 | A | O |
| ATOM | 441 | OE2 | GLU | A | 181 | 28.084 | 2.097 | 20.460 | 1.00 | 63.68 | A | O |
| ATOM | 442 | C | GLU | A | 181 | 31.969 | −0.791 | 16.715 | 1.00 | 42.69 | A | C |
| ATOM | 443 | O | GLU | A | 181 | 33.184 | −0.823 | 17.021 | 1.00 | 37.91 | A | O |
| ATOM | 444 | N | VAL | A | 182 | 31.376 | −1.737 | 15.991 | 1.00 | 42.84 | A | N |
| ATOM | 445 | CA | VAL | A | 182 | 32.154 | −2.836 | 15.461 | 1.00 | 42.24 | A | C |
| ATOM | 446 | CB | VAL | A | 182 | 31.247 | −3.804 | 14.673 | 1.00 | 47.58 | A | C |
| ATOM | 447 | CG1 | VAL | A | 182 | 32.032 | −4.689 | 13.755 | 1.00 | 47.22 | A | C |
| ATOM | 448 | CG2 | VAL | A | 182 | 30.453 | −4.643 | 15.654 | 1.00 | 48.70 | A | C |
| ATOM | 449 | C | VAL | A | 182 | 33.273 | −2.287 | 14.624 | 1.00 | 41.67 | A | C |
| ATOM | 450 | O | VAL | A | 182 | 34.421 | −2.681 | 14.815 | 1.00 | 36.66 | A | O |
| ATOM | 451 | N | GLU | A | 183 | 32.964 | −1.370 | 13.703 | 1.00 | 38.95 | A | N |
| ATOM | 452 | CA | GLU | A | 183 | 34.032 | −0.856 | 12.850 | 1.00 | 44.05 | A | C |
| ATOM | 453 | CB | GLU | A | 183 | 33.519 | −0.001 | 11.696 | 1.00 | 47.75 | A | C |
| ATOM | 454 | CG | GLU | A | 183 | 34.628 | 0.135 | 10.645 | 1.00 | 60.17 | A | C |
| ATOM | 455 | CD | GLU | A | 183 | 34.213 | 0.701 | 9.298 | 1.00 | 72.52 | A | C |
| ATOM | 456 | OE1 | GLU | A | 183 | 33.004 | 0.627 | 8.860 | 1.00 | 70.14 | A | O |
| ATOM | 457 | OE2 | GLU | A | 183 | 35.173 | 1.220 | 8.671 | 1.00 | 63.28 | A | O |
| ATOM | 458 | C | GLU | A | 183 | 35.069 | −0.070 | 13.622 | 1.00 | 41.92 | A | C |
| ATOM | 459 | O | GLU | A | 183 | 36.269 | −0.156 | 13.327 | 1.00 | 40.22 | A | O |
| ATOM | 460 | N | ILE | A | 184 | 34.609 | 0.734 | 14.590 | 1.00 | 43.74 | A | N |
| ATOM | 461 | CA | ILE | A | 184 | 35.564 | 1.454 | 15.429 | 1.00 | 41.33 | A | C |
| ATOM | 462 | CB | ILE | A | 184 | 34.852 | 2.324 | 16.475 | 1.00 | 40.43 | A | C |
| ATOM | 463 | CG1 | ILE | A | 184 | 34.176 | 3.493 | 15.790 | 1.00 | 42.27 | A | C |
| ATOM | 464 | CD1 | ILE | A | 184 | 32.967 | 4.030 | 16.531 | 1.00 | 48.22 | A | C |
| ATOM | 465 | CG2 | ILE | A | 184 | 35.862 | 2.852 | 17.493 | 1.00 | 42.33 | A | C |
| ATOM | 466 | C | ILE | A | 184 | 36.465 | 0.454 | 16.119 | 1.00 | 41.11 | A | C |
| ATOM | 467 | O | ILE | A | 184 | 37.704 | 0.555 | 16.081 | 1.00 | 40.32 | A | O |
| ATOM | 468 | N | GLN | A | 185 | 35.835 | −0.542 | 16.746 | 1.00 | 48.28 | A | N |
| ATOM | 469 | CA | GLN | A | 185 | 36.571 | −1.419 | 17.647 | 1.00 | 47.19 | A | C |
| ATOM | 470 | CB | GLN | A | 185 | 35.629 | −2.272 | 18.523 | 1.00 | 49.54 | A | C |
| ATOM | 471 | CG | GLN | A | 185 | 36.107 | −2.417 | 19.977 | 1.00 | 48.96 | A | C |
| ATOM | 472 | CD | GLN | A | 185 | 35.923 | −1.154 | 20.833 | 1.00 | 55.92 | A | C |
| ATOM | 473 | OE1 | GLN | A | 185 | 35.266 | −0.157 | 20.438 | 1.00 | 58.71 | A | O |
| ATOM | 474 | NE2 | GLN | A | 185 | 36.526 | −1.181 | 22.026 | 1.00 | 63.25 | A | N |
| ATOM | 475 | C | GLN | A | 185 | 37.563 | −2.264 | 16.855 | 1.00 | 43.76 | A | C |
| ATOM | 476 | O | GLN | A | 185 | 38.580 | −2.597 | 17.386 | 1.00 | 43.51 | A | O |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 477 | N | SER | A | 186 | 37.263 | −2.564 | 15.586 | 1.00 | 46.27 | A | N |
| ATOM | 478 | CA | SER | A | 186 | 38.214 | −3.225 | 14.650 | 1.00 | 48.30 | A | C |
| ATOM | 479 | CB | SER | A | 186 | 37.731 | −3.094 | 13.215 | 1.00 | 43.87 | A | C |
| ATOM | 480 | OG | SER | A | 186 | 36.396 | −3.456 | 13.246 | 1.00 | 53.92 | A | O |
| ATOM | 481 | C | SER | A | 186 | 39.598 | −2.685 | 14.651 | 1.00 | 46.76 | A | C |
| ATOM | 482 | O | SER | A | 186 | 40.542 | −3.452 | 14.670 | 1.00 | 54.32 | A | O |
| ATOM | 483 | N | HIS | A | 187 | 39.719 | −1.366 | 14.586 | 1.00 | 51.63 | A | N |
| ATOM | 484 | CA | HIS | A | 187 | 41.016 | −0.701 | 14.318 | 1.00 | 49.11 | A | C |
| ATOM | 485 | CB | HIS | A | 187 | 40.808 | 0.680 | 13.678 | 1.00 | 50.76 | A | C |
| ATOM | 486 | CG | HIS | A | 187 | 39.903 | 0.677 | 12.479 | 1.00 | 59.12 | A | C |
| ATOM | 487 | ND1 | HIS | A | 187 | 40.102 | −0.140 | 11.384 | 1.00 | 61.48 | A | N |
| ATOM | 488 | CE1 | HIS | A | 187 | 39.162 | 0.092 | 10.483 | 1.00 | 55.98 | A | C |
| ATOM | 489 | NE2 | HIS | A | 187 | 38.358 | 1.027 | 10.956 | 1.00 | 55.93 | A | N |
| ATOM | 490 | CD2 | HIS | A | 187 | 38.800 | 1.412 | 12.199 | 1.00 | 57.41 | A | C |
| ATOM | 491 | C | HIS | A | 187 | 41.830 | −0.497 | 15.582 | 1.00 | 50.47 | A | C |
| ATOM | 492 | O | HIS | A | 187 | 42.911 | 0.106 | 15.521 | 1.00 | 48.23 | A | O |
| ATOM | 493 | N | LEU | A | 188 | 41.301 | −0.932 | 16.737 | 1.00 | 51.79 | A | N |
| ATOM | 494 | CA | LEU | A | 188 | 41.975 | −0.703 | 18.030 | 1.00 | 52.94 | A | C |
| ATOM | 495 | CB | LEU | A | 188 | 40.958 | −0.402 | 19.140 | 1.00 | 50.66 | A | C |
| ATOM | 496 | CG | LEU | A | 188 | 40.022 | 0.801 | 18.891 | 1.00 | 46.53 | A | C |
| ATOM | 497 | CD1 | LEU | A | 188 | 39.094 | 0.953 | 20.072 | 1.00 | 42.40 | A | C |
| ATOM | 498 | CD2 | LEU | A | 188 | 40.771 | 2.101 | 18.553 | 1.00 | 43.57 | A | C |
| ATOM | 499 | C | LEU | A | 188 | 42.883 | −1.855 | 18.438 | 1.00 | 51.14 | A | C |
| ATOM | 500 | O | LEU | A | 188 | 42.435 | −2.971 | 18.708 | 1.00 | 52.75 | A | O |
| ATOM | 501 | N | ARG | A | 189 | 44.150 | −1.499 | 18.555 | 1.00 | 52.67 | A | N |
| ATOM | 502 | CA | ARG | A | 189 | 45.264 | −2.377 | 18.770 | 1.00 | 52.14 | A | C |
| ATOM | 503 | CB | ARG | A | 189 | 46.246 | −2.189 | 17.594 | 1.00 | 58.87 | A | C |
| ATOM | 504 | CG | ARG | A | 189 | 45.732 | −2.716 | 16.276 | 1.00 | 65.91 | A | C |
| ATOM | 505 | CD | ARG | A | 189 | 45.488 | −4.215 | 16.346 | 1.00 | 60.26 | A | C |
| ATOM | 506 | NE | ARG | A | 189 | 45.279 | −4.691 | 14.992 | 1.00 | 64.94 | A | N |
| ATOM | 507 | CZ | ARG | A | 189 | 44.155 | −4.542 | 14.303 | 1.00 | 67.81 | A | C |
| ATOM | 508 | NH1 | ARG | A | 189 | 43.088 | −3.918 | 14.825 | 1.00 | 68.47 | A | N |
| ATOM | 509 | NH2 | ARG | A | 189 | 44.098 | −5.014 | 13.066 | 1.00 | 72.55 | A | N |
| ATOM | 510 | C | ARG | A | 189 | 46.022 | −2.007 | 20.030 | 1.00 | 44.94 | A | C |
| ATOM | 511 | O | ARG | A | 189 | 46.923 | −1.181 | 19.961 | 1.00 | 41.07 | A | O |
| ATOM | 512 | N | HIS | A | 190 | 45.741 | −2.672 | 21.156 | 1.00 | 41.83 | A | N |
| ATOM | 513 | CA | HIS | A | 190 | 46.460 | −2.383 | 22.397 | 1.00 | 36.18 | A | C |
| ATOM | 514 | CB | HIS | A | 190 | 45.887 | −1.061 | 22.992 | 1.00 | 39.98 | A | C |
| ATOM | 515 | CG | HIS | A | 190 | 46.675 | −0.497 | 24.129 | 1.00 | 37.89 | A | C |
| ATOM | 516 | ND1 | HIS | A | 190 | 46.534 | −0.956 | 25.419 | 1.00 | 36.30 | A | N |
| ATOM | 517 | CE1 | HIS | A | 190 | 47.362 | −0.294 | 26.215 | 1.00 | 34.59 | A | C |
| ATOM | 518 | NE2 | HIS | A | 190 | 48.018 | 0.587 | 25.488 | 1.00 | 34.81 | A | N |
| ATOM | 519 | CD2 | HIS | A | 190 | 47.612 | 0.480 | 24.179 | 1.00 | 35.05 | A | C |
| ATOM | 520 | C | HIS | A | 190 | 46.284 | −3.586 | 23.344 | 1.00 | 38.17 | A | C |
| ATOM | 521 | O | HIS | A | 190 | 45.202 | −4.158 | 23.376 | 1.00 | 35.27 | A | O |
| ATOM | 522 | N | PRO | A | 191 | 47.336 | −3.964 | 24.120 | 1.00 | 41.44 | A | N |
| ATOM | 523 | CA | PRO | A | 191 | 47.214 | −5.116 | 25.068 | 1.00 | 47.99 | A | C |
| ATOM | 524 | CB | PRO | A | 191 | 48.572 | −5.138 | 25.783 | 1.00 | 48.16 | A | C |
| ATOM | 525 | CG | PRO | A | 191 | 49.208 | −3.817 | 25.515 | 1.00 | 47.97 | A | C |
| ATOM | 526 | CD | PRO | A | 191 | 48.667 | −3.328 | 24.209 | 1.00 | 44.34 | A | C |
| ATOM | 527 | C | PRO | A | 191 | 46.077 | −5.025 | 26.114 | 1.00 | 45.47 | A | C |
| ATOM | 528 | O | PRO | A | 191 | 45.490 | −6.039 | 26.522 | 1.00 | 46.59 | A | O |
| ATOM | 529 | N | ASN | A | 192 | 45.773 | −3.814 | 26.540 | 1.00 | 43.02 | A | N |
| ATOM | 530 | CA | ASN | A | 192 | 44.656 | −3.569 | 27.444 | 1.00 | 37.76 | A | C |
| ATOM | 531 | CB | ASN | A | 192 | 45.065 | −2.503 | 28.425 | 1.00 | 40.85 | A | C |
| ATOM | 532 | CG | ASN | A | 192 | 46.358 | −2.868 | 29.152 | 1.00 | 41.31 | A | C |
| ATOM | 533 | OD1 | ASN | A | 192 | 47.384 | −2.231 | 28.975 | 1.00 | 41.68 | A | O |
| ATOM | 534 | ND2 | ASN | A | 192 | 46.291 | −3.900 | 29.981 | 1.00 | 43.23 | A | N |
| ATOM | 535 | C | ASN | A | 192 | 43.314 | −3.285 | 26.812 | 1.00 | 39.86 | A | C |
| ATOM | 536 | O | ASN | A | 192 | 42.357 | −2.925 | 27.532 | 1.00 | 38.59 | A | O |
| ATOM | 537 | N | ILE | A | 193 | 43.220 | −3.488 | 25.494 | 1.00 | 37.15 | A | N |
| ATOM | 538 | CA | ILE | A | 193 | 41.939 | −3.425 | 24.784 | 1.00 | 39.14 | A | C |
| ATOM | 539 | CB | ILE | A | 193 | 41.880 | −2.223 | 23.780 | 1.00 | 35.47 | A | C |
| ATOM | 540 | CG1 | ILE | A | 193 | 42.267 | −0.880 | 24.462 | 1.00 | 34.08 | A | C |
| ATOM | 541 | CD1 | ILE | A | 193 | 42.317 | 0.322 | 23.502 | 1.00 | 33.88 | A | C |
| ATOM | 542 | CG2 | ILE | A | 193 | 40.506 | −2.189 | 23.124 | 1.00 | 36.21 | A | C |
| ATOM | 543 | C | ILE | A | 193 | 41.618 | −4.746 | 24.043 | 1.00 | 37.42 | A | C |
| ATOM | 544 | O | ILE | A | 193 | 42.379 | −5.194 | 23.215 | 1.00 | 42.30 | A | O |
| ATOM | 545 | N | LEU | A | 194 | 40.440 | −5.285 | 24.315 | 1.00 | 35.05 | A | N |
| ATOM | 546 | CA | LEU | A | 194 | 40.014 | −6.562 | 23.838 | 1.00 | 37.59 | A | C |
| ATOM | 547 | CB | LEU | A | 194 | 38.670 | −6.953 | 24.453 | 1.00 | 38.20 | A | C |
| ATOM | 548 | CG | LEU | A | 194 | 38.255 | −8.426 | 24.227 | 1.00 | 38.26 | A | C |
| ATOM | 549 | CD1 | LEU | A | 194 | 38.922 | −9.324 | 25.246 | 1.00 | 41.02 | A | C |
| ATOM | 550 | CD2 | LEU | A | 194 | 36.754 | −8.663 | 24.233 | 1.00 | 37.77 | A | C |
| ATOM | 551 | C | LEU | A | 194 | 39.864 | −6.479 | 22.347 | 1.00 | 39.94 | A | C |
| ATOM | 552 | O | LEU | A | 194 | 39.186 | −5.574 | 21.853 | 1.00 | 39.12 | A | O |
| ATOM | 553 | N | ARG | A | 195 | 40.497 | −7.419 | 21.628 | 1.00 | 43.86 | A | N |
| ATOM | 554 | CA | ARG | A | 195 | 40.545 | −7.373 | 20.175 | 1.00 | 43.07 | A | C |

APPENDIX A-continued

| Atomic coordinates of Aurora A + Inhibitory Monobody Mb60 + Danusertib | | | | | | | | | | | |
|---|---|---|---|---|---|---|---|---|---|---|---|
| ATOM | 555 | CB | ARG | A | 195 | 41.701 | −8.188 | 19.605 | 1.00 | 48.45 | A | C |
| ATOM | 556 | CG | ARG | A | 195 | 43.060 | −7.563 | 19.864 | 1.00 | 53.91 | A | C |
| ATOM | 557 | CD | ARG | A | 195 | 43.395 | −6.490 | 18.849 | 1.00 | 56.36 | A | C |
| ATOM | 558 | NE | ARG | A | 195 | 43.832 | −7.104 | 17.600 | 1.00 | 68.94 | A | N |
| ATOM | 559 | CZ | ARG | A | 195 | 43.143 | −7.190 | 16.449 | 1.00 | 70.20 | A | C |
| ATOM | 560 | NH1 | ARG | A | 195 | 43.726 | −7.801 | 15.416 | 1.00 | 71.19 | A | N |
| ATOM | 561 | NH2 | ARG | A | 195 | 41.909 | −6.682 | 16.284 | 1.00 | 69.90 | A | N |
| ATOM | 562 | C | ARG | A | 195 | 39.247 | −7.848 | 19.666 | 1.00 | 39.05 | A | C |
| ATOM | 563 | O | ARG | A | 195 | 38.687 | −8.731 | 20.242 | 1.00 | 38.49 | A | O |
| ATOM | 564 | N | LEU | A | 196 | 38.734 | −7.180 | 18.631 | 1.00 | 39.14 | A | N |
| ATOM | 565 | CA | LEU | A | 196 | 37.574 | −7.609 | 17.847 | 1.00 | 42.67 | A | C |
| ATOM | 566 | CB | LEU | A | 196 | 36.514 | −6.509 | 17.682 | 1.00 | 45.70 | A | C |
| ATOM | 567 | CG | LEU | A | 196 | 35.259 | −6.708 | 16.813 | 1.00 | 46.20 | A | C |
| ATOM | 568 | CD1 | LEU | A | 196 | 34.789 | −8.129 | 16.778 | 1.00 | 54.00 | A | C |
| ATOM | 569 | CD2 | LEU | A | 196 | 34.100 | −5.874 | 17.339 | 1.00 | 50.02 | A | C |
| ATOM | 570 | C | LEU | A | 196 | 38.128 | −7.958 | 16.493 | 1.00 | 47.49 | A | C |
| ATOM | 571 | O | LEU | A | 196 | 38.616 | −7.077 | 15.804 | 1.00 | 39.61 | A | O |
| ATOM | 572 | N | TYR | A | 197 | 38.036 | −9.241 | 16.142 | 1.00 | 43.44 | A | N |
| ATOM | 573 | CA | TYR | A | 197 | 38.726 | −9.833 | 14.992 | 1.00 | 46.25 | A | C |
| ATOM | 574 | CB | TYR | A | 197 | 39.183 | −11.314 | 15.346 | 1.00 | 42.36 | A | C |
| ATOM | 575 | CG | TYR | A | 197 | 40.246 | −11.377 | 16.423 | 1.00 | 36.75 | A | C |
| ATOM | 576 | CD1 | TYR | A | 197 | 41.453 | −10.778 | 16.204 | 1.00 | 40.93 | A | C |
| ATOM | 577 | CE1 | TYR | A | 197 | 42.461 | −10.780 | 17.147 | 1.00 | 44.77 | A | C |
| ATOM | 578 | CZ | TYR | A | 197 | 42.311 | −11.431 | 18.344 | 1.00 | 41.57 | A | C |
| ATOM | 579 | OH | TYR | A | 197 | 43.422 | −11.335 | 19.190 | 1.00 | 47.57 | A | O |
| ATOM | 580 | CE2 | TYR | A | 197 | 41.130 | −12.089 | 18.598 | 1.00 | 40.14 | A | C |
| ATOM | 581 | CD2 | TYR | A | 197 | 40.073 | −12.043 | 17.635 | 1.00 | 38.96 | A | C |
| ATOM | 582 | C | TYR | A | 197 | 37.835 | −9.788 | 13.726 | 1.00 | 46.79 | A | C |
| ATOM | 583 | O | TYR | A | 197 | 38.329 | −9.590 | 12.621 | 1.00 | 52.46 | A | O |
| ATOM | 584 | N | GLY | A | 198 | 36.535 | −9.935 | 13.875 | 1.00 | 42.28 | A | N |
| ATOM | 585 | CA | GLY | A | 198 | 35.638 | −9.830 | 12.730 | 1.00 | 37.83 | A | C |
| ATOM | 586 | C | GLY | A | 198 | 34.225 | −10.064 | 13.171 | 1.00 | 39.44 | A | C |
| ATOM | 587 | O | GLY | A | 198 | 33.888 | −10.074 | 14.393 | 1.00 | 44.04 | A | O |
| ATOM | 588 | N | TYR | A | 199 | 33.371 | −10.230 | 12.185 | 1.00 | 39.40 | A | N |
| ATOM | 589 | CA | TYR | A | 199 | 31.988 | −10.531 | 12.421 | 1.00 | 41.51 | A | C |
| ATOM | 590 | CB | TYR | A | 199 | 31.206 | −9.272 | 12.705 | 1.00 | 47.49 | A | C |
| ATOM | 591 | CG | TYR | A | 199 | 31.313 | −8.229 | 11.620 | 1.00 | 51.95 | A | C |
| ATOM | 592 | CD1 | TYR | A | 199 | 32.377 | −7.321 | 11.615 | 1.00 | 52.69 | A | C |
| ATOM | 593 | CE1 | TYR | A | 199 | 32.485 | −6.357 | 10.634 | 1.00 | 55.63 | A | C |
| ATOM | 594 | CZ | TYR | A | 199 | 31.523 | −6.261 | 9.663 | 1.00 | 60.38 | A | C |
| ATOM | 595 | OH | TYR | A | 199 | 31.671 | −5.277 | 8.717 | 1.00 | 83.24 | A | O |
| ATOM | 596 | CE2 | TYR | A | 199 | 30.439 | −7.127 | 9.642 | 1.00 | 63.89 | A | C |
| ATOM | 597 | CD2 | TYR | A | 199 | 30.339 | −8.113 | 10.623 | 1.00 | 59.86 | A | C |
| ATOM | 598 | C | TYR | A | 199 | 31.361 | −11.226 | 11.234 | 1.00 | 41.51 | A | C |
| ATOM | 599 | O | TYR | A | 199 | 31.959 | −11.360 | 10.202 | 1.00 | 44.86 | A | O |
| ATOM | 600 | N | PHE | A | 200 | 30.152 | −11.690 | 11.431 | 1.00 | 43.99 | A | N |
| ATOM | 601 | CA | PHE | A | 200 | 29.363 | −12.319 | 10.382 | 1.00 | 48.01 | A | C |
| ATOM | 602 | CB | PHE | A | 200 | 29.930 | −13.694 | 9.944 | 1.00 | 54.62 | A | C |
| ATOM | 603 | CG | PHE | A | 200 | 30.122 | −14.688 | 11.068 | 1.00 | 55.94 | A | C |
| ATOM | 604 | CD1 | PHE | A | 200 | 31.368 | −14.851 | 11.660 | 1.00 | 63.58 | A | C |
| ATOM | 605 | CE1 | PHE | A | 200 | 31.553 | −15.767 | 12.691 | 1.00 | 59.68 | A | C |
| ATOM | 606 | CZ | PHE | A | 200 | 30.500 | −16.553 | 13.117 | 1.00 | 57.48 | A | C |
| ATOM | 607 | CE2 | PHE | A | 200 | 29.258 | −16.417 | 12.530 | 1.00 | 62.70 | A | C |
| ATOM | 608 | CD2 | PHE | A | 200 | 29.070 | −15.487 | 11.510 | 1.00 | 58.47 | A | C |
| ATOM | 609 | C | PHE | A | 200 | 27.991 | −12.463 | 10.979 | 1.00 | 48.08 | A | C |
| ATOM | 610 | O | PHE | A | 200 | 27.788 | −12.152 | 12.166 | 1.00 | 51.87 | A | O |
| ATOM | 611 | N | HIS | A | 201 | 27.037 | −12.884 | 10.176 | 1.00 | 47.84 | A | N |
| ATOM | 612 | CA | HIS | A | 201 | 25.650 | −12.899 | 10.631 | 1.00 | 50.83 | A | C |
| ATOM | 613 | CB | HIS | A | 201 | 25.050 | −11.500 | 10.395 | 1.00 | 46.67 | A | C |
| ATOM | 614 | CG | HIS | A | 201 | 24.884 | −11.151 | 8.955 | 1.00 | 40.57 | A | C |
| ATOM | 615 | ND1 | HIS | A | 201 | 23.647 | −10.981 | 8.375 | 1.00 | 40.07 | A | N |
| ATOM | 616 | CE1 | HIS | A | 201 | 23.797 | −10.672 | 7.106 | 1.00 | 36.80 | A | C |
| ATOM | 617 | NE2 | HIS | A | 201 | 25.090 | −10.649 | 6.832 | 1.00 | 37.42 | A | N |
| ATOM | 618 | CD2 | HIS | A | 201 | 25.793 | −10.955 | 7.974 | 1.00 | 39.54 | A | C |
| ATOM | 619 | C | HIS | A | 201 | 24.811 | −13.953 | 9.917 | 1.00 | 46.94 | A | C |
| ATOM | 620 | O | HIS | A | 201 | 25.298 | −14.618 | 9.053 | 1.00 | 52.46 | A | O |
| ATOM | 621 | N | ASP | A | 202 | 23.534 | −14.024 | 10.256 | 1.00 | 52.50 | A | N |
| ATOM | 622 | CA | ASP | A | 202 | 22.602 | −14.957 | 9.670 | 1.00 | 62.28 | A | C |
| ATOM | 623 | CB | ASP | A | 202 | 22.817 | −16.367 | 10.273 | 1.00 | 66.29 | A | C |
| ATOM | 624 | CG | ASP | A | 202 | 22.330 | −16.503 | 11.742 | 1.00 | 59.54 | A | C |
| ATOM | 625 | OD1 | ASP | A | 202 | 21.341 | −15.860 | 12.188 | 1.00 | 65.86 | A | O |
| ATOM | 626 | OD2 | ASP | A | 202 | 22.919 | −17.341 | 12.441 | 1.00 | 63.32 | A | O |
| ATOM | 627 | C | ASP | A | 202 | 21.173 | −14.476 | 9.890 | 1.00 | 64.15 | A | C |
| ATOM | 628 | O | ASP | A | 202 | 20.941 | −13.386 | 10.425 | 1.00 | 61.59 | A | O |
| ATOM | 629 | N | ALA | A | 203 | 20.223 | −15.306 | 9.466 | 1.00 | 69.51 | A | N |
| ATOM | 630 | CA | ALA | A | 203 | 18.794 | −15.031 | 9.564 | 1.00 | 71.58 | A | C |
| ATOM | 631 | CB | ALA | A | 203 | 18.010 | −16.344 | 9.541 | 1.00 | 80.48 | A | C |
| ATOM | 632 | C | ALA | A | 203 | 18.425 | −14.258 | 10.798 | 1.00 | 66.52 | A | C |

APPENDIX A-continued

Atomic coordinates of Aurora A + Inhibitory Monobody Mb60 + Danusertib

| | | | | | | | | | | | |
|---|---|---|---|---|---|---|---|---|---|---|---|
| ATOM | 633 | O | ALA | A | 203 | 17.675 | −13.323 | 10.703 | 1.00 | 58.03 | A | O |
| ATOM | 634 | N | THR | A | 204 | 18.960 | −14.672 | 11.947 | 1.00 | 65.68 | A | N |
| ATOM | 635 | CA | THR | A | 204 | 18.528 | −14.164 | 13.246 | 1.00 | 65.31 | A | C |
| ATOM | 636 | CB | THR | A | 204 | 18.034 | −15.347 | 14.089 | 1.00 | 67.21 | A | C |
| ATOM | 637 | OG1 | THR | A | 204 | 19.026 | −16.384 | 14.047 | 1.00 | 67.35 | A | O |
| ATOM | 638 | CG2 | THR | A | 204 | 16.750 | −15.883 | 13.524 | 1.00 | 66.20 | A | C |
| ATOM | 639 | C | THR | A | 204 | 19.586 | −13.440 | 14.080 | 1.00 | 54.55 | A | C |
| ATOM | 640 | O | THR | A | 204 | 19.239 | −12.770 | 15.045 | 1.00 | 55.63 | A | O |
| ATOM | 641 | N | ARG | A | 205 | 20.859 | −13.590 | 13.749 | 1.00 | 52.88 | A | N |
| ATOM | 642 | CA | ARG | A | 205 | 21.918 | −13.190 | 14.678 | 1.00 | 54.63 | A | C |
| ATOM | 643 | CB | ARG | A | 205 | 22.429 | −14.420 | 15.429 | 1.00 | 61.76 | A | C |
| ATOM | 644 | CG | ARG | A | 205 | 21.421 | −15.046 | 16.386 | 1.00 | 65.39 | A | C |
| ATOM | 645 | CD | ARG | A | 205 | 21.795 | −16.476 | 16.728 | 1.00 | 66.82 | A | C |
| ATOM | 646 | NE | ARG | A | 205 | 21.698 | −17.361 | 15.569 | 1.00 | 70.52 | A | N |
| ATOM | 647 | CZ | ARG | A | 205 | 21.483 | −18.674 | 15.614 | 1.00 | 72.77 | A | C |
| ATOM | 648 | NH1 | ARG | A | 205 | 21.309 | −19.322 | 16.765 | 1.00 | 71.16 | A | N |
| ATOM | 649 | NH2 | ARG | A | 205 | 21.449 | −19.348 | 14.473 | 1.00 | 68.83 | A | N |
| ATOM | 650 | C | ARG | A | 205 | 23.121 | −12.517 | 14.039 | 1.00 | 56.45 | A | C |
| ATOM | 651 | O | ARG | A | 205 | 23.404 | −12.714 | 12.855 | 1.00 | 59.66 | A | O |
| ATOM | 652 | N | VAL | A | 206 | 23.870 | −11.780 | 14.869 | 1.00 | 45.63 | A | N |
| ATOM | 653 | CA | VAL | A | 206 | 25.119 | −11.161 | 14.465 | 1.00 | 45.93 | A | C |
| ATOM | 654 | CB | VAL | A | 206 | 25.071 | −9.601 | 14.662 | 1.00 | 43.23 | A | C |
| ATOM | 655 | CG1 | VAL | A | 206 | 26.385 | −8.933 | 14.250 | 1.00 | 41.68 | A | C |
| ATOM | 656 | CG2 | VAL | A | 206 | 23.861 | −8.989 | 13.946 | 1.00 | 43.18 | A | C |
| ATOM | 657 | C | VAL | A | 206 | 26.118 | −11.761 | 15.399 | 1.00 | 40.54 | A | C |
| ATOM | 658 | O | VAL | A | 206 | 25.799 | −11.956 | 16.564 | 1.00 | 41.85 | A | O |
| ATOM | 659 | N | TYR | A | 207 | 27.317 | −12.015 | 14.901 | 1.00 | 44.34 | A | N |
| ATOM | 660 | CA | TYR | A | 207 | 28.334 | −12.789 | 15.606 | 1.00 | 50.34 | A | C |
| ATOM | 661 | CB | TYR | A | 207 | 28.658 | −14.121 | 14.855 | 1.00 | 55.18 | A | C |
| ATOM | 662 | CG | TYR | A | 207 | 27.493 | −15.108 | 14.792 | 1.00 | 59.29 | A | C |
| ATOM | 663 | CD1 | TYR | A | 207 | 26.508 | −14.980 | 13.823 | 1.00 | 59.78 | A | C |
| ATOM | 664 | CE1 | TYR | A | 207 | 25.438 | −15.847 | 13.757 | 1.00 | 56.62 | A | C |
| ATOM | 665 | CZ | TYR | A | 207 | 25.326 | −16.891 | 14.653 | 1.00 | 60.81 | A | C |
| ATOM | 666 | OH | TYR | A | 207 | 24.226 | −17.729 | 14.560 | 1.00 | 56.62 | A | O |
| ATOM | 667 | CE2 | TYR | A | 207 | 26.293 | −17.063 | 15.632 | 1.00 | 62.87 | A | C |
| ATOM | 668 | CD2 | TYR | A | 207 | 27.381 | −16.179 | 15.692 | 1.00 | 65.75 | A | C |
| ATOM | 669 | C | TYR | A | 207 | 29.553 | −11.958 | 15.582 | 1.00 | 46.10 | A | C |
| ATOM | 670 | O | TYR | A | 207 | 29.922 | −11.507 | 14.513 | 1.00 | 47.53 | A | O |
| ATOM | 671 | N | LEU | A | 208 | 30.189 | −11.741 | 16.726 | 1.00 | 41.20 | A | N |
| ATOM | 672 | CA | LEU | A | 208 | 31.454 | −11.024 | 16.755 | 1.00 | 43.23 | A | C |
| ATOM | 673 | CB | LEU | A | 208 | 31.443 | −9.804 | 17.719 | 1.00 | 43.15 | A | C |
| ATOM | 674 | CG | LEU | A | 208 | 30.192 | −8.931 | 17.682 | 1.00 | 44.13 | A | C |
| ATOM | 675 | CD1 | LEU | A | 208 | 30.407 | −7.678 | 18.547 | 1.00 | 47.02 | A | C |
| ATOM | 676 | CD2 | LEU | A | 208 | 29.838 | −8.555 | 16.250 | 1.00 | 48.61 | A | C |
| ATOM | 677 | C | LEU | A | 208 | 32.476 | −11.998 | 17.209 | 1.00 | 43.09 | A | C |
| ATOM | 678 | O | LEU | A | 208 | 32.180 | −12.852 | 18.062 | 1.00 | 47.66 | A | O |
| ATOM | 679 | N | ILE | A | 209 | 33.690 | −11.828 | 16.713 | 1.00 | 43.31 | A | N |
| ATOM | 680 | CA | ILE | A | 209 | 34.759 | −12.745 | 16.985 | 1.00 | 41.71 | A | C |
| ATOM | 681 | CB | ILE | A | 209 | 35.357 | −13.298 | 15.706 | 1.00 | 40.48 | A | C |
| ATOM | 682 | CG1 | ILE | A | 209 | 34.269 | −13.868 | 14.818 | 1.00 | 48.60 | A | C |
| ATOM | 683 | CD1 | ILE | A | 209 | 34.682 | −13.924 | 13.352 | 1.00 | 50.75 | A | C |
| ATOM | 684 | CG2 | ILE | A | 209 | 36.423 | −14.319 | 16.047 | 1.00 | 45.21 | A | C |
| ATOM | 685 | C | ILE | A | 209 | 35.800 | −11.992 | 17.747 | 1.00 | 42.05 | A | C |
| ATOM | 686 | O | ILE | A | 209 | 36.401 | −11.045 | 17.226 | 1.00 | 50.23 | A | O |
| ATOM | 687 | N | LEU | A | 210 | 36.011 | −12.413 | 18.989 | 1.00 | 39.04 | A | N |
| ATOM | 688 | CA | LEU | A | 210 | 36.603 | −11.580 | 20.020 | 1.00 | 38.65 | A | C |
| ATOM | 689 | CB | LEU | A | 210 | 35.529 | −11.222 | 21.049 | 1.00 | 38.30 | A | C |
| ATOM | 690 | CG | LEU | A | 210 | 34.372 | −10.275 | 20.581 | 1.00 | 43.66 | A | C |
| ATOM | 691 | CD1 | LEU | A | 210 | 33.221 | −10.196 | 21.567 | 1.00 | 40.57 | A | C |
| ATOM | 692 | CD2 | LEU | A | 210 | 34.851 | −8.836 | 20.362 | 1.00 | 45.51 | A | C |
| ATOM | 693 | C | LEU | A | 210 | 37.766 | −12.313 | 20.643 | 1.00 | 40.31 | A | C |
| ATOM | 694 | O | LEU | A | 210 | 37.798 | −13.556 | 20.666 | 1.00 | 43.78 | A | O |
| ATOM | 695 | N | GLU | A | 211 | 38.727 | −11.555 | 21.127 | 1.00 | 37.77 | A | N |
| ATOM | 696 | CA | GLU | A | 211 | 39.786 | −12.092 | 21.948 | 1.00 | 41.02 | A | C |
| ATOM | 697 | CB | GLU | A | 211 | 40.719 | −10.975 | 22.355 | 1.00 | 40.19 | A | C |
| ATOM | 698 | CG | GLU | A | 211 | 41.862 | −11.324 | 23.281 | 1.00 | 39.79 | A | C |
| ATOM | 699 | CD | GLU | A | 211 | 42.624 | −10.097 | 23.709 | 1.00 | 48.67 | A | C |
| ATOM | 700 | OE1 | GLU | A | 211 | 42.428 | −8.990 | 23.087 | 1.00 | 47.40 | A | O |
| ATOM | 701 | OE2 | GLU | A | 211 | 43.430 | −10.232 | 24.676 | 1.00 | 44.81 | A | O |
| ATOM | 702 | C | GLU | A | 211 | 39.164 | −12.743 | 23.191 | 1.00 | 48.56 | A | C |
| ATOM | 703 | O | GLU | A | 211 | 38.168 | −12.242 | 23.736 | 1.00 | 49.05 | A | O |
| ATOM | 704 | N | TYR | A | 212 | 39.732 | −13.873 | 23.615 | 1.00 | 50.43 | A | N |
| ATOM | 705 | CA | TYR | A | 212 | 39.281 | −14.523 | 24.821 | 1.00 | 52.69 | A | C |
| ATOM | 706 | CB | TYR | A | 212 | 39.425 | −16.033 | 24.710 | 1.00 | 50.82 | A | C |
| ATOM | 707 | CG | TYR | A | 212 | 39.178 | −16.778 | 26.004 | 1.00 | 47.18 | A | C |
| ATOM | 708 | CD1 | TYR | A | 212 | 37.955 | −16.690 | 26.682 | 1.00 | 44.18 | A | C |
| ATOM | 709 | CE1 | TYR | A | 212 | 37.749 | −17.413 | 27.860 | 1.00 | 50.07 | A | C |
| ATOM | 710 | CZ | TYR | A | 212 | 38.789 | −18.230 | 28.346 | 1.00 | 48.82 | A | C |

APPENDIX A-continued

Atomic coordinates of Aurora A + Inhibitory Monobody Mb60 + Danusertib

| | | | | | | | | | | | |
|---|---|---|---|---|---|---|---|---|---|---|---|
| ATOM | 711 | OH | TYR | A | 212 | 38.694 | −18.929 | 29.499 | 1.00 | 58.76 | A | O |
| ATOM | 712 | CE2 | TYR | A | 212 | 39.986 | −18.308 | 27.700 | 1.00 | 46.31 | A | C |
| ATOM | 713 | CD2 | TYR | A | 212 | 40.182 | −17.580 | 26.549 | 1.00 | 49.89 | A | C |
| ATOM | 714 | C | TYR | A | 212 | 40.053 | −13.969 | 26.018 | 1.00 | 55.62 | A | C |
| ATOM | 715 | O | TYR | A | 212 | 41.271 | −13.927 | 26.017 | 1.00 | 54.29 | A | O |
| ATOM | 716 | N | ALA | A | 213 | 39.295 | −13.514 | 27.016 | 1.00 | 54.73 | A | N |
| ATOM | 717 | CA | ALA | A | 213 | 39.827 | −13.034 | 28.284 | 1.00 | 53.07 | A | C |
| ATOM | 718 | CB | ALA | A | 213 | 39.190 | −11.703 | 28.635 | 1.00 | 49.57 | A | C |
| ATOM | 719 | C | ALA | A | 213 | 39.445 | −14.122 | 29.327 | 1.00 | 50.81 | A | C |
| ATOM | 720 | O | ALA | A | 213 | 38.241 | −14.266 | 29.646 | 1.00 | 46.05 | A | O |
| ATOM | 721 | N | PRO | A | 214 | 40.445 | −14.913 | 29.778 | 1.00 | 50.37 | A | N |
| ATOM | 722 | CA | PRO | A | 214 | 40.221 | −16.129 | 30.596 | 1.00 | 53.96 | A | C |
| ATOM | 723 | CB | PRO | A | 214 | 41.572 | −16.869 | 30.559 | 1.00 | 52.33 | A | C |
| ATOM | 724 | CG | PRO | A | 214 | 42.562 | −15.874 | 30.139 | 1.00 | 57.19 | A | C |
| ATOM | 725 | CD | PRO | A | 214 | 41.857 | −14.784 | 29.375 | 1.00 | 53.88 | A | C |
| ATOM | 726 | C | PRO | A | 214 | 39.820 | −15.872 | 32.021 | 1.00 | 54.14 | A | C |
| ATOM | 727 | O | PRO | A | 214 | 38.964 | −16.582 | 32.570 | 1.00 | 51.95 | A | O |
| ATOM | 728 | N | LEU | A | 215 | 40.396 | −14.834 | 32.611 | 1.00 | 56.96 | A | N |
| ATOM | 729 | CA | LEU | A | 215 | 40.130 | −14.530 | 34.005 | 1.00 | 48.93 | A | C |
| ATOM | 730 | CB | LEU | A | 215 | 41.327 | −13.823 | 34.636 | 1.00 | 52.30 | A | C |
| ATOM | 731 | CG | LEU | A | 215 | 42.488 | −14.766 | 34.992 | 1.00 | 56.71 | A | C |
| ATOM | 732 | CD1 | LEU | A | 215 | 42.876 | −15.779 | 33.905 | 1.00 | 59.95 | A | C |
| ATOM | 733 | CD2 | LEU | A | 215 | 43.687 | −13.924 | 35.394 | 1.00 | 59.28 | A | C |
| ATOM | 734 | C | LEU | A | 215 | 38.850 | −13.799 | 34.265 | 1.00 | 48.43 | A | C |
| ATOM | 735 | O | LEU | A | 215 | 38.647 | −13.403 | 35.398 | 1.00 | 53.89 | A | O |
| ATOM | 736 | N | GLY | A | 216 | 37.968 | −13.617 | 33.275 | 1.00 | 48.83 | A | N |
| ATOM | 737 | CA | GLY | A | 216 | 36.628 | −13.025 | 33.524 | 1.00 | 49.65 | A | C |
| ATOM | 738 | C | GLY | A | 216 | 36.588 | −11.560 | 33.959 | 1.00 | 44.91 | A | C |
| ATOM | 739 | O | GLY | A | 216 | 37.583 | −10.831 | 33.784 | 1.00 | 49.74 | A | O |
| ATOM | 740 | N | THR | A | 217 | 35.445 | −11.119 | 34.492 | 1.00 | 46.79 | A | N |
| ATOM | 741 | CA | THR | A | 217 | 35.260 | −9.699 | 34.796 | 1.00 | 49.11 | A | C |
| ATOM | 742 | CB | THR | A | 217 | 33.777 | −9.169 | 34.894 | 1.00 | 49.50 | A | C |
| ATOM | 743 | OG1 | THR | A | 217 | 33.119 | −9.632 | 36.070 | 1.00 | 52.26 | A | O |
| ATOM | 744 | CG2 | THR | A | 217 | 32.967 | −9.575 | 33.729 | 1.00 | 51.77 | A | C |
| ATOM | 745 | C | THR | A | 217 | 36.038 | −9.245 | 36.011 | 1.00 | 49.97 | A | C |
| ATOM | 746 | O | THR | A | 217 | 36.360 | −10.025 | 36.919 | 1.00 | 52.16 | A | O |
| ATOM | 747 | N | VAL | A | 218 | 36.338 | −7.962 | 36.019 | 1.00 | 43.98 | A | N |
| ATOM | 748 | CA | VAL | A | 218 | 37.016 | −7.390 | 37.139 | 1.00 | 46.84 | A | C |
| ATOM | 749 | CB | VAL | A | 218 | 37.681 | −6.048 | 36.819 | 1.00 | 52.22 | A | C |
| ATOM | 750 | CG1 | VAL | A | 218 | 38.609 | −5.600 | 37.951 | 1.00 | 53.17 | A | C |
| ATOM | 751 | CG2 | VAL | A | 218 | 38.488 | −6.178 | 35.562 | 1.00 | 69.20 | A | C |
| ATOM | 752 | C | VAL | A | 218 | 35.948 | −7.183 | 38.184 | 1.00 | 47.68 | A | C |
| ATOM | 753 | O | VAL | A | 218 | 36.252 | −7.199 | 39.359 | 1.00 | 44.28 | A | O |
| ATOM | 754 | N | TYR | A | 219 | 34.703 | −6.969 | 37.758 | 1.00 | 49.81 | A | N |
| ATOM | 755 | CA | TYR | A | 219 | 33.613 | −6.796 | 38.708 | 1.00 | 56.59 | A | C |
| ATOM | 756 | CB | TYR | A | 219 | 32.285 | −6.649 | 37.996 | 1.00 | 53.79 | A | C |
| ATOM | 757 | CG | TYR | A | 219 | 31.154 | −6.348 | 38.959 | 1.00 | 59.25 | A | C |
| ATOM | 758 | CD1 | TYR | A | 219 | 31.180 | −5.186 | 39.747 | 1.00 | 59.99 | A | C |
| ATOM | 759 | CE1 | TYR | A | 219 | 30.161 | −4.889 | 40.643 | 1.00 | 65.09 | A | C |
| ATOM | 760 | CZ | TYR | A | 219 | 29.090 | −5.777 | 40.777 | 1.00 | 72.54 | A | C |
| ATOM | 761 | OH | TYR | A | 219 | 28.075 | −5.482 | 41.664 | 1.00 | 79.93 | A | O |
| ATOM | 762 | CE2 | TYR | A | 219 | 29.041 | −6.948 | 40.017 | 1.00 | 67.16 | A | C |
| ATOM | 763 | CD2 | TYR | A | 219 | 30.078 | −7.232 | 39.116 | 1.00 | 67.59 | A | C |
| ATOM | 764 | C | TYR | A | 219 | 33.433 | −7.954 | 39.709 | 1.00 | 60.21 | A | C |
| ATOM | 765 | O | TYR | A | 219 | 33.163 | −7.733 | 40.899 | 1.00 | 56.51 | A | O |
| ATOM | 766 | N | ARG | A | 220 | 33.506 | −9.172 | 39.198 | 1.00 | 52.40 | A | N |
| ATOM | 767 | CA | ARG | A | 220 | 33.277 | −10.325 | 40.023 | 1.00 | 67.81 | A | C |
| ATOM | 768 | CB | ARG | A | 220 | 32.872 | −11.523 | 39.126 | 1.00 | 79.06 | A | C |
| ATOM | 769 | CG | ARG | A | 220 | 32.658 | −12.891 | 39.808 | 1.00 | 91.40 | A | C |
| ATOM | 770 | CD | ARG | A | 220 | 33.042 | −14.070 | 38.904 | 1.00 | 100.14 | A | C |
| ATOM | 771 | NE | ARG | A | 220 | 34.049 | −13.677 | 37.900 | 1.00 | 118.49 | A | N |
| ATOM | 772 | CZ | ARG | A | 220 | 35.343 | −13.391 | 38.139 | 1.00 | 117.49 | A | C |
| ATOM | 773 | NH1 | ARG | A | 220 | 35.866 | −13.470 | 39.368 | 1.00 | 107.72 | A | N |
| ATOM | 774 | NH2 | ARG | A | 220 | 36.125 | −13.005 | 37.128 | 1.00 | 105.75 | A | N |
| ATOM | 775 | C | ARG | A | 220 | 34.527 | −10.513 | 40.931 | 1.00 | 54.49 | A | C |
| ATOM | 776 | O | ARG | A | 220 | 34.380 | −10.954 | 42.072 | 1.00 | 51.76 | A | O |
| ATOM | 777 | N | GLU | A | 221 | 35.722 | −10.123 | 40.464 | 1.00 | 46.20 | A | N |
| ATOM | 778 | CA | GLU | A | 221 | 36.905 | −10.096 | 41.333 | 1.00 | 47.86 | A | C |
| ATOM | 779 | CB | GLU | A | 221 | 38.204 | −9.730 | 40.611 | 1.00 | 51.67 | A | C |
| ATOM | 780 | CG | GLU | A | 221 | 38.711 | −10.768 | 39.645 | 1.00 | 57.96 | A | C |
| ATOM | 781 | CD | GLU | A | 221 | 39.115 | −12.034 | 40.347 | 1.00 | 63.72 | A | C |
| ATOM | 782 | OE1 | GLU | A | 221 | 40.248 | −12.028 | 40.923 | 1.00 | 58.31 | A | O |
| ATOM | 783 | OE2 | GLU | A | 221 | 38.263 | −12.983 | 40.337 | 1.00 | 57.14 | A | O |
| ATOM | 784 | C | GLU | A | 221 | 36.734 | −9.145 | 42.496 | 1.00 | 52.17 | A | C |
| ATOM | 785 | O | GLU | A | 221 | 37.133 | −9.472 | 43.611 | 1.00 | 48.77 | A | O |
| ATOM | 786 | N | LEU | A | 222 | 36.193 | −7.961 | 42.226 | 1.00 | 47.05 | A | N |
| ATOM | 787 | CA | LEU | A | 222 | 36.017 | −6.934 | 43.264 | 1.00 | 49.46 | A | C |
| ATOM | 788 | CB | LEU | A | 222 | 35.582 | −5.593 | 42.643 | 1.00 | 44.78 | A | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 789 | CG | LEU | A | 222 | 35.317 | −4.393 | 43.568 | 1.00 | 44.27 | A | C |
| ATOM | 790 | CD1 | LEU | A | 222 | 36.629 | −3.829 | 44.051 | 1.00 | 49.18 | A | C |
| ATOM | 791 | CD2 | LEU | A | 222 | 34.512 | −3.313 | 42.852 | 1.00 | 50.09 | A | C |
| ATOM | 792 | C | LEU | A | 222 | 34.961 | −7.406 | 44.261 | 1.00 | 54.88 | A | C |
| ATOM | 793 | O | LEU | A | 222 | 35.047 | −7.067 | 45.439 | 1.00 | 57.86 | A | O |
| ATOM | 794 | N | GLN | A | 223 | 33.946 | −8.129 | 43.774 | 1.00 | 54.65 | A | N |
| ATOM | 795 | CA | GLN | A | 223 | 32.927 | −8.707 | 44.643 | 1.00 | 59.34 | A | C |
| ATOM | 796 | CB | GLN | A | 223 | 31.794 | −9.304 | 43.833 | 1.00 | 65.22 | A | C |
| ATOM | 797 | CG | GLN | A | 223 | 30.747 | −8.274 | 43.453 | 1.00 | 76.69 | A | C |
| ATOM | 798 | CD | GLN | A | 223 | 29.534 | −8.929 | 42.831 | 1.00 | 89.57 | A | C |
| ATOM | 799 | OE1 | GLN | A | 223 | 29.620 | −10.053 | 42.305 | 1.00 | 91.92 | A | O |
| ATOM | 800 | NE2 | GLN | A | 223 | 28.389 | −8.242 | 42.889 | 1.00 | 91.33 | A | N |
| ATOM | 801 | C | GLN | A | 223 | 33.501 | −9.778 | 45.564 | 1.00 | 53.44 | A | C |
| ATOM | 802 | O | GLN | A | 223 | 33.324 | −9.702 | 46.740 | 1.00 | 49.91 | A | O |
| ATOM | 803 | N | LYS | A | 224 | 34.184 | −10.768 | 45.007 | 1.00 | 53.88 | A | N |
| ATOM | 804 | CA | LYS | A | 224 | 34.857 | −11.781 | 45.811 | 1.00 | 53.55 | A | C |
| ATOM | 805 | CB | LYS | A | 224 | 35.648 | −12.747 | 44.910 | 1.00 | 55.57 | A | C |
| ATOM | 806 | CG | LYS | A | 224 | 35.007 | −14.127 | 44.758 | 1.00 | 62.73 | A | C |
| ATOM | 807 | CD | LYS | A | 224 | 35.041 | −14.679 | 43.345 | 1.00 | 65.37 | A | C |
| ATOM | 808 | CE | LYS | A | 224 | 36.448 | −14.742 | 42.796 | 1.00 | 71.76 | A | C |
| ATOM | 809 | NZ | LYS | A | 224 | 36.474 | −15.690 | 41.648 | 1.00 | 83.24 | A | N |
| ATOM | 810 | C | LYS | A | 224 | 35.757 | −11.164 | 46.900 | 1.00 | 57.26 | A | C |
| ATOM | 811 | O | LYS | A | 224 | 35.759 | −11.641 | 48.026 | 1.00 | 64.83 | A | O |
| ATOM | 812 | N | LEU | A | 225 | 36.481 | −10.092 | 46.563 | 1.00 | 51.47 | A | N |
| ATOM | 813 | CA | LEU | A | 225 | 37.394 | −9.412 | 47.470 | 1.00 | 46.17 | A | C |
| ATOM | 814 | CB | LEU | A | 225 | 38.679 | −8.971 | 46.730 | 1.00 | 50.88 | A | C |
| ATOM | 815 | CG | LEU | A | 225 | 39.890 | −9.885 | 46.492 | 1.00 | 58.79 | A | C |
| ATOM | 816 | CD1 | LEU | A | 225 | 39.588 | −11.052 | 45.538 | 1.00 | 63.53 | A | C |
| ATOM | 817 | CD2 | LEU | A | 225 | 41.044 | −9.078 | 45.911 | 1.00 | 59.42 | A | C |
| ATOM | 818 | C | LEU | A | 225 | 36.828 | −8.181 | 48.155 | 1.00 | 43.71 | A | C |
| ATOM | 819 | O | LEU | A | 225 | 37.552 | −7.577 | 48.912 | 1.00 | 47.39 | A | O |
| ATOM | 820 | N | SER | A | 226 | 35.586 | −7.773 | 47.877 | 1.00 | 51.34 | A | N |
| ATOM | 821 | CA | SER | A | 226 | 35.002 | −6.474 | 48.314 | 1.00 | 47.94 | A | C |
| ATOM | 822 | CB | SER | A | 226 | 34.908 | −6.371 | 49.832 | 1.00 | 52.72 | A | C |
| ATOM | 823 | OG | SER | A | 226 | 34.578 | −7.597 | 50.406 | 1.00 | 60.59 | A | O |
| ATOM | 824 | C | SER | A | 226 | 35.685 | −5.170 | 47.825 | 1.00 | 48.94 | A | C |
| ATOM | 825 | O | SER | A | 226 | 35.014 | −4.252 | 47.367 | 1.00 | 49.74 | A | O |
| ATOM | 826 | N | LYS | A | 227 | 36.985 | −5.055 | 48.048 | 1.00 | 49.61 | A | N |
| ATOM | 827 | CA | LYS | A | 227 | 37.786 | −3.929 | 47.566 | 1.00 | 52.65 | A | C |
| ATOM | 828 | CB | LYS | A | 227 | 37.781 | −2.797 | 48.581 | 1.00 | 55.79 | A | C |
| ATOM | 829 | CG | LYS | A | 227 | 37.793 | −3.246 | 50.037 | 1.00 | 61.34 | A | C |
| ATOM | 830 | CD | LYS | A | 227 | 38.274 | −2.151 | 50.965 | 1.00 | 62.30 | A | C |
| ATOM | 831 | CE | LYS | A | 227 | 37.890 | −2.440 | 52.401 | 1.00 | 71.44 | A | C |
| ATOM | 832 | NZ | LYS | A | 227 | 38.913 | −1.900 | 53.349 | 1.00 | 75.82 | A | N |
| ATOM | 833 | C | LYS | A | 227 | 39.195 | −4.407 | 47.266 | 1.00 | 48.73 | A | C |
| ATOM | 834 | O | LYS | A | 227 | 39.583 | −5.472 | 47.737 | 1.00 | 57.69 | A | O |
| ATOM | 835 | N | PHE | A | 228 | 39.946 | −3.645 | 46.471 | 1.00 | 44.01 | A | N |
| ATOM | 836 | CA | PHE | A | 228 | 41.334 | −3.986 | 46.124 | 1.00 | 42.71 | A | C |
| ATOM | 837 | CB | PHE | A | 228 | 41.637 | −3.791 | 44.618 | 1.00 | 44.72 | A | C |
| ATOM | 838 | CG | PHE | A | 228 | 40.773 | −4.622 | 43.703 | 1.00 | 47.47 | A | C |
| ATOM | 839 | CD1 | PHE | A | 228 | 40.436 | −5.936 | 44.022 | 1.00 | 46.46 | A | C |
| ATOM | 840 | CE1 | PHE | A | 228 | 39.627 | −6.682 | 43.186 | 1.00 | 43.29 | A | C |
| ATOM | 841 | CZ | PHE | A | 228 | 39.161 | −6.145 | 42.001 | 1.00 | 44.04 | A | C |
| ATOM | 842 | CE2 | PHE | A | 228 | 39.501 | −4.867 | 41.657 | 1.00 | 41.72 | A | C |
| ATOM | 843 | CD2 | PHE | A | 228 | 40.304 | −4.104 | 42.494 | 1.00 | 46.88 | A | C |
| ATOM | 844 | C | PHE | A | 228 | 42.306 | −3.146 | 46.903 | 1.00 | 43.00 | A | C |
| ATOM | 845 | O | PHE | A | 228 | 42.010 | −2.052 | 47.366 | 1.00 | 43.25 | A | O |
| ATOM | 846 | N | ASP | A | 229 | 43.494 | −3.684 | 47.048 | 1.00 | 39.74 | A | N |
| ATOM | 847 | CA | ASP | A | 229 | 44.517 | −2.986 | 47.783 | 1.00 | 43.97 | A | C |
| ATOM | 848 | CB | ASP | A | 229 | 45.547 | −3.975 | 48.324 | 1.00 | 48.37 | A | C |
| ATOM | 849 | CG | ASP | A | 229 | 46.081 | −4.872 | 47.239 | 1.00 | 57.05 | A | C |
| ATOM | 850 | OD1 | ASP | A | 229 | 47.196 | −4.617 | 46.767 | 1.00 | 60.57 | A | O |
| ATOM | 851 | OD2 | ASP | A | 229 | 45.319 | −5.760 | 46.792 | 1.00 | 64.59 | A | O |
| ATOM | 852 | C | ASP | A | 229 | 45.188 | −2.028 | 46.821 | 1.00 | 47.51 | A | C |
| ATOM | 853 | O | ASP | A | 229 | 44.967 | −2.053 | 45.593 | 1.00 | 46.90 | A | O |
| ATOM | 854 | N | GLU | A | 230 | 46.043 | −1.198 | 47.393 | 1.00 | 47.72 | A | N |
| ATOM | 855 | CA | GLU | A | 230 | 46.703 | −0.140 | 46.681 | 1.00 | 44.50 | A | C |
| ATOM | 856 | CB | GLU | A | 230 | 47.489 | 0.720 | 47.657 | 1.00 | 43.26 | A | C |
| ATOM | 857 | CG | GLU | A | 230 | 46.556 | 1.542 | 48.548 | 1.00 | 44.30 | A | C |
| ATOM | 858 | CD | GLU | A | 230 | 47.277 | 2.643 | 49.300 | 1.00 | 50.25 | A | C |
| ATOM | 859 | OE1 | GLU | A | 230 | 48.317 | 2.280 | 49.881 | 1.00 | 52.56 | A | O |
| ATOM | 860 | OE2 | GLU | A | 230 | 46.806 | 3.833 | 49.351 | 1.00 | 44.56 | A | O |
| ATOM | 861 | C | GLU | A | 230 | 47.552 | −0.600 | 45.493 | 1.00 | 50.63 | A | C |
| ATOM | 862 | O | GLU | A | 230 | 47.588 | 0.122 | 44.468 | 1.00 | 51.76 | A | O |
| ATOM | 863 | N | GLN | A | 231 | 48.153 | −1.790 | 45.558 | 1.00 | 41.23 | A | N |
| ATOM | 864 | CA | GLN | A | 231 | 49.097 | −2.185 | 44.502 | 1.00 | 45.24 | A | C |
| ATOM | 865 | CB | GLN | A | 231 | 50.228 | −3.125 | 44.971 | 1.00 | 49.22 | A | C |
| ATOM | 866 | CG | GLN | A | 231 | 51.077 | −2.605 | 46.159 | 1.00 | 53.27 | A | C |

APPENDIX A-continued

| Atomic coordinates of Aurora A + Inhibitory Monobody Mb60 + Danusertib | | | | | | | | | | | | |
|---|---|---|---|---|---|---|---|---|---|---|---|---|
| ATOM | 867 | CD | GLN | A | 231 | 50.325 | −2.666 | 47.521 | 1.00 | 57.88 | A | C |
| ATOM | 868 | OE1 | GLN | A | 231 | 50.231 | −1.679 | 48.243 | 1.00 | 58.72 | A | O |
| ATOM | 869 | NE2 | GLN | A | 231 | 49.753 | −3.823 | 47.832 | 1.00 | 61.59 | A | N |
| ATOM | 870 | C | GLN | A | 231 | 48.329 | −2.744 | 43.288 | 1.00 | 46.05 | A | C |
| ATOM | 871 | O | GLN | A | 231 | 48.630 | −2.387 | 42.159 | 1.00 | 43.06 | A | O |
| ATOM | 872 | N | ARG | A | 232 | 47.309 | −3.555 | 43.521 | 1.00 | 39.46 | A | N |
| ATOM | 873 | CA | ARG | A | 232 | 46.517 | −4.056 | 42.448 | 1.00 | 43.03 | A | C |
| ATOM | 874 | CB | ARG | A | 232 | 45.500 | −5.047 | 42.983 | 1.00 | 49.53 | A | C |
| ATOM | 875 | CG | ARG | A | 232 | 44.877 | −5.911 | 41.918 | 1.00 | 58.01 | A | C |
| ATOM | 876 | CD | ARG | A | 232 | 43.464 | −6.329 | 42.297 | 1.00 | 62.16 | A | C |
| ATOM | 877 | NE | ARG | A | 232 | 43.386 | −7.660 | 42.890 | 1.00 | 66.55 | A | N |
| ATOM | 878 | CZ | ARG | A | 232 | 42.860 | −8.750 | 42.330 | 1.00 | 63.88 | A | C |
| ATOM | 879 | NH1 | ARG | A | 232 | 42.338 | −8.750 | 41.107 | 1.00 | 59.94 | A | N |
| ATOM | 880 | NH2 | ARG | A | 232 | 42.837 | −9.867 | 43.037 | 1.00 | 70.47 | A | N |
| ATOM | 881 | C | ARG | A | 232 | 45.754 | −2.906 | 41.748 | 1.00 | 46.03 | A | C |
| ATOM | 882 | O | ARG | A | 232 | 45.532 | −2.980 | 40.557 | 1.00 | 40.11 | A | O |
| ATOM | 883 | N | THR | A | 233 | 45.315 | −1.900 | 42.524 | 1.00 | 42.15 | A | N |
| ATOM | 884 | CA | THR | A | 233 | 44.478 | −0.812 | 42.008 | 1.00 | 41.49 | A | C |
| ATOM | 885 | CB | THR | A | 233 | 43.795 | 0.040 | 43.133 | 1.00 | 43.47 | A | C |
| ATOM | 886 | OG1 | THR | A | 233 | 42.822 | −0.722 | 43.893 | 1.00 | 41.79 | A | O |
| ATOM | 887 | CG2 | THR | A | 233 | 43.079 | 1.267 | 42.516 | 1.00 | 42.32 | A | C |
| ATOM | 888 | C | THR | A | 233 | 45.347 | 0.115 | 41.165 | 1.00 | 42.23 | A | C |
| ATOM | 889 | O | THR | A | 233 | 44.990 | 0.491 | 40.071 | 1.00 | 40.98 | A | O |
| ATOM | 890 | N | ALA | A | 234 | 46.503 | 0.492 | 41.689 | 1.00 | 43.09 | A | N |
| ATOM | 891 | CA | ALA | A | 234 | 47.409 | 1.374 | 40.957 | 1.00 | 44.13 | A | C |
| ATOM | 892 | CB | ALA | A | 234 | 48.564 | 1.841 | 41.823 | 1.00 | 43.56 | A | C |
| ATOM | 893 | C | ALA | A | 234 | 47.934 | 0.721 | 39.693 | 1.00 | 41.34 | A | C |
| ATOM | 894 | O | ALA | A | 234 | 48.212 | 1.413 | 38.694 | 1.00 | 47.32 | A | O |
| ATOM | 895 | N | THR | A | 235 | 48.052 | −0.593 | 39.719 | 1.00 | 40.28 | A | N |
| ATOM | 896 | CA | THR | A | 235 | 48.496 | −1.326 | 38.567 | 1.00 | 39.88 | A | C |
| ATOM | 897 | CB | THR | A | 235 | 48.862 | −2.780 | 38.942 | 1.00 | 43.13 | A | C |
| ATOM | 898 | OG1 | THR | A | 235 | 49.847 | −2.769 | 39.990 | 1.00 | 44.60 | A | O |
| ATOM | 899 | CG2 | THR | A | 235 | 49.404 | −3.473 | 37.747 | 1.00 | 40.17 | A | C |
| ATOM | 900 | C | THR | A | 235 | 47.403 | −1.283 | 37.478 | 1.00 | 41.49 | A | C |
| ATOM | 901 | O | THR | A | 235 | 47.732 | −0.977 | 36.339 | 1.00 | 39.10 | A | O |
| ATOM | 902 | N | TYR | A | 236 | 46.136 | −1.585 | 37.828 | 1.00 | 37.35 | A | N |
| ATOM | 903 | CA | TYR | A | 236 | 44.982 | −1.354 | 36.945 | 1.00 | 38.46 | A | C |
| ATOM | 904 | CB | TYR | A | 236 | 43.671 | −1.640 | 37.671 | 1.00 | 39.48 | A | C |
| ATOM | 905 | CG | TYR | A | 236 | 43.381 | −3.096 | 37.966 | 1.00 | 40.91 | A | C |
| ATOM | 906 | CD1 | TYR | A | 236 | 43.977 | −4.122 | 37.239 | 1.00 | 43.82 | A | C |
| ATOM | 907 | CE1 | TYR | A | 236 | 43.685 | −5.430 | 37.504 | 1.00 | 43.07 | A | C |
| ATOM | 908 | CZ | TYR | A | 236 | 42.834 | −5.736 | 38.524 | 1.00 | 43.33 | A | C |
| ATOM | 909 | OH | TYR | A | 236 | 42.560 | −7.036 | 38.758 | 1.00 | 44.17 | A | O |
| ATOM | 910 | CE2 | TYR | A | 236 | 42.227 | −4.751 | 39.279 | 1.00 | 45.33 | A | C |
| ATOM | 911 | CD2 | TYR | A | 236 | 42.503 | −3.444 | 39.003 | 1.00 | 41.04 | A | C |
| ATOM | 912 | C | TYR | A | 236 | 44.858 | 0.064 | 36.360 | 1.00 | 38.83 | A | C |
| ATOM | 913 | O | TYR | A | 236 | 44.664 | 0.246 | 35.166 | 1.00 | 38.34 | A | O |
| ATOM | 914 | N | ILE | A | 237 | 44.990 | 1.067 | 37.200 | 1.00 | 34.85 | A | N |
| ATOM | 915 | CA | ILE | A | 237 | 44.861 | 2.411 | 36.741 | 1.00 | 37.18 | A | C |
| ATOM | 916 | CB | ILE | A | 237 | 44.843 | 3.390 | 37.917 | 1.00 | 35.86 | A | C |
| ATOM | 917 | CG1 | ILE | A | 237 | 43.577 | 3.177 | 38.789 | 1.00 | 39.28 | A | C |
| ATOM | 918 | CD1 | ILE | A | 237 | 42.229 | 3.356 | 38.078 | 1.00 | 38.59 | A | C |
| ATOM | 919 | CG2 | ILE | A | 237 | 44.903 | 4.820 | 37.472 | 1.00 | 36.62 | A | C |
| ATOM | 920 | C | ILE | A | 237 | 45.956 | 2.661 | 35.700 | 1.00 | 40.22 | A | C |
| ATOM | 921 | O | ILE | A | 237 | 45.693 | 3.300 | 34.668 | 1.00 | 34.22 | A | O |
| ATOM | 922 | N | THR | A | 238 | 47.167 | 2.174 | 35.946 | 1.00 | 38.54 | A | N |
| ATOM | 923 | CA | THR | A | 238 | 48.272 | 2.326 | 34.971 | 1.00 | 42.63 | A | C |
| ATOM | 924 | CB | THR | A | 238 | 49.599 | 1.701 | 35.485 | 1.00 | 44.49 | A | C |
| ATOM | 925 | OG1 | THR | A | 238 | 49.944 | 2.333 | 36.703 | 1.00 | 50.52 | A | O |
| ATOM | 926 | CG2 | THR | A | 238 | 50.755 | 1.934 | 34.494 | 1.00 | 48.52 | A | C |
| ATOM | 927 | C | THR | A | 238 | 47.905 | 1.670 | 33.643 | 1.00 | 38.67 | A | C |
| ATOM | 928 | O | THR | A | 238 | 48.103 | 2.234 | 32.583 | 1.00 | 36.32 | A | O |
| ATOM | 929 | N | GLU | A | 239 | 47.305 | 0.503 | 33.702 | 1.00 | 34.67 | A | N |
| ATOM | 930 | CA | GLU | A | 239 | 46.921 | −0.176 | 32.481 | 1.00 | 40.48 | A | C |
| ATOM | 931 | CB | GLU | A | 239 | 46.404 | −1.576 | 32.827 | 1.00 | 43.65 | A | C |
| ATOM | 932 | CG | GLU | A | 239 | 47.483 | −2.481 | 33.464 | 1.00 | 47.31 | A | C |
| ATOM | 933 | CD | GLU | A | 239 | 46.929 | −3.718 | 34.136 | 1.00 | 52.53 | A | C |
| ATOM | 934 | OE1 | GLU | A | 239 | 45.668 | −3.903 | 34.181 | 1.00 | 49.12 | A | O |
| ATOM | 935 | OE2 | GLU | A | 239 | 47.773 | −4.526 | 34.607 | 1.00 | 57.06 | A | O |
| ATOM | 936 | C | GLU | A | 239 | 45.865 | 0.618 | 31.674 | 1.00 | 40.60 | A | C |
| ATOM | 937 | O | GLU | A | 239 | 45.906 | 0.708 | 30.439 | 1.00 | 37.99 | A | O |
| ATOM | 938 | N | LEU | A | 240 | 44.902 | 1.173 | 32.376 | 1.00 | 37.54 | A | N |
| ATOM | 939 | CA | LEU | A | 240 | 43.824 | 1.896 | 31.714 | 1.00 | 35.94 | A | C |
| ATOM | 940 | CB | LEU | A | 240 | 42.632 | 2.112 | 32.631 | 1.00 | 34.40 | A | C |
| ATOM | 941 | CG | LEU | A | 240 | 42.023 | 0.788 | 32.967 | 1.00 | 33.89 | A | C |
| ATOM | 942 | CD1 | LEU | A | 240 | 40.993 | 0.988 | 34.055 | 1.00 | 37.58 | A | C |
| ATOM | 943 | CD2 | LEU | A | 240 | 41.400 | 0.080 | 31.760 | 1.00 | 38.71 | A | C |
| ATOM | 944 | C | LEU | A | 240 | 44.334 | 3.206 | 31.228 | 1.00 | 33.16 | A | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 945 | O | LEU | A | 240 | 43.926 | 3.679 | 30.181 | 1.00 | 36.16 | A | O |
| ATOM | 946 | N | ALA | A | 241 | 45.213 | 3.824 | 31.981 | 1.00 | 32.92 | A | N |
| ATOM | 947 | CA | ALA | A | 241 | 45.750 | 5.060 | 31.505 | 1.00 | 34.46 | A | C |
| ATOM | 948 | CB | ALA | A | 241 | 46.603 | 5.785 | 32.525 | 1.00 | 31.94 | A | C |
| ATOM | 949 | C | ALA | A | 241 | 46.474 | 4.801 | 30.197 | 1.00 | 37.54 | A | C |
| ATOM | 950 | O | ALA | A | 241 | 46.313 | 5.605 | 29.259 | 1.00 | 37.33 | A | O |
| ATOM | 951 | N | ASN | A | 242 | 47.207 | 3.694 | 30.072 | 1.00 | 37.27 | A | N |
| ATOM | 952 | CA | ASN | A | 242 | 47.894 | 3.470 | 28.791 | 1.00 | 41.08 | A | C |
| ATOM | 953 | CB | ASN | A | 242 | 49.000 | 2.376 | 28.850 | 1.00 | 44.60 | A | C |
| ATOM | 954 | CG | ASN | A | 242 | 50.029 | 2.608 | 29.952 | 1.00 | 46.23 | A | C |
| ATOM | 955 | OD1 | ASN | A | 242 | 50.467 | 3.737 | 30.197 | 1.00 | 46.97 | A | O |
| ATOM | 956 | ND2 | ASN | A | 242 | 50.367 | 1.521 | 30.681 | 1.00 | 41.64 | A | N |
| ATOM | 957 | C | ASN | A | 242 | 46.864 | 3.169 | 27.677 | 1.00 | 40.48 | A | C |
| ATOM | 958 | O | ASN | A | 242 | 46.998 | 3.677 | 26.571 | 1.00 | 36.69 | A | O |
| ATOM | 959 | N | ALA | A | 243 | 45.851 | 2.349 | 27.963 | 1.00 | 35.10 | A | N |
| ATOM | 960 | CA | ALA | A | 243 | 44.794 | 2.091 | 26.989 | 1.00 | 35.67 | A | C |
| ATOM | 961 | CB | ALA | A | 243 | 43.717 | 1.185 | 27.560 | 1.00 | 37.04 | A | C |
| ATOM | 962 | C | ALA | A | 243 | 44.151 | 3.408 | 26.559 | 1.00 | 37.83 | A | C |
| ATOM | 963 | O | ALA | A | 243 | 43.949 | 3.642 | 25.371 | 1.00 | 36.76 | A | O |
| ATOM | 964 | N | LEU | A | 244 | 43.848 | 4.273 | 27.521 | 1.00 | 34.97 | A | N |
| ATOM | 965 | CA | LEU | A | 244 | 43.174 | 5.548 | 27.183 | 1.00 | 38.78 | A | C |
| ATOM | 966 | CB | LEU | A | 244 | 42.622 | 6.240 | 28.451 | 1.00 | 37.50 | A | C |
| ATOM | 967 | CG | LEU | A | 244 | 41.553 | 5.424 | 29.197 | 1.00 | 37.17 | A | C |
| ATOM | 968 | CD1 | LEU | A | 244 | 41.326 | 5.994 | 30.583 | 1.00 | 36.65 | A | C |
| ATOM | 969 | CD2 | LEU | A | 244 | 40.251 | 5.368 | 28.406 | 1.00 | 40.36 | A | C |
| ATOM | 970 | C | LEU | A | 244 | 44.071 | 6.503 | 26.386 | 1.00 | 35.37 | A | C |
| ATOM | 971 | O | LEU | A | 244 | 43.583 | 7.172 | 25.492 | 1.00 | 39.05 | A | O |
| ATOM | 972 | N | SER | A | 245 | 45.366 | 6.551 | 26.705 | 1.00 | 37.75 | A | N |
| ATOM | 973 | CA | SER | A | 245 | 46.366 | 7.299 | 25.902 | 1.00 | 37.65 | A | C |
| ATOM | 974 | CB | SER | A | 245 | 47.793 | 7.142 | 26.450 | 1.00 | 39.12 | A | C |
| ATOM | 975 | OG | SER | A | 245 | 47.921 | 7.883 | 27.639 | 1.00 | 47.94 | A | O |
| ATOM | 976 | C | SER | A | 245 | 46.391 | 6.823 | 24.462 | 1.00 | 34.68 | A | C |
| ATOM | 977 | O | SER | A | 245 | 46.483 | 7.632 | 23.521 | 1.00 | 32.94 | A | O |
| ATOM | 978 | N | TYR | A | 246 | 46.353 | 5.508 | 24.269 | 1.00 | 31.25 | A | N |
| ATOM | 979 | CA | TYR | A | 246 | 46.287 | 4.987 | 22.921 | 1.00 | 33.69 | A | C |
| ATOM | 980 | CB | TYR | A | 246 | 46.286 | 3.486 | 22.989 | 1.00 | 35.75 | A | C |
| ATOM | 981 | CG | TYR | A | 246 | 46.060 | 2.871 | 21.650 | 1.00 | 35.28 | A | C |
| ATOM | 982 | CD1 | TYR | A | 246 | 44.840 | 2.317 | 21.350 | 1.00 | 43.48 | A | C |
| ATOM | 983 | CE1 | TYR | A | 246 | 44.592 | 1.744 | 20.125 | 1.00 | 43.72 | A | C |
| ATOM | 984 | CZ | TYR | A | 246 | 45.580 | 1.727 | 19.172 | 1.00 | 44.33 | A | C |
| ATOM | 985 | OH | TYR | A | 246 | 45.233 | 1.132 | 17.985 | 1.00 | 47.64 | A | O |
| ATOM | 986 | CE2 | TYR | A | 246 | 46.820 | 2.290 | 19.443 | 1.00 | 39.60 | A | C |
| ATOM | 987 | CD2 | TYR | A | 246 | 47.038 | 2.876 | 20.680 | 1.00 | 36.13 | A | C |
| ATOM | 988 | C | TYR | A | 246 | 45.018 | 5.469 | 22.201 | 1.00 | 36.52 | A | C |
| ATOM | 989 | O | TYR | A | 246 | 45.065 | 6.019 | 21.076 | 1.00 | 34.94 | A | O |
| ATOM | 990 | N | CYS | A | 247 | 43.881 | 5.259 | 22.860 | 1.00 | 34.35 | A | N |
| ATOM | 991 | CA | CYS | A | 247 | 42.602 | 5.683 | 22.280 | 1.00 | 37.04 | A | C |
| ATOM | 992 | CB | CYS | A | 247 | 41.420 | 5.385 | 23.186 | 1.00 | 35.81 | A | C |
| ATOM | 993 | SG | CYS | A | 247 | 41.059 | 3.650 | 23.458 | 1.00 | 36.00 | A | S |
| ATOM | 994 | C | CYS | A | 247 | 42.630 | 7.163 | 21.919 | 1.00 | 30.54 | A | C |
| ATOM | 995 | O | CYS | A | 247 | 42.299 | 7.528 | 20.818 | 1.00 | 31.32 | A | O |
| ATOM | 996 | N | HIS | A | 248 | 43.102 | 7.986 | 22.820 | 1.00 | 27.96 | A | N |
| ATOM | 997 | CA | HIS | A | 248 | 43.107 | 9.407 | 22.561 | 1.00 | 28.69 | A | C |
| ATOM | 998 | CB | HIS | A | 248 | 43.534 | 10.176 | 23.787 | 1.00 | 28.64 | A | C |
| ATOM | 999 | CG | HIS | A | 248 | 42.539 | 10.127 | 24.880 | 1.00 | 30.89 | A | C |
| ATOM | 1000 | ND1 | HIS | A | 248 | 42.737 | 10.757 | 26.082 | 1.00 | 32.17 | A | N |
| ATOM | 1001 | CE1 | HIS | A | 248 | 41.702 | 10.542 | 26.862 | 1.00 | 31.81 | A | C |
| ATOM | 1002 | NE2 | HIS | A | 248 | 40.813 | 9.828 | 26.182 | 1.00 | 33.81 | A | N |
| ATOM | 1003 | CD2 | HIS | A | 248 | 41.335 | 9.511 | 24.961 | 1.00 | 31.21 | A | C |
| ATOM | 1004 | C | HIS | A | 248 | 44.040 | 9.782 | 21.426 | 1.00 | 34.47 | A | C |
| ATOM | 1005 | O | HIS | A | 248 | 43.723 | 10.682 | 20.706 | 1.00 | 31.83 | A | O |
| ATOM | 1006 | N | SER | A | 249 | 45.145 | 9.043 | 21.229 | 1.00 | 33.33 | A | N |
| ATOM | 1007 | CA | SER | A | 249 | 46.073 | 9.291 | 20.121 | 1.00 | 34.99 | A | C |
| ATOM | 1008 | CB | SER | A | 249 | 47.311 | 8.331 | 20.101 | 1.00 | 33.13 | A | C |
| ATOM | 1009 | OG | SER | A | 249 | 46.849 | 6.968 | 19.931 | 1.00 | 31.90 | A | O |
| ATOM | 1010 | C | SER | A | 249 | 45.347 | 9.136 | 18.826 | 1.00 | 31.79 | A | C |
| ATOM | 1011 | O | SER | A | 249 | 45.729 | 9.797 | 17.873 | 1.00 | 34.14 | A | O |
| ATOM | 1012 | N | LYS | A | 250 | 44.398 | 8.208 | 18.810 | 1.00 | 29.13 | A | N |
| ATOM | 1013 | CA | LYS | A | 250 | 43.466 | 7.961 | 17.711 | 1.00 | 34.10 | A | C |
| ATOM | 1014 | CB | LYS | A | 250 | 43.111 | 6.463 | 17.668 | 1.00 | 37.08 | A | C |
| ATOM | 1015 | CG | LYS | A | 250 | 44.283 | 5.490 | 17.640 | 1.00 | 43.78 | A | C |
| ATOM | 1016 | CD | LYS | A | 250 | 45.136 | 5.669 | 16.415 | 1.00 | 51.07 | A | C |
| ATOM | 1017 | CE | LYS | A | 250 | 46.628 | 5.431 | 16.668 | 1.00 | 60.31 | A | C |
| ATOM | 1018 | NZ | LYS | A | 250 | 47.009 | 4.178 | 15.978 | 1.00 | 64.89 | A | N |
| ATOM | 1019 | C | LYS | A | 250 | 42.170 | 8.772 | 17.736 | 1.00 | 30.33 | A | C |
| ATOM | 1020 | O | LYS | A | 250 | 41.262 | 8.511 | 16.957 | 1.00 | 30.33 | A | O |
| ATOM | 1021 | N | ARG | A | 251 | 42.077 | 9.739 | 18.641 | 1.00 | 32.37 | A | N |
| ATOM | 1022 | CA | ARG | A | 251 | 40.938 | 10.649 | 18.745 | 1.00 | 33.93 | A | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 1023 | CB | ARG | A | 251 | 40.797 | 11.546 | 17.489 | 1.00 | 35.48 | A | C |
| ATOM | 1024 | CG | ARG | A | 251 | 42.005 | 12.446 | 17.244 | 1.00 | 34.51 | A | C |
| ATOM | 1025 | CD | ARG | A | 251 | 41.841 | 13.214 | 15.929 | 1.00 | 37.96 | A | C |
| ATOM | 1026 | NE | ARG | A | 251 | 41.941 | 12.333 | 14.757 | 1.00 | 37.52 | A | N |
| ATOM | 1027 | CZ | ARG | A | 251 | 41.616 | 12.645 | 13.495 | 1.00 | 41.51 | A | C |
| ATOM | 1028 | NH1 | ARG | A | 251 | 41.109 | 13.829 | 13.149 | 1.00 | 44.13 | A | N |
| ATOM | 1029 | NH2 | ARG | A | 251 | 41.781 | 11.750 | 12.553 | 1.00 | 45.24 | A | N |
| ATOM | 1030 | C | ARG | A | 251 | 39.639 | 9.896 | 19.065 | 1.00 | 32.66 | A | C |
| ATOM | 1031 | O | ARG | A | 251 | 38.531 | 10.364 | 18.739 | 1.00 | 30.21 | A | O |
| ATOM | 1032 | N | VAL | A | 252 | 39.776 | 8.807 | 19.821 | 1.00 | 29.90 | A | N |
| ATOM | 1033 | CA | VAL | A | 252 | 38.636 | 8.045 | 20.341 | 1.00 | 33.35 | A | C |
| ATOM | 1034 | CB | VAL | A | 252 | 38.751 | 6.554 | 19.968 | 1.00 | 36.19 | A | C |
| ATOM | 1035 | CG1 | VAL | A | 252 | 37.614 | 5.759 | 20.572 | 1.00 | 37.36 | A | C |
| ATOM | 1036 | CG2 | VAL | A | 252 | 38.735 | 6.419 | 18.449 | 1.00 | 38.87 | A | C |
| ATOM | 1037 | C | VAL | A | 252 | 38.540 | 8.208 | 21.834 | 1.00 | 32.28 | A | C |
| ATOM | 1038 | O | VAL | A | 252 | 39.468 | 7.859 | 22.545 | 1.00 | 33.39 | A | O |
| ATOM | 1039 | N | ILE | A | 253 | 37.387 | 8.704 | 22.293 | 1.00 | 30.83 | A | N |
| ATOM | 1040 | CA | ILE | A | 253 | 37.188 | 9.107 | 23.667 | 1.00 | 32.95 | A | C |
| ATOM | 1041 | CB | ILE | A | 253 | 37.105 | 10.623 | 23.767 | 1.00 | 34.83 | A | C |
| ATOM | 1042 | CG1 | ILE | A | 253 | 35.905 | 11.199 | 22.954 | 1.00 | 32.00 | A | C |
| ATOM | 1043 | CD1 | ILE | A | 253 | 35.412 | 12.470 | 23.600 | 1.00 | 35.40 | A | C |
| ATOM | 1044 | CG2 | ILE | A | 253 | 38.445 | 11.247 | 23.333 | 1.00 | 37.75 | A | C |
| ATOM | 1045 | C | ILE | A | 253 | 35.974 | 8.448 | 24.288 | 1.00 | 33.07 | A | C |
| ATOM | 1046 | O | ILE | A | 253 | 35.248 | 7.669 | 23.638 | 1.00 | 31.90 | A | O |
| ATOM | 1047 | N | HIS | A | 254 | 35.794 | 8.722 | 25.573 | 1.00 | 32.75 | A | N |
| ATOM | 1048 | CA | HIS | A | 254 | 34.723 | 8.147 | 26.379 | 1.00 | 34.46 | A | C |
| ATOM | 1049 | CB | HIS | A | 254 | 33.376 | 8.768 | 25.947 | 1.00 | 37.16 | A | C |
| ATOM | 1050 | CG | HIS | A | 254 | 32.222 | 8.471 | 26.868 | 1.00 | 41.82 | A | C |
| ATOM | 1051 | ND1 | HIS | A | 254 | 32.352 | 8.353 | 28.240 | 1.00 | 43.76 | A | N |
| ATOM | 1052 | CE1 | HIS | A | 254 | 31.164 | 8.153 | 28.783 | 1.00 | 41.39 | A | C |
| ATOM | 1053 | NE2 | HIS | A | 254 | 30.266 | 8.128 | 27.811 | 1.00 | 43.08 | A | N |
| ATOM | 1054 | CD2 | HIS | A | 254 | 30.896 | 8.356 | 26.610 | 1.00 | 40.76 | A | C |
| ATOM | 1055 | C | HIS | A | 254 | 34.650 | 6.621 | 26.307 | 1.00 | 37.38 | A | C |
| ATOM | 1056 | O | HIS | A | 254 | 33.649 | 6.073 | 25.853 | 1.00 | 33.30 | A | O |
| ATOM | 1057 | N | ARG | A | 255 | 35.663 | 5.906 | 26.770 | 1.00 | 34.68 | A | N |
| ATOM | 1058 | CA | ARG | A | 255 | 35.537 | 4.450 | 26.793 | 1.00 | 37.73 | A | C |
| ATOM | 1059 | CB | ARG | A | 255 | 36.911 | 3.757 | 26.768 | 1.00 | 38.00 | A | C |
| ATOM | 1060 | CG | ARG | A | 255 | 37.815 | 4.131 | 25.618 | 1.00 | 43.10 | A | C |
| ATOM | 1061 | CD | ARG | A | 255 | 37.404 | 3.455 | 24.331 | 1.00 | 42.97 | A | C |
| ATOM | 1062 | NE | ARG | A | 255 | 36.426 | 4.271 | 23.685 | 1.00 | 46.20 | A | N |
| ATOM | 1063 | CZ | ARG | A | 255 | 35.590 | 3.890 | 22.722 | 1.00 | 51.36 | A | C |
| ATOM | 1064 | NH1 | ARG | A | 255 | 35.579 | 2.653 | 22.220 | 1.00 | 47.85 | A | N |
| ATOM | 1065 | NH2 | ARG | A | 255 | 34.755 | 4.820 | 22.237 | 1.00 | 50.01 | A | N |
| ATOM | 1066 | C | ARG | A | 255 | 34.751 | 3.993 | 28.030 | 1.00 | 32.54 | A | C |
| ATOM | 1067 | O | ARG | A | 255 | 34.785 | 4.597 | 29.057 | 1.00 | 41.45 | A | O |
| ATOM | 1068 | N | ASP | A | 256 | 34.033 | 2.922 | 27.911 | 1.00 | 37.33 | A | N |
| ATOM | 1069 | CA | ASP | A | 256 | 33.368 | 2.285 | 29.046 | 1.00 | 41.17 | A | C |
| ATOM | 1070 | CB | ASP | A | 256 | 32.320 | 1.328 | 28.498 | 1.00 | 45.93 | A | C |
| ATOM | 1071 | CG | ASP | A | 256 | 31.319 | 0.905 | 29.554 | 1.00 | 53.97 | A | C |
| ATOM | 1072 | OD1 | ASP | A | 256 | 31.703 | 0.702 | 30.729 | 1.00 | 52.64 | A | O |
| ATOM | 1073 | OD2 | ASP | A | 256 | 30.132 | 0.816 | 29.221 | 1.00 | 60.30 | A | O |
| ATOM | 1074 | C | ASP | A | 256 | 34.407 | 1.535 | 29.963 | 1.00 | 42.59 | A | C |
| ATOM | 1075 | O | ASP | A | 256 | 34.919 | 0.462 | 29.616 | 1.00 | 47.30 | A | O |
| ATOM | 1076 | N | ILE | A | 257 | 34.759 | 2.123 | 31.111 | 1.00 | 38.82 | A | N |
| ATOM | 1077 | CA | ILE | A | 257 | 35.731 | 1.480 | 31.998 | 1.00 | 39.28 | A | C |
| ATOM | 1078 | CB | ILE | A | 257 | 37.049 | 2.297 | 32.226 | 1.00 | 38.42 | A | C |
| ATOM | 1079 | CG1 | ILE | A | 257 | 36.759 | 3.653 | 32.862 | 1.00 | 37.13 | A | C |
| ATOM | 1080 | CD1 | ILE | A | 257 | 38.029 | 4.432 | 33.174 | 1.00 | 38.42 | A | C |
| ATOM | 1081 | CG2 | ILE | A | 257 | 37.884 | 2.524 | 30.927 | 1.00 | 39.85 | A | C |
| ATOM | 1082 | C | ILE | A | 257 | 35.064 | 1.191 | 33.344 | 1.00 | 41.18 | A | C |
| ATOM | 1083 | O | ILE | A | 257 | 35.722 | 1.203 | 34.405 | 1.00 | 40.19 | A | O |
| ATOM | 1084 | N | LYS | A | 258 | 33.776 | 0.922 | 33.317 | 1.00 | 36.41 | A | N |
| ATOM | 1085 | CA | LYS | A | 258 | 33.125 | 0.410 | 34.498 | 1.00 | 41.23 | A | C |
| ATOM | 1086 | CB | LYS | A | 258 | 31.634 | 0.409 | 34.318 | 1.00 | 43.63 | A | C |
| ATOM | 1087 | CG | LYS | A | 258 | 31.056 | 1.804 | 34.262 | 1.00 | 49.72 | A | C |
| ATOM | 1088 | CD | LYS | A | 258 | 29.538 | 1.821 | 34.523 | 1.00 | 57.63 | A | C |
| ATOM | 1089 | CE | LYS | A | 258 | 28.757 | 0.905 | 33.567 | 1.00 | 58.17 | A | C |
| ATOM | 1090 | NZ | LYS | A | 258 | 28.963 | 1.257 | 32.118 | 1.00 | 56.00 | A | N |
| ATOM | 1091 | C | LYS | A | 258 | 33.638 | −1.015 | 34.799 | 1.00 | 39.22 | A | C |
| ATOM | 1092 | O | LYS | A | 258 | 33.990 | −1.766 | 33.903 | 1.00 | 39.38 | A | O |
| ATOM | 1093 | N | PRO | A | 259 | 33.722 | −1.367 | 36.083 | 1.00 | 39.78 | A | N |
| ATOM | 1094 | CA | PRO | A | 259 | 34.237 | −2.685 | 36.448 | 1.00 | 40.62 | A | C |
| ATOM | 1095 | CB | PRO | A | 259 | 34.195 | −2.679 | 37.996 | 1.00 | 40.25 | A | C |
| ATOM | 1096 | CG | PRO | A | 259 | 33.643 | −1.352 | 38.437 | 1.00 | 37.73 | A | C |
| ATOM | 1097 | CD | PRO | A | 259 | 33.302 | −0.551 | 37.238 | 1.00 | 37.77 | A | C |
| ATOM | 1098 | C | PRO | A | 259 | 33.443 | −3.882 | 35.810 | 1.00 | 37.29 | A | C |
| ATOM | 1099 | O | PRO | A | 259 | 34.035 | −4.872 | 35.408 | 1.00 | 34.88 | A | O |
| ATOM | 1100 | N | GLU | A | 260 | 32.142 | −3.747 | 35.666 | 1.00 | 38.80 | A | N |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 1101 | CA | GLU | A | 260 | 31.303 | −4.779 | 35.025 | 1.00 | 41.47 | A | C |
| ATOM | 1102 | CB | GLU | A | 260 | 29.839 | −4.567 | 35.361 | 1.00 | 45.29 | A | C |
| ATOM | 1103 | CG | GLU | A | 260 | 29.162 | −3.255 | 34.948 | 1.00 | 49.17 | A | C |
| ATOM | 1104 | CD | GLU | A | 260 | 29.313 | −2.109 | 35.981 | 1.00 | 53.41 | A | C |
| ATOM | 1105 | OE1 | GLU | A | 260 | 28.370 | −1.311 | 36.145 | 1.00 | 56.36 | A | O |
| ATOM | 1106 | OE2 | GLU | A | 260 | 30.393 | −1.953 | 36.597 | 1.00 | 43.77 | A | O |
| ATOM | 1107 | C | GLU | A | 260 | 31.533 | −4.986 | 33.517 | 1.00 | 43.91 | A | C |
| ATOM | 1108 | O | GLU | A | 260 | 31.077 | −5.949 | 32.938 | 1.00 | 42.63 | A | O |
| ATOM | 1109 | N | ASN | A | 261 | 32.302 | −4.094 | 32.912 | 1.00 | 45.98 | A | N |
| ATOM | 1110 | CA | ASN | A | 261 | 32.617 | −4.137 | 31.519 | 1.00 | 44.34 | A | C |
| ATOM | 1111 | CB | ASN | A | 261 | 32.024 | −2.907 | 30.827 | 1.00 | 47.88 | A | C |
| ATOM | 1112 | CG | ASN | A | 261 | 30.520 | −2.801 | 31.040 | 1.00 | 56.67 | A | C |
| ATOM | 1113 | OD1 | ASN | A | 261 | 29.828 | −3.780 | 31.396 | 1.00 | 58.98 | A | O |
| ATOM | 1114 | ND2 | ASN | A | 261 | 30.014 | −1.621 | 30.858 | 1.00 | 55.84 | A | N |
| ATOM | 1115 | C | ASN | A | 261 | 34.091 | −4.176 | 31.292 | 1.00 | 40.77 | A | C |
| ATOM | 1116 | O | ASN | A | 261 | 34.522 | −3.861 | 30.208 | 1.00 | 44.48 | A | O |
| ATOM | 1117 | N | LEU | A | 262 | 34.880 | −4.557 | 32.293 | 1.00 | 35.89 | A | N |
| ATOM | 1118 | CA | LEU | A | 262 | 36.287 | −4.776 | 32.085 | 1.00 | 35.56 | A | C |
| ATOM | 1119 | CB | LEU | A | 262 | 37.115 | −3.978 | 33.082 | 1.00 | 35.08 | A | C |
| ATOM | 1120 | CG | LEU | A | 262 | 37.087 | −2.436 | 32.957 | 1.00 | 40.18 | A | C |
| ATOM | 1121 | CD1 | LEU | A | 262 | 37.695 | −1.757 | 34.155 | 1.00 | 40.22 | A | C |
| ATOM | 1122 | CD2 | LEU | A | 262 | 37.816 | −1.943 | 31.715 | 1.00 | 40.96 | A | C |
| ATOM | 1123 | C | LEU | A | 262 | 36.547 | −6.278 | 32.278 | 1.00 | 44.24 | A | C |
| ATOM | 1124 | O | LEU | A | 262 | 36.028 | −6.882 | 33.215 | 1.00 | 42.88 | A | O |
| ATOM | 1125 | N | LEU | A | 263 | 37.347 | −6.872 | 31.396 | 1.00 | 37.63 | A | N |
| ATOM | 1126 | CA | LEU | A | 263 | 37.696 | −8.273 | 31.480 | 1.00 | 41.84 | A | C |
| ATOM | 1127 | CB | LEU | A | 263 | 37.454 | −8.917 | 30.123 | 1.00 | 39.52 | A | C |
| ATOM | 1128 | CG | LEU | A | 263 | 35.984 | −9.118 | 29.793 | 1.00 | 39.79 | A | C |
| ATOM | 1129 | CD1 | LEU | A | 263 | 35.829 | −9.274 | 28.277 | 1.00 | 42.99 | A | C |
| ATOM | 1130 | CD2 | LEU | A | 263 | 35.351 | −10.285 | 30.559 | 1.00 | 40.04 | A | C |
| ATOM | 1131 | C | LEU | A | 263 | 39.138 | −8.399 | 31.895 | 1.00 | 43.41 | A | C |
| ATOM | 1132 | O | LEU | A | 263 | 39.872 | −7.407 | 31.968 | 1.00 | 48.14 | A | O |
| ATOM | 1133 | N | LEU | A | 264 | 39.581 | −9.614 | 32.145 | 1.00 | 44.88 | A | N |
| ATOM | 1134 | CA | LEU | A | 264 | 40.950 | −9.811 | 32.640 | 1.00 | 45.36 | A | C |
| ATOM | 1135 | CB | LEU | A | 264 | 40.928 | −10.358 | 34.065 | 1.00 | 47.03 | A | C |
| ATOM | 1136 | CG | LEU | A | 264 | 40.515 | −9.298 | 35.097 | 1.00 | 46.40 | A | C |
| ATOM | 1137 | CD1 | LEU | A | 264 | 39.847 | −9.952 | 36.309 | 1.00 | 52.24 | A | C |
| ATOM | 1138 | CD2 | LEU | A | 264 | 41.686 | −8.437 | 35.488 | 1.00 | 45.91 | A | C |
| ATOM | 1139 | C | LEU | A | 264 | 41.652 | −10.791 | 31.771 | 1.00 | 46.50 | A | C |
| ATOM | 1140 | O | LEU | A | 264 | 41.109 | −11.846 | 31.480 | 1.00 | 45.90 | A | O |
| ATOM | 1141 | N | GLY | A | 265 | 42.881 | −10.458 | 31.407 | 1.00 | 52.09 | A | N |
| ATOM | 1142 | CA | GLY | A | 265 | 43.673 | −11.278 | 30.522 | 1.00 | 55.75 | A | C |
| ATOM | 1143 | C | GLY | A | 265 | 44.431 | −12.290 | 31.341 | 1.00 | 60.01 | A | C |
| ATOM | 1144 | O | GLY | A | 265 | 44.476 | −12.167 | 32.567 | 1.00 | 65.56 | A | O |
| ATOM | 1145 | N | SER | A | 266 | 45.034 | −13.261 | 30.652 | 1.00 | 53.10 | A | N |
| ATOM | 1146 | CA | SER | A | 266 | 45.850 | −14.352 | 31.262 | 1.00 | 55.81 | A | C |
| ATOM | 1147 | CB | SER | A | 266 | 46.697 | −15.056 | 30.191 | 1.00 | 52.13 | A | C |
| ATOM | 1148 | OG | SER | A | 266 | 47.821 | −14.247 | 29.839 | 1.00 | 55.21 | A | O |
| ATOM | 1149 | C | SER | A | 266 | 46.763 | −13.893 | 32.437 | 1.00 | 55.85 | A | C |
| ATOM | 1150 | O | SER | A | 266 | 46.798 | −14.537 | 33.488 | 1.00 | 58.90 | A | O |
| ATOM | 1151 | N | ALA | A | 267 | 47.456 | −12.767 | 32.251 | 1.00 | 50.02 | A | N |
| ATOM | 1152 | CA | ALA | A | 267 | 48.302 | −12.163 | 33.263 | 1.00 | 45.49 | A | C |
| ATOM | 1153 | CB | ALA | A | 267 | 49.427 | −11.359 | 32.576 | 1.00 | 44.84 | A | C |
| ATOM | 1154 | C | ALA | A | 267 | 47.583 | −11.277 | 34.293 | 1.00 | 44.66 | A | C |
| ATOM | 1155 | O | ALA | A | 267 | 48.240 | −10.496 | 34.942 | 1.00 | 52.34 | A | O |
| ATOM | 1156 | N | GLY | A | 268 | 46.261 | −11.375 | 34.445 | 1.00 | 49.28 | A | N |
| ATOM | 1157 | CA | GLY | A | 268 | 45.471 | −10.440 | 35.304 | 1.00 | 52.76 | A | C |
| ATOM | 1158 | C | GLY | A | 268 | 45.520 | −8.959 | 34.912 | 1.00 | 54.16 | A | C |
| ATOM | 1159 | O | GLY | A | 268 | 45.458 | −8.053 | 35.767 | 1.00 | 51.81 | A | O |
| ATOM | 1160 | N | GLU | A | 269 | 45.701 | −8.709 | 33.623 | 1.00 | 53.02 | A | N |
| ATOM | 1161 | CA | GLU | A | 269 | 45.768 | −7.353 | 33.100 | 1.00 | 50.23 | A | C |
| ATOM | 1162 | CB | GLU | A | 269 | 46.883 | −7.187 | 32.063 | 1.00 | 52.43 | A | C |
| ATOM | 1163 | CG | GLU | A | 269 | 46.652 | −7.731 | 30.662 | 1.00 | 53.59 | A | C |
| ATOM | 1164 | CD | GLU | A | 269 | 46.760 | −9.240 | 30.515 | 1.00 | 57.20 | A | C |
| ATOM | 1165 | OE1 | GLU | A | 269 | 46.593 | −10.019 | 31.487 | 1.00 | 56.51 | A | O |
| ATOM | 1166 | OE2 | GLU | A | 269 | 46.982 | −9.657 | 29.379 | 1.00 | 59.03 | A | O |
| ATOM | 1167 | C | GLU | A | 269 | 44.397 | −7.076 | 32.536 | 1.00 | 47.65 | A | C |
| ATOM | 1168 | O | GLU | A | 269 | 43.744 | −7.961 | 31.977 | 1.00 | 46.07 | A | O |
| ATOM | 1169 | N | LEU | A | 270 | 43.948 | −5.851 | 32.739 | 1.00 | 44.80 | A | N |
| ATOM | 1170 | CA | LEU | A | 270 | 42.627 | −5.379 | 32.268 | 1.00 | 41.66 | A | C |
| ATOM | 1171 | CB | LEU | A | 270 | 42.430 | −3.952 | 32.739 | 1.00 | 45.46 | A | C |
| ATOM | 1172 | CG | LEU | A | 270 | 42.134 | −3.841 | 34.224 | 1.00 | 43.15 | A | C |
| ATOM | 1173 | CD1 | LEU | A | 270 | 41.857 | −2.409 | 34.558 | 1.00 | 41.85 | A | C |
| ATOM | 1174 | CD2 | LEU | A | 270 | 40.919 | −4.662 | 34.542 | 1.00 | 47.36 | A | C |
| ATOM | 1175 | C | LEU | A | 270 | 42.471 | −5.356 | 30.772 | 1.00 | 35.31 | A | C |
| ATOM | 1176 | O | LEU | A | 270 | 43.419 | −5.039 | 30.079 | 1.00 | 34.03 | A | O |
| ATOM | 1177 | N | LYS | A | 271 | 41.286 | −5.735 | 30.316 | 1.00 | 34.62 | A | N |
| ATOM | 1178 | CA | LYS | A | 271 | 40.853 | −5.633 | 28.919 | 1.00 | 39.36 | A | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 1179 | CB | LYS | A | 271 | 40.564 | −7.016 | 28.318 | 1.00 | 36.32 | A | C |
| ATOM | 1180 | CG | LYS | A | 271 | 41.747 | −7.977 | 28.388 | 1.00 | 39.13 | A | C |
| ATOM | 1181 | CD | LYS | A | 271 | 42.700 | −7.827 | 27.221 | 1.00 | 39.44 | A | C |
| ATOM | 1182 | CE | LYS | A | 271 | 44.063 | −8.381 | 27.584 | 1.00 | 41.85 | A | C |
| ATOM | 1183 | NZ | LYS | A | 271 | 44.859 | −8.573 | 26.346 | 1.00 | 43.33 | A | N |
| ATOM | 1184 | C | LYS | A | 271 | 39.569 | −4.805 | 28.846 | 1.00 | 37.14 | A | C |
| ATOM | 1185 | O | LYS | A | 271 | 38.531 | −5.183 | 29.395 | 1.00 | 39.82 | A | O |
| ATOM | 1186 | N | ILE | A | 272 | 39.614 | −3.691 | 28.140 | 1.00 | 40.09 | A | N |
| ATOM | 1187 | CA | ILE | A | 272 | 38.404 | −2.908 | 27.942 | 1.00 | 39.68 | A | C |
| ATOM | 1188 | CB | ILE | A | 272 | 38.702 | −1.448 | 27.468 | 1.00 | 39.19 | A | C |
| ATOM | 1189 | CG1 | ILE | A | 272 | 39.606 | −0.716 | 28.452 | 1.00 | 39.82 | A | C |
| ATOM | 1190 | CD1 | ILE | A | 272 | 40.046 | 0.692 | 28.027 | 1.00 | 38.01 | A | C |
| ATOM | 1191 | CG2 | ILE | A | 272 | 37.382 | −0.699 | 27.255 | 1.00 | 38.61 | A | C |
| ATOM | 1192 | C | ILE | A | 272 | 37.626 | −3.609 | 26.841 | 1.00 | 36.39 | A | C |
| ATOM | 1193 | O | ILE | A | 272 | 38.206 | −3.862 | 25.777 | 1.00 | 30.54 | A | O |
| ATOM | 1194 | N | ALA | A | 273 | 36.337 | −3.847 | 27.092 | 1.00 | 38.75 | A | N |
| ATOM | 1195 | CA | ALA | A | 273 | 35.361 | −4.403 | 26.138 | 1.00 | 44.74 | A | C |
| ATOM | 1196 | CB | ALA | A | 273 | 34.339 | −5.168 | 26.917 | 1.00 | 41.29 | A | C |
| ATOM | 1197 | C | ALA | A | 273 | 34.561 | −3.394 | 25.281 | 1.00 | 52.75 | A | C |
| ATOM | 1198 | O | ALA | A | 273 | 34.232 | −3.676 | 24.127 | 1.00 | 52.66 | A | O |
| ATOM | 1199 | N | ASP | A | 274 | 34.145 | −2.279 | 25.888 | 1.00 | 54.97 | A | N |
| ATOM | 1200 | CA | ASP | A | 274 | 33.061 | −1.405 | 25.331 | 1.00 | 57.31 | A | C |
| ATOM | 1201 | CB | ASP | A | 274 | 33.580 | −0.488 | 24.191 | 1.00 | 55.25 | A | C |
| ATOM | 1202 | CG | ASP | A | 274 | 34.620 | 0.539 | 24.685 | 1.00 | 66.54 | A | C |
| ATOM | 1203 | OD1 | ASP | A | 274 | 34.280 | 1.387 | 25.571 | 1.00 | 60.81 | A | O |
| ATOM | 1204 | OD2 | ASP | A | 274 | 35.773 | 0.512 | 24.169 | 1.00 | 58.00 | A | O |
| ATOM | 1205 | C | ASP | A | 274 | 31.826 | −2.265 | 24.955 | 1.00 | 52.84 | A | C |
| ATOM | 1206 | O | ASP | A | 274 | 31.622 | −3.347 | 25.550 | 1.00 | 53.00 | A | O |
| ATOM | 1207 | N | PHE | A | 275 | 30.997 | −1.804 | 24.012 | 1.00 | 50.24 | A | N |
| ATOM | 1208 | CA | PHE | A | 275 | 29.667 | −2.388 | 23.797 | 1.00 | 51.35 | A | C |
| ATOM | 1209 | CB | PHE | A | 275 | 29.781 | −3.733 | 23.070 | 1.00 | 57.15 | A | C |
| ATOM | 1210 | CG | PHE | A | 275 | 30.660 | −3.687 | 21.859 | 1.00 | 62.32 | A | C |
| ATOM | 1211 | CD1 | PHE | A | 275 | 30.144 | −3.309 | 20.613 | 1.00 | 62.61 | A | C |
| ATOM | 1212 | CE1 | PHE | A | 275 | 30.961 | −3.267 | 19.496 | 1.00 | 62.09 | A | C |
| ATOM | 1213 | CZ | PHE | A | 275 | 32.307 | −3.587 | 19.618 | 1.00 | 61.83 | A | C |
| ATOM | 1214 | CE2 | PHE | A | 275 | 32.823 | −3.961 | 20.850 | 1.00 | 62.54 | A | C |
| ATOM | 1215 | CD2 | PHE | A | 275 | 31.996 | −4.004 | 21.958 | 1.00 | 66.56 | A | C |
| ATOM | 1216 | C | PHE | A | 275 | 28.954 | −2.567 | 25.140 | 1.00 | 47.33 | A | C |
| ATOM | 1217 | O | PHE | A | 275 | 28.282 | −3.579 | 25.363 | 1.00 | 49.65 | A | O |
| ATOM | 1218 | N | GLY | A | 276 | 29.121 | −1.572 | 26.017 | 1.00 | 50.81 | A | N |
| ATOM | 1219 | CA | GLY | A | 276 | 28.553 | −1.533 | 27.374 | 1.00 | 49.32 | A | C |
| ATOM | 1220 | C | GLY | A | 276 | 27.077 | −1.818 | 27.437 | 1.00 | 50.25 | A | C |
| ATOM | 1221 | O | GLY | A | 276 | 26.608 | −2.585 | 28.292 | 1.00 | 61.98 | A | O |
| ATOM | 1222 | N | TRP | A | 277 | 26.351 | −1.203 | 26.520 | 1.00 | 45.45 | A | N |
| ATOM | 1223 | CA | TRP | A | 277 | 24.903 | −1.420 | 26.350 | 1.00 | 47.73 | A | C |
| ATOM | 1224 | CB | TRP | A | 277 | 24.363 | −0.443 | 25.295 | 1.00 | 51.54 | A | C |
| ATOM | 1225 | CG | TRP | A | 277 | 25.101 | −0.536 | 24.035 | 1.00 | 57.70 | A | C |
| ATOM | 1226 | CD1 | TRP | A | 277 | 26.193 | 0.208 | 23.651 | 1.00 | 58.31 | A | C |
| ATOM | 1227 | NE1 | TRP | A | 277 | 26.629 | −0.205 | 22.437 | 1.00 | 63.21 | A | N |
| ATOM | 1228 | CE2 | TRP | A | 277 | 25.832 | −1.228 | 21.993 | 1.00 | 66.70 | A | C |
| ATOM | 1229 | CD2 | TRP | A | 277 | 24.859 | −1.468 | 22.994 | 1.00 | 63.16 | A | C |
| ATOM | 1230 | CE3 | TRP | A | 277 | 23.898 | −2.473 | 22.796 | 1.00 | 63.26 | A | C |
| ATOM | 1231 | CZ3 | TRP | A | 277 | 23.937 | −3.209 | 21.617 | 1.00 | 68.75 | A | C |
| ATOM | 1232 | CH2 | TRP | A | 277 | 24.926 | −2.949 | 20.629 | 1.00 | 75.29 | A | C |
| ATOM | 1233 | CZ2 | TRP | A | 277 | 25.876 | −1.959 | 20.795 | 1.00 | 68.37 | A | C |
| ATOM | 1234 | C | TRP | A | 277 | 24.490 | −2.883 | 26.033 | 1.00 | 48.23 | A | C |
| ATOM | 1235 | O | TRP | A | 277 | 23.356 | −3.266 | 26.286 | 1.00 | 54.72 | A | O |
| ATOM | 1236 | N | SER | A | 278 | 25.430 | −3.677 | 25.505 | 1.00 | 56.00 | A | N |
| ATOM | 1237 | CA | SER | A | 278 | 25.301 | −5.140 | 25.307 | 1.00 | 57.07 | A | C |
| ATOM | 1238 | CB | SER | A | 278 | 26.220 | −5.583 | 24.142 | 1.00 | 55.04 | A | C |
| ATOM | 1239 | OG | SER | A | 278 | 27.580 | −5.714 | 24.555 | 1.00 | 50.89 | A | O |
| ATOM | 1240 | C | SER | A | 278 | 25.572 | −6.079 | 26.528 | 1.00 | 66.35 | A | C |
| ATOM | 1241 | O | SER | A | 278 | 25.386 | −7.306 | 26.413 | 1.00 | 65.38 | A | O |
| ATOM | 1242 | N | VAL | A | 279 | 26.016 | −5.533 | 27.666 | 1.00 | 66.32 | A | N |
| ATOM | 1243 | CA | VAL | A | 279 | 26.426 | −6.353 | 28.825 | 1.00 | 63.82 | A | C |
| ATOM | 1244 | CB | VAL | A | 279 | 27.679 | −5.736 | 29.460 | 1.00 | 58.43 | A | C |
| ATOM | 1245 | CG1 | VAL | A | 279 | 28.192 | −6.593 | 30.615 | 1.00 | 56.84 | A | C |
| ATOM | 1246 | CG2 | VAL | A | 279 | 28.756 | −5.543 | 28.388 | 1.00 | 55.52 | A | C |
| ATOM | 1247 | C | VAL | A | 279 | 25.236 | −6.478 | 29.824 | 1.00 | 74.83 | A | C |
| ATOM | 1248 | O | VAL | A | 279 | 24.302 | −5.684 | 29.729 | 1.00 | 75.79 | A | O |
| ATOM | 1249 | N | HIS | A | 280 | 25.258 | −7.477 | 30.732 | 1.00 | 80.50 | A | N |
| ATOM | 1250 | CA | HIS | A | 280 | 24.110 | −7.862 | 31.630 | 1.00 | 87.05 | A | C |
| ATOM | 1251 | CB | HIS | A | 280 | 23.420 | −6.663 | 32.355 | 1.00 | 91.25 | A | C |
| ATOM | 1252 | CG | HIS | A | 280 | 24.017 | −6.310 | 33.686 | 1.00 | 102.28 | A | C |
| ATOM | 1253 | ND1 | HIS | A | 280 | 23.243 | −5.987 | 34.783 | 1.00 | 107.80 | A | N |
| ATOM | 1254 | CE1 | HIS | A | 280 | 24.028 | −5.719 | 35.813 | 1.00 | 108.50 | A | C |
| ATOM | 1255 | NE2 | HIS | A | 280 | 25.284 | −5.856 | 35.426 | 1.00 | 110.37 | A | N |
| ATOM | 1256 | CD2 | HIS | A | 280 | 25.306 | −6.224 | 34.098 | 1.00 | 111.78 | A | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 1257 | C | HIS | A | 280 | 23.089 | −8.696 | 30.829 | 1.00 | 80.44 | A | C |
| ATOM | 1258 | O | HIS | A | 280 | 21.958 | −8.937 | 31.253 | 1.00 | 70.42 | A | O |
| ATOM | 1259 | N | LEU | A | 293 | 26.480 | 6.100 | 34.424 | 1.00 | 39.36 | A | N |
| ATOM | 1260 | CA | LEU | A | 293 | 25.506 | 6.776 | 35.346 | 1.00 | 44.30 | A | C |
| ATOM | 1261 | CB | LEU | A | 293 | 24.372 | 5.821 | 35.712 | 1.00 | 54.36 | A | C |
| ATOM | 1262 | CG | LEU | A | 293 | 24.502 | 4.262 | 35.987 | 1.00 | 65.80 | A | C |
| ATOM | 1263 | CD1 | LEU | A | 293 | 25.613 | 3.496 | 35.212 | 1.00 | 67.75 | A | C |
| ATOM | 1264 | CD2 | LEU | A | 293 | 24.579 | 3.892 | 37.493 | 1.00 | 59.31 | A | C |
| ATOM | 1265 | C | LEU | A | 293 | 26.272 | 7.312 | 36.588 | 1.00 | 36.56 | A | C |
| ATOM | 1266 | O | LEU | A | 293 | 26.618 | 8.474 | 36.717 | 1.00 | 29.85 | A | O |
| ATOM | 1267 | N | ASP | A | 294 | 26.695 | 6.389 | 37.422 | 1.00 | 34.38 | A | N |
| ATOM | 1268 | CA | ASP | A | 294 | 27.645 | 6.653 | 38.474 | 1.00 | 35.51 | A | C |
| ATOM | 1269 | CB | ASP | A | 294 | 27.860 | 5.341 | 39.263 | 1.00 | 38.40 | A | C |
| ATOM | 1270 | CG | ASP | A | 294 | 26.749 | 5.076 | 40.243 | 1.00 | 40.83 | A | C |
| ATOM | 1271 | OD1 | ASP | A | 294 | 26.481 | 5.996 | 41.002 | 1.00 | 40.92 | A | O |
| ATOM | 1272 | OD2 | ASP | A | 294 | 26.130 | 3.970 | 40.230 | 1.00 | 48.21 | A | O |
| ATOM | 1273 | C | ASP | A | 294 | 28.988 | 7.132 | 37.883 | 1.00 | 32.36 | A | C |
| ATOM | 1274 | O | ASP | A | 294 | 29.758 | 7.785 | 38.557 | 1.00 | 32.28 | A | O |
| ATOM | 1275 | N | TYR | A | 295 | 29.266 | 6.741 | 36.643 | 1.00 | 26.17 | A | N |
| ATOM | 1276 | CA | TYR | A | 295 | 30.546 | 7.054 | 35.988 | 1.00 | 30.57 | A | C |
| ATOM | 1277 | CB | TYR | A | 295 | 31.021 | 5.827 | 35.188 | 1.00 | 28.04 | A | C |
| ATOM | 1278 | CG | TYR | A | 295 | 31.714 | 4.826 | 36.104 | 1.00 | 29.04 | A | C |
| ATOM | 1279 | CD1 | TYR | A | 295 | 31.010 | 4.074 | 36.997 | 1.00 | 28.79 | A | C |
| ATOM | 1280 | CE1 | TYR | A | 295 | 31.648 | 3.241 | 37.913 | 1.00 | 29.59 | A | C |
| ATOM | 1281 | CZ | TYR | A | 295 | 33.021 | 3.152 | 37.897 | 1.00 | 33.73 | A | C |
| ATOM | 1282 | OH | TYR | A | 295 | 33.707 | 2.348 | 38.774 | 1.00 | 38.31 | A | O |
| ATOM | 1283 | CE2 | TYR | A | 295 | 33.739 | 3.923 | 37.040 | 1.00 | 32.23 | A | C |
| ATOM | 1284 | CD2 | TYR | A | 295 | 33.090 | 4.764 | 36.146 | 1.00 | 30.29 | A | C |
| ATOM | 1285 | C | TYR | A | 295 | 30.505 | 8.305 | 35.094 | 1.00 | 33.57 | A | C |
| ATOM | 1286 | O | TYR | A | 295 | 31.533 | 8.751 | 34.585 | 1.00 | 31.97 | A | O |
| ATOM | 1287 | N | LEU | A | 296 | 29.323 | 8.864 | 34.885 | 1.00 | 30.27 | A | N |
| ATOM | 1288 | CA | LEU | A | 296 | 29.230 | 10.002 | 34.012 | 1.00 | 32.74 | A | C |
| ATOM | 1289 | CB | LEU | A | 296 | 27.781 | 10.218 | 33.586 | 1.00 | 31.60 | A | C |
| ATOM | 1290 | CG | LEU | A | 296 | 27.189 | 9.201 | 32.605 | 1.00 | 35.53 | A | C |
| ATOM | 1291 | CD1 | LEU | A | 296 | 25.752 | 9.654 | 32.395 | 1.00 | 39.02 | A | C |
| ATOM | 1292 | CD2 | LEU | A | 296 | 27.990 | 9.174 | 31.307 | 1.00 | 37.06 | A | C |
| ATOM | 1293 | C | LEU | A | 296 | 29.741 | 11.297 | 34.635 | 1.00 | 32.11 | A | C |
| ATOM | 1294 | O | LEU | A | 296 | 29.407 | 11.631 | 35.777 | 1.00 | 29.11 | A | O |
| ATOM | 1295 | N | PRO | A | 297 | 30.528 | 12.067 | 33.870 | 1.00 | 29.02 | A | N |
| ATOM | 1296 | CA | PRO | A | 297 | 30.961 | 13.364 | 34.346 | 1.00 | 28.45 | A | C |
| ATOM | 1297 | CB | PRO | A | 297 | 32.077 | 13.747 | 33.422 | 1.00 | 29.45 | A | C |
| ATOM | 1298 | CG | PRO | A | 297 | 32.080 | 12.770 | 32.344 | 1.00 | 32.76 | A | C |
| ATOM | 1299 | CD | PRO | A | 297 | 31.183 | 11.628 | 32.651 | 1.00 | 33.22 | A | C |
| ATOM | 1300 | C | PRO | A | 297 | 29.867 | 14.428 | 34.317 | 1.00 | 29.07 | A | C |
| ATOM | 1301 | O | PRO | A | 297 | 28.897 | 14.263 | 33.605 | 1.00 | 32.51 | A | O |
| ATOM | 1302 | N | PRO | A | 298 | 30.056 | 15.546 | 35.060 | 1.00 | 29.92 | A | N |
| ATOM | 1303 | CA | PRO | A | 298 | 29.072 | 16.608 | 35.108 | 1.00 | 31.75 | A | C |
| ATOM | 1304 | CB | PRO | A | 298 | 29.754 | 17.684 | 35.923 | 1.00 | 31.87 | A | C |
| ATOM | 1305 | CG | PRO | A | 298 | 30.563 | 16.849 | 36.882 | 1.00 | 33.48 | A | C |
| ATOM | 1306 | CD | PRO | A | 298 | 31.175 | 15.848 | 35.963 | 1.00 | 32.56 | A | C |
| ATOM | 1307 | C | PRO | A | 298 | 28.720 | 17.098 | 33.736 | 1.00 | 31.98 | A | C |
| ATOM | 1308 | O | PRO | A | 298 | 27.553 | 17.238 | 33.470 | 1.00 | 29.79 | A | O |
| ATOM | 1309 | N | GLU | A | 299 | 29.717 | 17.204 | 32.847 | 1.00 | 33.22 | A | N |
| ATOM | 1310 | CA | GLU | A | 299 | 29.458 | 17.729 | 31.506 | 1.00 | 31.58 | A | C |
| ATOM | 1311 | CB | GLU | A | 299 | 30.729 | 18.091 | 30.756 | 1.00 | 30.11 | A | C |
| ATOM | 1312 | CG | GLU | A | 299 | 31.701 | 16.943 | 30.495 | 1.00 | 26.95 | A | C |
| ATOM | 1313 | CD | GLU | A | 299 | 32.820 | 16.804 | 31.515 | 1.00 | 27.34 | A | C |
| ATOM | 1314 | OE1 | GLU | A | 299 | 32.548 | 17.043 | 32.705 | 1.00 | 29.03 | A | O |
| ATOM | 1315 | OE2 | GLU | A | 299 | 33.961 | 16.406 | 31.127 | 1.00 | 25.11 | A | O |
| ATOM | 1316 | C | GLU | A | 299 | 28.571 | 16.793 | 30.676 | 1.00 | 34.30 | A | C |
| ATOM | 1317 | O | GLU | A | 299 | 27.726 | 17.253 | 29.911 | 1.00 | 35.78 | A | O |
| ATOM | 1318 | N | MET | A | 300 | 28.732 | 15.497 | 30.858 | 1.00 | 33.58 | A | N |
| ATOM | 1319 | CA | MET | A | 300 | 27.867 | 14.554 | 30.207 | 1.00 | 36.76 | A | C |
| ATOM | 1320 | CB | MET | A | 300 | 28.567 | 13.251 | 29.998 | 1.00 | 41.77 | A | C |
| ATOM | 1321 | CG | MET | A | 300 | 29.751 | 13.431 | 29.062 | 1.00 | 42.60 | A | C |
| ATOM | 1322 | SD | MET | A | 300 | 30.416 | 11.819 | 28.789 | 1.00 | 42.12 | A | S |
| ATOM | 1323 | CE | MET | A | 300 | 29.182 | 11.372 | 27.527 | 1.00 | 45.27 | A | C |
| ATOM | 1324 | C | MET | A | 300 | 26.527 | 14.351 | 30.925 | 1.00 | 36.73 | A | C |
| ATOM | 1325 | O | MET | A | 300 | 25.533 | 14.252 | 30.252 | 1.00 | 31.67 | A | O |
| ATOM | 1326 | N | ILE | A | 301 | 26.436 | 14.360 | 32.263 | 1.00 | 38.10 | A | N |
| ATOM | 1327 | CA | ILE | A | 301 | 25.051 | 14.345 | 32.829 | 1.00 | 38.45 | A | C |
| ATOM | 1328 | CB | ILE | A | 301 | 24.985 | 14.071 | 34.333 | 1.00 | 37.66 | A | C |
| ATOM | 1329 | CG1 | ILE | A | 301 | 25.528 | 15.240 | 35.112 | 1.00 | 42.69 | A | C |
| ATOM | 1330 | CD1 | ILE | A | 301 | 25.327 | 15.135 | 36.625 | 1.00 | 47.66 | A | C |
| ATOM | 1331 | CG2 | ILE | A | 301 | 25.703 | 12.765 | 34.636 | 1.00 | 43.52 | A | C |
| ATOM | 1332 | C | ILE | A | 301 | 24.202 | 15.584 | 32.381 | 1.00 | 36.48 | A | C |
| ATOM | 1333 | O | ILE | A | 301 | 23.010 | 15.454 | 32.154 | 1.00 | 35.38 | A | O |
| ATOM | 1334 | N | GLU | A | 302 | 24.849 | 16.713 | 32.106 | 1.00 | 34.37 | A | N |

APPENDIX A-continued

| Atomic coordinates of Aurora A + Inhibitory Monobody Mb60 + Danusertib | | | | | | | | | | | | |
|---|---|---|---|---|---|---|---|---|---|---|---|---|
| ATOM | 1335 | CA | GLU | A | 302 | 24.156 | 17.922 | 31.580 | 1.00 | 37.70 | A | C |
| ATOM | 1336 | CB | GLU | A | 302 | 24.815 | 19.183 | 32.155 | 1.00 | 38.76 | A | C |
| ATOM | 1337 | CG | GLU | A | 302 | 24.911 | 19.106 | 33.648 | 1.00 | 38.80 | A | C |
| ATOM | 1338 | CD | GLU | A | 302 | 25.453 | 20.356 | 34.231 | 1.00 | 45.48 | A | C |
| ATOM | 1339 | OE1 | GLU | A | 302 | 26.390 | 20.945 | 33.645 | 1.00 | 46.72 | A | O |
| ATOM | 1340 | OE2 | GLU | A | 302 | 24.882 | 20.734 | 35.265 | 1.00 | 44.08 | A | O |
| ATOM | 1341 | C | GLU | A | 302 | 24.066 | 18.081 | 30.086 | 1.00 | 35.69 | A | C |
| ATOM | 1342 | O | GLU | A | 302 | 23.619 | 19.105 | 29.605 | 1.00 | 47.37 | A | O |
| ATOM | 1343 | N | GLY | A | 303 | 24.577 | 17.104 | 29.357 | 1.00 | 32.36 | A | N |
| ATOM | 1344 | CA | GLY | A | 303 | 24.406 | 16.982 | 27.951 | 1.00 | 35.47 | A | C |
| ATOM | 1345 | C | GLY | A | 303 | 25.180 | 17.966 | 27.108 | 1.00 | 32.93 | A | C |
| ATOM | 1346 | O | GLY | A | 303 | 24.658 | 18.387 | 26.102 | 1.00 | 30.31 | A | O |
| ATOM | 1347 | N | ARG | A | 304 | 26.381 | 18.335 | 27.540 | 1.00 | 30.20 | A | N |
| ATOM | 1348 | CA | ARG | A | 304 | 27.084 | 19.491 | 26.978 | 1.00 | 31.48 | A | C |
| ATOM | 1349 | CB | ARG | A | 304 | 27.578 | 20.465 | 28.051 | 1.00 | 31.28 | A | C |
| ATOM | 1350 | CG | ARG | A | 304 | 26.494 | 21.132 | 28.901 | 1.00 | 34.84 | A | C |
| ATOM | 1351 | CD | ARG | A | 304 | 27.066 | 22.200 | 29.872 | 1.00 | 35.24 | A | C |
| ATOM | 1352 | NE | ARG | A | 304 | 27.625 | 21.660 | 31.129 | 1.00 | 33.36 | A | N |
| ATOM | 1353 | CZ | ARG | A | 304 | 28.931 | 21.432 | 31.420 | 1.00 | 34.34 | A | C |
| ATOM | 1354 | NH1 | ARG | A | 304 | 29.236 | 21.033 | 32.646 | 1.00 | 32.16 | A | N |
| ATOM | 1355 | NH2 | ARG | A | 304 | 29.923 | 21.588 | 30.530 | 1.00 | 33.83 | A | N |
| ATOM | 1356 | C | ARG | A | 304 | 28.244 | 18.936 | 26.261 | 1.00 | 32.44 | A | C |
| ATOM | 1357 | O | ARG | A | 304 | 28.573 | 17.746 | 26.397 | 1.00 | 37.51 | A | O |
| ATOM | 1358 | N | MET | A | 305 | 28.859 | 19.793 | 25.485 | 1.00 | 32.45 | A | N |
| ATOM | 1359 | CA | MET | A | 305 | 29.991 | 19.402 | 24.710 | 1.00 | 33.08 | A | C |
| ATOM | 1360 | CB | MET | A | 305 | 30.520 | 20.600 | 23.966 | 1.00 | 33.39 | A | C |
| ATOM | 1361 | CG | MET | A | 305 | 31.652 | 20.209 | 23.044 | 1.00 | 35.18 | A | C |
| ATOM | 1362 | SD | MET | A | 305 | 32.001 | 21.488 | 21.815 | 1.00 | 35.97 | A | S |
| ATOM | 1363 | CE | MET | A | 305 | 32.453 | 22.863 | 22.834 | 1.00 | 39.58 | A | C |
| ATOM | 1364 | C | MET | A | 305 | 31.036 | 18.841 | 25.665 | 1.00 | 29.76 | A | C |
| ATOM | 1365 | O | MET | A | 305 | 31.283 | 19.394 | 26.725 | 1.00 | 28.44 | A | O |
| ATOM | 1366 | N | HIS | A | 306 | 31.587 | 17.723 | 25.308 | 1.00 | 31.29 | A | N |
| ATOM | 1367 | CA | HIS | A | 306 | 32.638 | 17.102 | 26.103 | 1.00 | 36.60 | A | C |
| ATOM | 1368 | CB | HIS | A | 306 | 32.113 | 15.853 | 26.813 | 1.00 | 33.40 | A | C |
| ATOM | 1369 | CG | HIS | A | 306 | 31.661 | 14.777 | 25.887 | 1.00 | 36.96 | A | C |
| ATOM | 1370 | ND1 | HIS | A | 306 | 30.381 | 14.731 | 25.382 | 1.00 | 33.71 | A | N |
| ATOM | 1371 | CE1 | HIS | A | 306 | 30.257 | 13.662 | 24.610 | 1.00 | 35.45 | A | C |
| ATOM | 1372 | NE2 | HIS | A | 306 | 31.421 | 13.030 | 24.575 | 1.00 | 37.41 | A | N |
| ATOM | 1373 | CD2 | HIS | A | 306 | 32.317 | 13.709 | 25.364 | 1.00 | 35.98 | A | C |
| ATOM | 1374 | C | HIS | A | 306 | 33.832 | 16.739 | 25.258 | 1.00 | 37.85 | A | C |
| ATOM | 1375 | O | HIS | A | 306 | 33.774 | 16.765 | 24.044 | 1.00 | 34.83 | A | O |
| ATOM | 1376 | N | ASP | A | 307 | 34.913 | 16.378 | 25.934 | 1.00 | 33.18 | A | N |
| ATOM | 1377 | CA | ASP | A | 307 | 36.171 | 16.118 | 25.291 | 1.00 | 32.32 | A | C |
| ATOM | 1378 | CB | ASP | A | 307 | 36.996 | 17.419 | 25.238 | 1.00 | 31.89 | A | C |
| ATOM | 1379 | CG | ASP | A | 307 | 37.473 | 17.910 | 26.601 | 1.00 | 35.11 | A | C |
| ATOM | 1380 | OD1 | ASP | A | 307 | 37.415 | 17.222 | 27.658 | 1.00 | 31.36 | A | O |
| ATOM | 1381 | OD2 | ASP | A | 307 | 37.989 | 19.037 | 26.599 | 1.00 | 36.30 | A | O |
| ATOM | 1382 | C | ASP | A | 307 | 36.872 | 14.948 | 25.997 | 1.00 | 29.42 | A | C |
| ATOM | 1383 | O | ASP | A | 307 | 36.273 | 14.271 | 26.831 | 1.00 | 30.69 | A | O |
| ATOM | 1384 | N | GLU | A | 308 | 38.114 | 14.684 | 25.649 | 1.00 | 31.15 | A | N |
| ATOM | 1385 | CA | GLU | A | 308 | 38.867 | 13.554 | 26.178 | 1.00 | 29.83 | A | C |
| ATOM | 1386 | CB | GLU | A | 308 | 40.294 | 13.460 | 25.576 | 1.00 | 32.87 | A | C |
| ATOM | 1387 | CG | GLU | A | 308 | 41.382 | 14.391 | 26.116 | 1.00 | 35.10 | A | C |
| ATOM | 1388 | CD | GLU | A | 308 | 41.244 | 15.849 | 25.683 | 1.00 | 36.59 | A | C |
| ATOM | 1389 | OE1 | GLU | A | 308 | 41.976 | 16.666 | 26.248 | 1.00 | 50.55 | A | O |
| ATOM | 1390 | OE2 | GLU | A | 308 | 40.409 | 16.226 | 24.850 | 1.00 | 38.06 | A | O |
| ATOM | 1391 | C | GLU | A | 308 | 38.965 | 13.524 | 27.666 | 1.00 | 28.77 | A | C |
| ATOM | 1392 | O | GLU | A | 308 | 39.144 | 12.463 | 28.216 | 1.00 | 30.06 | A | O |
| ATOM | 1393 | N | LYS | A | 309 | 38.844 | 14.674 | 28.317 | 1.00 | 27.95 | A | N |
| ATOM | 1394 | CA | LYS | A | 309 | 38.839 | 14.740 | 29.764 | 1.00 | 28.99 | A | C |
| ATOM | 1395 | CB | LYS | A | 309 | 38.726 | 16.209 | 30.290 | 1.00 | 29.56 | A | C |
| ATOM | 1396 | CG | LYS | A | 309 | 39.822 | 17.169 | 29.860 | 1.00 | 32.47 | A | C |
| ATOM | 1397 | CD | LYS | A | 309 | 41.191 | 16.599 | 30.300 | 1.00 | 35.82 | A | C |
| ATOM | 1398 | CE | LYS | A | 309 | 42.195 | 17.677 | 30.725 | 1.00 | 37.72 | A | C |
| ATOM | 1399 | NZ | LYS | A | 309 | 43.544 | 17.047 | 30.737 | 1.00 | 37.01 | A | N |
| ATOM | 1400 | C | LYS | A | 309 | 37.727 | 13.963 | 30.408 | 1.00 | 28.93 | A | C |
| ATOM | 1401 | O | LYS | A | 309 | 37.785 | 13.788 | 31.600 | 1.00 | 26.36 | A | O |
| ATOM | 1402 | N | VAL | A | 310 | 36.687 | 13.527 | 29.672 | 1.00 | 25.66 | A | N |
| ATOM | 1403 | CA | VAL | A | 310 | 35.703 | 12.644 | 30.332 | 1.00 | 30.68 | A | C |
| ATOM | 1404 | CB | VAL | A | 310 | 34.483 | 12.245 | 29.464 | 1.00 | 27.91 | A | C |
| ATOM | 1405 | CG1 | VAL | A | 310 | 34.876 | 11.412 | 28.238 | 1.00 | 26.57 | A | C |
| ATOM | 1406 | CG2 | VAL | A | 310 | 33.754 | 13.508 | 29.052 | 1.00 | 27.77 | A | C |
| ATOM | 1407 | C | VAL | A | 310 | 36.372 | 11.381 | 30.834 | 1.00 | 30.75 | A | C |
| ATOM | 1408 | O | VAL | A | 310 | 35.965 | 10.841 | 31.865 | 1.00 | 28.52 | A | O |
| ATOM | 1409 | N | ASP | A | 311 | 37.368 | 10.897 | 30.089 | 1.00 | 30.25 | A | N |
| ATOM | 1410 | CA | ASP | A | 311 | 38.040 | 9.645 | 30.484 | 1.00 | 32.51 | A | C |
| ATOM | 1411 | CB | ASP | A | 311 | 38.889 | 9.135 | 29.334 | 1.00 | 30.77 | A | C |
| ATOM | 1412 | CG | ASP | A | 311 | 38.061 | 8.646 | 28.155 | 1.00 | 31.46 | A | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 1413 | OD1 | ASP | A | 311 | 37.126 | 7.860 | 28.381 | 1.00 | 29.52 | A | O |
| ATOM | 1414 | OD2 | ASP | A | 311 | 38.323 | 9.055 | 26.997 | 1.00 | 30.90 | A | O |
| ATOM | 1415 | C | ASP | A | 311 | 38.885 | 9.802 | 31.755 | 1.00 | 29.54 | A | C |
| ATOM | 1416 | O | ASP | A | 311 | 39.090 | 8.819 | 32.489 | 1.00 | 29.64 | A | O |
| ATOM | 1417 | N | LEU | A | 312 | 39.297 | 11.037 | 32.066 | 1.00 | 30.52 | A | N |
| ATOM | 1418 | CA | LEU | A | 312 | 40.050 | 11.307 | 33.304 | 1.00 | 31.42 | A | C |
| ATOM | 1419 | CB | LEU | A | 312 | 40.769 | 12.653 | 33.302 | 1.00 | 34.12 | A | C |
| ATOM | 1420 | CG | LEU | A | 312 | 42.119 | 12.740 | 32.554 | 1.00 | 32.65 | A | C |
| ATOM | 1421 | CD1 | LEU | A | 312 | 43.251 | 11.876 | 33.154 | 1.00 | 34.55 | A | C |
| ATOM | 1422 | CD2 | LEU | A | 312 | 41.950 | 12.349 | 31.099 | 1.00 | 34.67 | A | C |
| ATOM | 1423 | C | LEU | A | 312 | 39.090 | 11.231 | 34.468 | 1.00 | 32.28 | A | C |
| ATOM | 1424 | O | LEU | A | 312 | 39.388 | 10.596 | 35.455 | 1.00 | 28.45 | A | O |
| ATOM | 1425 | N | TRP | A | 313 | 37.906 | 11.819 | 34.316 | 1.00 | 33.86 | A | N |
| ATOM | 1426 | CA | TRP | A | 313 | 36.863 | 11.743 | 35.340 | 1.00 | 30.59 | A | C |
| ATOM | 1427 | CB | TRP | A | 313 | 35.620 | 12.521 | 34.921 | 1.00 | 31.64 | A | C |
| ATOM | 1428 | CG | TRP | A | 313 | 34.478 | 12.351 | 35.825 | 1.00 | 29.22 | A | C |
| ATOM | 1429 | CD1 | TRP | A | 313 | 33.602 | 11.318 | 35.828 | 1.00 | 30.33 | A | C |
| ATOM | 1430 | NE1 | TRP | A | 313 | 32.685 | 11.467 | 36.787 | 1.00 | 26.50 | A | N |
| ATOM | 1431 | CE2 | TRP | A | 313 | 32.913 | 12.653 | 37.423 | 1.00 | 30.32 | A | C |
| ATOM | 1432 | CD2 | TRP | A | 313 | 34.056 | 13.228 | 36.840 | 1.00 | 30.89 | A | C |
| ATOM | 1433 | CE3 | TRP | A | 313 | 34.527 | 14.448 | 37.326 | 1.00 | 33.13 | A | C |
| ATOM | 1434 | CZ3 | TRP | A | 313 | 33.846 | 15.063 | 38.349 | 1.00 | 36.74 | A | C |
| ATOM | 1435 | CH2 | TRP | A | 313 | 32.699 | 14.457 | 38.936 | 1.00 | 35.99 | A | C |
| ATOM | 1436 | CZ2 | TRP | A | 313 | 32.222 | 13.258 | 38.476 | 1.00 | 34.19 | A | C |
| ATOM | 1437 | C | TRP | A | 313 | 36.530 | 10.294 | 35.629 | 1.00 | 30.79 | A | C |
| ATOM | 1438 | O | TRP | A | 313 | 36.531 | 9.903 | 36.798 | 1.00 | 32.50 | A | O |
| ATOM | 1439 | N | SER | A | 314 | 36.384 | 9.495 | 34.575 | 1.00 | 27.65 | A | N |
| ATOM | 1440 | CA | SER | A | 314 | 36.035 | 8.095 | 34.703 | 1.00 | 30.70 | A | C |
| ATOM | 1441 | CB | SER | A | 314 | 35.867 | 7.372 | 33.348 | 1.00 | 31.02 | A | C |
| ATOM | 1442 | OG | SER | A | 314 | 34.697 | 7.813 | 32.781 | 1.00 | 35.86 | A | O |
| ATOM | 1443 | C | SER | A | 314 | 37.043 | 7.321 | 35.465 | 1.00 | 32.53 | A | C |
| ATOM | 1444 | O | SER | A | 314 | 36.663 | 6.405 | 36.174 | 1.00 | 27.90 | A | O |
| ATOM | 1445 | N | LEU | A | 315 | 38.322 | 7.652 | 35.273 | 1.00 | 34.51 | A | N |
| ATOM | 1446 | CA | LEU | A | 315 | 39.408 | 6.966 | 35.999 | 1.00 | 33.57 | A | C |
| ATOM | 1447 | CB | LEU | A | 315 | 40.801 | 7.402 | 35.539 | 1.00 | 36.33 | A | C |
| ATOM | 1448 | CG | LEU | A | 315 | 41.414 | 6.669 | 34.387 | 1.00 | 40.89 | A | C |
| ATOM | 1449 | CD1 | LEU | A | 315 | 42.726 | 7.350 | 33.995 | 1.00 | 44.03 | A | C |
| ATOM | 1450 | CD2 | LEU | A | 315 | 41.610 | 5.218 | 34.725 | 1.00 | 40.54 | A | C |
| ATOM | 1451 | C | LEU | A | 315 | 39.329 | 7.218 | 37.461 | 1.00 | 33.28 | A | C |
| ATOM | 1452 | O | LEU | A | 315 | 39.643 | 6.317 | 38.233 | 1.00 | 30.71 | A | O |
| ATOM | 1453 | N | GLY | A | 316 | 39.043 | 8.484 | 37.831 | 1.00 | 32.91 | A | N |
| ATOM | 1454 | CA | GLY | A | 316 | 38.753 | 8.852 | 39.196 | 1.00 | 31.74 | A | C |
| ATOM | 1455 | C | GLY | A | 316 | 37.678 | 8.038 | 39.886 | 1.00 | 36.05 | A | C |
| ATOM | 1456 | O | GLY | A | 316 | 37.875 | 7.507 | 40.988 | 1.00 | 36.50 | A | O |
| ATOM | 1457 | N | VAL | A | 317 | 36.524 | 7.915 | 39.234 | 1.00 | 32.93 | A | N |
| ATOM | 1458 | CA | VAL | A | 317 | 35.436 | 7.113 | 39.781 | 1.00 | 31.22 | A | C |
| ATOM | 1459 | CB | VAL | A | 317 | 34.222 | 7.158 | 38.874 | 1.00 | 28.15 | A | C |
| ATOM | 1460 | CG1 | VAL | A | 317 | 33.084 | 6.310 | 39.399 | 1.00 | 29.28 | A | C |
| ATOM | 1461 | CG2 | VAL | A | 317 | 33.739 | 8.591 | 38.684 | 1.00 | 26.67 | A | C |
| ATOM | 1462 | C | VAL | A | 317 | 35.886 | 5.678 | 39.912 | 1.00 | 32.91 | A | C |
| ATOM | 1463 | O | VAL | A | 317 | 35.657 | 5.006 | 40.925 | 1.00 | 38.29 | A | O |
| ATOM | 1464 | N | LEU | A | 318 | 36.504 | 5.152 | 38.885 | 1.00 | 29.57 | A | N |
| ATOM | 1465 | CA | LEU | A | 318 | 36.937 | 3.749 | 38.990 | 1.00 | 28.56 | A | C |
| ATOM | 1466 | CB | LEU | A | 318 | 37.446 | 3.292 | 37.646 | 1.00 | 27.18 | A | C |
| ATOM | 1467 | CG | LEU | A | 318 | 37.907 | 1.848 | 37.610 | 1.00 | 33.68 | A | C |
| ATOM | 1468 | CD1 | LEU | A | 318 | 36.730 | 0.897 | 37.727 | 1.00 | 35.87 | A | C |
| ATOM | 1469 | CD2 | LEU | A | 318 | 38.664 | 1.627 | 36.332 | 1.00 | 35.75 | A | C |
| ATOM | 1470 | C | LEU | A | 318 | 38.034 | 3.544 | 40.078 | 1.00 | 32.43 | A | C |
| ATOM | 1471 | O | LEU | A | 318 | 38.013 | 2.570 | 40.833 | 1.00 | 31.41 | A | O |
| ATOM | 1472 | N | CYS | A | 319 | 39.035 | 4.411 | 40.106 | 1.00 | 31.76 | A | N |
| ATOM | 1473 | CA | CYS | A | 319 | 40.055 | 4.319 | 41.143 | 1.00 | 35.07 | A | C |
| ATOM | 1474 | CB | CYS | A | 319 | 41.042 | 5.488 | 41.063 | 1.00 | 34.34 | A | C |
| ATOM | 1475 | SG | CYS | A | 319 | 42.482 | 5.214 | 42.145 | 1.00 | 35.34 | A | S |
| ATOM | 1476 | C | CYS | A | 319 | 39.386 | 4.317 | 42.530 | 1.00 | 37.22 | A | C |
| ATOM | 1477 | O | CYS | A | 319 | 39.710 | 3.502 | 43.381 | 1.00 | 31.41 | A | O |
| ATOM | 1478 | N | TYR | A | 320 | 38.436 | 5.225 | 42.740 | 1.00 | 31.70 | A | N |
| ATOM | 1479 | CA | TYR | A | 320 | 37.656 | 5.201 | 43.953 | 1.00 | 32.61 | A | C |
| ATOM | 1480 | CB | TYR | A | 320 | 36.684 | 6.369 | 43.985 | 1.00 | 34.80 | A | C |
| ATOM | 1481 | CG | TYR | A | 320 | 35.901 | 6.490 | 45.264 | 1.00 | 35.74 | A | C |
| ATOM | 1482 | CD1 | TYR | A | 320 | 34.869 | 5.580 | 45.588 | 1.00 | 35.99 | A | C |
| ATOM | 1483 | CE1 | TYR | A | 320 | 34.179 | 5.679 | 46.774 | 1.00 | 38.96 | A | C |
| ATOM | 1484 | CZ | TYR | A | 320 | 34.484 | 6.744 | 47.643 | 1.00 | 37.99 | A | C |
| ATOM | 1485 | OH | TYR | A | 320 | 33.821 | 6.914 | 48.800 | 1.00 | 30.42 | A | O |
| ATOM | 1486 | CE2 | TYR | A | 320 | 35.497 | 7.613 | 47.337 | 1.00 | 35.53 | A | C |
| ATOM | 1487 | CD2 | TYR | A | 320 | 36.196 | 7.471 | 46.154 | 1.00 | 33.65 | A | C |
| ATOM | 1488 | C | TYR | A | 320 | 36.931 | 3.860 | 44.132 | 1.00 | 36.49 | A | C |
| ATOM | 1489 | O | TYR | A | 320 | 37.061 | 3.214 | 45.183 | 1.00 | 31.10 | A | O |
| ATOM | 1490 | N | GLU | A | 321 | 36.179 | 3.413 | 43.126 | 1.00 | 35.75 | A | N |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 1491 | CA | GLU | A | 321 | 35.437 | 2.174 | 43.287 | 1.00 | 34.52 | A | C |
| ATOM | 1492 | CB | GLU | A | 321 | 34.536 | 1.861 | 42.113 | 1.00 | 34.61 | A | C |
| ATOM | 1493 | CG | GLU | A | 321 | 33.799 | 0.524 | 42.283 | 1.00 | 38.77 | A | C |
| ATOM | 1494 | CD | GLU | A | 321 | 32.522 | 0.394 | 41.435 | 1.00 | 40.09 | A | C |
| ATOM | 1495 | OE1 | GLU | A | 321 | 32.406 | 0.981 | 40.330 | 1.00 | 39.38 | A | O |
| ATOM | 1496 | OE2 | GLU | A | 321 | 31.611 | −0.266 | 41.926 | 1.00 | 43.97 | A | O |
| ATOM | 1497 | C | GLU | A | 321 | 36.349 | 0.970 | 43.622 | 1.00 | 39.23 | A | C |
| ATOM | 1498 | O | GLU | A | 321 | 35.968 | 0.172 | 44.484 | 1.00 | 39.61 | A | O |
| ATOM | 1499 | N | PHE | A | 322 | 37.521 | 0.855 | 42.979 | 1.00 | 32.64 | A | N |
| ATOM | 1500 | CA | PHE | A | 322 | 38.461 | −0.211 | 43.271 | 1.00 | 37.81 | A | C |
| ATOM | 1501 | CB | PHE | A | 322 | 39.703 | −0.145 | 42.353 | 1.00 | 39.16 | A | C |
| ATOM | 1502 | CG | PHE | A | 322 | 39.487 | −0.618 | 40.928 | 1.00 | 37.98 | A | C |
| ATOM | 1503 | CD1 | PHE | A | 322 | 38.472 | −1.532 | 40.578 | 1.00 | 38.71 | A | C |
| ATOM | 1504 | CE1 | PHE | A | 322 | 38.318 | −1.969 | 39.265 | 1.00 | 34.53 | A | C |
| ATOM | 1505 | CZ | PHE | A | 322 | 39.186 | −1.512 | 38.281 | 1.00 | 34.76 | A | C |
| ATOM | 1506 | CE2 | PHE | A | 322 | 40.171 | −0.584 | 38.591 | 1.00 | 34.67 | A | C |
| ATOM | 1507 | CD2 | PHE | A | 322 | 40.321 | −0.142 | 39.909 | 1.00 | 35.05 | A | C |
| ATOM | 1508 | C | PHE | A | 322 | 38.937 | −0.183 | 44.751 | 1.00 | 39.87 | A | C |
| ATOM | 1509 | O | PHE | A | 322 | 39.017 | −1.234 | 45.416 | 1.00 | 35.86 | A | O |
| ATOM | 1510 | N | LEU | A | 323 | 39.258 | 1.007 | 45.252 | 1.00 | 37.33 | A | N |
| ATOM | 1511 | CA | LEU | A | 323 | 39.784 | 1.137 | 46.613 | 1.00 | 37.77 | A | C |
| ATOM | 1512 | CB | LEU | A | 323 | 40.444 | 2.479 | 46.793 | 1.00 | 36.33 | A | C |
| ATOM | 1513 | CG | LEU | A | 323 | 41.742 | 2.614 | 46.015 | 1.00 | 36.11 | A | C |
| ATOM | 1514 | CD1 | LEU | A | 323 | 42.181 | 4.035 | 46.194 | 1.00 | 40.44 | A | C |
| ATOM | 1515 | CD2 | LEU | A | 323 | 42.820 | 1.636 | 46.435 | 1.00 | 39.45 | A | C |
| ATOM | 1516 | C | LEU | A | 323 | 38.711 | 0.975 | 47.678 | 1.00 | 41.47 | A | C |
| ATOM | 1517 | O | LEU | A | 323 | 38..88 | 0.416 | 48.741 | 1.00 | 44.93 | A | O |
| ATOM | 1518 | N | VAL | A | 324 | 37.511 | 1.486 | 47.406 | 1.00 | 35.62 | A | N |
| ATOM | 1519 | CA | VAL | A | 324 | 36.458 | 1.531 | 48.392 | 1.00 | 35.57 | A | C |
| ATOM | 1520 | CB | VAL | A | 324 | 35.766 | 2.890 | 48.377 | 1.00 | 33.49 | A | C |
| ATOM | 1521 | CG1 | VAL | A | 324 | 34.546 | 2.917 | 49.302 | 1.00 | 35.47 | A | C |
| ATOM | 1522 | CG2 | VAL | A | 324 | 36.772 | 3.995 | 48.726 | 1.00 | 31.63 | A | C |
| ATOM | 1523 | C | VAL | A | 324 | 35.477 | 0.410 | 48.203 | 1.00 | 40.95 | A | C |
| ATOM | 1524 | O | VAL | A | 324 | 34.927 | −0.040 | 49.165 | 1.00 | 46.10 | A | O |
| ATOM | 1525 | N | GLY | A | 325 | 35.254 | −0.048 | 46.976 | 1.00 | 41.91 | A | N |
| ATOM | 1526 | CA | GLY | A | 325 | 34.284 | −1.093 | 46.685 | 1.00 | 38.64 | A | C |
| ATOM | 1527 | C | GLY | A | 325 | 32.911 | −0.577 | 46.314 | 1.00 | 39.52 | A | C |
| ATOM | 1528 | O | GLY | A | 325 | 32.033 | −1.357 | 46.054 | 1.00 | 49.60 | A | O |
| ATOM | 1529 | N | LYS | A | 326 | 32.719 | 0.724 | 46.226 | 1.00 | 41.19 | A | N |
| ATOM | 1530 | CA | LYS | A | 326 | 31.471 | 1.311 | 45.728 | 1.00 | 45.42 | A | C |
| ATOM | 1531 | CB | LYS | A | 326 | 30.540 | 1.681 | 46.891 | 1.00 | 51.75 | A | C |
| ATOM | 1532 | CG | LYS | A | 326 | 30.103 | 0.513 | 47.777 | 1.00 | 66.91 | A | C |
| ATOM | 1533 | CD | LYS | A | 326 | 29.267 | −0.543 | 47.020 | 1.00 | 69.56 | A | C |
| ATOM | 1534 | CE | LYS | A | 326 | 27.949 | −0.835 | 47.742 | 1.00 | 70.10 | A | C |
| ATOM | 1535 | NZ | LYS | A | 326 | 26.884 | −1.234 | 46.789 | 1.00 | 67.62 | A | N |
| ATOM | 1536 | C | LYS | A | 326 | 31.851 | 2.596 | 44.990 | 1.00 | 38.97 | A | C |
| ATOM | 1537 | O | LYS | A | 326 | 32.790 | 3.230 | 45.361 | 1.00 | 40.43 | A | O |
| ATOM | 1538 | N | PRO | A | 327 | 31.123 | 2.993 | 43.949 | 1.00 | 38.31 | A | N |
| ATOM | 1539 | CA | PRO | A | 327 | 31.483 | 4.256 | 43.342 | 1.00 | 34.26 | A | C |
| ATOM | 1540 | CB | PRO | A | 327 | 30.664 | 4.256 | 42.065 | 1.00 | 38.15 | A | C |
| ATOM | 1541 | CG | PRO | A | 327 | 29.439 | 3.511 | 42.442 | 1.00 | 36.05 | A | C |
| ATOM | 1542 | CD | PRO | A | 327 | 29.969 | 2.380 | 43.256 | 1.00 | 41.41 | A | C |
| ATOM | 1543 | C | PRO | A | 327 | 31.070 | 5.426 | 44.224 | 1.00 | 37.00 | A | C |
| ATOM | 1544 | O | PRO | A | 327 | 30.158 | 5.282 | 45.051 | 1.00 | 36.03 | A | O |
| ATOM | 1545 | N | PRO | A | 328 | 31.703 | 6.584 | 44.020 | 1.00 | 33.24 | A | N |
| ATOM | 1546 | CA | PRO | A | 328 | 31.717 | 7.605 | 45.026 | 1.00 | 33.95 | A | C |
| ATOM | 1547 | CB | PRO | A | 328 | 32.857 | 8.559 | 44.586 | 1.00 | 32.85 | A | C |
| ATOM | 1548 | CG | PRO | A | 328 | 32.975 | 8.328 | 43.094 | 1.00 | 34.02 | A | C |
| ATOM | 1549 | CD | PRO | A | 328 | 32.620 | 6.895 | 42.888 | 1.00 | 34.93 | A | C |
| ATOM | 1550 | C | PRO | A | 328 | 30.495 | 8.374 | 45.098 | 1.00 | 34.64 | A | C |
| ATOM | 1551 | O | PRO | A | 328 | 30.280 | 8.972 | 46.153 | 1.00 | 37.63 | A | O |
| ATOM | 1552 | N | PHE | A | 329 | 29.731 | 8.462 | 44.006 | 1.00 | 38.10 | A | N |
| ATOM | 1553 | CA | PHE | A | 329 | 28.520 | 9.295 | 43.984 | 1.00 | 33.46 | A | C |
| ATOM | 1554 | CB | PHE | A | 329 | 28.426 | 10.189 | 42.744 | 1.00 | 32.06 | A | C |
| ATOM | 1555 | CG | PHE | A | 329 | 29.655 | 11.033 | 42.550 | 1.00 | 36.83 | A | C |
| ATOM | 1556 | CD1 | PHE | A | 329 | 29.974 | 12.035 | 43.459 | 1.00 | 32.66 | A | C |
| ATOM | 1557 | CE1 | PHE | A | 329 | 31.139 | 12.785 | 43.314 | 1.00 | 35.18 | A | C |
| ATOM | 1558 | CZ | PHE | A | 329 | 31.985 | 12.561 | 42.251 | 1.00 | 33.63 | A | C |
| ATOM | 1559 | CE2 | PHE | A | 329 | 31.673 | 11.569 | 41.343 | 1.00 | 36.03 | A | C |
| ATOM | 1560 | CD2 | PHE | A | 329 | 30.518 | 10.798 | 41.505 | 1.00 | 34.21 | A | C |
| ATOM | 1561 | C | PHE | A | 329 | 27.267 | 8.511 | 44.156 | 1.00 | 38.74 | A | C |
| ATOM | 1562 | O | PHE | A | 329 | 26.197 | 9.055 | 43.948 | 1.00 | 40.86 | A | O |
| ATOM | 1563 | N | GLU | A | 330 | 27.395 | 7.248 | 44.544 | 1.00 | 42.28 | A | N |
| ATOM | 1564 | CA | GLU | A | 330 | 26.267 | 6.338 | 44.617 | 1.00 | 47.57 | A | C |
| ATOM | 1565 | CB | GLU | A | 330 | 26.712 | 4.991 | 45.189 | 1.00 | 51.20 | A | C |
| ATOM | 1566 | CG | GLU | A | 330 | 25.806 | 3.859 | 44.799 | 1.00 | 59.22 | A | C |
| ATOM | 1567 | CD | GLU | A | 330 | 26.296 | 2.550 | 45.355 | 1.00 | 61.29 | A | C |
| ATOM | 1568 | OE1 | GLU | A | 330 | 26.318 | 2.391 | 46.601 | 1.00 | 67.05 | A | O |

APPENDIX A-continued

| Atomic coordinates of Aurora A + Inhibitory Monobody Mb60 + Danusertib | | | | | | | | | | | |
|---|---|---|---|---|---|---|---|---|---|---|---|
| ATOM | 1569 | OE2 | GLU | A | 330 | 26.666 | 1.701 | 44.534 | 1.00 | 63.36 | A | O |
| ATOM | 1570 | C | GLU | A | 330 | 25.226 | 6.952 | 45.530 | 1.00 | 44.32 | A | C |
| ATOM | 1571 | O | GLU | A | 330 | 25.582 | 7.519 | 46.548 | 1.00 | 38.09 | A | O |
| ATOM | 1572 | N | ALA | A | 331 | 23.970 | 6.909 | 45.108 | 1.00 | 40.44 | A | N |
| ATOM | 1573 | CA | ALA | A | 331 | 22.823 | 7.347 | 45.923 | 1.00 | 40.47 | A | C |
| ATOM | 1574 | CB | ALA | A | 331 | 22.596 | 8.834 | 45.799 | 1.00 | 38.46 | A | C |
| ATOM | 1575 | C | ALA | A | 331 | 21.570 | 6.558 | 45.495 | 1.00 | 44.28 | A | C |
| ATOM | 1576 | O | ALA | A | 331 | 21.599 | 5.794 | 44.502 | 1.00 | 40.45 | A | O |
| ATOM | 1577 | N | ASN | A | 332 | 20.493 | 6.725 | 46.260 | 1.00 | 45.59 | A | N |
| ATOM | 1578 | CA | ASN | A | 332 | 19.233 | 5.968 | 46.085 | 1.00 | 46.41 | A | C |
| ATOM | 1579 | CB | ASN | A | 332 | 18.250 | 6.288 | 47.251 | 1.00 | 52.08 | A | C |
| ATOM | 1580 | CG | ASN | A | 332 | 18.379 | 5.332 | 48.402 | 1.00 | 66.35 | A | C |
| ATOM | 1581 | OD1 | ASN | A | 332 | 19.329 | 4.549 | 48.478 | 1.00 | 75.48 | A | O |
| ATOM | 1582 | ND2 | ASN | A | 332 | 17.415 | 5.386 | 49.318 | 1.00 | 79.53 | A | N |
| ATOM | 1583 | C | ASN | A | 332 | 18.449 | 6.289 | 44.849 | 1.00 | 42.35 | A | C |
| ATOM | 1584 | O | ASN | A | 332 | 17.679 | 5.452 | 44.395 | 1.00 | 37.89 | A | O |
| ATOM | 1585 | N | THR | A | 333 | 18.496 | 7.547 | 44.436 | 1.00 | 37.89 | A | N |
| ATOM | 1586 | CA | THR | A | 333 | 17.688 | 8.011 | 43.323 | 1.00 | 41.33 | A | C |
| ATOM | 1587 | CB | THR | A | 333 | 16.656 | 9.041 | 43.789 | 1.00 | 39.26 | A | C |
| ATOM | 1588 | OG1 | THR | A | 333 | 17.322 | 10.218 | 44.249 | 1.00 | 35.09 | A | O |
| ATOM | 1589 | CG2 | THR | A | 333 | 15.779 | 8.381 | 44.944 | 1.00 | 43.69 | A | C |
| ATOM | 1590 | C | THR | A | 333 | 18.554 | 8.669 | 42.264 | 1.00 | 42.33 | A | C |
| ATOM | 1591 | O | THR | A | 333 | 19.715 | 9.006 | 42.527 | 1.00 | 35.87 | A | O |
| ATOM | 1592 | N | TYR | A | 334 | 17.942 | 8.885 | 41.102 | 1.00 | 37.38 | A | N |
| ATOM | 1593 | CA | TYR | A | 334 | 18.583 | 9.573 | 40.010 | 1.00 | 36.75 | A | C |
| ATOM | 1594 | CB | TYR | A | 334 | 17.700 | 9.629 | 38.724 | 1.00 | 36.19 | A | C |
| ATOM | 1595 | CG | TYR | A | 334 | 18.353 | 10.396 | 37.580 | 1.00 | 34.25 | A | C |
| ATOM | 1596 | CD1 | TYR | A | 334 | 18.156 | 11.767 | 37.439 | 1.00 | 36.73 | A | C |
| ATOM | 1597 | CE1 | TYR | A | 334 | 18.768 | 12.480 | 36.424 | 1.00 | 34.35 | A | C |
| ATOM | 1598 | CZ | TYR | A | 334 | 19.606 | 11.810 | 35.512 | 1.00 | 39.09 | A | C |
| ATOM | 1599 | OH | TYR | A | 334 | 20.223 | 12.560 | 34.498 | 1.00 | 34.00 | A | O |
| ATOM | 1600 | CE2 | TYR | A | 334 | 19.819 | 10.420 | 35.634 | 1.00 | 35.95 | A | C |
| ATOM | 1601 | CD2 | TYR | A | 334 | 19.205 | 9.737 | 36.664 | 1.00 | 33.82 | A | C |
| ATOM | 1602 | C | TYR | A | 334 | 18.869 | 10.962 | 40.485 | 1.00 | 38.89 | A | C |
| ATOM | 1603 | O | TYR | A | 334 | 20.020 | 11.389 | 40.423 | 1.00 | 34.68 | A | O |
| ATOM | 1604 | N | GLN | A | 335 | 17.850 | 11.683 | 40.950 | 1.00 | 37.84 | A | N |
| ATOM | 1605 | CA | GLN | A | 335 | 18.068 | 13.097 | 41.230 | 1.00 | 42.67 | A | C |
| ATOM | 1606 | CB | GLN | A | 335 | 16.777 | 13.837 | 41.608 | 1.00 | 45.47 | A | C |
| ATOM | 1607 | CG | GLN | A | 335 | 16.865 | 15.391 | 41.561 | 1.00 | 55.22 | A | C |
| ATOM | 1608 | CD | GLN | A | 335 | 17.920 | 15.942 | 40.567 | 1.00 | 64.62 | A | C |
| ATOM | 1609 | OE1 | GLN | A | 335 | 17.729 | 15.930 | 39.344 | 1.00 | 65.12 | A | O |
| ATOM | 1610 | NE2 | GLN | A | 335 | 19.056 | 16.375 | 41.095 | 1.00 | 68.74 | A | N |
| ATOM | 1611 | C | GLN | A | 335 | 19.162 | 13.290 | 42.305 | 1.00 | 44.66 | A | C |
| ATOM | 1612 | O | GLN | A | 335 | 19.973 | 14.208 | 42.217 | 1.00 | 35.46 | A | O |
| ATOM | 1613 | N | GLU | A | 336 | 19.188 | 12.415 | 43.302 | 1.00 | 41.22 | A | N |
| ATOM | 1614 | CA | GLU | A | 336 | 20.209 | 12.512 | 44.320 | 1.00 | 45.79 | A | C |
| ATOM | 1615 | CB | GLU | A | 336 | 19.851 | 11.576 | 45.504 | 1.00 | 53.50 | A | C |
| ATOM | 1616 | CG | GLU | A | 336 | 20.737 | 11.733 | 46.721 | 1.00 | 62.76 | A | C |
| ATOM | 1617 | CD | GLU | A | 336 | 20.796 | 13.175 | 47.229 | 1.00 | 75.01 | A | C |
| ATOM | 1618 | OE1 | GLU | A | 336 | 19.737 | 13.879 | 47.148 | 1.00 | 78.21 | A | O |
| ATOM | 1619 | OE2 | GLU | A | 336 | 21.901 | 13.597 | 47.688 | 1.00 | 73.26 | A | O |
| ATOM | 1620 | C | GLU | A | 336 | 21.630 | 12.208 | 43.760 | 1.00 | 39.11 | A | C |
| ATOM | 1621 | O | GLU | A | 336 | 22.596 | 12.853 | 44.157 | 1.00 | 35.76 | A | O |
| ATOM | 1622 | N | THR | A | 337 | 21.757 | 11.212 | 42.886 | 1.00 | 33.33 | A | N |
| ATOM | 1623 | CA | THR | A | 337 | 23.074 | 10.908 | 42.271 | 1.00 | 38.99 | A | C |
| ATOM | 1624 | CB | THR | A | 337 | 23.003 | 9.641 | 41.420 | 1.00 | 40.76 | A | C |
| ATOM | 1625 | OG1 | THR | A | 337 | 22.536 | 8.566 | 42.245 | 1.00 | 43.05 | A | O |
| ATOM | 1626 | CG2 | THR | A | 337 | 24.379 | 9.281 | 40.822 | 1.00 | 37.90 | A | C |
| ATOM | 1627 | C | THR | A | 337 | 23.555 | 12.076 | 41.424 | 1.00 | 34.49 | A | C |
| ATOM | 1628 | O | THR | A | 337 | 24.675 | 12.511 | 41.520 | 1.00 | 37.03 | A | O |
| ATOM | 1629 | N | TYR | A | 338 | 22.648 | 12.624 | 40.645 | 1.00 | 38.89 | A | N |
| ATOM | 1630 | CA | TYR | A | 338 | 22.929 | 13.755 | 39.803 | 1.00 | 36.10 | A | C |
| ATOM | 1631 | CB | TYR | A | 338 | 21.651 | 14.155 | 39.108 | 1.00 | 37.42 | A | C |
| ATOM | 1632 | CG | TYR | A | 338 | 21.779 | 15.290 | 38.151 | 1.00 | 38.32 | A | C |
| ATOM | 1633 | CD1 | TYR | A | 338 | 21.632 | 16.605 | 38.573 | 1.00 | 42.12 | A | C |
| ATOM | 1634 | CE1 | TYR | A | 338 | 21.726 | 17.661 | 37.689 | 1.00 | 44.66 | A | C |
| ATOM | 1635 | CZ | TYR | A | 338 | 21.945 | 17.410 | 36.336 | 1.00 | 47.63 | A | C |
| ATOM | 1636 | OH | TYR | A | 338 | 22.046 | 18.442 | 35.449 | 1.00 | 50.82 | A | O |
| ATOM | 1637 | CE2 | TYR | A | 338 | 22.072 | 16.118 | 35.878 | 1.00 | 41.51 | A | C |
| ATOM | 1638 | CD2 | TYR | A | 338 | 21.961 | 15.053 | 36.786 | 1.00 | 42.12 | A | C |
| ATOM | 1639 | C | TYR | A | 338 | 23.435 | 14.947 | 40.606 | 1.00 | 38.08 | A | C |
| ATOM | 1640 | O | TYR | A | 338 | 24.378 | 15.592 | 40.259 | 1.00 | 34.70 | A | O |
| ATOM | 1641 | N | LYS | A | 339 | 22.729 | 15.271 | 41.655 | 1.00 | 36.66 | A | N |
| ATOM | 1642 | CA | LYS | A | 339 | 23.116 | 16.386 | 42.443 | 1.00 | 42.86 | A | C |
| ATOM | 1643 | CB | LYS | A | 339 | 22.036 | 16.602 | 43.501 | 1.00 | 51.07 | A | C |
| ATOM | 1644 | CG | LYS | A | 339 | 22.095 | 17.939 | 44.182 | 1.00 | 61.56 | A | C |
| ATOM | 1645 | CD | LYS | A | 339 | 22.106 | 17.773 | 45.697 | 1.00 | 75.10 | A | C |
| ATOM | 1646 | CE | LYS | A | 339 | 23.294 | 16.938 | 46.188 | 1.00 | 75.70 | A | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 1647 | NZ | LYS | A | 339 | 23.585 | 17.206 | 47.619 | 1.00 | 78.31 | A | N |
| ATOM | 1648 | C | LYS | A | 339 | 24.532 | 16.145 | 43.028 | 1.00 | 35.27 | A | C |
| ATOM | 1649 | O | LYS | A | 339 | 25.420 | 16.992 | 42.964 | 1.00 | 35.87 | A | O |
| ATOM | 1650 | N | ARG | A | 340 | 24.784 | 14.960 | 43.513 | 1.00 | 31.78 | A | N |
| ATOM | 1651 | CA | ARG | A | 340 | 26.112 | 14.664 | 44.033 | 1.00 | 32.56 | A | C |
| ATOM | 1652 | CB | ARG | A | 340 | 26.094 | 13.305 | 44.700 | 1.00 | 37.55 | A | C |
| ATOM | 1653 | CG | ARG | A | 340 | 25.391 | 13.326 | 46.054 | 1.00 | 42.26 | A | C |
| ATOM | 1654 | CD | ARG | A | 340 | 25.543 | 12.039 | 46.839 | 1.00 | 49.91 | A | C |
| ATOM | 1655 | NE | ARG | A | 340 | 26.970 | 11.773 | 47.026 | 1.00 | 63.21 | A | N |
| ATOM | 1656 | CZ | ARG | A | 340 | 27.502 | 10.668 | 47.545 | 1.00 | 64.15 | A | C |
| ATOM | 1657 | NH1 | ARG | A | 340 | 26.746 | 9.669 | 47.982 | 1.00 | 66.73 | A | N |
| ATOM | 1658 | NH2 | ARG | A | 340 | 28.819 | 10.583 | 47.640 | 1.00 | 68.55 | A | N |
| ATOM | 1659 | C | ARG | A | 340 | 27.221 | 14.786 | 42.978 | 1.00 | 36.49 | A | C |
| ATOM | 1660 | O | ARG | A | 340 | 28.279 | 15.442 | 43.227 | 1.00 | 37.03 | A | O |
| ATOM | 1661 | N | ILE | A | 341 | 26.993 | 14.185 | 41.795 | 1.00 | 32.68 | A | N |
| ATOM | 1662 | CA | ILE | A | 341 | 27.934 | 14.360 | 40.665 | 1.00 | 32.54 | A | C |
| ATOM | 1663 | CB | ILE | A | 341 | 27.476 | 13.608 | 39.409 | 1.00 | 30.58 | A | C |
| ATOM | 1664 | CG1 | ILE | A | 341 | 27.558 | 12.129 | 39.668 | 1.00 | 26.59 | A | C |
| ATOM | 1665 | CD1 | ILE | A | 341 | 26.894 | 11.272 | 38.636 | 1.00 | 27.53 | A | C |
| ATOM | 1666 | CG2 | ILE | A | 341 | 28.344 | 14.003 | 38.177 | 1.00 | 30.28 | A | C |
| ATOM | 1667 | C | ILE | A | 341 | 28.147 | 15.846 | 40.319 | 1.00 | 30.82 | A | C |
| ATOM | 1668 | O | ILE | A | 341 | 29.252 | 16.328 | 40.292 | 1.00 | 28.96 | A | O |
| ATOM | 1669 | N | SER | A | 342 | 27.065 | 16.556 | 40.113 | 1.00 | 33.11 | A | N |
| ATOM | 1670 | CA | SER | A | 342 | 27.070 | 17.991 | 39.715 | 1.00 | 34.31 | A | C |
| ATOM | 1671 | CB | SER | A | 342 | 25.598 | 18.373 | 39.542 | 1.00 | 37.08 | A | C |
| ATOM | 1672 | OG | SER | A | 342 | 25.408 | 19.738 | 39.264 | 1.00 | 46.41 | A | O |
| ATOM | 1673 | C | SER | A | 342 | 27.783 | 18.914 | 40.741 | 1.00 | 36.42 | A | C |
| ATOM | 1674 | O | SER | A | 342 | 28.384 | 19.935 | 40.395 | 1.00 | 39.99 | A | O |
| ATOM | 1675 | N | ARG | A | 343 | 27.744 | 18.532 | 42.000 | 1.00 | 35.56 | A | N |
| ATOM | 1676 | CA | ARG | A | 343 | 28.421 | 19.282 | 43.070 | 1.00 | 39.78 | A | C |
| ATOM | 1677 | CB | ARG | A | 343 | 27.499 | 19.358 | 44.277 | 1.00 | 38.44 | A | C |
| ATOM | 1678 | CG | ARG | A | 343 | 26.175 | 19.989 | 43.964 | 1.00 | 42.28 | A | C |
| ATOM | 1679 | CD | ARG | A | 343 | 25.224 | 19.901 | 45.139 | 1.00 | 47.25 | A | C |
| ATOM | 1680 | NE | ARG | A | 343 | 24.693 | 21.239 | 45.421 | 1.00 | 59.35 | A | N |
| ATOM | 1681 | CZ | ARG | A | 343 | 24.937 | 21.979 | 46.511 | 1.00 | 55.18 | A | C |
| ATOM | 1682 | NH1 | ARG | A | 343 | 25.692 | 21.550 | 47.524 | 1.00 | 47.28 | A | N |
| ATOM | 1683 | NH2 | ARG | A | 343 | 24.381 | 23.189 | 46.585 | 1.00 | 66.42 | A | N |
| ATOM | 1684 | C | ARG | A | 343 | 29.751 | 18.645 | 43.494 | 1.00 | 38.99 | A | C |
| ATOM | 1685 | O | ARG | A | 343 | 30.342 | 19.084 | 44.450 | 1.00 | 39.95 | A | O |
| ATOM | 1686 | N | VAL | A | 344 | 30.158 | 17.577 | 42.806 | 1.00 | 35.58 | A | N |
| ATOM | 1687 | CA | VAL | A | 344 | 31.319 | 16.784 | 43.147 | 1.00 | 37.04 | A | C |
| ATOM | 1688 | CB | VAL | A | 344 | 32.612 | 17.405 | 42.630 | 1.00 | 34.28 | A | C |
| ATOM | 1689 | CG1 | VAL | A | 344 | 33.709 | 16.352 | 42.622 | 1.00 | 34.23 | A | C |
| ATOM | 1690 | CG2 | VAL | A | 344 | 32.419 | 17.952 | 41.223 | 1.00 | 35.43 | A | C |
| ATOM | 1691 | C | VAL | A | 344 | 31.357 | 16.541 | 44.648 | 1.00 | 36.22 | A | C |
| ATOM | 1692 | O | VAL | A | 344 | 32.325 | 16.828 | 45.293 | 1.00 | 39.82 | A | O |
| ATOM | 1693 | N | GLU | A | 345 | 30.278 | 15.966 | 45.164 | 1.00 | 36.46 | A | N |
| ATOM | 1694 | CA | GLU | A | 345 | 30.086 | 15.735 | 46.580 | 1.00 | 39.44 | A | C |
| ATOM | 1695 | CB | GLU | A | 345 | 28.652 | 16.139 | 46.949 | 1.00 | 44.70 | A | C |
| ATOM | 1696 | CG | GLU | A | 345 | 28.516 | 17.107 | 48.111 | 1.00 | 54.99 | A | C |
| ATOM | 1697 | CD | GLU | A | 345 | 27.181 | 17.855 | 48.066 | 1.00 | 56.79 | A | C |
| ATOM | 1698 | OE1 | GLU | A | 345 | 26.152 | 17.155 | 48.041 | 1.00 | 55.02 | A | O |
| ATOM | 1699 | OE2 | GLU | A | 345 | 27.161 | 19.119 | 48.009 | 1.00 | 53.09 | A | O |
| ATOM | 1700 | C | GLU | A | 345 | 30.329 | 14.271 | 46.887 | 1.00 | 37.19 | A | C |
| ATOM | 1701 | O | GLU | A | 345 | 29.502 | 13.411 | 46.582 | 1.00 | 35.77 | A | O |
| ATOM | 1702 | N | PHE | A | 346 | 31.437 | 13.970 | 47.538 | 1.00 | 39.72 | A | N |
| ATOM | 1703 | CA | PHE | A | 346 | 31.722 | 12.592 | 47.918 | 1.00 | 38.90 | A | C |
| ATOM | 1704 | CB | PHE | A | 346 | 32.353 | 11.812 | 46.746 | 1.00 | 41.27 | A | C |
| ATOM | 1705 | CG | PHE | A | 346 | 33.755 | 12.226 | 46.422 | 1.00 | 37.27 | A | C |
| ATOM | 1706 | CD1 | PHE | A | 346 | 33.996 | 13.365 | 45.695 | 1.00 | 42.10 | A | C |
| ATOM | 1707 | CE1 | PHE | A | 346 | 35.266 | 13.762 | 45.376 | 1.00 | 37.45 | A | C |
| ATOM | 1708 | CZ | PHE | A | 346 | 36.329 | 13.030 | 45.828 | 1.00 | 40.21 | A | C |
| ATOM | 1709 | CE2 | PHE | A | 346 | 36.117 | 11.889 | 46.565 | 1.00 | 40.57 | A | C |
| ATOM | 1710 | CD2 | PHE | A | 346 | 34.819 | 11.485 | 46.854 | 1.00 | 43.15 | A | C |
| ATOM | 1711 | C | PHE | A | 346 | 32.639 | 12.540 | 49.104 | 1.00 | 40.58 | A | C |
| ATOM | 1712 | O | PHE | A | 346 | 33.322 | 13.497 | 49.345 | 1.00 | 36.80 | A | O |
| ATOM | 1713 | N | THR | A | 347 | 32.688 | 11.410 | 49.817 | 1.00 | 37.24 | A | N |
| ATOM | 1714 | CA | THR | A | 347 | 33.586 | 11.332 | 50.955 | 1.00 | 41.50 | A | C |
| ATOM | 1715 | CB | THR | A | 347 | 32.830 | 11.133 | 52.270 | 1.00 | 43.02 | A | C |
| ATOM | 1716 | OG1 | THR | A | 347 | 31.819 | 10.137 | 52.059 | 1.00 | 43.54 | A | O |
| ATOM | 1717 | CG2 | THR | A | 347 | 32.193 | 12.431 | 52.694 | 1.00 | 43.48 | A | C |
| ATOM | 1718 | C | THR | A | 347 | 34.483 | 10.194 | 50.775 | 1.00 | 36.57 | A | C |
| ATOM | 1719 | O | THR | A | 347 | 34.176 | 9.260 | 50.052 | 1.00 | 44.01 | A | O |
| ATOM | 1720 | N | PHE | A | 348 | 35.575 | 10.225 | 51.498 | 1.00 | 39.10 | A | N |
| ATOM | 1721 | CA | PHE | A | 348 | 36.439 | 9.049 | 51.626 | 1.00 | 38.40 | A | C |
| ATOM | 1722 | CB | PHE | A | 348 | 37.893 | 9.475 | 51.584 | 1.00 | 41.38 | A | C |
| ATOM | 1723 | CG | PHE | A | 348 | 38.323 | 10.069 | 50.286 | 1.00 | 44.63 | A | C |
| ATOM | 1724 | CD1 | PHE | A | 348 | 38.583 | 9.244 | 49.183 | 1.00 | 39.60 | A | C |

APPENDIX A-continued

Atomic coordinates of Aurora A + Inhibitory Monobody Mb60 + Danusertib

| | | | | | | | | | | | |
|---|---|---|---|---|---|---|---|---|---|---|---|
| ATOM | 1725 | CE1 | PHE | A | 348 | 39.023 | 9.799 | 47.968 | 1.00 | 40.93 | A | C |
| ATOM | 1726 | CZ | PHE | A | 348 | 39.224 | 11.167 | 47.844 | 1.00 | 38.94 | A | C |
| ATOM | 1727 | CE2 | PHE | A | 348 | 38.958 | 11.995 | 48.945 | 1.00 | 44.06 | A | C |
| ATOM | 1728 | CD2 | PHE | A | 348 | 38.512 | 11.447 | 50.161 | 1.00 | 41.01 | A | C |
| ATOM | 1729 | C | PHE | A | 348 | 36.293 | 8.351 | 52.959 | 1.00 | 40.25 | A | C |
| ATOM | 1730 | O | PHE | A | 348 | 36.235 | 9.003 | 53.980 | 1.00 | 40.43 | A | O |
| ATOM | 1731 | N | PRO | A | 349 | 36.301 | 7.026 | 52.976 | 1.00 | 46.88 | A | N |
| ATOM | 1732 | CA | PRO | A | 349 | 36.540 | 6.380 | 54.274 | 1.00 | 45.79 | A | C |
| ATOM | 1733 | CB | PRO | A | 349 | 36.294 | 4.891 | 54.011 | 1.00 | 41.91 | A | C |
| ATOM | 1734 | CG | PRO | A | 349 | 36.175 | 4.749 | 52.526 | 1.00 | 43.33 | A | C |
| ATOM | 1735 | CD | PRO | A | 349 | 35.902 | 6.080 | 51.920 | 1.00 | 43.43 | A | C |
| ATOM | 1736 | C | PRO | A | 349 | 37.965 | 6.594 | 54.776 | 1.00 | 50.24 | A | C |
| ATOM | 1737 | O | PRO | A | 349 | 38.865 | 6.986 | 54.005 | 1.00 | 47.09 | A | O |
| ATOM | 1738 | N | ASP | A | 350 | 38.145 | 6.297 | 56.067 | 1.00 | 49.87 | A | N |
| ATOM | 1739 | CA | ASP | A | 350 | 39.373 | 6.575 | 56.796 | 1.00 | 50.40 | A | C |
| ATOM | 1740 | CB | ASP | A | 350 | 39.210 | 6.239 | 58.295 | 1.00 | 55.72 | A | C |
| ATOM | 1741 | CG | ASP | A | 350 | 38.473 | 7.329 | 59.072 | 1.00 | 56.33 | A | C |
| ATOM | 1742 | OD1 | ASP | A | 350 | 38.363 | 8.464 | 58.578 | 1.00 | 61.21 | A | O |
| ATOM | 1743 | OD2 | ASP | A | 350 | 38.025 | 7.062 | 60.211 | 1.00 | 65.14 | A | O |
| ATOM | 1744 | C | ASP | A | 350 | 40.582 | 5.864 | 56.252 | 1.00 | 45.19 | A | C |
| ATOM | 1745 | O | ASP | A | 350 | 41.651 | 6.470 | 56.160 | 1.00 | 50.22 | A | O |
| ATOM | 1746 | N | PHE | A | 351 | 40.415 | 4.609 | 55.847 | 1.00 | 42.89 | A | N |
| ATOM | 1747 | CA | PHE | A | 351 | 41.553 | 3.836 | 55.340 | 1.00 | 43.77 | A | C |
| ATOM | 1748 | CB | PHE | A | 351 | 41.220 | 2.345 | 55.226 | 1.00 | 49.05 | A | C |
| ATOM | 1749 | CG | PHE | A | 351 | 40.111 | 2.036 | 54.269 | 1.00 | 51.78 | A | C |
| ATOM | 1750 | CD1 | PHE | A | 351 | 40.382 | 1.833 | 52.915 | 1.00 | 50.11 | A | C |
| ATOM | 1751 | CE1 | PHE | A | 351 | 39.363 | 1.549 | 52.035 | 1.00 | 52.56 | A | C |
| ATOM | 1752 | CZ | PHE | A | 351 | 38.039 | 1.464 | 52.482 | 1.00 | 53.68 | A | C |
| ATOM | 1753 | CE2 | PHE | A | 351 | 37.762 | 1.664 | 53.826 | 1.00 | 58.58 | A | C |
| ATOM | 1754 | CD2 | PHE | A | 351 | 38.805 | 1.951 | 54.716 | 1.00 | 51.24 | A | C |
| ATOM | 1755 | C | PHE | A | 351 | 42.143 | 4.318 | 54.010 | 1.00 | 44.94 | A | C |
| ATOM | 1756 | O | PHE | A | 351 | 43.311 | 4.059 | 53.742 | 1.00 | 42.73 | A | O |
| ATOM | 1757 | N | VAL | A | 352 | 41.378 | 5.044 | 53.193 | 1.00 | 43.43 | A | N |
| ATOM | 1758 | CA | VAL | A | 352 | 41.932 | 5.510 | 51.925 | 1.00 | 40.98 | A | C |
| ATOM | 1759 | CB | VAL | A | 352 | 40.901 | 6.225 | 51.062 | 1.00 | 40.76 | A | C |
| ATOM | 1760 | CG1 | VAL | A | 352 | 41.575 | 6.816 | 49.814 | 1.00 | 39.28 | A | C |
| ATOM | 1761 | CG2 | VAL | A | 352 | 39.816 | 5.246 | 50.664 | 1.00 | 37.80 | A | C |
| ATOM | 1762 | C | VAL | A | 352 | 43.048 | 6.493 | 52.234 | 1.00 | 41.21 | A | C |
| ATOM | 1763 | O | VAL | A | 352 | 42.769 | 7.570 | 52.795 | 1.00 | 41.36 | A | O |
| ATOM | 1764 | N | THR | A | 353 | 44.277 | 6.134 | 51.848 | 1.00 | 37.17 | A | N |
| ATOM | 1765 | CA | THR | A | 353 | 45.447 | 6.971 | 52.115 | 1.00 | 42.40 | A | C |
| ATOM | 1766 | CB | THR | A | 353 | 46.737 | 6.322 | 51.649 | 1.00 | 42.71 | A | C |
| ATOM | 1767 | OG1 | THR | A | 353 | 46.689 | 6.150 | 50.221 | 1.00 | 47.33 | A | O |
| ATOM | 1768 | CG2 | THR | A | 353 | 46.955 | 4.988 | 52.358 | 1.00 | 45.29 | A | C |
| ATOM | 1769 | C | THR | A | 353 | 45.437 | 8.293 | 51.406 | 1.00 | 46.63 | A | C |
| ATOM | 1770 | O | THR | A | 353 | 44.641 | 8.531 | 50.486 | 1.00 | 48.58 | A | O |
| ATOM | 1771 | N | GLU | A | 354 | 46.369 | 9.149 | 51.795 | 1.00 | 47.33 | A | N |
| ATOM | 1772 | CA | GLU | A | 354 | 46.373 | 10.553 | 51.329 | 1.00 | 56.49 | A | C |
| ATOM | 1773 | CB | GLU | A | 354 | 47.118 | 11.463 | 52.354 | 1.00 | 54.65 | A | C |
| ATOM | 1774 | CG | GLU | A | 354 | 47.870 | 12.679 | 51.813 | 1.00 | 66.74 | A | C |
| ATOM | 1775 | CD | GLU | A | 354 | 49.205 | 12.337 | 51.133 | 1.00 | 77.39 | A | C |
| ATOM | 1776 | OE1 | GLU | A | 354 | 49.821 | 11.298 | 51.475 | 1.00 | 80.91 | A | O |
| ATOM | 1777 | OE2 | GLU | A | 354 | 49.649 | 13.114 | 50.249 | 1.00 | 80.71 | A | O |
| ATOM | 1778 | C | GLU | A | 354 | 46.810 | 10.713 | 49.835 | 1.00 | 52.88 | A | C |
| ATOM | 1779 | O | GLU | A | 354 | 46.412 | 11.692 | 49.170 | 1.00 | 48.74 | A | O |
| ATOM | 1780 | N | GLY | A | 355 | 47.603 | 9.757 | 49.339 | 1.00 | 49.35 | A | N |
| ATOM | 1781 | CA | GLY | A | 355 | 48.063 | 9.711 | 47.945 | 1.00 | 47.27 | A | C |
| ATOM | 1782 | C | GLY | A | 355 | 46.900 | 9.352 | 47.017 | 1.00 | 47.30 | A | C |
| ATOM | 1783 | O | GLY | A | 355 | 46.728 | 9.996 | 45.996 | 1.00 | 43.21 | A | O |
| ATOM | 1784 | N | ALA | A | 356 | 46.110 | 8.332 | 47.377 | 1.00 | 44.63 | A | N |
| ATOM | 1785 | CA | ALA | A | 356 | 44.919 | 7.944 | 46.615 | 1.00 | 43.83 | A | C |
| ATOM | 1786 | CB | ALA | A | 356 | 44.225 | 6.757 | 47.227 | 1.00 | 47.68 | A | C |
| ATOM | 1787 | C | ALA | A | 356 | 43.983 | 9.122 | 46.575 | 1.00 | 46.48 | A | C |
| ATOM | 1788 | O | ALA | A | 356 | 43.473 | 9.476 | 45.480 | 1.00 | 44.19 | A | O |
| ATOM | 1789 | N | ARG | A | 357 | 43.813 | 9.777 | 47.734 | 1.00 | 41.82 | A | N |
| ATOM | 1790 | CA | ARG | A | 357 | 42.923 | 10.930 | 47.832 | 1.00 | 43.43 | A | C |
| ATOM | 1791 | CB | ARG | A | 357 | 42.858 | 11.511 | 49.239 | 1.00 | 44.54 | A | C |
| ATOM | 1792 | CG | ARG | A | 357 | 42.130 | 10.634 | 50.224 | 1.00 | 49.54 | A | C |
| ATOM | 1793 | CD | ARG | A | 357 | 42.386 | 11.046 | 51.685 | 1.00 | 51.03 | A | C |
| ATOM | 1794 | NE | ARG | A | 357 | 41.837 | 10.023 | 52.590 | 1.00 | 45.14 | A | N |
| ATOM | 1795 | CZ | ARG | A | 357 | 40.894 | 10.207 | 53.505 | 1.00 | 48.10 | A | C |
| ATOM | 1796 | NH1 | ARG | A | 357 | 40.383 | 11.410 | 53.736 | 1.00 | 47.45 | A | N |
| ATOM | 1797 | NH2 | ARG | A | 357 | 40.469 | 9.161 | 54.215 | 1.00 | 52.33 | A | N |
| ATOM | 1798 | C | ARG | A | 357 | 43.334 | 12.042 | 46.887 | 1.00 | 45.48 | A | C |
| ATOM | 1799 | O | ARG | A | 357 | 42.491 | 12.813 | 46.374 | 1.00 | 40.07 | A | O |
| ATOM | 1800 | N | ASP | A | 358 | 44.636 | 12.155 | 46.705 | 1.00 | 41.32 | A | N |
| ATOM | 1801 | CA | ASP | A | 358 | 45.142 | 13.230 | 45.956 | 1.00 | 42.24 | A | C |
| ATOM | 1802 | CB | ASP | A | 358 | 46.632 | 13.368 | 46.190 | 1.00 | 45.06 | A | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 1803 | CG | ASP | A | 358 | 47.195 | 14.511 | 45.415 | 1.00 | 40.08 | A | C |
| ATOM | 1804 | OD1 | ASP | A | 358 | 46.933 | 15.618 | 45.834 | 1.00 | 41.00 | A | O |
| ATOM | 1805 | OD2 | ASP | A | 358 | 47.809 | 14.260 | 44.360 | 1.00 | 41.87 | A | O |
| ATOM | 1806 | C | ASP | A | 358 | 44.841 | 13.007 | 44.467 | 1.00 | 38.48 | A | C |
| ATOM | 1807 | O | ASP | A | 358 | 44.265 | 13.882 | 43.803 | 1.00 | 35.95 | A | O |
| ATOM | 1808 | N | LEU | A | 359 | 45.189 | 11.820 | 43.986 | 1.00 | 35.18 | A | N |
| ATOM | 1809 | CA | LEU | A | 359 | 44.881 | 11.400 | 42.627 | 1.00 | 38.10 | A | C |
| ATOM | 1810 | CB | LEU | A | 359 | 45.408 | 9.986 | 42.380 | 1.00 | 39.17 | A | C |
| ATOM | 1811 | CG | LEU | A | 359 | 45.097 | 9.451 | 40.988 | 1.00 | 38.13 | A | C |
| ATOM | 1812 | CD1 | LEU | A | 359 | 45.680 | 10.396 | 39.957 | 1.00 | 42.14 | A | C |
| ATOM | 1813 | CD2 | LEU | A | 359 | 45.586 | 8.024 | 40.814 | 1.00 | 37.65 | A | C |
| ATOM | 1814 | C | LEU | A | 359 | 43.369 | 11.484 | 42.317 | 1.00 | 36.13 | A | C |
| ATOM | 1815 | O | LEU | A | 359 | 42.950 | 12.261 | 41.476 | 1.00 | 32.77 | A | O |
| ATOM | 1816 | N | ILE | A | 360 | 42.571 | 10.698 | 43.025 | 1.00 | 37.15 | A | N |
| ATOM | 1817 | CA | ILE | A | 360 | 41.106 | 10.742 | 42.892 | 1.00 | 34.22 | A | C |
| ATOM | 1818 | CB | ILE | A | 360 | 40.424 | 9.921 | 43.995 | 1.00 | 33.06 | A | C |
| ATOM | 1819 | CG1 | ILE | A | 360 | 40.749 | 8.440 | 43.777 | 1.00 | 34.23 | A | C |
| ATOM | 1820 | CD1 | ILE | A | 360 | 40.415 | 7.521 | 44.920 | 1.00 | 34.04 | A | C |
| ATOM | 1821 | CG2 | ILE | A | 360 | 38.903 | 10.213 | 44.011 | 1.00 | 30.86 | A | C |
| ATOM | 1822 | C | ILE | A | 360 | 40.550 | 12.182 | 42.895 | 1.00 | 36.93 | A | C |
| ATOM | 1823 | O | ILE | A | 360 | 39.740 | 12.574 | 42.039 | 1.00 | 35.99 | A | O |
| ATOM | 1824 | N | SER | A | 361 | 40.991 | 12.983 | 43.839 | 1.00 | 37.86 | A | N |
| ATOM | 1825 | CA | SER | A | 361 | 40.485 | 14.342 | 43.926 | 1.00 | 39.12 | A | C |
| ATOM | 1826 | CB | SER | A | 361 | 40.926 | 15.025 | 45.218 | 1.00 | 44.82 | A | C |
| ATOM | 1827 | OG | SER | A | 361 | 40.308 | 14.377 | 46.302 | 1.00 | 43.74 | A | O |
| ATOM | 1828 | C | SER | A | 361 | 40.894 | 15.153 | 42.740 | 1.00 | 37.47 | A | C |
| ATOM | 1829 | O | SER | A | 361 | 40.124 | 15.974 | 42.277 | 1.00 | 38.77 | A | O |
| ATOM | 1830 | N | ARG | A | 362 | 42.111 | 14.937 | 42.264 | 1.00 | 33.14 | A | N |
| ATOM | 1831 | CA | ARG | A | 362 | 42.547 | 15.616 | 41.085 | 1.00 | 39.01 | A | C |
| ATOM | 1832 | CB | ARG | A | 362 | 44.010 | 15.321 | 40.809 | 1.00 | 42.29 | A | C |
| ATOM | 1833 | CG | ARG | A | 362 | 44.970 | 16.136 | 41.660 | 1.00 | 46.17 | A | C |
| ATOM | 1834 | CD | ARG | A | 362 | 46.316 | 15.401 | 41.733 | 1.00 | 50.66 | A | C |
| ATOM | 1835 | NE | ARG | A | 362 | 47.391 | 16.354 | 41.783 | 1.00 | 55.57 | A | N |
| ATOM | 1836 | CZ | ARG | A | 362 | 47.728 | 17.130 | 40.758 | 1.00 | 65.43 | A | C |
| ATOM | 1837 | NH1 | ARG | A | 362 | 47.106 | 17.041 | 39.571 | 1.00 | 73.72 | A | N |
| ATOM | 1838 | NH2 | ARG | A | 362 | 48.681 | 18.020 | 40.925 | 1.00 | 74.46 | A | N |
| ATOM | 1839 | C | ARG | A | 362 | 41.701 | 15.203 | 39.857 | 1.00 | 35.98 | A | C |
| ATOM | 1840 | O | ARG | A | 362 | 41.502 | 15.998 | 39.001 | 1.00 | 35.42 | A | O |
| ATOM | 1841 | N | LEU | A | 363 | 41.269 | 13.948 | 39.765 | 1.00 | 33.40 | A | N |
| ATOM | 1842 | CA | LEU | A | 363 | 40.544 | 13.499 | 38.587 | 1.00 | 31.46 | A | C |
| ATOM | 1843 | CB | LEU | A | 363 | 40.595 | 12.021 | 38.442 | 1.00 | 28.91 | A | C |
| ATOM | 1844 | CG | LEU | A | 363 | 42.011 | 11.520 | 38.222 | 1.00 | 32.55 | A | C |
| ATOM | 1845 | CD1 | LEU | A | 363 | 42.153 | 10.064 | 38.617 | 1.00 | 33.55 | A | C |
| ATOM | 1846 | CD2 | LEU | A | 363 | 42.417 | 11.656 | 36.747 | 1.00 | 34.85 | A | C |
| ATOM | 1847 | C | LEU | A | 363 | 39.129 | 13.979 | 38.703 | 1.00 | 31.17 | A | C |
| ATOM | 1848 | O | LEU | A | 363 | 38.545 | 14.455 | 37.722 | 1.00 | 31.38 | A | O |
| ATOM | 1849 | N | LEU | A | 364 | 38.565 | 13.916 | 39.881 | 1.00 | 27.39 | A | N |
| ATOM | 1850 | CA | LEU | A | 364 | 37.185 | 14.339 | 39.997 | 1.00 | 27.68 | A | C |
| ATOM | 1851 | CB | LEU | A | 364 | 36.500 | 13.592 | 41.109 | 1.00 | 30.79 | A | C |
| ATOM | 1852 | CG | LEU | A | 364 | 36.668 | 12.093 | 40.988 | 1.00 | 29.11 | A | C |
| ATOM | 1853 | CD1 | LEU | A | 364 | 36.026 | 11.516 | 42.206 | 1.00 | 31.91 | A | C |
| ATOM | 1854 | CD2 | LEU | A | 364 | 36.056 | 11.527 | 39.718 | 1.00 | 28.10 | A | C |
| ATOM | 1855 | C | LEU | A | 364 | 36.966 | 15.827 | 40.101 | 1.00 | 33.21 | A | C |
| ATOM | 1856 | O | LEU | A | 364 | 36.496 | 16.334 | 41.109 | 1.00 | 37.70 | A | O |
| ATOM | 1857 | N | LYS | A | 365 | 37.261 | 16.550 | 39.031 | 1.00 | 35.36 | A | N |
| ATOM | 1858 | CA | LYS | A | 365 | 37.059 | 17.973 | 39.062 | 1.00 | 32.86 | A | C |
| ATOM | 1859 | CB | LYS | A | 365 | 38.312 | 18.729 | 38.616 | 1.00 | 37.37 | A | C |
| ATOM | 1860 | CG | LYS | A | 365 | 39.556 | 18.432 | 39.434 | 1.00 | 42.58 | A | C |
| ATOM | 1861 | CD | LYS | A | 365 | 39.519 | 18.986 | 40.847 | 1.00 | 49.25 | A | C |
| ATOM | 1862 | CE | LYS | A | 365 | 39.616 | 20.512 | 40.870 | 1.00 | 54.49 | A | C |
| ATOM | 1863 | NZ | LYS | A | 365 | 40.895 | 21.023 | 41.434 | 1.00 | 59.37 | A | N |
| ATOM | 1864 | C | LYS | A | 365 | 35.938 | 18.296 | 38.130 | 1.00 | 29.56 | A | C |
| ATOM | 1865 | O | LYS | A | 365 | 35.898 | 17.762 | 37.028 | 1.00 | 28.90 | A | O |
| ATOM | 1866 | N | HIS | A | 366 | 35.067 | 19.204 | 38.574 | 1.00 | 28.45 | A | N |
| ATOM | 1867 | CA | HIS | A | 366 | 33.915 | 19.633 | 37.827 | 1.00 | 30.43 | A | C |
| ATOM | 1868 | CB | HIS | A | 366 | 33.058 | 20.578 | 38.609 | 1.00 | 30.88 | A | C |
| ATOM | 1869 | CG | HIS | A | 366 | 31.770 | 20.893 | 37.935 | 1.00 | 29.49 | A | C |
| ATOM | 1870 | ND1 | HIS | A | 366 | 31.674 | 21.823 | 36.931 | 1.00 | 31.47 | A | N |
| ATOM | 1871 | CE1 | HIS | A | 366 | 30.416 | 21.898 | 36.532 | 1.00 | 30.28 | A | C |
| ATOM | 1872 | NE2 | HIS | A | 366 | 29.707 | 21.027 | 37.233 | 1.00 | 29.28 | A | N |
| ATOM | 1873 | CD2 | HIS | A | 366 | 30.530 | 20.405 | 38.121 | 1.00 | 30.05 | A | C |
| ATOM | 1874 | C | HIS | A | 366 | 34.354 | 20.256 | 36.526 | 1.00 | 32.39 | A | C |
| ATOM | 1875 | O | HIS | A | 366 | 33.850 | 19.874 | 35.449 | 1.00 | 32.02 | A | O |
| ATOM | 1876 | N | ASN | A | 367 | 35.353 | 21.131 | 36.607 | 1.00 | 33.90 | A | N |
| ATOM | 1877 | CA | ASN | A | 367 | 35.949 | 21.703 | 35.419 | 1.00 | 34.39 | A | C |
| ATOM | 1878 | CB | ASN | A | 367 | 36.649 | 22.989 | 35.802 | 1.00 | 39.18 | A | C |
| ATOM | 1879 | CG | ASN | A | 367 | 37.143 | 23.780 | 34.606 | 1.00 | 41.31 | A | C |
| ATOM | 1880 | OD1 | ASN | A | 367 | 37.542 | 23.223 | 33.561 | 1.00 | 40.32 | A | O |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 1881 | ND2 | ASN | A | 367 | 37.118 | 25.083 | 34.752 | 1.00 | 36.46 | A | N |
| ATOM | 1882 | C | ASN | A | 367 | 36.907 | 20.690 | 34.726 | 1.00 | 30.16 | A | C |
| ATOM | 1883 | O | ASN | A | 367 | 37.933 | 20.344 | 35.243 | 1.00 | 32.12 | A | O |
| ATOM | 1884 | N | PRO | A | 368 | 36.592 | 20.249 | 33.509 | 1.00 | 30.38 | A | N |
| ATOM | 1885 | CA | PRO | A | 368 | 37.450 | 19.210 | 32.903 | 1.00 | 32.01 | A | C |
| ATOM | 1886 | CB | PRO | A | 368 | 36.701 | 18.816 | 31.612 | 1.00 | 31.77 | A | C |
| ATOM | 1887 | CG | PRO | A | 368 | 35.715 | 19.891 | 31.386 | 1.00 | 32.81 | A | C |
| ATOM | 1888 | CD | PRO | A | 368 | 35.390 | 20.537 | 32.696 | 1.00 | 33.47 | A | C |
| ATOM | 1889 | C | PRO | A | 368 | 38.856 | 19.691 | 32.579 | 1.00 | 33.10 | A | C |
| ATOM | 1890 | O | PRO | A | 368 | 39.787 | 18.913 | 32.629 | 1.00 | 34.37 | A | O |
| ATOM | 1891 | N | SER | A | 369 | 39.015 | 20.958 | 32.244 | 1.00 | 35.52 | A | N |
| ATOM | 1892 | CA | SER | A | 369 | 40.364 | 21.446 | 31.962 | 1.00 | 41.01 | A | C |
| ATOM | 1893 | CB | SER | A | 369 | 40.357 | 22.834 | 31.387 | 1.00 | 38.90 | A | C |
| ATOM | 1894 | OG | SER | A | 369 | 39.810 | 23.662 | 32.354 | 1.00 | 39.39 | A | O |
| ATOM | 1895 | C | SER | A | 369 | 41.216 | 21.420 | 33.231 | 1.00 | 35.13 | A | C |
| ATOM | 1896 | O | SER | A | 369 | 42.366 | 21.290 | 33.108 | 1.00 | 36.30 | A | O |
| ATOM | 1897 | N | GLN | A | 370 | 40.636 | 21.421 | 34.433 | 1.00 | 42.78 | A | N |
| ATOM | 1898 | CA | GLN | A | 370 | 41.412 | 21.180 | 35.669 | 1.00 | 37.54 | A | C |
| ATOM | 1899 | CB | GLN | A | 370 | 40.678 | 21.700 | 36.914 | 1.00 | 38.58 | A | C |
| ATOM | 1900 | CG | GLN | A | 370 | 40.617 | 23.212 | 36.947 | 1.00 | 40.06 | A | C |
| ATOM | 1901 | CD | GLN | A | 370 | 39.631 | 23.777 | 37.950 | 1.00 | 43.89 | A | C |
| ATOM | 1902 | OE1 | GLN | A | 370 | 38.856 | 23.061 | 38.548 | 1.00 | 49.10 | A | O |
| ATOM | 1903 | NE2 | GLN | A | 370 | 39.682 | 25.067 | 38.150 | 1.00 | 46.34 | A | N |
| ATOM | 1904 | C | GLN | A | 370 | 41.820 | 19.735 | 35.907 | 1.00 | 36.80 | A | C |
| ATOM | 1905 | O | GLN | A | 370 | 42.614 | 19.486 | 36.801 | 1.00 | 36.18 | A | O |
| ATOM | 1906 | N | ARG | A | 371 | 41.302 | 18.778 | 35.135 | 1.00 | 35.24 | A | N |
| ATOM | 1907 | CA | ARG | A | 371 | 41.695 | 17.378 | 35.342 | 1.00 | 35.87 | A | C |
| ATOM | 1908 | CB | ARG | A | 371 | 40.744 | 16.369 | 34.683 | 1.00 | 33.50 | A | C |
| ATOM | 1909 | CG | ARG | A | 371 | 39.325 | 16.497 | 35.215 | 1.00 | 34.83 | A | C |
| ATOM | 1910 | CD | ARG | A | 371 | 38.244 | 15.649 | 34.521 | 1.00 | 35.86 | A | C |
| ATOM | 1911 | NE | ARG | A | 371 | 36.974 | 16.310 | 34.832 | 1.00 | 35.69 | A | N |
| ATOM | 1912 | CZ | ARG | A | 371 | 35.868 | 16.250 | 34.110 | 1.00 | 35.14 | A | C |
| ATOM | 1913 | NH1 | ARG | A | 371 | 35.854 | 15.501 | 33.058 | 1.00 | 33.77 | A | N |
| ATOM | 1914 | NH2 | ARG | A | 371 | 34.788 | 16.989 | 34.458 | 1.00 | 35.83 | A | N |
| ATOM | 1915 | C | ARG | A | 371 | 43.079 | 17.223 | 34.731 | 1.00 | 35.72 | A | C |
| ATOM | 1916 | O | ARG | A | 371 | 43.399 | 17.820 | 33.703 | 1.00 | 36.96 | A | O |
| ATOM | 1917 | N | PRO | A | 372 | 43.887 | 16.397 | 35.323 | 1.00 | 37.47 | A | N |
| ATOM | 1918 | CA | PRO | A | 372 | 45.224 | 16.207 | 34.756 | 1.00 | 38.59 | A | C |
| ATOM | 1919 | CB | PRO | A | 372 | 45.853 | 15.223 | 35.698 | 1.00 | 39.80 | A | C |
| ATOM | 1920 | CG | PRO | A | 372 | 44.722 | 14.576 | 36.449 | 1.00 | 39.14 | A | C |
| ATOM | 1921 | CD | PRO | A | 372 | 43.655 | 15.603 | 36.536 | 1.00 | 37.81 | A | C |
| ATOM | 1922 | C | PRO | A | 372 | 45.250 | 15.604 | 33.364 | 1.00 | 41.75 | A | C |
| ATOM | 1923 | O | PRO | A | 372 | 44.257 | 15.050 | 32.898 | 1.00 | 41.04 | A | O |
| ATOM | 1924 | N | MET | A | 373 | 46.413 | 15.669 | 32.732 | 1.00 | 36.47 | A | N |
| ATOM | 1925 | CA | MET | A | 373 | 46.719 | 14.806 | 31.601 | 1.00 | 38.42 | A | C |
| ATOM | 1926 | CB | MET | A | 373 | 47.922 | 15.358 | 30.862 | 1.00 | 48.89 | A | C |
| ATOM | 1927 | CG | MET | A | 373 | 47.569 | 16.561 | 29.989 | 1.00 | 55.96 | A | C |
| ATOM | 1928 | SD | MET | A | 373 | 49.110 | 17.203 | 29.312 | 1.00 | 67.07 | A | S |
| ATOM | 1929 | CE | MET | A | 373 | 49.473 | 18.522 | 30.481 | 1.00 | 69.01 | A | C |
| ATOM | 1930 | C | MET | A | 373 | 46.978 | 13.359 | 32.038 | 1.00 | 36.14 | A | C |
| ATOM | 1931 | O | MET | A | 373 | 47.389 | 13.115 | 33.199 | 1.00 | 35.69 | A | O |
| ATOM | 1932 | N | LEU | A | 374 | 46.765 | 12.403 | 31.117 | 1.00 | 33.92 | A | N |
| ATOM | 1933 | CA | LEU | A | 374 | 47.010 | 11.016 | 31.411 | 1.00 | 32.69 | A | C |
| ATOM | 1934 | CB | LEU | A | 374 | 46.677 | 10.086 | 30.237 | 1.00 | 35.37 | A | C |
| ATOM | 1935 | CG | LEU | A | 374 | 45.175 | 9.869 | 30.029 | 1.00 | 35.93 | A | C |
| ATOM | 1936 | CD1 | LEU | A | 374 | 44.880 | 9.099 | 28.726 | 1.00 | 36.96 | A | C |
| ATOM | 1937 | CD2 | LEU | A | 374 | 44.557 | 9.110 | 31.186 | 1.00 | 32.50 | A | C |
| ATOM | 1938 | C | LEU | A | 374 | 48.424 | 10.742 | 31.880 | 1.00 | 39.44 | A | C |
| ATOM | 1939 | O | LEU | A | 374 | 48.650 | 9.892 | 32.764 | 1.00 | 39.64 | A | O |
| ATOM | 1940 | N | ARG | A | 375 | 49.373 | 11.443 | 31.301 | 1.00 | 42.37 | A | N |
| ATOM | 1941 | CA | ARG | A | 375 | 50.759 | 11.214 | 31.652 | 1.00 | 49.01 | A | C |
| ATOM | 1942 | CB | ARG | A | 375 | 51.668 | 11.936 | 30.659 | 1.00 | 54.40 | A | C |
| ATOM | 1943 | CG | ARG | A | 375 | 53.125 | 11.466 | 30.663 | 1.00 | 66.93 | A | C |
| ATOM | 1944 | CD | ARG | A | 375 | 54.022 | 12.597 | 30.164 | 1.00 | 75.98 | A | C |
| ATOM | 1945 | NE | ARG | A | 375 | 54.100 | 13.758 | 31.093 | 1.00 | 89.30 | A | N |
| ATOM | 1946 | CZ | ARG | A | 375 | 53.433 | 14.931 | 31.006 | 1.00 | 93.86 | A | C |
| ATOM | 1947 | NH1 | ARG | A | 375 | 52.568 | 15.204 | 30.016 | 1.00 | 97.55 | A | N |
| ATOM | 1948 | NH2 | ARG | A | 375 | 53.634 | 15.863 | 31.943 | 1.00 | 88.09 | A | N |
| ATOM | 1949 | C | ARG | A | 375 | 50.979 | 11.655 | 33.121 | 1.00 | 46.74 | A | C |
| ATOM | 1950 | O | ARG | A | 375 | 51.800 | 11.046 | 33.821 | 1.00 | 40.72 | A | O |
| ATOM | 1951 | N | GLU | A | 376 | 50.231 | 12.666 | 33.588 | 1.00 | 39.38 | A | N |
| ATOM | 1952 | CA | GLU | A | 376 | 50.338 | 13.150 | 34.977 | 1.00 | 43.65 | A | C |
| ATOM | 1953 | CB | GLU | A | 376 | 49.628 | 14.474 | 35.165 | 1.00 | 43.81 | A | C |
| ATOM | 1954 | CG | GLU | A | 376 | 50.354 | 15.614 | 34.474 | 1.00 | 51.84 | A | C |
| ATOM | 1955 | CD | GLU | A | 376 | 49.651 | 16.954 | 34.663 | 1.00 | 55.31 | A | C |
| ATOM | 1956 | OE1 | GLU | A | 376 | 50.340 | 17.917 | 35.070 | 1.00 | 63.32 | A | O |
| ATOM | 1957 | OE2 | GLU | A | 376 | 40.427 | 17.057 | 34.373 | 1.00 | 52.63 | A | O |
| ATOM | 1958 | C | GLU | A | 376 | 49.799 | 12.110 | 35.970 | 1.00 | 48.35 | A | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 1959 | O | GLU | A | 376 | 50.291 | 12.001 | 37.102 | 1.00 | 48.53 | A | O |
| ATOM | 1960 | N | VAL | A | 377 | 48.824 | 11.332 | 35.500 | 1.00 | 41.51 | A | N |
| ATOM | 1961 | CA | VAL | A | 377 | 48.328 | 10.151 | 36.190 | 1.00 | 39.89 | A | C |
| ATOM | 1962 | CB | VAL | A | 377 | 47.058 | 9.520 | 35.536 | 1.00 | 37.02 | A | C |
| ATOM | 1963 | CG1 | VAL | A | 377 | 46.593 | 8.303 | 36.314 | 1.00 | 35.63 | A | C |
| ATOM | 1964 | CG2 | VAL | A | 377 | 45.917 | 10.543 | 35.420 | 1.00 | 35.92 | A | C |
| ATOM | 1965 | C | VAL | A | 377 | 49.422 | 9.105 | 36.190 | 1.00 | 38.35 | A | C |
| ATOM | 1966 | O | VAL | A | 377 | 49.738 | 8.595 | 37.238 | 1.00 | 38.33 | A | O |
| ATOM | 1967 | N | LEU | A | 378 | 50.005 | 8.787 | 35.039 | 1.00 | 36.34 | A | N |
| ATOM | 1968 | CA | LEU | A | 378 | 51.045 | 7.741 | 35.012 | 1.00 | 39.51 | A | C |
| ATOM | 1969 | CB | LEU | A | 378 | 51.462 | 7.466 | 33.585 | 1.00 | 43.17 | A | C |
| ATOM | 1970 | CG | LEU | A | 378 | 50.413 | 6.777 | 32.746 | 1.00 | 40.53 | A | C |
| ATOM | 1971 | CD1 | LEU | A | 378 | 50.766 | 6.814 | 31.243 | 1.00 | 40.35 | A | C |
| ATOM | 1972 | CD2 | LEU | A | 378 | 50.217 | 5.360 | 33.211 | 1.00 | 38.88 | A | C |
| ATOM | 1973 | C | LEU | A | 378 | 52.290 | 8.071 | 35.907 | 1.00 | 40.25 | A | C |
| ATOM | 1974 | O | LEU | A | 378 | 52.936 | 7.175 | 36.399 | 1.00 | 47.74 | A | O |
| ATOM | 1975 | N | GLU | A | 379 | 52.521 | 9.351 | 36.158 | 1.00 | 41.82 | A | N |
| ATOM | 1976 | CA | GLU | A | 379 | 53.569 | 9.874 | 37.002 | 1.00 | 48.70 | A | C |
| ATOM | 1977 | CB | GLU | A | 379 | 54.255 | 11.040 | 36.252 | 1.00 | 53.04 | A | C |
| ATOM | 1978 | CG | GLU | A | 379 | 54.904 | 10.614 | 34.932 | 1.00 | 58.23 | A | C |
| ATOM | 1979 | CD | GLU | A | 379 | 55.552 | 11.773 | 34.150 | 1.00 | 70.35 | A | C |
| ATOM | 1980 | OE1 | GLU | A | 379 | 56.069 | 11.490 | 33.042 | 1.00 | 72.80 | A | O |
| ATOM | 1981 | OE2 | GLU | A | 379 | 55.555 | 12.945 | 34.617 | 1.00 | 63.84 | A | O |
| ATOM | 1982 | C | GLU | A | 379 | 53.074 | 10.373 | 38.368 | 1.00 | 50.11 | A | C |
| ATOM | 1983 | O | GLU | A | 379 | 53.792 | 11.094 | 39.075 | 1.00 | 44.39 | A | O |
| ATOM | 1984 | N | HIS | A | 380 | 51.868 | 10.003 | 38.790 | 1.00 | 41.46 | A | N |
| ATOM | 1985 | CA | HIS | A | 380 | 51.441 | 10.441 | 40.110 | 1.00 | 42.00 | A | C |
| ATOM | 1986 | CB | HIS | A | 380 | 49.941 | 10.188 | 40.354 | 1.00 | 42.78 | A | C |
| ATOM | 1987 | CG | HIS | A | 380 | 49.397 | 10.970 | 41.493 | 1.00 | 37.47 | A | C |
| ATOM | 1988 | ND1 | HIS | A | 380 | 49.471 | 10.519 | 42.786 | 1.00 | 37.28 | A | N |
| ATOM | 1989 | CE1 | HIS | A | 380 | 48.927 | 11.406 | 43.599 | 1.00 | 40.68 | A | C |
| ATOM | 1990 | NE2 | HIS | A | 380 | 48.566 | 12.453 | 42.880 | 1.00 | 43.06 | A | N |
| ATOM | 1991 | CD2 | HIS | A | 380 | 48.883 | 12.211 | 41.560 | 1.00 | 40.67 | A | C |
| ATOM | 1992 | C | HIS | A | 380 | 52.306 | 9.656 | 41.132 | 1.00 | 40.79 | A | C |
| ATOM | 1993 | O | HIS | A | 380 | 52.574 | 8.467 | 40.875 | 1.00 | 46.18 | A | O |
| ATOM | 1994 | N | PRO | A | 381 | 52.776 | 10.324 | 42.212 | 1.00 | 41.05 | A | N |
| ATOM | 1995 | CA | PRO | A | 381 | 53.612 | 9.650 | 43.231 | 1.00 | 49.63 | A | C |
| ATOM | 1996 | CB | PRO | A | 381 | 53.781 | 10.724 | 44.336 | 1.00 | 53.37 | A | C |
| ATOM | 1997 | CG | PRO | A | 381 | 53.448 | 12.053 | 43.711 | 1.00 | 49.06 | A | C |
| ATOM | 1998 | CD | PRO | A | 381 | 52.556 | 11.764 | 42.528 | 1.00 | 44.55 | A | C |
| ATOM | 1999 | C | PRO | A | 381 | 52.953 | 8.374 | 43.822 | 1.00 | 48.50 | A | C |
| ATOM | 2000 | O | PRO | A | 381 | 53.611 | 7.372 | 44.004 | 1.00 | 49.04 | A | O |
| ATOM | 2001 | N | TRP | A | 382 | 51.658 | 8.440 | 44.139 | 1.00 | 51.34 | A | N |
| ATOM | 2002 | CA | TRP | A | 382 | 50.845 | 7.256 | 44.493 | 1.00 | 43.27 | A | C |
| ATOM | 2003 | CB | TRP | A | 382 | 49.400 | 7.649 | 44.781 | 1.00 | 46.23 | A | C |
| ATOM | 2004 | CG | TRP | A | 382 | 48.620 | 6.556 | 45.408 | 1.00 | 46.73 | A | C |
| ATOM | 2005 | CD1 | TRP | A | 382 | 48.612 | 6.208 | 46.725 | 1.00 | 48.24 | A | C |
| ATOM | 2006 | NE1 | TRP | A | 382 | 47.769 | 5.135 | 46.930 | 1.00 | 44.81 | A | N |
| ATOM | 2007 | CE2 | TRP | A | 382 | 47.203 | 4.775 | 45.739 | 1.00 | 48.52 | A | C |
| ATOM | 2008 | CD2 | TRP | A | 382 | 47.712 | 5.657 | 44.748 | 1.00 | 48.01 | A | C |
| ATOM | 2009 | CE3 | TRP | A | 382 | 47.266 | 5.515 | 43.418 | 1.00 | 46.21 | A | C |
| ATOM | 2010 | CZ3 | TRP | A | 382 | 46.371 | 4.493 | 43.115 | 1.00 | 40.61 | A | C |
| ATOM | 2011 | CH2 | TRP | A | 382 | 45.864 | 3.639 | 44.128 | 1.00 | 41.95 | A | C |
| ATOM | 2012 | CZ2 | TRP | A | 382 | 46.276 | 3.749 | 45.434 | 1.00 | 45.69 | A | C |
| ATOM | 2013 | C | TRP | A | 382 | 50.868 | 6.160 | 43.471 | 1.00 | 41.39 | A | C |
| ATOM | 2014 | O | TRP | A | 382 | 50.899 | 4.992 | 43.818 | 1.00 | 38.20 | A | O |
| ATOM | 2015 | N | ILE | A | 383 | 50.844 | 6.515 | 42.196 | 1.00 | 38.33 | A | N |
| ATOM | 2016 | CA | ILE | A | 383 | 50.871 | 5.511 | 41.162 | 1.00 | 37.22 | A | C |
| ATOM | 2017 | CB | ILE | A | 383 | 50.439 | 6.097 | 39.803 | 1.00 | 41.25 | A | C |
| ATOM | 2018 | CG1 | ILE | A | 383 | 48.964 | 6.516 | 39.863 | 1.00 | 41.72 | A | C |
| ATOM | 2019 | CD1 | ILE | A | 383 | 47.997 | 5.369 | 39.620 | 1.00 | 41.99 | A | C |
| ATOM | 2020 | CG2 | ILE | A | 383 | 50.691 | 5.099 | 38.660 | 1.00 | 34.21 | A | C |
| ATOM | 2021 | C | ILE | A | 383 | 52.280 | 4.945 | 40.990 | 1.00 | 40.79 | A | C |
| ATOM | 2022 | O | ILE | A | 383 | 52.444 | 3.721 | 40.837 | 1.00 | 42.17 | A | O |
| ATOM | 2023 | N | THR | A | 384 | 53.279 | 5.837 | 40.902 | 1.00 | 40.77 | A | N |
| ATOM | 2024 | CA | THR | A | 384 | 54.691 | 5.367 | 40.752 | 1.00 | 44.52 | A | C |
| ATOM | 2025 | CB | THR | A | 384 | 55.671 | 6.528 | 40.593 | 1.00 | 41.17 | A | C |
| ATOM | 2026 | OG1 | THR | A | 384 | 55.395 | 7.517 | 41.586 | 1.00 | 46.19 | A | O |
| ATOM | 2027 | CG2 | THR | A | 384 | 55.512 | 7.133 | 39.262 | 1.00 | 41.43 | A | C |
| ATOM | 2028 | C | THR | A | 384 | 55.062 | 4.529 | 41.974 | 1.00 | 42.57 | A | C |
| ATOM | 2029 | O | THR | A | 384 | 55.545 | 3.393 | 41.836 | 1.00 | 47.78 | A | O |
| ATOM | 2030 | N | ALA | A | 385 | 54.687 | 5.023 | 43.162 | 1.00 | 43.02 | A | N |
| ATOM | 2031 | CA | ALA | A | 385 | 54.972 | 4.292 | 44.429 | 1.00 | 46.76 | A | C |
| ATOM | 2032 | CB | ALA | A | 385 | 54.784 | 5.188 | 45.651 | 1.00 | 43.55 | A | C |
| ATOM | 2033 | C | ALA | A | 385 | 54.200 | 2.994 | 44.625 | 1.00 | 45.48 | A | C |
| ATOM | 2034 | O | ALA | A | 385 | 54.608 | 2.216 | 45.440 | 1.00 | 55.95 | A | O |
| ATOM | 2035 | N | ASN | A | 386 | 53.119 | 2.740 | 43.887 | 1.00 | 42.77 | A | N |
| ATOM | 2036 | CA | ASN | A | 386 | 52.313 | 1.526 | 44.073 | 1.00 | 43.19 | A | C |

APPENDIX A-continued

| Atomic coordinates of Aurora A + Inhibitory Monobody Mb60 + Danusertib | | | | | | | | | | | |
|---|---|---|---|---|---|---|---|---|---|---|---|
| ATOM | 2037 | CB | ASN | A | 386 | 50.953 | 1.942 | 44.644 | 1.00 | 45.14 | A | C |
| ATOM | 2038 | CG | ASN | A | 386 | 51.057 | 2.448 | 46.086 | 1.00 | 47.12 | A | C |
| ATOM | 2039 | OD1 | ASN | A | 386 | 51.344 | 1.667 | 46.988 | 1.00 | 59.72 | A | O |
| ATOM | 2040 | ND2 | ASN | A | 386 | 50.763 | 3.718 | 46.320 | 1.00 | 47.43 | A | N |
| ATOM | 2041 | C | ASN | A | 386 | 52.112 | 0.604 | 42.854 | 1.00 | 45.83 | A | C |
| ATOM | 2042 | O | ASN | A | 386 | 51.744 | −0.562 | 43.007 | 1.00 | 48.40 | A | O |
| ATOM | 2043 | N | SER | A | 387 | 52.332 | 1.108 | 41.646 | 1.00 | 47.49 | A | N |
| ATOM | 2044 | CA | SER | A | 387 | 52.124 | 0.298 | 40.466 | 1.00 | 54.76 | A | C |
| ATOM | 2045 | CB | SER | A | 387 | 52.047 | 1.227 | 39.244 | 1.00 | 55.40 | A | C |
| ATOM | 2046 | OG | SER | A | 387 | 51.809 | 0.469 | 38.087 | 1.00 | 62.36 | A | O |
| ATOM | 2047 | C | SER | A | 387 | 53.237 | −0.743 | 40.258 | 1.00 | 56.16 | A | C |
| ATOM | 2048 | O | SER | A | 387 | 54.408 | −0.393 | 40.324 | 1.00 | 62.53 | A | O |
| ATOM | 2049 | N | SER | A | 388 | 52.860 | −1.997 | 39.988 | 1.00 | 56.98 | A | N |
| ATOM | 2050 | CA | SER | A | 388 | 53.775 | −3.045 | 39.491 | 1.00 | 59.99 | A | C |
| ATOM | 2051 | CB | SER | A | 388 | 52.966 | −4.202 | 38.928 | 1.00 | 60.34 | A | C |
| ATOM | 2052 | OG | SER | A | 388 | 52.224 | −4.797 | 39.954 | 1.00 | 70.06 | A | O |
| ATOM | 2053 | C | SER | A | 388 | 54.705 | −2.587 | 38.380 | 1.00 | 61.78 | A | C |
| ATOM | 2054 | O | SER | A | 388 | 54.271 | −2.455 | 37.243 | 1.00 | 66.97 | A | O |
| TER | 2055 | | SER | A | 388 | | | | | | | |
| ATOM | 2056 | N | SER | B | 4 | 23.038 | −23.646 | 6.925 | 1.00 | 80.71 | B | N |
| ATOM | 2057 | CA | SER | B | 4 | 22.204 | −22.392 | 6.796 | 1.00 | 74.09 | B | C |
| ATOM | 2058 | CB | SER | B | 4 | 22.080 | −21.694 | 8.130 | 1.00 | 69.45 | B | C |
| ATOM | 2059 | OG | SER | B | 4 | 21.426 | −22.537 | 9.043 | 1.00 | 76.62 | B | O |
| ATOM | 2060 | C | SER | B | 4 | 22.759 | −21.403 | 5.769 | 1.00 | 76.84 | B | C |
| ATOM | 2061 | O | SER | B | 4 | 23.986 | −21.296 | 5.597 | 1.00 | 65.35 | B | O |
| ATOM | 2062 | N | SER | B | 5 | 21.834 | −20.706 | 5.091 | 1.00 | 77.58 | B | N |
| ATOM | 2063 | CA | SER | B | 5 | 22.141 | −19.785 | 3.980 | 1.00 | 74.15 | B | C |
| ATOM | 2064 | CB | SER | B | 5 | 22.359 | −20.552 | 2.660 | 1.00 | 75.23 | B | C |
| ATOM | 2065 | OG | SER | B | 5 | 21.129 | −20.885 | 2.050 | 1.00 | 78.67 | B | O |
| ATOM | 2066 | C | SER | B | 5 | 21.011 | −18.778 | 3.803 | 1.00 | 69.54 | B | C |
| ATOM | 2067 | O | SER | B | 5 | 19.929 | −18.954 | 4.369 | 1.00 | 69.94 | B | O |
| ATOM | 2068 | N | VAL | B | 6 | 21.276 | −17.706 | 3.052 | 1.00 | 67.57 | B | N |
| ATOM | 2069 | CA | VAL | B | 6 | 20.208 | −16.780 | 2.616 | 1.00 | 62.42 | B | C |
| ATOM | 2070 | CB | VAL | B | 6 | 19.972 | −15.545 | 3.564 | 1.00 | 63.60 | B | C |
| ATOM | 2071 | CG1 | VAL | B | 6 | 18.781 | −14.693 | 3.111 | 1.00 | 61.70 | B | C |
| ATOM | 2072 | CG2 | VAL | B | 6 | 19.690 | −15.981 | 5.002 | 1.00 | 55.43 | B | C |
| ATOM | 2073 | C | VAL | B | 6 | 20.557 | −16.380 | 1.178 | 1.00 | 60.54 | B | C |
| ATOM | 2074 | O | VAL | B | 6 | 21.674 | −15.894 | 0.915 | 1.00 | 69.32 | B | O |
| ATOM | 2075 | N | PRO | B | 7 | 19.649 | −16.645 | 0.233 | 1.00 | 55.33 | B | N |
| ATOM | 2076 | CA | PRO | B | 7 | 18.375 | −17.330 | 0.490 | 1.00 | 56.66 | B | C |
| ATOM | 2077 | CB | PRO | B | 7 | 17.566 | −17.038 | −0.775 | 1.00 | 52.80 | B | C |
| ATOM | 2078 | CG | PRO | B | 7 | 18.552 | −16.528 | −1.794 | 1.00 | 47.73 | B | C |
| ATOM | 2079 | CD | PRO | B | 7 | 19.929 | −16.593 | −1.209 | 1.00 | 50.61 | B | C |
| ATOM | 2080 | C | PRO | B | 7 | 18.554 | −18.855 | 0.767 | 1.00 | 58.38 | B | C |
| ATOM | 2081 | O | PRO | B | 7 | 19.680 | −19.409 | 0.642 | 1.00 | 53.14 | B | O |
| ATOM | 2082 | N | THR | B | 8 | 17.472 | −19.494 | 1.200 | 1.00 | 61.63 | B | N |
| ATOM | 2083 | CA | THR | B | 8 | 17.547 | −20.854 | 1.762 | 1.00 | 67.38 | B | C |
| ATOM | 2084 | CB | THR | B | 8 | 16.378 | −21.138 | 2.687 | 1.00 | 61.37 | B | C |
| ATOM | 2085 | OG1 | THR | B | 8 | 15.172 | −20.703 | 2.044 | 1.00 | 68.40 | B | O |
| ATOM | 2086 | CG2 | THR | B | 8 | 16.573 | −20.407 | 4.002 | 1.00 | 68.34 | B | C |
| ATOM | 2087 | C | THR | B | 8 | 17.525 | −21.934 | 0.700 | 1.00 | 78.59 | B | C |
| ATOM | 2088 | O | THR | B | 8 | 18.317 | −22.892 | 0.787 | 1.00 | 82.93 | B | O |
| ATOM | 2089 | N | LYS | B | 9 | 16.586 | −21.825 | −0.249 | 1.00 | 72.67 | B | N |
| ATOM | 2090 | CA | LYS | B | 9 | 16.541 | −22.767 | −1.383 | 1.00 | 74.10 | B | C |
| ATOM | 2091 | CB | LYS | B | 9 | 15.222 | −23.544 | −1.482 | 1.00 | 67.48 | B | C |
| ATOM | 2092 | CG | LYS | B | 9 | 13.970 | −22.740 | −1.784 | 1.00 | 68.61 | B | C |
| ATOM | 2093 | CD | LYS | B | 9 | 13.648 | −22.585 | −3.262 | 1.00 | 66.66 | B | C |
| ATOM | 2094 | CE | LYS | B | 9 | 12.259 | −21.954 | −3.432 | 1.00 | 70.29 | B | C |
| ATOM | 2095 | NZ | LYS | B | 9 | 11.975 | −21.468 | −4.812 | 1.00 | 67.67 | B | N |
| ATOM | 2096 | C | LYS | B | 9 | 16.847 | −22.006 | −2.650 | 1.00 | 76.76 | B | C |
| ATOM | 2097 | O | LYS | B | 9 | 16.908 | −20.774 | −2.632 | 1.00 | 92.02 | B | O |
| ATOM | 2098 | N | LEU | B | 10 | 17.071 | −22.746 | −3.727 | 1.00 | 68.49 | B | N |
| ATOM | 2099 | CA | LEU | B | 10 | 17.381 | −22.164 | −5.018 | 1.00 | 70.84 | B | C |
| ATOM | 2100 | CB | LEU | B | 10 | 18.816 | −21.592 | −5.015 | 1.00 | 62.69 | B | C |
| ATOM | 2101 | CG | LEU | B | 10 | 19.431 | −21.112 | −6.349 | 1.00 | 59.30 | B | C |
| ATOM | 2102 | CD1 | LEU | B | 10 | 18.611 | −19.989 | −6.979 | 1.00 | 57.68 | B | C |
| ATOM | 2103 | CD2 | LEU | B | 10 | 20.901 | −20.710 | −6.193 | 1.00 | 61.09 | B | C |
| ATOM | 2104 | C | LEU | B | 10 | 17.239 | −23.226 | −6.117 | 1.00 | 67.90 | B | C |
| ATOM | 2105 | O | LEU | B | 10 | 17.968 | −24.226 | −6.085 | 1.00 | 64.35 | B | O |
| ATOM | 2106 | N | GLU | B | 11 | 16.354 | −22.987 | −7.094 | 1.00 | 73.07 | B | N |
| ATOM | 2107 | CA | GLU | B | 11 | 16.299 | −23.816 | −8.327 | 1.00 | 73.74 | B | C |
| ATOM | 2108 | CB | GLU | B | 11 | 15.223 | −24.926 | −8.221 | 1.00 | 78.77 | B | C |
| ATOM | 2109 | CG | GLU | B | 11 | 13.759 | −24.508 | −8.447 | 1.00 | 84.61 | B | C |
| ATOM | 2110 | CD | GLU | B | 11 | 13.111 | −23.862 | −7.231 | 1.00 | 87.59 | B | C |
| ATOM | 2111 | OE1 | GLU | B | 11 | 11.860 | −23.889 | −7.138 | 1.00 | 77.21 | B | O |
| ATOM | 2112 | OE2 | GLU | B | 11 | 13.844 | −23.341 | −6.360 | 1.00 | 101.05 | B | O |
| ATOM | 2113 | C | GLU | B | 11 | 16.104 | −23.092 | −9.663 | 1.00 | 62.30 | B | C |
| ATOM | 2114 | O | GLU | B | 11 | 15.608 | −21.983 | −9.742 | 1.00 | 53.98 | B | O |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 2115 | N | VAL | B | 12 | 16.489 | −23.808 | −10.709 | 1.00 | 66.64 | B | N |
| ATOM | 2116 | CA | VAL | B | 12 | 15.970 | −23.624 | −12.048 | 1.00 | 68.12 | B | C |
| ATOM | 2117 | CB | VAL | B | 12 | 16.785 | −24.428 | −13.094 | 1.00 | 66.88 | B | C |
| ATOM | 2118 | CG1 | VAL | B | 12 | 16.123 | −24.331 | −14.466 | 1.00 | 64.51 | B | C |
| ATOM | 2119 | CG2 | VAL | B | 12 | 18.231 | −23.955 | −13.144 | 1.00 | 70.14 | B | C |
| ATOM | 2120 | C | VAL | B | 12 | 14.546 | −24.189 | −12.074 | 1.00 | 66.76 | B | C |
| ATOM | 2121 | O | VAL | B | 12 | 14.325 | −25.351 | −11.706 | 1.00 | 69.57 | B | O |
| ATOM | 2122 | N | VAL | B | 13 | 13.603 | −23.370 | −12.511 | 1.00 | 61.64 | B | N |
| ATOM | 2123 | CA | VAL | B | 13 | 12.207 | −23.774 | −12.580 | 1.00 | 68.63 | B | C |
| ATOM | 2124 | CB | VAL | B | 13 | 11.327 | −22.834 | −11.718 | 1.00 | 77.62 | B | C |
| ATOM | 2125 | CG1 | VAL | B | 13 | 9.947 | −23.447 | −11.497 | 1.00 | 86.70 | B | C |
| ATOM | 2126 | CG2 | VAL | B | 13 | 11.216 | −21.430 | −12.307 | 1.00 | 72.41 | B | C |
| ATOM | 2127 | C | VAL | B | 13 | 11.679 | −23.921 | −14.027 | 1.00 | 66.74 | B | C |
| ATOM | 2128 | O | VAL | B | 13 | 10.635 | −24.566 | −14.268 | 1.00 | 67.33 | B | O |
| ATOM | 2129 | N | ALA | B | 14 | 12.404 | −23.336 | −14.974 | 1.00 | 58.41 | B | N |
| ATOM | 2130 | CA | ALA | B | 14 | 12.108 | −23.459 | −16.396 | 1.00 | 60.14 | B | C |
| ATOM | 2131 | CB | ALA | B | 14 | 10.873 | −22.659 | −16.755 | 1.00 | 56.33 | B | C |
| ATOM | 2132 | C | ALA | B | 14 | 13.327 | −22.937 | −17.162 | 1.00 | 62.98 | B | C |
| ATOM | 2133 | O | ALA | B | 14 | 14.140 | −22.167 | −16.602 | 1.00 | 59.45 | B | O |
| ATOM | 2134 | N | ALA | B | 15 | 13.477 | −23.365 | −18.413 | 1.00 | 57.37 | B | N |
| ATOM | 2135 | CA | ALA | B | 15 | 14.651 | −22.987 | −19.204 | 1.00 | 58.29 | B | C |
| ATOM | 2136 | CB | ALA | B | 15 | 15.815 | −23.907 | −18.854 | 1.00 | 55.12 | B | C |
| ATOM | 2137 | C | ALA | B | 15 | 14.431 | −22.946 | −20.726 | 1.00 | 58.47 | B | C |
| ATOM | 2138 | O | ALA | B | 15 | 13.508 | −23.540 | −21.251 | 1.00 | 50.67 | B | O |
| ATOM | 2139 | N | THR | B | 16 | 15.294 | −22.192 | −21.397 | 1.00 | 62.61 | B | N |
| ATOM | 2140 | CA | THR | B | 16 | 15.440 | −22.184 | −22.854 | 1.00 | 65.67 | B | C |
| ATOM | 2141 | CB | THR | B | 16 | 15.206 | −20.758 | −23.389 | 1.00 | 64.79 | B | C |
| ATOM | 2142 | OG1 | THR | B | 16 | 13.878 | −20.366 | −23.045 | 1.00 | 61.10 | B | O |
| ATOM | 2143 | CG2 | THR | B | 16 | 15.351 | −20.591 | −24.881 | 1.00 | 73.61 | B | C |
| ATOM | 2144 | C | THR | B | 16 | 16.860 | −22.653 | −23.058 | 1.00 | 66.41 | B | C |
| ATOM | 2145 | O | THR | B | 16 | 17.576 | −22.829 | −22.093 | 1.00 | 64.10 | B | O |
| ATOM | 2146 | N | PRO | B | 17 | 17.265 | −22.956 | −24.298 | 1.00 | 79.83 | B | N |
| ATOM | 2147 | CA | PRO | B | 17 | 18.696 | −23.250 | −24.506 | 1.00 | 82.36 | B | C |
| ATOM | 2148 | CB | PRO | B | 17 | 18.777 | −23.504 | −26.033 | 1.00 | 83.51 | B | C |
| ATOM | 2149 | CG | PRO | B | 17 | 17.386 | −23.268 | −26.576 | 1.00 | 80.76 | B | C |
| ATOM | 2150 | CD | PRO | B | 17 | 16.472 | −23.497 | −25.413 | 1.00 | 81.23 | B | C |
| ATOM | 2151 | C | PRO | B | 17 | 19.678 | −22.132 | −24.085 | 1.00 | 79.68 | B | C |
| ATOM | 2152 | O | PRO | B | 17 | 20.811 | −22.424 | −23.701 | 1.00 | 66.94 | B | O |
| ATOM | 2153 | N | THR | B | 18 | 19.226 | −20.877 | −24.164 | 1.00 | 85.14 | B | N |
| ATOM | 2154 | CA | THR | B | 18 | 20.054 | −19.699 | −23.888 | 1.00 | 87.03 | B | C |
| ATOM | 2155 | CB | THR | B | 18 | 20.279 | −18.885 | −25.180 | 1.00 | 84.11 | B | C |
| ATOM | 2156 | OG1 | THR | B | 18 | 21.153 | −17.784 | −24.900 | 1.00 | 95.56 | B | O |
| ATOM | 2157 | CG2 | THR | B | 18 | 18.945 | −18.381 | −25.789 | 1.00 | 79.38 | B | C |
| ATOM | 2158 | C | THR | B | 18 | 19.493 | −18.772 | −22.784 | 1.00 | 88.64 | B | C |
| ATOM | 2159 | O | THR | B | 18 | 20.059 | −17.710 | −22.530 | 1.00 | 89.08 | B | O |
| ATOM | 2160 | N | SER | B | 19 | 18.433 | −19.205 | −22.103 | 1.00 | 83.51 | B | N |
| ATOM | 2161 | CA | SER | B | 19 | 17.760 | −18.422 | −21.072 | 1.00 | 75.18 | B | C |
| ATOM | 2162 | CB | SER | B | 19 | 16.392 | −17.934 | −21.587 | 1.00 | 71.04 | B | C |
| ATOM | 2163 | OG | SER | B | 19 | 15.784 | −16.987 | −20.740 | 1.00 | 71.05 | B | O |
| ATOM | 2164 | C | SER | B | 19 | 17.582 | −19.363 | −19.883 | 1.00 | 83.12 | B | C |
| ATOM | 2165 | O | SER | B | 19 | 17.527 | −20.594 | −20.032 | 1.00 | 76.49 | B | O |
| ATOM | 2166 | N | LEU | B | 20 | 17.479 | −18.790 | −18.695 | 1.00 | 83.85 | B | N |
| ATOM | 2167 | CA | LEU | B | 20 | 17.341 | −19.605 | −17.505 | 1.00 | 78.66 | B | C |
| ATOM | 2168 | CB | LEU | B | 20 | 18.717 | −20.026 | −17.048 | 1.00 | 79.19 | B | C |
| ATOM | 2169 | CG | LEU | B | 20 | 18.747 | −21.096 | −15.972 | 1.00 | 89.87 | B | C |
| ATOM | 2170 | CD1 | LEU | B | 20 | 17.916 | −22.306 | −16.389 | 1.00 | 96.60 | B | C |
| ATOM | 2171 | CD2 | LEU | B | 20 | 20.193 | −21.487 | −15.700 | 1.00 | 82.86 | B | C |
| ATOM | 2172 | C | LEU | B | 20 | 16.596 | −18.878 | −16.395 | 1.00 | 74.04 | B | C |
| ATOM | 2173 | O | LEU | B | 20 | 17.027 | −17.806 | −15.954 | 1.00 | 72.86 | B | O |
| ATOM | 2174 | N | LEU | B | 21 | 15.469 | −19.461 | −15.981 | 1.00 | 66.53 | B | N |
| ATOM | 2175 | CA | LEU | B | 21 | 14.612 | −18.884 | −14.963 | 1.00 | 67.28 | B | C |
| ATOM | 2176 | CB | LEU | B | 21 | 13.137 | −19.062 | −15.319 | 1.00 | 67.24 | B | C |
| ATOM | 2177 | CG | LEU | B | 21 | 12.179 | −18.574 | −14.228 | 1.00 | 72.22 | B | C |
| ATOM | 2178 | CD1 | LEU | B | 21 | 12.458 | −17.121 | −13.869 | 1.00 | 70.28 | B | C |
| ATOM | 2179 | CD2 | LEU | B | 21 | 10.719 | −18.771 | −14.610 | 1.00 | 73.40 | B | C |
| ATOM | 2180 | C | LEU | B | 21 | 14.934 | −19.542 | −13.620 | 1.00 | 64.80 | B | C |
| ATOM | 2181 | O | LEU | B | 21 | 14.860 | −20.753 | −13.523 | 1.00 | 64.68 | B | O |
| ATOM | 2182 | N | ILE | B | 22 | 15.307 | −18.742 | −12.604 | 1.00 | 61.04 | B | N |
| ATOM | 2183 | CA | ILE | B | 22 | 15.604 | −19.261 | −11.253 | 1.00 | 57.80 | B | C |
| ATOM | 2184 | CB | ILE | B | 22 | 17.058 | −19.066 | −10.800 | 1.00 | 60.08 | B | C |
| ATOM | 2185 | CG1 | ILE | B | 22 | 17.441 | −17.590 | −10.773 | 1.00 | 64.97 | B | C |
| ATOM | 2186 | CD1 | ILE | B | 22 | 18.772 | −17.349 | −10.117 | 1.00 | 67.25 | B | C |
| ATOM | 2187 | CG2 | ILE | B | 22 | 17.997 | −19.836 | −11.717 | 1.00 | 66.51 | B | C |
| ATOM | 2188 | C | ILE | B | 22 | 14.693 | −18.679 | −10.196 | 1.00 | 58.60 | B | C |
| ATOM | 2189 | O | ILE | B | 22 | 14.077 | −17.629 | −10.402 | 1.00 | 50.14 | B | O |
| ATOM | 2190 | N | SER | B | 23 | 14.625 | −19.393 | −9.077 | 1.00 | 52.14 | B | N |
| ATOM | 2191 | CA | SER | B | 23 | 13.765 | −19.048 | −7.985 | 1.00 | 55.42 | B | C |
| ATOM | 2192 | CB | SER | B | 23 | 12.428 | −19.748 | −8.145 | 1.00 | 56.58 | B | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 2193 | OG | SER | B | 23 | 11.442 | −19.032 | −7.435 | 1.00 | 59.82 | B | O |
| ATOM | 2194 | C | SER | B | 23 | 14.410 | −19.420 | −6.641 | 1.00 | 54.89 | B | C |
| ATOM | 2195 | O | SER | B | 23 | 15.267 | −20.294 | −6.574 | 1.00 | 49.63 | B | O |
| ATOM | 2196 | N | TRP | B | 24 | 14.001 | −18.711 | −5.586 | 1.00 | 58.62 | B | N |
| ATOM | 2197 | CA | TRP | B | 24 | 14.485 | −18.956 | −4.233 | 1.00 | 58.50 | B | C |
| ATOM | 2198 | CB | TRP | B | 24 | 15.810 | −18.194 | −3.972 | 1.00 | 61.58 | B | C |
| ATOM | 2199 | CG | TRP | B | 24 | 15.752 | −16.725 | −4.216 | 1.00 | 57.17 | B | C |
| ATOM | 2200 | CD1 | TRP | B | 24 | 15.295 | −15.773 | −3.353 | 1.00 | 60.87 | B | C |
| ATOM | 2201 | NE1 | TRP | B | 24 | 15.393 | −14.530 | −3.922 | 1.00 | 56.27 | B | N |
| ATOM | 2202 | CE2 | TRP | B | 24 | 15.941 | −14.659 | −5.169 | 1.00 | 56.64 | B | C |
| ATOM | 2203 | CD2 | TRP | B | 24 | 16.177 | −16.031 | −5.389 | 1.00 | 55.24 | B | C |
| ATOM | 2204 | CE3 | TRP | B | 24 | 16.724 | −16.436 | −6.611 | 1.00 | 57.32 | B | C |
| ATOM | 2205 | CZ3 | TRP | B | 24 | 17.000 | −15.467 | −7.579 | 1.00 | 59.81 | B | C |
| ATOM | 2206 | CH2 | TRP | B | 24 | 16.748 | −14.111 | −7.332 | 1.00 | 62.63 | B | C |
| ATOM | 2207 | CZ2 | TRP | B | 24 | 16.213 | −13.686 | −6.136 | 1.00 | 59.54 | B | C |
| ATOM | 2208 | C | TRP | B | 24 | 13.401 | −18.596 | −3.216 | 1.00 | 62.58 | B | C |
| ATOM | 2209 | O | TRP | B | 24 | 12.373 | −18.015 | −3.580 | 1.00 | 54.82 | B | O |
| ATOM | 2210 | N | ASP | B | 25 | 13.626 | −18.965 | −1.954 | 1.00 | 69.44 | B | N |
| ATOM | 2211 | CA | ASP | B | 25 | 12.651 | −18.706 | −0.888 | 1.00 | 77.61 | B | C |
| ATOM | 2212 | CB | ASP | B | 25 | 12.836 | −19.701 | 0.280 | 1.00 | 85.32 | B | C |
| ATOM | 2213 | CG | ASP | B | 25 | 11.810 | −20.857 | 0.263 | 1.00 | 95.75 | B | C |
| ATOM | 2214 | OD1 | ASP | B | 25 | 10.629 | −20.640 | −0.120 | 1.00 | 93.61 | B | O |
| ATOM | 2215 | OD2 | ASP | B | 25 | 12.191 | −21.987 | 0.660 | 1.00 | 91.52 | B | O |
| ATOM | 2216 | C | ASP | B | 25 | 12.776 | −17.279 | −0.369 | 1.00 | 79.27 | B | C |
| ATOM | 2217 | O | ASP | B | 25 | 13.835 | −16.906 | 0.144 | 1.00 | 81.63 | B | O |
| ATOM | 2218 | N | ALA | B | 26 | 11.690 | −16.502 | −0.491 | 1.00 | 81.76 | B | N |
| ATOM | 2219 | CA | ALA | B | 26 | 11.614 | −15.116 | 0.021 | 1.00 | 82.98 | B | C |
| ATOM | 2220 | CB | ALA | B | 26 | 10.257 | −14.497 | −0.315 | 1.00 | 77.28 | B | C |
| ATOM | 2221 | C | ALA | B | 26 | 11.827 | −15.103 | 1.535 | 1.00 | 83.59 | B | C |
| ATOM | 2222 | O | ALA | B | 26 | 11.031 | −15.705 | 2.246 | 1.00 | 100.16 | B | O |
| ATOM | 2223 | N | PRO | B | 27 | 12.883 | −14.425 | 2.041 | 1.00 | 75.98 | B | N |
| ATOM | 2224 | CA | PRO | B | 27 | 13.173 | −14.573 | 3.483 | 1.00 | 76.87 | B | C |
| ATOM | 2225 | CB | PRO | B | 27 | 14.664 | −14.184 | 3.603 | 1.00 | 77.76 | B | C |
| ATOM | 2226 | CG | PRO | B | 27 | 15.049 | −13.628 | 2.258 | 1.00 | 79.67 | B | C |
| ATOM | 2227 | CD | PRO | B | 27 | 13.800 | −13.459 | 1.425 | 1.00 | 76.17 | B | C |
| ATOM | 2228 | C | PRO | B | 27 | 12.290 | −13.700 | 4.386 | 1.00 | 73.64 | B | C |
| ATOM | 2229 | O | PRO | R | 27 | 11.436 | −12.911 | 3.894 | 1.00 | 60.43 | B | O |
| ATOM | 2230 | N | ALA | B | 28 | 12.496 | −13.866 | 5.692 | 1.00 | 72.46 | B | N |
| ATOM | 2231 | CA | ALA | B | 28 | 11.719 | −13.141 | 6.707 | 1.00 | 76.73 | B | C |
| ATOM | 2232 | CB | ALA | B | 28 | 11.685 | −13.925 | 8.008 | 1.00 | 73.81 | B | C |
| ATOM | 2233 | C | ALA | B | 28 | 12.311 | −11.742 | 6.921 | 1.00 | 78.33 | B | C |
| ATOM | 2234 | O | ALA | B | 28 | 11.628 | −10.718 | 6.780 | 1.00 | 78.93 | B | O |
| ATOM | 2235 | N | VAL | B | 29 | 13.598 | −11.717 | 7.244 | 1.00 | 77.03 | B | N |
| ATOM | 2236 | CA | VAL | B | 29 | 14.369 | −10.477 | 7.262 | 1.00 | 72.99 | B | C |
| ATOM | 2237 | CB | VAL | B | 29 | 15.766 | −10.704 | 7.912 | 1.00 | 75.89 | B | C |
| ATOM | 2238 | CG1 | VAL | B | 29 | 16.388 | −9.380 | 8.385 | 1.00 | 77.74 | B | C |
| ATOM | 2239 | CG2 | VAL | B | 29 | 16.695 | −11.493 | 6.995 | 1.00 | 75.17 | B | C |
| ATOM | 2240 | C | VAL | B | 29 | 14.473 | −9.915 | 5.828 | 1.00 | 70.87 | B | C |
| ATOM | 2241 | O | VAL | B | 29 | 14.824 | −10.657 | 4.912 | 1.00 | 78.32 | B | O |
| ATOM | 2242 | N | THR | B | 30 | 14.111 | −8.642 | 5.633 | 1.00 | 61.79 | B | N |
| ATOM | 2243 | CA | THR | B | 30 | 14.228 | −8.001 | 4.329 | 1.00 | 60.66 | B | C |
| ATOM | 2244 | CB | THR | B | 30 | 13.429 | −6.669 | 4.213 | 1.00 | 66.24 | B | C |
| ATOM | 2245 | OG1 | THR | B | 30 | 13.965 | −5.711 | 5.124 | 1.00 | 59.94 | B | O |
| ATOM | 2246 | CG2 | THR | B | 30 | 11.893 | −6.862 | 4.466 | 1.00 | 67.61 | B | C |
| ATOM | 2247 | C | THR | B | 30 | 15.714 | −7.758 | 3.936 | 1.00 | 55.28 | B | C |
| ATOM | 2248 | O | THR | B | 30 | 16.602 | −7.622 | 4.762 | 1.00 | 49.73 | B | O |
| ATOM | 2249 | N | VAL | B | 31 | 15.929 | −7.683 | 2.634 | 1.00 | 53.45 | B | N |
| ATOM | 2250 | CA | VAL | B | 31 | 17.220 | −7.773 | 2.007 | 1.00 | 49.83 | B | C |
| ATOM | 2251 | CB | VAL | B | 31 | 17.308 | −9.142 | 1.284 | 1.00 | 58.60 | B | C |
| ATOM | 2252 | CG1 | VAL | B | 31 | 18.260 | −9.159 | 0.097 | 1.00 | 61.76 | B | C |
| ATOM | 2253 | CG2 | VAL | B | 31 | 17.724 | −10.200 | 2.291 | 1.00 | 61.12 | B | C |
| ATOM | 2254 | C | VAL | B | 31 | 17.290 | −6.604 | 1.055 | 1.00 | 52.42 | B | C |
| ATOM | 2255 | O | VAL | B | 31 | 16.284 | −6.196 | 0.456 | 1.00 | 51.91 | B | O |
| ATOM | 2256 | N | VAL | B | 32 | 18.481 | −6.051 | 0.906 | 1.00 | 47.76 | B | N |
| ATOM | 2257 | CA | VAL | B | 32 | 18.636 | −4.898 | 0.058 | 1.00 | 49.94 | B | C |
| ATOM | 2258 | CB | VAL | B | 32 | 19.953 | −4.140 | 0.368 | 1.00 | 50.77 | B | C |
| ATOM | 2259 | CG1 | VAL | B | 32 | 20.220 | −3.074 | −0.700 | 1.00 | 44.38 | B | C |
| ATOM | 2260 | CG2 | VAL | B | 32 | 19.877 | −3.536 | 1.777 | 1.00 | 45.34 | B | C |
| ATOM | 2261 | C | VAL | B | 32 | 18.561 | −5.335 | −1.404 | 1.00 | 48.63 | B | C |
| ATOM | 2262 | O | VAL | B | 32 | 17.782 | −4.777 | −2.191 | 1.00 | 49.15 | B | O |
| ATOM | 2263 | N | HIS | B | 33 | 19.394 | −6.297 | −1.757 | 1.00 | 45.98 | B | N |
| ATOM | 2264 | CA | HIS | B | 33 | 19.338 | −6.904 | −3.074 | 1.00 | 48.73 | B | C |
| ATOM | 2265 | CB | HIS | B | 33 | 19.974 | −6.008 | −4.150 | 1.00 | 47.94 | B | C |
| ATOM | 2266 | CG | HIS | B | 33 | 21.421 | −5.689 | −3.960 | 1.00 | 52.39 | B | C |
| ATOM | 2267 | ND1 | HIS | B | 33 | 22.416 | −6.640 | −4.018 | 1.00 | 57.42 | B | N |
| ATOM | 2268 | CE1 | HIS | B | 33 | 23.594 | −6.057 | −3.875 | 1.00 | 57.71 | B | C |
| ATOM | 2269 | NE2 | HIS | B | 33 | 23.402 | −4.757 | −3.764 | 1.00 | 53.86 | B | N |
| ATOM | 2270 | CD2 | HIS | B | 33 | 22.056 | −4.493 | −3.852 | 1.00 | 53.13 | B | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 2271 | C | HIS | B | 33 | 19.968 | −8.268 | −3.056 | 1.00 | 49.67 | B | C |
| ATOM | 2272 | O | HIS | B | 33 | 20.559 | −8.638 | −2.051 | 1.00 | 50.46 | B | O |
| ATOM | 2273 | N | TYR | B | 34 | 19.893 | −8.990 | −4.182 | 1.00 | 50.32 | B | N |
| ATOM | 2274 | CA | TYR | B | 34 | 20.606 | −10.264 | −4.313 | 1.00 | 49.72 | B | C |
| ATOM | 2275 | CB | TYR | B | 34 | 19.668 | −11.423 | −4.632 | 1.00 | 51.61 | B | C |
| ATOM | 2276 | CG | TYR | B | 34 | 18.534 | −11.619 | −3.650 | 1.00 | 46.74 | B | C |
| ATOM | 2277 | CD1 | TYR | B | 34 | 17.325 | −10.944 | −3.810 | 1.00 | 46.14 | B | C |
| ATOM | 2278 | CE1 | TYR | B | 34 | 16.281 | −11.136 | −2.931 | 1.00 | 45.26 | B | C |
| ATOM | 2279 | CZ | TYR | B | 34 | 16.430 | −12.001 | −1.902 | 1.00 | 43.00 | B | C |
| ATOM | 2280 | OH | TYR | B | 34 | 15.412 | −12.176 | −1.013 | 1.00 | 46.75 | B | O |
| ATOM | 2281 | CE2 | TYR | B | 34 | 17.615 | −12.686 | −1.715 | 1.00 | 49.45 | B | C |
| ATOM | 2282 | CD2 | TYR | B | 34 | 18.659 | −12.495 | −2.601 | 1.00 | 47.03 | B | C |
| ATOM | 2283 | C | TYR | B | 34 | 21.583 | −10.166 | −5.426 | 1.00 | 49.20 | B | C |
| ATOM | 2284 | O | TYR | B | 34 | 21.238 | −9.655 | −6.477 | 1.00 | 57.07 | B | O |
| ATOM | 2285 | N | VAL | B | 35 | 22.783 | −10.656 | −5.183 | 1.00 | 46.65 | B | N |
| ATOM | 2286 | CA | VAL | B | 35 | 23.803 | −10.822 | −6.203 | 1.00 | 54.76 | B | C |
| ATOM | 2287 | CB | VAL | B | 35 | 25.243 | −10.667 | −5.628 | 1.00 | 59.48 | B | C |
| ATOM | 2288 | CG1 | VAL | B | 35 | 26.311 | −10.730 | −6.729 | 1.00 | 56.45 | B | C |
| ATOM | 2289 | CG2 | VAL | B | 35 | 25.349 | −9.359 | −4.841 | 1.00 | 57.13 | B | C |
| ATOM | 2290 | C | VAL | B | 35 | 23.645 | −12.241 | −6.761 | 1.00 | 61.86 | B | C |
| ATOM | 2291 | O | VAL | B | 35 | 23.615 | −13.275 | −6.012 | 1.00 | 51.08 | B | O |
| ATOM | 2292 | N | ILE | B | 36 | 23.538 | −12.287 | −8.077 | 1.00 | 52.47 | B | N |
| ATOM | 2293 | CA | ILE | B | 36 | 23.462 | −13.544 | −8.742 | 1.00 | 62.98 | B | C |
| ATOM | 2294 | CB | ILE | B | 36 | 22.175 | −13.638 | −9.540 | 1.00 | 68.54 | B | C |
| ATOM | 2295 | CG1 | ILE | B | 36 | 20.999 | −13.500 | −8.573 | 1.00 | 69.68 | B | C |
| ATOM | 2296 | CD1 | ILE | B | 36 | 19.670 | −13.309 | −9.246 | 1.00 | 75.30 | B | C |
| ATOM | 2297 | CG2 | ILE | B | 36 | 22.123 | −14.974 | −10.266 | 1.00 | 73.83 | B | C |
| ATOM | 2298 | C | ILE | B | 36 | 24.677 | −13.642 | −9.614 | 1.00 | 62.71 | B | C |
| ATOM | 2299 | O | ILE | B | 36 | 24.872 | −12.795 | −10.497 | 1.00 | 62.59 | B | O |
| ATOM | 2300 | N | THR | B | 37 | 25.521 | −14.620 | −9.318 | 1.00 | 57.19 | B | N |
| ATOM | 2301 | CA | THR | B | 37 | 26.703 | −14.874 | −10.128 | 1.00 | 70.63 | B | C |
| ATOM | 2302 | CB | THR | B | 37 | 28.000 | −14.828 | −9.313 | 1.00 | 72.45 | B | C |
| ATOM | 2303 | OG1 | THR | B | 37 | 28.122 | −16.027 | −8.533 | 1.00 | 67.61 | B | O |
| ATOM | 2304 | CG2 | THR | B | 37 | 28.062 | −13.571 | −8.410 | 1.00 | 72.25 | B | C |
| ATOM | 2305 | C | THR | B | 37 | 26.589 | −16.257 | −10.791 | 1.00 | 80.62 | B | C |
| ATOM | 2306 | O | THR | B | 37 | 26.015 | −17.200 | −10.212 | 1.00 | 72.75 | B | O |
| ATOM | 2307 | N | TYR | B | 38 | 27.146 | −16.369 | −11.997 | 1.00 | 85.55 | B | N |
| ATOM | 2308 | CA | TYR | B | 38 | 26.996 | −17.578 | −12.797 | 1.00 | 84.73 | B | C |
| ATOM | 2309 | CB | TYR | B | 38 | 25.654 | −17.539 | −13.532 | 1.00 | 80.58 | B | C |
| ATOM | 2310 | CG | TYR | B | 38 | 25.531 | −16.464 | −14.589 | 1.00 | 84.54 | B | C |
| ATOM | 2311 | CD1 | TYR | B | 38 | 24.948 | −15.220 | −14.309 | 1.00 | 86.18 | B | C |
| ATOM | 2312 | CE1 | TYR | B | 38 | 24.828 | −14.247 | −15.302 | 1.00 | 80.66 | B | C |
| ATOM | 2313 | CZ | TYR | B | 38 | 25.290 | −14.526 | −16.588 | 1.00 | 76.76 | B | C |
| ATOM | 2314 | OH | TYR | B | 38 | 25.189 | −13.623 | −17.600 | 1.00 | 70.47 | B | O |
| ATOM | 2315 | CE2 | TYR | B | 38 | 25.864 | −15.740 | −16.881 | 1.00 | 75.09 | B | C |
| ATOM | 2316 | CD2 | TYR | B | 38 | 25.977 | −16.699 | −15.891 | 1.00 | 83.43 | B | C |
| ATOM | 2317 | C | TYR | B | 38 | 28.146 | −17.859 | −13.773 | 1.00 | 77.28 | B | C |
| ATOM | 2318 | O | TYR | B | 38 | 28.704 | −16.935 | −14.346 | 1.00 | 73.96 | B | O |
| ATOM | 2319 | N | GLN | B | 48 | 31.263 | −13.928 | −13.339 | 1.00 | 77.48 | B | N |
| ATOM | 2320 | CA | GLN | B | 48 | 30.211 | −13.227 | −14.089 | 1.00 | 86.60 | B | C |
| ATOM | 2321 | CB | GLN | B | 48 | 29.923 | −14.015 | −15.378 | 1.00 | 93.58 | B | C |
| ATOM | 2322 | CG | GLN | B | 48 | 28.798 | −13.498 | −16.276 | 1.00 | 105.59 | B | C |
| ATOM | 2323 | CD | GLN | B | 48 | 29.083 | −12.131 | −16.893 | 1.00 | 112.34 | B | C |
| ATOM | 2324 | OE1 | GLN | B | 48 | 30.149 | −11.551 | −16.688 | 1.00 | 115.65 | B | O |
| ATOM | 2325 | NE2 | GLN | B | 48 | 28.124 | −11.612 | −17.657 | 1.00 | 111.25 | B | N |
| ATOM | 2326 | C | GLN | B | 48 | 28.920 | −12.995 | −13.246 | 1.00 | 83.46 | B | C |
| ATOM | 2327 | O | GLN | B | 48 | 28.318 | −13.955 | −12.772 | 1.00 | 84.54 | B | O |
| ATOM | 2328 | N | GLU | B | 49 | 28.495 | −11.732 | −13.085 | 1.00 | 78.35 | B | N |
| ATOM | 2329 | CA | GLU | B | 49 | 27.441 | −11.381 | −12.122 | 1.00 | 73.76 | B | C |
| ATOM | 2330 | CB | GLU | B | 49 | 28.049 | −11.091 | −10.747 | 1.00 | 73.98 | B | C |
| ATOM | 2331 | CG | GLU | B | 49 | 28.445 | −9.637 | −10.465 | 1.00 | 77.38 | B | C |
| ATOM | 2332 | CD | GLU | B | 49 | 29.190 | −9.465 | −9.141 | 1.00 | 75.60 | B | C |
| ATOM | 2333 | OE1 | GLU | B | 49 | 29.242 | −8.323 | −8.630 | 1.00 | 78.04 | B | O |
| ATOM | 2334 | OE2 | GLU | B | 49 | 29.713 | −10.468 | −8.606 | 1.00 | 68.67 | B | O |
| ATOM | 2335 | C | GLU | B | 49 | 26.532 | −10.221 | −12.476 | 1.00 | 67.42 | B | C |
| ATOM | 2336 | O | GLU | B | 49 | 26.848 | −9.392 | −13.313 | 1.00 | 68.47 | B | O |
| ATOM | 2337 | N | PHE | B | 50 | 25.399 | −10.185 | −11.783 | 1.00 | 64.20 | B | N |
| ATOM | 2338 | CA | PHE | B | 50 | 24.459 | −9.063 | −11.815 | 1.00 | 60.24 | B | C |
| ATOM | 2339 | CB | PHE | B | 50 | 23.554 | −9.119 | −13.056 | 1.00 | 66.10 | B | C |
| ATOM | 2340 | CG | PHE | B | 50 | 22.497 | −10.201 | −13.016 | 1.00 | 68.71 | B | C |
| ATOM | 2341 | CD1 | PHE | B | 50 | 21.157 | −9.893 | −12.706 | 1.00 | 73.37 | B | C |
| ATOM | 2342 | CE1 | PHE | B | 50 | 20.170 | −10.896 | −12.688 | 1.00 | 69.86 | B | C |
| ATOM | 2343 | CZ | PHE | B | 50 | 20.522 | −12.217 | −12.974 | 1.00 | 61.83 | B | C |
| ATOM | 2344 | CE2 | PHE | B | 50 | 21.845 | −12.528 | −13.289 | 1.00 | 65.34 | B | C |
| ATOM | 2345 | CD2 | PHE | B | 50 | 22.824 | −11.528 | −13.304 | 1.00 | 66.96 | B | C |
| ATOM | 2346 | C | PHE | B | 50 | 23.650 | −9.080 | −10.520 | 1.00 | 55.82 | B | C |
| ATOM | 2347 | O | PHE | B | 50 | 23.895 | −9.917 | −9.653 | 1.00 | 51.47 | B | O |
| ATOM | 2348 | N | THR | B | 51 | 22.709 | −8.157 | −10.365 | 1.00 | 53.23 | B | N |

APPENDIX A-continued

| Atomic coordinates of Aurora A + Inhibitory Monobody Mb60 + Danusertib | | | | | | | | | | | | |
|---|---|---|---|---|---|---|---|---|---|---|---|---|
| ATOM | 2349 | CA | THR | B | 51 | 21.986 | −8.074 | −9.127 | 1.00 | 52.95 | B | C |
| ATOM | 2350 | CB | THR | B | 51 | 22.495 | −6.924 | −8.241 | 1.00 | 60.84 | B | C |
| ATOM | 2351 | OG1 | THR | B | 51 | 21.882 | −5.698 | −8.662 | 1.00 | 61.37 | B | O |
| ATOM | 2352 | CG2 | THR | B | 51 | 24.024 | −6.806 | −8.274 | 1.00 | 58.40 | B | C |
| ATOM | 2353 | C | THR | B | 51 | 20.511 | −7.840 | −9.350 | 1.00 | 60.96 | B | C |
| ATOM | 2354 | O | THR | B | 51 | 20.101 | −7.314 | −10.386 | 1.00 | 60.03 | B | O |
| ATOM | 2355 | N | VAL | B | 52 | 19.732 | −8.163 | −8.323 | 1.00 | 57.83 | B | N |
| ATOM | 2356 | CA | VAL | B | 52 | 18.273 | −8.128 | −8.380 | 1.00 | 60.96 | B | C |
| ATOM | 2357 | CB | VAL | B | 52 | 17.731 | −9.584 | −8.402 | 1.00 | 63.12 | B | C |
| ATOM | 2358 | CG1 | VAL | B | 52 | 16.199 | −9.652 | −8.490 | 1.00 | 64.76 | B | C |
| ATOM | 2359 | CG2 | VAL | B | 52 | 18.361 | −10.329 | −9.563 | 1.00 | 67.99 | B | C |
| ATOM | 2360 | C | VAL | B | 52 | 17.724 | −7.407 | −7.139 | 1.00 | 53.92 | B | C |
| ATOM | 2361 | O | VAL | B | 52 | 18.227 | −7.626 | −6.039 | 1.00 | 55.61 | B | O |
| ATOM | 2362 | N | PRO | B | 53 | 16.650 | −6.616 | −7.303 | 1.00 | 47.32 | B | N |
| ATOM | 2363 | CA | PRO | B | 53 | 16.029 | −5.994 | −6.161 | 1.00 | 45.54 | B | C |
| ATOM | 2364 | CB | PRO | B | 53 | 14.705 | −5.460 | −6.731 | 1.00 | 44.88 | B | C |
| ATOM | 2365 | CG | PRO | B | 53 | 14.952 | −5.217 | −8.169 | 1.00 | 47.11 | B | C |
| ATOM | 2366 | CD | PRO | B | 53 | 16.038 | −6.171 | −8.580 | 1.00 | 48.47 | B | C |
| ATOM | 2367 | C | PRO | B | 53 | 15.763 | −6.999 | −5.034 | 1.00 | 52.06 | B | C |
| ATOM | 2368 | O | PRO | B | 53 | 15.450 | −8.173 | −5.284 | 1.00 | 52.21 | B | O |
| ATOM | 2369 | N | GLY | B | 54 | 15.861 | −6.529 | −3.802 | 1.00 | 46.96 | B | N |
| ATOM | 2370 | CA | GLY | B | 54 | 15.547 | −7.329 | −2.633 | 1.00 | 45.35 | B | C |
| ATOM | 2371 | C | GLY | B | 54 | 14.127 | −7.800 | −2.561 | 1.00 | 46.45 | B | C |
| ATOM | 2372 | O | GLY | B | 54 | 13.839 | −8.747 | −1.848 | 1.00 | 49.24 | B | O |
| ATOM | 2373 | N | SER | B | 55 | 13.213 | −7.138 | −3.252 | 1.00 | 54.75 | B | N |
| ATOM | 2374 | CA | SER | B | 55 | 11.817 | −7.581 | −3.223 | 1.00 | 59.17 | B | C |
| ATOM | 2375 | CB | SER | B | 55 | 10.899 | −6.446 | −3.625 | 1.00 | 53.97 | B | C |
| ATOM | 2376 | OG | SER | B | 55 | 11.421 | −5.894 | −4.804 | 1.00 | 55.70 | B | O |
| ATOM | 2377 | C | SER | B | 55 | 11.551 | −8.806 | −4.137 | 1.00 | 60.55 | B | C |
| ATOM | 2378 | O | SER | B | 55 | 10.540 | −9.454 | −3.964 | 1.00 | 63.05 | B | O |
| ATOM | 2379 | N | LYS | B | 56 | 12.423 | −9.097 | −5.104 | 1.00 | 63.46 | B | N |
| ATOM | 2380 | CA | LYS | B | 56 | 12.208 | −10.223 | −6.031 | 1.00 | 62.15 | B | C |
| ATOM | 2381 | CB | LYS | B | 56 | 13.063 | −10.093 | −7.304 | 1.00 | 61.08 | B | C |
| ATOM | 2382 | CG | LYS | B | 56 | 12.839 | −8.871 | −8.191 | 1.00 | 58.71 | B | C |
| ATOM | 2383 | CD | LYS | B | 56 | 11.373 | −8.483 | −8.322 | 1.00 | 65.73 | B | C |
| ATOM | 2384 | CE | LYS | B | 56 | 11.160 | −7.268 | −9.235 | 1.00 | 66.74 | B | C |
| ATOM | 2385 | NZ | LYS | B | 56 | 11.564 | −7.494 | −10.661 | 1.00 | 64.26 | B | N |
| ATOM | 2386 | C | LYS | B | 56 | 12.584 | −11.532 | −5.366 | 1.00 | 62.37 | B | C |
| ATOM | 2387 | O | LYS | B | 56 | 13.362 | −11.545 | −4.422 | 1.00 | 68.21 | B | O |
| ATOM | 2388 | N | SER | B | 57 | 12.027 | −12.625 | −5.884 | 1.00 | 60.16 | B | N |
| ATOM | 2389 | CA | SER | B | 57 | 12.379 | −13.996 | −5.494 | 1.00 | 60.85 | B | C |
| ATOM | 2390 | CB | SER | B | 57 | 11.307 | −14.555 | −4.543 | 1.00 | 57.55 | B | C |
| ATOM | 2391 | OG | SER | B | 57 | 10.017 | −14.335 | −5.067 | 1.00 | 59.06 | B | O |
| ATOM | 2392 | C | SER | B | 57 | 12.621 | −14.942 | −6.705 | 1.00 | 63.20 | B | C |
| ATOM | 2393 | O | SER | B | 57 | 12.638 | −16.176 | −6.545 | 1.00 | 63.08 | B | O |
| ATOM | 2394 | N | THR | B | 58 | 12.850 | −14.359 | −7.889 | 1.00 | 58.10 | B | N |
| ATOM | 2395 | CA | THR | B | 58 | 13.112 | −15.088 | −9.136 | 1.00 | 58.61 | B | C |
| ATOM | 2396 | CB | THR | B | 58 | 11.804 | −15.456 | −9.902 | 1.00 | 64.92 | B | C |
| ATOM | 2397 | OG1 | THR | B | 58 | 11.257 | −14.285 | −10.534 | 1.00 | 75.79 | B | O |
| ATOM | 2398 | CG2 | THR | B | 58 | 10.733 | −16.059 | −8.994 | 1.00 | 67.24 | B | C |
| ATOM | 2399 | C | THR | B | 58 | 13.904 | −14.216 | −10.099 | 1.00 | 56.35 | B | C |
| ATOM | 2400 | O | THR | B | 58 | 13.852 | −13.008 | −9.998 | 1.00 | 58.66 | B | O |
| ATOM | 2401 | N | ALA | B | 59 | 14.556 | −14.823 | −11.079 | 1.00 | 60.08 | B | N |
| ATOM | 2402 | CA | ALA | B | 59 | 15.261 | −14.067 | −12.118 | 1.00 | 68.06 | B | C |
| ATOM | 2403 | CB | ALA | B | 59 | 16.570 | −13.522 | −11.553 | 1.00 | 68.36 | B | C |
| ATOM | 2404 | C | ALA | B | 59 | 15.564 | −14.882 | −13.377 | 1.00 | 63.64 | B | C |
| ATOM | 2405 | O | ALA | B | 59 | 15.745 | −16.091 | −13.314 | 1.00 | 57.99 | B | O |
| ATOM | 2406 | N | THR | B | 60 | 15.664 | −14.176 | −14.496 | 1.00 | 62.61 | B | N |
| ATOM | 2407 | CA | THR | B | 60 | 16.095 | −14.719 | −15.784 | 1.00 | 62.04 | B | C |
| ATOM | 2408 | CB | THR | B | 60 | 15.358 | −14.005 | −16.941 | 1.00 | 65.85 | B | C |
| ATOM | 2409 | OG1 | THR | B | 60 | 13.946 | −14.188 | −16.799 | 1.00 | 71.05 | B | O |
| ATOM | 2410 | CG2 | THR | B | 60 | 15.801 | −14.512 | −18.323 | 1.00 | 67.55 | B | C |
| ATOM | 2411 | C | THR | B | 60 | 17.592 | −14.461 | −15.905 | 1.00 | 63.58 | B | C |
| ATOM | 2412 | O | THR | B | 60 | 18.081 | −13.434 | −15.452 | 1.00 | 72.30 | B | O |
| ATOM | 2413 | N | ILE | B | 61 | 18.316 | −15.388 | −16.519 | 1.00 | 70.83 | B | N |
| ATOM | 2414 | CA | ILE | B | 61 | 19.765 | −15.283 | −16.671 | 1.00 | 69.80 | B | C |
| ATOM | 2415 | CB | ILE | B | 61 | 20.436 | −16.551 | −16.111 | 1.00 | 66.67 | B | C |
| ATOM | 2416 | CG1 | ILE | B | 61 | 20.526 | −16.403 | −14.585 | 1.00 | 64.00 | B | C |
| ATOM | 2417 | CD1 | ILE | B | 61 | 21.409 | −17.394 | −13.866 | 1.00 | 64.50 | B | C |
| ATOM | 2418 | CG2 | ILE | B | 61 | 21.804 | −16.808 | −16.737 | 1.00 | 72.51 | B | C |
| ATOM | 2419 | C | ILE | B | 61 | 20.250 | −14.847 | −18.085 | 1.00 | 83.61 | B | C |
| ATOM | 2420 | O | ILE | B | 61 | 21.044 | −13.902 | −18.180 | 1.00 | 97.26 | B | O |
| ATOM | 2421 | N | SER | B | 62 | 19.792 | −15.503 | −19.157 | 1.00 | 83.72 | B | N |
| ATOM | 2422 | CA | SER | B | 62 | 20.097 | −15.095 | −20.576 | 1.00 | 74.48 | B | C |
| ATOM | 2423 | CB | SER | B | 62 | 19.627 | −13.672 | −20.908 | 1.00 | 69.98 | B | C |
| ATOM | 2424 | OG | SER | B | 62 | 18.221 | −13.549 | −20.778 | 1.00 | 71.26 | B | O |
| ATOM | 2425 | C | SER | B | 62 | 21.553 | −15.251 | −21.032 | 1.00 | 73.03 | B | C |
| ATOM | 2426 | O | SER | B | 62 | 22.485 | −15.211 | −20.217 | 1.00 | 72.04 | B | O |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 2427 | N | GLY | B | 63 | 21.712 | −15.462 | −22.345 | 1.00 | 69.16 | B | N |
| ATOM | 2428 | CA | GLY | B | 63 | 23.012 | −15.494 | −23.030 | 1.00 | 70.97 | B | C |
| ATOM | 2429 | C | GLY | B | 63 | 24.033 | −16.558 | −22.642 | 1.00 | 76.73 | B | C |
| ATOM | 2430 | O | GLY | B | 63 | 25.239 | −16.322 | −22.785 | 1.00 | 78.30 | B | O |
| ATOM | 2431 | N | LEU | B | 64 | 23.576 | −17.737 | −22.211 | 1.00 | 73.64 | B | N |
| ATOM | 2432 | CA | LEU | B | 64 | 24.495 | −18.808 | −21.756 | 1.00 | 76.78 | B | C |
| ATOM | 2433 | CB | LEU | B | 64 | 23.836 | −19.736 | −20.728 | 1.00 | 80.26 | B | C |
| ATOM | 2434 | CG | LEU | B | 64 | 22.635 | −19.203 | −19.916 | 1.00 | 84.10 | B | C |
| ATOM | 2435 | CD1 | LEU | B | 64 | 21.314 | −19.701 | −20.478 | 1.00 | 86.43 | B | C |
| ATOM | 2436 | CD2 | LEU | B | 64 | 22.732 | −19.622 | −18.461 | 1.00 | 85.16 | B | C |
| ATOM | 2437 | C | LEU | B | 64 | 24.979 | −19.638 | −22.940 | 1.00 | 71.03 | B | C |
| ATOM | 2438 | O | LEU | B | 64 | 24.231 | −19.813 | −23.908 | 1.00 | 64.01 | B | O |
| ATOM | 2439 | N | THR | B | 71 | 28.369 | −22.833 | −10.839 | 1.00 | 83.13 | B | N |
| ATOM | 2440 | CA | THR | B | 71 | 27.668 | −22.483 | −12.055 | 1.00 | 83.32 | B | C |
| ATOM | 2441 | CB | THR | B | 71 | 26.800 | −23.654 | −12.634 | 1.00 | 83.31 | B | C |
| ATOM | 2442 | OG1 | THR | B | 71 | 27.246 | −24.899 | −12.092 | 1.00 | 86.85 | B | O |
| ATOM | 2443 | CG2 | THR | B | 71 | 26.831 | −23.711 | −14.219 | 1.00 | 70.65 | B | C |
| ATOM | 2444 | C | THR | B | 71 | 26.782 | −21.291 | −11.716 | 1.00 | 80.29 | B | C |
| ATOM | 2445 | O | THR | B | 71 | 26.900 | −20.276 | −12.398 | 1.00 | 74.38 | B | O |
| ATOM | 2446 | N | ILE | B | 72 | 25.903 | −21.426 | −10.695 | 1.00 | 73.15 | B | N |
| ATOM | 2447 | CA | ILE | B | 72 | 24.907 | −20.376 | −10.329 | 1.00 | 67.76 | B | C |
| ATOM | 2448 | CB | ILE | B | 72 | 23.480 | −20.683 | −10.837 | 1.00 | 74.48 | B | C |
| ATOM | 2449 | CG1 | ILE | B | 72 | 23.476 | −20.980 | −12.336 | 1.00 | 74.89 | B | C |
| ATOM | 2450 | CD1 | ILE | B | 72 | 22.136 | −21.487 | −12.833 | 1.00 | 74.04 | B | C |
| ATOM | 2451 | CG2 | ILE | B | 72 | 22.524 | −19.512 | −10.527 | 1.00 | 70.18 | B | C |
| ATOM | 2452 | C | ILE | B | 72 | 24.749 | −20.122 | −8.831 | 1.00 | 64.59 | B | C |
| ATOM | 2453 | O | ILE | B | 72 | 24.092 | −20.895 | −8.119 | 1.00 | 63.45 | B | O |
| ATOM | 2454 | N | THR | B | 73 | 25.276 | −18.994 | −8.379 | 1.00 | 62.78 | B | N |
| ATOM | 2455 | CA | THR | B | 73 | 25.270 | −18.651 | −6.953 | 1.00 | 68.60 | B | C |
| ATOM | 2456 | CB | THR | B | 73 | 26.667 | −18.231 | −6.519 | 1.00 | 72.25 | B | C |
| ATOM | 2457 | OG1 | THR | B | 73 | 27.627 | −18.899 | −7.350 | 1.00 | 81.08 | B | O |
| ATOM | 2458 | CG2 | THR | B | 73 | 26.878 | −18.579 | −5.041 | 1.00 | 78.39 | B | C |
| ATOM | 2459 | C | THR | B | 73 | 24.371 | −17.481 | −6.604 | 1.00 | 59.62 | B | C |
| ATOM | 2460 | O | THR | B | 73 | 24.384 | −16.477 | −7.314 | 1.00 | 60.98 | B | O |
| ATOM | 2461 | N | VAL | B | 74 | 23.633 | −17.596 | −5.494 | 1.00 | 60.94 | B | N |
| ATOM | 2462 | CA | VAL | B | 74 | 22.812 | −16.481 | −5.010 | 1.00 | 55.82 | B | C |
| ATOM | 2463 | CB | VAL | B | 74 | 21.333 | −16.814 | −5.151 | 1.00 | 53.50 | B | C |
| ATOM | 2464 | CG1 | VAL | B | 74 | 20.470 | −15.642 | −4.724 | 1.00 | 55.44 | B | C |
| ATOM | 2465 | CG2 | VAL | B | 74 | 21.016 | −17.133 | −6.606 | 1.00 | 56.12 | B | C |
| ATOM | 2466 | C | VAL | B | 74 | 23.162 | −15.955 | −3.581 | 1.00 | 58.45 | B | C |
| ATOM | 2467 | O | VAL | B | 74 | 23.092 | −16.685 | −2.573 | 1.00 | 59.85 | B | O |
| ATOM | 2468 | N | TYR | B | 75 | 23.504 | −14.666 | −3.528 | 1.00 | 52.37 | B | N |
| ATOM | 2469 | CA | TYR | B | 75 | 23.899 | −13.952 | −2.295 | 1.00 | 55.77 | B | C |
| ATOM | 2470 | CB | TYR | B | 75 | 25.170 | −13.083 | −2.507 | 1.00 | 60.21 | B | C |
| ATOM | 2471 | CG | TYR | B | 75 | 26.470 | −13.760 | −2.870 | 1.00 | 73.64 | B | C |
| ATOM | 2472 | CD1 | TYR | B | 75 | 26.516 | −14.806 | −3.802 | 1.00 | 85.20 | B | C |
| ATOM | 2473 | CE1 | TYR | B | 75 | 27.714 | −15.427 | −4.135 | 1.00 | 93.68 | B | C |
| ATOM | 2474 | CZ | TYR | B | 75 | 28.902 | −14.998 | −3.571 | 1.00 | 91.63 | B | C |
| ATOM | 2475 | OH | TYR | B | 75 | 30.049 | −15.658 | −3.959 | 1.00 | 80.12 | B | O |
| ATOM | 2476 | CE2 | TYR | B | 75 | 28.899 | −13.934 | −2.661 | 1.00 | 90.80 | B | C |
| ATOM | 2477 | CD2 | TYR | B | 75 | 27.689 | −13.313 | −2.327 | 1.00 | 83.66 | B | C |
| ATOM | 2478 | C | TYR | B | 75 | 22.795 | −12.951 | −1.934 | 1.00 | 48.83 | B | C |
| ATOM | 2479 | O | TYR | B | 75 | 22.386 | −12.135 | −2.765 | 1.00 | 52.63 | B | O |
| ATOM | 2480 | N | ALA | B | 76 | 22.344 | −12.972 | −0.698 | 1.00 | 43.76 | B | N |
| ATOM | 2481 | CA | ALA | B | 76 | 21.463 | −11.936 | −0.185 | 1.00 | 41.56 | B | C |
| ATOM | 2482 | CB | ALA | B | 76 | 20.471 | −12.520 | 0.734 | 1.00 | 40.71 | B | C |
| ATOM | 2483 | C | ALA | B | 76 | 22.311 | −10.911 | 0.577 | 1.00 | 46.41 | B | C |
| ATOM | 2484 | O | ALA | B | 76 | 23.191 | −11.273 | 1.363 | 1.00 | 44.73 | B | O |
| ATOM | 2485 | N | ILE | B | 77 | 22.048 | −9.639 | 0.343 | 1.00 | 46.76 | B | N |
| ATOM | 2486 | CA | ILE | B | 77 | 22.848 | −8.563 | 0.962 | 1.00 | 46.76 | B | C |
| ATOM | 2487 | CB | ILE | B | 77 | 23.356 | −7.616 | −0.130 | 1.00 | 53.01 | B | C |
| ATOM | 2488 | CG1 | ILE | B | 77 | 24.359 | −8.352 | −1.031 | 1.00 | 53.63 | B | C |
| ATOM | 2489 | CD1 | ILE | B | 77 | 25.734 | −8.563 | −0.423 | 1.00 | 55.14 | B | C |
| ATOM | 2490 | CG2 | ILE | B | 77 | 23.973 | −6.349 | 0.461 | 1.00 | 57.39 | B | C |
| ATOM | 2491 | C | ILE | B | 77 | 22.003 | −7.820 | 1.993 | 1.00 | 42.13 | B | C |
| ATOM | 2492 | O | ILE | B | 77 | 20.924 | −7.289 | 1.673 | 1.00 | 42.05 | B | O |
| ATOM | 2493 | N | ASP | B | 78 | 22.463 | −7.853 | 3.233 | 1.00 | 38.65 | B | N |
| ATOM | 2494 | CA | ASP | B | 78 | 21.889 | −7.062 | 4.331 | 1.00 | 42.98 | B | C |
| ATOM | 2495 | CB | ASP | B | 78 | 22.249 | −7.689 | 5.670 | 1.00 | 43.15 | B | C |
| ATOM | 2496 | CG | ASP | B | 78 | 21.701 | −6.904 | 6.825 | 1.00 | 42.58 | B | C |
| ATOM | 2497 | OD1 | ASP | B | 78 | 20.471 | −6.843 | 6.933 | 1.00 | 47.50 | B | O |
| ATOM | 2498 | OD2 | ASP | B | 78 | 22.491 | −6.302 | 7.567 | 1.00 | 40.87 | B | O |
| ATOM | 2499 | C | ASP | B | 78 | 22.438 | −5.624 | 4.375 | 1.00 | 41.36 | B | C |
| ATOM | 2500 | O | ASP | B | 78 | 23.660 | −5.424 | 4.224 | 1.00 | 33.35 | B | O |
| ATOM | 2501 | N | PHE | B | 79 | 21.561 | −4.663 | 4.694 | 1.00 | 43.22 | B | N |
| ATOM | 2502 | CA | PHE | B | 79 | 21.966 | −3.246 | 4.847 | 1.00 | 42.47 | B | C |
| ATOM | 2503 | CB | PHE | B | 79 | 20.835 | −2.362 | 5.396 | 1.00 | 44.10 | B | C |
| ATOM | 2504 | CG | PHE | B | 79 | 21.165 | −0.884 | 5.350 | 1.00 | 43.14 | B | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 2505 | CD1 | PHE | B | 79 | 21.649 | −0.222 | 6.487 | 1.00 | 40.90 | B | C |
| ATOM | 2506 | CE1 | PHE | B | 79 | 21.986 | 1.125 | 6.437 | 1.00 | 42.22 | B | C |
| ATOM | 2507 | CZ | PHE | B | 79 | 21.826 | 1.826 | 5.243 | 1.00 | 42.39 | B | C |
| ATOM | 2508 | CE2 | PHE | B | 79 | 21.350 | 1.181 | 4.105 | 1.00 | 42.18 | B | C |
| ATOM | 2509 | CD2 | PHE | B | 79 | 21.023 | −0.163 | 4.166 | 1.00 | 39.06 | B | C |
| ATOM | 2510 | C | PHE | B | 79 | 23.219 | −3.025 | 5.683 | 1.00 | 40.85 | B | C |
| ATOM | 2511 | O | PHE | B | 79 | 24.149 | −2.388 | 5.213 | 1.00 | 34.28 | B | O |
| ATOM | 2512 | N | TYR | B | 80 | 23.249 | −3.567 | 6.902 | 1.00 | 41.48 | B | N |
| ATOM | 2513 | CA | TYR | B | 80 | 24.337 | −3.280 | 7.852 | 1.00 | 38.66 | B | C |
| ATOM | 2514 | CB | TYR | B | 80 | 23.825 | −3.290 | 9.283 | 1.00 | 43.13 | B | C |
| ATOM | 2515 | CG | TYR | B | 80 | 22.880 | −2.109 | 9.609 | 1.00 | 43.75 | B | C |
| ATOM | 2516 | CD1 | TYR | B | 80 | 23.395 | −0.811 | 9.834 | 1.00 | 47.85 | B | C |
| ATOM | 2517 | CE1 | TYR | B | 80 | 22.554 | 0.264 | 10.127 | 1.00 | 47.00 | B | C |
| ATOM | 2518 | CZ | TYR | B | 80 | 21.190 | 0.066 | 10.177 | 1.00 | 48.45 | B | C |
| ATOM | 2519 | OH | TYR | B | 80 | 20.349 | 1.141 | 10.448 | 1.00 | 49.32 | B | O |
| ATOM | 2520 | CE2 | TYR | B | 80 | 20.656 | −1.213 | 9.959 | 1.00 | 49.57 | B | C |
| ATOM | 2521 | CD2 | TYR | B | 80 | 21.507 | −2.292 | 9.689 | 1.00 | 45.07 | B | C |
| ATOM | 2522 | C | TYR | B | 80 | 25.462 | −4.242 | 7.751 | 1.00 | 43.13 | B | C |
| ATOM | 2523 | O | TYR | B | 80 | 26.620 | −3.823 | 7.784 | 1.00 | 38.52 | B | O |
| ATOM | 2524 | N | TRP | B | 81 | 25.137 | −5.536 | 7.633 | 1.00 | 42.82 | B | N |
| ATOM | 2525 | CA | TRP | B | 81 | 26.110 | −6.602 | 7.830 | 1.00 | 42.82 | B | C |
| ATOM | 2526 | CB | TRP | B | 81 | 25.511 | −7.672 | 8.778 | 1.00 | 46.52 | B | C |
| ATOM | 2527 | CG | TRP | B | 81 | 24.982 | −7.010 | 10.050 | 1.00 | 41.81 | B | C |
| ATOM | 2528 | CD1 | TRP | B | 81 | 23.689 | −6.761 | 10.363 | 1.00 | 40.26 | B | C |
| ATOM | 2529 | NE1 | TRP | B | 81 | 23.612 | −6.116 | 11.563 | 1.00 | 42.06 | B | N |
| ATOM | 2530 | CE2 | TRP | B | 81 | 24.882 | −5.934 | 12.049 | 1.00 | 40.81 | B | C |
| ATOM | 2531 | CD2 | TRP | B | 81 | 25.766 | −6.505 | 11.125 | 1.00 | 39.01 | B | C |
| ATOM | 2532 | CE3 | TRP | B | 81 | 27.148 | −6.462 | 11.386 | 1.00 | 45.44 | B | C |
| ATOM | 2533 | CZ3 | TRP | B | 81 | 27.590 | −5.857 | 12.594 | 1.00 | 43.73 | B | C |
| ATOM | 2534 | CH2 | TRP | B | 81 | 26.671 | −5.300 | 13.485 | 1.00 | 39.19 | B | C |
| ATOM | 2535 | CZ2 | TRP | B | 81 | 25.325 | −5.297 | 13.224 | 1.00 | 39.33 | B | C |
| ATOM | 2536 | C | TRP | B | 81 | 26.634 | −7.215 | 6.520 | 1.00 | 45.92 | B | C |
| ATOM | 2537 | O | TRP | B | 81 | 27.431 | −8.122 | 6.571 | 1.00 | 44.98 | B | O |
| ATOM | 2538 | N | GLY | B | 82 | 26.245 | −6.688 | 5.356 | 1.00 | 47.24 | B | N |
| ATOM | 2539 | CA | GLY | B | 82 | 26.722 | −7.252 | 4.085 | 1.00 | 52.04 | B | C |
| ATOM | 2540 | C | GLY | B | 82 | 26.082 | −8.595 | 3.752 | 1.00 | 49.07 | B | C |
| ATOM | 2541 | O | GLY | B | 82 | 24.926 | −8.873 | 4.122 | 1.00 | 48.76 | B | O |
| ATOM | 2542 | N | SER | B | 83 | 26.832 | −9.434 | 3.059 | 1.00 | 51.01 | B | N |
| ATOM | 2543 | CA | SER | B | 83 | 26.292 | −10.716 | 2.558 | 1.00 | 51.71 | B | C |
| ATOM | 2544 | CB | SER | B | 83 | 27.222 | −11.304 | 1.526 | 1.00 | 50.61 | B | C |
| ATOM | 2545 | OG | SER | B | 83 | 28.517 | −11.326 | 2.040 | 1.00 | 51.70 | B | O |
| ATOM | 2546 | C | SER | B | 83 | 26.061 | −11.769 | 3.618 | 1.00 | 51.36 | B | C |
| ATOM | 2547 | O | SER | B | 83 | 26.850 | −11.936 | 4.541 | 1.00 | 50.51 | B | O |
| ATOM | 2548 | N | TYR | B | 84 | 24.962 | −12.490 | 3.461 | 1.00 | 58.09 | B | N |
| ATOM | 2549 | CA | TYR | B | 84 | 24.743 | −13.753 | 4.174 | 1.00 | 53.88 | B | C |
| ATOM | 2550 | CB | TYR | B | 84 | 23.298 | −14.167 | 4.046 | 1.00 | 50.46 | B | C |
| ATOM | 2551 | CG | TYR | B | 84 | 22.339 | −13.257 | 4.779 | 1.00 | 50.64 | B | C |
| ATOM | 2552 | CD1 | TYR | B | 84 | 21.925 | −13.553 | 6.059 | 1.00 | 50.23 | B | C |
| ATOM | 2553 | CE1 | TYR | B | 84 | 21.034 | −12.736 | 6.746 | 1.00 | 48.04 | B | C |
| ATOM | 2554 | CZ | TYR | B | 84 | 20.542 | −11.614 | 6.153 | 1.00 | 45.70 | B | C |
| ATOM | 2555 | OH | TYR | B | 84 | 19.665 | −10.847 | 6.873 | 1.00 | 52.66 | B | O |
| ATOM | 2556 | CE2 | TYR | B | 84 | 20.920 | −11.285 | 4.871 | 1.00 | 50.90 | B | C |
| ATOM | 2557 | CD2 | TYR | B | 84 | 21.825 | −12.104 | 4.188 | 1.00 | 57.44 | B | C |
| ATOM | 2558 | C | TYR | B | 84 | 25.634 | −14.845 | 3.583 | 1.00 | 51.72 | B | C |
| ATOM | 2559 | O | TYR | B | 84 | 26.255 | −14.661 | 2.516 | 1.00 | 49.89 | B | O |
| ATOM | 2560 | N | SER | B | 85 | 25.734 | −15.979 | 4.277 | 1.00 | 69.02 | B | N |
| ATOM | 2561 | CA | SER | B | 85 | 26.395 | −17.163 | 3.679 | 1.00 | 67.55 | B | C |
| ATOM | 2562 | CB | SER | B | 85 | 26.552 | −18.319 | 4.693 | 1.00 | 70.41 | B | C |
| ATOM | 2563 | OG | SER | B | 85 | 25.326 | −18.979 | 4.953 | 1.00 | 71.39 | B | O |
| ATOM | 2564 | C | SER | B | 85 | 25.547 | −17.528 | 2.420 | 1.00 | 61.23 | B | C |
| ATOM | 2565 | O | SER | B | 85 | 24.286 | −17.532 | 2.487 | 1.00 | 54.20 | B | O |
| ATOM | 2566 | N | PRO | B | 86 | 26.219 | −17.713 | 1.262 | 1.00 | 56.25 | B | N |
| ATOM | 2567 | CA | PRO | B | 86 | 25.487 | −17.876 | 0.007 | 1.00 | 59.88 | B | C |
| ATOM | 2568 | CB | PRO | B | 86 | 26.535 | −17.497 | −1.041 | 1.00 | 56.16 | B | C |
| ATOM | 2569 | CG | PRO | B | 86 | 27.831 | −17.945 | −0.430 | 1.00 | 55.07 | B | C |
| ATOM | 2570 | CD | PRO | B | 86 | 27.681 | −17.856 | 1.060 | 1.00 | 54.15 | B | C |
| ATOM | 2571 | C | PRO | B | 86 | 24.949 | −19.311 | −0.240 | 1.00 | 67.34 | B | C |
| ATOM | 2572 | O | PRO | B | 86 | 25.161 | −20.245 | 0.551 | 1.00 | 61.93 | B | O |
| ATOM | 2573 | N | ILE | B | 87 | 24.226 | −19.444 | −1.339 | 1.00 | 73.03 | B | N |
| ATOM | 2574 | CA | ILE | B | 87 | 23.679 | −20.713 | −1.782 | 1.00 | 73.97 | B | C |
| ATOM | 2575 | CB | ILE | B | 87 | 22.148 | −20.745 | −1.656 | 1.00 | 70.83 | B | C |
| ATOM | 2576 | CG1 | ILE | B | 87 | 21.638 | −22.181 | −1.900 | 1.00 | 71.07 | B | C |
| ATOM | 2577 | CD1 | ILE | B | 87 | 20.202 | −22.382 | −1.475 | 1.00 | 68.00 | B | C |
| ATOM | 2578 | CG2 | ILE | B | 87 | 21.473 | −19.760 | −2.609 | 1.00 | 63.85 | B | C |
| ATOM | 2579 | C | ILE | B | 87 | 24.097 | −20.952 | −3.226 | 1.00 | 77.02 | B | C |
| ATOM | 2580 | O | ILE | B | 87 | 24.126 | −20.010 | −4.038 | 1.00 | 83.24 | B | O |
| ATOM | 2581 | N | SER | B | 88 | 24.417 | −22.204 | −3.547 | 1.00 | 75.60 | B | N |
| ATOM | 2582 | CA | SER | B | 88 | 24.802 | −22.539 | −4.916 | 1.00 | 76.51 | B | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 2583 | CB | SER | B | 88 | 26.314 | −22.772 | −5.001 | 1.00 | 71.28 | B | C |
| ATOM | 2584 | OG | SER | B | 88 | 26.863 | −21.889 | −5.972 | 1.00 | 69.69 | B | O |
| ATOM | 2585 | C | SER | B | 88 | 24.004 | −23.729 | −5.451 | 1.00 | 72.61 | B | C |
| ATOM | 2586 | O | SER | B | 88 | 23.427 | −24.508 | −4.662 | 1.00 | 58.53 | B | O |
| ATOM | 2587 | N | ILE | B | 89 | 23.936 | −23.803 | −6.788 | 1.00 | 72.35 | B | N |
| ATOM | 2588 | CA | ILE | B | 89 | 23.479 | −24.995 | −7.544 | 1.00 | 66.00 | B | C |
| ATOM | 2589 | CB | ILE | B | 89 | 21.928 | −25.076 | −7.724 | 1.00 | 63.87 | B | C |
| ATOM | 2590 | CG1 | ILE | B | 89 | 21.411 | −23.919 | −8.601 | 1.00 | 65.55 | B | C |
| ATOM | 2591 | CD1 | ILE | B | 89 | 19.976 | −24.084 | −9.006 | 1.00 | 66.99 | B | C |
| ATOM | 2592 | CG2 | ILE | B | 89 | 21.178 | −25.201 | −6.405 | 1.00 | 60.54 | B | C |
| ATOM | 2593 | C | ILE | B | 89 | 24.071 | −25.019 | −8.962 | 1.00 | 72.32 | B | C |
| ATOM | 2594 | O | ILE | B | 89 | 24.761 | −24.068 | −9.405 | 1.00 | 67.51 | B | O |
| ATOM | 2595 | N | ASN | B | 90 | 23.752 | −26.124 | −9.665 | 1.00 | 85.64 | B | N |
| ATOM | 2596 | CA | ASN | B | 90 | 24.022 | −26.348 | −11.099 | 1.00 | 80.19 | B | C |
| ATOM | 2597 | CB | ASN | B | 90 | 25.292 | −27.189 | −11.258 | 1.00 | 82.70 | B | C |
| ATOM | 2598 | CG | ASN | B | 90 | 26.123 | −27.246 | −9.971 | 1.00 | 79.86 | B | C |
| ATOM | 2599 | OD1 | ASN | B | 90 | 25.962 | −28.162 | −9.167 | 1.00 | 81.90 | B | O |
| ATOM | 2600 | ND2 | ASN | B | 90 | 26.960 | −26.237 | −9.742 | 1.00 | 74.12 | B | N |
| ATOM | 2601 | C | ASN | B | 90 | 22.837 | −27.079 | −11.768 | 1.00 | 70.53 | B | C |
| ATOM | 2602 | O | ASN | B | 90 | 22.555 | −26.880 | −12.954 | 1.00 | 60.34 | B | O |
| TER | 2603 | | ASN | B | 90 | | | | | | | |
| HETATM | 2604 | O26 | 627 | C | 1 | 31.698 | −9.513 | 25.053 | 1.00 | 45.93 | C | O |
| HETATM | 2605 | C25 | 627 | C | 1 | 31.743 | −10.182 | 26.054 | 1.00 | 52.46 | C | C |
| HETATM | 2606 | C20 | 627 | C | 1 | 30.644 | −9.951 | 27.053 | 1.00 | 60.17 | C | C |
| HETATM | 2607 | O34 | 627 | C | 1 | 29.605 | −9.115 | 26.504 | 1.00 | 57.33 | C | O |
| HETATM | 2608 | C36 | 627 | C | 1 | 28.305 | −9.487 | 26.944 | 1.00 | 60.87 | C | C |
| HETATM | 2609 | C27 | 627 | C | 1 | 31.193 | −9.235 | 28.216 | 1.00 | 61.17 | C | C |
| HETATM | 2610 | C29 | 627 | C | 1 | 31.965 | −8.077 | 28.052 | 1.00 | 59.67 | C | C |
| HETATM | 2611 | C33 | 627 | C | 1 | 32.458 | −7.414 | 29.169 | 1.00 | 66.40 | C | C |
| HETATM | 2612 | C35 | 627 | C | 1 | 32.182 | −7.906 | 30.449 | 1.00 | 66.06 | C | C |
| HETATM | 2613 | C31 | 627 | C | 1 | 31.403 | −9.056 | 30.601 | 1.00 | 60.13 | C | C |
| HETATM | 2614 | C28 | 627 | C | 1 | 30.900 | −9.719 | 29.489 | 1.00 | 59.22 | C | C |
| HETATM | 2615 | N1 | 627 | C | 1 | 32.827 | −10.993 | 26.267 | 1.00 | 48.87 | C | N |
| HETATM | 2616 | C16 | 627 | C | 1 | 33.915 | −10.955 | 25.442 | 1.00 | 47.58 | C | C |
| HETATM | 2617 | C13 | 627 | C | 1 | 34.815 | −11.848 | 26.003 | 1.00 | 48.74 | C | C |
| HETATM | 2618 | N2 | 627 | C | 1 | 36.115 | −12.325 | 25.739 | 1.00 | 44.57 | C | N |
| HETATM | 2619 | C15 | 627 | C | 1 | 33.009 | −11.800 | 27.347 | 1.00 | 49.51 | C | C |
| HETATM | 2620 | C14 | 627 | C | 1 | 34.298 | −12.321 | 27.134 | 1.00 | 49.40 | C | C |
| HETATM | 2621 | C3 | 627 | C | 1 | 35.347 | −13.233 | 27.671 | 1.00 | 52.22 | C | C |
| HETATM | 2622 | N4 | 627 | C | 1 | 36.433 | −13.200 | 26.837 | 1.00 | 51.07 | C | N |
| HETATM | 2623 | N5 | 627 | C | 1 | 35.369 | −13.978 | 28.812 | 1.00 | 55.39 | C | N |
| HETATM | 2624 | C6 | 627 | C | 1 | 34.346 | −14.198 | 29.669 | 1.00 | 56.49 | C | C |
| HETATM | 2625 | O8 | 627 | C | 1 | 33.178 | −13.922 | 29.435 | 1.00 | 47.86 | C | O |
| HETATM | 2626 | C7 | 627 | C | 1 | 34.577 | −15.028 | 30.892 | 1.00 | 55.95 | C | C |
| HETATM | 2627 | C12 | 627 | C | 1 | 33.630 | −15.085 | 31.920 | 1.00 | 56.23 | C | C |
| HETATM | 2628 | C11 | 627 | C | 1 | 33.867 | −15.873 | 33.051 | 1.00 | 59.90 | C | C |
| HETATM | 2629 | C24 | 627 | C | 1 | 35.045 | −16.638 | 33.193 | 1.00 | 60.77 | C | C |
| HETATM | 2630 | C10 | 627 | C | 1 | 35.961 | −16.550 | 32.124 | 1.00 | 64.78 | C | C |
| HETATM | 2631 | C9 | 627 | C | 1 | 35.745 | −15.766 | 31.000 | 1.00 | 60.97 | C | C |
| HETATM | 2632 | N17 | 627 | C | 1 | 35.322 | −17.450 | 34.363 | 1.00 | 66.42 | C | N |
| HETATM | 2633 | C22 | 627 | C | 1 | 36.796 | −17.614 | 34.582 | 1.00 | 63.40 | C | C |
| HETATM | 2634 | C21 | 627 | C | 1 | 37.201 | −18.352 | 35.848 | 1.00 | 67.04 | C | C |
| HETATM | 2635 | N20 | 627 | C | 1 | 36.607 | −17.746 | 37.043 | 1.00 | 71.96 | C | N |
| HETATM | 2636 | C23 | 627 | C | 1 | 36.920 | −18.638 | 38.177 | 1.00 | 75.44 | C | C |
| HETATM | 2637 | C19 | 627 | C | 1 | 35.144 | −17.555 | 36.924 | 1.00 | 70.78 | C | C |
| HETATM | 2638 | C18 | 627 | C | 1 | 34.677 | −16.911 | 35.602 | 1.00 | 69.22 | C | C |
| TER | 2639 | | 627 | C | 1 | | | | | | | |
| ATOM | 2640 | N | TRP | D | 128 | 2.993 | 21.503 | 37.295 | 1.00 | 59.58 | D | N |
| ATOM | 2641 | CA | TRP | D | 128 | 2.009 | 20.875 | 36.318 | 1.00 | 56.93 | D | C |
| ATOM | 2642 | CB | TRP | D | 128 | 2.495 | 20.952 | 34.867 | 1.00 | 58.57 | D | C |
| ATOM | 2643 | CG | TRP | D | 128 | 2.482 | 22.255 | 34.152 | 1.00 | 63.61 | D | C |
| ATOM | 2644 | CD1 | TRP | D | 128 | 3.502 | 22.773 | 33.405 | 1.00 | 61.43 | D | C |
| ATOM | 2645 | NE1 | TRP | D | 128 | 3.128 | 23.970 | 32.861 | 1.00 | 64.87 | D | N |
| ATOM | 2646 | CE2 | TRP | D | 128 | 1.842 | 24.247 | 33.238 | 1.00 | 67.57 | D | C |
| ATOM | 2647 | CD2 | TRP | D | 128 | 1.397 | 23.181 | 34.049 | 1.00 | 58.44 | D | C |
| ATOM | 2648 | CE3 | TRP | D | 128 | 0.115 | 23.232 | 34.591 | 1.00 | 60.61 | D | C |
| ATOM | 2649 | CZ3 | TRP | D | 128 | −0.676 | 24.305 | 34.304 | 1.00 | 66.60 | D | C |
| ATOM | 2650 | CH2 | TRP | D | 128 | −0.212 | 25.359 | 33.488 | 1.00 | 73.31 | D | C |
| ATOM | 2651 | CZ2 | TRP | D | 128 | 1.045 | 25.351 | 32.952 | 1.00 | 67.78 | D | C |
| ATOM | 2652 | C | TRP | D | 128 | 1.852 | 19.390 | 36.577 | 1.00 | 49.70 | D | C |
| ATOM | 2653 | O | TRP | D | 128 | 2.851 | 18.690 | 36.704 | 1.00 | 41.90 | D | O |
| ATOM | 2654 | N | ALA | D | 129 | 0.626 | 18.888 | 36.591 | 1.00 | 46.08 | D | N |
| ATOM | 2655 | CA | ALA | D | 129 | 0.383 | 17.433 | 36.787 | 1.00 | 43.93 | D | C |
| ATOM | 2656 | CB | ALA | D | 129 | −0.068 | 17.159 | 38.195 | 1.00 | 42.40 | D | C |
| ATOM | 2657 | C | ALA | D | 129 | −0.680 | 16.986 | 35.821 | 1.00 | 41.16 | D | C |
| ATOM | 2658 | O | ALA | D | 129 | −1.334 | 17.841 | 35.234 | 1.00 | 42.12 | D | O |
| ATOM | 2659 | N | LEU | D | 130 | −0.854 | 15.671 | 35.665 | 1.00 | 40.07 | D | N |
| ATOM | 2660 | CA | LEU | D | 130 | −1.833 | 15.087 | 34.735 | 1.00 | 50.40 | D | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 2661 | CB | LEU | D | 130 | −2.075 | 13.620 | 35.047 | 1.00 | 51.05 | D | C |
| ATOM | 2662 | CG | LEU | D | 130 | −3.196 | 12.913 | 34.262 | 1.00 | 57.82 | D | C |
| ATOM | 2663 | CD1 | LEU | D | 130 | −2.805 | 11.442 | 34.153 | 1.00 | 55.54 | D | C |
| ATOM | 2664 | CD2 | LEU | D | 130 | −4.639 | 13.088 | 34.851 | 1.00 | 57.44 | D | C |
| ATOM | 2665 | C | LEU | D | 130 | −3.173 | 15.800 | 34.809 | 1.00 | 55.71 | D | C |
| ATOM | 2666 | O | LEU | D | 130 | −3.765 | 16.211 | 33.794 | 1.00 | 54.12 | D | O |
| ATOM | 2667 | N | GLU | D | 131 | −3.635 | 15.977 | 36.036 | 1.00 | 53.38 | D | N |
| ATOM | 2668 | CA | GLU | D | 131 | −4.988 | 16.441 | 36.253 | 1.00 | 50.30 | D | C |
| ATOM | 2669 | CB | GLU | D | 131 | −5.342 | 16.308 | 37.744 | 1.00 | 53.22 | D | C |
| ATOM | 2670 | CG | GLU | D | 131 | −4.676 | 17.379 | 38.601 | 1.00 | 56.12 | D | C |
| ATOM | 2671 | CD | GLU | D | 131 | −4.951 | 17.237 | 40.068 | 1.00 | 59.63 | D | C |
| ATOM | 2672 | OE1 | GLU | D | 131 | −6.149 | 17.136 | 40.454 | 1.00 | 70.80 | D | O |
| ATOM | 2673 | OE2 | GLU | D | 131 | −3.953 | 17.253 | 40.827 | 1.00 | 61.66 | D | O |
| ATOM | 2674 | C | GLU | D | 131 | −5.222 | 17.866 | 35.746 | 1.00 | 44.73 | D | C |
| ATOM | 2675 | O | GLU | D | 131 | −6.357 | 18.322 | 35.740 | 1.00 | 46.01 | D | O |
| ATOM | 2676 | N | ASP | D | 132 | −4.180 | 18.580 | 35.332 | 1.00 | 43.13 | D | N |
| ATOM | 2677 | CA | ASP | D | 132 | −4.347 | 19.928 | 34.792 | 1.00 | 46.08 | D | C |
| ATOM | 2678 | CB | ASP | D | 132 | −3.057 | 20.720 | 34.964 | 1.00 | 50.67 | D | C |
| ATOM | 2679 | CG | ASP | D | 132 | −2.641 | 20.866 | 36.439 | 1.00 | 62.80 | D | C |
| ATOM | 2680 | OD1 | ASP | D | 132 | −3.277 | 21.664 | 37.171 | 1.00 | 72.75 | D | O |
| ATOM | 2681 | OD2 | ASP | D | 132 | −1.663 | 20.201 | 36.862 | 1.00 | 56.96 | D | O |
| ATOM | 2682 | C | ASP | D | 132 | −4.781 | 19.981 | 33.310 | 1.00 | 43.08 | D | C |
| ATOM | 2683 | O | ASP | D | 132 | −5.054 | 21.062 | 32.798 | 1.00 | 49.05 | D | O |
| ATOM | 2684 | N | PHE | D | 133 | −4.858 | 18.825 | 32.652 | 1.00 | 38.24 | D | N |
| ATOM | 2685 | CA | PHE | D | 133 | −5.001 | 18.739 | 31.215 | 1.00 | 43.09 | D | C |
| ATOM | 2686 | CB | PHE | D | 133 | −3.711 | 18.199 | 30.558 | 1.00 | 41.26 | D | C |
| ATOM | 2687 | CG | PHE | D | 133 | −2.501 | 19.013 | 30.920 | 1.00 | 40.86 | D | C |
| ATOM | 2688 | CD1 | PHE | D | 133 | −2.348 | 20.307 | 30.429 | 1.00 | 39.51 | D | C |
| ATOM | 2689 | CE1 | PHE | D | 133 | −1.256 | 21.094 | 30.818 | 1.00 | 39.56 | D | C |
| ATOM | 2690 | CZ | PHE | D | 133 | −0.338 | 20.604 | 31.719 | 1.00 | 41.96 | D | C |
| ATOM | 2691 | CE2 | PHE | D | 133 | −0.488 | 19.302 | 32.229 | 1.00 | 41.39 | D | C |
| ATOM | 2692 | CD2 | PHE | D | 133 | −1.582 | 18.530 | 31.853 | 1.00 | 40.75 | D | C |
| ATOM | 2693 | C | PHE | D | 133 | −6.163 | 17.861 | 30.801 | 1.00 | 43.86 | D | C |
| ATOM | 2694 | O | PHE | D | 133 | −6.304 | 16.746 | 31.250 | 1.00 | 44.31 | D | O |
| ATOM | 2695 | N | GLU | D | 134 | −6.982 | 18.415 | 29.930 | 1.00 | 45.50 | D | N |
| ATOM | 2696 | CA | GLU | D | 134 | −7.944 | 17.649 | 29.174 | 1.00 | 50.12 | D | C |
| ATOM | 2697 | CB | GLU | D | 134 | −9.080 | 18.615 | 28.807 | 1.00 | 56.62 | D | C |
| ATOM | 2698 | CG | GLU | D | 134 | −10.304 | 17.937 | 28.234 | 1.00 | 66.41 | D | C |
| ATOM | 2699 | CD | GLU | D | 134 | −11.455 | 18.900 | 28.055 | 1.00 | 75.64 | D | C |
| ATOM | 2700 | OE1 | GLU | D | 134 | −11.184 | 20.131 | 27.910 | 1.00 | 67.98 | D | O |
| ATOM | 2701 | OE2 | GLU | D | 134 | −12.613 | 18.405 | 28.066 | 1.00 | 75.52 | D | O |
| ATOM | 2702 | C | GLU | D | 134 | −7.297 | 17.067 | 27.908 | 1.00 | 45.84 | D | C |
| ATOM | 2703 | O | GLU | D | 134 | −6.852 | 17.809 | 27.035 | 1.00 | 43.81 | D | O |
| ATOM | 2704 | N | ILE | D | 135 | −7.281 | 15.749 | 27.790 | 1.00 | 41.26 | D | N |
| ATOM | 2705 | CA | ILE | D | 135 | −6.647 | 15.072 | 26.666 | 1.00 | 48.74 | D | C |
| ATOM | 2706 | CB | ILE | D | 135 | −6.172 | 13.677 | 27.103 | 1.00 | 50.73 | D | C |
| ATOM | 2707 | CG1 | ILE | D | 135 | −5.165 | 13.806 | 28.236 | 1.00 | 53.36 | D | C |
| ATOM | 2708 | CD1 | ILE | D | 135 | −4.938 | 12.497 | 28.956 | 1.00 | 58.04 | D | C |
| ATOM | 2709 | CG2 | ILE | D | 135 | −5.551 | 12.899 | 25.949 | 1.00 | 54.23 | D | C |
| ATOM | 2710 | C | ILE | D | 135 | −7.551 | 14.961 | 25.410 | 1.00 | 54.38 | D | C |
| ATOM | 2711 | O | ILE | D | 135 | −8.501 | 14.184 | 25.382 | 1.00 | 60.30 | D | O |
| ATOM | 2712 | N | GLY | D | 136 | −7.201 | 15.690 | 24.347 | 1.00 | 50.10 | D | N |
| ATOM | 2713 | CA | GLY | D | 136 | −7.855 | 15.582 | 23.046 | 1.00 | 39.74 | D | C |
| ATOM | 2714 | C | GLY | D | 136 | −7.366 | 14.456 | 22.186 | 1.00 | 41.57 | D | C |
| ATOM | 2715 | O | GLY | D | 136 | −6.966 | 13.436 | 22.690 | 1.00 | 41.13 | D | O |
| ATOM | 2716 | N | ARG | D | 137 | −7.374 | 14.653 | 20.867 | 1.00 | 41.83 | D | N |
| ATOM | 2717 | CA | ARG | D | 137 | −7.139 | 13.541 | 19.907 | 1.00 | 42.09 | D | C |
| ATOM | 2718 | CB | ARG | D | 137 | −7.725 | 13.859 | 18.541 | 1.00 | 48.48 | D | C |
| ATOM | 2719 | CG | ARG | D | 137 | −7.383 | 15.244 | 18.048 | 1.00 | 49.34 | D | C |
| ATOM | 2720 | CD | ARG | D | 137 | −7.677 | 15.457 | 16.582 | 1.00 | 48.39 | D | C |
| ATOM | 2721 | NE | ARG | D | 137 | −7.198 | 16.822 | 16.302 | 1.00 | 51.30 | D | N |
| ATOM | 2722 | CZ | ARG | D | 137 | −6.046 | 17.115 | 15.699 | 1.00 | 44.14 | D | C |
| ATOM | 2723 | NH1 | ARG | D | 137 | −5.242 | 16.141 | 15.301 | 1.00 | 48.12 | D | N |
| ATOM | 2724 | NH2 | ARG | D | 137 | −5.675 | 18.383 | 15.534 | 1.00 | 40.74 | D | N |
| ATOM | 2725 | C | ARG | D | 137 | −5.660 | 13.274 | 19.733 | 1.00 | 41.08 | D | C |
| ATOM | 2726 | O | ARG | D | 137 | −4.846 | 14.140 | 20.041 | 1.00 | 38.77 | D | O |
| ATOM | 2727 | N | PRO | D | 138 | −5.314 | 12.068 | 19.299 | 1.00 | 43.00 | D | N |
| ATOM | 2728 | CA | PRO | D | 138 | −3.928 | 11.789 | 19.085 | 1.00 | 42.33 | D | C |
| ATOM | 2729 | CB | PRO | D | 138 | −3.901 | 10.282 | 18.738 | 1.00 | 43.52 | D | C |
| ATOM | 2730 | CG | PRO | D | 138 | −5.297 | 9.950 | 18.297 | 1.00 | 44.49 | D | C |
| ATOM | 2731 | CD | PRO | D | 138 | −6.157 | 10.860 | 19.116 | 1.00 | 44.24 | D | C |
| ATOM | 2732 | C | PRO | D | 138 | −3.420 | 12.651 | 17.916 | 1.00 | 47.70 | D | C |
| ATOM | 2733 | O | PRO | D | 138 | −4.122 | 12.850 | 16.938 | 1.00 | 47.42 | D | O |
| ATOM | 2734 | N | LEU | D | 139 | −2.215 | 13.192 | 18.063 | 1.00 | 44.33 | D | N |
| ATOM | 2735 | CA | LEU | D | 139 | −1.577 | 13.936 | 17.007 | 1.00 | 36.07 | D | C |
| ATOM | 2736 | CB | LEU | D | 139 | −0.742 | 15.076 | 17.599 | 1.00 | 35.57 | D | C |
| ATOM | 2737 | CG | LEU | D | 139 | −1.565 | 16.284 | 18.034 | 1.00 | 33.91 | D | C |
| ATOM | 2738 | CD1 | LEU | D | 139 | −0.689 | 17.332 | 18.693 | 1.00 | 39.37 | D | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 2739 | CD2 | LEU | D | 139 | −2.334 | 16.938 | 16.879 | 1.00 | 35.86 | D | C |
| ATOM | 2740 | C | LEU | D | 139 | −0.759 | 12.993 | 16.154 | 1.00 | 36.99 | D | C |
| ATOM | 2741 | O | LEU | D | 139 | −0.569 | 13.250 | 14.981 | 1.00 | 40.90 | D | O |
| ATOM | 2742 | N | GLY | D | 140 | −0.233 | 11.938 | 16.764 | 1.00 | 35.49 | D | N |
| ATOM | 2743 | CA | GLY | D | 140 | 0.484 | 10.888 | 16.092 | 1.00 | 37.14 | D | C |
| ATOM | 2744 | C | GLY | D | 140 | 0.970 | 9.924 | 17.162 | 1.00 | 40.98 | D | C |
| ATOM | 2745 | O | GLY | D | 140 | 0.566 | 10.013 | 18.307 | 1.00 | 48.93 | D | O |
| ATOM | 2746 | N | LYS | D | 141 | 1.806 | 8.979 | 16.786 | 1.00 | 42.61 | D | N |
| ATOM | 2747 | CA | LYS | D | 141 | 2.271 | 7.980 | 17.705 | 1.00 | 42.84 | D | C |
| ATOM | 2748 | CB | LYS | D | 141 | 1.659 | 6.604 | 17.405 | 1.00 | 49.76 | D | C |
| ATOM | 2749 | CG | LYS | D | 141 | 2.514 | 5.647 | 16.608 | 1.00 | 57.13 | D | C |
| ATOM | 2750 | CD | LYS | D | 141 | 1.823 | 4.325 | 16.353 | 1.00 | 66.40 | D | C |
| ATOM | 2751 | CE | LYS | D | 141 | 2.319 | 3.698 | 15.057 | 1.00 | 72.65 | D | C |
| ATOM | 2752 | NZ | LYS | D | 141 | 2.095 | 2.219 | 15.010 | 1.00 | 77.76 | D | N |
| ATOM | 2753 | C | LYS | D | 141 | 3.773 | 7.991 | 17.614 | 1.00 | 45.52 | D | C |
| ATOM | 2754 | O | LYS | D | 141 | 4.315 | 8.038 | 16.517 | 1.00 | 45.38 | D | O |
| ATOM | 2755 | N | GLY | D | 142 | 4.415 | 7.963 | 18.779 | 1.00 | 40.94 | D | N |
| ATOM | 2756 | CA | GLY | D | 142 | 5.870 | 7.834 | 18.940 | 1.00 | 43.39 | D | C |
| ATOM | 2757 | C | GLY | D | 142 | 6.258 | 6.386 | 19.024 | 1.00 | 44.31 | D | C |
| ATOM | 2758 | O | GLY | D | 142 | 5.398 | 5.505 | 18.986 | 1.00 | 47.90 | D | O |
| ATOM | 2759 | N | LYS | D | 143 | 7.552 | 6.107 | 19.094 | 1.00 | 42.35 | D | N |
| ATOM | 2760 | CA | LYS | D | 143 | 7.968 | 4.750 | 19.321 | 1.00 | 45.23 | D | C |
| ATOM | 2761 | CB | LYS | D | 143 | 9.490 | 4.601 | 19.310 | 1.00 | 51.08 | D | C |
| ATOM | 2762 | CG | LYS | D | 143 | 9.928 | 3.138 | 19.345 | 1.00 | 55.05 | D | C |
| ATOM | 2763 | CD | LYS | D | 143 | 11.427 | 3.029 | 19.142 | 1.00 | 60.45 | D | C |
| ATOM | 2764 | CE | LYS | D | 143 | 11.975 | 1.691 | 19.621 | 1.00 | 62.36 | D | C |
| ATOM | 2765 | NZ | LYS | D | 143 | 13.471 | 1.650 | 19.578 | 1.00 | 59.46 | D | N |
| ATOM | 2766 | C | LYS | D | 143 | 7.397 | 4.213 | 20.659 | 1.00 | 47.09 | D | C |
| ATOM | 2767 | O | LYS | D | 143 | 7.137 | 3.032 | 20.760 | 1.00 | 42.24 | D | O |
| ATOM | 2768 | N | PHE | D | 144 | 7.247 | 5.073 | 21.672 | 1.00 | 48.37 | D | N |
| ATOM | 2769 | CA | PHE | D | 144 | 7.012 | 4.631 | 23.061 | 1.00 | 40.90 | D | C |
| ATOM | 2770 | CB | PHE | D | 144 | 8.122 | 5.179 | 23.979 | 1.00 | 41.99 | D | C |
| ATOM | 2771 | CG | PHE | D | 144 | 9.496 | 4.628 | 23.638 | 1.00 | 43.01 | D | C |
| ATOM | 2772 | CD1 | PHE | D | 144 | 9.888 | 3.356 | 24.106 | 1.00 | 47.59 | D | C |
| ATOM | 2773 | CE1 | PHE | D | 144 | 11.128 | 2.801 | 23.789 | 1.00 | 48.01 | D | C |
| ATOM | 2774 | CZ | PHE | D | 144 | 11.999 | 3.533 | 22.982 | 1.00 | 49.35 | D | C |
| ATOM | 2775 | CE2 | PHE | D | 144 | 11.627 | 4.814 | 22.521 | 1.00 | 42.55 | D | C |
| ATOM | 2776 | CD2 | PHE | D | 144 | 10.379 | 5.348 | 22.848 | 1.00 | 41.01 | D | C |
| ATOM | 2777 | C | PHE | D | 144 | 5.605 | 4.980 | 23.585 | 1.00 | 42.13 | D | C |
| ATOM | 2778 | O | PHE | D | 144 | 5.311 | 4.641 | 24.702 | 1.00 | 40.52 | D | O |
| ATOM | 2779 | N | GLY | D | 145 | 4.754 | 5.603 | 22.762 | 1.00 | 38.30 | D | N |
| ATOM | 2780 | CA | GLY | D | 145 | 3.331 | 5.899 | 23.095 | 1.00 | 38.33 | D | C |
| ATOM | 2781 | C | GLY | D | 145 | 2.869 | 7.086 | 22.263 | 1.00 | 40.05 | D | C |
| ATOM | 2782 | O | GLY | D | 145 | 3.607 | 7.597 | 21.434 | 1.00 | 41.42 | D | O |
| ATOM | 2783 | N | ASN | D | 146 | 1.660 | 7.552 | 22.495 | 1.00 | 40.08 | D | N |
| ATOM | 2784 | CA | ASN | D | 146 | 1.081 | 8.563 | 21.655 | 1.00 | 41.56 | D | C |
| ATOM | 2785 | CB | ASN | D | 146 | −0.428 | 8.405 | 21.590 | 1.00 | 49.11 | D | C |
| ATOM | 2786 | CG | ASN | D | 146 | −0.831 | 7.030 | 21.129 | 1.00 | 57.72 | D | C |
| ATOM | 2787 | OD1 | ASN | D | 146 | −0.192 | 6.425 | 20.247 | 1.00 | 60.53 | D | O |
| ATOM | 2788 | ND2 | ASN | D | 146 | −1.870 | 6.506 | 21.747 | 1.00 | 63.13 | D | N |
| ATOM | 2789 | C | ASN | D | 146 | 1.407 | 9.928 | 22.109 | 1.00 | 39.85 | D | C |
| ATOM | 2790 | O | ASN | D | 146 | 1.895 | 10.099 | 23.216 | 1.00 | 36.62 | D | O |
| ATOM | 2791 | N | VAL | D | 147 | 1.142 | 10.890 | 21.228 | 1.00 | 35.36 | D | N |
| ATOM | 2792 | CA | VAL | D | 147 | 1.160 | 12.299 | 21.567 | 1.00 | 33.15 | D | C |
| ATOM | 2793 | CB | VAL | D | 147 | 2.138 | 13.045 | 20.622 | 1.00 | 33.09 | D | C |
| ATOM | 2794 | CG1 | VAL | D | 147 | 2.309 | 14.468 | 21.043 | 1.00 | 28.18 | D | C |
| ATOM | 2795 | CG2 | VAL | D | 147 | 3.494 | 12.321 | 20.638 | 1.00 | 35.36 | D | C |
| ATOM | 2796 | C | VAL | D | 147 | −0.213 | 12.829 | 21.328 | 1.00 | 34.98 | D | C |
| ATOM | 2797 | O | VAL | D | 147 | −0.756 | 12.579 | 20.257 | 1.00 | 40.10 | D | O |
| ATOM | 2798 | N | TYR | D | 148 | −0.763 | 13.575 | 22.294 | 1.00 | 34.97 | D | N |
| ATOM | 2799 | CA | TYR | D | 148 | −2.126 | 14.047 | 22.245 | 1.00 | 33.75 | D | C |
| ATOM | 2800 | CB | TYR | D | 148 | −2.915 | 13.607 | 23.480 | 1.00 | 32.30 | D | C |
| ATOM | 2801 | CG | TYR | D | 148 | −2.941 | 12.134 | 23.631 | 1.00 | 36.03 | D | C |
| ATOM | 2802 | CD1 | TYR | D | 148 | −3.934 | 11.395 | 23.006 | 1.00 | 37.09 | D | C |
| ATOM | 2803 | CE1 | TYR | D | 148 | −3.956 | 10.027 | 23.055 | 1.00 | 35.41 | D | C |
| ATOM | 2804 | CZ | TYR | D | 148 | −3.036 | 9.358 | 23.799 | 1.00 | 42.33 | D | C |
| ATOM | 2805 | OH | TYR | D | 148 | −3.130 | 7.963 | 23.783 | 1.00 | 39.11 | D | O |
| ATOM | 2806 | CE2 | TYR | D | 148 | −1.989 | 10.058 | 24.425 | 1.00 | 40.74 | D | C |
| ATOM | 2807 | CD2 | TYR | D | 148 | −1.955 | 11.449 | 24.331 | 1.00 | 40.04 | D | C |
| ATOM | 2808 | C | TYR | D | 148 | −2.090 | 15.506 | 22.257 | 1.00 | 33.49 | D | C |
| ATOM | 2809 | O | TYR | D | 148 | −1.283 | 16.094 | 22.947 | 1.00 | 34.46 | D | O |
| ATOM | 2810 | N | LEU | D | 149 | −3.040 | 16.082 | 21.534 | 1.00 | 35.22 | D | N |
| ATOM | 2811 | CA | LEU | D | 149 | −3.455 | 17.453 | 21.703 | 1.00 | 39.25 | D | C |
| ATOM | 2812 | CB | LEU | D | 149 | −4.415 | 17.790 | 20.568 | 1.00 | 42.20 | D | C |
| ATOM | 2813 | CG | LEU | D | 149 | −4.734 | 19.232 | 20.237 | 1.00 | 55.05 | D | C |
| ATOM | 2814 | CD1 | LEU | D | 149 | −5.524 | 19.911 | 21.363 | 1.00 | 67.70 | D | C |
| ATOM | 2815 | CD2 | LEU | D | 149 | −3.454 | 19.981 | 19.920 | 1.00 | 49.25 | D | C |
| ATOM | 2816 | C | LEU | D | 149 | −4.095 | 17.504 | 23.093 | 1.00 | 38.67 | D | C |

APPENDIX A-continued

| Atomic coordinates of Aurora A + Inhibitory Monobody Mb60 + Danusertib | | | | | | | | | | | |
|---|---|---|---|---|---|---|---|---|---|---|---|
| ATOM | 2817 | O | LEU | D | 149 | −4.755 | 16.564 | 23.522 | 1.00 | 42.30 | D | O |
| ATOM | 2818 | N | ALA | D | 150 | −3.843 | 18.553 | 23.831 | 1.00 | 38.77 | D | N |
| ATOM | 2819 | CA | ALA | D | 150 | −4.216 | 18.593 | 25.244 | 1.00 | 37.34 | D | C |
| ATOM | 2820 | CB | ALA | D | 150 | −3.101 | 18.050 | 26.131 | 1.00 | 38.30 | D | C |
| ATOM | 2821 | C | ALA | D | 150 | −4.476 | 20.043 | 25.558 | 1.00 | 38.20 | D | C |
| ATOM | 2822 | O | ALA | D | 150 | −4.075 | 20.882 | 24.767 | 1.00 | 44.92 | D | O |
| ATOM | 2823 | N | ARG | D | 151 | −5.272 | 20.304 | 26.609 | 1.00 | 39.75 | D | N |
| ATOM | 2824 | CA | ARG | D | 151 | −5.694 | 21.646 | 26.983 | 1.00 | 41.80 | D | C |
| ATOM | 2825 | CB | ARG | D | 151 | −7.159 | 21.923 | 26.614 | 1.00 | 50.76 | D | C |
| ATOM | 2826 | CG | ARG | D | 151 | −7.387 | 22.462 | 25.208 | 1.00 | 66.48 | D | C |
| ATOM | 2827 | CD | ARG | D | 151 | −8.489 | 21.704 | 24.433 | 1.00 | 79.22 | D | C |
| ATOM | 2828 | NE | ARG | D | 151 | −9.746 | 21.695 | 25.180 | 1.00 | 85.05 | D | N |
| ATOM | 2829 | CZ | ARG | D | 151 | −10.572 | 22.738 | 25.304 | 1.00 | 97.74 | D | C |
| ATOM | 2830 | NH1 | ARG | D | 151 | −10.309 | 23.912 | 24.711 | 1.00 | 104.55 | D | N |
| ATOM | 2831 | NH2 | ARG | D | 151 | −11.681 | 22.612 | 26.032 | 1.00 | 96.25 | D | N |
| ATOM | 2832 | C | ARG | D | 151 | −5.515 | 21.760 | 28.455 | 1.00 | 41.48 | D | C |
| ATOM | 2833 | O | ARG | D | 151 | −5.953 | 20.884 | 29.223 | 1.00 | 44.67 | D | O |
| ATOM | 2834 | N | GLU | D | 152 | −4.915 | 22.866 | 28.860 | 1.00 | 43.77 | D | N |
| ATOM | 2835 | CA | GLU | D | 152 | −4.854 | 23.236 | 30.260 | 1.00 | 48.25 | D | C |
| ATOM | 2836 | CB | GLU | D | 152 | −3.927 | 24.424 | 30.445 | 1.00 | 49.80 | D | C |
| ATOM | 2837 | CG | GLU | D | 152 | −3.473 | 24.605 | 31.883 | 1.00 | 55.79 | D | C |
| ATOM | 2838 | CD | GLU | D | 152 | −4.539 | 25.251 | 32.743 | 1.00 | 62.11 | D | C |
| ATOM | 2839 | OE1 | GLU | D | 152 | −4.843 | 26.469 | 32.527 | 1.00 | 59.13 | D | O |
| ATOM | 2840 | OE2 | GLU | D | 152 | −5.075 | 24.520 | 33.615 | 1.00 | 61.77 | D | O |
| ATOM | 2841 | C | GLU | D | 152 | −6.285 | 23.571 | 30.766 | 1.00 | 47.59 | D | C |
| ATOM | 2842 | O | GLU | D | 152 | −6.849 | 24.596 | 30.386 | 1.00 | 41.54 | D | O |
| ATOM | 2843 | N | LYS | D | 153 | −6.840 | 22.710 | 31.619 | 1.00 | 46.50 | D | N |
| ATOM | 2844 | CA | LYS | D | 153 | −8.228 | 22.900 | 32.163 | 1.00 | 47.15 | D | C |
| ATOM | 2845 | CB | LYS | D | 153 | −8.502 | 21.994 | 33.345 | 1.00 | 45.61 | D | C |
| ATOM | 2846 | CG | LYS | D | 153 | −8.716 | 20.572 | 32.931 | 1.00 | 47.45 | D | C |
| ATOM | 2847 | CD | LYS | D | 153 | −8.985 | 19.665 | 34.121 | 1.00 | 53.80 | D | C |
| ATOM | 2848 | CE | LYS | D | 153 | −8.806 | 18.215 | 33.705 | 1.00 | 52.34 | D | C |
| ATOM | 2849 | NZ | LYS | D | 153 | −8.663 | 17.320 | 34.875 | 1.00 | 57.59 | D | N |
| ATOM | 2850 | C | LYS | D | 153 | −8.613 | 24.322 | 32.529 | 1.00 | 48.78 | D | C |
| ATOM | 2851 | O | LYS | D | 153 | −9.582 | 24.813 | 32.007 | 1.00 | 53.88 | D | O |
| ATOM | 2852 | N | GLN | D | 154 | −7.840 | 24.995 | 33.384 | 1.00 | 55.03 | D | N |
| ATOM | 2853 | CA | GLN | D | 154 | −8.135 | 26.392 | 33.743 | 1.00 | 57.16 | D | C |
| ATOM | 2854 | CB | GLN | D | 154 | −7.099 | 26.998 | 34.699 | 1.00 | 67.37 | D | C |
| ATOM | 2855 | CG | GLN | D | 154 | −7.264 | 26.653 | 36.172 | 1.00 | 71.13 | D | C |
| ATOM | 2856 | CD | GLN | D | 154 | −6.392 | 27.543 | 37.065 | 1.00 | 70.74 | D | C |
| ATOM | 2857 | OE1 | GLN | D | 154 | −5.266 | 27.184 | 37.425 | 1.00 | 77.28 | D | O |
| ATOM | 2858 | NE2 | GLN | D | 154 | −6.897 | 28.714 | 37.391 | 1.00 | 60.08 | D | N |
| ATOM | 2859 | C | GLN | D | 154 | −8.302 | 27.356 | 32.593 | 1.00 | 57.63 | D | C |
| ATOM | 2860 | O | GLN | D | 154 | −9.375 | 27.898 | 32.472 | 1.00 | 59.60 | D | O |
| ATOM | 2861 | N | SER | D | 155 | −7.238 | 27.590 | 31.797 | 1.00 | 52.49 | D | N |
| ATOM | 2862 | CA | SER | D | 155 | −7.230 | 28.539 | 30.627 | 1.00 | 45.43 | D | C |
| ATOM | 2863 | CB | SER | D | 155 | −5.818 | 28.991 | 30.378 | 1.00 | 46.83 | D | C |
| ATOM | 2864 | OG | SER | D | 155 | −4.937 | 27.877 | 30.266 | 1.00 | 47.01 | D | O |
| ATOM | 2865 | C | SER | D | 155 | −7.724 | 28.021 | 29.275 | 1.00 | 43.85 | D | C |
| ATOM | 2866 | O | SER | D | 155 | −8.109 | 28.802 | 28.400 | 1.00 | 43.33 | D | O |
| ATOM | 2867 | N | LYS | D | 156 | −7.678 | 26.718 | 29.082 | 1.00 | 39.16 | D | N |
| ATOM | 2868 | CA | LYS | D | 156 | −7.924 | 26.087 | 27.785 | 1.00 | 46.77 | D | C |
| ATOM | 2869 | CB | LYS | D | 156 | −9.278 | 26.517 | 27.149 | 1.00 | 48.72 | D | C |
| ATOM | 2870 | CG | LYS | D | 156 | −10.451 | 25.642 | 27.559 | 1.00 | 57.40 | D | C |
| ATOM | 2871 | CD | LYS | D | 156 | −10.646 | 25.487 | 29.062 | 1.00 | 56.67 | D | C |
| ATOM | 2872 | CE | LYS | D | 156 | −11.849 | 24.594 | 29.375 | 1.00 | 58.98 | D | C |
| ATOM | 2873 | NZ | LYS | D | 156 | −11.652 | 23.859 | 30.656 | 1.00 | 56.77 | D | N |
| ATOM | 2874 | C | LYS | D | 156 | −6.746 | 26.232 | 26.793 | 1.00 | 43.18 | D | C |
| ATOM | 2875 | O | LYS | D | 156 | −6.858 | 25.851 | 25.635 | 1.00 | 43.19 | D | O |
| ATOM | 2876 | N | PHE | D | 157 | −5.606 | 26.700 | 27.281 | 1.00 | 43.62 | D | N |
| ATOM | 2877 | CA | PHE | D | 157 | −4.408 | 26.839 | 26.480 | 1.00 | 39.88 | D | C |
| ATOM | 2878 | CB | PHE | D | 157 | −3.259 | 27.387 | 27.317 | 1.00 | 42.44 | D | C |
| ATOM | 2879 | CG | PHE | D | 157 | −2.133 | 27.930 | 26.507 | 1.00 | 43.00 | D | C |
| ATOM | 2880 | CD1 | PHE | D | 157 | −2.215 | 29.186 | 25.978 | 1.00 | 42.79 | D | C |
| ATOM | 2881 | CE1 | PHE | D | 157 | −1.164 | 29.694 | 25.241 | 1.00 | 45.85 | D | C |
| ATOM | 2882 | CZ | PHE | D | 157 | −0.041 | 28.922 | 25.011 | 1.00 | 36.87 | D | C |
| ATOM | 2883 | CE2 | PHE | D | 157 | 0.028 | 27.653 | 25.524 | 1.00 | 37.00 | D | C |
| ATOM | 2884 | CD2 | PHE | D | 157 | −1.003 | 27.173 | 26.273 | 1.00 | 39.44 | D | C |
| ATOM | 2885 | C | PHE | D | 157 | −4.014 | 25.493 | 25.955 | 1.00 | 35.19 | D | C |
| ATOM | 2886 | O | PHE | D | 157 | −3.931 | 24.484 | 26.709 | 1.00 | 33.08 | D | O |
| ATOM | 2887 | N | ILE | D | 158 | −3.750 | 25.489 | 24.660 | 1.00 | 34.45 | D | N |
| ATOM | 2888 | CA | ILE | D | 158 | −3.479 | 24.278 | 23.896 | 1.00 | 37.95 | D | C |
| ATOM | 2889 | CB | ILE | D | 158 | −3.773 | 24.490 | 22.397 | 1.00 | 39.81 | D | C |
| ATOM | 2890 | CG1 | ILE | D | 158 | −5.159 | 25.141 | 22.147 | 1.00 | 47.07 | D | C |
| ATOM | 2891 | CD1 | ILE | D | 158 | −6.368 | 24.222 | 22.169 | 1.00 | 46.77 | D | C |
| ATOM | 2892 | CG2 | ILE | D | 158 | −3.541 | 23.182 | 21.658 | 1.00 | 43.19 | D | C |
| ATOM | 2893 | C | ILE | D | 158 | −1.988 | 23.910 | 23.981 | 1.00 | 39.26 | D | C |
| ATOM | 2894 | O | ILE | D | 158 | −1.118 | 24.767 | 23.739 | 1.00 | 33.31 | D | O |

APPENDIX A-continued

| Atomic coordinates of Aurora A + Inhibitory Monobody Mb60 + Danusertib | | | | | | | | | | | | |
|---|---|---|---|---|---|---|---|---|---|---|---|---|
| ATOM | 2895 | N | LEU | D | 159 | −1.731 | 22.637 | 24.290 | 1.00 | 39.56 | D | N |
| ATOM | 2896 | CA | LEU | D | 159 | −0.391 | 22.062 | 24.448 | 1.00 | 37.32 | D | C |
| ATOM | 2897 | CB | LEU | D | 159 | −0.016 | 21.953 | 25.934 | 1.00 | 39.31 | D | C |
| ATOM | 2898 | CG | LEU | D | 159 | 0.036 | 23.296 | 26.693 | 1.00 | 43.37 | D | C |
| ATOM | 2899 | CD1 | LEU | D | 159 | 0.074 | 23.058 | 28.198 | 1.00 | 44.87 | D | C |
| ATOM | 2900 | CD2 | LEU | D | 159 | 1.235 | 24.143 | 26.293 | 1.00 | 44.15 | D | C |
| ATOM | 2901 | C | LEU | D | 159 | −0.426 | 20.692 | 23.855 | 1.00 | 33.70 | D | C |
| ATOM | 2902 | O | LEU | D | 159 | −1.489 | 20.224 | 23.393 | 1.00 | 32.77 | D | O |
| ATOM | 2903 | N | ALA | D | 160 | 0.725 | 20.036 | 23.854 | 1.00 | 31.54 | D | N |
| ATOM | 2904 | CA | ALA | D | 160 | 0.824 | 18.641 | 23.445 | 1.00 | 32.20 | D | C |
| ATOM | 2905 | CB | ALA | D | 160 | 1.779 | 18.520 | 22.271 | 1.00 | 32.34 | D | C |
| ATOM | 2906 | C | ALA | D | 160 | 1.299 | 17.791 | 24.605 | 1.00 | 34.25 | D | C |
| ATOM | 2907 | O | ALA | D | 160 | 2.181 | 18.201 | 25.335 | 1.00 | 36.65 | D | O |
| ATOM | 2908 | N | LEU | D | 161 | 0.757 | 16.577 | 24.726 | 1.00 | 34.67 | D | N |
| ATOM | 2909 | CA | LEU | D | 161 | 1.085 | 15.693 | 25.798 | 1.00 | 31.11 | D | C |
| ATOM | 2910 | CB | LEU | D | 161 | −0.202 | 15.366 | 26.604 | 1.00 | 37.88 | D | C |
| ATOM | 2911 | CG | LEU | D | 161 | −0.005 | 14.448 | 27.831 | 1.00 | 42.63 | D | C |
| ATOM | 2912 | CD1 | LEU | D | 161 | 0.720 | 15.177 | 28.945 | 1.00 | 41.59 | D | C |
| ATOM | 2913 | CD2 | LEU | D | 161 | −1.385 | 13.987 | 28.306 | 1.00 | 51.08 | D | C |
| ATOM | 2914 | C | LEU | D | 161 | 1.628 | 14.427 | 25.224 | 1.00 | 35.20 | D | C |
| ATOM | 2915 | O | LEU | D | 161 | 0.914 | 13.705 | 24.522 | 1.00 | 38.03 | D | O |
| ATOM | 2916 | N | LYS | D | 162 | 2.882 | 14.146 | 25.536 | 1.00 | 30.58 | D | N |
| ATOM | 2917 | CA | LYS | D | 162 | 3.554 | 13.018 | 25.020 | 1.00 | 31.91 | D | C |
| ATOM | 2918 | CB | LYS | D | 162 | 4.976 | 13.420 | 24.577 | 1.00 | 30.33 | D | C |
| ATOM | 2919 | CG | LYS | D | 162 | 5.782 | 12.301 | 23.945 | 1.00 | 30.85 | D | C |
| ATOM | 2920 | CD | LYS | D | 162 | 6.920 | 12.889 | 23.091 | 1.00 | 35.01 | D | C |
| ATOM | 2921 | CE | LYS | D | 162 | 7.826 | 11.834 | 22.468 | 1.00 | 34.51 | D | C |
| ATOM | 2922 | NZ | LYS | D | 162 | 8.949 | 12.408 | 21.653 | 1.00 | 34.21 | D | N |
| ATOM | 2923 | C | LYS | D | 162 | 3.648 | 11.954 | 26.133 | 1.00 | 34.95 | D | C |
| ATOM | 2924 | O | LYS | D | 162 | 4.132 | 12.246 | 27.262 | 1.00 | 41.83 | D | O |
| ATOM | 2925 | N | VAL | D | 163 | 3.327 | 10.722 | 25.782 | 1.00 | 34.56 | D | N |
| ATOM | 2926 | CA | VAL | D | 163 | 3.300 | 9.601 | 26.705 | 1.00 | 35.04 | D | C |
| ATOM | 2927 | CB | VAL | D | 163 | 1.948 | 8.877 | 26.552 | 1.00 | 35.95 | D | C |
| ATOM | 2928 | CG1 | VAL | D | 163 | 1.883 | 7.565 | 27.347 | 1.00 | 41.71 | D | C |
| ATOM | 2929 | CG2 | VAL | D | 163 | 0.851 | 9.841 | 26.943 | 1.00 | 40.61 | D | C |
| ATOM | 2930 | C | VAL | D | 163 | 4.444 | 8.698 | 26.283 | 1.00 | 39.54 | D | C |
| ATOM | 2931 | O | VAL | D | 163 | 4.605 | 8.458 | 25.104 | 1.00 | 44.18 | D | O |
| ATOM | 2932 | N | LEU | D | 164 | 5.264 | 8.230 | 27.230 | 1.00 | 34.55 | D | N |
| ATOM | 2933 | CA | LEU | D | 164 | 6.150 | 7.130 | 26.982 | 1.00 | 40.67 | D | C |
| ATOM | 2934 | CB | LEU | D | 164 | 7.604 | 7.650 | 26.917 | 1.00 | 40.50 | D | C |
| ATOM | 2935 | CG | LEU | D | 164 | 7.843 | 8.899 | 26.061 | 1.00 | 37.82 | D | C |
| ATOM | 2936 | CD1 | LEU | D | 164 | 7.577 | 10.181 | 26.828 | 1.00 | 36.40 | D | C |
| ATOM | 2937 | CD2 | LEU | D | 164 | 9.268 | 8.893 | 25.479 | 1.00 | 38.74 | D | C |
| ATOM | 2938 | C | LEU | D | 164 | 5.966 | 6.065 | 28.088 | 1.00 | 43.40 | D | C |
| ATOM | 2939 | O | LEU | D | 164 | 6.011 | 6.360 | 29.264 | 1.00 | 50.70 | D | O |
| ATOM | 2940 | N | PHE | D | 165 | 5.745 | 4.836 | 27.701 | 1.00 | 41.58 | D | N |
| ATOM | 2941 | CA | PHE | D | 165 | 5.504 | 3.775 | 28.644 | 1.00 | 43.83 | D | C |
| ATOM | 2942 | CB | PHE | D | 165 | 4.734 | 2.634 | 27.945 | 1.00 | 47.76 | D | C |
| ATOM | 2943 | CG | PHE | D | 165 | 3.258 | 2.924 | 27.806 | 1.00 | 49.43 | D | C |
| ATOM | 2944 | CD1 | PHE | D | 165 | 2.361 | 2.599 | 28.831 | 1.00 | 54.51 | D | C |
| ATOM | 2945 | CE1 | PHE | D | 165 | 0.988 | 2.887 | 28.706 | 1.00 | 52.38 | D | C |
| ATOM | 2946 | CZ | PHE | D | 165 | 0.515 | 3.533 | 27.564 | 1.00 | 46.13 | D | C |
| ATOM | 2947 | CE2 | PHE | D | 165 | 1.390 | 3.864 | 26.554 | 1.00 | 48.59 | D | C |
| ATOM | 2948 | CD2 | PHE | D | 165 | 2.758 | 3.567 | 26.676 | 1.00 | 51.00 | D | C |
| ATOM | 2949 | C | PHE | D | 165 | 6.830 | 3.274 | 29.256 | 1.00 | 45.79 | D | C |
| ATOM | 2950 | O | PHE | D | 165 | 7.812 | 2.965 | 28.546 | 1.00 | 36.67 | D | O |
| ATOM | 2951 | N | LYS | D | 166 | 6.844 | 3.188 | 30.583 | 1.00 | 43.13 | D | N |
| ATOM | 2952 | CA | LYS | D | 166 | 8.074 | 2.897 | 31.295 | 1.00 | 37.20 | D | C |
| ATOM | 2953 | CB | LYS | D | 166 | 7.875 | 3.032 | 32.816 | 1.00 | 35.91 | D | C |
| ATOM | 2954 | CG | LYS | D | 166 | 7.481 | 4.423 | 33.310 | 1.00 | 37.82 | D | C |
| ATOM | 2955 | CD | LYS | D | 166 | 7.250 | 4.410 | 34.825 | 1.00 | 40.10 | D | C |
| ATOM | 2956 | CE | LYS | D | 166 | 7.091 | 5.798 | 35.457 | 1.00 | 41.19 | D | C |
| ATOM | 2957 | NZ | LYS | D | 166 | 6.886 | 5.713 | 36.958 | 1.00 | 38.25 | D | N |
| ATOM | 2958 | C | LYS | D | 166 | 8.576 | 1.528 | 30.926 | 1.00 | 40.46 | D | C |
| ATOM | 2959 | O | LYS | D | 166 | 9.776 | 1.311 | 30.735 | 1.00 | 51.12 | D | O |
| ATOM | 2960 | N | ALA | D | 167 | 7.674 | 0.574 | 30.840 | 1.00 | 41.62 | D | N |
| ATOM | 2961 | CA | ALA | D | 167 | 8.062 | −0.805 | 30.531 | 1.00 | 41.49 | D | C |
| ATOM | 2962 | CB | ALA | D | 167 | 6.810 | −1.651 | 30.391 | 1.00 | 41.32 | D | C |
| ATOM | 2963 | C | ALA | D | 167 | 8.867 | −0.843 | 29.254 | 1.00 | 46.24 | D | C |
| ATOM | 2964 | O | ALA | D | 167 | 9.928 | −1.510 | 29.138 | 1.00 | 51.54 | D | O |
| ATOM | 2965 | N | GLN | D | 168 | 8.353 | −0.081 | 28.294 | 1.00 | 50.67 | D | N |
| ATOM | 2966 | CA | GLN | D | 168 | 8.943 | 0.009 | 26.987 | 1.00 | 46.26 | D | C |
| ATOM | 2967 | CB | GLN | D | 168 | 7.996 | 0.735 | 26.065 | 1.00 | 53.72 | D | C |
| ATOM | 2968 | CG | GLN | D | 168 | 7.342 | −0.151 | 25.027 | 1.00 | 60.71 | D | C |
| ATOM | 2969 | CD | GLN | D | 168 | 6.929 | 0.692 | 23.853 | 1.00 | 62.82 | D | C |
| ATOM | 2970 | OE1 | GLN | D | 168 | 5.855 | 1.276 | 23.871 | 1.00 | 58.15 | D | O |
| ATOM | 2971 | NE2 | GLN | D | 168 | 7.825 | 0.827 | 22.860 | 1.00 | 63.19 | D | N |
| ATOM | 2972 | C | GLN | D | 168 | 10.275 | 0.722 | 27.026 | 1.00 | 44.28 | D | C |

APPENDIX A-continued

| Atomic coordinates of Aurora A + Inhibitory Monobody Mb60 + Danusertib | | | | | | | | | | | |
|---|---|---|---|---|---|---|---|---|---|---|---|
| ATOM | 2973 | O | GLN | D | 168 | 11.243 | 0.223 | 26.467 | 1.00 | 40.42 | D | O |
| ATOM | 2974 | N | LEU | D | 169 | 10.314 | 1.910 | 27.647 | 1.00 | 40.19 | D | N |
| ATOM | 2975 | CA | LEU | D | 169 | 11.604 | 2.606 | 27.826 | 1.00 | 40.92 | D | C |
| ATOM | 2976 | CB | LEU | D | 169 | 11.409 | 3.803 | 28.731 | 1.00 | 40.53 | D | C |
| ATOM | 2977 | CG | LEU | D | 169 | 10.492 | 4.927 | 28.280 | 1.00 | 39.70 | D | C |
| ATOM | 2978 | CD1 | LEU | D | 169 | 10.305 | 5.852 | 29.474 | 1.00 | 42.19 | D | C |
| ATOM | 2979 | CD2 | LEU | D | 169 | 11.155 | 5.678 | 27.101 | 1.00 | 39.61 | D | C |
| ATOM | 2980 | C | LEU | D | 169 | 12.688 | 1.690 | 28.453 | 1.00 | 43.19 | D | C |
| ATOM | 2981 | O | LEU | D | 169 | 13.865 | 1.671 | 28.030 | 1.00 | 42.06 | D | O |
| ATOM | 2982 | N | GLU | D | 170 | 12.264 | 0.917 | 29.442 | 1.00 | 43.50 | D | N |
| ATOM | 2983 | CA | GLU | D | 170 | 13.146 | 0.006 | 30.166 | 1.00 | 55.72 | D | C |
| ATOM | 2984 | CB | GLU | D | 170 | 12.411 | −0.652 | 31.366 | 1.00 | 62.03 | D | C |
| ATOM | 2985 | CG | GLU | D | 170 | 13.302 | −1.438 | 32.330 | 1.00 | 70.15 | D | C |
| ATOM | 2986 | CD | GLU | D | 170 | 13.834 | −2.755 | 31.750 | 1.00 | 82.65 | D | C |
| ATOM | 2987 | OE1 | GLU | D | 170 | 13.073 | −3.467 | 31.060 | 1.00 | 93.71 | D | O |
| ATOM | 2988 | OE2 | GLU | D | 170 | 15.022 | −3.100 | 31.974 | 1.00 | 92.77 | D | O |
| ATOM | 2989 | C | GLU | D | 170 | 13.654 | −1.047 | 29.199 | 1.00 | 56.12 | D | C |
| ATOM | 2990 | O | GLU | D | 170 | 14.870 | −1.170 | 28.998 | 1.00 | 51.93 | D | O |
| ATOM | 2991 | N | LYS | D | 171 | 12.713 | −1.767 | 28.581 | 1.00 | 56.71 | D | N |
| ATOM | 2992 | CA | LYS | D | 171 | 13.022 | −2.804 | 27.604 | 1.00 | 60.81 | D | C |
| ATOM | 2993 | CB | LYS | D | 171 | 11.720 | −3.309 | 26.982 | 1.00 | 67.84 | D | C |
| ATOM | 2994 | CG | LYS | D | 171 | 11.922 | −4.377 | 25.937 | 1.00 | 79.88 | D | C |
| ATOM | 2995 | CD | LYS | D | 171 | 10.695 | −5.271 | 25.769 | 1.00 | 87.49 | D | C |
| ATOM | 2996 | CE | LYS | D | 171 | 10.883 | −6.265 | 24.626 | 1.00 | 90.11 | D | C |
| ATOM | 2997 | NZ | LYS | D | 171 | 12.175 | −7.017 | 24.722 | 1.00 | 97.22 | D | N |
| ATOM | 2998 | C | LYS | D | 171 | 14.004 | −2.278 | 26.540 | 1.00 | 57.31 | D | C |
| ATOM | 2999 | O | LYS | D | 171 | 14.978 | −2.927 | 26.219 | 1.00 | 52.90 | D | O |
| ATOM | 3000 | N | ALA | D | 172 | 13.781 | −1.057 | 26.069 | 1.00 | 53.06 | D | N |
| ATOM | 3001 | CA | ALA | D | 172 | 14.656 | −0.459 | 25.071 | 1.00 | 55.39 | D | C |
| ATOM | 3002 | CB | ALA | D | 172 | 13.893 | 0.595 | 24.272 | 1.00 | 54.84 | D | C |
| ATOM | 3003 | C | ALA | D | 172 | 15.967 | 0.110 | 25.665 | 1.00 | 55.85 | D | C |
| ATOM | 3004 | O | ALA | D | 172 | 16.884 | 0.466 | 24.923 | 1.00 | 54.20 | D | O |
| ATOM | 3005 | N | GLY | D | 173 | 16.066 | 0.202 | 26.987 | 1.00 | 52.98 | D | N |
| ATOM | 3006 | CA | GLY | D | 173 | 17.290 | 0.689 | 27.630 | 1.00 | 50.16 | D | C |
| ATOM | 3007 | C | GLY | D | 173 | 17.527 | 2.175 | 27.422 | 1.00 | 43.10 | D | C |
| ATOM | 3008 | O | GLY | D | 173 | 18.653 | 2.638 | 27.364 | 1.00 | 41.64 | D | O |
| ATOM | 3009 | N | VAL | D | 174 | 16.460 | 2.926 | 27.350 | 1.00 | 41.34 | D | N |
| ATOM | 3010 | CA | VAL | D | 174 | 16.536 | 4.371 | 27.105 | 1.00 | 43.05 | D | C |
| ATOM | 3011 | CB | VAL | D | 174 | 15.853 | 4.756 | 25.778 | 1.00 | 47.15 | D | C |
| ATOM | 3012 | CG1 | VAL | D | 174 | 16.666 | 4.182 | 24.602 | 1.00 | 44.35 | D | C |
| ATOM | 3013 | CG2 | VAL | D | 174 | 14.385 | 4.301 | 25.778 | 1.00 | 43.67 | D | C |
| ATOM | 3014 | C | VAL | D | 174 | 15.913 | 5.216 | 28.178 | 1.00 | 35.74 | D | C |
| ATOM | 3015 | O | VAL | D | 174 | 15.822 | 6.364 | 27.995 | 1.00 | 35.17 | D | O |
| ATOM | 3016 | N | GLU | D | 175 | 15.491 | 4.658 | 29.306 | 1.00 | 39.13 | D | N |
| ATOM | 3017 | CA | GLU | D | 175 | 14.791 | 5.460 | 30.367 | 1.00 | 40.31 | D | C |
| ATOM | 3018 | CB | GLU | D | 175 | 14.232 | 4.502 | 31.463 | 1.00 | 39.95 | D | C |
| ATOM | 3019 | CG | GLU | D | 175 | 13.314 | 5.193 | 32.447 | 1.00 | 45.49 | D | C |
| ATOM | 3020 | CD | GLU | D | 175 | 12.382 | 4.273 | 33.246 | 1.00 | 44.81 | D | C |
| ATOM | 3021 | OE1 | GLU | D | 175 | 12.565 | 3.023 | 33.221 | 1.00 | 44.89 | D | O |
| ATOM | 3022 | OE2 | GLU | D | 175 | 11.445 | 4.859 | 33.873 | 1.00 | 43.59 | D | O |
| ATOM | 3023 | C | GLU | D | 175 | 15.707 | 6.535 | 30.987 | 1.00 | 37.07 | D | C |
| ATOM | 3024 | O | GLU | D | 175 | 15.366 | 7.722 | 31.157 | 1.00 | 35.15 | D | O |
| ATOM | 3025 | N | HIS | D | 176 | 16.910 | 6.087 | 31.296 | 1.00 | 38.61 | D | N |
| ATOM | 3026 | CA | HIS | D | 176 | 17.954 | 6.944 | 31.838 | 1.00 | 31.58 | D | C |
| ATOM | 3027 | CB | HIS | D | 176 | 19.233 | 6.084 | 32.001 | 1.00 | 34.84 | D | C |
| ATOM | 3028 | CG | HIS | D | 176 | 20.428 | 6.865 | 32.447 | 1.00 | 38.01 | D | C |
| ATOM | 3029 | ND1 | HIS | D | 176 | 21.701 | 6.329 | 32.484 | 1.00 | 40.83 | D | N |
| ATOM | 3030 | CE1 | HIS | D | 176 | 22.556 | 7.246 | 32.908 | 1.00 | 40.45 | D | C |
| ATOM | 3031 | NE2 | HIS | D | 176 | 21.881 | 8.361 | 33.153 | 1.00 | 46.29 | D | N |
| ATOM | 3032 | CD2 | HIS | D | 176 | 20.553 | 8.157 | 32.855 | 1.00 | 43.52 | D | C |
| ATOM | 3033 | C | HIS | D | 176 | 18.177 | 8.076 | 30.882 | 1.00 | 29.91 | D | C |
| ATOM | 3034 | O | HIS | D | 176 | 18.140 | 9.245 | 31.225 | 1.00 | 31.80 | D | O |
| ATOM | 3035 | N | GLN | D | 177 | 18.372 | 7.716 | 29.640 | 1.00 | 31.14 | D | N |
| ATOM | 3036 | CA | GLN | D | 177 | 18.480 | 8.719 | 28.577 | 1.00 | 34.59 | D | C |
| ATOM | 3037 | CB | GLN | D | 177 | 18.592 | 7.995 | 27.277 | 1.00 | 38.53 | D | C |
| ATOM | 3038 | CG | GLN | D | 177 | 18.835 | 8.934 | 26.121 | 1.00 | 41.48 | D | C |
| ATOM | 3039 | CD | GLN | D | 177 | 19.056 | 8.181 | 24.853 | 1.00 | 40.00 | D | C |
| ATOM | 3040 | OE1 | GLN | D | 177 | 18.752 | 6.996 | 24.747 | 1.00 | 44.70 | D | O |
| ATOM | 3041 | NE2 | GLN | D | 177 | 19.563 | 8.870 | 23.869 | 1.00 | 41.95 | D | N |
| ATOM | 3042 | C | GLN | D | 177 | 17.343 | 9.742 | 28.502 | 1.00 | 36.09 | D | C |
| ATOM | 3043 | O | GLN | D | 177 | 17.574 | 10.958 | 28.325 | 1.00 | 38.73 | D | O |
| ATOM | 3044 | N | LEU | D | 178 | 16.112 | 9.264 | 28.589 | 1.00 | 34.32 | D | N |
| ATOM | 3045 | CA | LEU | D | 178 | 14.978 | 10.201 | 28.696 | 1.00 | 34.82 | D | C |
| ATOM | 3046 | CB | LEU | D | 178 | 13.697 | 9.419 | 28.753 | 1.00 | 34.14 | D | C |
| ATOM | 3047 | CG | LEU | D | 178 | 12.402 | 10.207 | 28.868 | 1.00 | 37.14 | D | C |
| ATOM | 3048 | CD1 | LEU | D | 178 | 12.187 | 11.065 | 27.644 | 1.00 | 36.63 | D | C |
| ATOM | 3049 | CD2 | LEU | D | 178 | 11.278 | 9.215 | 28.989 | 1.00 | 38.72 | D | C |
| ATOM | 3050 | C | LEU | D | 178 | 15.081 | 11.115 | 29.924 | 1.00 | 33.70 | D | C |

APPENDIX A-continued

| Atomic coordinates of Aurora A + Inhibitory Monobody Mb60 + Danusertib | | | | | | | | | | | | |
|---|---|---|---|---|---|---|---|---|---|---|---|---|
| ATOM | 3051 | O | LEU | D | 178 | 14.896 | 12.308 | 29.823 | 1.00 | 38.75 | D | O |
| ATOM | 3052 | N | ARG | D | 179 | 15.388 | 10.549 | 31.092 | 1.00 | 35.42 | D | N |
| ATOM | 3053 | CA | ARG | D | 179 | 15.350 | 11.364 | 32.288 | 1.00 | 34.38 | D | C |
| ATOM | 3054 | CB | ARG | D | 179 | 15.515 | 10.480 | 33.527 | 1.00 | 38.59 | D | C |
| ATOM | 3055 | CG | ARG | D | 179 | 15.657 | 11.209 | 34.838 | 1.00 | 40.73 | D | C |
| ATOM | 3056 | CD | ARG | D | 179 | 14.456 | 12.079 | 35.147 | 1.00 | 44.61 | D | C |
| ATOM | 3057 | NE | ARG | D | 179 | 14.693 | 12.792 | 36.407 | 1.00 | 41.37 | D | N |
| ATOM | 3058 | CZ | ARG | D | 179 | 15.445 | 13.886 | 36.521 | 1.00 | 40.78 | D | C |
| ATOM | 3059 | NH1 | ARG | D | 179 | 16.081 | 14.384 | 35.480 | 1.00 | 35.50 | D | N |
| ATOM | 3060 | NH2 | ARG | D | 179 | 15.618 | 14.441 | 37.704 | 1.00 | 38.86 | D | N |
| ATOM | 3061 | C | ARG | D | 179 | 16.403 | 12.479 | 32.169 | 1.00 | 37.10 | D | C |
| ATOM | 3062 | O | ARG | D | 179 | 16.170 | 13.575 | 32.616 | 1.00 | 33.24 | D | O |
| ATOM | 3063 | N | ARG | D | 180 | 17.562 | 12.174 | 31.556 | 1.00 | 37.94 | D | N |
| ATOM | 3064 | CA | ARG | D | 180 | 18.645 | 13.179 | 31.363 | 1.00 | 38.37 | D | C |
| ATOM | 3065 | CB | ARG | D | 180 | 19.923 | 12.480 | 30.875 | 1.00 | 38.54 | D | C |
| ATOM | 3066 | CG | ARG | D | 180 | 21.109 | 13.409 | 30.564 | 1.00 | 44.89 | D | C |
| ATOM | 3067 | CD | ARG | D | 180 | 22.121 | 12.808 | 29.571 | 1.00 | 45.51 | D | C |
| ATOM | 3068 | NE | ARG | D | 180 | 22.478 | 11.507 | 30.086 | 1.00 | 49.53 | D | N |
| ATOM | 3069 | CZ | ARG | D | 180 | 22.423 | 10.337 | 29.465 | 1.00 | 47.10 | D | C |
| ATOM | 3070 | NH1 | ARG | D | 180 | 22.171 | 10.229 | 28.172 | 1.00 | 43.67 | D | N |
| ATOM | 3071 | NH2 | ARG | D | 180 | 22.717 | 9.245 | 30.178 | 1.00 | 50.16 | D | N |
| ATOM | 3072 | C | ARG | D | 180 | 18.140 | 14.193 | 30.361 | 1.00 | 31.56 | D | C |
| ATOM | 3073 | O | ARG | D | 180 | 18.187 | 15.379 | 30.563 | 1.00 | 30.45 | D | O |
| ATOM | 3074 | N | GLU | D | 181 | 17.521 | 13.687 | 29.308 | 1.00 | 31.75 | D | N |
| ATOM | 3075 | CA | GLU | D | 181 | 17.180 | 14.546 | 28.195 | 1.00 | 35.31 | D | C |
| ATOM | 3076 | CB | GLU | D | 181 | 17.016 | 13.747 | 26.887 | 1.00 | 36.68 | D | C |
| ATOM | 3077 | CG | GLU | D | 181 | 18.373 | 13.273 | 26.356 | 1.00 | 40.28 | D | C |
| ATOM | 3078 | CD | GLU | D | 181 | 18.291 | 12.358 | 25.100 | 1.00 | 44.09 | D | C |
| ATOM | 3079 | OE1 | GLU | D | 181 | 17.230 | 12.363 | 24.411 | 1.00 | 39.53 | D | O |
| ATOM | 3080 | OE2 | GLU | D | 181 | 19.308 | 11.667 | 24.775 | 1.00 | 42.40 | D | O |
| ATOM | 3081 | C | GLU | D | 181 | 16.032 | 15.451 | 28.475 | 1.00 | 35.08 | D | C |
| ATOM | 3082 | O | GLU | D | 181 | 16.032 | 16.542 | 27.965 | 1.00 | 35.81 | D | O |
| ATOM | 3083 | N | VAL | D | 182 | 15.085 | 15.068 | 29.324 | 1.00 | 31.22 | D | N |
| ATOM | 3084 | CA | VAL | D | 182 | 14.073 | 16.081 | 29.656 | 1.00 | 32.47 | D | C |
| ATOM | 3085 | CB | VAL | D | 182 | 12.837 | 15.473 | 30.394 | 1.00 | 35.89 | D | C |
| ATOM | 3086 | CG1 | VAL | D | 182 | 12.141 | 14.481 | 29.464 | 1.00 | 33.87 | D | C |
| ATOM | 3087 | CG2 | VAL | D | 182 | 13.192 | 14.807 | 31.747 | 1.00 | 37.39 | D | C |
| ATOM | 3088 | C | VAL | D | 182 | 14.613 | 17.269 | 30.403 | 1.00 | 33.93 | D | C |
| ATOM | 3089 | O | VAL | D | 182 | 14.119 | 18.377 | 30.232 | 1.00 | 34.51 | D | O |
| ATOM | 3090 | N | GLU | D | 183 | 15.606 | 17.027 | 31.263 | 1.00 | 34.74 | D | N |
| ATOM | 3091 | CA | GLU | D | 183 | 16.193 | 18.085 | 32.079 | 1.00 | 39.79 | D | C |
| ATOM | 3092 | CB | GLU | D | 183 | 17.162 | 17.444 | 33.112 | 1.00 | 46.66 | D | C |
| ATOM | 3093 | CG | GLU | D | 183 | 17.704 | 18.321 | 34.241 | 1.00 | 53.95 | D | C |
| ATOM | 3094 | CD | GLU | D | 183 | 16.583 | 18.975 | 35.058 | 1.00 | 64.75 | D | C |
| ATOM | 3095 | OE1 | GLU | D | 183 | 15.523 | 18.308 | 35.247 | 1.00 | 72.90 | D | O |
| ATOM | 3096 | OE2 | GLU | D | 183 | 16.744 | 20.155 | 35.472 | 1.00 | 53.92 | D | O |
| ATOM | 3097 | C | GLU | D | 183 | 16.923 | 19.038 | 31.146 | 1.00 | 35.65 | D | C |
| ATOM | 3098 | O | GLU | D | 183 | 16.830 | 20.280 | 31.225 | 1.00 | 37.16 | D | O |
| ATOM | 3099 | N | ILE | D | 184 | 17.691 | 18.446 | 30.248 | 1.00 | 34.08 | D | N |
| ATOM | 3100 | CA | ILE | D | 184 | 18.469 | 19.258 | 29.323 | 1.00 | 32.61 | D | C |
| ATOM | 3101 | CB | ILE | D | 184 | 19.284 | 18.359 | 28.358 | 1.00 | 28.97 | D | C |
| ATOM | 3102 | CG1 | ILE | D | 184 | 20.387 | 17.650 | 29.134 | 1.00 | 31.69 | D | C |
| ATOM | 3103 | CD1 | ILE | D | 184 | 20.832 | 16.378 | 28.428 | 1.00 | 37.06 | D | C |
| ATOM | 3104 | CG2 | ILE | D | 184 | 19.830 | 19.163 | 27.193 | 1.00 | 30.62 | D | C |
| ATOM | 3105 | C | ILE | D | 184 | 17.509 | 20.098 | 28.501 | 1.00 | 33.33 | D | C |
| ATOM | 3106 | O | ILE | D | 184 | 17.713 | 21.314 | 28.363 | 1.00 | 29.70 | D | O |
| ATOM | 3107 | N | GLN | D | 185 | 16.483 | 19.437 | 27.934 | 1.00 | 33.07 | D | N |
| ATOM | 3108 | CA | GLN | D | 185 | 15.597 | 20.129 | 27.013 | 1.00 | 37.05 | D | C |
| ATOM | 3109 | CB | GLN | D | 185 | 14.734 | 19.148 | 26.219 | 1.00 | 37.74 | D | C |
| ATOM | 3110 | CG | GLN | D | 185 | 14.369 | 19.664 | 24.787 | 1.00 | 42.83 | D | C |
| ATOM | 3111 | CD | GLN | D | 185 | 15.528 | 19.497 | 23.827 | 1.00 | 41.74 | D | C |
| ATOM | 3112 | OE1 | GLN | D | 185 | 16.575 | 18.952 | 24.221 | 1.00 | 41.60 | D | O |
| ATOM | 3113 | NE2 | GLN | D | 185 | 15.383 | 19.974 | 22.590 | 1.00 | 41.64 | D | N |
| ATOM | 3114 | C | GLN | D | 185 | 14.767 | 21.223 | 27.739 | 1.00 | 35.20 | D | C |
| ATOM | 3115 | O | GLN | D | 185 | 14.514 | 22.251 | 27.175 | 1.00 | 31.85 | D | O |
| ATOM | 3116 | N | SER | D | 186 | 14.438 | 20.992 | 29.004 | 1.00 | 35.77 | D | N |
| ATOM | 3117 | CA | SER | D | 186 | 13.715 | 21.964 | 29.847 | 1.00 | 39.48 | D | C |
| ATOM | 3118 | CB | SER | D | 186 | 13.532 | 21.428 | 31.300 | 1.00 | 42.61 | D | C |
| ATOM | 3119 | OG | SER | D | 186 | 14.726 | 21.591 | 32.126 | 1.00 | 47.63 | D | O |
| ATOM | 3120 | C | SER | D | 186 | 14.354 | 23.336 | 29.904 | 1.00 | 39.84 | D | C |
| ATOM | 3121 | O | SER | D | 186 | 13.637 | 24.328 | 30.036 | 1.00 | 42.48 | D | O |
| ATOM | 3122 | N | HIS | D | 187 | 15.669 | 23.443 | 29.759 | 1.00 | 40.95 | D | N |
| ATOM | 3123 | CA | HIS | D | 187 | 16.353 | 24.772 | 29.866 | 1.00 | 40.55 | D | C |
| ATOM | 3124 | CB | HIS | D | 187 | 17.768 | 24.570 | 30.440 | 1.00 | 42.87 | D | C |
| ATOM | 3125 | CG | HIS | D | 187 | 17.781 | 23.869 | 31.757 | 1.00 | 48.92 | D | C |
| ATOM | 3126 | ND1 | HIS | D | 187 | 17.096 | 24.338 | 32.857 | 1.00 | 55.07 | D | N |
| ATOM | 3127 | CE1 | HIS | D | 187 | 17.269 | 23.508 | 33.873 | 1.00 | 54.04 | D | C |
| ATOM | 3128 | NE2 | HIS | D | 187 | 18.049 | 22.518 | 33.469 | 1.00 | 54.79 | D | N |

APPENDIX A-continued

| Atomic coordinates of Aurora A + Inhibitory Monobody Mb60 + Danusertib | | | | | | | | | | | |
|---|---|---|---|---|---|---|---|---|---|---|---|
| ATOM | 3129 | CD2 | HIS | D | 187 | 18.383 | 22.719 | 32.153 | 1.00 | 53.42 | D | C |
| ATOM | 3130 | C | HIS | D | 187 | 16.434 | 25.577 | 28.548 | 1.00 | 43.84 | D | C |
| ATOM | 3131 | O | HIS | D | 187 | 16.799 | 26.763 | 28.523 | 1.00 | 45.05 | D | O |
| ATOM | 3132 | N | LEU | D | 188 | 16.099 | 24.935 | 27.440 | 1.00 | 43.68 | D | N |
| ATOM | 3133 | CA | LEU | D | 188 | 16.338 | 25.524 | 26.127 | 1.00 | 40.55 | D | C |
| ATOM | 3134 | CB | LEU | D | 188 | 16.543 | 24.402 | 25.116 | 1.00 | 35.23 | D | C |
| ATOM | 3135 | CG | LEU | D | 188 | 17.678 | 23.442 | 25.356 | 1.00 | 34.82 | D | C |
| ATOM | 3136 | CD1 | LEU | D | 188 | 17.783 | 22.526 | 24.158 | 1.00 | 37.52 | D | C |
| ATOM | 3137 | CD2 | LEU | D | 188 | 18.999 | 24.152 | 25.609 | 1.00 | 39.05 | D | C |
| ATOM | 3138 | C | LEU | D | 188 | 15.122 | 26.383 | 25.706 | 1.00 | 41.48 | D | C |
| ATOM | 3139 | O | LEU | D | 188 | 14.083 | 25.827 | 25.376 | 1.00 | 46.28 | D | O |
| ATOM | 3140 | N | ARG | D | 189 | 15.256 | 27.712 | 25.731 | 1.00 | 39.14 | D | N |
| ATOM | 3141 | CA | ARG | D | 189 | 14.153 | 28.655 | 25.402 | 1.00 | 39.09 | D | C |
| ATOM | 3142 | CB | ARG | D | 189 | 13.936 | 29.667 | 26.535 | 1.00 | 41.98 | D | C |
| ATOM | 3143 | CG | ARG | D | 189 | 12.729 | 29.448 | 27.426 | 1.00 | 51.32 | D | C |
| ATOM | 3144 | CD | ARG | D | 189 | 13.007 | 28.553 | 28.618 | 1.00 | 62.12 | D | C |
| ATOM | 3145 | NE | ARG | D | 189 | 12.204 | 28.941 | 29.781 | 1.00 | 67.88 | D | N |
| ATOM | 3146 | CZ | ARG | D | 189 | 12.253 | 28.345 | 30.976 | 1.00 | 74.47 | D | C |
| ATOM | 3147 | NH1 | ARG | D | 189 | 13.070 | 27.311 | 31.207 | 1.00 | 65.00 | D | N |
| ATOM | 3148 | NH2 | ARG | D | 189 | 11.463 | 28.785 | 31.962 | 1.00 | 84.94 | D | N |
| ATOM | 3149 | C | ARG | D | 189 | 14.519 | 29.386 | 24.151 | 1.00 | 33.71 | D | C |
| ATOM | 3150 | O | ARG | D | 189 | 15.416 | 30.180 | 24.151 | 1.00 | 36.97 | D | O |
| ATOM | 3151 | N | HIS | D | 190 | 13.857 | 29.060 | 23.056 | 1.00 | 32.79 | D | N |
| ATOM | 3152 | CA | HIS | D | 190 | 14.158 | 29.704 | 21.787 | 1.00 | 32.76 | D | C |
| ATOM | 3153 | CB | HIS | D | 190 | 15.451 | 29.150 | 21.206 | 1.00 | 30.47 | D | C |
| ATOM | 3154 | CG | HIS | D | 190 | 15.917 | 29.871 | 19.988 | 1.00 | 28.54 | D | C |
| ATOM | 3155 | ND1 | HIS | D | 190 | 15.387 | 29.652 | 18.752 | 1.00 | 30.05 | D | N |
| ATOM | 3156 | CE1 | HIS | D | 190 | 15.993 | 30.400 | 17.857 | 1.00 | 25.24 | D | C |
| ATOM | 3157 | NE2 | HIS | D | 190 | 16.894 | 31.111 | 18.489 | 1.00 | 27.89 | D | N |
| ATOM | 3158 | CD2 | HIS | D | 190 | 16.890 | 30.770 | 19.809 | 1.00 | 26.71 | D | C |
| ATOM | 3159 | C | HIS | D | 190 | 12.969 | 29.476 | 20.871 | 1.00 | 26.45 | D | C |
| ATOM | 3160 | O | HIS | D | 190 | 12.375 | 28.417 | 20.944 | 1.00 | 29.83 | D | O |
| ATOM | 3161 | N | PRO | D | 191 | 12.641 | 30.460 | 20.024 | 1.00 | 28.25 | D | N |
| ATOM | 3162 | CA | PRO | D | 191 | 11.458 | 30.362 | 19.136 | 1.00 | 28.11 | D | C |
| ATOM | 3163 | CB | PRO | D | 191 | 11.338 | 31.745 | 18.497 | 1.00 | 28.76 | D | C |
| ATOM | 3164 | CG | PRO | D | 191 | 12.603 | 32.512 | 18.869 | 1.00 | 30.32 | D | C |
| ATOM | 3165 | CD | PRO | D | 191 | 13.258 | 31.817 | 20.021 | 1.00 | 29.15 | D | C |
| ATOM | 3166 | C | PRO | D | 191 | 11.481 | 29.223 | 18.096 | 1.00 | 28.43 | D | C |
| ATOM | 3167 | O | PRO | D | 191 | 10.416 | 28.803 | 17.633 | 1.00 | 26.88 | D | O |
| ATOM | 3168 | N | ASN | D | 192 | 12.647 | 28.607 | 17.871 | 1.00 | 26.93 | D | N |
| ATOM | 3169 | CA | ASN | D | 192 | 12.789 | 27.557 | 16.901 | 1.00 | 25.78 | D | C |
| ATOM | 3170 | CB | ASN | D | 192 | 13.762 | 28.018 | 15.831 | 1.00 | 26.51 | D | C |
| ATOM | 3171 | CG | ASN | D | 192 | 13.286 | 29.247 | 15.123 | 1.00 | 25.74 | D | C |
| ATOM | 3172 | OD1 | ASN | D | 192 | 13.855 | 30.272 | 15.222 | 1.00 | 30.37 | D | O |
| ATOM | 3173 | ND2 | ASN | D | 192 | 12.300 | 29.082 | 14.306 | 1.00 | 28.11 | D | N |
| ATOM | 3174 | C | ASN | D | 192 | 13.253 | 26.316 | 17.578 | 1.00 | 26.16 | D | C |
| ATOM | 3175 | O | ASN | D | 192 | 13.790 | 25.409 | 16.928 | 1.00 | 27.32 | D | O |
| ATOM | 3176 | N | ILE | D | 193 | 13.029 | 26.236 | 18.899 | 1.00 | 24.96 | D | N |
| ATOM | 3177 | CA | ILE | D | 193 | 13.193 | 25.001 | 19.638 | 1.00 | 26.02 | D | C |
| ATOM | 3178 | CB | ILE | D | 193 | 14.275 | 25.131 | 20.729 | 1.00 | 26.30 | D | C |
| ATOM | 3179 | CG1 | ILE | D | 193 | 15.593 | 25.480 | 20.036 | 1.00 | 25.56 | D | C |
| ATOM | 3180 | CD1 | ILE | D | 193 | 16.836 | 25.531 | 20.889 | 1.00 | 24.03 | D | C |
| ATOM | 3181 | CG2 | ILE | D | 193 | 14.307 | 23.845 | 21.550 | 1.00 | 27.91 | D | C |
| ATOM | 3182 | C | ILE | D | 193 | 11.889 | 24.709 | 20.344 | 1.00 | 26.76 | D | C |
| ATOM | 3183 | O | ILE | D | 193 | 11.382 | 25.547 | 21.031 | 1.00 | 28.27 | D | O |
| ATOM | 3184 | N | LEU | D | 194 | 11.381 | 23.504 | 20.193 | 1.00 | 31.04 | D | N |
| ATOM | 3185 | CA | LEU | D | 194 | 10.062 | 23.176 | 20.779 | 1.00 | 30.63 | D | C |
| ATOM | 3186 | CB | LEU | D | 194 | 9.651 | 21.750 | 20.377 | 1.00 | 28.19 | D | C |
| ATOM | 3187 | CG | LEU | D | 194 | 8.165 | 21.524 | 20.643 | 1.00 | 30.41 | D | C |
| ATOM | 3188 | CD1 | LEU | D | 194 | 7.328 | 22.311 | 19.632 | 1.00 | 31.67 | D | C |
| ATOM | 3189 | CD2 | LEU | D | 194 | 7.827 | 20.066 | 20.588 | 1.00 | 29.19 | D | C |
| ATOM | 3190 | C | LEU | D | 194 | 10.141 | 23.272 | 22.300 | 1.00 | 28.48 | D | C |
| ATOM | 3191 | O | LEU | D | 194 | 11.045 | 22.662 | 22.863 | 1.00 | 25.97 | D | O |
| ATOM | 3192 | N | ARG | D | 195 | 9.253 | 24.032 | 22.980 | 1.00 | 28.50 | D | N |
| ATOM | 3193 | CA | ARG | D | 195 | 9.289 | 24.083 | 24.468 | 1.00 | 30.97 | D | C |
| ATOM | 3194 | CB | ARG | D | 195 | 8.429 | 25.200 | 25.059 | 1.00 | 37.96 | D | C |
| ATOM | 3195 | CG | ARG | D | 195 | 8.933 | 26.608 | 24.758 | 1.00 | 40.25 | D | C |
| ATOM | 3196 | CD | ARG | D | 195 | 10.070 | 27.067 | 25.686 | 1.00 | 47.90 | D | C |
| ATOM | 3197 | NE | ARG | D | 195 | 9.664 | 27.295 | 27.080 | 1.00 | 58.51 | D | N |
| ATOM | 3198 | CZ | ARG | D | 195 | 10.042 | 26.580 | 28.156 | 1.00 | 62.40 | D | C |
| ATOM | 3199 | NH1 | ARG | D | 195 | 9.592 | 26.930 | 29.360 | 1.00 | 64.60 | D | N |
| ATOM | 3200 | NH2 | ARG | D | 195 | 10.885 | 25.549 | 28.082 | 1.00 | 61.42 | D | N |
| ATOM | 3201 | C | ARG | D | 195 | 8.868 | 22.804 | 25.127 | 1.00 | 31.60 | D | C |
| ATOM | 3202 | O | ARG | D | 195 | 7.860 | 22.163 | 24.749 | 1.00 | 25.73 | D | O |
| ATOM | 3203 | N | LEU | D | 196 | 9.661 | 22.394 | 26.101 | 1.00 | 31.00 | D | N |
| ATOM | 3204 | CA | LEU | D | 196 | 9.253 | 21.333 | 27.019 | 1.00 | 33.89 | D | C |
| ATOM | 3205 | CB | LEU | D | 196 | 10.316 | 20.257 | 27.183 | 1.00 | 32.73 | D | C |
| ATOM | 3206 | CG | LEU | D | 196 | 10.109 | 19.227 | 28.290 | 1.00 | 33.90 | D | C |

APPENDIX A-continued

| Atomic coordinates of Aurora A + Inhibitory Monobody Mb60 + Danusertib | | | | | | | | | | | |
|---|---|---|---|---|---|---|---|---|---|---|---|
| ATOM | 3207 | CD1 | LEU | D | 196 | 8.919 | 18.355 | 27.999 | 1.00 | 36.99 | D | C |
| ATOM | 3208 | CD2 | LEU | D | 196 | 11.309 | 18.339 | 28.418 | 1.00 | 38.63 | D | C |
| ATOM | 3209 | C | LEU | D | 196 | 8.946 | 22.017 | 28.338 | 1.00 | 33.61 | D | C |
| ATOM | 3210 | O | LEU | D | 196 | 9.828 | 22.564 | 28.929 | 1.00 | 31.99 | D | O |
| ATOM | 3211 | N | TYR | D | 197 | 7.684 | 21.987 | 28.773 | 1.00 | 34.53 | D | N |
| ATOM | 3212 | CA | TYR | D | 197 | 7.272 | 22.784 | 29.916 | 1.00 | 35.09 | D | C |
| ATOM | 3213 | CB | TYR | D | 197 | 5.831 | 23.230 | 29.780 | 1.00 | 33.48 | D | C |
| ATOM | 3214 | CG | TYR | D | 197 | 5.647 | 24.177 | 28.674 | 1.00 | 30.80 | D | C |
| ATOM | 3215 | CD1 | TYR | D | 197 | 6.095 | 25.472 | 28.769 | 1.00 | 33.96 | D | C |
| ATOM | 3216 | CE1 | TYR | D | 197 | 5.921 | 26.363 | 27.718 | 1.00 | 37.91 | D | C |
| ATOM | 3217 | CZ | TYR | D | 197 | 5.255 | 25.932 | 26.537 | 1.00 | 37.04 | D | C |
| ATOM | 3218 | OH | TYR | D | 197 | 5.031 | 26.776 | 25.481 | 1.00 | 35.20 | D | O |
| ATOM | 3219 | CE2 | TYR | D | 197 | 4.821 | 24.645 | 26.433 | 1.00 | 33.20 | D | C |
| ATOM | 3220 | CD2 | TYR | D | 197 | 5.030 | 23.768 | 27.475 | 1.00 | 33.65 | D | C |
| ATOM | 3221 | C | TYR | D | 197 | 7.461 | 22.018 | 31.179 | 1.00 | 35.60 | D | C |
| ATOM | 3222 | O | TYR | D | 197 | 7.757 | 22.592 | 32.193 | 1.00 | 34.91 | D | O |
| ATOM | 3223 | N | GLY | D | 198 | 7.265 | 20.722 | 31.144 | 1.00 | 34.84 | D | N |
| ATOM | 3224 | CA | GLY | D | 198 | 7.397 | 19.956 | 32.348 | 1.00 | 34.14 | D | C |
| ATOM | 3225 | C | GLY | D | 198 | 7.219 | 18.499 | 32.017 | 1.00 | 38.01 | D | C |
| ATOM | 3226 | O | GLY | D | 198 | 6.935 | 18.099 | 30.848 | 1.00 | 36.68 | D | O |
| ATOM | 3227 | N | TYR | D | 199 | 7.420 | 17.695 | 33.045 | 1.00 | 33.46 | D | N |
| ATOM | 3228 | CA | TYR | D | 199 | 7.177 | 16.307 | 32.974 | 1.00 | 37.21 | D | C |
| ATOM | 3229 | CB | TYR | D | 199 | 8.456 | 15.614 | 32.556 | 1.00 | 35.62 | D | C |
| ATOM | 3230 | CG | TYR | D | 199 | 9.698 | 15.852 | 33.447 | 1.00 | 38.84 | D | C |
| ATOM | 3231 | CD1 | TYR | D | 199 | 10.519 | 16.974 | 33.282 | 1.00 | 41.88 | D | C |
| ATOM | 3232 | CE1 | TYR | D | 199 | 11.684 | 17.150 | 34.065 | 1.00 | 44.95 | D | C |
| ATOM | 3233 | CZ | TYR | D | 199 | 12.034 | 16.179 | 34.999 | 1.00 | 43.24 | D | C |
| ATOM | 3234 | OH | TYR | D | 199 | 13.173 | 16.287 | 35.787 | 1.00 | 47.76 | D | O |
| ATOM | 3235 | CE2 | TYR | D | 199 | 11.225 | 15.064 | 35.152 | 1.00 | 41.94 | D | C |
| ATOM | 3236 | CD2 | TYR | D | 199 | 10.087 | 14.901 | 34.381 | 1.00 | 38.84 | D | C |
| ATOM | 3237 | C | TYR | D | 199 | 6.653 | 15.710 | 34.281 | 1.00 | 36.44 | D | C |
| ATOM | 3238 | O | TYR | D | 199 | 6.795 | 16.264 | 35.320 | 1.00 | 34.30 | D | O |
| ATOM | 3239 | N | PHE | D | 200 | 6.083 | 14.535 | 34.200 | 1.00 | 35.25 | D | N |
| ATOM | 3240 | CA | PHE | D | 200 | 5.542 | 13.892 | 35.422 | 1.00 | 37.95 | D | C |
| ATOM | 3241 | CB | PHE | D | 200 | 4.306 | 14.636 | 35.935 | 1.00 | 33.93 | D | C |
| ATOM | 3242 | CG | PHE | D | 200 | 3.244 | 14.858 | 34.884 | 1.00 | 42.26 | D | C |
| ATOM | 3243 | CD1 | PHE | D | 200 | 3.160 | 16.063 | 34.187 | 1.00 | 44.38 | D | C |
| ATOM | 3244 | CE1 | PHE | D | 200 | 2.175 | 16.253 | 33.223 | 1.00 | 44.93 | D | C |
| ATOM | 3245 | CZ | PHE | D | 200 | 1.277 | 15.265 | 32.941 | 1.00 | 43.40 | D | C |
| ATOM | 3246 | CE2 | PHE | D | 200 | 1.333 | 14.074 | 33.640 | 1.00 | 48.38 | D | C |
| ATOM | 3247 | CD2 | PHE | D | 200 | 2.323 | 13.871 | 34.592 | 1.00 | 40.52 | D | C |
| ATOM | 3248 | C | PHE | D | 200 | 5.233 | 12.462 | 35.028 | 1.00 | 36.58 | D | C |
| ATOM | 3249 | O | PHE | D | 200 | 5.477 | 12.095 | 33.880 | 1.00 | 38.49 | D | O |
| ATOM | 3250 | N | HIS | D | 201 | 4.674 | 11.677 | 35.933 | 1.00 | 32.72 | D | N |
| ATOM | 3251 | CA | HIS | D | 201 | 4.584 | 10.253 | 35.708 | 1.00 | 33.28 | D | C |
| ATOM | 3252 | CB | HIS | D | 201 | 5.896 | 9.587 | 36.036 | 1.00 | 34.22 | D | C |
| ATOM | 3253 | CG | HIS | D | 201 | 6.200 | 9.606 | 37.486 | 1.00 | 34.78 | D | C |
| ATOM | 3254 | ND1 | HIS | D | 201 | 6.385 | 8.459 | 38.204 | 1.00 | 35.48 | D | N |
| ATOM | 3255 | CE1 | HIS | D | 201 | 6.606 | 8.762 | 39.470 | 1.00 | 36.44 | D | C |
| ATOM | 3256 | NE2 | HIS | D | 201 | 6.565 | 10.073 | 39.596 | 1.00 | 35.82 | D | N |
| ATOM | 3257 | CD2 | HIS | D | 201 | 6.272 | 10.626 | 38.375 | 1.00 | 37.06 | D | C |
| ATOM | 3258 | C | HIS | D | 201 | 3.480 | 9.630 | 36.543 | 1.00 | 34.99 | D | C |
| ATOM | 3259 | O | HIS | D | 201 | 2.910 | 10.282 | 37.389 | 1.00 | 34.17 | D | O |
| ATOM | 3260 | N | ASP | D | 202 | 3.172 | 8.377 | 36.232 | 1.00 | 35.02 | D | N |
| ATOM | 3261 | CA | ASP | D | 202 | 2.312 | 7.557 | 37.046 | 1.00 | 36.01 | D | C |
| ATOM | 3262 | CB | ASP | D | 202 | 0.850 | 7.658 | 36.572 | 1.00 | 37.46 | D | C |
| ATOM | 3263 | CG | ASP | D | 202 | 0.609 | 7.071 | 35.148 | 1.00 | 40.53 | D | C |
| ATOM | 3264 | OD1 | ASP | D | 202 | 1.357 | 6.190 | 34.590 | 1.00 | 43.07 | D | O |
| ATOM | 3265 | OD2 | ASP | D | 202 | −0.405 | 7.511 | 34.580 | 1.00 | 38.28 | D | O |
| ATOM | 3266 | C | ASP | D | 202 | 2.932 | 6.169 | 36.965 | 1.00 | 39.46 | D | C |
| ATOM | 3267 | O | ASP | D | 202 | 4.082 | 6.042 | 36.493 | 1.00 | 36.38 | D | O |
| ATOM | 3268 | N | ALA | D | 203 | 2.190 | 5.139 | 37.376 | 1.00 | 39.93 | D | N |
| ATOM | 3269 | CA | ALA | D | 203 | 2.747 | 3.789 | 37.516 | 1.00 | 41.75 | D | C |
| ATOM | 3270 | CB | ALA | D | 203 | 1.688 | 2.835 | 38.103 | 1.00 | 41.17 | D | C |
| ATOM | 3271 | C | ALA | D | 203 | 3.306 | 3.203 | 36.233 | 1.00 | 43.54 | D | C |
| ATOM | 3272 | O | ALA | D | 203 | 4.302 | 2.459 | 36.269 | 1.00 | 46.74 | D | O |
| ATOM | 3273 | N | THR | D | 204 | 2.653 | 3.506 | 35.108 | 1.00 | 45.60 | D | N |
| ATOM | 3274 | CA | THR | D | 204 | 3.005 | 2.890 | 33.803 | 1.00 | 42.83 | D | C |
| ATOM | 3275 | CB | THR | D | 204 | 1.754 | 2.190 | 33.167 | 1.00 | 42.57 | D | C |
| ATOM | 3276 | OG1 | THR | D | 204 | 0.582 | 3.032 | 33.297 | 1.00 | 39.95 | D | O |
| ATOM | 3277 | CG2 | THR | D | 204 | 1.481 | 0.827 | 33.915 | 1.00 | 41.36 | D | C |
| ATOM | 3278 | C | THR | D | 204 | 3.672 | 3.866 | 32.783 | 1.00 | 40.29 | D | C |
| ATOM | 3279 | O | THR | D | 204 | 4.291 | 3.433 | 31.806 | 1.00 | 44.42 | D | O |
| ATOM | 3280 | N | ARG | D | 205 | 3.555 | 5.155 | 33.029 | 1.00 | 38.73 | D | N |
| ATOM | 3281 | CA | ARG | D | 205 | 3.875 | 6.167 | 32.025 | 1.00 | 40.26 | D | C |
| ATOM | 3282 | CB | ARG | D | 205 | 2.577 | 6.718 | 31.425 | 1.00 | 37.59 | D | C |
| ATOM | 3283 | CG | ARG | D | 205 | 1.929 | 5.696 | 30.508 | 1.00 | 44.65 | D | C |
| ATOM | 3284 | CD | ARG | D | 205 | 0.448 | 5.906 | 30.303 | 1.00 | 44.76 | D | C |

APPENDIX A-continued

| Atomic coordinates of Aurora A + Inhibitory Monobody Mb60 + Danusertib | | | | | | | | | | | |
|---|---|---|---|---|---|---|---|---|---|---|---|
| ATOM | 3285 | NE | ARG | D | 205 | −0.249 | 5.749 | 31.536 | 1.00 | 47.86 | D | N |
| ATOM | 3286 | CZ | ARG | D | 205 | −1.571 | 5.663 | 31.652 | 1.00 | 50.92 | D | C |
| ATOM | 3287 | NH1 | ARG | D | 205 | −2.374 | 5.705 | 30.586 | 1.00 | 52.40 | D | N |
| ATOM | 3288 | NH2 | ARG | D | 205 | −2.083 | 5.562 | 32.863 | 1.00 | 47.10 | D | N |
| ATOM | 3289 | C | ARG | D | 205 | 4.679 | 7.345 | 32.544 | 1.00 | 36.86 | D | C |
| ATOM | 3290 | O | ARG | D | 205 | 4.550 | 7.779 | 33.708 | 1.00 | 37.40 | D | O |
| ATOM | 3291 | N | VAL | D | 206 | 5.458 | 7.899 | 31.610 | 1.00 | 34.70 | D | N |
| ATOM | 3292 | CA | VAL | D | 206 | 6.039 | 9.187 | 31.744 | 1.00 | 33.34 | D | C |
| ATOM | 3293 | CB | VAL | D | 206 | 7.528 | 9.156 | 31.411 | 1.00 | 33.69 | D | C |
| ATOM | 3294 | CG1 | VAL | D | 206 | 8.106 | 10.514 | 31.687 | 1.00 | 34.10 | D | C |
| ATOM | 3295 | CG2 | VAL | D | 206 | 8.226 | 8.026 | 32.177 | 1.00 | 34.91 | D | C |
| ATOM | 3296 | C | VAL | D | 206 | 5.336 | 10.072 | 30.737 | 1.00 | 31.61 | D | C |
| ATOM | 3297 | O | VAL | D | 206 | 5.136 | 9.702 | 29.566 | 1.00 | 33.29 | D | O |
| ATOM | 3298 | N | TYR | D | 207 | 4.983 | 11.259 | 31.210 | 1.00 | 33.42 | D | N |
| ATOM | 3299 | CA | TYR | D | 207 | 4.290 | 12.256 | 30.475 | 1.00 | 33.40 | D | C |
| ATOM | 3300 | CB | TYR | D | 207 | 3.082 | 12.727 | 31.271 | 1.00 | 34.26 | D | C |
| ATOM | 3301 | CG | TYR | D | 207 | 2.073 | 11.643 | 31.508 | 1.00 | 41.60 | D | C |
| ATOM | 3302 | CD1 | TYR | D | 207 | 2.068 | 10.896 | 32.685 | 1.00 | 39.72 | D | C |
| ATOM | 3303 | CE1 | TYR | D | 207 | 1.134 | 9.898 | 32.881 | 1.00 | 41.78 | D | C |
| ATOM | 3304 | CZ | TYR | D | 207 | 0.168 | 9.659 | 31.914 | 1.00 | 45.10 | D | C |
| ATOM | 3305 | OH | TYR | D | 207 | −0.759 | 8.679 | 32.068 | 1.00 | 43.94 | D | O |
| ATOM | 3306 | CE2 | TYR | D | 207 | 0.155 | 10.373 | 30.739 | 1.00 | 46.10 | D | C |
| ATOM | 3307 | CD2 | TYR | D | 207 | 1.104 | 11.343 | 30.532 | 1.00 | 43.84 | D | C |
| ATOM | 3308 | C | TYR | D | 207 | 5.244 | 13.463 | 30.302 | 1.00 | 37.46 | D | C |
| ATOM | 3309 | O | TYR | D | 207 | 5.929 | 13.824 | 31.274 | 1.00 | 35.82 | D | O |
| ATOM | 3310 | N | LEU | D | 208 | 5.253 | 14.059 | 29.091 | 1.00 | 35.09 | D | N |
| ATOM | 3311 | CA | LEU | D | 208 | 5.928 | 15.321 | 28.806 | 1.00 | 32.21 | D | C |
| ATOM | 3312 | CB | LEU | D | 208 | 7.009 | 15.169 | 27.753 | 1.00 | 36.32 | D | C |
| ATOM | 3313 | CG | LEU | D | 208 | 8.368 | 14.637 | 28.168 | 1.00 | 38.51 | D | C |
| ATOM | 3314 | CD1 | LEU | D | 208 | 8.286 | 13.335 | 28.925 | 1.00 | 42.55 | D | C |
| ATOM | 3315 | CD2 | LEU | D | 208 | 9.209 | 14.452 | 26.922 | 1.00 | 39.18 | D | C |
| ATOM | 3316 | C | LEU | D | 208 | 4.889 | 16.229 | 28.316 | 1.00 | 30.76 | D | C |
| ATOM | 3317 | O | LEU | D | 208 | 4.033 | 15.806 | 27.512 | 1.00 | 35.13 | D | O |
| ATOM | 3318 | N | ILE | D | 209 | 4.910 | 17.460 | 28.822 | 1.00 | 28.59 | D | N |
| ATOM | 3319 | CA | ILE | D | 209 | 4.029 | 18.544 | 28.377 | 1.00 | 31.08 | D | C |
| ATOM | 3320 | CB | ILE | D | 209 | 3.588 | 19.492 | 29.527 | 1.00 | 37.65 | D | C |
| ATOM | 3321 | CG1 | ILE | D | 209 | 2.896 | 18.700 | 30.640 | 1.00 | 50.19 | D | C |
| ATOM | 3322 | CD1 | ILE | D | 209 | 3.114 | 19.316 | 32.006 | 1.00 | 58.07 | D | C |
| ATOM | 3323 | CG2 | ILE | D | 209 | 2.603 | 20.541 | 29.032 | 1.00 | 35.72 | D | C |
| ATOM | 3324 | C | ILE | D | 209 | 4.837 | 19.417 | 27.455 | 1.00 | 31.28 | D | C |
| ATOM | 3325 | O | ILE | D | 209 | 5.816 | 20.035 | 27.868 | 1.00 | 31.58 | D | O |
| ATOM | 3326 | N | LEU | D | 210 | 4.425 | 19.487 | 26.205 | 1.00 | 29.10 | D | N |
| ATOM | 3327 | CA | LEU | D | 210 | 5.188 | 20.188 | 25.187 | 1.00 | 28.09 | D | C |
| ATOM | 3328 | CB | LEU | D | 210 | 5.646 | 19.132 | 24.185 | 1.00 | 29.45 | D | C |
| ATOM | 3329 | CG | LEU | D | 210 | 6.639 | 18.090 | 24.685 | 1.00 | 29.50 | D | C |
| ATOM | 3330 | CD1 | LEU | D | 210 | 6.543 | 16.792 | 23.935 | 1.00 | 32.32 | D | C |
| ATOM | 3331 | CD2 | LEU | D | 210 | 8.067 | 18.551 | 24.501 | 1.00 | 30.49 | D | C |
| ATOM | 3332 | C | LEU | D | 210 | 4.385 | 21.256 | 24.473 | 1.00 | 26.25 | D | C |
| ATOM | 3333 | O | LEU | D | 210 | 3.176 | 21.209 | 24.424 | 1.00 | 31.81 | D | O |
| ATOM | 3334 | N | GLU | D | 211 | 5.067 | 22.220 | 23.902 | 1.00 | 30.22 | D | N |
| ATOM | 3335 | CA | GLU | D | 211 | 4.455 | 23.133 | 22.959 | 1.00 | 26.86 | D | C |
| ATOM | 3336 | CB | GLU | D | 211 | 5.531 | 24.065 | 22.429 | 1.00 | 27.56 | D | C |
| ATOM | 3337 | CG | GLU | D | 211 | 5.127 | 25.116 | 21.418 | 1.00 | 28.25 | D | C |
| ATOM | 3338 | CD | GLU | D | 211 | 6.329 | 25.880 | 20.901 | 1.00 | 30.09 | D | C |
| ATOM | 3339 | OE1 | GLU | D | 211 | 7.490 | 25.565 | 21.334 | 1.00 | 27.11 | D | O |
| ATOM | 3340 | OE2 | GLU | D | 211 | 6.147 | 26.764 | 20.013 | 1.00 | 29.89 | D | O |
| ATOM | 3341 | C | GLU | D | 211 | 3.792 | 22.354 | 21.786 | 1.00 | 28.29 | D | C |
| ATOM | 3342 | O | GLU | D | 211 | 4.331 | 21.328 | 21.289 | 1.00 | 26.18 | D | O |
| ATOM | 3343 | N | TYR | D | 212 | 2.644 | 22.882 | 21.331 | 1.00 | 26.21 | D | N |
| ATOM | 3344 | CA | TYR | D | 212 | 1.931 | 22.299 | 20.227 | 1.00 | 27.72 | D | C |
| ATOM | 3345 | CB | TYR | D | 212 | 0.451 | 22.480 | 20.422 | 1.00 | 29.36 | D | C |
| ATOM | 3346 | CG | TYR | D | 212 | −0.386 | 22.173 | 19.237 | 1.00 | 29.40 | D | C |
| ATOM | 3347 | CD1 | TYR | D | 212 | −0.290 | 20.951 | 18.614 | 1.00 | 28.05 | D | C |
| ATOM | 3348 | CE1 | TYR | D | 212 | −1.088 | 20.643 | 17.536 | 1.00 | 36.04 | D | C |
| ATOM | 3349 | CZ | TYR | D | 212 | −2.028 | 21.559 | 17.091 | 1.00 | 33.41 | D | C |
| ATOM | 3350 | OH | TYR | D | 212 | −2.733 | 21.207 | 16.013 | 1.00 | 34.70 | D | O |
| ATOM | 3351 | CE2 | TYR | D | 212 | −2.168 | 22.788 | 17.687 | 1.00 | 33.62 | D | C |
| ATOM | 3352 | CD2 | TYR | D | 212 | −1.319 | 23.103 | 18.760 | 1.00 | 33.17 | D | C |
| ATOM | 3353 | C | TYR | D | 212 | 2.443 | 22.957 | 18.943 | 1.00 | 25.28 | D | C |
| ATOM | 3354 | O | TYR | D | 212 | 2.497 | 24.192 | 18.817 | 1.00 | 24.28 | D | O |
| ATOM | 3355 | N | ALA | D | 213 | 2.890 | 22.126 | 18.007 | 1.00 | 27.14 | D | N |
| ATOM | 3356 | CA | ALA | D | 213 | 3.355 | 22.685 | 16.721 | 1.00 | 29.09 | D | C |
| ATOM | 3357 | CB | ALA | D | 213 | 4.726 | 22.167 | 16.395 | 1.00 | 29.41 | D | C |
| ATOM | 3358 | C | ALA | D | 213 | 2.300 | 22.221 | 15.704 | 1.00 | 28.21 | D | C |
| ATOM | 3359 | O | ALA | D | 213 | 2.233 | 21.033 | 15.362 | 1.00 | 29.51 | D | O |
| ATOM | 3360 | N | PRO | D | 214 | 1.419 | 23.147 | 15.290 | 1.00 | 29.02 | D | N |
| ATOM | 3361 | CA | PRO | D | 214 | 0.213 | 22.721 | 14.536 | 1.00 | 32.04 | D | C |
| ATOM | 3362 | CB | PRO | D | 214 | −0.698 | 23.975 | 14.569 | 1.00 | 33.72 | D | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 3363 | CG | PRO | D | 214 | 0.200 | 25.103 | 14.930 | 1.00 | 32.15 | D | C |
| ATOM | 3364 | CD | PRO | D | 214 | 1.340 | 24.541 | 15.702 | 1.00 | 29.34 | D | C |
| ATOM | 3365 | C | PRO | D | 214 | 0.469 | 22.322 | 13.081 | 1.00 | 32.79 | D | C |
| ATOM | 3366 | O | PRO | D | 214 | −0.430 | 21.743 | 12.459 | 1.00 | 31.88 | D | O |
| ATOM | 3367 | N | LEU | D | 215 | 1.642 | 22.635 | 12.507 | 1.00 | 30.16 | D | N |
| ATOM | 3368 | CA | LEU | D | 215 | 1.820 | 22.329 | 11.053 | 1.00 | 28.84 | D | C |
| ATOM | 3369 | CB | LEU | D | 215 | 2.413 | 23.510 | 10.336 | 1.00 | 28.94 | D | C |
| ATOM | 3370 | CG | LEU | D | 215 | 1.418 | 24.489 | 9.759 | 1.00 | 33.83 | D | C |
| ATOM | 3371 | CD1 | LEU | D | 215 | 0.388 | 24.918 | 10.780 | 1.00 | 38.67 | D | C |
| ATOM | 3372 | CD2 | LEU | D | 215 | 2.167 | 25.701 | 9.174 | 1.00 | 36.59 | D | C |
| ATOM | 3373 | C | LEU | D | 215 | 2.561 | 21.038 | 10.788 | 1.00 | 28.50 | D | C |
| ATOM | 3374 | O | LEU | D | 215 | 2.844 | 20.676 | 9.646 | 1.00 | 30.18 | D | O |
| ATOM | 3375 | N | GLY | D | 216 | 2.826 | 20.281 | 11.844 | 1.00 | 28.85 | D | N |
| ATOM | 3376 | CA | GLY | D | 216 | 3.334 | 18.963 | 11.697 | 1.00 | 27.95 | D | C |
| ATOM | 3377 | C | GLY | D | 216 | 4.819 | 19.017 | 11.412 | 1.00 | 27.75 | D | C |
| ATOM | 3378 | O | GLY | D | 216 | 5.475 | 20.042 | 11.733 | 1.00 | 28.82 | D | O |
| ATOM | 3379 | N | THR | D | 217 | 5.319 | 17.943 | 10.802 | 1.00 | 28.13 | D | N |
| ATOM | 3380 | CA | THR | D | 217 | 6.686 | 17.795 | 10.452 | 1.00 | 27.88 | D | C |
| ATOM | 3381 | CB | THR | D | 217 | 7.176 | 16.334 | 10.473 | 1.00 | 30.27 | D | C |
| ATOM | 3382 | OG1 | THR | D | 217 | 6.693 | 15.590 | 9.354 | 1.00 | 31.67 | D | O |
| ATOM | 3383 | CG2 | THR | D | 217 | 6.781 | 15.605 | 11.718 | 1.00 | 29.99 | D | C |
| ATOM | 3384 | C | THR | D | 217 | 7.087 | 18.411 | 9.112 | 1.00 | 29.32 | D | C |
| ATOM | 3385 | O | THR | D | 217 | 6.366 | 18.383 | 8.126 | 1.00 | 27.69 | D | O |
| ATOM | 3386 | N | VAL | D | 218 | 8.297 | 18.930 | 9.065 | 1.00 | 27.52 | D | N |
| ATOM | 3387 | CA | VAL | D | 218 | 8.799 | 19.458 | 7.818 | 1.00 | 27.19 | D | C |
| ATOM | 3388 | CB | VAL | D | 218 | 10.060 | 20.346 | 8.010 | 1.00 | 28.69 | D | C |
| ATOM | 3389 | CG1 | VAL | D | 218 | 11.277 | 19.484 | 8.223 | 1.00 | 31.53 | D | C |
| ATOM | 3390 | CG2 | VAL | D | 218 | 10.326 | 21.151 | 6.775 | 1.00 | 29.11 | D | C |
| ATOM | 3391 | C | VAL | D | 218 | 9.010 | 18.320 | 6.839 | 1.00 | 23.08 | D | C |
| ATOM | 3392 | O | VAL | D | 218 | 8.944 | 18.531 | 5.607 | 1.00 | 25.13 | D | O |
| ATOM | 3393 | N | TYR | D | 219 | 9.248 | 17.108 | 7.329 | 1.00 | 23.03 | D | N |
| ATOM | 3394 | CA | TYR | D | 219 | 9.300 | 15.960 | 6.458 | 1.00 | 24.09 | D | C |
| ATOM | 3395 | CB | TYR | D | 219 | 9.475 | 14.708 | 7.265 | 1.00 | 29.89 | D | C |
| ATOM | 3396 | CG | TYR | D | 219 | 9.685 | 13.514 | 6.382 | 1.00 | 37.74 | D | C |
| ATOM | 3397 | CD1 | TYR | D | 219 | 10.886 | 13.365 | 5.739 | 1.00 | 39.90 | D | C |
| ATOM | 3398 | CE1 | TYR | D | 219 | 11.123 | 12.321 | 4.888 | 1.00 | 45.20 | D | C |
| ATOM | 3399 | CZ | TYR | D | 219 | 10.167 | 11.388 | 4.672 | 1.00 | 46.44 | D | C |
| ATOM | 3400 | OH | TYR | D | 219 | 10.537 | 10.407 | 3.783 | 1.00 | 58.95 | D | O |
| ATOM | 3401 | CE2 | TYR | D | 219 | 8.911 | 11.479 | 5.293 | 1.00 | 44.31 | D | C |
| ATOM | 3402 | CD2 | TYR | D | 219 | 8.672 | 12.566 | 6.143 | 1.00 | 39.62 | D | C |
| ATOM | 3403 | C | TYR | D | 219 | 8.012 | 15.749 | 5.599 | 1.00 | 28.24 | D | C |
| ATOM | 3404 | O | TYR | D | 219 | 8.086 | 15.397 | 4.430 | 1.00 | 22.63 | D | O |
| ATOM | 3405 | N | ARG | D | 220 | 6.838 | 15.887 | 6.199 | 1.00 | 27.10 | D | N |
| ATOM | 3406 | CA | ARG | D | 220 | 5.615 | 15.690 | 5.438 | 1.00 | 29.14 | D | C |
| ATOM | 3407 | CB | ARG | D | 220 | 4.358 | 15.620 | 6.355 | 1.00 | 32.98 | D | C |
| ATOM | 3408 | CG | ARG | D | 220 | 4.188 | 14.430 | 7.297 | 1.00 | 43.33 | D | C |
| ATOM | 3409 | CD | ARG | D | 220 | 3.951 | 13.043 | 6.669 | 1.00 | 51.23 | D | C |
| ATOM | 3410 | NE | ARG | D | 220 | 4.514 | 12.012 | 7.570 | 1.00 | 67.30 | D | N |
| ATOM | 3411 | CZ | ARG | D | 220 | 4.804 | 10.734 | 7.262 | 1.00 | 73.77 | D | C |
| ATOM | 3412 | NH1 | ARG | D | 220 | 5.358 | 9.945 | 8.197 | 1.00 | 75.28 | D | N |
| ATOM | 3413 | NH2 | ARG | D | 220 | 4.552 | 10.225 | 6.055 | 1.00 | 69.17 | D | N |
| ATOM | 3414 | C | ARG | D | 220 | 5.466 | 16.850 | 4.420 | 1.00 | 27.70 | D | C |
| ATOM | 3415 | O | ARG | D | 220 | 4.953 | 16.698 | 3.327 | 1.00 | 24.80 | D | O |
| ATOM | 3416 | N | GLU | D | 221 | 5.881 | 18.027 | 4.784 | 1.00 | 25.65 | D | N |
| ATOM | 3417 | CA | GLU | D | 221 | 5.870 | 19.082 | 3.811 | 1.00 | 28.33 | D | C |
| ATOM | 3418 | CB | GLU | D | 221 | 6.291 | 20.376 | 4.429 | 1.00 | 27.03 | D | C |
| ATOM | 3419 | CG | GLU | D | 221 | 5.191 | 20.936 | 5.316 | 1.00 | 28.50 | D | C |
| ATOM | 3420 | CD | GLU | D | 221 | 4.068 | 21.592 | 4.497 | 1.00 | 30.94 | D | C |
| ATOM | 3421 | OE1 | GLU | D | 221 | 4.367 | 22.337 | 3.543 | 1.00 | 33.26 | D | O |
| ATOM | 3422 | OE2 | GLU | D | 221 | 2.915 | 21.298 | 4.805 | 1.00 | 29.42 | D | O |
| ATOM | 3423 | C | GLU | D | 221 | 6.790 | 18.720 | 2.623 | 1.00 | 27.12 | D | C |
| ATOM | 3424 | O | GLU | D | 221 | 6.471 | 18.960 | 1.449 | 1.00 | 26.07 | D | O |
| ATOM | 3425 | N | LEU | D | 222 | 7.955 | 18.203 | 2.915 | 1.00 | 28.32 | D | N |
| ATOM | 3426 | CA | LEU | D | 222 | 8.912 | 17.911 | 1.835 | 1.00 | 30.69 | D | C |
| ATOM | 3427 | CB | LEU | D | 222 | 10.245 | 17.407 | 2.372 | 1.00 | 28.83 | D | C |
| ATOM | 3428 | CG | LEU | D | 222 | 11.412 | 17.408 | 1.408 | 1.00 | 29.12 | D | C |
| ATOM | 3429 | CD1 | LEU | D | 222 | 11.617 | 18.771 | 0.810 | 1.00 | 27.50 | D | C |
| ATOM | 3430 | CD2 | LEU | D | 222 | 12.697 | 16.995 | 2.133 | 1.00 | 34.00 | D | C |
| ATOM | 3431 | C | LEU | D | 222 | 8.352 | 16.872 | 0.890 | 1.00 | 26.29 | D | C |
| ATOM | 3432 | O | LEU | D | 222 | 8.567 | 16.959 | −0.292 | 1.00 | 28.46 | D | O |
| ATOM | 3433 | N | GLN | D | 223 | 7.665 | 15.862 | 1.437 | 1.00 | 27.94 | D | N |
| ATOM | 3434 | CA | GLN | D | 223 | 7.007 | 14.800 | 0.657 | 1.00 | 28.84 | D | C |
| ATOM | 3435 | CB | GLN | D | 223 | 6.360 | 13.757 | 1.563 | 1.00 | 30.63 | D | C |
| ATOM | 3436 | CG | GLN | D | 223 | 7.378 | 12.914 | 2.326 | 1.00 | 38.73 | D | C |
| ATOM | 3437 | CD | GLN | D | 223 | 7.022 | 11.423 | 2.293 | 1.00 | 52.14 | D | C |
| ATOM | 3438 | OE1 | GLN | D | 223 | 6.545 | 10.875 | 3.295 | 1.00 | 67.54 | D | O |
| ATOM | 3439 | NE2 | GLN | D | 223 | 7.196 | 10.777 | 1.125 | 1.00 | 53.23 | D | N |
| ATOM | 3440 | C | GLN | D | 223 | 5.901 | 15.362 | −0.201 | 1.00 | 26.57 | D | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 3441 | O | GLN | D | 223 | 5.736 | 14.934 | −1.339 | 1.00 | 22.88 | D | O |
| ATOM | 3442 | N | LYS | D | 224 | 5.205 | 16.358 | 0.334 | 1.00 | 23.50 | D | N |
| ATOM | 3443 | CA | LYS | D | 224 | 4.150 | 16.994 | −0.405 | 1.00 | 24.67 | D | C |
| ATOM | 3444 | CB | LYS | D | 224 | 3.318 | 17.759 | 0.607 | 1.00 | 27.41 | D | C |
| ATOM | 3445 | CG | LYS | D | 224 | 2.219 | 18.645 | 0.035 | 1.00 | 27.69 | D | C |
| ATOM | 3446 | CD | LYS | D | 224 | 1.349 | 19.113 | 1.196 | 1.00 | 24.96 | D | C |
| ATOM | 3447 | CE | LYS | D | 224 | 1.966 | 20.322 | 1.827 | 1.00 | 27.32 | D | C |
| ATOM | 3448 | NZ | LYS | D | 224 | 1.010 | 20.809 | 2.812 | 1.00 | 28.93 | D | N |
| ATOM | 3449 | C | LYS | D | 224 | 4.660 | 17.915 | −1.560 | 1.00 | 22.65 | D | C |
| ATOM | 3450 | O | LYS | D | 224 | 4.112 | 17.888 | −2.667 | 1.00 | 19.86 | D | O |
| ATOM | 3451 | N | LEU | D | 225 | 5.731 | 18.672 | −1.347 | 1.00 | 22.90 | D | N |
| ATOM | 3452 | CA | LEU | D | 225 | 6.224 | 19.595 | −2.337 | 1.00 | 23.80 | D | C |
| ATOM | 3453 | CB | LEU | D | 225 | 6.738 | 20.859 | −1.677 | 1.00 | 29.27 | N | C |
| ATOM | 3454 | CG | LEU | D | 225 | 5.641 | 21.710 | −0.979 | 1.00 | 36.10 | D | C |
| ATOM | 3455 | CD1 | LEU | D | 225 | 6.265 | 22.890 | −0.323 | 1.00 | 42.85 | D | C |
| ATOM | 3456 | CD2 | LEU | D | 225 | 4.601 | 22.248 | −1.909 | 1.00 | 41.68 | D | C |
| ATOM | 3457 | C | LEU | D | 225 | 7.309 | 18.983 | −3.192 | 1.00 | 26.72 | D | C |
| ATOM | 3458 | O | LEU | D | 225 | 7.603 | 19.572 | −4.186 | 1.00 | 26.71 | D | O |
| ATOM | 3459 | N | SER | D | 226 | 7.883 | 17.843 | −2.766 | 1.00 | 27.85 | D | N |
| ATOM | 3460 | CA | SER | D | 226 | 9.104 | 17.119 | −3.308 | 1.00 | 32.82 | D | C |
| ATOM | 3461 | CB | SER | D | 226 | 9.118 | 16.860 | −4.845 | 1.00 | 33.66 | D | C |
| ATOM | 3462 | OG | SER | D | 226 | 8.022 | 16.035 | −5.134 | 1.00 | 38.86 | D | O |
| ATOM | 3463 | C | SER | D | 226 | 10.405 | 17.767 | −2.967 | 1.00 | 28.82 | D | C |
| ATOM | 3464 | O | SER | D | 226 | 11.322 | 17.093 | −2.647 | 1.00 | 29.90 | D | O |
| ATOM | 3465 | N | LYS | D | 227 | 10.486 | 19.055 | −3.175 | 1.00 | 25.91 | D | N |
| ATOM | 3466 | CA | LYS | D | 227 | 11.645 | 19.830 | −2.782 | 1.00 | 25.86 | D | C |
| ATOM | 3467 | CB | LYS | D | 227 | 12.672 | 19.789 | −3.941 | 1.00 | 28.08 | D | C |
| ATOM | 3468 | CG | LYS | D | 227 | 12.235 | 20.337 | −5.299 | 1.00 | 29.31 | D | C |
| ATOM | 3469 | CD | LYS | D | 227 | 13.258 | 19.874 | −6.404 | 1.00 | 30.08 | D | C |
| ATOM | 3470 | CE | LYS | D | 227 | 12.966 | 20.402 | −7.780 | 1.00 | 31.86 | D | C |
| ATOM | 3471 | NZ | LYS | D | 227 | 12.936 | 21.905 | −7.688 | 1.00 | 38.68 | D | N |
| ATOM | 3472 | C | LYS | D | 227 | 11.173 | 21.194 | −2.475 | 1.00 | 26.80 | D | C |
| ATOM | 3473 | O | LYS | D | 227 | 10.047 | 21.552 | −2.863 | 1.00 | 27.65 | D | O |
| ATOM | 3474 | N | PHE | D | 228 | 11.969 | 21.970 | −1.734 | 1.00 | 25.63 | D | N |
| ATOM | 3475 | CA | PHE | D | 228 | 11.591 | 23.364 | −1.412 | 1.00 | 24.89 | D | C |
| ATOM | 3476 | CB | PHE | D | 228 | 11.884 | 23.700 | 0.027 | 1.00 | 24.70 | D | C |
| ATOM | 3477 | CG | PHE | D | 228 | 11.120 | 22.869 | 1.017 | 1.00 | 27.27 | D | C |
| ATOM | 3478 | CD1 | PHE | D | 228 | 9.783 | 22.534 | 0.813 | 1.00 | 27.55 | D | C |
| ATOM | 3479 | CE1 | PHE | D | 228 | 9.120 | 21.762 | 1.729 | 1.00 | 26.48 | D | C |
| ATOM | 3480 | CZ | PHE | D | 228 | 9.767 | 21.289 | 2.871 | 1.00 | 25.01 | D | C |
| ATOM | 3481 | CE2 | PHE | D | 228 | 11.086 | 21.542 | 3.057 | 1.00 | 25.99 | D | C |
| ATOM | 3482 | CD2 | PHE | D | 228 | 11.767 | 22.367 | 2.163 | 1.00 | 26.58 | D | C |
| ATOM | 3483 | C | PHE | D | 228 | 12.313 | 24.331 | −2.286 | 1.00 | 26.54 | D | C |
| ATOM | 3484 | O | PHE | D | 228 | 13.376 | 24.027 | −2.757 | 1.00 | 34.94 | D | O |
| ATOM | 3485 | N | ASP | D | 229 | 11.749 | 25.482 | −2.549 | 1.00 | 24.29 | D | N |
| ATOM | 3486 | CA | ASP | D | 229 | 12.427 | 26.481 | −3.307 | 1.00 | 27.98 | D | C |
| ATOM | 3487 | CB | ASP | D | 229 | 11.454 | 27.451 | −3.992 | 1.00 | 26.33 | D | C |
| ATOM | 3488 | CG | ASP | D | 229 | 10.661 | 28.306 | −3.003 | 1.00 | 31.36 | D | C |
| ATOM | 3489 | OD1 | ASP | D | 229 | 11.092 | 28.684 | −1.899 | 1.00 | 33.06 | D | O |
| ATOM | 3490 | OD2 | ASP | D | 229 | 9.565 | 28.629 | −3.371 | 1.00 | 31.60 | D | O |
| ATOM | 3491 | C | ASP | D | 229 | 13.450 | 27.217 | −2.408 | 1.00 | 27.79 | D | C |
| ATOM | 3492 | O | ASP | D | 229 | 13.564 | 26.934 | −1.252 | 1.00 | 29.63 | D | O |
| ATOM | 3493 | N | GLU | D | 230 | 14.188 | 28.135 | −3.010 | 1.00 | 27.80 | D | N |
| ATOM | 3494 | CA | GLU | D | 230 | 15.312 | 28.781 | −2.402 | 1.00 | 29.97 | D | C |
| ATOM | 3495 | CB | GLU | D | 230 | 16.056 | 29.561 | −3.453 | 1.00 | 30.03 | D | C |
| ATOM | 3496 | CG | GLU | D | 230 | 16.669 | 28.653 | −4.501 | 1.00 | 31.87 | D | C |
| ATOM | 3497 | CD | GLU | D | 230 | 17.829 | 29.338 | −5.246 | 1.00 | 35.17 | D | C |
| ATOM | 3498 | OE1 | GLU | D | 230 | 17.599 | 30.307 | −5.990 | 1.00 | 37.63 | D | O |
| ATOM | 3499 | OE2 | GLU | D | 230 | 18.993 | 28.911 | −5.078 | 1.00 | 32.89 | D | O |
| ATOM | 3500 | C | GLU | D | 230 | 14.929 | 29.650 | −1.244 | 1.00 | 29.14 | D | C |
| ATOM | 3501 | O | GLU | D | 230 | 15.637 | 29.712 | −0.211 | 1.00 | 28.42 | D | O |
| ATOM | 3502 | N | GLN | D | 231 | 13.765 | 30.280 | −1.357 | 1.00 | 31.67 | D | N |
| ATOM | 3503 | CA | GLN | D | 231 | 13.334 | 31.212 | −0.326 | 1.00 | 30.80 | D | C |
| ATOM | 3504 | CB | GLN | D | 231 | 12.175 | 32.065 | −0.831 | 1.00 | 34.04 | D | C |
| ATOM | 3505 | CG | GLN | D | 231 | 12.581 | 33.072 | −1.934 | 1.00 | 42.11 | D | C |
| ATOM | 3506 | CD | GLN | D | 231 | 13.081 | 32.496 | −3.309 | 1.00 | 48.36 | D | C |
| ATOM | 3507 | OE1 | GLN | D | 231 | 12.532 | 31.521 | −3.920 | 1.00 | 36.98 | D | O |
| ATOM | 3508 | NE2 | GLN | D | 231 | 14.148 | 33.133 | −3.809 | 1.00 | 45.47 | D | N |
| ATOM | 3509 | C | GLN | D | 231 | 12.924 | 30.403 | 0.895 | 1.00 | 27.20 | D | C |
| ATOM | 3510 | O | GLN | D | 231 | 13.267 | 30.751 | 2.024 | 1.00 | 28.42 | D | O |
| ATOM | 3511 | N | ARG | D | 232 | 12.164 | 29.346 | 0.675 | 1.00 | 26.47 | D | N |
| ATOM | 3512 | CA | ARG | D | 232 | 11.669 | 28.518 | 1.793 | 1.00 | 27.37 | D | C |
| ATOM | 3513 | CB | ARG | D | 232 | 10.652 | 27.450 | 1.347 | 1.00 | 31.49 | D | C |
| ATOM | 3514 | CG | ARG | D | 232 | 10.018 | 26.857 | 2.598 | 1.00 | 37.86 | D | C |
| ATOM | 3515 | CD | ARG | D | 232 | 9.374 | 25.509 | 2.534 | 1.00 | 43.75 | D | C |
| ATOM | 3516 | NE | ARG | D | 232 | 8.039 | 25.581 | 2.082 | 1.00 | 42.84 | D | N |
| ATOM | 3517 | CZ | ARG | D | 232 | 6.941 | 24.995 | 2.579 | 1.00 | 37.92 | D | C |
| ATOM | 3518 | NH1 | ARG | D | 232 | 6.890 | 24.173 | 3.598 | 1.00 | 30.80 | D | N |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 3519 | NH2 | ARG | D | 232 | 5.830 | 25.238 | 1.926 | 1.00 | 41.04 | D | N |
| ATOM | 3520 | C | ARG | D | 232 | 12.867 | 27.871 | 2.493 | 1.00 | 23.60 | D | C |
| ATOM | 3521 | O | ARG | D | 232 | 12.964 | 27.830 | 3.716 | 1.00 | 26.78 | D | O |
| ATOM | 3522 | N | THR | D | 233 | 13.788 | 27.390 | 1.680 | 1.00 | 22.69 | D | N |
| ATOM | 3523 | CA | THR | D | 233 | 14.979 | 26.762 | 2.156 | 1.00 | 25.94 | D | C |
| ATOM | 3524 | CB | THR | D | 233 | 15.767 | 26.054 | 1.018 | 1.00 | 25.42 | D | C |
| ATOM | 3525 | OG1 | THR | D | 233 | 14.960 | 25.017 | 0.443 | 1.00 | 25.00 | D | O |
| ATOM | 3526 | CG2 | THR | D | 233 | 16.982 | 25.385 | 1.569 | 1.00 | 28.66 | D | C |
| ATOM | 3527 | C | THR | D | 233 | 15.846 | 27.730 | 2.944 | 1.00 | 22.97 | D | C |
| ATOM | 3528 | O | THR | D | 233 | 16.136 | 27.475 | 4.116 | 1.00 | 21.66 | D | O |
| ATOM | 3529 | N | ALA | D | 234 | 16.162 | 28.873 | 2.370 | 1.00 | 24.39 | D | N |
| ATOM | 3530 | CA | ALA | D | 234 | 17.072 | 29.812 | 3.065 | 1.00 | 25.48 | D | C |
| ATOM | 3531 | CB | ALA | D | 234 | 17.509 | 30.975 | 2.182 | 1.00 | 25.23 | D | C |
| ATOM | 3532 | C | ALA | D | 234 | 16.448 | 30.293 | 4.349 | 1.00 | 22.20 | D | C |
| ATOM | 3533 | O | ALA | D | 234 | 17.156 | 30.417 | 5.366 | 1.00 | 23.61 | D | O |
| ATOM | 3534 | N | THR | D | 235 | 15.127 | 30.371 | 4.374 | 1.00 | 21.76 | D | N |
| ATOM | 3535 | CA | THR | D | 235 | 14.437 | 30.770 | 5.589 | 1.00 | 23.69 | D | C |
| ATOM | 3536 | CB | THR | D | 235 | 12.971 | 31.166 | 5.265 | 1.00 | 24.70 | D | C |
| ATOM | 3537 | OG1 | THR | D | 235 | 12.979 | 32.157 | 4.229 | 1.00 | 26.21 | D | O |
| ATOM | 3538 | CG2 | THR | D | 235 | 12.258 | 31.668 | 6.458 | 1.00 | 23.87 | D | C |
| ATOM | 3539 | C | THR | D | 235 | 14.547 | 29.660 | 6.672 | 1.00 | 24.17 | D | C |
| ATOM | 3540 | O | THR | D | 235 | 14.836 | 29.924 | 7.830 | 1.00 | 23.71 | D | O |
| ATOM | 3541 | N | TYR | D | 236 | 14.328 | 28.406 | 6.313 | 1.00 | 25.19 | D | N |
| ATOM | 3542 | CA | TYR | D | 236 | 14.509 | 27.375 | 7.291 | 1.00 | 24.82 | D | C |
| ATOM | 3543 | CB | TYR | D | 236 | 14.220 | 26.003 | 6.699 | 1.00 | 26.69 | D | C |
| ATOM | 3544 | CG | TYR | D | 236 | 12.788 | 25.679 | 6.464 | 1.00 | 28.00 | D | C |
| ATOM | 3545 | CD1 | TYR | D | 236 | 11.727 | 26.205 | 7.260 | 1.00 | 24.27 | D | C |
| ATOM | 3546 | CE1 | TYR | D | 236 | 10.394 | 25.870 | 7.007 | 1.00 | 26.05 | D | C |
| ATOM | 3547 | CZ | TYR | D | 236 | 10.097 | 24.994 | 6.014 | 1.00 | 28.10 | D | C |
| ATOM | 3548 | OH | TYR | D | 236 | 8.768 | 24.674 | 5.705 | 1.00 | 31.00 | D | O |
| ATOM | 3549 | CE2 | TYR | D | 236 | 11.117 | 24.465 | 5.220 | 1.00 | 29.59 | D | C |
| ATOM | 3550 | CD2 | TYR | D | 236 | 12.455 | 24.822 | 5.442 | 1.00 | 27.41 | D | C |
| ATOM | 3551 | C | TYR | D | 236 | 15.968 | 27.359 | 7.815 | 1.00 | 25.95 | D | C |
| ATOM | 3552 | O | TYR | D | 236 | 16.195 | 27.161 | 9.010 | 1.00 | 23.73 | D | O |
| ATOM | 3553 | N | ILE | D | 237 | 16.932 | 27.578 | 6.928 | 1.00 | 25.08 | D | N |
| ATOM | 3554 | CA | ILE | D | 237 | 18.334 | 27.543 | 7.349 | 1.00 | 25.42 | D | C |
| ATOM | 3555 | CB | ILE | D | 237 | 19.240 | 27.358 | 6.146 | 1.00 | 26.57 | D | C |
| ATOM | 3556 | CG1 | ILE | D | 237 | 19.102 | 25.855 | 5.715 | 1.00 | 31.07 | D | C |
| ATOM | 3557 | CD1 | ILE | D | 237 | 18.844 | 25.822 | 4.292 | 1.00 | 40.22 | D | C |
| ATOM | 3558 | CG2 | ILE | D | 237 | 20.693 | 27.572 | 6.467 | 1.00 | 24.27 | D | C |
| ATOM | 3559 | C | ILE | D | 237 | 18.642 | 28.623 | 8.347 | 1.00 | 26.85 | D | C |
| ATOM | 3560 | O | ILE | D | 237 | 19.311 | 28.331 | 9.328 | 1.00 | 26.86 | D | O |
| ATOM | 3561 | N | THR | D | 238 | 18.142 | 29.841 | 8.124 | 1.00 | 25.08 | D | N |
| ATOM | 3562 | CA | THR | D | 238 | 18.210 | 30.943 | 9.102 | 1.00 | 24.52 | D | C |
| ATOM | 3563 | CB | THR | D | 238 | 17.455 | 32.197 | 8.544 | 1.00 | 25.54 | D | C |
| ATOM | 3564 | OG1 | THR | D | 238 | 18.178 | 32.665 | 7.411 | 1.00 | 26.34 | D | O |
| ATOM | 3565 | CG2 | THR | D | 238 | 17.379 | 33.295 | 9.547 | 1.00 | 26.67 | D | C |
| ATOM | 3566 | C | THR | D | 238 | 17.682 | 30.553 | 10.457 | 1.00 | 22.11 | D | C |
| ATOM | 3567 | O | THR | D | 238 | 18.320 | 30.731 | 11.491 | 1.00 | 23.99 | D | O |
| ATOM | 3568 | N | GLU | D | 239 | 16.487 | 29.992 | 10.456 | 1.00 | 23.43 | D | N |
| ATOM | 3569 | CA | GLU | D | 239 | 15.856 | 29.554 | 11.711 | 1.00 | 24.53 | D | C |
| ATOM | 3570 | CB | GLU | D | 239 | 14.467 | 28.971 | 11.404 | 1.00 | 23.98 | D | C |
| ATOM | 3571 | CG | GLU | D | 239 | 13.468 | 30.026 | 10.912 | 1.00 | 26.14 | D | C |
| ATOM | 3572 | CD | GLU | D | 239 | 12.229 | 29.397 | 10.226 | 1.00 | 34.10 | D | C |
| ATOM | 3573 | OE1 | GLU | D | 239 | 12.043 | 28.143 | 10.279 | 1.00 | 35.10 | D | O |
| ATOM | 3574 | OE2 | GLU | D | 239 | 11.443 | 30.138 | 9.610 | 1.00 | 45.04 | D | O |
| ATOM | 3575 | C | GLU | D | 239 | 16.697 | 28.535 | 12.489 | 1.00 | 25.34 | D | C |
| ATOM | 3576 | O | GLU | D | 239 | 16.974 | 28.713 | 13.682 | 1.00 | 22.92 | D | O |
| ATOM | 3577 | N | LEU | D | 240 | 17.135 | 27.475 | 11.791 | 1.00 | 23.59 | D | N |
| ATOM | 3578 | CA | LEU | D | 240 | 18.001 | 26.505 | 12.408 | 1.00 | 24.29 | D | C |
| ATOM | 3579 | CB | LEU | D | 240 | 18.259 | 25.278 | 11.462 | 1.00 | 24.52 | D | C |
| ATOM | 3580 | CG | LEU | D | 240 | 16.936 | 24.561 | 11.282 | 1.00 | 27.48 | D' | C |
| ATOM | 3581 | CD1 | LEU | D | 240 | 17.147 | 23.554 | 10.213 | 1.00 | 30.48 | D | C |
| ATOM | 3582 | CD2 | LEU | D | 240 | 16.412 | 23.915 | 12.526 | 1.00 | 25.93 | D | C |
| ATOM | 3583 | C | LEU | D | 240 | 19.320 | 27.102 | 12.814 | 1.00 | 22.82 | D | C |
| ATOM | 3584 | O | LEU | D | 240 | 19.886 | 26.724 | 13.854 | 1.00 | 24.27 | D | O |
| ATOM | 3585 | N | ALA | D | 241 | 19.893 | 27.966 | 11.982 | 1.00 | 23.83 | D | N |
| ATOM | 3586 | CA | ALA | D | 241 | 21.152 | 28.562 | 12.383 | 1.00 | 26.58 | D | C |
| ATOM | 3587 | CB | ALA | D | 241 | 21.807 | 29.310 | 11.225 | 1.00 | 28.02 | D | C |
| ATOM | 3588 | C | ALA | D | 241 | 21.038 | 29.425 | 13.632 | 1.00 | 27.85 | D | C |
| ATOM | 3589 | O | ALA | D | 241 | 21.932 | 29.429 | 14.520 | 1.00 | 26.72 | D | O |
| ATOM | 3590 | N | ASN | D | 242 | 19.931 | 30.140 | 13.761 | 1.00 | 27.82 | D | N |
| ATOM | 3591 | CA | ASN | D | 242 | 19.700 | 30.869 | 15.017 | 1.00 | 26.66 | D | C |
| ATOM | 3592 | CB | ASN | D | 242 | 18.444 | 31.741 | 14.939 | 1.00 | 29.19 | D | C |
| ATOM | 3593 | CG | ASN | D | 242 | 18.634 | 32.898 | 14.039 | 1.00 | 28.03 | D | C |
| ATOM | 3594 | OD1 | ASN | D | 242 | 19.694 | 33.429 | 13.930 | 1.00 | 35.94 | D | O |
| ATOM | 3595 | ND2 | ASN | D | 242 | 17.598 | 33.266 | 13.355 | 1.00 | 32.20 | D | N |
| ATOM | 3596 | C | ASN | D | 242 | 19.595 | 29.953 | 16.197 | 1.00 | 26.29 | D | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 3597 | O | ASN | D | 242 | 20.247 | 30.161 | 17.234 | 1.00 | 29.42 | D | O |
| ATOM | 3598 | N | ALA | D | 243 | 18.784 | 28.934 | 16.029 | 1.00 | 27.61 | D | N |
| ATOM | 3599 | CA | ALA | D | 243 | 18.591 | 27.988 | 17.073 | 1.00 | 28.90 | D | C |
| ATOM | 3600 | CB | ALA | D | 243 | 17.517 | 27.015 | 16.699 | 1.00 | 29.15 | D | C |
| ATOM | 3601 | C | ALA | D | 243 | 19.872 | 27.221 | 17.462 | 1.00 | 25.33 | D | C |
| ATOM | 3602 | O | ALA | D | 243 | 20.062 | 26.941 | 18.674 | 1.00 | 25.16 | D | O |
| ATOM | 3603 | N | LEU | D | 244 | 20.708 | 26.863 | 16.482 | 1.00 | 25.80 | D | N |
| ATOM | 3604 | CA | LEU | D | 244 | 21.917 | 26.133 | 16.844 | 1.00 | 25.63 | D | C |
| ATOM | 3605 | CB | LEU | D | 244 | 22.559 | 25.406 | 15.624 | 1.00 | 24.67 | D | C |
| ATOM | 3606 | CG | LEU | D | 244 | 21.717 | 24.272 | 15.019 | 1.00 | 21.78 | D | C |
| ATOM | 3607 | CD1 | LEU | D | 244 | 22.156 | 24.049 | 13.602 | 1.00 | 20.85 | D | C |
| ATOM | 3608 | CD2 | LEU | D | 244 | 21.750 | 22.982 | 15.848 | 1.00 | 24.65 | D | C |
| ATOM | 3609 | C | LEU | D | 244 | 22.916 | 27.094 | 17.554 | 1.00 | 24.82 | D | C |
| ATOM | 3610 | O | LEU | D | 244 | 23.640 | 26.644 | 18.445 | 1.00 | 26.12 | D | O |
| ATOM | 3611 | N | SER | D | 245 | 22.925 | 28.388 | 17.221 | 1.00 | 26.53 | D | N |
| ATOM | 3612 | CA | SER | D | 245 | 23.834 | 29.371 | 17.937 | 1.00 | 32.10 | D | C |
| ATOM | 3613 | CB | SER | D | 245 | 23.853 | 30.855 | 17.444 | 1.00 | 31.27 | D | C |
| ATOM | 3614 | OG | SER | D | 245 | 23.727 | 30.964 | 16.076 | 1.00 | 38.08 | D | O |
| ATOM | 3615 | C | SER | D | 245 | 23.441 | 29.481 | 19.373 | 1.00 | 27.41 | D | C |
| ATOM | 3616 | O | SER | D | 245 | 24.299 | 29.656 | 20.203 | 1.00 | 33.44 | D | O |
| ATOM | 3617 | N | TYR | D | 246 | 22.126 | 29.508 | 19.623 | 1.00 | 28.57 | D | N |
| ATOM | 3618 | CA | TYR | D | 246 | 21.604 | 29.545 | 20.949 | 1.00 | 27.91 | D | C |
| ATOM | 3619 | CB | TYR | D | 246 | 20.077 | 29.810 | 20.899 | 1.00 | 28.86 | D | C |
| ATOM | 3620 | CG | TYR | D | 246 | 19.448 | 29.618 | 22.238 | 1.00 | 29.09 | D | C |
| ATOM | 3621 | CD1 | TYR | D | 246 | 18.953 | 28.387 | 22.573 | 1.00 | 27.83 | D | C |
| ATOM | 3622 | CE1 | TYR | D | 246 | 18.408 | 28.132 | 23.819 | 1.00 | 28.46 | D | C |
| ATOM | 3623 | CZ | TYR | D | 246 | 18.342 | 29.154 | 24.767 | 1.00 | 32.70 | D | C |
| ATOM | 3624 | OH | TYR | D | 246 | 17.765 | 28.799 | 25.961 | 1.00 | 30.93 | D | O |
| ATOM | 3625 | CE2 | TYR | D | 246 | 18.812 | 30.420 | 24.460 | 1.00 | 30.81 | D | C |
| ATOM | 3626 | CD2 | TYR | D | 246 | 19.366 | 30.668 | 23.206 | 1.00 | 29.23 | D | C |
| ATOM | 3627 | C | TYR | D | 246 | 22.042 | 28.238 | 21.685 | 1.00 | 30.22 | D | C |
| ATOM | 3628 | O | TYR | D | 246 | 22.679 | 28.296 | 22.761 | 1.00 | 31.72 | D | O |
| ATOM | 3629 | N | CYS | D | 247 | 21.801 | 27.072 | 21.111 | 1.00 | 24.85 | D | N |
| ATOM | 3630 | CA | CYS | D | 247 | 22.329 | 25.823 | 21.731 | 1.00 | 27.26 | D | C |
| ATOM | 3631 | CB | CYS | D | 247 | 22.003 | 24.591 | 20.903 | 1.00 | 28.12 | D | C |
| ATOM | 3632 | SG | CYS | D | 247 | 20.229 | 24.304 | 20.755 | 1.00 | 29.92 | D | S |
| ATOM | 3633 | C | CYS | D | 247 | 23.833 | 25.895 | 22.022 | 1.00 | 26.92 | D | C |
| ATOM | 3634 | O | CYS | D | 247 | 24.302 | 25.636 | 23.165 | 1.00 | 27.36 | D | O |
| ATOM | 3635 | N | HIS | D | 248 | 24.597 | 26.348 | 21.038 | 1.00 | 28.48 | D | N |
| ATOM | 3636 | CA | HIS | D | 248 | 26.071 | 26.477 | 21.225 | 1.00 | 28.96 | D | C |
| ATOM | 3637 | CB | HIS | D | 248 | 26.770 | 26.852 | 19.950 | 1.00 | 27.36 | D | C |
| ATOM | 3638 | CG | HIS | D | 248 | 26.690 | 25.788 | 18.896 | 1.00 | 29.41 | D | C |
| ATOM | 3639 | ND1 | HIS | D | 248 | 27.325 | 25.891 | 17.681 | 1.00 | 30.53 | D | N |
| ATOM | 3640 | CE1 | HIS | D | 248 | 27.082 | 24.819 | 16.961 | 1.00 | 27.23 | D | C |
| ATOM | 3641 | NE2 | HIS | D | 248 | 26.338 | 24.000 | 17.689 | 1.00 | 28.76 | D | N |
| ATOM | 3642 | CD2 | HIS | D | 248 | 26.080 | 24.583 | 18.899 | 1.00 | 27.34 | D | C |
| ATOM | 3643 | C | HIS | D | 248 | 26.432 | 27.441 | 22.357 | 1.00 | 30.99 | D | C |
| ATOM | 3644 | O | HIS | D | 248 | 27.358 | 27.142 | 23.135 | 1.00 | 28.26 | D | O |
| ATOM | 3645 | N | SER | D | 249 | 25.670 | 28.528 | 22.512 | 1.00 | 31.13 | D | N |
| ATOM | 3646 | CA | SER | D | 249 | 25.932 | 29.497 | 23.603 | 1.00 | 31.66 | D | C |
| ATOM | 3647 | CB | SER | D | 249 | 25.054 | 30.754 | 23.503 | 1.00 | 33.24 | D | C |
| ATOM | 3648 | OG | SER | D | 249 | 23.670 | 30.494 | 23.888 | 1.00 | 35.32 | D | O |
| ATOM | 3649 | C | SER | D | 249 | 25.720 | 28.829 | 24.954 | 1.00 | 35.74 | D | C |
| ATOM | 3650 | O | SER | D | 249 | 26.246 | 29.285 | 25.920 | 1.00 | 33.89 | D | O |
| ATOM | 3651 | N | LYS | D | 250 | 24.944 | 27.747 | 24.997 | 1.00 | 29.07 | D | N |
| ATOM | 3652 | CA | LYS | D | 250 | 24.710 | 27.012 | 26.191 | 1.00 | 30.01 | D | C |
| ATOM | 3653 | CB | LYS | D | 250 | 23.258 | 26.535 | 26.217 | 1.00 | 28.22 | D | C |
| ATOM | 3654 | CG | LYS | D | 250 | 22.219 | 27.616 | 26.090 | 1.00 | 36.62 | D | C |
| ATOM | 3655 | CD | LYS | D | 250 | 22.233 | 28.555 | 27.252 | 1.00 | 40.99 | D | C |
| ATOM | 3656 | CE | LYS | D | 250 | 21.010 | 29.461 | 27.252 | 1.00 | 52.63 | D | C |
| ATOM | 3657 | NZ | LYS | D | 250 | 21.342 | 30.803 | 27.858 | 1.00 | 56.20 | D | N |
| ATOM | 3658 | C | LYS | D | 250 | 25.602 | 25.773 | 26.244 | 1.00 | 30.88 | D | C |
| ATOM | 3659 | O | LYS | D | 250 | 25.365 | 24.895 | 27.062 | 1.00 | 30.12 | D | O |
| ATOM | 3660 | N | ARG | D | 251 | 26.560 | 25.649 | 25.332 | 1.00 | 30.99 | D | N |
| ATOM | 3661 | CA | ARG | D | 251 | 27.315 | 24.443 | 25.199 | 1.00 | 30.73 | D | C |
| ATOM | 3662 | CB | ARG | D | 251 | 28.241 | 24.321 | 26.402 | 1.00 | 35.75 | D | C |
| ATOM | 3663 | CG | ARG | D | 251 | 29.072 | 25.587 | 26.486 | 1.00 | 40.68 | D | C |
| ATOM | 3664 | CD | ARG | D | 251 | 30.222 | 25.543 | 27.471 | 1.00 | 41.28 | D | C |
| ATOM | 3665 | NE | ARG | D | 251 | 29.935 | 25.179 | 28.836 | 1.00 | 44.79 | D | N |
| ATOM | 3666 | CZ | ARG | D | 251 | 29.029 | 25.704 | 29.658 | 1.00 | 54.18 | D | C |
| ATOM | 3667 | NH1 | ARG | D | 251 | 28.154 | 26.642 | 29.258 | 1.00 | 67.13 | D | N |
| ATOM | 3668 | NH2 | ARG | D | 251 | 28.971 | 25.238 | 30.927 | 1.00 | 51.70 | D | N |
| ATOM | 3669 | C | ARG | D | 251 | 26.577 | 23.147 | 24.941 | 1.00 | 32.01 | D | C |
| ATOM | 3670 | O | ARG | D | 251 | 27.083 | 22.099 | 25.268 | 1.00 | 30.67 | D | O |
| ATOM | 3671 | N | VAL | D | 252 | 25.423 | 23.215 | 24.281 | 1.00 | 28.53 | D | N |
| ATOM | 3672 | CA | VAL | D | 252 | 24.692 | 22.025 | 23.866 | 1.00 | 28.21 | D | C |
| ATOM | 3673 | CB | VAL | D | 252 | 23.193 | 22.132 | 24.217 | 1.00 | 28.45 | D | C |
| ATOM | 3674 | CG1 | VAL | D | 252 | 22.356 | 21.007 | 23.618 | 1.00 | 29.55 | D | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 3675 | CG2 | VAL | D | 252 | 23.017 | 22.092 | 25.738 | 1.00 | 33.36 | D | C |
| ATOM | 3676 | C | VAL | D | 252 | 24.866 | 21.942 | 22.397 | 1.00 | 25.73 | D | C |
| ATOM | 3677 | O | VAL | D | 252 | 24.728 | 22.960 | 21.733 | 1.00 | 26.96 | D | O |
| ATOM | 3678 | N | ILE | D | 253 | 25.227 | 20.760 | 21.892 | 1.00 | 23.71 | D | N |
| ATOM | 3679 | CA | ILE | D | 253 | 25.633 | 20.566 | 20.500 | 1.00 | 26.90 | D | C |
| ATOM | 3680 | CB | ILE | D | 253 | 27.203 | 20.419 | 20.291 | 1.00 | 28.46 | D | C |
| ATOM | 3681 | CG1 | ILE | D | 253 | 27.779 | 19.219 | 21.062 | 1.00 | 32.35 | D | C |
| ATOM | 3682 | CD1 | ILE | D | 253 | 29.209 | 18.855 | 20.620 | 1.00 | 33.06 | D | C |
| ATOM | 3683 | CG2 | ILE | D | 253 | 27.931 | 21.674 | 20.718 | 1.00 | 30.62 | D | C |
| ATOM | 3684 | C | ILE | D | 253 | 24.938 | 19.317 | 19.962 | 1.00 | 26.31 | D | C |
| ATOM | 3685 | O | ILE | D | 253 | 24.333 | 18.547 | 20.709 | 1.00 | 26.59 | D | O |
| ATOM | 3686 | N | HIS | D | 254 | 25.071 | 19.117 | 18.669 | 1.00 | 26.61 | D | N |
| ATOM | 3687 | CA | HIS | D | 254 | 24.591 | 17.926 | 17.960 | 1.00 | 31.46 | D | C |
| ATOM | 3688 | CB | HIS | D | 254 | 25.339 | 16.685 | 18.460 | 1.00 | 32.17 | D | C |
| ATOM | 3689 | CG | HIS | D | 254 | 25.036 | 15.446 | 17.695 | 1.00 | 32.19 | D | C |
| ATOM | 3690 | ND1 | HIS | D | 254 | 24.956 | 15.415 | 16.318 | 1.00 | 34.18 | D | N |
| ATOM | 3691 | CE1 | HIS | D | 254 | 24.718 | 14.181 | 15.923 | 1.00 | 32.95 | D | C |
| ATOM | 3692 | NE2 | HIS | D | 254 | 24.611 | 13.425 | 16.997 | 1.00 | 38.09 | D | N |
| ATOM | 3693 | CD2 | HIS | D | 254 | 24.785 | 14.194 | 18.117 | 1.00 | 33.08 | D | C |
| ATOM | 3694 | C | HIS | D | 254 | 23.076 | 17.782 | 18.181 | 1.00 | 31.47 | D | C |
| ATOM | 3695 | O | HIS | D | 254 | 22.613 | 16.832 | 18.753 | 1.00 | 30.20 | D | O |
| ATOM | 3696 | N | ARG | D | 255 | 22.338 | 18.744 | 17.693 | 1.00 | 29.63 | D | N |
| ATOM | 3697 | CA | ARG | D | 255 | 20.906 | 18.686 | 17.784 | 1.00 | 30.14 | D | C |
| ATOM | 3698 | CB | ARG | D | 255 | 20.326 | 20.099 | 17.714 | 1.00 | 29.10 | D | C |
| ATOM | 3699 | CG | ARG | D | 255 | 20.670 | 21.018 | 18.868 | 1.00 | 37.45 | D | C |
| ATOM | 3700 | CD | ARG | D | 255 | 20.005 | 20.554 | 20.170 | 1.00 | 41.22 | D | C |
| ATOM | 3701 | NE | ARG | D | 255 | 20.926 | 19.696 | 20.831 | 1.00 | 37.22 | D | N |
| ATOM | 3702 | CZ | ARG | D | 255 | 20.690 | 18.832 | 21.815 | 1.00 | 37.06 | D | C |
| ATOM | 3703 | NH1 | ARG | D | 255 | 19.482 | 18.669 | 22.369 | 1.00 | 38.94 | D | N |
| ATOM | 3704 | NH2 | ARG | D | 255 | 21.767 | 18.141 | 22.271 | 1.00 | 29.99 | D | N |
| ATOM | 3705 | C | ARG | D | 255 | 20.412 | 17.878 | 16.593 | 1.00 | 27.80 | D | C |
| ATOM | 3706 | O | ARG | D | 255 | 21.043 | 17.809 | 15.563 | 1.00 | 27.55 | D | O |
| ATOM | 3707 | N | ASP | D | 256 | 19.244 | 17.293 | 16.730 | 1.00 | 30.82 | D | N |
| ATOM | 3708 | CA | ASP | D | 256 | 18.660 | 16.479 | 15.656 | 1.00 | 34.08 | D | C |
| ATOM | 3709 | CB | ASP | D | 256 | 17.738 | 15.462 | 16.275 | 1.00 | 34.84 | D | C |
| ATOM | 3710 | CG | ASP | D | 256 | 17.353 | 14.392 | 15.346 | 1.00 | 37.75 | D | C |
| ATOM | 3711 | OD1 | ASP | D | 256 | 17.429 | 14.573 | 14.107 | 1.00 | 35.53 | D | O |
| ATOM | 3712 | OD2 | ASP | D | 256 | 16.908 | 13.348 | 15.870 | 1.00 | 43.97 | D | O |
| ATOM | 3713 | C | ASP | D | 256 | 17.887 | 17.393 | 14.707 | 1.00 | 33.32 | D | C |
| ATOM | 3714 | O | ASP | D | 256 | 16.843 | 18.020 | 15.088 | 1.00 | 33.98 | D | O |
| ATOM | 3715 | N | ILE | D | 257 | 18.386 | 17.517 | 13.487 | 1.00 | 25.63 | D | N |
| ATOM | 3716 | CA | ILE | D | 257 | 17.765 | 18.467 | 12.548 | 1.00 | 26.25 | D | C |
| ATOM | 3717 | CB | ILE | D | 257 | 18.559 | 19.743 | 12.302 | 1.00 | 25.89 | D | C |
| ATOM | 3718 | CG1 | ILE | D | 257 | 19.908 | 19.481 | 11.688 | 1.00 | 27.07 | D | C |
| ATOM | 3719 | CD1 | ILE | D | 257 | 20.510 | 20.745 | 11.163 | 1.00 | 29.92 | D | C |
| ATOM | 3720 | CG2 | ILE | D | 257 | 18.710 | 20.560 | 13.574 | 1.00 | 27.76 | D | C |
| ATOM | 3721 | C | ILE | D | 257 | 17.350 | 17.775 | 11.274 | 1.00 | 27.33 | D | C |
| ATOM | 3722 | O | ILE | D | 257 | 17.123 | 18.422 | 10.274 | 1.00 | 27.87 | D | O |
| ATOM | 3723 | N | LYS | D | 258 | 17.194 | 16.476 | 11.337 | 1.00 | 23.51 | D | N |
| ATOM | 3724 | CA | LYS | D | 258 | 16.569 | 15.785 | 10.229 | 1.00 | 27.03 | D | C |
| ATOM | 3725 | CB | LYS | D | 258 | 16.549 | 14.314 | 10.514 | 1.00 | 31.17 | D | C |
| ATOM | 3726 | CG | LYS | D | 258 | 17.894 | 13.677 | 10.468 | 1.00 | 38.38 | D | C |
| ATOM | 3727 | CD | LYS | D | 258 | 17.735 | 12.166 | 10.587 | 1.00 | 48.31 | D | C |
| ATOM | 3728 | CE | LYS | D | 258 | 18.235 | 11.620 | 11.907 | 1.00 | 47.46 | D | C |
| ATOM | 3729 | NZ | LYS | D | 258 | 17.639 | 12.128 | 13.161 | 1.00 | 44.76 | D | N |
| ATOM | 3730 | C | LYS | D | 258 | 15.116 | 16.228 | 10.028 | 1.00 | 28.09 | D | C |
| ATOM | 3731 | O | LYS | D | 258 | 14.398 | 16.495 | 11.003 | 1.00 | 25.75 | D | O |
| ATOM | 3732 | N | PRO | D | 259 | 14.649 | 16.251 | 8.789 | 1.00 | 28.75 | D | N |
| ATOM | 3733 | CA | PRO | D | 259 | 13.289 | 16.743 | 8.571 | 1.00 | 29.25 | D | C |
| ATOM | 3734 | CB | PRO | D | 259 | 13.091 | 16.616 | 7.068 | 1.00 | 31.69 | D | C |
| ATOM | 3735 | CG | PRO | D | 259 | 14.342 | 16.089 | 6.513 | 1.00 | 31.25 | D | C |
| ATOM | 3736 | CD | PRO | D | 259 | 15.333 | 15.889 | 7.553 | 1.00 | 29.25 | D | C |
| ATOM | 3737 | C | PRO | D | 259 | 12.190 | 15.939 | 9.271 | 1.00 | 28.46 | D | C |
| ATOM | 3738 | O | PRO | D | 259 | 11.189 | 16.531 | 9.675 | 1.00 | 23.04 | D | O |
| ATOM | 3739 | N | GLU | D | 260 | 12.382 | 14.625 | 9.409 | 1.00 | 28.00 | D | N |
| ATOM | 3740 | CA | GLU | D | 260 | 11.441 | 13.807 | 10.231 | 1.00 | 33.55 | D | C |
| ATOM | 3741 | CB | GLU | D | 260 | 11.654 | 12.293 | 9.998 | 1.00 | 36.42 | D | C |
| ATOM | 3742 | CG | GLU | D | 260 | 13.037 | 11.747 | 10.309 | 1.00 | 43.50 | D | C |
| ATOM | 3743 | CD | GLU | D | 260 | 14.052 | 11.842 | 9.164 | 1.00 | 49.80 | D | C |
| ATOM | 3744 | OE1 | GLU | D | 260 | 14.057 | 12.895 | 8.460 | 1.00 | 43.32 | D | O |
| ATOM | 3745 | OE2 | GLU | D | 260 | 14.877 | 10.875 | 8.999 | 1.00 | 47.96 | D | O |
| ATOM | 3746 | C | GLU | D | 260 | 11.343 | 14.205 | 11.710 | 1.00 | 33.53 | D | C |
| ATOM | 3747 | O | GLU | D | 260 | 10.347 | 13.912 | 12.366 | 1.00 | 27.99 | D | O |
| ATOM | 3748 | N | ASN | D | 261 | 12.312 | 15.000 | 12.225 | 1.00 | 32.28 | D | N |
| ATOM | 3749 | CA | ASN | D | 261 | 12.311 | 15.389 | 13.620 | 1.00 | 30.35 | D | C |
| ATOM | 3750 | CB | ASN | D | 261 | 13.542 | 14.815 | 14.333 | 1.00 | 38.23 | D | C |
| ATOM | 3751 | CG | ASN | D | 261 | 13.586 | 13.285 | 14.240 | 1.00 | 41.30 | D | C |
| ATOM | 3752 | OD1 | ASN | D | 261 | 12.596 | 12.609 | 13.897 | 1.00 | 47.88 | D | O |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 3753 | ND2 | ASN | D | 261 | 14.731 | 12.744 | 14.492 | 1.00 | 46.72 | D | N |
| ATOM | 3754 | C | ASN | D | 261 | 12.169 | 16.829 | 13.829 | 1.00 | 29.98 | D | C |
| ATOM | 3755 | O | ASN | D | 261 | 12.276 | 17.288 | 14.948 | 1.00 | 29.26 | D | O |
| ATOM | 3756 | N | LEU | D | 262 | 11.824 | 17.554 | 12.777 | 1.00 | 27.81 | D | N |
| ATOM | 3757 | CA | LEU | D | 262 | 11.510 | 18.952 | 12.901 | 1.00 | 26.06 | D | C |
| ATOM | 3758 | CB | LEU | D | 262 | 12.214 | 19.762 | 11.821 | 1.00 | 28.92 | D | C |
| ATOM | 3759 | CG | LEU | D | 262 | 13.736 | 19.621 | 11.850 | 1.00 | 26.05 | D | C |
| ATOM | 3760 | CD1 | LEU | D | 262 | 14.387 | 20.196 | 10.614 | 1.00 | 28.46 | D | C |
| ATOM | 3761 | CD2 | LEU | D | 262 | 14.282 | 20.276 | 13.064 | 1.00 | 27.14 | D | C |
| ATOM | 3762 | C | LEU | D | 262 | 10.008 | 19.201 | 12.741 | 1.00 | 27.84 | D | C |
| ATOM | 3763 | O | LEU | D | 262 | 9.384 | 18.788 | 11.763 | 1.00 | 24.79 | D | O |
| ATOM | 3764 | N | LEU | D | 263 | 9.479 | 19.983 | 13.647 | 1.00 | 26.44 | D | N |
| ATOM | 3765 | CA | LEU | D | 263 | 8.091 | 20.381 | 13.606 | 1.00 | 29.30 | D | C |
| ATOM | 3766 | CB | LEU | D | 263 | 7.478 | 20.215 | 14.992 | 1.00 | 24.87 | D | C |
| ATOM | 3767 | CG | LEU | D | 263 | 7.345 | 18.777 | 15.454 | 1.00 | 30.29 | D | C |
| ATOM | 3768 | CD1 | LEU | D | 263 | 7.127 | 18.722 | 16.954 | 1.00 | 30.45 | D | C |
| ATOM | 3769 | CD2 | LEU | D | 263 | 6.159 | 18.115 | 14.763 | 1.00 | 33.92 | D | C |
| ATOM | 3770 | C | LEU | D | 263 | 7.970 | 21.822 | 13.159 | 1.00 | 26.44 | D | C |
| ATOM | 3771 | O | LEU | D | 263 | 8.979 | 22.585 | 13.040 | 1.00 | 28.54 | D | O |
| ATOM | 3772 | N | LEU | D | 264 | 6.715 | 22.196 | 12.903 | 1.00 | 25.51 | D | N |
| ATOM | 3773 | CA | LEU | D | 264 | 6.402 | 23.471 | 12.296 | 1.00 | 25.14 | D | C |
| ATOM | 3774 | CB | LEU | D | 264 | 5.956 | 23.287 | 10.847 | 1.00 | 29.99 | D | C |
| ATOM | 3775 | CG | LEU | D | 264 | 7.043 | 22.812 | 9.831 | 1.00 | 26.58 | D | C |
| ATOM | 3776 | CD1 | LEU | D | 264 | 6.372 | 22.390 | 8.557 | 1.00 | 26.05 | D | C |
| ATOM | 3777 | CD2 | LEU | D | 264 | 8.036 | 23.913 | 9.569 | 1.00 | 24.94 | D | C |
| ATOM | 3778 | C | LEU | D | 264 | 5.339 | 24.152 | 13.128 | 1.00 | 30.43 | D | C |
| ATOM | 3779 | O | LEU | D | 264 | 4.266 | 23.562 | 13.415 | 1.00 | 27.28 | D | O |
| ATOM | 3780 | N | GLY | D | 265 | 5.672 | 25.387 | 13.514 | 1.00 | 28.40 | D | N |
| ATOM | 3781 | CA | GLY | D | 265 | 4.823 | 26.212 | 14.308 | 1.00 | 33.92 | D | C |
| ATOM | 3782 | C | GLY | D | 265 | 3.779 | 26.875 | 13.458 | 1.00 | 34.64 | D | C |
| ATOM | 3783 | O | GLY | D | 265 | 3.726 | 26.665 | 12.264 | 1.00 | 34.92 | D | O |
| ATOM | 3784 | N | SER | D | 266 | 2.926 | 27.654 | 14.095 | 1.00 | 33.84 | D | N |
| ATOM | 3785 | CA | SER | D | 266 | 1.741 | 28.271 | 13.427 | 1.00 | 34.01 | D | C |
| ATOM | 3786 | CB | SER | D | 266 | 0.852 | 29.020 | 14.460 | 1.00 | 33.71 | D | C |
| ATOM | 3787 | OG | SER | D | 266 | 1.588 | 29.998 | 15.200 | 1.00 | 36.95 | D | O |
| ATOM | 3788 | C | SER | D | 266 | 2.114 | 29.199 | 12.277 | 1.00 | 34.41 | D | C |
| ATOM | 3789 | O | SER | D | 266 | 1.396 | 29.289 | 11.299 | 1.00 | 34.70 | D | O |
| ATOM | 3790 | N | ALA | D | 267 | 3.250 | 29.861 | 12.350 | 1.00 | 32.34 | D | N |
| ATOM | 3791 | CA | ALA | D | 267 | 3.690 | 30.724 | 11.248 | 1.00 | 33.43 | D | C |
| ATOM | 3792 | CB | ALA | D | 267 | 4.379 | 31.955 | 11.829 | 1.00 | 32.55 | D | C |
| ATOM | 3793 | C | ALA | D | 267 | 4.601 | 29.994 | 10.249 | 1.00 | 34.18 | D | C |
| ATOM | 3794 | O | ALA | D | 267 | 5.240 | 30.609 | 9.401 | 1.00 | 39.05 | D | O |
| ATOM | 3795 | N | GLY | D | 268 | 4.623 | 28.662 | 10.327 | 1.00 | 36.02 | D | N |
| ATOM | 3796 | CA | GLY | D | 268 | 5.425 | 27.830 | 9.460 | 1.00 | 33.53 | D | C |
| ATOM | 3797 | C | GLY | D | 268 | 6.909 | 27.833 | 9.788 | 1.00 | 32.77 | D | C |
| ATOM | 3798 | O | GLY | D | 268 | 7.726 | 27.489 | 8.933 | 1.00 | 36.25 | D | O |
| ATOM | 3799 | N | GLU | D | 269 | 7.259 | 28.181 | 11.013 | 1.00 | 33.86 | D | N |
| ATOM | 3800 | CA | GLU | D | 269 | 8.669 | 28.323 | 11.397 | 1.00 | 33.06 | D | C |
| ATOM | 3801 | CB | GLU | D | 269 | 8.843 | 29.569 | 12.257 | 1.00 | 34.30 | D | C |
| ATOM | 3802 | CG | GLU | D | 269 | 8.495 | 29.429 | 13.707 | 1.00 | 35.97 | D | C |
| ATOM | 3803 | CD | GLU | D | 269 | 7.023 | 29.430 | 14.009 | 1.00 | 39.46 | D | C |
| ATOM | 3804 | OE1 | GLU | D | 269 | 6.167 | 29.273 | 13.114 | 1.00 | 43.77 | D | O |
| ATOM | 3805 | OE2 | GLU | D | 269 | 6.711 | 29.526 | 15.176 | 1.00 | 43.70 | D | O |
| ATOM | 3806 | C | GLU | D | 269 | 9.125 | 27.001 | 12.057 | 1.00 | 32.21 | D | C |
| ATOM | 3807 | O | GLU | D | 269 | 8.324 | 26.258 | 12.694 | 1.00 | 29.63 | D | O |
| ATOM | 3808 | N | LEU | D | 270 | 10.375 | 26.635 | 11.834 | 1.00 | 30.19 | D | N |
| ATOM | 3809 | CA | LEU | D | 270 | 10.846 | 25.371 | 12.347 | 1.00 | 30.05 | D | C |
| ATOM | 3810 | CB | LEU | D | 270 | 12.214 | 24.953 | 11.737 | 1.00 | 29.71 | D | C |
| ATOM | 3811 | CG | LEU | D | 270 | 12.139 | 24.470 | 10.307 | 1.00 | 29.09 | D | C |
| ATOM | 3812 | CD1 | LEU | D | 270 | 13.488 | 24.514 | 9.622 | 1.00 | 27.80 | D | C |
| ATOM | 3813 | CD2 | LEU | D | 270 | 11.567 | 23.044 | 10.225 | 1.00 | 29.01 | D | C |
| ATOM | 3814 | C | LEU | D | 270 | 10.920 | 25.356 | 13.869 | 1.00 | 26.70 | D | C |
| ATOM | 3815 | O | LEU | D | 270 | 11.179 | 26.381 | 14.517 | 1.00 | 29.82 | D | O |
| ATOM | 3816 | N | LYS | D | 271 | 10.672 | 24.158 | 14.404 | 1.00 | 24.54 | D | N |
| ATOM | 3817 | CA | LYS | D | 271 | 10.865 | 23.789 | 15.810 | 1.00 | 25.66 | D | C |
| ATOM | 3818 | CB | LYS | D | 271 | 9.518 | 23.525 | 16.437 | 1.00 | 26.28 | D | C |
| ATOM | 3819 | CG | LYS | D | 271 | 8.480 | 24.648 | 16.262 | 1.00 | 26.31 | D | C |
| ATOM | 3820 | CD | LYS | D | 271 | 8.813 | 25.768 | 17.237 | 1.00 | 24.78 | D | C |
| ATOM | 3821 | CE | LYS | D | 271 | 7.812 | 26.870 | 17.082 | 1.00 | 26.73 | D | C |
| ATOM | 3822 | NZ | LYS | D | 271 | 7.952 | 27.864 | 18.143 | 1.00 | 26.97 | D | N |
| ATOM | 3823 | C | LYS | D | 271 | 11.669 | 22.510 | 15.950 | 1.00 | 23.56 | D | C |
| ATOM | 3824 | O | LYS | D | 271 | 11.207 | 21.453 | 15.607 | 1.00 | 27.45 | D | O |
| ATOM | 3825 | N | ILE | D | 272 | 12.853 | 22.605 | 16.526 | 1.00 | 23.62 | D | N |
| ATOM | 3826 | CA | ILE | D | 272 | 13.639 | 21.452 | 16.843 | 1.00 | 25.53 | D | C |
| ATOM | 3827 | CB | ILE | D | 272 | 15.057 | 21.874 | 17.199 | 1.00 | 26.27 | D | C |
| ATOM | 3828 | CG1 | ILE | D | 272 | 15.701 | 22.593 | 15.999 | 1.00 | 24.77 | D | C |
| ATOM | 3829 | CD1 | ILE | D | 272 | 17.122 | 23.069 | 16.333 | 1.00 | 24.46 | D | C |
| ATOM | 3830 | CG2 | ILE | D | 272 | 15.830 | 20.687 | 17.720 | 1.00 | 27.38 | D | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 3831 | C | ILE | D | 272 | 13.021 | 20.733 | 18.019 | 1.00 | 26.88 | D | C |
| ATOM | 3832 | O | ILE | D | 272 | 12.694 | 21.390 | 19.015 | 1.00 | 25.70 | D | O |
| ATOM | 3833 | N | ALA | D | 273 | 12.864 | 19.419 | 17.881 | 1.00 | 29.61 | D | N |
| ATOM | 3834 | CA | ALA | D | 273 | 12.300 | 18.532 | 18.903 | 1.00 | 33.35 | D | C |
| ATOM | 3835 | CB | ALA | D | 273 | 11.350 | 17.570 | 18.230 | 1.00 | 34.32 | D | C |
| ATOM | 3836 | C | ALA | D | 273 | 13.312 | 17.709 | 19.716 | 1.00 | 32.93 | D | C |
| ATOM | 3837 | O | ALA | D | 273 | 13.082 | 17.384 | 20.891 | 1.00 | 33.77 | D | O |
| ATOM | 3838 | N | ASP | D | 274 | 14.381 | 17.271 | 19.077 | 1.00 | 36.08 | D | N |
| ATOM | 3839 | CA | ASP | D | 274 | 15.310 | 16.250 | 19.638 | 1.00 | 38.73 | D | C |
| ATOM | 3840 | CB | ASP | D | 274 | 16.255 | 16.859 | 20.719 | 1.00 | 39.20 | D | C |
| ATOM | 3841 | CG | ASP | D | 274 | 17.193 | 17.941 | 20.144 | 1.00 | 43.89 | D | C |
| ATOM | 3842 | OD1 | ASP | D | 274 | 17.834 | 17.622 | 19.099 | 1.00 | 41.82 | D | O |
| ATOM | 3843 | OD2 | ASP | D | 274 | 17.258 | 19.092 | 20.732 | 1.00 | 36.67 | D | O |
| ATOM | 3844 | C | ASP | D | 274 | 14.544 | 14.996 | 20.090 | 1.00 | 36.39 | D | C |
| ATOM | 3845 | O | ASP | D | 274 | 13.502 | 14.693 | 19.528 | 1.00 | 37.17 | D | O |
| ATOM | 3846 | N | PHE | D | 275 | 15.044 | 14.258 | 21.077 | 1.00 | 41.52 | D | N |
| ATOM | 3847 | CA | PHE | D | 275 | 14.542 | 12.909 | 21.427 | 1.00 | 40.88 | D | C |
| ATOM | 3848 | CB | PHE | D | 275 | 13.249 | 12.997 | 22.224 | 1.00 | 41.50 | D | C |
| ATOM | 3849 | CG | PHE | D | 275 | 13.333 | 13.858 | 23.440 | 1.00 | 41.36 | D | C |
| ATOM | 3850 | CD1 | PHE | D | 275 | 13.625 | 13.296 | 24.698 | 1.00 | 43.32 | D | C |
| ATOM | 3851 | CE1 | PHE | D | 275 | 13.677 | 14.086 | 25.828 | 1.00 | 42.86 | D | C |
| ATOM | 3852 | CZ | PHE | D | 275 | 13.421 | 15.452 | 25.722 | 1.00 | 38.29 | D | C |
| ATOM | 3853 | CE2 | PHE | D | 275 | 13.133 | 15.997 | 24.486 | 1.00 | 43.58 | D | C |
| ATOM | 3854 | CD2 | PHE | D | 275 | 13.059 | 15.190 | 23.357 | 1.00 | 39.04 | D | C |
| ATOM | 3855 | C | PHE | D | 275 | 14.261 | 11.996 | 20.200 | 1.00 | 44.60 | D | C |
| ATOM | 3856 | O | PHE | D | 275 | 13.346 | 11.150 | 20.261 | 1.00 | 36.04 | D | O |
| ATOM | 3857 | N | GLY | D | 276 | 15.025 | 12.171 | 19.105 | 1.00 | 44.54 | D | N |
| ATOM | 3858 | CA | GLY | D | 276 | 14.820 | 11.449 | 17.841 | 1.00 | 42.96 | D | C |
| ATOM | 3859 | C | GLY | D | 276 | 14.605 | 9.963 | 17.979 | 1.00 | 42.73 | D | C |
| ATOM | 3860 | O | GLY | D | 276 | 13.721 | 9.392 | 17.306 | 1.00 | 40.18 | D | O |
| ATOM | 3861 | N | TRP | D | 277 | 15.390 | 9.348 | 18.884 | 1.00 | 42.00 | D | N |
| ATOM | 3862 | CA | TRP | D | 277 | 15.189 | 7.945 | 19.280 | 1.00 | 40.08 | D | C |
| ATOM | 3863 | CB | TRP | D | 277 | 16.159 | 7.505 | 20.407 | 1.00 | 36.92 | D | C |
| ATOM | 3864 | CG | TRP | D | 277 | 16.041 | 8.320 | 21.601 | 1.00 | 42.23 | D | C |
| ATOM | 3865 | CD1 | TRP | D | 277 | 16.807 | 9.431 | 21.939 | 1.00 | 45.59 | D | C |
| ATOM | 3866 | NE1 | TRP | D | 277 | 16.375 | 9.944 | 23.156 | 1.00 | 43.82 | D | N |
| ATOM | 3867 | CE2 | TRP | D | 277 | 15.304 | 9.201 | 23.593 | 1.00 | 42.88 | D | C |
| ATOM | 3868 | CD2 | TRP | D | 277 | 15.085 | 8.152 | 22.652 | 1.00 | 42.98 | D | C |
| ATOM | 3869 | CE3 | TRP | D | 277 | 14.078 | 7.199 | 22.908 | 1.00 | 46.23 | D | C |
| ATOM | 3870 | CZ3 | TRP | D | 277 | 13.307 | 7.327 | 24.063 | 1.00 | 41.72 | D | C |
| ATOM | 3871 | CH2 | TRP | D | 277 | 13.545 | 8.381 | 24.969 | 1.00 | 46.23 | D | C |
| ATOM | 3872 | CZ2 | TRP | D | 277 | 14.535 | 9.334 | 24.750 | 1.00 | 42.81 | D | C |
| ATOM | 3873 | C | TRP | D | 277 | 13.742 | 7.627 | 19.667 | 1.00 | 40.89 | D | C |
| ATOM | 3874 | O | TRP | D | 277 | 13.368 | 6.484 | 19.648 | 1.00 | 39.25 | D | O |
| ATOM | 3875 | N | SER | D | 278 | 12.962 | 8.641 | 20.060 | 1.00 | 46.32 | D | N |
| ATOM | 3876 | CA | SER | D | 278 | 11.561 | 8.478 | 20.464 | 1.00 | 45.29 | D | C |
| ATOM | 3877 | CB | SER | D | 278 | 11.176 | 9.491 | 21.569 | 1.00 | 41.33 | D | C |
| ATOM | 3878 | OG | SER | D | 278 | 10.941 | 10.799 | 21.074 | 1.00 | 42.58 | D | O |
| ATOM | 3879 | C | SER | D | 278 | 10.575 | 8.577 | 19.319 | 1.00 | 44.27 | D | C |
| ATOM | 3880 | O | SER | D | 278 | 9.391 | 8.273 | 19.521 | 1.00 | 41.63 | D | O |
| ATOM | 3881 | N | VAL | D | 279 | 11.029 | 8.968 | 18.132 | 1.00 | 41.98 | D | N |
| ATOM | 3882 | CA | VAL | D | 279 | 10.104 | 9.268 | 17.016 | 1.00 | 50.25 | D | C |
| ATOM | 3883 | CB | VAL | D | 279 | 10.692 | 10.406 | 16.139 | 1.00 | 52.90 | D | C |
| ATOM | 3884 | CG1 | VAL | D | 279 | 9.826 | 10.699 | 14.921 | 1.00 | 50.48 | D | C |
| ATOM | 3885 | CG2 | VAL | D | 279 | 10.856 | 11.651 | 17.006 | 1.00 | 56.08 | D | C |
| ATOM | 3886 | C | VAL | D | 279 | 9.840 | 8.015 | 16.163 | 1.00 | 53.95 | D | C |
| ATOM | 3887 | O | VAL | D | 279 | 10.768 | 7.248 | 15.925 | 1.00 | 53.13 | D | O |
| ATOM | 3888 | N | HIS | D | 280 | 8.589 | 7.809 | 15.736 | 1.00 | 57.29 | D | N |
| ATOM | 3889 | CA | HIS | D | 280 | 8.273 | 7.011 | 14.522 | 1.00 | 73.14 | D | C |
| ATOM | 3890 | CB | HIS | D | 280 | 8.943 | 7.676 | 13.271 | 1.00 | 79.25 | D | C |
| ATOM | 3891 | CG | HIS | D | 280 | 8.983 | 6.835 | 12.025 | 1.00 | 88.64 | D | C |
| ATOM | 3892 | ND1 | HIS | D | 280 | 10.078 | 6.064 | 11.682 | 1.00 | 80.52 | D | N |
| ATOM | 3893 | CE1 | HIS | D | 280 | 9.848 | 5.464 | 10.528 | 1.00 | 80.18 | D | C |
| ATOM | 3894 | NE2 | HIS | D | 280 | 8.657 | 5.840 | 10.092 | 1.00 | 87.70 | D | N |
| ATOM | 3895 | CD2 | HIS | D | 280 | 8.102 | 6.709 | 11.000 | 1.00 | 92.48 | D | C |
| ATOM | 3896 | C | HIS | D | 280 | 8.612 | 5.526 | 14.692 | 1.00 | 76.31 | D | C |
| ATOM | 3897 | O | HIS | D | 280 | 7.745 | 4.733 | 15.108 | 1.00 | 79.30 | D | O |
| ATOM | 3898 | N | THR | D | 292 | 20.088 | 9.447 | 12.191 | 1.00 | 54.54 | D | N |
| ATOM | 3899 | CA | THR | D | 292 | 20.460 | 8.411 | 11.293 | 1.00 | 46.47 | D | C |
| ATOM | 3900 | CB | THR | D | 292 | 19.356 | 8.051 | 10.262 | 1.00 | 55.05 | D | C |
| ATOM | 3901 | OG1 | THR | D | 292 | 18.996 | 9.215 | 9.477 | 1.00 | 50.36 | D | O |
| ATOM | 3902 | CG2 | THR | D | 292 | 18.114 | 7.277 | 10.947 | 1.00 | 58.27 | D | C |
| ATOM | 3903 | C | THR | D | 292 | 21.756 | 8.765 | 10.547 | 1.00 | 40.54 | D | C |
| ATOM | 3904 | O | THR | D | 292 | 22.239 | 9.933 | 10.498 | 1.00 | 31.06 | D | O |
| ATOM | 3905 | N | LEU | D | 293 | 22.249 | 7.713 | 9.913 | 1.00 | 35.73 | D | N |
| ATOM | 3906 | CA | LEU | D | 293 | 23.455 | 7.705 | 9.132 | 1.00 | 34.34 | D | C |
| ATOM | 3907 | CB | LEU | D | 293 | 23.471 | 6.420 | 8.356 | 1.00 | 38.16 | D | C |
| ATOM | 3908 | CG | LEU | D | 293 | 24.823 | 6.083 | 7.734 | 1.00 | 40.33 | D | C |

APPENDIX A-continued

Atomic coordinates of Aurora A + Inhibitory Monobody Mb60 + Danusertib

| | | | | | | | | | | | |
|---|---|---|---|---|---|---|---|---|---|---|---|
| ATOM | 3909 | CD1 | LEU | D | 293 | 25.964 | 6.105 | 8.750 | 1.00 | 41.68 | D | C |
| ATOM | 3910 | CD2 | LEU | D | 293 | 24.681 | 4.710 | 7.096 | 1.00 | 46.00 | D | C |
| ATOM | 3911 | C | LEU | D | 293 | 23.594 | 8.881 | 8.193 | 1.00 | 29.28 | D | C |
| ATOM | 3912 | O | LEU | D | 293 | 24.608 | 9.519 | 8.151 | 1.00 | 25.22 | D | O |
| ATOM | 3913 | N | ASP | D | 294 | 22.539 | 9.177 | 7.484 | 1.00 | 27.95 | D | N |
| ATOM | 3914 | CA | ASP | D | 294 | 22.614 | 10.124 | 6.437 | 1.00 | 29.34 | D | C |
| ATOM | 3915 | CB | ASP | D | 294 | 21.247 | 10.233 | 5.732 | 1.00 | 34.10 | D | C |
| ATOM | 3916 | CG | ASP | D | 294 | 21.051 | 9.176 | 4.638 | 1.00 | 38.04 | D | C |
| ATOM | 3917 | OD1 | ASP | D | 294 | 21.919 | 9.027 | 3.742 | 1.00 | 38.13 | D | O |
| ATOM | 3918 | OD2 | ASP | D | 294 | 19.970 | 8.588 | 4.619 | 1.00 | 40.54 | D | O |
| ATOM | 3919 | C | ASP | D | 294 | 23.096 | 11.493 | 6.846 | 1.00 | 28.13 | D | C |
| ATOM | 3920 | O | ASP | D | 294 | 23.616 | 12.236 | 5.998 | 1.00 | 28.01 | D | O |
| ATOM | 3921 | N | TYR | D | 295 | 22.883 | 11.837 | 8.111 | 1.00 | 25.52 | D | N |
| ATOM | 3922 | CA | TYR | D | 295 | 23.163 | 13.157 | 8.656 | 1.00 | 26.59 | D | C |
| ATOM | 3923 | CB | TYR | D | 295 | 21.959 | 13.679 | 9.437 | 1.00 | 26.37 | D | C |
| ATOM | 3924 | CG | TYR | D | 295 | 20.932 | 14.337 | 8.531 | 1.00 | 29.38 | D | C |
| ATOM | 3925 | CD1 | TYR | D | 295 | 20.077 | 13.599 | 7.736 | 1.00 | 32.21 | D | C |
| ATOM | 3926 | CE1 | TYR | D | 295 | 19.149 | 14.213 | 6.877 | 1.00 | 29.57 | D | C |
| ATOM | 3927 | CZ | TYR | D | 295 | 19.089 | 15.587 | 6.852 | 1.00 | 29.83 | D | C |
| ATOM | 3928 | OH | TYR | D | 295 | 18.239 | 16.296 | 6.019 | 1.00 | 36.19 | D | O |
| ATOM | 3929 | CE2 | TYR | D | 295 | 19.910 | 16.335 | 7.648 | 1.00 | 32.76 | D | C |
| ATOM | 3930 | CD2 | TYR | D | 295 | 20.815 | 15.716 | 8.493 | 1.00 | 30.29 | D | C |
| ATOM | 3931 | C | TYR | D | 295 | 24.456 | 13.263 | 9.490 | 1.00 | 27.63 | D | C |
| ATOM | 3932 | O | TYR | D | 295 | 24.851 | 14.370 | 9.913 | 1.00 | 29.44 | D | O |
| ATOM | 3933 | N | LEU | D | 296 | 25.151 | 12.162 | 9.620 | 1.00 | 25.62 | D | N |
| ATOM | 3934 | CA | LEU | D | 296 | 26.315 | 12.079 | 10.515 | 1.00 | 26.66 | D | C |
| ATOM | 3935 | CB | LEU | D | 296 | 26.552 | 10.659 | 11.071 | 1.00 | 28.93 | D | C |
| ATOM | 3936 | CG | LEU | D | 296 | 25.488 | 10.038 | 11.988 | 1.00 | 31.40 | D | C |
| ATOM | 3937 | CD1 | LEU | D | 296 | 25.979 | 8.685 | 12.465 | 1.00 | 34.14 | D | C |
| ATOM | 3938 | CD2 | LEU | D | 296 | 25.226 | 10.947 | 13.191 | 1.00 | 37.47 | D | C |
| ATOM | 3939 | C | LEU | D | 296 | 27.550 | 12.560 | 9.794 | 1.00 | 22.58 | D | C |
| ATOM | 3940 | O | LEU | D | 296 | 27.779 | 12.206 | 8.638 | 1.00 | 23.34 | D | O |
| ATOM | 3941 | N | PRO | D | 297 | 28.323 | 13.395 | 10.454 | 1.00 | 22.71 | D | N |
| ATOM | 3942 | CA | PRO | D | 297 | 29.591 | 13.828 | 9.876 | 1.00 | 21.80 | D | C |
| ATOM | 3943 | CB | PRO | D | 297 | 29.997 | 15.040 | 10.710 | 1.00 | 21.24 | D | C |
| ATOM | 3944 | CG | PRO | D | 297 | 29.082 | 15.138 | 11.800 | 1.00 | 25.35 | D | C |
| ATOM | 3945 | CD | PRO | D | 297 | 27.906 | 14.246 | 11.589 | 1.00 | 23.52 | D | C |
| ATOM | 3946 | C | PRO | D | 297 | 30.634 | 12.768 | 9.944 | 1.00 | 20.96 | D | C |
| ATOM | 3947 | O | PRO | D | 297 | 30.511 | 11.787 | 10.723 | 1.00 | 25.28 | D | O |
| ATOM | 3948 | N | PRO | D | 298 | 31.697 | 12.939 | 9.178 | 1.00 | 25.91 | D | N |
| ATOM | 3949 | CA | PRO | D | 298 | 32.788 | 11.947 | 9.125 | 1.00 | 26.05 | D | C |
| ATOM | 3950 | CB | PRO | D | 298 | 33.864 | 12.636 | 8.260 | 1.00 | 23.53 | D | C |
| ATOM | 3951 | CG | PRO | D | 298 | 33.000 | 13.404 | 7.310 | 1.00 | 24.75 | D | C |
| ATOM | 3952 | CD | PRO | D | 298 | 31.916 | 13.994 | 8.181 | 1.00 | 24.09 | D | C |
| ATOM | 3953 | C | PRO | D | 298 | 33.352 | 11.629 | 10.461 | 1.00 | 25.11 | D | C |
| ATOM | 3954 | O | PRO | D | 298 | 33.623 | 10.452 | 10.740 | 1.00 | 33.17 | D | O |
| ATOM | 3955 | N | GLU | D | 299 | 33.451 | 12.612 | 11.315 | 1.00 | 26.52 | D | N |
| ATOM | 3956 | CA | GLU | D | 299 | 34.054 | 12.349 | 12.659 | 1.00 | 24.49 | D | C |
| ATOM | 3957 | CB | GLU | D | 299 | 34.471 | 13.656 | 13.365 | 1.00 | 26.46 | D | C |
| ATOM | 3958 | CG | GLU | D | 299 | 33.345 | 14.689 | 13.650 | 1.00 | 23.24 | D | C |
| ATOM | 3959 | CD | GLU | D | 299 | 33.092 | 15.708 | 12.520 | 1.00 | 23.51 | D | C |
| ATOM | 3960 | OE1 | GLU | D | 299 | 33.344 | 15.478 | 11.305 | 1.00 | 24.32 | D | O |
| ATOM | 3961 | OE2 | GLU | D | 299 | 32.599 | 16.763 | 12.856 | 1.00 | 20.92 | D | O |
| ATOM | 3962 | C | GLU | D | 299 | 33.135 | 11.517 | 13.533 | 1.00 | 26.03 | D | C |
| ATOM | 3963 | O | GLU | D | 299 | 33.589 | 10.675 | 14.326 | 1.00 | 28.45 | D | O |
| ATOM | 3964 | N | MET | D | 300 | 31.837 | 11.666 | 13.367 | 1.00 | 24.80 | D | N |
| ATOM | 3965 | CA | MET | D | 300 | 30.910 | 10.840 | 14.140 | 1.00 | 27.07 | D | C |
| ATOM | 3966 | CB | MET | D | 300 | 29.554 | 11.518 | 14.319 | 1.00 | 27.44 | D | C |
| ATOM | 3967 | CG | MET | D | 300 | 29.715 | 12.758 | 15.203 | 1.00 | 33.02 | D | C |
| ATOM | 3968 | SD | MET | D | 300 | 28.138 | 13.467 | 15.630 | 1.00 | 34.71 | D | S |
| ATOM | 3969 | CE | MET | D | 300 | 27.610 | 12.254 | 16.822 | 1.00 | 36.50 | D | C |
| ATOM | 3970 | C | MET | D | 300 | 30.704 | 9.435 | 13.555 | 1.00 | 28.29 | D | C |
| ATOM | 3971 | O | MET | D | 300 | 30.537 | 8.514 | 14.309 | 1.00 | 28.72 | D | O |
| ATOM | 3972 | N | ILE | D | 301 | 30.688 | 9.247 | 12.251 | 1.00 | 28.74 | D | N |
| ATOM | 3973 | CA | ILE | D | 301 | 30.650 | 7.916 | 11.769 | 1.00 | 31.71 | D | C |
| ATOM | 3974 | CB | ILE | D | 301 | 30.457 | 7.762 | 10.256 | 1.00 | 35.18 | D | C |
| ATOM | 3975 | CG1 | ILE | D | 301 | 31.578 | 8.446 | 9.494 | 1.00 | 36.43 | D | C |
| ATOM | 3976 | CD1 | ILE | D | 301 | 31.542 | 8.069 | 8.034 | 1.00 | 43.53 | D | C |
| ATOM | 3977 | CG2 | ILE | D | 301 | 29.052 | 8.148 | 9.844 | 1.00 | 38.58 | D | C |
| ATOM | 3978 | C | ILE | D | 301 | 31.919 | 7.155 | 12.140 | 1.00 | 33.23 | D | C |
| ATOM | 3979 | O | ILE | D | 301 | 31.852 | 5.965 | 12.235 | 1.00 | 32.09 | D | O |
| ATOM | 3980 | N | GLU | D | 302 | 33.060 | 7.852 | 12.297 | 1.00 | 33.31 | D | N |
| ATOM | 3981 | CA | GLU | D | 302 | 34.275 | 7.196 | 12.770 | 1.00 | 36.00 | D | C |
| ATOM | 3982 | CB | GLU | D | 302 | 35.488 | 7.891 | 12.186 | 1.00 | 35.63 | D | C |
| ATOM | 3983 | CG | GLU | D | 302 | 35.506 | 7.777 | 10.674 | 1.00 | 35.22 | D | C |
| ATOM | 3984 | CD | GLU | D | 302 | 36.681 | 8.474 | 10.032 | 1.00 | 37.45 | D | C |
| ATOM | 3985 | OE1 | GLU | D | 302 | 37.407 | 9.273 | 10.665 | 1.00 | 39.39 | D | O |
| ATOM | 3986 | OE2 | GLU | D | 302 | 36.821 | 8.273 | 8.829 | 1.00 | 46.40 | D | O |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 3987 | C | GLU | D | 302 | 34.400 | 7.125 | 14.280 | 1.00 | 36.09 | D | C |
| ATOM | 3988 | O | GLU | D | 302 | 35.414 | 6.682 | 14.778 | 1.00 | 37.97 | D | O |
| ATOM | 3989 | N | GLY | D | 303 | 33.395 | 7.606 | 15.004 | 1.00 | 36.71 | D | N |
| ATOM | 3990 | CA | GLY | D | 303 | 33.367 | 7.541 | 16.456 | 1.00 | 35.99 | D | C |
| ATOM | 3991 | C | GLY | D | 303 | 34.486 | 8.296 | 17.106 | 1.00 | 34.99 | D | C |
| ATOM | 3992 | O | GLY | D | 303 | 34.974 | 7.895 | 18.146 | 1.00 | 34.87 | D | O |
| ATOM | 3993 | N | ARG | D | 304 | 34.919 | 9.381 | 16.478 | 1.00 | 35.90 | D | N |
| ATOM | 3994 | CA | ARG | D | 304 | 35.952 | 10.203 | 17.047 | 1.00 | 30.86 | D | C |
| ATOM | 3995 | CB | ARG | D | 304 | 36.870 | 10.714 | 15.977 | 1.00 | 31.04 | D | C |
| ATOM | 3996 | CG | ARG | D | 304 | 37.615 | 9.560 | 15.305 | 1.00 | 32.48 | D | C |
| ATOM | 3997 | CD | ARG | D | 304 | 38.636 | 10.044 | 14.305 | 1.00 | 31.76 | D | C |
| ATOM | 3998 | NE | ARG | D | 304 | 38.048 | 10.527 | 13.018 | 1.00 | 35.84 | D | N |
| ATOM | 3999 | CZ | ARG | D | 304 | 37.822 | 11.811 | 12.651 | 1.00 | 30.98 | D | C |
| ATOM | 4000 | NH1 | ARG | D | 304 | 38.026 | 12.785 | 13.448 | 1.00 | 31.56 | D | N |
| ATOM | 4001 | NH2 | ARG | D | 304 | 37.368 | 12.104 | 11.451 | 1.00 | 33.63 | D | N |
| ATOM | 4002 | C | ARG | D | 304 | 35.365 | 11.315 | 17.853 | 1.00 | 29.65 | D | C |
| ATOM | 4003 | O | ARG | D | 304 | 34.177 | 11.506 | 17.853 | 1.00 | 29.09 | D | O |
| ATOM | 4004 | N | MET | D | 305 | 36.230 | 12.004 | 18.590 | 1.00 | 28.45 | D | N |
| ATOM | 4005 | CA | MET | D | 305 | 35.870 | 13.155 | 19.380 | 1.00 | 30.18 | D | C |
| ATOM | 4006 | CB | MET | D | 305 | 37.094 | 13.744 | 20.059 | 1.00 | 30.09 | D | C |
| ATOM | 4007 | CG | MET | D | 305 | 36.737 | 14.895 | 20.959 | 1.00 | 34.46 | D | C |
| ATOM | 4008 | SD | MET | D | 305 | 38.112 | 15.367 | 22.053 | 1.00 | 39.14 | D | S |
| ATOM | 4009 | CE | MET | D | 305 | 39.405 | 15.891 | 20.906 | 1.00 | 36.45 | D | C |
| ATOM | 4010 | C | MET | D | 305 | 35.268 | 14.171 | 18.435 | 1.00 | 28.70 | D | C |
| ATOM | 4011 | O | MET | D | 305 | 35.788 | 14.374 | 17.338 | 1.00 | 25.19 | D | O |
| ATOM | 4012 | N | HIS | D | 306 | 34.196 | 14.815 | 18.852 | 1.00 | 30.20 | D | N |
| ATOM | 4013 | CA | HIS | D | 306 | 33.528 | 15.746 | 17.962 | 1.00 | 31.76 | D | C |
| ATOM | 4014 | CB | HIS | D | 306 | 32.330 | 15.050 | 17.335 | 1.00 | 31.61 | D | C |
| ATOM | 4015 | CG | HIS | D | 306 | 31.225 | 14.798 | 18.295 | 1.00 | 31.48 | D | C |
| ATOM | 4016 | ND1 | HIS | D | 306 | 31.012 | 13.577 | 18.902 | 1.00 | 34.30 | D | N |
| ATOM | 4017 | CE1 | HIS | D | 306 | 29.970 | 13.680 | 19.712 | 1.00 | 37.76 | D | C |
| ATOM | 4018 | NE2 | HIS | D | 306 | 29.484 | 14.912 | 19.619 | 1.00 | 32.81 | D | N |
| ATOM | 4019 | CD2 | HIS | D | 306 | 30.244 | 15.620 | 18.733 | 1.00 | 32.00 | D | C |
| ATOM | 4020 | C | HIS | D | 306 | 33.188 | 17.018 | 18.733 | 1.00 | 29.71 | D | C |
| ATOM | 4021 | O | HIS | D | 306 | 33.333 | 17.069 | 19.935 | 1.00 | 30.39 | D | O |
| ATOM | 4022 | N | ASP | D | 307 | 32.837 | 18.089 | 18.046 | 1.00 | 29.04 | D | N |
| ATOM | 4023 | CA | ASP | D | 307 | 32.573 | 19.351 | 18.731 | 1.00 | 27.49 | D | C |
| ATOM | 4024 | CB | ASP | D | 307 | 33.890 | 20.228 | 18.725 | 1.00 | 27.66 | D | C |
| ATOM | 4025 | CG | ASP | D | 307 | 34.332 | 20.613 | 17.343 | 1.00 | 28.00 | D | C |
| ATOM | 4026 | OD1 | ASP | D | 307 | 33.530 | 20.512 | 16.378 | 1.00 | 25.05 | D | O |
| ATOM | 4027 | OD2 | ASP | D | 307 | 35.510 | 20.914 | 17.112 | 1.00 | 27.60 | D | O |
| ATOM | 4028 | C | ASP | D | 307 | 31.380 | 20.013 | 18.017 | 1.00 | 28.64 | D | C |
| ATOM | 4029 | O | ASP | D | 307 | 30.653 | 19.357 | 17.229 | 1.00 | 23.81 | D | O |
| ATOM | 4030 | N | GLU | D | 308 | 31.184 | 21.307 | 18.259 | 1.00 | 23.28 | D | N |
| ATOM | 4031 | CA | GLU | D | 308 | 30.028 | 21.964 | 17.744 | 1.00 | 26.64 | D | C |
| ATOM | 4032 | CB | GLU | D | 308 | 29.866 | 23.332 | 18.374 | 1.00 | 28.17 | D | C |
| ATOM | 4033 | CG | GLU | D | 308 | 30.689 | 24.448 | 17.747 | 1.00 | 32.80 | D | C |
| ATOM | 4034 | CD | GLU | D | 308 | 32.163 | 24.374 | 18.065 | 1.00 | 35.13 | D | C |
| ATOM | 4035 | OE1 | GLU | D | 308 | 32.875 | 25.208 | 17.464 | 1.00 | 46.24 | D | O |
| ATOM | 4036 | OE2 | GLU | D | 308 | 32.605 | 23.564 | 18.940 | 1.00 | 32.99 | D | O |
| ATOM | 4037 | C | GLU | D | 308 | 29.927 | 22.014 | 16.206 | 1.00 | 26.90 | D | C |
| ATOM | 4038 | O | GLU | D | 308 | 28.830 | 22.284 | 15.633 | 1.00 | 22.26 | D | O |
| ATOM | 4039 | N | LYS | D | 309 | 31.050 | 21.756 | 15.535 | 1.00 | 24.70 | D | N |
| ATOM | 4040 | CA | LYS | D | 309 | 31.075 | 21.811 | 14.092 | 1.00 | 28.62 | D | C |
| ATOM | 4041 | CB | LYS | D | 309 | 32.519 | 21.805 | 13.551 | 1.00 | 26.33 | D | C |
| ATOM | 4042 | CG | LYS | D | 309 | 33.356 | 22.998 | 14.008 | 1.00 | 26.06 | D | C |
| ATOM | 4043 | CD | LYS | D | 309 | 32.733 | 24.336 | 13.567 | 1.00 | 26.51 | D | C |
| ATOM | 4044 | CE | LYS | D | 309 | 33.812 | 25.397 | 13.406 | 1.00 | 27.96 | D | C |
| ATOM | 4045 | NZ | LYS | D | 309 | 33.259 | 26.689 | 12.925 | 1.00 | 30.01 | D | N |
| ATOM | 4046 | C | LYS | D | 309 | 30.283 | 20.679 | 13.469 | 1.00 | 26.45 | D | C |
| ATOM | 4047 | O | LYS | D | 309 | 30.026 | 20.725 | 12.269 | 1.00 | 25.63 | D | O |
| ATOM | 4048 | N | VAL | D | 310 | 29.922 | 19.663 | 14.248 | 1.00 | 23.81 | D | N |
| ATOM | 4049 | CA | VAL | D | 310 | 28.956 | 18.677 | 13.716 | 1.00 | 24.04 | D | C |
| ATOM | 4050 | CB | VAL | D | 310 | 28.651 | 17.496 | 14.673 | 1.00 | 24.32 | D | C |
| ATOM | 4051 | CG1 | VAL | D | 310 | 29.940 | 16.792 | 15.111 | 1.00 | 27.05 | D | C |
| ATOM | 4052 | CG2 | VAL | D | 310 | 27.817 | 17.871 | 15.918 | 1.00 | 23.92 | D | C |
| ATOM | 4053 | C | VAL | D | 310 | 27.633 | 19.330 | 13.240 | 1.00 | 24.32 | D | C |
| ATOM | 4054 | O | VAL | D | 310 | 26.980 | 18.852 | 12.260 | 1.00 | 22.96 | D | O |
| ATOM | 4055 | N | ASP | D | 311 | 27.198 | 20.359 | 13.941 | 1.00 | 22.75 | D | N |
| ATOM | 4056 | CA | ASP | D | 311 | 25.957 | 21.014 | 13.563 | 1.00 | 23.58 | D | C |
| ATOM | 4057 | CB | ASP | D | 311 | 25.427 | 21.934 | 14.686 | 1.00 | 26.05 | D | C |
| ATOM | 4058 | CG | ASP | D | 311 | 25.011 | 21.137 | 15.914 | 1.00 | 28.70 | D | C |
| ATOM | 4059 | OD1 | ASP | D | 311 | 24.232 | 20.173 | 15.781 | 1.00 | 24.77 | D | O |
| ATOM | 4060 | OD2 | ASP | D | 311 | 25.535 | 21.414 | 17.017 | 1.00 | 28.18 | D | O |
| ATOM | 4061 | C | ASP | D | 311 | 26.053 | 21.749 | 12.277 | 1.00 | 21.95 | D | C |
| ATOM | 4062 | O | ASP | D | 311 | 25.061 | 21.937 | 11.571 | 1.00 | 20.26 | D | O |
| ATOM | 4063 | N | LEU | D | 312 | 27.245 | 22.153 | 11.917 | 1.00 | 20.90 | D | N |
| ATOM | 4064 | CA | LEU | D | 312 | 27.425 | 22.798 | 10.646 | 1.00 | 20.54 | D | C |

APPENDIX A-continued

| Atomic coordinates of Aurora A + Inhibitory Monobody Mb60 + Danusertib | | | | | | | | | | | |
|---|---|---|---|---|---|---|---|---|---|---|---|
| ATOM | 4065 | CB | LEU | D | 312 | 28.756 | 23.565 | 10.606 | 1.00 | 22.29 | D | C |
| ATOM | 4066 | CG | LEU | D | 312 | 28.873 | 24.878 | 11.343 | 1.00 | 21.82 | D | C |
| ATOM | 4067 | CD1 | LEU | D | 312 | 28.072 | 25.975 | 10.663 | 1.00 | 24.00 | D | C |
| ATOM | 4068 | CD2 | LEU | D | 312 | 28.449 | 24.802 | 12.802 | 1.00 | 22.89 | D | C |
| ATOM | 4069 | C | LEU | D | 312 | 27.383 | 21.835 | 9.519 | 1.00 | 20.17 | D | C |
| ATOM | 4070 | O | LEU | D | 312 | 26.771 | 22.157 | 8.514 | 1.00 | 21.63 | D | O |
| ATOM | 4071 | N | TRP | D | 313 | 27.983 | 20.629 | 9.666 | 1.00 | 19.91 | D | N |
| ATOM | 4072 | CA | TRP | D | 313 | 27.857 | 19.582 | 8.656 | 1.00 | 19.02 | D | C |
| ATOM | 4073 | CB | TRP | D | 313 | 28.608 | 18.364 | 9.133 | 1.00 | 21.09 | D | C |
| ATOM | 4074 | CG | TRP | D | 313 | 28.408 | 17.186 | 8.282 | 1.00 | 21.31 | D | C |
| ATOM | 4075 | CD1 | TRP | D | 313 | 27.392 | 16.285 | 8.365 | 1.00 | 19.37 | D | C |
| ATOM | 4076 | NE1 | TRP | D | 313 | 27.530 | 15.349 | 7.437 | 1.00 | 20.31 | D | N |
| ATOM | 4077 | CE2 | TRP | D | 313 | 28.687 | 15.569 | 6.744 | 1.00 | 21.85 | D | C |
| ATOM | 4078 | CD2 | TRP | D | 313 | 29.278 | 16.714 | 7.278 | 1.00 | 22.97 | D | C |
| ATOM | 4079 | CE3 | TRP | D | 313 | 30.481 | 17.193 | 6.719 | 1.00 | 22.61 | D | C |
| ATOM | 4080 | CZ3 | TRP | D | 313 | 31.066 | 16.469 | 5.734 | 1.00 | 24.10 | D | C |
| ATOM | 4081 | CH2 | TRP | D | 313 | 30.466 | 15.308 | 5.224 | 1.00 | 25.27 | D | C |
| ATOM | 4082 | CZ2 | TRP | D | 313 | 29.260 | 14.849 | 5.724 | 1.00 | 25.13 | D | C |
| ATOM | 4083 | C | TRP | D | 313 | 26.348 | 19.211 | 8.476 | 1.00 | 20.22 | D | C |
| ATOM | 4084 | O | TRP | D | 313 | 25.826 | 19.131 | 7.408 | 1.00 | 20.24 | D | O |
| ATOM | 4085 | N | SER | D | 314 | 25.688 | 19.003 | 9.573 | 1.00 | 20.20 | D | N |
| ATOM | 4086 | CA | SER | D | 314 | 24.300 | 18.545 | 9.489 | 1.00 | 28.56 | D | C |
| ATOM | 4087 | CB | SER | D | 314 | 23.783 | 18.049 | 10.864 | 1.00 | 26.69 | D | C |
| ATOM | 4088 | OG | SER | D | 314 | 23.472 | 19.142 | 11.636 | 1.00 | 40.74 | D | O |
| ATOM | 4089 | C | SER | D | 314 | 23.434 | 19.619 | 8.790 | 1.00 | 24.79 | D | C |
| ATOM | 4090 | O | SER | D | 314 | 22.514 | 19.311 | 8.034 | 1.00 | 23.01 | D | O |
| ATOM | 4091 | N | LEU | D | 315 | 23.747 | 20.882 | 9.004 | 1.00 | 27.00 | D | N |
| ATOM | 4092 | CA | LEU | D | 315 | 23.063 | 21.941 | 8.313 | 1.00 | 25.08 | D | C |
| ATOM | 4093 | CB | LEU | D | 315 | 23.511 | 23.259 | 8.914 | 1.00 | 31.03 | D | C |
| ATOM | 4094 | CG | LEU | D | 315 | 22.693 | 24.509 | 8.887 | 1.00 | 31.25 | D | C |
| ATOM | 4095 | CD1 | LEU | D | 315 | 21.308 | 24.267 | 9.441 | 1.00 | 27.94 | D | C |
| ATOM | 4096 | CD2 | LEU | D | 315 | 23.379 | 25.487 | 9.850 | 1.00 | 31.96 | D | C |
| ATOM | 4097 | C | LEU | D | 315 | 23.260 | 21.910 | 6.813 | 1.00 | 25.34 | D | C |
| ATOM | 4098 | O | LEU | D | 315 | 22.316 | 22.177 | 5.975 | 1.00 | 27.04 | D | O |
| ATOM | 4099 | N | GLY | D | 316 | 24.471 | 21.608 | 6.410 | 1.00 | 25.78 | D | N |
| ATOM | 4100 | CA | GLY | D | 316 | 24.729 | 21.360 | 4.968 | 1.00 | 25.38 | D | C |
| ATOM | 4101 | C | GLY | D | 316 | 23.889 | 20.195 | 4.399 | 1.00 | 23.24 | D | C |
| ATOM | 4102 | O | GLY | D | 316 | 23.362 | 20.304 | 3.308 | 1.00 | 24.49 | D | O |
| ATOM | 4103 | N | VAL | D | 317 | 23.882 | 19.064 | 5.088 | 1.00 | 19.60 | D | N |
| ATOM | 4104 | CA | VAL | D | 317 | 23.155 | 17.961 | 4.642 | 1.00 | 21.85 | D | C |
| ATOM | 4105 | CB | VAL | D | 317 | 23.314 | 16.782 | 5.613 | 1.00 | 22.15 | D | C |
| ATOM | 4106 | CG1 | VAL | D | 317 | 22.368 | 15.658 | 5.277 | 1.00 | 23.48 | D | C |
| ATOM | 4107 | CG2 | VAL | D | 317 | 24.752 | 16.245 | 5.611 | 1.00 | 21.08 | D | C |
| ATOM | 4108 | C | VAL | D | 317 | 21.666 | 18.390 | 4.492 | 1.00 | 24.54 | D | C |
| ATOM | 4109 | O | VAL | D | 317 | 21.006 | 18.013 | 3.539 | 1.00 | 20.38 | D | O |
| ATOM | 4110 | N | LEU | D | 318 | 21.146 | 19.139 | 5.453 | 1.00 | 24.69 | D | N |
| ATOM | 4111 | CA | LEU | D | 318 | 19.729 | 19.481 | 5.449 | 1.00 | 25.10 | D | C |
| ATOM | 4112 | CB | LEU | D | 318 | 19.361 | 20.063 | 6.817 | 1.00 | 25.36 | D | C |
| ATOM | 4113 | CG | LEU | D | 318 | 17.899 | 20.397 | 6.973 | 1.00 | 28.12 | D | C |
| ATOM | 4114 | CD1 | LEU | D | 318 | 16.998 | 19.156 | 6.940 | 1.00 | 25.74 | D | C |
| ATOM | 4115 | CD2 | LEU | D | 318 | 17.760 | 21.176 | 8.282 | 1.00 | 31.60 | D | C |
| ATOM | 4116 | C | LEU | D | 318 | 19.429 | 20.477 | 4.348 | 1.00 | 23.99 | D | C |
| ATOM | 4117 | O | LEU | D | 318 | 18.416 | 20.348 | 3.676 | 1.00 | 22.29 | D | O |
| ATOM | 4118 | N | CYS | D | 319 | 20.311 | 21.491 | 4.176 | 1.00 | 23.87 | D | N |
| ATOM | 4119 | CA | CYS | D | 319 | 20.177 | 22.466 | 3.090 | 1.00 | 22.15 | D | C |
| ATOM | 4120 | CB | CYS | D | 319 | 21.331 | 23.434 | 3.071 | 1.00 | 23.25 | D | C |
| ATOM | 4121 | SG | CYS | D | 319 | 20.993 | 24.768 | 1.923 | 1.00 | 24.63 | D | S |
| ATOM | 4122 | C | CYS | D | 319 | 20.041 | 21.798 | 1.712 | 1.00 | 24.21 | D | C |
| ATOM | 4123 | O | CYS | D | 319 | 19.162 | 22.157 | 0.941 | 1.00 | 22.28 | D | O |
| ATOM | 4124 | N | TYR | D | 320 | 20.820 | 20.718 | 1.511 | 1.00 | 24.43 | D | N |
| ATOM | 4125 | CA | TYR | D | 320 | 20.818 | 19.972 | 0.276 | 1.00 | 25.06 | D | C |
| ATOM | 4126 | CB | TYR | D | 320 | 22.024 | 18.979 | 0.255 | 1.00 | 22.98 | D | C |
| ATOM | 4127 | CG | TYR | D | 320 | 22.147 | 18.062 | −0.967 | 1.00 | 21.56 | D | C |
| ATOM | 4128 | CD1 | TYR | D | 320 | 21.346 | 16.969 | −1.130 | 1.00 | 20.68 | D | C |
| ATOM | 4129 | CE1 | TYR | D | 320 | 21.448 | 16.193 | −2.270 | 1.00 | 23.61 | D | C |
| ATOM | 4130 | CZ | TYR | D | 320 | 22.377 | 16.498 | −3.221 | 1.00 | 22.34 | D | C |
| ATOM | 4131 | OH | TYR | D | 320 | 22.544 | 15.760 | −4.303 | 1.00 | 25.27 | D | O |
| ATOM | 4132 | CE2 | TYR | D | 320 | 23.231 | 17.538 | −3.052 | 1.00 | 23.03 | D | C |
| ATOM | 4133 | CD2 | TYR | D | 320 | 23.095 | 18.311 | −1.941 | 1.00 | 21.95 | D | C |
| ATOM | 4134 | C | TYR | D | 320 | 19.483 | 19.219 | 0.161 | 1.00 | 23.96 | D | C |
| ATOM | 4135 | O | TYR | D | 320 | 18.833 | 19.253 | −0.886 | 1.00 | 22.01 | D | O |
| ATOM | 4136 | N | GLU | D | 321 | 19.117 | 18.528 | 1.232 | 1.00 | 25.28 | D | N |
| ATOM | 4137 | CA | GLU | D | 321 | 17.939 | 17.719 | 1.221 | 1.00 | 23.71 | D | C |
| ATOM | 4138 | CB | GLU | D | 321 | 17.822 | 16.844 | 2.507 | 1.00 | 24.07 | D | C |
| ATOM | 4139 | CG | GLU | D | 321 | 16.531 | 16.020 | 2.436 | 1.00 | 27.33 | D | C |
| ATOM | 4140 | CD | GLU | D | 321 | 16.423 | 14.848 | 3.387 | 1.00 | 33.88 | D | C |
| ATOM | 4141 | OE1 | GLU | D | 321 | 17.104 | 14.795 | 4.439 | 1.00 | 35.45 | D | O |
| ATOM | 4142 | OE2 | GLU | D | 321 | 15.603 | 13.969 | 3.037 | 1.00 | 37.17 | D | O |

APPENDIX A-continued

| Atomic coordinates of Aurora A + Inhibitory Monobody Mb60 + Danusertib | | | | | | | | | | | |
|---|---|---|---|---|---|---|---|---|---|---|---|
| ATOM | 4143 | C | GLU | D | 321 | 16.672 | 18.553 | 0.950 | 1.00 | 24.70 | D | C |
| ATOM | 4144 | O | GLU | D | 321 | 15.817 | 18.125 | 0.205 | 1.00 | 24.65 | D | O |
| ATOM | 4145 | N | PHE | D | 322 | 16.581 | 19.753 | 1.533 | 1.00 | 25.20 | D | N |
| ATOM | 4146 | CA | PHE | D | 322 | 15.494 | 20.682 | 1.251 | 1.00 | 23.09 | D | C |
| ATOM | 4147 | CB | PHE | D | 322 | 15.656 | 21.937 | 2.107 | 1.00 | 22.91 | D | C |
| ATOM | 4148 | CG | PHE | D | 322 | 15.311 | 21.776 | 3.554 | 1.00 | 23.46 | D | C |
| ATOM | 4149 | CD1 | PHE | D | 322 | 14.412 | 20.821 | 4.007 | 1.00 | 24.92 | D | C |
| ATOM | 4150 | CE1 | PHE | D | 322 | 14.054 | 20.779 | 5.339 | 1.00 | 26.37 | D | C |
| ATOM | 4151 | CZ | PHE | D | 322 | 14.571 | 21.709 | 6.222 | 1.00 | 25.50 | D | C |
| ATOM | 4152 | CE2 | PHE | D | 322 | 15.429 | 22.661 | 5.791 | 1.00 | 25.14 | D | C |
| ATOM | 4153 | CD2 | PHE | D | 322 | 15.796 | 22.685 | 4.453 | 1.00 | 25.46 | D | C |
| ATOM | 4154 | C | PHE | D | 322 | 15.381 | 21.150 | −0.206 | 1.00 | 26.83 | D | C |
| ATOM | 4155 | O | PHE | D | 322 | 14.301 | 21.207 | −0.796 | 1.00 | 22.54 | D | O |
| ATOM | 4156 | N | LEU | D | 323 | 16.514 | 21.484 | −0.787 | 1.00 | 24.36 | D | N |
| ATOM | 4157 | CA | LEU | D | 323 | 16.584 | 21.842 | −2.170 | 1.00 | 24.84 | D | C |
| ATOM | 4158 | CB | LEU | D | 323 | 17.910 | 22.529 | −2.480 | 1.00 | 25.14 | D | C |
| ATOM | 4159 | CG | LEU | D | 323 | 18.132 | 23.843 | −1.740 | 1.00 | 27.06 | D | C |
| ATOM | 4160 | CD1 | LEU | D | 323 | 19.568 | 24.303 | −1.925 | 1.00 | 28.30 | D | C |
| ATOM | 4161 | CD2 | LEU | D | 323 | 17.155 | 24.913 | −2.268 | 1.00 | 30.09 | D | C |
| ATOM | 4162 | C | LEU | D | 323 | 16.422 | 20.723 | −3.169 | 1.00 | 24.72 | D | C |
| ATOM | 4163 | O | LEU | D | 323 | 15.873 | 20.972 | −4.247 | 1.00 | 22.19 | D | O |
| ATOM | 4164 | N | VAL | D | 324 | 16.941 | 19.537 | −2.845 | 1.00 | 23.40 | D | N |
| ATOM | 4165 | CA | VAL | D | 324 | 16.991 | 18.399 | −3.771 | 1.00 | 24.96 | D | C |
| ATOM | 4166 | CB | VAL | D | 324 | 18.391 | 17.722 | −3.749 | 1.00 | 24.62 | D | C |
| ATOM | 4167 | CG1 | VAL | D | 324 | 18.464 | 16.507 | −4.653 | 1.00 | 24.06 | D | C |
| ATOM | 4168 | CG2 | VAL | D | 324 | 19.384 | 18.751 | −4.281 | 1.00 | 23.95 | D | C |
| ATOM | 4169 | C | VAL | D | 324 | 15.889 | 17.375 | −3.545 | 1.00 | 26.26 | D | C |
| ATOM | 4170 | O | VAL | D | 324 | 15.433 | 16.758 | −4.498 | 1.00 | 27.06 | D | O |
| ATOM | 4171 | N | GLY | D | 325 | 15.448 | 17.226 | −2.317 | 1.00 | 25.61 | D | N |
| ATOM | 4172 | CA | GLY | D | 325 | 14.388 | 16.267 | −1.974 | 1.00 | 27.70 | D | C |
| ATOM | 4173 | C | GLY | D | 325 | 14.899 | 14.997 | −1.349 | 1.00 | 27.54 | D | C |
| ATOM | 4174 | O | GLY | D | 325 | 14.112 | 14.212 | −0.896 | 1.00 | 23.79 | D | O |
| ATOM | 4175 | N | LYS | D | 326 | 16.219 | 14.777 | −1.375 | 1.00 | 29.64 | D | N |
| ATOM | 4176 | CA | LYS | D | 326 | 16.895 | 13.641 | −0.790 | 1.00 | 32.32 | D | C |
| ATOM | 4177 | CB | LYS | D | 326 | 17.219 | 12.599 | −1.874 | 1.00 | 40.24 | D | C |
| ATOM | 4178 | CG | LYS | D | 326 | 16.066 | 12.082 | −2.663 | 1.00 | 50.41 | D | C |
| ATOM | 4179 | CD | LYS | D | 326 | 16.057 | 10.558 | −2.867 | 1.00 | 60.77 | D | C |
| ATOM | 4180 | CE | LYS | D | 326 | 15.446 | 9.809 | −1.672 | 1.00 | 61.37 | D | C |
| ATOM | 4181 | NZ | LYS | D | 326 | 14.065 | 10.259 | −1.381 | 1.00 | 66.61 | D | N |
| ATOM | 4182 | C | LYS | D | 326 | 18.256 | 14.077 | −0.198 | 1.00 | 29.58 | D | C |
| ATOM | 4183 | O | LYS | D | 326 | 18.865 | 15.035 | −0.674 | 1.00 | 26.29 | D | O |
| ATOM | 4184 | N | PRO | D | 327 | 18.775 | 13.331 | 0.767 | 1.00 | 28.24 | D | N |
| ATOM | 4185 | CA | PRO | D | 327 | 20.066 | 13.716 | 1.360 | 1.00 | 28.34 | D | C |
| ATOM | 4186 | CB | PRO | D | 327 | 20.136 | 12.904 | 2.646 | 1.00 | 26.96 | D | C |
| ATOM | 4187 | CG | PRO | D | 327 | 19.177 | 11.770 | 2.451 | 1.00 | 29.30 | D | C |
| ATOM | 4188 | CD | PRO | D | 327 | 18.149 | 12.186 | 1.454 | 1.00 | 29.62 | D | C |
| ATOM | 4189 | C | PRO | D | 327 | 21.241 | 13.353 | 0.453 | 1.00 | 26.83 | D | C |
| ATOM | 4190 | O | PRO | D | 327 | 21.131 | 12.504 | −0.319 | 1.00 | 25.34 | D | O |
| ATOM | 4191 | N | PRO | D | 328 | 22.363 | 14.058 | 0.566 | 1.00 | 29.12 | D | N |
| ATOM | 4192 | CA | PRO | D | 328 | 23.445 | 13.956 | −0.414 | 1.00 | 27.05 | D | C |
| ATOM | 4193 | CB | PRO | D | 328 | 24.339 | 15.163 | −0.061 | 1.00 | 27.88 | D | C |
| ATOM | 4194 | CG | PRO | D | 328 | 24.081 | 15.427 | 1.379 | 1.00 | 29.52 | D | C |
| ATOM | 4195 | CD | PRO | D | 328 | 22.615 | 15.108 | 1.577 | 1.00 | 27.39 | D | C |
| ATOM | 4196 | C | PRO | D | 328 | 24.245 | 12.632 | −0.475 | 1.00 | 27.81 | D | C |
| ATOM | 4197 | O | PRO | D | 328 | 24.801 | 12.318 | −1.539 | 1.00 | 27.24 | D | O |
| ATOM | 4198 | N | PHE | D | 329 | 24.276 | 11.844 | 0.596 | 1.00 | 26.25 | D | N |
| ATOM | 4199 | CA | PHE | D | 329 | 25.164 | 10.659 | 0.659 | 1.00 | 29.66 | D | C |
| ATOM | 4200 | CB | PHE | D | 329 | 26.067 | 10.744 | 1.901 | 1.00 | 25.79 | D | C |
| ATOM | 4201 | CG | PHE | D | 329 | 26.811 | 12.061 | 2.000 | 1.00 | 23.09 | D | C |
| ATOM | 4202 | CD1 | PHE | D | 329 | 27.794 | 12.342 | 1.114 | 1.00 | 22.44 | D | C |
| ATOM | 4203 | CE1 | PHE | D | 329 | 28.500 | 13.538 | 1.150 | 1.00 | 24.40 | D | C |
| ATOM | 4204 | CZ | PHE | D | 329 | 28.207 | 14.459 | 2.127 | 1.00 | 24.54 | D | C |
| ATOM | 4205 | CE2 | PHE | D | 329 | 27.193 | 14.170 | 3.037 | 1.00 | 24.68 | D | C |
| ATOM | 4206 | CD2 | PHE | D | 329 | 26.522 | 12.960 | 2.974 | 1.00 | 24.02 | D | C |
| ATOM | 4207 | C | PHE | D | 329 | 24.370 | 9.377 | 0.679 | 1.00 | 29.72 | D | C |
| ATOM | 4208 | O | PHE | D | 329 | 24.904 | 8.298 | 0.980 | 1.00 | 36.39 | D | O |
| ATOM | 4209 | N | GLU | D | 330 | 23.116 | 9.486 | 0.312 | 1.00 | 28.70 | D | N |
| ATOM | 4210 | CA | GLU | D | 330 | 22.206 | 8.337 | 0.404 | 1.00 | 34.79 | D | C |
| ATOM | 4211 | CB | GLU | D | 330 | 20.831 | 8.747 | −0.115 | 1.00 | 38.00 | D | C |
| ATOM | 4212 | CG | GLU | D | 330 | 19.697 | 7.877 | 0.358 | 1.00 | 47.48 | D | C |
| ATOM | 4213 | CD | GLU | D | 330 | 18.352 | 8.470 | −0.051 | 1.00 | 45.54 | D | C |
| ATOM | 4214 | OE1 | GLU | D | 330 | 18.127 | 8.641 | −1.260 | 1.00 | 52.99 | D | O |
| ATOM | 4215 | OE2 | GLU | D | 330 | 17.560 | 8.806 | 0.841 | 1.00 | 50.98 | D | O |
| ATOM | 4216 | C | GLU | D | 330 | 22.774 | 7.221 | −0.439 | 1.00 | 33.36 | D | C |
| ATOM | 4217 | O | GLU | D | 330 | 23.176 | 7.432 | −1.549 | 1.00 | 32.35 | D | O |
| ATOM | 4218 | N | ALA | D | 331 | 22.853 | 6.028 | 0.085 | 1.00 | 33.82 | D | N |
| ATOM | 4219 | CA | ALA | D | 331 | 23.257 | 4.878 | −0.733 | 1.00 | 35.67 | D | C |
| ATOM | 4220 | CB | ALA | D | 331 | 24.775 | 4.701 | −0.731 | 1.00 | 36.89 | D | C |

APPENDIX A-continued

| Atomic coordinates of Aurora A + Inhibitory Monobody Mb60 + Danusertib | | | | | | | | | | | |
|---|---|---|---|---|---|---|---|---|---|---|---|
| ATOM | 4221 | C | ALA | D | 331 | 22.538 | 3.633 | −0.244 | 1.00 | 35.22 | D | C |
| ATOM | 4222 | O | ALA | D | 331 | 21.874 | 3.662 | 0.763 | 1.00 | 35.11 | D | O |
| ATOM | 4223 | N | ASN | D | 332 | 22.671 | 2.517 | −0.938 | 1.00 | 37.36 | D | N |
| ATOM | 4224 | CA | ASN | D | 332 | 21.759 | 1.392 | −0.640 | 1.00 | 43.15 | D | C |
| ATOM | 4225 | CB | ASN | D | 332 | 21.357 | 0.654 | −1.916 | 1.00 | 43.66 | D | C |
| ATOM | 4226 | CG | ASN | D | 332 | 22.548 | 0.091 | −2.654 | 1.00 | 53.22 | D | C |
| ATOM | 4227 | OD1 | ASN | D | 332 | 23.573 | −0.286 | −2.050 | 1.00 | 59.96 | D | O |
| ATOM | 4228 | ND2 | ASN | D | 332 | 22.454 | 0.078 | −3.968 | 1.00 | 60.85 | D | N |
| ATOM | 4229 | C | ASN | D | 332 | 22.288 | 0.454 | 0.439 | 1.00 | 38.31 | D | C |
| ATOM | 4230 | O | ASN | D | 332 | 21.551 | −0.378 | 0.928 | 1.00 | 35.08 | D | O |
| ATOM | 4231 | N | THR | D | 333 | 23.553 | 0.620 | 0.836 | 1.00 | 38.58 | D | N |
| ATOM | 4232 | CA | THR | D | 333 | 24.075 | −0.030 | 2.016 | 1.00 | 36.09 | D | C |
| ATOM | 4233 | CB | THR | D | 333 | 25.072 | −1.124 | 1.645 | 1.00 | 36.46 | D | C |
| ATOM | 4234 | OG1 | THR | D | 333 | 26.294 | −0.575 | 1.150 | 1.00 | 35.94 | D | O |
| ATOM | 4235 | CG2 | THR | D | 333 | 24.479 | −2.136 | 0.647 | 1.00 | 35.21 | D | C |
| ATOM | 4236 | C | THR | D | 333 | 24.774 | 0.900 | 3.030 | 1.00 | 39.11 | D | C |
| ATOM | 4237 | O | THR | D | 333 | 25.155 | 2.048 | 2.713 | 1.00 | 40.18 | D | O |
| ATOM | 4238 | N | TYR | D | 334 | 25.005 | 0.339 | 4.208 | 1.00 | 36.26 | D | N |
| ATOM | 4239 | CA | TYR | D | 334 | 25.671 | 1.018 | 5.283 | 1.00 | 34.49 | D | C |
| ATOM | 4240 | CB | TYR | D | 334 | 25.595 | 0.234 | 6.595 | 1.00 | 34.53 | D | C |
| ATOM | 4241 | CG | TYR | D | 334 | 26.399 | 0.934 | 7.692 | 1.00 | 35.57 | D | C |
| ATOM | 4242 | CD1 | TYR | D | 334 | 27.736 | 0.701 | 7.821 | 1.00 | 35.65 | D | C |
| ATOM | 4243 | CE1 | TYR | D | 334 | 28.495 | 1.360 | 8.757 | 1.00 | 38.89 | D | C |
| ATOM | 4244 | CZ | TYR | D | 334 | 27.924 | 2.254 | 9.601 | 1.00 | 36.14 | D | C |
| ATOM | 4245 | OH | TYR | D | 334 | 28.762 | 2.851 | 10.496 | 1.00 | 42.12 | D | O |
| ATOM | 4246 | CE2 | TYR | D | 334 | 26.578 | 2.522 | 9.521 | 1.00 | 38.15 | D | C |
| ATOM | 4247 | CD2 | TYR | D | 334 | 25.804 | 1.839 | 8.576 | 1.00 | 34.67 | D | C |
| ATOM | 4248 | C | TYR | D | 334 | 27.107 | 1.295 | 4.833 | 1.00 | 39.48 | D | C |
| ATOM | 4249 | O | TYR | D | 334 | 27.590 | 2.440 | 4.913 | 1.00 | 39.01 | D | O |
| ATOM | 4250 | N | GLN | D | 335 | 27.758 | 0.297 | 4.281 | 1.00 | 34.40 | D | N |
| ATOM | 4251 | CA | GLN | D | 335 | 29.124 | 0.448 | 3.889 | 1.00 | 37.78 | D | C |
| ATOM | 4252 | CB | GLN | D | 335 | 29.792 | −0.894 | 3.487 | 1.00 | 39.58 | D | C |
| ATOM | 4253 | CG | GLN | D | 335 | 31.304 | −0.782 | 3.197 | 1.00 | 49.74 | D | C |
| ATOM | 4254 | CD | GLN | D | 335 | 32.142 | −0.043 | 4.293 | 1.00 | 62.08 | D | C |
| ATOM | 4255 | OE1 | GLN | D | 335 | 32.098 | −0.391 | 5.495 | 1.00 | 72.57 | D | O |
| ATOM | 4256 | NE2 | GLN | D | 335 | 32.889 | 0.988 | 3.883 | 1.00 | 58.93 | D | N |
| ATOM | 4257 | C | GLN | D | 335 | 29.282 | 1.472 | 2.767 | 1.00 | 35.54 | D | C |
| ATOM | 4258 | O | GLN | D | 335 | 30.303 | 2.211 | 2.752 | 1.00 | 32.77 | D | O |
| ATOM | 4259 | N | GLU | D | 336 | 28.329 | 1.510 | 1.832 | 1.00 | 34.11 | D | N |
| ATOM | 4260 | CA | GLU | D | 336 | 28.434 | 2.459 | 0.729 | 1.00 | 37.29 | D | C |
| ATOM | 4261 | CB | GLU | D | 336 | 27.509 | 2.060 | −0.413 | 1.00 | 42.48 | D | C |
| ATOM | 4262 | CG | GLU | D | 336 | 27.682 | 2.848 | −1.714 | 1.00 | 53.48 | D | C |
| ATOM | 4263 | CD | GLU | D | 336 | 29.134 | 2.957 | −2.185 | 1.00 | 63.48 | D | C |
| ATOM | 4264 | OE1 | GLU | D | 336 | 29.891 | 1.925 | −2.156 | 1.00 | 61.92 | D | O |
| ATOM | 4265 | OE2 | GLU | D | 336 | 29.510 | 4.102 | −2.557 | 1.00 | 61.06 | D | O |
| ATOM | 4266 | C | GLU | D | 336 | 28.142 | 3.884 | 1.255 | 1.00 | 36.10 | D | C |
| ATOM | 4267 | O | GLU | D | 336 | 28.815 | 4.874 | 0.868 | 1.00 | 30.16 | D | O |
| ATOM | 4268 | N | THR | D | 337 | 27.171 | 3.974 | 2.173 | 1.00 | 31.53 | D | N |
| ATOM | 4269 | CA | THR | D | 337 | 26.819 | 5.248 | 2.763 | 1.00 | 32.08 | D | C |
| ATOM | 4270 | CB | THR | D | 337 | 25.533 | 5.175 | 3.626 | 1.00 | 32.61 | D | C |
| ATOM | 4271 | OG1 | THR | D | 337 | 24.469 | 4.595 | 2.867 | 1.00 | 31.57 | D | O |
| ATOM | 4272 | CG2 | THR | D | 337 | 25.105 | 6.594 | 4.031 | 1.00 | 32.37 | D | C |
| ATOM | 4273 | C | THR | D | 337 | 28.000 | 5.854 | 3.528 | 1.00 | 28.71 | D | C |
| ATOM | 4274 | O | THR | D | 337 | 28.360 | 7.000 | 3.321 | 1.00 | 27.55 | D | O |
| ATOM | 4275 | N | TYR | D | 338 | 28.613 | 5.022 | 4.349 | 1.00 | 28.99 | D | N |
| ATOM | 4276 | CA | TYR | D | 338 | 29.818 | 5.299 | 5.121 | 1.00 | 30.13 | D | C |
| ATOM | 4277 | CB | TYR | D | 338 | 30.222 | 4.025 | 5.869 | 1.00 | 30.04 | D | C |
| ATOM | 4278 | CG | TYR | D | 338 | 31.365 | 4.206 | 6.803 | 1.00 | 31.65 | D | C |
| ATOM | 4279 | CD1 | TYR | D | 338 | 32.667 | 4.210 | 6.323 | 1.00 | 36.54 | D | C |
| ATOM | 4280 | CE1 | TYR | D | 338 | 33.770 | 4.393 | 7.172 | 1.00 | 38.21 | D | C |
| ATOM | 4281 | CZ | TYR | D | 338 | 33.557 | 4.573 | 8.513 | 1.00 | 37.17 | D | C |
| ATOM | 4282 | OH | TYR | D | 338 | 34.674 | 4.706 | 9.264 | 1.00 | 43.67 | D | O |
| ATOM | 4283 | CE2 | TYR | D | 338 | 32.260 | 4.531 | 9.051 | 1.00 | 39.41 | D | C |
| ATOM | 4284 | CD2 | TYR | D | 338 | 31.161 | 4.336 | 8.194 | 1.00 | 34.74 | D | C |
| ATOM | 4285 | C | TYR | D | 338 | 30.969 | 5.816 | 4.254 | 1.00 | 31.02 | D | C |
| ATOM | 4286 | O | TYR | D | 338 | 31.585 | 6.830 | 4.553 | 1.00 | 26.77 | D | O |
| ATOM | 4287 | N | LYS | D | 339 | 31.236 | 5.104 | 3.171 | 1.00 | 28.84 | D | N |
| ATOM | 4288 | CA | LYS | D | 339 | 32.265 | 5.463 | 2.277 | 1.00 | 33.29 | D | C |
| ATOM | 4289 | CB | LYS | D | 339 | 32.340 | 4.381 | 1.205 | 1.00 | 41.85 | D | C |
| ATOM | 4290 | CG | LYS | D | 339 | 33.496 | 4.488 | 0.253 | 1.00 | 53.31 | D | C |
| ATOM | 4291 | CD | LYS | D | 339 | 33.690 | 3.145 | −0.468 | 1.00 | 69.56 | D | C |
| ATOM | 4292 | CE | LYS | D | 339 | 34.946 | 3.108 | −1.341 | 1.00 | 80.15 | D | C |
| ATOM | 4293 | NZ | LYS | D | 339 | 34.893 | 4.114 | −2.443 | 1.00 | 85.23 | D | N |
| ATOM | 4294 | C | LYS | D | 339 | 31.968 | 6.845 | 1.641 | 1.00 | 30.17 | D | C |
| ATOM | 4295 | O | LYS | D | 339 | 32.847 | 7.661 | 1.540 | 1.00 | 28.17 | D | O |
| ATOM | 4296 | N | ARG | D | 340 | 30.733 | 7.073 | 1.232 | 1.00 | 25.09 | D | N |
| ATOM | 4297 | CA | ARG | D | 340 | 30.313 | 8.366 | 0.684 | 1.00 | 28.53 | D | C |
| ATOM | 4298 | CB | ARG | D | 340 | 28.833 | 8.364 | 0.266 | 1.00 | 29.89 | D | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 4299 | CG | ARG | D | 340 | 28.439 | 7.293 | −0.762 | 1.00 | 37.27 | D | C |
| ATOM | 4300 | CD | ARG | D | 340 | 28.790 | 7.631 | −2.169 | 1.00 | 40.22 | D | C |
| ATOM | 4301 | NE | ARG | D | 340 | 28.156 | 8.877 | −2.446 | 1.00 | 50.75 | D | N |
| ATOM | 4302 | CZ | ARG | D | 340 | 26.870 | 9.066 | −2.701 | 1.00 | 50.69 | D | C |
| ATOM | 4303 | NH1 | ARG | D | 340 | 26.038 | 8.024 | −2.831 | 1.00 | 53.27 | D | N |
| ATOM | 4304 | NH2 | ARG | D | 340 | 26.444 | 10.336 | −2.856 | 1.00 | 39.08 | D | N |
| ATOM | 4305 | C | ARG | D | 340 | 30.519 | 9.542 | 1.639 | 1.00 | 24.13 | D | C |
| ATOM | 4306 | O | ARG | D | 340 | 31.051 | 10.598 | 1.231 | 1.00 | 27.94 | D | O |
| ATOM | 4307 | N | ILE | D | 341 | 30.083 | 9.372 | 2.868 | 1.00 | 23.46 | D | N |
| ATOM | 4308 | CA | ILE | D | 341 | 30.182 | 10.404 | 3.899 | 1.00 | 23.84 | D | C |
| ATOM | 4309 | CB | ILE | D | 341 | 29.495 | 10.036 | 5.204 | 1.00 | 23.92 | D | C |
| ATOM | 4310 | CG1 | ILE | D | 341 | 27.984 | 10.169 | 5.034 | 1.00 | 24.21 | D | C |
| ATOM | 4311 | CD1 | ILE | D | 341 | 27.214 | 9.355 | 6.086 | 1.00 | 28.47 | D | C |
| ATOM | 4312 | CG2 | ILE | D | 341 | 29.897 | 11.020 | 6.321 | 1.00 | 21.46 | D | C |
| ATOM | 4313 | C | ILE | D | 341 | 31.670 | 10.610 | 4.190 | 1.00 | 25.67 | D | C |
| ATOM | 4314 | O | ILE | D | 341 | 32.164 | 11.737 | 4.150 | 1.00 | 24.27 | D | O |
| ATOM | 4315 | N | SER | D | 342 | 32.367 | 9.507 | 4.373 | 1.00 | 25.79 | D | N |
| ATOM | 4316 | CA | SER | D | 342 | 33.799 | 9.544 | 4.692 | 1.00 | 30.28 | D | C |
| ATOM | 4317 | CB | SER | D | 342 | 34.291 | 8.115 | 4.821 | 1.00 | 28.51 | D | C |
| ATOM | 4318 | OG | SER | D | 342 | 35.441 | 8.202 | 5.536 | 1.00 | 48.89 | D | O |
| ATOM | 4319 | C | SER | D | 342 | 34.644 | 10.294 | 3.630 | 1.00 | 28.69 | D | C |
| ATOM | 4320 | O | SER | D | 342 | 35.648 | 10.917 | 3.946 | 1.00 | 25.89 | D | O |
| ATOM | 4321 | N | ARG | D | 343 | 34.232 | 10.193 | 2.368 | 1.00 | 26.28 | D | N |
| ATOM | 4322 | CA | ARG | D | 343 | 34.958 | 10.814 | 1.240 | 1.00 | 26.71 | D | C |
| ATOM | 4323 | CB | ARG | D | 343 | 34.979 | 9.829 | 0.081 | 1.00 | 29.24 | D | C |
| ATOM | 4324 | CG | ARG | D | 343 | 35.700 | 8.512 | 0.386 | 1.00 | 31.82 | D | C |
| ATOM | 4325 | CD | ARG | D | 343 | 35.717 | 7.534 | −0.777 | 1.00 | 36.78 | D | C |
| ATOM | 4326 | NE | ARG | D | 343 | 37.046 | 7.465 | −1.374 | 1.00 | 48.85 | D | N |
| ATOM | 4327 | CZ | ARG | D | 343 | 37.421 | 8.080 | −2.487 | 1.00 | 55.86 | D | C |
| ATOM | 4328 | NH1 | ARG | D | 343 | 36.573 | 8.818 | −3.200 | 1.00 | 67.69 | D | N |
| ATOM | 4329 | NH2 | ARG | D | 343 | 38.664 | 7.973 | −2.887 | 1.00 | 50.87 | D | N |
| ATOM | 4330 | C | ARG | D | 343 | 34.325 | 12.100 | 0.796 | 1.00 | 27.03 | D | C |
| ATOM | 4331 | O | ARG | D | 343 | 34.812 | 12.749 | −0.122 | 1.00 | 25.30 | D | O |
| ATOM | 4332 | N | VAL | D | 344 | 33.229 | 12.477 | 1.473 | 1.00 | 25.62 | D | N |
| ATOM | 4333 | CA | VAL | D | 344 | 32.377 | 13.623 | 1.125 | 1.00 | 27.34 | D | C |
| ATOM | 4334 | CB | VAL | D | 344 | 32.934 | 14.970 | 1.620 | 1.00 | 31.57 | D | C |
| ATOM | 4335 | CG1 | VAL | D | 344 | 31.792 | 15.975 | 1.705 | 1.00 | 33.23 | D | C |
| ATOM | 4336 | CG2 | VAL | D | 344 | 33.653 | 14.795 | 2.955 | 1.00 | 32.44 | D | C |
| ATOM | 4337 | C | VAL | D | 344 | 32.026 | 13.639 | −0.345 | 1.00 | 23.90 | D | C |
| ATOM | 4338 | O | VAL | D | 344 | 32.185 | 14.625 | −1.087 | 1.00 | 23.32 | D | O |
| ATOM | 4339 | N | GLU | D | 345 | 31.559 | 12.488 | −0.737 | 1.00 | 24.40 | D | N |
| ATOM | 4340 | CA | GLU | D | 345 | 31.244 | 12.162 | −2.106 | 1.00 | 30.58 | D | C |
| ATOM | 4341 | CB | GLU | D | 345 | 31.588 | 10.682 | −2.314 | 1.00 | 37.32 | D | C |
| ATOM | 4342 | CG | GLU | D | 345 | 32.086 | 10.234 | −3.652 | 1.00 | 44.89 | D | C |
| ATOM | 4343 | CD | GLU | D | 345 | 32.851 | 8.883 | −3.509 | 1.00 | 53.91 | D | C |
| ATOM | 4344 | OE1 | GLU | D | 345 | 32.272 | 7.896 | −2.991 | 1.00 | 55.68 | D | O |
| ATOM | 4345 | OE2 | GLU | D | 345 | 34.054 | 8.815 | −3.864 | 1.00 | 50.66 | D | O |
| ATOM | 4346 | C | GLU | D | 345 | 29.769 | 12.411 | −2.368 | 1.00 | 27.64 | D | C |
| ATOM | 4347 | O | GLU | D | 345 | 28.909 | 11.661 | −1.953 | 1.00 | 26.76 | D | O |
| ATOM | 4348 | N | PHE | D | 346 | 29.498 | 13.470 | −3.090 | 1.00 | 27.59 | D | N |
| ATOM | 4349 | CA | PHE | D | 346 | 28.166 | 13.737 | −3.527 | 1.00 | 28.89 | D | C |
| ATOM | 4350 | CB | PHE | D | 346 | 27.438 | 14.435 | −2.400 | 1.00 | 29.97 | D | C |
| ATOM | 4351 | CG | PHE | D | 346 | 27.865 | 15.855 | −2.205 | 1.00 | 30.83 | D | C |
| ATOM | 4352 | CD1 | PHE | D | 346 | 29.076 | 16.157 | −1.572 | 1.00 | 30.52 | D | C |
| ATOM | 4353 | CE1 | PHE | D | 346 | 29.483 | 17.476 | −1.367 | 1.00 | 29.62 | D | C |
| ATOM | 4354 | CZ | PHE | D | 346 | 28.715 | 18.504 | −1.861 | 1.00 | 31.52 | D | C |
| ATOM | 4355 | CE2 | PHE | D | 346 | 27.516 | 18.209 | −2.481 | 1.00 | 33.95 | D | C |
| ATOM | 4356 | CD2 | PHE | D | 346 | 27.080 | 16.892 | −2.637 | 1.00 | 32.95 | D | C |
| ATOM | 4357 | C | PHE | D | 346 | 28.189 | 14.643 | −4.733 | 1.00 | 29.40 | D | C |
| ATOM | 4358 | O | PHE | D | 346 | 29.212 | 15.236 | −5.073 | 1.00 | 30.24 | D | O |
| ATOM | 4359 | N | THR | D | 347 | 27.041 | 14.781 | −5.387 | 1.00 | 29.39 | D | N |
| ATOM | 4360 | CA | THR | D | 347 | 26.920 | 15.602 | −6.577 | 1.00 | 30.95 | D | C |
| ATOM | 4361 | CB | THR | D | 347 | 26.762 | 14.730 | −7.846 | 1.00 | 35.44 | D | C |
| ATOM | 4362 | OG1 | THR | D | 347 | 25.647 | 13.905 | −7.649 | 1.00 | 37.27 | D | O |
| ATOM | 4363 | CG2 | THR | D | 347 | 27.942 | 13.853 | −8.039 | 1.00 | 38.48 | D | C |
| ATOM | 4364 | C | THR | D | 347 | 25.672 | 16.462 | −6.465 | 1.00 | 29.64 | D | C |
| ATOM | 4365 | O | THR | D | 347 | 24.786 | 16.180 | −5.714 | 1.00 | 27.51 | D | O |
| ATOM | 4366 | N | PHE | D | 348 | 25.619 | 17.541 | −7.212 | 1.00 | 28.03 | D | N |
| ATOM | 4367 | CA | PHE | D | 348 | 24.430 | 18.314 | −7.277 | 1.00 | 25.61 | D | C |
| ATOM | 4368 | CB | PHE | D | 348 | 24.822 | 19.788 | −7.251 | 1.00 | 29.57 | D | C |
| ATOM | 4369 | CG | PHE | D | 348 | 25.520 | 20.263 | −5.996 | 1.00 | 28.29 | D | C |
| ATOM | 4370 | CD1 | PHE | D | 348 | 24.792 | 20.694 | −4.893 | 1.00 | 27.06 | D | C |
| ATOM | 4371 | CE1 | PHE | D | 348 | 25.429 | 21.182 | −3.780 | 1.00 | 27.03 | D | C |
| ATOM | 4372 | CZ | PHE | D | 348 | 26.815 | 21.405 | −3.798 | 1.00 | 27.07 | D | C |
| ATOM | 4373 | CE2 | PHE | D | 348 | 27.517 | 21.035 | −4.917 | 1.00 | 25.40 | D | C |
| ATOM | 4374 | CD2 | PHE | D | 348 | 26.878 | 20.499 | −5.989 | 1.00 | 25.22 | D | C |
| ATOM | 4375 | C | PHE | D | 348 | 23.706 | 18.091 | −8.596 | 1.00 | 27.81 | D | C |
| ATOM | 4376 | O | PHE | D | 348 | 24.331 | 18.066 | −9.659 | 1.00 | 29.36 | D | O |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 4377 | N | PRO | D | 349 | 22.358 | 18.018 | −8.564 | 1.00 | 27.16 | D | N |
| ATOM | 4378 | CA | PRO | D | 349 | 21.585 | 18.264 | −9.735 | 1.00 | 26.57 | D | C |
| ATOM | 4379 | CB | PRO | D | 349 | 20.144 | 18.145 | −9.252 | 1.00 | 30.26 | D | C |
| ATOM | 4380 | CG | PRO | D | 349 | 20.192 | 17.417 | −7.983 | 1.00 | 27.60 | D | C |
| ATOM | 4381 | CD | PRO | D | 349 | 21.525 | 17.654 | −7.405 | 1.00 | 25.97 | D | C |
| ATOM | 4382 | C | PRO | D | 349 | 21.815 | 19.666 | −10.324 | 1.00 | 26.37 | D | C |
| ATOM | 4383 | O | PRO | D | 349 | 22.057 | 20.643 | −9.609 | 1.00 | 28.06 | D | O |
| ATOM | 4384 | N | ASP | D | 350 | 21.639 | 19.730 | −11.631 | 1.00 | 31.62 | D | N |
| ATOM | 4385 | CA | ASP | D | 350 | 21.798 | 20.951 | −12.481 | 1.00 | 33.39 | D | C |
| ATOM | 4386 | CB | ASP | D | 350 | 21.330 | 20.590 | −13.951 | 1.00 | 36.43 | D | C |
| ATOM | 4387 | CG | ASP | D | 350 | 22.290 | 19.578 | −14.644 | 1.00 | 45.07 | D | C |
| ATOM | 4388 | OD1 | ASP | D | 350 | 23.433 | 19.367 | −14.157 | 1.00 | 45.58 | D | O |
| ATOM | 4389 | OD2 | ASP | D | 350 | 21.940 | 18.998 | −15.692 | 1.00 | 53.13 | D | O |
| ATOM | 4390 | C | ASP | D | 350 | 21.076 | 22.143 | −11.988 | 1.00 | 29.48 | D | C |
| ATOM | 4391 | O | ASP | D | 350 | 21.593 | 23.249 | −12.029 | 1.00 | 30.27 | D | O |
| ATOM | 4392 | N | PHE | D | 351 | 19.875 | 21.948 | −11.443 | 1.00 | 29.34 | D | N |
| ATOM | 4393 | CA | PHE | D | 351 | 19.064 | 23.084 | −10.988 | 1.00 | 29.62 | D | C |
| ATOM | 4394 | CB | PHE | D | 351 | 17.564 | 22.760 | −10.845 | 1.00 | 30.75 | D | C |
| ATOM | 4395 | CG | PHE | D | 351 | 17.293 | 21.718 | −9.826 | 1.00 | 28.12 | D | C |
| ATOM | 4396 | CD1 | PHE | D | 351 | 17.274 | 22.053 | −8.448 | 1.00 | 27.93 | D | C |
| ATOM | 4397 | CE1 | PHE | D | 351 | 17.062 | 21.097 | −7.492 | 1.00 | 23.01 | D | C |
| ATOM | 4398 | CZ | PHE | D | 351 | 16.879 | 19.764 | −7.880 | 1.00 | 29.15 | D | C |
| ATOM | 4399 | CE2 | PHE | D | 351 | 16.937 | 19.406 | −9.233 | 1.00 | 28.21 | D | C |
| ATOM | 4400 | CD2 | PHE | D | 351 | 17.136 | 20.411 | −10.200 | 1.00 | 26.71 | D | C |
| ATOM | 4401 | C | PHE | D | 351 | 19.571 | 23.694 | −9.702 | 1.00 | 30.44 | D | C |
| ATOM | 4402 | O | PHE | D | 351 | 19.222 | 24.793 | −9.403 | 1.00 | 28.21 | D | O |
| ATOM | 4403 | N | VAL | D | 352 | 20.461 | 23.044 | −8.956 | 1.00 | 31.08 | D | N |
| ATOM | 4404 | CA | VAL | D | 352 | 20.955 | 23.687 | −7.763 | 1.00 | 28.69 | D | C |
| ATOM | 4405 | CB | VAL | D | 352 | 21.705 | 22.703 | −6.862 | 1.00 | 27.38 | D | C |
| ATOM | 4406 | CG1 | VAL | D | 352 | 22.224 | 23.447 | −5.641 | 1.00 | 25.96 | D | C |
| ATOM | 4407 | CG2 | VAL | D | 352 | 20.728 | 21.605 | −6.417 | 1.00 | 30.13 | D | C |
| ATOM | 4408 | C | VAL | D | 352 | 21.844 | 24.865 | −8.153 | 1.00 | 27.28 | D | C |
| ATOM | 4409 | O | VAL | D | 352 | 22.752 | 24.681 | −8.878 | 1.00 | 27.21 | D | O |
| ATOM | 4410 | N | THR | D | 353 | 21.561 | 26.048 | −7.664 | 1.00 | 27.78 | D | N |
| ATOM | 4411 | CA | THR | D | 353 | 22.157 | 27.253 | −8.162 | 1.00 | 28.83 | D | C |
| ATOM | 4412 | CB | THR | D | 353 | 21.365 | 28.496 | −7.769 | 1.00 | 32.04 | D | C |
| ATOM | 4413 | OG1 | THR | D | 353 | 21.424 | 28.693 | −6.351 | 1.00 | 31.03 | D | O |
| ATOM | 4414 | CG2 | THR | D | 353 | 19.933 | 28.448 | −8.334 | 1.00 | 34.87 | D | C |
| ATOM | 4415 | C | THR | D | 353 | 23.519 | 27.415 | −7.549 | 1.00 | 30.97 | D | C |
| ATOM | 4416 | O | THR | D | 353 | 23.847 | 26.757 | −6.549 | 1.00 | 30.06 | D | O |
| ATOM | 4417 | N | GLU | D | 354 | 24.293 | 28.317 | −8.122 | 1.00 | 29.97 | D | N |
| ATOM | 4418 | CA | GLU | D | 354 | 25.696 | 28.554 | −7.679 | 1.00 | 34.09 | D | C |
| ATOM | 4419 | CB | GLU | D | 354 | 26.387 | 29.536 | −8.632 | 1.00 | 40.61 | D | C |
| ATOM | 4420 | CG | GLU | D | 354 | 27.624 | 30.248 | −8.101 | 1.00 | 48.65 | D | C |
| ATOM | 4421 | CD | GLU | D | 354 | 28.353 | 31.051 | −9.184 | 1.00 | 64.63 | D | C |
| ATOM | 4422 | OE1 | GLU | D | 354 | 27.720 | 31.912 | −9.868 | 1.00 | 60.82 | D | O |
| ATOM | 4423 | OE2 | GLU | D | 354 | 29.576 | 30.804 | −9.358 | 1.00 | 68.65 | D | O |
| ATOM | 4424 | C | GLU | D | 354 | 25.814 | 29.008 | −6.213 | 1.00 | 30.35 | D | C |
| ATOM | 4425 | O | GLU | D | 354 | 26.680 | 28.558 | −5.491 | 1.00 | 27.23 | D | O |
| ATOM | 4426 | N | GLY | D | 355 | 24.975 | 29.924 | −5.775 | 1.00 | 27.03 | D | N |
| ATOM | 4427 | CA | GLY | D | 355 | 24.965 | 30.336 | −4.372 | 1.00 | 26.83 | D | C |
| ATOM | 4428 | C | GLY | D | 355 | 24.632 | 29.203 | −3.388 | 1.00 | 27.62 | D | C |
| ATOM | 4429 | O | GLY | D | 355 | 25.263 | 29.104 | −2.310 | 1.00 | 27.79 | D | O |
| ATOM | 4430 | N | ALA | D | 356 | 23.663 | 28.346 | −3.750 | 1.00 | 26.38 | D | N |
| ATOM | 4431 | CA | ALA | D | 356 | 23.282 | 27.232 | −2.910 | 1.00 | 26.78 | D | C |
| ATOM | 4432 | CB | ALA | D | 356 | 22.041 | 26.536 | −3.443 | 1.00 | 29.32 | D | C |
| ATOM | 4433 | C | ALA | D | 356 | 24.466 | 26.205 | −2.857 | 1.00 | 23.01 | D | C |
| ATOM | 4434 | O | ALA | D | 356 | 24.831 | 25.744 | −1.810 | 1.00 | 24.14 | D | O |
| ATOM | 4435 | N | ARG | D | 357 | 25.050 | 25.909 | −3.991 | 1.00 | 24.33 | D | N |
| ATOM | 4436 | CA | ARG | D | 357 | 26.251 | 25.048 | −4.046 | 1.00 | 27.33 | D | C |
| ATOM | 4437 | CB | ARG | D | 357 | 26.787 | 24.927 | −5.484 | 1.00 | 28.33 | D | C |
| ATOM | 4438 | CG | ARG | D | 357 | 25.942 | 24.017 | −6.356 | 1.00 | 30.96 | D | C |
| ATOM | 4439 | CD | ARG | D | 357 | 26.272 | 24.210 | −7.835 | 1.00 | 32.63 | D | C |
| ATOM | 4440 | NE | ARG | D | 357 | 25.320 | 23.493 | −8.688 | 1.00 | 29.03 | D | N |
| ATOM | 4441 | CZ | ARG | D | 357 | 25.640 | 22.577 | −9.602 | 1.00 | 31.66 | D | C |
| ATOM | 4442 | NH1 | ARG | D | 357 | 26.879 | 22.221 | −9.799 | 1.00 | 27.86 | D | N |
| ATOM | 4443 | NH2 | ARG | D | 357 | 24.714 | 21.996 | −10.320 | 1.00 | 29.31 | D | N |
| ATOM | 4444 | C | ARG | D | 357 | 27.366 | 25.570 | −3.162 | 1.00 | 24.84 | D | C |
| ATOM | 4445 | O | ARG | D | 357 | 28.055 | 24.810 | −2.508 | 1.00 | 25.91 | D | O |
| ATOM | 4446 | N | ASP | D | 358 | 27.552 | 26.875 | −3.191 | 1.00 | 27.42 | D | N |
| ATOM | 4447 | CA | ASP | D | 358 | 28.605 | 27.494 | −2.412 | 1.00 | 28.08 | D | C |
| ATOM | 4448 | CB | ASP | D | 358 | 28.694 | 29.014 | −2.712 | 1.00 | 28.71 | D | C |
| ATOM | 4449 | CG | ASP | D | 358 | 29.891 | 29.685 | −2.019 | 1.00 | 29.19 | D | C |
| ATOM | 4450 | OD1 | ASP | D | 358 | 30.949 | 29.670 | −2.599 | 1.00 | 34.05 | D | O |
| ATOM | 4451 | OD2 | ASP | D | 358 | 29.815 | 30.189 | −0.904 | 1.00 | 28.82 | D | O |
| ATOM | 4452 | C | ASP | D | 358 | 28.374 | 27.262 | −0.927 | 1.00 | 24.63 | D | C |
| ATOM | 4453 | O | ASP | D | 358 | 29.302 | 26.905 | −0.196 | 1.00 | 25.88 | D | O |
| ATOM | 4454 | N | LEU | D | 359 | 27.174 | 27.556 | −0.431 | 1.00 | 24.02 | D | N |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 4455 | CA | LEU | D | 359 | 26.920 | 27.406 | 0.978 | 1.00 | 26.54 | D | C |
| ATOM | 4456 | CB | LEU | D | 359 | 25.524 | 27.939 | 1.380 | 1.00 | 28.27 | D | C |
| ATOM | 4457 | CG | LEU | D | 359 | 24.999 | 27.525 | 2.771 | 1.00 | 28.22 | D | C |
| ATOM | 4458 | CD1 | LEU | D | 359 | 25.905 | 28.100 | 3.789 | 1.00 | 27.60 | D | C |
| ATOM | 4459 | CD2 | LEU | D | 359 | 23.567 | 28.024 | 2.995 | 1.00 | 30.74 | D | C |
| ATOM | 4460 | C | LEU | D | 359 | 27.074 | 25.919 | 1.400 | 1.00 | 27.15 | D | C |
| ATOM | 4461 | O | LEU | D | 359 | 27.801 | 25.580 | 2.335 | 1.00 | 25.29 | D | O |
| ATOM | 4462 | N | ILE | D | 360 | 26.421 | 25.042 | 0.665 | 1.00 | 24.42 | D | N |
| ATOM | 4463 | CA | ILE | D | 360 | 26.529 | 23.632 | 0.972 | 1.00 | 25.18 | D | C |
| ATOM | 4464 | CB | ILE | D | 360 | 25.672 | 22.820 | 0.023 | 1.00 | 22.73 | D | C |
| ATOM | 4465 | CG1 | ILE | D | 360 | 24.203 | 23.075 | 0.396 | 1.00 | 22.01 | D | C |
| ATOM | 4466 | CD1 | ILE | D | 360 | 23.310 | 22.684 | −0.753 | 1.00 | 21.87 | D | C |
| ATOM | 4467 | CG2 | ILE | D | 360 | 25.964 | 21.322 | 0.079 | 1.00 | 24.54 | D | C |
| ATOM | 4468 | C | ILE | D | 360 | 27.969 | 23.100 | 0.970 | 1.00 | 23.37 | D | C |
| ATOM | 4469 | O | ILE | D | 360 | 28.299 | 22.276 | 1.838 | 1.00 | 18.58 | D | O |
| ATOM | 4470 | N | SER | D | 361 | 28.746 | 23.497 | −0.032 | 1.00 | 24.86 | D | N |
| ATOM | 4471 | CA | SER | D | 361 | 30.141 | 23.012 | −0.130 | 1.00 | 24.96 | D | C |
| ATOM | 4472 | CB | SER | D | 361 | 30.828 | 23.242 | −1.466 | 1.00 | 27.15 | D | C |
| ATOM | 4473 | OG | SER | D | 361 | 30.089 | 22.650 | −2.494 | 1.00 | 28.01 | D | O |
| ATOM | 4474 | C | SER | D | 361 | 30.919 | 23.621 | 0.978 | 1.00 | 26.66 | D | C |
| ATOM | 4475 | O | SER | D | 361 | 31.800 | 22.913 | 1.492 | 1.00 | 26.56 | D | O |
| ATOM | 4476 | N | ARG | D | 362 | 30.594 | 24.864 | 1.384 | 1.00 | 26.21 | D | N |
| ATOM | 4477 | CA | ARG | D | 362 | 31.271 | 25.412 | 2.574 | 1.00 | 27.76 | D | C |
| ATOM | 4478 | CB | ARG | D | 362 | 30.934 | 26.855 | 2.823 | 1.00 | 32.94 | D | C |
| ATOM | 4479 | CG | ARG | D | 362 | 31.717 | 27.849 | 1.943 | 1.00 | 36.95 | D | C |
| ATOM | 4480 | CD | ARG | D | 362 | 31.214 | 29.270 | 2.153 | 1.00 | 45.90 | D | C |
| ATOM | 4481 | NE | ARG | D | 362 | 31.772 | 30.235 | 1.175 | 1.00 | 50.29 | D | N |
| ATOM | 4482 | CZ | ARG | D | 362 | 33.008 | 30.744 | 1.247 | 1.00 | 63.24 | D | C |
| ATOM | 4483 | NH1 | ARG | D | 362 | 33.831 | 30.422 | 2.274 | 1.00 | 67.38 | D | N |
| ATOM | 4484 | NH2 | ARG | D | 362 | 33.436 | 31.593 | 0.305 | 1.00 | 57.25 | D | N |
| ATOM | 4485 | C | ARG | D | 362 | 31.031 | 24.559 | 3.823 | 1.00 | 28.83 | D | C |
| ATOM | 4486 | O | ARG | D | 362 | 31.957 | 24.343 | 4.661 | 1.00 | 28.91 | D | O |
| ATOM | 4487 | N | LEU | D | 363 | 29.824 | 24.027 | 3.962 | 1.00 | 20.50 | D | N |
| ATOM | 4488 | CA | LEU | D | 363 | 29.467 | 23.328 | 5.172 | 1.00 | 20.53 | D | C |
| ATOM | 4489 | CB | LEU | D | 363 | 27.934 | 23.374 | 5.349 | 1.00 | 20.89 | D | C |
| ATOM | 4490 | CG | LEU | D | 363 | 27.280 | 24.772 | 5.565 | 1.00 | 20.81 | D | C |
| ATOM | 4491 | CD1 | LEU | D | 363 | 25.737 | 24.790 | 5.302 | 1.00 | 21.73 | D | C |
| ATOM | 4492 | CD2 | LEU | D | 363 | 27.517 | 25.199 | 6.963 | 1.00 | 21.49 | D | C |
| ATOM | 4493 | C | LEU | D | 363 | 29.952 | 21.909 | 5.132 | 1.00 | 19.08 | D | C |
| ATOM | 4494 | O | LEU | D | 363 | 30.235 | 21.328 | 6.173 | 1.00 | 23.61 | D | O |
| ATOM | 4495 | N | LEU | D | 364 | 29.975 | 21.274 | 4.000 | 1.00 | 21.47 | D | N |
| ATOM | 4496 | CA | LEU | D | 364 | 30.400 | 19.888 | 3.960 | 1.00 | 21.99 | D | C |
| ATOM | 4497 | CB | LEU | D | 364 | 29.610 | 19.161 | 2.913 | 1.00 | 23.32 | D | C |
| ATOM | 4498 | CG | LEU | D | 364 | 28.079 | 19.200 | 3.098 | 1.00 | 24.96 | D | C |
| ATOM | 4499 | CD1 | LEU | D | 364 | 27.482 | 18.338 | 2.002 | 1.00 | 27.10 | D | C |
| ATOM | 4500 | CD2 | LEU | D | 364 | 27.691 | 18.600 | 4.435 | 1.00 | 23.70 | D | C |
| ATOM | 4501 | C | LEU | D | 364 | 31.897 | 19.770 | 3.743 | 1.00 | 22.66 | D | C |
| ATOM | 4502 | O | LEU | D | 364 | 32.392 | 19.350 | 2.647 | 1.00 | 23.76 | D | O |
| ATOM | 4503 | N | LYS | D | 365 | 32.624 | 20.083 | 4.794 | 1.00 | 25.04 | D | N |
| ATOM | 4504 | CA | LYS | D | 365 | 34.086 | 19.921 | 4.805 | 1.00 | 24.11 | D | C |
| ATOM | 4505 | CB | LYS | D | 365 | 34.770 | 21.130 | 5.407 | 1.00 | 28.80 | D | C |
| ATOM | 4506 | CG | LYS | D | 365 | 34.536 | 22.398 | 4.654 | 1.00 | 28.86 | D | C |
| ATOM | 4507 | CD | LYS | D | 365 | 35.342 | 22.453 | 3.392 | 1.00 | 29.32 | D | C |
| ATOM | 4508 | CE | LYS | D | 365 | 35.355 | 23.842 | 2.849 | 1.00 | 37.54 | D | C |
| ATOM | 4509 | NZ | LYS | D | 365 | 36.307 | 23.795 | 1.729 | 1.00 | 40.92 | D | N |
| ATOM | 4510 | C | LYS | D | 365 | 34.364 | 18.771 | 5.696 | 1.00 | 25.38 | D | C |
| ATOM | 4511 | O | LYS | D | 365 | 33.726 | 18.656 | 6.736 | 1.00 | 25.02 | D | O |
| ATOM | 4512 | N | HIS | D | 366 | 35.306 | 17.905 | 5.287 | 1.00 | 22.34 | D | N |
| ATOM | 4513 | CA | HIS | D | 366 | 35.688 | 16.759 | 6.041 | 1.00 | 22.85 | D | C |
| ATOM | 4514 | CB | HIS | D | 366 | 36.706 | 15.920 | 5.248 | 1.00 | 24.53 | D | C |
| ATOM | 4515 | CG | HIS | D | 366 | 37.029 | 14.629 | 5.897 | 1.00 | 25.46 | D | C |
| ATOM | 4516 | ND1 | HIS | D | 366 | 37.995 | 14.524 | 6.873 | 1.00 | 27.52 | D | N |
| ATOM | 4517 | CE1 | HIS | D | 366 | 38.052 | 13.274 | 7.296 | 1.00 | 26.65 | D | C |
| ATOM | 4518 | NE2 | HIS | D | 366 | 37.149 | 12.575 | 6.647 | 1.00 | 28.99 | D | N |
| ATOM | 4519 | CD2 | HIS | D | 366 | 36.487 | 13.401 | 5.769 | 1.00 | 28.06 | D | C |
| ATOM | 4520 | C | HIS | D | 366 | 36.268 | 17.226 | 7.353 | 1.00 | 21.02 | D | C |
| ATOM | 4521 | O | HIS | D | 366 | 35.969 | 16.675 | 8.418 | 1.00 | 23.32 | D | O |
| ATOM | 4522 | N | ASN | D | 367 | 37.065 | 18.258 | 7.309 | 1.00 | 22.47 | D | N |
| ATOM | 4523 | CA | ASN | D | 367 | 37.712 | 18.724 | 8.539 | 1.00 | 23.54 | D | C |
| ATOM | 4524 | CB | ASN | D | 367 | 39.096 | 19.259 | 8.179 | 1.00 | 26.92 | D | C |
| ATOM | 4525 | CG | ASN | D | 367 | 39.836 | 19.934 | 9.347 | 1.00 | 29.69 | D | C |
| ATOM | 4526 | OD1 | ASN | D | 367 | 39.307 | 20.170 | 10.418 | 1.00 | 30.55 | D | O |
| ATOM | 4527 | ND2 | ASN | D | 367 | 41.062 | 20.340 | 9.068 | 1.00 | 36.06 | D | N |
| ATOM | 4528 | C | ASN | D | 367 | 36.824 | 19.776 | 9.191 | 1.00 | 22.77 | D | C |
| ATOM | 4529 | O | ASN | D | 367 | 36.611 | 20.885 | 8.626 | 1.00 | 22.79 | D | O |
| ATOM | 4530 | N | PRO | D | 368 | 36.371 | 19.492 | 10.400 | 1.00 | 24.70 | D | N |
| ATOM | 4531 | CA | PRO | D | 368 | 35.392 | 20.336 | 11.084 | 1.00 | 23.97 | D | C |
| ATOM | 4532 | CB | PRO | D | 368 | 35.233 | 19.679 | 12.454 | 1.00 | 24.20 | D | C |

APPENDIX A-continued

Atomic coordinates of Aurora A + Inhibitory Monobody Mb60 + Danusertib

| | | | | | | | | | | | |
|---|---|---|---|---|---|---|---|---|---|---|---|
| ATOM | 4533 | CG | PRO | D | 368 | 35.782 | 18.340 | 12.314 | 1.00 | 25.81 | D | C |
| ATOM | 4534 | CD | PRO | D | 368 | 36.715 | 18.300 | 11.182 | 1.00 | 26.01 | D | C |
| ATOM | 4535 | C | PRO | D | 368 | 35.856 | 21.741 | 11.290 | 1.00 | 26.85 | D | C |
| ATOM | 4536 | O | PRO | D | 368 | 35.025 | 22.621 | 11.283 | 1.00 | 24.28 | D | O |
| ATOM | 4537 | N | SER | D | 369 | 37.159 | 21.945 | 11.527 | 1.00 | 24.85 | D | N |
| ATOM | 4538 | CA | SER | D | 369 | 37.697 | 23.257 | 11.813 | 1.00 | 26.72 | D | C |
| ATOM | 4539 | CB | SER | D | 369 | 39.164 | 23.181 | 12.286 | 1.00 | 28.23 | D | C |
| ATOM | 4540 | OG | SER | D | 369 | 39.984 | 22.930 | 11.182 | 1.00 | 28.73 | D | O |
| ATOM | 4541 | C | SER | D | 369 | 37.570 | 24.138 | 10.558 | 1.00 | 25.55 | D | C |
| ATOM | 4542 | O | SER | D | 369 | 37.566 | 25.335 | 10.639 | 1.00 | 29.73 | D | O |
| ATOM | 4543 | N | GLN | D | 370 | 37.430 | 23.542 | 9.398 | 1.00 | 26.06 | D | N |
| ATOM | 4544 | CA | GLN | D | 370 | 37.230 | 24.298 | 8.186 | 1.00 | 25.51 | D | C |
| ATOM | 4545 | CB | GLN | D | 370 | 37.923 | 23.640 | 7.037 | 1.00 | 28.90 | D | C |
| ATOM | 4546 | CG | GLN | D | 370 | 39.413 | 23.791 | 7.323 | 1.00 | 41.21 | D | C |
| ATOM | 4547 | CD | GLN | D | 370 | 40.230 | 23.125 | 6.310 | 1.00 | 53.78 | D | C |
| ATOM | 4548 | OE1 | GLN | D | 370 | 39.698 | 22.490 | 5.402 | 1.00 | 64.94 | D | O |
| ATOM | 4549 | NE2 | GLN | D | 370 | 41.537 | 23.217 | 6.457 | 1.00 | 57.71 | D | N |
| ATOM | 4550 | C | GLN | D | 370 | 35.798 | 24.576 | 7.848 | 1.00 | 24.67 | D | C |
| ATOM | 4551 | O | GLN | D | 370 | 35.533 | 25.228 | 6.844 | 1.00 | 22.37 | D | O |
| ATOM | 4552 | N | ARG | D | 371 | 34.874 | 24.123 | 8.677 | 1.00 | 29.83 | D | N |
| ATOM | 4553 | CA | ARG | D | 371 | 33.452 | 24.470 | 8.448 | 1.00 | 28.33 | D | C |
| ATOM | 4554 | CB | ARG | D | 371 | 32.492 | 23.430 | 9.096 | 1.00 | 26.85 | D | C |
| ATOM | 4555 | CG | ARG | D | 371 | 32.674 | 21.999 | 8.535 | 1.00 | 23.38 | D | C |
| ATOM | 4556 | CD | ARG | D | 371 | 31.835 | 20.980 | 9.270 | 1.00 | 23.02 | D | C |
| ATOM | 4557 | NE | ARG | D | 371 | 32.415 | 19.670 | 8.994 | 1.00 | 23.53 | D | N |
| ATOM | 4558 | CZ | ARG | D | 371 | 32.438 | 18.657 | 9.819 | 1.00 | 20.25 | D | C |
| ATOM | 4559 | NH1 | ARG | D | 371 | 31.853 | 18.687 | 11.019 | 1.00 | 22.03 | D | N |
| ATOM | 4560 | NH2 | ARG | D | 371 | 33.117 | 17.616 | 9.446 | 1.00 | 24.50 | D | N |
| ATOM | 4561 | C | ARG | D | 371 | 33.263 | 25.865 | 9.024 | 1.00 | 29.24 | D | C |
| ATOM | 4562 | O | ARG | D | 371 | 34.018 | 26.310 | 9.876 | 1.00 | 31.82 | D | O |
| ATOM | 4563 | N | PRO | D | 372 | 32.282 | 26.599 | 8.521 | 1.00 | 27.93 | D | N |
| ATOM | 4564 | CA | PRO | D | 372 | 32.144 | 27.967 | 8.971 | 1.00 | 28.14 | D | C |
| ATOM | 4565 | CB | PRO | D | 372 | 31.224 | 28.603 | 7.937 | 1.00 | 31.47 | D | C |
| ATOM | 4566 | CG | PRO | D | 372 | 30.636 | 27.511 | 7.155 | 1.00 | 29.03 | D | C |
| ATOM | 4567 | CD | PRO | D | 372 | 31.376 | 26.251 | 7.415 | 1.00 | 29.44 | D | C |
| ATOM | 4568 | C | PRO | D | 372 | 31.534 | 28.125 | 10.331 | 1.00 | 27.92 | D | C |
| ATOM | 4569 | O | PRO | D | 372 | 31.003 | 27.174 | 10.855 | 1.00 | 28.23 | D | O |
| ATOM | 4570 | N | MET | D | 373 | 31.650 | 29.335 | 10.898 | 1.00 | 30.09 | D | N |
| ATOM | 4571 | CA | MET | D | 373 | 30.849 | 29.771 | 12.004 | 1.00 | 29.11 | D | C |
| ATOM | 4572 | CB | MET | D | 373 | 31.289 | 31.182 | 12.429 | 1.00 | 36.94 | D | C |
| ATOM | 4573 | CG | MET | D | 373 | 32.754 | 31.426 | 12.872 | 1.00 | 42.05 | D | C |
| ATOM | 4574 | SD | MET | D | 373 | 33.316 | 30.321 | 14.155 | 1.00 | 55.20 | D | S |
| ATOM | 4575 | CE | MET | D | 373 | 32.217 | 30.659 | 15.549 | 1.00 | 53.36 | D | C |
| ATOM | 4576 | C | MET | D | 373 | 29.389 | 29.848 | 11.595 | 1.00 | 26.83 | D | C |
| ATOM | 4577 | O | MET | D | 373 | 29.075 | 30.218 | 10.496 | 1.00 | 29.16 | D | O |
| ATOM | 4578 | N | LEU | D | 374 | 28.471 | 29.642 | 12.518 | 1.00 | 28.57 | D | N |
| ATOM | 4579 | CA | LEU | D | 374 | 27.057 | 29.899 | 12.225 | 1.00 | 27.09 | D | C |
| ATOM | 4580 | CB | LEU | D | 374 | 26.273 | 29.592 | 13.446 | 1.00 | 28.46 | D | C |
| ATOM | 4581 | CG | LEU | D | 374 | 26.108 | 28.071 | 13.582 | 1.00 | 30.39 | D | C |
| ATOM | 4582 | CD1 | LEU | D | 374 | 25.519 | 27.764 | 14.946 | 1.00 | 32.54 | D | C |
| ATOM | 4583 | CD2 | LEU | D | 374 | 25.207 | 27.499 | 12.484 | 1.00 | 27.92 | D | C |
| ATOM | 4584 | C | LEU | D | 374 | 26.803 | 31.314 | 11.787 | 1.00 | 30.92 | D | C |
| ATOM | 4585 | O | LEU | D | 374 | 26.011 | 31.540 | 10.885 | 1.00 | 30.92 | D | O |
| ATOM | 4586 | N | ARG | D | 375 | 27.554 | 32.272 | 12.335 | 1.00 | 33.20 | D | N |
| ATOM | 4587 | CA | ARG | D | 375 | 27.431 | 33.650 | 11.876 | 1.00 | 37.16 | D | C |
| ATOM | 4588 | CB | ARG | D | 375 | 28.289 | 34.607 | 12.744 | 1.00 | 43.76 | D | C |
| ATOM | 4589 | CG | ARG | D | 375 | 28.251 | 36.106 | 12.344 | 1.00 | 50.81 | D | C |
| ATOM | 4590 | CD | ARG | D | 375 | 29.448 | 36.905 | 12.886 | 1.00 | 59.67 | D | C |
| ATOM | 4591 | NE | ARG | D | 375 | 30.741 | 36.383 | 12.373 | 1.00 | 73.91 | D | N |
| ATOM | 4592 | CZ | ARG | D | 375 | 31.592 | 35.551 | 13.007 | 1.00 | 73.32 | D | C |
| ATOM | 4593 | NH1 | ARG | D | 375 | 31.376 | 35.097 | 14.248 | 1.00 | 72.69 | D | N |
| ATOM | 4594 | NH2 | ARG | D | 375 | 32.690 | 35.150 | 12.372 | 1.00 | 85.70 | D | N |
| ATOM | 4595 | C | ARG | D | 375 | 27.777 | 33.777 | 10.395 | 1.00 | 34.57 | D | C |
| ATOM | 4596 | O | ARG | D | 375 | 27.096 | 34.514 | 9.715 | 1.00 | 30.05 | D | O |
| ATOM | 4597 | N | GLU | D | 376 | 28.788 | 33.061 | 9.872 | 1.00 | 31.73 | D | N |
| ATOM | 4598 | CA | GLU | D | 376 | 29.040 | 33.122 | 8.454 | 1.00 | 32.45 | D | C |
| ATOM | 4599 | CB | GLU | D | 376 | 30.389 | 32.548 | 8.033 | 1.00 | 33.61 | D | C |
| ATOM | 4600 | CG | GLU | D | 376 | 31.608 | 33.101 | 8.764 | 1.00 | 39.02 | D | C |
| ATOM | 4601 | CD | GLU | D | 376 | 32.799 | 32.144 | 8.594 | 1.00 | 37.58 | D | C |
| ATOM | 4602 | OE1 | GLU | D | 376 | 33.300 | 31.985 | 7.478 | 1.00 | 40.13 | D | O |
| ATOM | 4603 | OE2 | GLU | D | 376 | 33.136 | 31.437 | 9.527 | 1.00 | 40.03 | D | O |
| ATOM | 4604 | C | GLU | D | 376 | 27.909 | 32.466 | 7.638 | 1.00 | 33.12 | D | C |
| ATOM | 4605 | O | GLU | D | 376 | 27.650 | 32.885 | 6.539 | 1.00 | 32.96 | D | O |
| ATOM | 4606 | N | VAL | D | 377 | 27.202 | 31.467 | 8.167 | 1.00 | 30.53 | D | N |
| ATOM | 4607 | CA | VAL | D | 377 | 26.031 | 30.927 | 7.436 | 1.00 | 31.19 | D | C |
| ATOM | 4608 | CB | VAL | D | 377 | 25.430 | 29.673 | 8.116 | 1.00 | 32.59 | D | C |
| ATOM | 4609 | CG1 | VAL | D | 377 | 24.169 | 29.194 | 7.382 | 1.00 | 29.37 | D | C |
| ATOM | 4610 | CG2 | VAL | D | 377 | 26.492 | 28.579 | 8.241 | 1.00 | 33.34 | D | C |

APPENDIX A-continued

| Atomic coordinates of Aurora A + Inhibitory Monobody Mb60 + Danusertib | | | | | | | | | | | | |
|---|---|---|---|---|---|---|---|---|---|---|---|---|
| ATOM | 4611 | C | VAL | D | 377 | 24.928 | 32.001 | 7.376 | 1.00 | 30.71 | D | C |
| ATOM | 4612 | O | VAL | D | 377 | 24.379 | 32.247 | 6.301 | 1.00 | 30.68 | D | O |
| ATOM | 4613 | N | LEU | D | 378 | 24.642 | 32.648 | 8.522 | 1.00 | 28.72 | D | N |
| ATOM | 4614 | CA | LEU | D | 378 | 23.571 | 33.642 | 8.583 | 1.00 | 30.05 | D | C |
| ATOM | 4615 | CB | LEU | D | 378 | 23.341 | 34.127 | 10.013 | 1.00 | 31.35 | D | C |
| ATOM | 4616 | CG | LEU | D | 378 | 22.711 | 33.090 | 10.928 | 1.00 | 30.26 | D | C |
| ATOM | 4617 | CD1 | LEU | D | 378 | 23.016 | 33.333 | 12.368 | 1.00 | 30.74 | D | C |
| ATOM | 4618 | CD2 | LEU | D | 378 | 21.221 | 33.074 | 10.665 | 1.00 | 32.46 | D | C |
| ATOM | 4619 | C | LEU | D | 378 | 23.830 | 34.846 | 7.634 | 1.00 | 32.36 | D | C |
| ATOM | 4620 | O | LEU | D | 378 | 22.900 | 35.409 | 7.164 | 1.00 | 34.50 | D | O |
| ATOM | 4621 | N | GLU | D | 379 | 25.085 | 35.115 | 7.292 | 1.00 | 31.47 | D | N |
| ATOM | 4622 | CA | GLU | D | 379 | 25.555 | 36.244 | 6.474 | 1.00 | 39.90 | D | C |
| ATOM | 4623 | CB | GLU | D | 379 | 26.759 | 36.932 | 7.192 | 1.00 | 42.09 | D | C |
| ATOM | 4624 | CG | GLU | D | 379 | 26.326 | 37.898 | 8.277 | 1.00 | 47.19 | D | C |
| ATOM | 4625 | CD | GLU | D | 379 | 27.444 | 38.342 | 9.223 | 1.00 | 58.07 | D | C |
| ATOM | 4626 | OE1 | GLU | D | 379 | 27.082 | 38.889 | 10.292 | 1.00 | 60.49 | D | O |
| ATOM | 4627 | OE2 | GLU | D | 379 | 28.659 | 38.110 | 8.937 | 1.00 | 61.15 | D | O |
| ATOM | 4628 | C | GLU | D | 379 | 25.989 | 35.832 | 5.095 | 1.00 | 36.90 | D | C |
| ATOM | 4629 | O | GLU | D | 379 | 26.399 | 36.651 | 4.258 | 1.00 | 42.23 | D | O |
| ATOM | 4630 | N | HIS | D | 380 | 25.881 | 34.559 | 4.807 | 1.00 | 33.62 | D | N |
| ATOM | 4631 | CA | HIS | D | 380 | 26.221 | 34.095 | 3.502 | 1.00 | 30.29 | D | C |
| ATOM | 4632 | CB | HIS | D | 380 | 26.137 | 32.567 | 3.489 | 1.00 | 30.35 | D | C |
| ATOM | 4633 | CG | HIS | D | 380 | 26.571 | 31.960 | 2.223 | 1.00 | 28.13 | D | C |
| ATOM | 4634 | ND1 | HIS | D | 380 | 25.765 | 31.940 | 1.125 | 1.00 | 29.38 | D | N |
| ATOM | 4635 | CE1 | HIS | D | 380 | 26.403 | 31.398 | 0.115 | 1.00 | 26.67 | D | C |
| ATOM | 4636 | NE2 | HIS | D | 380 | 27.624 | 31.117 | 0.511 | 1.00 | 29.10 | D | N |
| ATOM | 4637 | CD2 | HIS | D | 380 | 27.756 | 31.460 | 1.826 | 1.00 | 28.39 | D | C |
| ATOM | 4638 | C | HIS | D | 380 | 25.276 | 34.769 | 2.470 | 1.00 | 30.16 | D | C |
| ATOM | 4639 | O | HIS | D | 380 | 24.056 | 34.889 | 2.684 | 1.00 | 27.93 | D | O |
| ATOM | 4640 | N | PRO | D | 381 | 25.837 | 35.228 | 1.355 | 1.00 | 33.26 | D | N |
| ATOM | 4641 | CA | PRO | D | 381 | 25.037 | 35.973 | 0.346 | 1.00 | 34.39 | D | C |
| ATOM | 4642 | CB | PRO | D | 381 | 26.022 | 36.205 | −0.825 | 1.00 | 31.77 | D | C |
| ATOM | 4643 | CG | PRO | D | 381 | 27.278 | 35.574 | −0.448 | 1.00 | 37.78 | D | C |
| ATOM | 4644 | CD | PRO | D | 381 | 27.267 | 35.145 | 1.005 | 1.00 | 36.05 | D | C |
| ATOM | 4645 | C | PRO | D | 381 | 23.793 | 35.223 | −0.189 | 1.00 | 31.58 | D | C |
| ATOM | 4646 | O | PRO | D | 381 | 22.755 | 35.803 | −0.444 | 1.00 | 33.93 | D | O |
| ATOM | 4647 | N | TRP | D | 382 | 23.915 | 33.930 | −0.403 | 1.00 | 34.14 | D | N |
| ATOM | 4648 | CA | TRP | D | 382 | 22.770 | 33.157 | −0.836 | 1.00 | 30.06 | D | C |
| ATOM | 4649 | CB | TRP | D | 382 | 23.161 | 31.788 | −1.262 | 1.00 | 31.36 | D | C |
| ATOM | 4650 | CG | TRP | D | 382 | 22.003 | 30.939 | −1.749 | 1.00 | 28.99 | D | C |
| ATOM | 4651 | CD1 | TRP | D | 382 | 21.486 | 30.932 | −2.972 | 1.00 | 28.50 | D | C |
| ATOM | 4652 | NE1 | TRP | D | 382 | 20.450 | 30.010 | −3.058 | 1.00 | 30.54 | D | N |
| ATOM | 4653 | CE2 | TRP | D | 382 | 20.304 | 29.403 | −1.845 | 1.00 | 28.48 | D | C |
| ATOM | 4654 | CD2 | TRP | D | 382 | 21.262 | 29.987 | −0.980 | 1.00 | 28.88 | D | C |
| ATOM | 4655 | CE3 | TRP | D | 382 | 21.310 | 29.572 | 0.360 | 1.00 | 28.85 | D | C |
| ATOM | 4656 | CZ3 | TRP | D | 382 | 20.411 | 28.553 | 0.783 | 1.00 | 31.42 | D | C |
| ATOM | 4657 | CH2 | TRP | D | 382 | 19.453 | 27.990 | −0.117 | 1.00 | 30.42 | D | C |
| ATOM | 4658 | CZ2 | TRP | D | 382 | 19.371 | 28.429 | −1.418 | 1.00 | 30.17 | D | C |
| ATOM | 4659 | C | TRP | D | 382 | 21.663 | 33.163 | 0.213 | 1.00 | 32.32 | D | C |
| ATOM | 4660 | O | TRP | D | 382 | 20.473 | 33.273 | −0.157 | 1.00 | 32.93 | D | O |
| ATOM | 4661 | N | ILE | D | 383 | 22.044 | 33.142 | 1.485 | 1.00 | 29.79 | D | N |
| ATOM | 4662 | CA | ILE | D | 383 | 21.078 | 33.190 | 2.562 | 1.00 | 31.49 | D | C |
| ATOM | 4663 | CB | ILE | D | 383 | 21.666 | 32.775 | 3.932 | 1.00 | 29.14 | D | C |
| ATOM | 4664 | CG1 | ILE | D | 383 | 21.949 | 31.240 | 4.005 | 1.00 | 30.22 | D | C |
| ATOM | 4665 | CD1 | ILE | D | 383 | 20.739 | 30.311 | 4.025 | 1.00 | 30.00 | D | C |
| ATOM | 4666 | CG2 | ILE | D | 383 | 20.832 | 33.272 | 5.109 | 1.00 | 27.84 | D | C |
| ATOM | 4667 | C | ILE | D | 383 | 20.441 | 34.580 | 2.642 | 1.00 | 31.95 | D | C |
| ATOM | 4668 | O | ILE | D | 383 | 19.229 | 34.673 | 2.744 | 1.00 | 33.99 | D | O |
| ATOM | 4669 | N | THR | D | 384 | 21.248 | 35.639 | 2.629 | 1.00 | 34.99 | D | N |
| ATOM | 4670 | CA | THR | D | 384 | 20.677 | 36.995 | 2.755 | 1.00 | 36.56 | D | C |
| ATOM | 4671 | CB | THR | D | 384 | 21.703 | 38.102 | 3.141 | 1.00 | 38.54 | D | C |
| ATOM | 4672 | OG1 | THR | D | 384 | 22.764 | 38.135 | 2.217 | 1.00 | 44.83 | D | O |
| ATOM | 4673 | CG2 | THR | D | 384 | 22.320 | 37.800 | 4.498 | 1.00 | 38.96 | D | C |
| ATOM | 4674 | C | THR | D | 384 | 19.873 | 37.322 | 1.530 | 1.00 | 36.00 | D | C |
| ATOM | 4675 | O | THR | D | 384 | 18.889 | 37.974 | 1.676 | 1.00 | 31.91 | D | O |
| ATOM | 4676 | N | ALA | D | 385 | 20.219 | 36.770 | 0.363 | 1.00 | 35.60 | D | N |
| ATOM | 4677 | CA | ALA | D | 385 | 19.423 | 37.011 | −0.822 | 1.00 | 40.00 | D | C |
| ATOM | 4678 | CB | ALA | D | 385 | 20.179 | 36.611 | −2.079 | 1.00 | 40.10 | D | C |
| ATOM | 4679 | C | ALA | D | 385 | 18.045 | 36.328 | −0.819 | 1.00 | 43.81 | D | C |
| ATOM | 4680 | O | ALA | D | 385 | 17.105 | 36.800 | −1.472 | 1.00 | 40.37 | D | O |
| ATOM | 4681 | N | ASN | D | 386 | 17.901 | 35.237 | −0.085 | 1.00 | 35.25 | D | N |
| ATOM | 4682 | CA | ASN | D | 386 | 16.699 | 34.437 | −0.206 | 1.00 | 36.53 | D | C |
| ATOM | 4683 | CB | ASN | D | 386 | 17.147 | 33.085 | −0.744 | 1.00 | 33.02 | D | C |
| ATOM | 4684 | CG | ASN | D | 386 | 17.599 | 33.186 | −2.169 | 1.00 | 30.67 | D | C |
| ATOM | 4685 | OD1 | ASN | D | 386 | 16.773 | 33.324 | −3.041 | 1.00 | 28.81 | D | O |
| ATOM | 4686 | ND2 | ASN | D | 386 | 18.904 | 33.111 | −2.425 | 1.00 | 33.11 | D | N |
| ATOM | 4687 | C | ASN | D | 386 | 15.838 | 34.324 | 1.023 | 1.00 | 33.16 | D | C |
| ATOM | 4688 | O | ASN | D | 386 | 14.727 | 33.875 | 0.937 | 1.00 | 30.69 | D | O |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 4689 | N | SER | D | 387 | 16.356 | 34.760 | 2.164 | 1.00 | 32.60 | D | N |
| ATOM | 4690 | CA | SER | D | 387 | 15.714 | 34.528 | 3.420 | 1.00 | 40.81 | D | C |
| ATOM | 4691 | CB | SER | D | 387 | 16.748 | 34.543 | 4.531 | 1.00 | 41.88 | D | C |
| ATOM | 4692 | OG | SER | D | 387 | 16.185 | 34.057 | 5.728 | 1.00 | 43.68 | D | O |
| ATOM | 4693 | C | SER | D | 387 | 14.687 | 35.638 | 3.679 | 1.00 | 44.63 | D | C |
| ATOM | 4694 | O | SER | D | 387 | 15.011 | 36.801 | 3.455 | 1.00 | 40.69 | D | O |
| ATOM | 4695 | N | SER | D | 388 | 13.486 | 35.263 | 4.139 | 1.00 | 40.56 | D | N |
| ATOM | 4696 | CA | SER | D | 388 | 12.496 | 36.217 | 4.758 | 1.00 | 43.80 | D | C |
| ATOM | 4697 | CB | SER | D | 388 | 11.287 | 35.410 | 5.234 | 1.00 | 44.77 | D | C |
| ATOM | 4698 | OG | SER | D | 388 | 10.699 | 34.741 | 4.147 | 1.00 | 46.54 | D | O |
| ATOM | 4699 | C | SER | D | 388 | 12.997 | 36.978 | 5.977 | 1.00 | 47.88 | D | C |
| ATOM | 4700 | O | SER | D | 388 | 13.623 | 36.364 | 6.903 | 1.00 | 51.13 | D | O |
| TER | 4701 | | SER | D | 388 | | | | | | | |
| ATOM | 4702 | N | VAL | E | 3 | −6.800 | 10.843 | 38.869 | 1.00 | 77.48 | E | N |
| ATOM | 4703 | CA | VAL | E | 3 | −5.721 | 10.803 | 39.913 | 1.00 | 73.40 | E | C |
| ATOM | 4704 | CB | VAL | E | 3 | −5.969 | 11.764 | 41.130 | 1.00 | 76.49 | E | C |
| ATOM | 4705 | CG1 | VAL | E | 3 | −6.512 | 13.133 | 40.688 | 1.00 | 79.95 | E | C |
| ATOM | 4706 | CG2 | VAL | E | 3 | −4.677 | 11.992 | 41.905 | 1.00 | 76.63 | E | C |
| ATOM | 4707 | C | VAL | E | 3 | −5.493 | 9.342 | 40.353 | 1.00 | 65.61 | E | C |
| ATOM | 4708 | O | VAL | E | 3 | −6.350 | 8.470 | 40.204 | 1.00 | 53.87 | E | O |
| ATOM | 4709 | N | SER | E | 4 | −4.279 | 9.067 | 40.802 | 1.00 | 59.29 | E | N |
| ATOM | 4710 | CA | SER | E | 4 | −3.909 | 7.737 | 41.215 | 1.00 | 58.35 | E | C |
| ATOM | 4711 | CB | SER | E | 4 | −3.192 | 7.030 | 40.073 | 1.00 | 59.58 | E | C |
| ATOM | 4712 | OG | SER | E | 4 | −1.926 | 7.651 | 39.852 | 1.00 | 61.71 | E | O |
| ATOM | 4713 | C | SER | E | 4 | −3.002 | 7.887 | 42.422 | 1.00 | 53.66 | E | C |
| ATOM | 4714 | O | SER | E | 4 | −2.806 | 8.995 | 42.920 | 1.00 | 58.54 | E | O |
| ATOM | 4715 | N | SER | E | 5 | −2.508 | 6.761 | 42.913 | 1.00 | 52.30 | E | N |
| ATOM | 4716 | CA | SER | E | 5 | −1.479 | 6.746 | 43.937 | 1.00 | 44.28 | E | C |
| ATOM | 4717 | CB | SER | E | 5 | −2.110 | 6.570 | 45.321 | 1.00 | 51.25 | E | C |
| ATOM | 4718 | OG | SER | E | 5 | −2.726 | 5.275 | 45.445 | 1.00 | 42.46 | E | O |
| ATOM | 4719 | C | SER | E | 5 | −0.633 | 5.566 | 43.592 | 1.00 | 42.97 | E | C |
| ATOM | 4720 | O | SER | E | 5 | −1.017 | 4.714 | 42.817 | 1.00 | 41.50 | E | O |
| ATOM | 4721 | N | VAL | E | 6 | 0.561 | 5.527 | 44.117 | 1.00 | 48.92 | E | N |
| ATOM | 4722 | CA | VAL | E | 6 | 1.250 | 4.244 | 44.216 | 1.00 | 43.70 | E | C |
| ATOM | 4723 | CB | VAL | E | 6 | 2.356 | 4.046 | 43.175 | 1.00 | 43.59 | E | C |
| ATOM | 4724 | CG1 | VAL | E | 6 | 2.999 | 2.680 | 43.346 | 1.00 | 39.93 | E | C |
| ATOM | 4725 | CG2 | VAL | E | 6 | 1.805 | 4.175 | 41.756 | 1.00 | 46.12 | E | C |
| ATOM | 4726 | C | VAL | E | 6 | 1.839 | 4.270 | 45.622 | 1.00 | 45.20 | E | C |
| ATOM | 4727 | O | VAL | E | 6 | 2.497 | 5.263 | 45.964 | 1.00 | 42.51 | E | O |
| ATOM | 4728 | N | PRO | E | 7 | 1.583 | 3.233 | 46.444 | 1.00 | 42.30 | E | N |
| ATOM | 4729 | CA | PRO | E | 7 | 0.780 | 2.041 | 46.101 | 1.00 | 40.54 | E | C |
| ATOM | 4730 | CB | PRO | E | 7 | 1.066 | 1.085 | 47.277 | 1.00 | 43.49 | E | C |
| ATOM | 4731 | CG | PRO | E | 7 | 1.408 | 1.981 | 48.426 | 1.00 | 38.74 | E | C |
| ATOM | 4732 | CD | PRO | E | 7 | 1.996 | 3.228 | 47.867 | 1.00 | 42.02 | E | C |
| ATOM | 4733 | C | PRO | E | 7 | −0.723 | 2.310 | 45.971 | 1.00 | 37.75 | E | C |
| ATOM | 4734 | O | PRO | E | 7 | −1.158 | 3.456 | 46.133 | 1.00 | 28.38 | E | O |
| ATOM | 4735 | N | THR | E | 8 | −1.498 | 1.272 | 45.656 | 1.00 | 40.91 | E | N |
| ATOM | 4736 | CA | THR | E | 8 | −2.978 | 1.469 | 45.563 | 1.00 | 46.86 | E | C |
| ATOM | 4737 | CB | THR | E | 8 | −3.528 | 0.944 | 44.264 | 1.00 | 39.91 | E | C |
| ATOM | 4738 | OG1 | THR | E | 8 | −2.981 | −0.369 | 44.055 | 1.00 | 44.49 | E | O |
| ATOM | 4739 | CG2 | THR | E | 8 | −3.142 | 1.913 | 43.140 | 1.00 | 44.23 | E | C |
| ATOM | 4740 | C | THR | E | 8 | −3.896 | 0.908 | 46.637 | 1.00 | 59.21 | E | C |
| ATOM | 4741 | O | THR | E | 8 | −4.906 | 1.564 | 46.961 | 1.00 | 69.76 | E | O |
| ATOM | 4742 | N | LYS | E | 9 | −3.662 | −0.286 | 47.157 | 1.00 | 46.97 | E | N |
| ATOM | 4743 | CA | LYS | E | 9 | −4.740 | −0.799 | 48.027 | 1.00 | 54.87 | E | C |
| ATOM | 4744 | CB | LYS | E | 9 | −5.383 | −2.036 | 47.412 | 1.00 | 59.28 | E | C |
| ATOM | 4745 | CG | LYS | E | 9 | −6.094 | −1.695 | 46.096 | 1.00 | 69.69 | E | C |
| ATOM | 4746 | CD | LYS | E | 9 | −7.455 | −2.381 | 45.932 | 1.00 | 76.98 | E | C |
| ATOM | 4747 | CE | LYS | E | 9 | −8.208 | −1.875 | 44.707 | 1.00 | 80.48 | E | C |
| ATOM | 4748 | NZ | LYS | E | 9 | −9.075 | −2.944 | 44.137 | 1.00 | 85.02 | E | N |
| ATOM | 4749 | C | LYS | E | 9 | −4.265 | −0.987 | 49.461 | 1.00 | 50.29 | E | C |
| ATOM | 4750 | O | LYS | E | 9 | −4.004 | −2.126 | 49.915 | 1.00 | 55.08 | E | O |
| ATOM | 4751 | N | LEU | E | 10 | −4.119 | 0.149 | 50.144 | 1.00 | 40.62 | E | N |
| ATOM | 4752 | CA | LEU | E | 10 | −3.510 | 0.167 | 51.481 | 1.00 | 43.70 | E | C |
| ATOM | 4753 | CB | LEU | E | 10 | −3.030 | 1.545 | 51.835 | 1.00 | 38.45 | E | C |
| ATOM | 4754 | CG | LEU | E | 10 | −2.343 | 1.693 | 53.189 | 1.00 | 38.86 | E | C |
| ATOM | 4755 | CD1 | LEU | E | 10 | −1.166 | 0.740 | 53.337 | 1.00 | 36.93 | E | C |
| ATOM | 4756 | CD2 | LEU | E | 10 | −1.937 | 3.137 | 53.399 | 1.00 | 43.56 | E | C |
| ATOM | 4757 | C | LEU | E | 10 | −4.489 | −0.274 | 52.580 | 1.00 | 46.72 | E | C |
| ATOM | 4758 | O | LEU | E | 10 | −5.551 | 0.341 | 52.717 | 1.00 | 45.40 | E | O |
| ATOM | 4759 | N | GLU | E | 11 | −4.070 | −1.219 | 53.434 | 1.00 | 43.29 | E | N |
| ATOM | 4760 | CA | GLU | E | 11 | −4.949 | −1.717 | 54.503 | 1.00 | 45.14 | E | C |
| ATOM | 4761 | CB | GLU | E | 11 | −5.848 | −2.828 | 53.931 | 1.00 | 45.25 | E | C |
| ATOM | 4762 | CG | GLU | E | 11 | −5.106 | −4.136 | 53.727 | 1.00 | 56.10 | E | C |
| ATOM | 4763 | CD | GLU | E | 11 | −5.610 | −5.020 | 52.586 | 1.00 | 67.77 | E | C |
| ATOM | 4764 | OE1 | GLU | E | 11 | −5.466 | −6.246 | 52.726 | 1.00 | 63.25 | E | O |
| ATOM | 4765 | OE2 | GLU | E | 11 | −6.092 | −4.509 | 51.545 | 1.00 | 75.33 | E | O |
| ATOM | 4766 | C | GLU | E | 11 | −4.200 | −2.235 | 55.722 | 1.00 | 42.49 | E | C |

APPENDIX A-continued

| Atomic coordinates of Aurora A + Inhibitory Monobody Mb60 + Danusertib | | | | | | | | | | | |
|---|---|---|---|---|---|---|---|---|---|---|---|
| ATOM | 4767 | O | GLU | E | 11 | −3.050 | −2.736 | 55.626 | 1.00 | 39.43 | E | O |
| ATOM | 4768 | N | VAL | E | 12 | −4.870 | −2.124 | 56.865 | 1.00 | 37.15 | E | N |
| ATOM | 4769 | CA | VAL | E | 12 | −4.402 | −2.716 | 58.109 | 1.00 | 38.74 | E | C |
| ATOM | 4770 | CB | VAL | E | 12 | −4.995 | −2.011 | 59.307 | 1.00 | 37.86 | E | C |
| ATOM | 4771 | CG1 | VAL | E | 12 | −4.662 | −2.769 | 60.592 | 1.00 | 38.91 | E | C |
| ATOM | 4772 | CG2 | VAL | E | 12 | −4.460 | −0.585 | 59.373 | 1.00 | 40.19 | E | C |
| ATOM | 4773 | C | VAL | E | 12 | −4.854 | −4.150 | 58.121 | 1.00 | 39.76 | E | C |
| ATOM | 4774 | O | VAL | E | 12 | −6.028 | −4.383 | 58.163 | 1.00 | 40.40 | E | O |
| ATOM | 4775 | N | VAL | E | 13 | −3.930 | −5.086 | 58.026 | 1.00 | 38.76 | E | N |
| ATOM | 4776 | CA | VAL | E | 13 | −4.269 | −6.506 | 57.963 | 1.00 | 43.17 | E | C |
| ATOM | 4777 | CB | VAL | E | 13 | −3.386 | −7.254 | 56.948 | 1.00 | 45.19 | E | C |
| ATOM | 4778 | CG1 | VAL | E | 13 | −1.927 | −7.303 | 57.349 | 1.00 | 45.87 | E | C |
| ATOM | 4779 | CG2 | VAL | E | 13 | −3.513 | −6.579 | 55.599 | 1.00 | 50.86 | E | C |
| ATOM | 4780 | C | VAL | E | 13 | −4.245 | −7.246 | 59.310 | 1.00 | 40.68 | E | C |
| ATOM | 4781 | O | VAL | E | 13 | −4.873 | −8.276 | 59.432 | 1.00 | 42.58 | E | O |
| ATOM | 4782 | N | ALA | E | 14 | −3.493 | −6.748 | 60.285 | 1.00 | 40.65 | E | N |
| ATOM | 4783 | CA | ALA | E | 14 | −3.587 | −7.232 | 61.674 | 1.00 | 42.05 | E | C |
| ATOM | 4784 | CB | ALA | E | 14 | −2.739 | −8.479 | 61.857 | 1.00 | 40.08 | E | C |
| ATOM | 4785 | C | ALA | E | 14 | −3.094 | −6.143 | 62.598 | 1.00 | 43.73 | E | C |
| ATOM | 4786 | O | ALA | E | 14 | −2.481 | −5.172 | 62.167 | 1.00 | 41.21 | E | O |
| ATOM | 4787 | N | ALA | E | 15 | −3.333 | −6.332 | 63.888 | 1.00 | 40.15 | E | N |
| ATOM | 4788 | CA | ALA | E | 15 | −3.090 | −5.297 | 64.848 | 1.00 | 39.64 | E | C |
| ATOM | 4789 | CB | ALA | E | 15 | −4.242 | −4.293 | 64.809 | 1.00 | 38.13 | E | C |
| ATOM | 4790 | C | ALA | E | 15 | −2.962 | −5.882 | 66.240 | 1.00 | 43.63 | E | C |
| ATOM | 4791 | O | ALA | E | 15 | −3.534 | −6.941 | 66.517 | 1.00 | 39.13 | E | O |
| ATOM | 4792 | N | THR | E | 16 | −2.204 | −5.181 | 67.087 | 1.00 | 40.73 | E | N |
| ATOM | 4793 | CA | THR | E | 16 | −2.206 | −5.333 | 68.518 | 1.00 | 42.27 | E | C |
| ATOM | 4794 | CB | THR | E | 16 | −0.843 | −5.780 | 69.086 | 1.00 | 43.38 | E | C |
| ATOM | 4795 | OG1 | THR | E | 16 | 0.068 | −4.657 | 69.190 | 1.00 | 38.67 | E | O |
| ATOM | 4796 | CG2 | THR | E | 16 | −0.224 | −6.985 | 68.251 | 1.00 | 43.04 | E | C |
| ATOM | 4797 | C | THR | E | 16 | −2.626 | −3.978 | 69.058 | 1.00 | 42.45 | E | C |
| ATOM | 4798 | O | THR | E | 16 | −2.833 | −3.080 | 68.286 | 1.00 | 42.36 | E | O |
| ATOM | 4799 | N | PRO | E | 17 | −2.786 | −3.842 | 70.396 | 1.00 | 51.84 | E | N |
| ATOM | 4800 | CA | PRO | E | 17 | −3.240 | −2.539 | 70.928 | 1.00 | 50.89 | E | C |
| ATOM | 4801 | CB | PRO | E | 17 | −3.310 | −2.778 | 72.460 | 1.00 | 50.39 | E | C |
| ATOM | 4802 | CG | PRO | E | 17 | −3.506 | −4.256 | 72.583 | 1.00 | 54.07 | E | C |
| ATOM | 4803 | CD | PRO | E | 17 | −2.682 | −4.857 | 71.471 | 1.00 | 48.82 | E | C |
| ATOM | 4804 | C | PRO | E | 17 | −2.286 | −1.393 | 70.600 | 1.00 | 43.55 | E | C |
| ATOM | 4805 | O | PRO | E | 17 | −2.710 | −0.269 | 70.522 | 1.00 | 49.45 | E | O |
| ATOM | 4806 | N | THR | E | 18 | −1.007 | −1.694 | 70.402 | 1.00 | 44.84 | E | N |
| ATOM | 4807 | CA | THR | E | 18 | −0.017 | −0.649 | 70.162 | 1.00 | 42.86 | E | C |
| ATOM | 4808 | CB | THR | E | 18 | 1.058 | −0.668 | 71.254 | 1.00 | 44.38 | E | C |
| ATOM | 4809 | OG1 | THR | E | 18 | 1.806 | −1.885 | 71.139 | 1.00 | 41.68 | E | O |
| ATOM | 4810 | CG2 | THR | E | 18 | 0.441 | −0.494 | 72.660 | 1.00 | 44.93 | E | C |
| ATOM | 4811 | C | THR | E | 18 | 0.719 | −0.779 | 68.809 | 1.00 | 47.34 | E | C |
| ATOM | 4812 | O | THR | E | 18 | 1.695 | −0.076 | 68.593 | 1.00 | 43.47 | E | O |
| ATOM | 4813 | N | SER | E | 19 | 0.217 | −1.634 | 67.907 | 1.00 | 46.02 | E | N |
| ATOM | 4814 | CA | SER | E | 19 | 0.928 | −2.064 | 66.709 | 1.00 | 43.82 | E | C |
| ATOM | 4815 | CB | SER | E | 19 | 1.625 | −3.386 | 66.989 | 1.00 | 47.63 | E | C |
| ATOM | 4816 | OG | SER | E | 19 | 2.696 | −3.570 | 66.117 | 1.00 | 59.03 | E | O |
| ATOM | 4817 | C | SER | E | 19 | −0.067 | −2.315 | 65.583 | 1.00 | 43.48 | E | C |
| ATOM | 4818 | O | SER | E | 19 | −1.220 | −2.795 | 65.827 | 1.00 | 40.30 | E | O |
| ATOM | 4819 | N | LEU | E | 20 | 0.383 | −2.011 | 64.365 | 1.00 | 40.00 | E | N |
| ATOM | 4820 | CA | LEU | E | 20 | −0.367 | −2.269 | 63.119 | 1.00 | 40.16 | E | C |
| ATOM | 4821 | CB | LEU | E | 20 | −0.788 | −0.958 | 62.483 | 1.00 | 42.51 | E | C |
| ATOM | 4822 | CG | LEU | E | 20 | −1.679 | −0.075 | 63.336 | 1.00 | 45.66 | E | C |
| ATOM | 4823 | CD1 | LEU | E | 20 | −2.078 | 1.132 | 62.500 | 1.00 | 47.44 | E | C |
| ATOM | 4824 | CD2 | LEU | E | 20 | −2.925 | −0.815 | 63.848 | 1.00 | 44.53 | E | C |
| ATOM | 4825 | C | LEU | E | 20 | 0.490 | −2.974 | 62.109 | 1.00 | 39.38 | E | C |
| ATOM | 4826 | O | LEU | E | 20 | 1.642 | −2.592 | 61.928 | 1.00 | 34.92 | E | O |
| ATOM | 4827 | N | LEU | E | 21 | −0.054 | −4.005 | 61.465 | 1.00 | 36.62 | E | N |
| ATOM | 4828 | CA | LEU | E | 21 | 0.571 | −4.598 | 60.280 | 1.00 | 37.08 | E | C |
| ATOM | 4829 | CB | LEU | E | 21 | 0.482 | −6.108 | 60.304 | 1.00 | 41.01 | E | C |
| ATOM | 4830 | CG | LEU | E | 21 | 1.127 | −6.890 | 59.159 | 1.00 | 44.84 | E | C |
| ATOM | 4831 | CD1 | LEU | E | 21 | 2.611 | −6.555 | 58.962 | 1.00 | 53.31 | E | C |
| ATOM | 4832 | CD2 | LEU | E | 21 | 1.008 | −8.352 | 59.469 | 1.00 | 45.25 | E | C |
| ATOM | 4833 | C | LEU | E | 21 | −0.173 | −4.058 | 59.079 | 1.00 | 38.02 | E | C |
| ATOM | 4834 | O | LEU | E | 21 | −1.360 | −4.365 | 58.894 | 1.00 | 38.32 | E | O |
| ATOM | 4835 | N | ILE | E | 22 | 0.503 | −3.223 | 58.272 | 1.00 | 36.57 | E | N |
| ATOM | 4836 | CA | ILE | E | 22 | −0.112 | −2.652 | 57.045 | 1.00 | 35.48 | E | C |
| ATOM | 4837 | CB | ILE | E | 22 | 0.148 | −1.151 | 56.820 | 1.00 | 38.95 | E | C |
| ATOM | 4838 | CG1 | ILE | E | 22 | 1.651 | −0.844 | 56.909 | 1.00 | 38.50 | E | C |
| ATOM | 4839 | CD1 | ILE | E | 22 | 1.969 | 0.550 | 56.463 | 1.00 | 43.54 | E | C |
| ATOM | 4840 | CG2 | ILE | E | 22 | −0.665 | −0.282 | 57.784 | 1.00 | 39.11 | E | C |
| ATOM | 4841 | C | ILE | E | 22 | 0.366 | −3.359 | 55.791 | 1.00 | 34.71 | E | C |
| ATOM | 4842 | O | ILE | E | 22 | 1.473 | −3.910 | 55.737 | 1.00 | 31.72 | E | O |
| ATOM | 4843 | N | SER | E | 23 | −0.460 | −3.276 | 54.773 | 1.00 | 35.14 | E | N |
| ATOM | 4844 | CA | SER | E | 23 | −0.246 | −4.018 | 53.542 | 1.00 | 41.48 | E | C |

APPENDIX A-continued

| | | | | | | | | | | | | |
|---|---|---|---|---|---|---|---|---|---|---|---|---|
| Atomic coordinates of Aurora A + Inhibitory Monobody Mb60 + Danusertib | | | | | | | | | | | | |
| ATOM | 4845 | CB | SER | E | 23 | −1.026 | −5.317 | 53.615 | 1.00 | 40.63 | E | C |
| ATOM | 4846 | OG | SER | E | 23 | −0.666 | −6.173 | 52.586 | 1.00 | 47.63 | E | O |
| ATOM | 4847 | C | SER | E | 23 | −0.717 | −3.219 | 52.342 | 1.00 | 34.46 | E | C |
| ATOM | 4848 | O | SER | E | 23 | −1.666 | −2.429 | 52.443 | 1.00 | 35.76 | E | O |
| ATOM | 4849 | N | TRP | E | 24 | −0.085 | −3.462 | 51.197 | 1.00 | 41.04 | E | N |
| ATOM | 4850 | CA | TRP | E | 24 | −0.454 | −2.733 | 49.942 | 1.00 | 45.08 | E | C |
| ATOM | 4851 | CB | TRP | E | 24 | 0.203 | −1.317 | 49.911 | 1.00 | 40.89 | E | C |
| ATOM | 4852 | CG | TRP | E | 24 | 1.660 | −1.409 | 49.911 | 1.00 | 43.81 | E | C |
| ATOM | 4853 | CD1 | TRP | E | 24 | 2.487 | −1.696 | 48.833 | 1.00 | 45.31 | E | C |
| ATOM | 4854 | NE1 | TRP | E | 24 | 3.814 | −1.714 | 49.246 | 1.00 | 46.20 | E | N |
| ATOM | 4855 | CE2 | TRP | E | 24 | 3.861 | −1.443 | 50.593 | 1.00 | 45.83 | E | C |
| ATOM | 4856 | CD2 | TRP | E | 24 | 2.519 | −1.273 | 51.050 | 1.00 | 45.89 | E | C |
| ATOM | 4857 | CE3 | TRP | E | 24 | 2.293 | −0.983 | 52.407 | 1.00 | 47.46 | E | C |
| ATOM | 4858 | CZ3 | TRP | E | 24 | 3.383 | −0.902 | 53.266 | 1.00 | 48.48 | E | C |
| ATOM | 4859 | CH2 | TRP | E | 24 | 4.702 | −1.120 | 52.782 | 1.00 | 48.05 | E | C |
| ATOM | 4860 | CZ2 | TRP | E | 24 | 4.948 | −1.395 | 51.456 | 1.00 | 43.27 | E | C |
| ATOM | 4861 | C | TRP | E | 24 | −0.102 | −3.534 | 48.674 | 1.00 | 42.89 | E | C |
| ATOM | 4862 | O | TRP | E | 24 | 0.721 | −4.453 | 48.712 | 1.00 | 45.36 | E | O |
| ATOM | 4863 | N | ASP | E | 25 | −0.749 | −3.158 | 47.576 | 1.00 | 48.28 | E | N |
| ATOM | 4864 | CA | ASP | E | 25 | −0.408 | −3.576 | 46.212 | 1.00 | 55.27 | E | C |
| ATOM | 4865 | CB | ASP | E | 25 | −1.635 | −3.496 | 45.287 | 1.00 | 61.15 | E | C |
| ATOM | 4866 | CG | ASP | E | 25 | −2.696 | −4.593 | 45.581 | 1.00 | 65.86 | E | C |
| ATOM | 4867 | OD1 | ASP | E | 25 | −2.521 | −5.380 | 46.544 | 1.00 | 64.04 | E | O |
| ATOM | 4868 | OD2 | ASP | E | 25 | −3.709 | −4.661 | 44.840 | 1.00 | 62.36 | E | O |
| ATOM | 4869 | C | ASP | E | 25 | 0.681 | −2.673 | 45.605 | 1.00 | 57.47 | E | C |
| ATOM | 4870 | O | ASP | E | 25 | 0.505 | −1.451 | 45.466 | 1.00 | 59.39 | E | O |
| ATOM | 4871 | N | ALA | E | 26 | 1.796 | −3.322 | 45.290 | 1.00 | 54.97 | E | N |
| ATOM | 4872 | CA | ALA | E | 26 | 2.881 | −2.788 | 44.478 | 1.00 | 56.67 | E | C |
| ATOM | 4873 | CB | ALA | E | 26 | 4.124 | −3.676 | 44.662 | 1.00 | 56.16 | E | C |
| ATOM | 4874 | C | ALA | E | 26 | 2.517 | −2.781 | 42.981 | 1.00 | 59.91 | E | C |
| ATOM | 4875 | O | ALA | E | 26 | 1.933 | −3.786 | 42.483 | 1.00 | 50.37 | E | O |
| ATOM | 4876 | N | PRO | E | 27 | 2.961 | −1.727 | 42.230 | 1.00 | 55.77 | E | N |
| ATOM | 4877 | CA | PRO | E | 27 | 2.682 | −1.683 | 40.792 | 1.00 | 53.45 | E | C |
| ATOM | 4878 | CB | PRO | E | 27 | 2.947 | −0.235 | 40.449 | 1.00 | 51.57 | E | C |
| ATOM | 4879 | CG | PRO | E | 27 | 4.147 | 0.070 | 41.305 | 1.00 | 53.92 | E | C |
| ATOM | 4880 | CD | PRO | E | 27 | 4.053 | −0.782 | 42.551 | 1.00 | 54.48 | E | C |
| ATOM | 4881 | C | PRO | E | 27 | 3.690 | −2.585 | 40.121 | 1.00 | 49.03 | E | C |
| ATOM | 4882 | O | PRO | E | 27 | 4.606 | −3.075 | 40.803 | 1.00 | 44.35 | E | O |
| ATOM | 4883 | N | ALA | E | 28 | 3.522 | −2.802 | 38.818 | 1.00 | 50.73 | E | N |
| ATOM | 4884 | CA | ALA | E | 28 | 4.396 | −3.689 | 38.050 | 1.00 | 49.00 | E | C |
| ATOM | 4885 | CB | ALA | E | 28 | 3.892 | −3.796 | 36.608 | 1.00 | 48.21 | E | C |
| ATOM | 4886 | C | ALA | E | 28 | 5.823 | −3.124 | 38.090 | 1.00 | 48.68 | E | C |
| ATOM | 4887 | O | ALA | E | 28 | 6.785 | −3.853 | 38.350 | 1.00 | 47.60 | E | O |
| ATOM | 4888 | N | VAL | E | 29 | 5.940 | −1.811 | 37.906 | 1.00 | 48.30 | E | N |
| ATOM | 4889 | CA | VAL | E | 29 | 7.255 | −1.160 | 37.838 | 1.00 | 48.52 | E | C |
| ATOM | 4890 | CB | VAL | E | 29 | 7.125 | 0.327 | 37.424 | 1.00 | 51.76 | E | C |
| ATOM | 4891 | CG1 | VAL | E | 29 | 8.464 | 0.880 | 36.942 | 1.00 | 51.39 | E | C |
| ATOM | 4892 | CG2 | VAL | E | 29 | 6.540 | 1.186 | 38.550 | 1.00 | 54.64 | E | C |
| ATOM | 4893 | C | VAL | E | 29 | 8.078 | −1.297 | 39.131 | 1.00 | 47.97 | E | C |
| ATOM | 4894 | O | VAL | E | 29 | 7.568 | −1.178 | 40.215 | 1.00 | 44.77 | E | O |
| ATOM | 4895 | N | THR | E | 30 | 9.371 | −1.505 | 38.992 | 1.00 | 47.60 | E | N |
| ATOM | 4896 | CA | THR | E | 30 | 10.255 | −1.534 | 40.135 | 1.00 | 51.48 | E | C |
| ATOM | 4897 | CB | THR | E | 30 | 11.712 | −1.912 | 39.752 | 1.00 | 52.97 | E | C |
| ATOM | 4898 | OG1 | THR | E | 30 | 12.524 | −1.755 | 40.907 | 1.00 | 53.98 | E | O |
| ATOM | 4899 | CG2 | THR | E | 30 | 12.310 | −0.997 | 38.674 | 1.00 | 63.72 | E | C |
| ATOM | 4900 | C | THR | E | 30 | 10.168 | −0.191 | 40.908 | 1.00 | 49.83 | E | C |
| ATOM | 4901 | O | THR | E | 30 | 9.882 | 0.864 | 40.336 | 1.00 | 46.36 | E | O |
| ATOM | 4902 | N | VAL | E | 31 | 10.322 | −0.261 | 42.227 | 1.00 | 42.43 | E | N |
| ATOM | 4903 | CA | VAL | E | 31 | 10.175 | 0.915 | 43.077 | 1.00 | 40.56 | E | C |
| ATOM | 4904 | CB | VAL | E | 31 | 8.856 | 0.806 | 43.888 | 1.00 | 39.91 | E | C |
| ATOM | 4905 | CG1 | VAL | E | 31 | 8.873 | 1.645 | 45.157 | 1.00 | 42.13 | E | C |
| ATOM | 4906 | CG2 | VAL | E | 31 | 7.689 | 1.143 | 42.994 | 1.00 | 42.44 | E | C |
| ATOM | 4907 | C | VAL | E | 31 | 11.389 | 0.967 | 43.992 | 1.00 | 39.39 | E | C |
| ATOM | 4908 | O | VAL | E | 31 | 11.888 | −0.087 | 44.399 | 1.00 | 45.05 | E | O |
| ATOM | 4909 | N | VAL | E | 32 | 11.841 | 2.172 | 44.347 | 1.00 | 38.86 | E | N |
| ATOM | 4910 | CA | VAL | E | 32 | 13.062 | 2.279 | 45.154 | 1.00 | 40.59 | E | C |
| ATOM | 4911 | CB | VAL | E | 32 | 13.682 | 3.696 | 45.152 | 1.00 | 41.16 | E | C |
| ATOM | 4912 | CG1 | VAL | E | 32 | 14.906 | 3.710 | 46.035 | 1.00 | 37.42 | E | C |
| ATOM | 4913 | CG2 | VAL | E | 32 | 14.042 | 4.192 | 43.736 | 1.00 | 41.60 | E | C |
| ATOM | 4914 | C | VAL | E | 32 | 12.714 | 1.884 | 46.587 | 1.00 | 43.41 | E | C |
| ATOM | 4915 | O | VAL | E | 32 | 13.226 | 0.914 | 47.131 | 1.00 | 44.73 | E | O |
| ATOM | 4916 | N | HIS | E | 33 | 11.818 | 2.648 | 47.177 | 1.00 | 44.93 | E | N |
| ATOM | 4917 | CA | HIS | E | 33 | 11.319 | 2.391 | 48.523 | 1.00 | 45.74 | E | C |
| ATOM | 4918 | CB | HIS | E | 33 | 12.315 | 2.869 | 49.600 | 1.00 | 39.78 | E | C |
| ATOM | 4919 | CG | HIS | E | 33 | 12.587 | 4.337 | 49.637 | 1.00 | 48.91 | E | C |
| ATOM | 4920 | ND1 | HIS | E | 33 | 13.869 | 4.836 | 49.700 | 1.00 | 51.50 | E | N |
| ATOM | 4921 | CE1 | HIS | E | 33 | 13.830 | 6.152 | 49.800 | 1.00 | 50.76 | E | C |
| ATOM | 4922 | NE2 | HIS | E | 33 | 12.566 | 6.531 | 49.812 | 1.00 | 48.06 | E | N |

APPENDIX A-continued

| Atomic coordinates of Aurora A + Inhibitory Monobody Mb60 + Danusertib | | | | | | | | | | | |
|---|---|---|---|---|---|---|---|---|---|---|---|
| ATOM | 4923 | CD2 | HIS | E | 33 | 11.767 | 5.413 | 49.756 | 1.00 | 53.95 | E | C |
| ATOM | 4924 | C | HIS | E | 33 | 9.950 | 3.058 | 48.691 | 1.00 | 42.77 | E | C |
| ATOM | 4925 | O | HIS | E | 33 | 9.527 | 3.855 | 47.836 | 1.00 | 38.11 | E | O |
| ATOM | 4926 | N | TYR | E | 34 | 9.301 | 2.780 | 49.815 | 1.00 | 42.16 | E | N |
| ATOM | 4927 | CA | TYR | E | 34 | 8.026 | 3.410 | 50.142 | 1.00 | 35.14 | E | C |
| ATOM | 4928 | CB | TYR | E | 34 | 7.007 | 2.349 | 50.529 | 1.00 | 38.72 | E | C |
| ATOM | 4929 | CG | TYR | E | 34 | 6.566 | 1.487 | 49.390 | 1.00 | 36.99 | E | C |
| ATOM | 4930 | CD1 | TYR | E | 34 | 7.248 | 0.330 | 49.076 | 1.00 | 36.10 | E | C |
| ATOM | 4931 | CE1 | TYR | E | 34 | 6.849 | −0.461 | 48.018 | 1.00 | 36.33 | E | C |
| ATOM | 4932 | CZ | TYR | E | 34 | 5.773 | −0.066 | 47.237 | 1.00 | 34.26 | E | C |
| ATOM | 4933 | OH | TYR | E | 34 | 5.377 | −0.841 | 46.175 | 1.00 | 39.68 | E | O |
| ATOM | 4934 | CE2 | TYR | E | 34 | 5.122 | 1.091 | 47.511 | 1.00 | 32.65 | E | C |
| ATOM | 4935 | CD2 | TYR | E | 34 | 5.506 | 1.857 | 48.597 | 1.00 | 32.12 | E | C |
| ATOM | 4936 | C | TYR | E | 34 | 8.262 | 4.277 | 51.325 | 1.00 | 36.50 | E | C |
| ATOM | 4937 | O | TYR | E | 34 | 8.973 | 3.852 | 52.247 | 1.00 | 42.24 | E | O |
| ATOM | 4938 | N | VAL | E | 35 | 7.637 | 5.458 | 51.324 | 1.00 | 35.29 | E | N |
| ATOM | 4939 | CA | VAL | E | 35 | 7.680 | 6.388 | 52.425 | 1.00 | 38.25 | E | C |
| ATOM | 4940 | CB | VAL | E | 35 | 7.833 | 7.846 | 51.946 | 1.00 | 39.82 | E | C |
| ATOM | 4941 | CG1 | VAL | E | 35 | 7.790 | 8.823 | 53.120 | 1.00 | 38.58 | E | C |
| ATOM | 4942 | CG2 | VAL | E | 35 | 9.119 | 8.018 | 51.108 | 1.00 | 39.01 | E | C |
| ATOM | 4943 | C | VAL | E | 35 | 6.364 | 6.211 | 53.174 | 1.00 | 36.65 | E | C |
| ATOM | 4944 | O | VAL | E | 35 | 5.275 | 6.315 | 52.601 | 1.00 | 39.49 | E | O |
| ATOM | 4945 | N | ILE | E | 36 | 6.483 | 5.943 | 54.463 | 1.00 | 40.82 | E | N |
| ATOM | 4946 | CA | ILE | E | 36 | 5.340 | 5.644 | 55.335 | 1.00 | 39.57 | E | C |
| ATOM | 4947 | CB | ILE | E | 36 | 5.487 | 4.271 | 55.980 | 1.00 | 37.62 | E | C |
| ATOM | 4948 | CG1 | ILE | E | 36 | 5.494 | 3.195 | 54.909 | 1.00 | 43.64 | E | C |
| ATOM | 4949 | CD1 | ILE | E | 36 | 6.007 | 1.870 | 55.372 | 1.00 | 45.83 | E | C |
| ATOM | 4950 | CG2 | ILE | E | 36 | 4.319 | 4.002 | 56.910 | 1.00 | 39.36 | E | C |
| ATOM | 4951 | C | ILE | E | 36 | 5.301 | 6.721 | 56.404 | 1.00 | 37.57 | E | C |
| ATOM | 4952 | O | ILE | E | 36 | 6.263 | 6.926 | 57.104 | 1.00 | 39.00 | E | O |
| ATOM | 4953 | N | THR | E | 37 | 4.200 | 7.418 | 56.501 | 1.00 | 37.97 | E | N |
| ATOM | 4954 | CA | THR | E | 37 | 4.011 | 8.352 | 57.586 | 1.00 | 47.26 | E | C |
| ATOM | 4955 | CB | THR | E | 37 | 3.638 | 9.756 | 57.091 | 1.00 | 46.50 | E | C |
| ATOM | 4956 | OG1 | THR | E | 37 | 2.433 | 9.644 | 56.337 | 1.00 | 55.38 | E | O |
| ATOM | 4957 | CG2 | THR | E | 37 | 4.752 | 10.383 | 56.240 | 1.00 | 47.28 | E | C |
| ATOM | 4958 | C | THR | E | 37 | 2.809 | 7.902 | 58.418 | 1.00 | 45.20 | E | C |
| ATOM | 4959 | O | THR | E | 37 | 1.825 | 7.355 | 57.877 | 1.00 | 45.21 | E | O |
| ATOM | 4960 | N | TYR | E | 38 | 2.863 | 8.252 | 59.700 | 1.00 | 44.58 | E | N |
| ATOM | 4961 | CA | TYR | E | 38 | 1.769 | 7.996 | 60.643 | 1.00 | 47.87 | E | C |
| ATOM | 4962 | CB | TYR | E | 38 | 1.826 | 6.565 | 61.231 | 1.00 | 45.22 | E | C |
| ATOM | 4963 | CG | TYR | E | 38 | 3.043 | 6.213 | 62.083 | 1.00 | 46.31 | E | C |
| ATOM | 4964 | CD1 | TYR | E | 38 | 4.232 | 5.814 | 61.496 | 1.00 | 43.06 | E | C |
| ATOM | 4965 | CE1 | TYR | E | 38 | 5.351 | 5.492 | 62.271 | 1.00 | 42.40 | E | C |
| ATOM | 4966 | CZ | TYR | E | 38 | 5.264 | 5.549 | 63.667 | 1.00 | 45.79 | E | C |
| ATOM | 4967 | OH | TYR | E | 38 | 6.370 | 5.219 | 64.440 | 1.00 | 44.89 | E | O |
| ATOM | 4968 | CE2 | TYR | E | 38 | 4.078 | 5.944 | 64.270 | 1.00 | 41.55 | E | C |
| ATOM | 4969 | CD2 | TYR | E | 38 | 2.994 | 6.290 | 63.487 | 1.00 | 44.55 | E | C |
| ATOM | 4970 | C | TYR | E | 38 | 1.775 | 9.014 | 61.779 | 1.00 | 53.23 | E | C |
| ATOM | 4971 | O | TYR | E | 38 | 2.851 | 9.321 | 62.347 | 1.00 | 48.92 | E | O |
| ATOM | 4972 | N | GLY | E | 39 | 0.570 | 9.509 | 62.103 | 1.00 | 48.52 | E | N |
| ATOM | 4973 | CA | GLY | E | 39 | 0.362 | 10.316 | 63.295 | 1.00 | 51.44 | E | C |
| ATOM | 4974 | C | GLY | E | 39 | −1.095 | 10.327 | 63.730 | 1.00 | 52.90 | E | C |
| ATOM | 4975 | O | GLY | E | 39 | −1.962 | 9.882 | 62.991 | 1.00 | 50.87 | E | O |
| ATOM | 4976 | N | GLU | E | 40 | −1.355 | 10.863 | 64.922 | 1.00 | 56.64 | E | N |
| ATOM | 4977 | CA | GLU | E | 40 | −2.717 | 10.954 | 65.477 | 1.00 | 58.55 | E | C |
| ATOM | 4978 | CB | GLU | E | 40 | −2.685 | 11.610 | 66.853 | 1.00 | 60.39 | E | C |
| ATOM | 4979 | CG | GLU | E | 40 | −1.903 | 10.821 | 67.904 | 1.00 | 65.41 | E | C |
| ATOM | 4980 | CD | GLU | E | 40 | −2.408 | 11.036 | 69.327 | 1.00 | 69.50 | E | C |
| ATOM | 4981 | OE1 | GLU | E | 40 | −3.609 | 11.367 | 69.501 | 1.00 | 66.21 | E | O |
| ATOM | 4982 | OE2 | GLU | E | 40 | −1.598 | 10.844 | 70.268 | 1.00 | 66.43 | E | O |
| ATOM | 4983 | C | GLU | E | 40 | −3.604 | 11.780 | 64.571 | 1.00 | 59.19 | E | C |
| ATOM | 4984 | O | GLU | E | 40 | −3.214 | 12.875 | 64.216 | 1.00 | 61.26 | E | O |
| ATOM | 4985 | N | THR | E | 41 | −4.776 | 11.275 | 64.178 | 1.00 | 57.63 | E | N |
| ATOM | 4986 | CA | THR | E | 41 | −5.585 | 12.003 | 63.186 | 1.00 | 67.20 | E | C |
| ATOM | 4987 | CB | THR | E | 41 | −6.844 | 11.222 | 62.709 | 1.00 | 69.22 | E | C |
| ATOM | 4988 | OG1 | THR | E | 41 | −6.497 | 9.888 | 62.285 | 1.00 | 65.94 | E | O |
| ATOM | 4989 | CG2 | THR | E | 41 | −7.532 | 11.948 | 61.533 | 1.00 | 66.24 | E | C |
| ATOM | 4990 | C | THR | E | 41 | −5.966 | 13.379 | 63.755 | 1.00 | 68.65 | E | C |
| ATOM | 4991 | O | THR | E | 41 | −6.037 | 13.559 | 64.975 | 1.00 | 65.86 | E | O |
| ATOM | 4992 | N | GLY | E | 42 | −6.135 | 14.355 | 62.870 | 1.00 | 77.99 | E | N |
| ATOM | 4993 | CA | GLY | E | 42 | −6.561 | 15.697 | 63.261 | 1.00 | 84.49 | E | C |
| ATOM | 4994 | C | GLY | E | 42 | −5.397 | 16.582 | 63.670 | 1.00 | 93.94 | E | C |
| ATOM | 4995 | O | GLY | E | 42 | −4.316 | 16.519 | 63.080 | 1.00 | 97.21 | E | O |
| ATOM | 4996 | N | GLY | E | 43 | −5.613 | 17.414 | 64.682 | 1.00 | 95.06 | E | N |
| ATOM | 4997 | CA | GLY | E | 43 | −4.637 | 18.427 | 65.045 | 1.00 | 95.37 | E | C |
| ATOM | 4998 | C | GLY | E | 43 | −3.339 | 17.886 | 65.620 | 1.00 | 97.85 | E | C |
| ATOM | 4999 | O | GLY | E | 43 | −3.282 | 16.754 | 66.121 | 1.00 | 94.12 | E | O |
| ATOM | 5000 | N | ASN | E | 44 | −2.292 | 18.701 | 65.481 | 1.00 | 95.09 | E | N |

APPENDIX A-continued

| Atomic coordinates of Aurora A + Inhibitory Monobody Mb60 + Danusertib | | | | | | | | | | | | |
|---|---|---|---|---|---|---|---|---|---|---|---|---|
| ATOM | 5001 | CA | ASN | E | 44 | −1.072 | 18.635 | 66.291 | 1.00 | 94.14 | E | C |
| ATOM | 5002 | CB | ASN | E | 44 | −1.375 | 19.215 | 67.695 | 1.00 | 93.15 | E | C |
| ATOM | 5003 | CG | ASN | E | 44 | −0.167 | 19.912 | 68.336 | 1.00 | 95.58 | E | C |
| ATOM | 5004 | OD1 | ASN | E | 44 | 0.602 | 20.640 | 67.687 | 1.00 | 85.48 | E | O |
| ATOM | 5005 | ND2 | ASN | E | 44 | 0.009 | 19.674 | 69.625 | 1.00 | 97.91 | E | N |
| ATOM | 5006 | C | ASN | E | 44 | −0.405 | 17.236 | 66.327 | 1.00 | 95.51 | E | C |
| ATOM | 5007 | O | ASN | E | 44 | −0.603 | 16.439 | 65.404 | 1.00 | 93.66 | E | O |
| ATOM | 5008 | N | SER | E | 45 | 0.407 | 16.960 | 67.353 | 1.00 | 91.42 | E | N |
| ATOM | 5009 | CA | SER | E | 45 | 1.172 | 15.715 | 67.481 | 1.00 | 93.33 | E | C |
| ATOM | 5010 | CB | SER | E | 45 | 0.259 | 14.471 | 67.517 | 1.00 | 96.89 | E | C |
| ATOM | 5011 | OG | SER | E | 45 | −0.451 | 14.407 | 68.736 | 1.00 | 94.09 | E | O |
| ATOM | 5012 | C | SER | E | 45 | 2.279 | 15.529 | 66.429 | 1.00 | 86.09 | E | C |
| ATOM | 5013 | O | SER | E | 45 | 2.193 | 16.039 | 65.306 | 1.00 | 72.14 | E | O |
| ATOM | 5014 | N | PRO | E | 46 | 3.338 | 14.792 | 66.804 | 1.00 | 87.82 | E | N |
| ATOM | 5015 | CA | PRO | E | 46 | 4.335 | 14.483 | 65.789 | 1.00 | 95.59 | E | C |
| ATOM | 5016 | CB | PRO | E | 46 | 5.417 | 13.730 | 66.582 | 1.00 | 97.91 | E | C |
| ATOM | 5017 | CG | PRO | E | 46 | 4.711 | 13.189 | 67.788 | 1.00 | 95.53 | E | C |
| ATOM | 5018 | CD | PRO | E | 46 | 3.697 | 14.232 | 68.127 | 1.00 | 88.36 | E | C |
| ATOM | 5019 | C | PRO | E | 46 | 3.761 | 13.602 | 64.657 | 1.00 | 94.69 | E | C |
| ATOM | 5020 | O | PRO | E | 46 | 2.913 | 12.726 | 64.918 | 1.00 | 100.15 | E | O |
| ATOM | 5021 | N | VAL | E | 47 | 4.183 | 13.879 | 63.420 | 1.00 | 78.64 | E | N |
| ATOM | 5022 | CA | VAL | E | 47 | 4.028 | 12.939 | 62.308 | 1.00 | 75.62 | E | C |
| ATOM | 5023 | CB | VAL | E | 47 | 3.764 | 13.666 | 60.988 | 1.00 | 78.65 | E | C |
| ATOM | 5024 | CG1 | VAL | E | 47 | 2.624 | 14.669 | 61.172 | 1.00 | 80.07 | E | C |
| ATOM | 5025 | CG2 | VAL | E | 47 | 3.469 | 12.661 | 59.871 | 1.00 | 72.95 | E | C |
| ATOM | 5026 | C | VAL | E | 47 | 5.330 | 12.144 | 62.221 | 1.00 | 68.15 | E | C |
| ATOM | 5027 | O | VAL | E | 47 | 6.392 | 12.725 | 62.064 | 1.00 | 62.90 | E | O |
| ATOM | 5028 | N | GLN | E | 48 | 5.258 | 10.826 | 62.381 | 1.00 | 61.83 | E | N |
| ATOM | 5029 | CA | GLN | E | 48 | 6.454 | 9.973 | 62.335 | 1.00 | 57.59 | E | C |
| ATOM | 5030 | CB | GLN | E | 48 | 6.295 | 8.727 | 63.196 | 1.00 | 64.94 | E | C |
| ATOM | 5031 | CG | GLN | E | 48 | 5.687 | 8.907 | 64.577 | 1.00 | 66.36 | E | C |
| ATOM | 5032 | CD | GLN | E | 48 | 6.611 | 9.552 | 65.520 | 1.00 | 65.72 | E | C |
| ATOM | 5033 | OE1 | GLN | E | 48 | 6.258 | 10.543 | 66.157 | 1.00 | 77.12 | E | O |
| ATOM | 5034 | NE2 | GLN | E | 48 | 7.810 | 8.988 | 65.652 | 1.00 | 63.94 | E | N |
| ATOM | 5035 | C | GLN | E | 48 | 6.631 | 9.533 | 60.875 | 1.00 | 54.40 | E | C |
| ATOM | 5036 | O | GLN | E | 48 | 5.645 | 9.377 | 60.166 | 1.00 | 50.95 | E | O |
| ATOM | 5037 | N | GLU | E | 49 | 7.875 | 9.316 | 60.441 | 1.00 | 57.16 | E | N |
| ATOM | 5038 | CA | GLU | E | 49 | 8.194 | 8.890 | 59.070 | 1.00 | 55.09 | E | C |
| ATOM | 5039 | CB | GLU | E | 49 | 8.717 | 10.075 | 58.256 | 1.00 | 56.36 | E | C |
| ATOM | 5040 | CG | GLU | E | 49 | 8.814 | 9.805 | 56.762 | 1.00 | 56.31 | E | C |
| ATOM | 5041 | CD | GLU | E | 49 | 8.849 | 11.085 | 55.920 | 1.00 | 57.95 | E | C |
| ATOM | 5042 | OE1 | GLU | E | 49 | 7.947 | 11.972 | 56.049 | 1.00 | 51.45 | E | O |
| ATOM | 5043 | OE2 | GLU | E | 49 | 9.775 | 11.185 | 55.098 | 1.00 | 51.17 | E | O |
| ATOM | 5044 | C | GLU | E | 49 | 9.227 | 7.771 | 59.049 | 1.00 | 49.74 | E | C |
| ATOM | 5045 | O | GLU | E | 49 | 10.157 | 7.782 | 59.814 | 1.00 | 51.34 | E | O |
| ATOM | 5046 | N | PHE | E | 50 | 9.050 | 6.810 | 58.167 | 1.00 | 43.25 | E | N |
| ATOM | 5047 | CA | PHE | E | 50 | 10.100 | 5.843 | 57.888 | 1.00 | 42.66 | E | C |
| ATOM | 5048 | CB | PHE | E | 50 | 10.190 | 4.782 | 58.981 | 1.00 | 43.31 | E | C |
| ATOM | 5049 | CG | PHE | E | 50 | 9.053 | 3.800 | 58.980 | 1.00 | 42.28 | E | C |
| ATOM | 5050 | CD1 | PHE | E | 50 | 9.242 | 2.516 | 58.523 | 1.00 | 39.32 | E | C |
| ATOM | 5051 | CE1 | PHE | E | 50 | 8.213 | 1.590 | 58.557 | 1.00 | 41.16 | E | C |
| ATOM | 5052 | CZ | PHE | E | 50 | 6.981 | 1.962 | 59.042 | 1.00 | 36.83 | E | C |
| ATOM | 5053 | CE2 | PHE | E | 50 | 6.769 | 3.247 | 59.503 | 1.00 | 39.48 | E | C |
| ATOM | 5054 | CD2 | PHE | E | 50 | 7.805 | 4.165 | 59.476 | 1.00 | 40.93 | E | C |
| ATOM | 5055 | C | PHE | E | 50 | 9.901 | 5.230 | 56.509 | 1.00 | 39.75 | E | C |
| ATOM | 5056 | O | PHE | E | 50 | 8.904 | 5.520 | 55.832 | 1.00 | 43.49 | E | O |
| ATOM | 5057 | N | THR | E | 51 | 10.862 | 4.417 | 56.081 | 1.00 | 36.31 | E | N |
| ATOM | 5058 | CA | THR | E | 51 | 10.845 | 3.919 | 54.742 | 1.00 | 37.05 | E | C |
| ATOM | 5059 | CB | THR | E | 51 | 11.982 | 4.519 | 53.832 | 1.00 | 44.94 | E | C |
| ATOM | 5060 | OG1 | THR | E | 51 | 13.201 | 3.800 | 54.061 | 1.00 | 45.32 | E | O |
| ATOM | 5061 | CG2 | THR | E | 51 | 12.187 | 5.985 | 54.103 | 1.00 | 43.26 | E | C |
| ATOM | 5062 | C | THR | E | 51 | 11.057 | 2.470 | 54.800 | 1.00 | 36.79 | E | C |
| ATOM | 5063 | O | THR | E | 51 | 11.563 | 1.980 | 55.722 | 1.00 | 39.43 | E | O |
| ATOM | 5064 | N | VAL | E | 52 | 10.723 | 1.811 | 53.715 | 1.00 | 40.50 | E | N |
| ATOM | 5065 | CA | VAL | E | 52 | 10.730 | 0.409 | 53.614 | 1.00 | 39.01 | E | C |
| ATOM | 5066 | CB | VAL | E | 52 | 9.310 | −0.088 | 53.906 | 1.00 | 45.13 | E | C |
| ATOM | 5067 | CG1 | VAL | E | 52 | 9.054 | −1.457 | 53.313 | 1.00 | 46.54 | E | C |
| ATOM | 5068 | CG2 | VAL | E | 52 | 9.036 | −0.071 | 55.411 | 1.00 | 47.12 | E | C |
| ATOM | 5069 | C | VAL | E | 52 | 11.097 | 0.137 | 52.140 | 1.00 | 43.46 | E | C |
| ATOM | 5070 | O | VAL | E | 52 | 10.565 | 0.789 | 51.216 | 1.00 | 45.85 | E | O |
| ATOM | 5071 | N | PRO | E | 53 | 11.997 | −0.818 | 51.906 | 1.00 | 47.33 | E | N |
| ATOM | 5072 | CA | PRO | E | 53 | 12.400 | −1.234 | 50.565 | 1.00 | 51.24 | E | C |
| ATOM | 5073 | CB | PRO | E | 53 | 13.154 | −2.543 | 50.828 | 1.00 | 51.84 | E | C |
| ATOM | 5074 | CG | PRO | E | 53 | 13.732 | −2.358 | 52.185 | 1.00 | 51.57 | E | C |
| ATOM | 5075 | CD | PRO | E | 53 | 12.807 | −1.472 | 52.952 | 1.00 | 50.97 | E | C |
| ATOM | 5076 | C | PRO | E | 53 | 11.250 | −1.530 | 49.598 | 1.00 | 50.63 | E | C |
| ATOM | 5077 | O | PRO | E | 53 | 10.213 | −2.085 | 50.010 | 1.00 | 41.94 | E | O |
| ATOM | 5078 | N | GLY | E | 54 | 11.492 | −1.234 | 48.315 | 1.00 | 48.70 | E | N |

APPENDIX A-continued

| Atomic coordinates of Aurora A + Inhibitory Monobody Mb60 + Danusertib | | | | | | | | | | | |
|---|---|---|---|---|---|---|---|---|---|---|---|
| ATOM | 5079 | CA | GLY | E | 54 | 10.553 | −1.497 | 47.213 | 1.00 | 45.68 | E | C |
| ATOM | 5080 | C | GLY | E | 54 | 10.213 | −2.952 | 46.987 | 1.00 | 45.97 | E | C |
| ATOM | 5081 | O | GLY | E | 54 | 9.164 | −3.287 | 46.445 | 1.00 | 47.00 | E | O |
| ATOM | 5082 | N | SER | E | 55 | 11.075 | −3.832 | 47.441 | 1.00 | 46.79 | E | N |
| ATOM | 5083 | CA | SER | E | 55 | 10.749 | −5.249 | 47.512 | 1.00 | 50.57 | E | C |
| ATOM | 5084 | CB | SER | E | 55 | 12.000 | −6.046 | 47.871 | 1.00 | 45.61 | E | C |
| ATOM | 5085 | OG | SER | E | 55 | 12.520 | 5.542 | 49.077 | 1.00 | 52.69 | E | O |
| ATOM | 5086 | C | SER | E | 55 | 9.661 | −5.616 | 48.529 | 1.00 | 52.88 | E | C |
| ATOM | 5087 | O | SER | E | 55 | 9.134 | −6.690 | 48.443 | 1.00 | 46.01 | E | O |
| ATOM | 5088 | N | LYS | E | 56 | 9.369 | −4.780 | 49.524 | 1.00 | 58.06 | E | N |
| ATOM | 5089 | CA | LYS | E | 56 | 8.386 | −5.161 | 50.557 | 1.00 | 56.48 | E | C |
| ATOM | 5090 | CB | LYS | E | 56 | 8.776 | −4.571 | 51.925 | 1.00 | 55.99 | E | C |
| ATOM | 5091 | CG | LYS | E | 56 | 10.188 | −4.914 | 52.424 | 1.00 | 59.75 | E | C |
| ATOM | 5092 | CD | LYS | E | 56 | 10.262 | −6.161 | 53.296 | 1.00 | 63.74 | E | C |
| ATOM | 5093 | CE | LYS | E | 56 | 11.424 | −7.052 | 52.875 | 1.00 | 68.89 | E | C |
| ATOM | 5094 | NZ | LYS | E | 56 | 11.325 | −8.391 | 53.513 | 1.00 | 74.00 | E | N |
| ATOM | 5095 | C | LYS | E | 56 | 7.006 | −4.668 | 50.137 | 1.00 | 47.75 | E | C |
| ATOM | 5096 | O | LYS | E | 56 | 6.906 | −3.565 | 49.576 | 1.00 | 51.03 | E | O |
| ATOM | 5097 | N | SER | E | 57 | 5.963 | −5.474 | 50.384 | 1.00 | 42.14 | E | N |
| ATOM | 5098 | CA | SER | E | 57 | 4.559 | −5.003 | 50.315 | 1.00 | 48.12 | E | C |
| ATOM | 5099 | CB | SER | E | 57 | 3.763 | −5.870 | 49.328 | 1.00 | 49.73 | E | C |
| ATOM | 5100 | OG | SER | E | 57 | 3.649 | −7.201 | 49.784 | 1.00 | 52.34 | E | O |
| ATOM | 5101 | C | SER | E | 57 | 3.817 | −4.878 | 51.689 | 1.00 | 50.67 | E | C |
| ATOM | 5102 | O | SER | E | 57 | 2.587 | −4.686 | 51.740 | 1.00 | 47.17 | E | O |
| ATOM | 5103 | N | THR | E | 58 | 4.566 | −4.921 | 52.790 | 1.00 | 47.81 | E | N |
| ATOM | 5104 | CA | THR | E | 58 | 3.987 | −4.769 | 54.128 | 1.00 | 47.69 | E | C |
| ATOM | 5105 | CB | THR | E | 58 | 3.628 | −6.121 | 54.771 | 1.00 | 51.60 | E | C |
| ATOM | 5106 | OG1 | THR | E | 58 | 4.831 | −6.879 | 54.935 | 1.00 | 51.74 | E | O |
| ATOM | 5107 | CG2 | THR | E | 58 | 2.565 | −6.921 | 53.948 | 1.00 | 50.52 | E | C |
| ATOM | 5108 | C | THR | E | 58 | 4.951 | −4.090 | 55.069 | 1.00 | 44.18 | E | C |
| ATOM | 5109 | O | THR | E | 58 | 6.141 | −3.992 | 54.799 | 1.00 | 47.86 | E | O |
| ATOM | 5110 | N | ALA | E | 59 | 4.433 | −3.645 | 56.196 | 1.00 | 40.09 | E | N |
| ATOM | 5111 | CA | ALA | E | 59 | 5.261 | −3.070 | 57.248 | 1.00 | 42.41 | E | C |
| ATOM | 5112 | CB | ALA | E | 59 | 5.612 | −1.627 | 56.904 | 1.00 | 40.85 | E | C |
| ATOM | 5113 | C | ALA | E | 59 | 4.502 | −3.093 | 58.565 | 1.00 | 41.50 | E | C |
| ATOM | 5114 | O | ALA | E | 59 | 3.268 | −3.094 | 58.574 | 1.00 | 42.14 | E | O |
| ATOM | 5115 | N | THR | E | 60 | 5.270 | −3.016 | 59.642 | 1.00 | 38.43 | E | N |
| ATOM | 5116 | CA | THR | E | 60 | 4.798 | −2.920 | 61.006 | 1.00 | 39.89 | E | C |
| ATOM | 5117 | CB | THR | E | 60 | 5.590 | −3.881 | 61.923 | 1.00 | 40.00 | E | C |
| ATOM | 5118 | OG1 | THR | E | 60 | 5.280 | −5.218 | 61.529 | 1.00 | 44.50 | E | O |
| ATOM | 5119 | CG2 | THR | E | 60 | 5.208 | −3.704 | 63.355 | 1.00 | 43.21 | E | C |
| ATOM | 5120 | C | THR | E | 60 | 4.999 | −1.501 | 61.438 | 1.00 | 38.95 | E | C |
| ATOM | 5121 | O | THR | E | 60 | 6.095 | −0.964 | 61.263 | 1.00 | 35.56 | E | O |
| ATOM | 5122 | N | ILE | E | 61 | 3.923 | −0.862 | 61.905 | 1.00 | 40.01 | E | N |
| ATOM | 5123 | CA | ILE | E | 61 | 4.004 | 0.416 | 62.601 | 1.00 | 40.69 | E | C |
| ATOM | 5124 | CB | ILE | E | 61 | 2.887 | 1.366 | 62.193 | 1.00 | 39.45 | E | C |
| ATOM | 5125 | CG1 | ILE | E | 61 | 3.081 | 1.748 | 60.733 | 1.00 | 38.79 | E | C |
| ATOM | 5126 | CD1 | ILE | E | 61 | 2.026 | 2.625 | 60.158 | 1.00 | 34.83 | E | C |
| ATOM | 5127 | CG2 | ILE | E | 61 | 2.919 | 2.635 | 63.029 | 1.00 | 39.25 | E | C |
| ATOM | 5128 | C | ILE | E | 61 | 3.832 | 0.050 | 64.060 | 1.00 | 50.01 | E | C |
| ATOM | 5129 | O | ILE | E | 61 | 2.843 | −0.635 | 64.410 | 1.00 | 45.26 | E | O |
| ATOM | 5130 | N | SER | E | 62 | 4.766 | 0.494 | 64.913 | 1.00 | 47.23 | E | N |
| ATOM | 5131 | CA | SER | E | 62 | 4.694 | 0.152 | 66.332 | 1.00 | 43.24 | E | C |
| ATOM | 5132 | CB | SER | E | 62 | 5.598 | −1.046 | 66.590 | 1.00 | 43.91 | E | C |
| ATOM | 5133 | OG | SER | E | 62 | 6.916 | −0.644 | 66.568 | 1.00 | 45.64 | E | O |
| ATOM | 5134 | C | SER | E | 62 | 4.919 | 1.302 | 67.300 | 1.00 | 44.26 | E | C |
| ATOM | 5135 | O | SER | E | 62 | 5.118 | 2.467 | 66.897 | 1.00 | 46.74 | E | O |
| ATOM | 5136 | N | GLY | E | 63 | 4.778 | 1.012 | 68.589 | 1.00 | 44.82 | E | N |
| ATOM | 5137 | CA | GLY | E | 63 | 4.886 | 2.050 | 69.623 | 1.00 | 41.86 | E | C |
| ATOM | 5138 | C | GLY | E | 63 | 3.736 | 3.023 | 69.648 | 1.00 | 42.81 | E | C |
| ATOM | 5139 | O | GLY | E | 63 | 3.899 | 4.179 | 70.018 | 1.00 | 47.36 | E | O |
| ATOM | 5140 | N | LEU | E | 64 | 2.554 | 2.578 | 69.248 | 1.00 | 46.15 | E | N |
| ATOM | 5141 | CA | LEU | E | 64 | 1.364 | 3.442 | 69.169 | 1.00 | 47.43 | E | C |
| ATOM | 5142 | CB | LEU | E | 64 | 0.407 | 2.927 | 68.090 | 1.00 | 47.27 | E | C |
| ATOM | 5143 | CG | LEU | E | 64 | 0.944 | 2.794 | 66.662 | 1.00 | 48.78 | E | C |
| ATOM | 5144 | CD1 | LEU | E | 64 | −0.153 | 2.288 | 65.753 | 1.00 | 47.91 | E | C |
| ATOM | 5145 | CD2 | LEU | E | 64 | 1.511 | 4.117 | 66.162 | 1.00 | 54.11 | E | C |
| ATOM | 5146 | C | LEU | E | 64 | 0.585 | 3.444 | 70.485 | 1.00 | 52.14 | E | C |
| ATOM | 5147 | O | LEU | E | 64 | 0.764 | 2.575 | 71.332 | 1.00 | 48.13 | E | O |
| ATOM | 5148 | N | LYS | E | 65 | −0.348 | 4.373 | 70.596 | 1.00 | 51.58 | E | N |
| ATOM | 5149 | CA | LYS | E | 65 | −1.181 | 4.464 | 71.777 | 1.00 | 58.49 | E | C |
| ATOM | 5150 | CB | LYS | E | 65 | −1.506 | 5.916 | 72.075 | 1.00 | 62.04 | E | C |
| ATOM | 5151 | CG | LYS | E | 65 | −0.305 | 6.691 | 72.571 | 1.00 | 66.70 | E | C |
| ATOM | 5152 | CD | LYS | E | 65 | −0.687 | 8.139 | 72.833 | 1.00 | 71.27 | E | C |
| ATOM | 5153 | CE | LYS | E | 65 | 0.440 | 8.858 | 73.551 | 1.00 | 75.55 | E | C |
| ATOM | 5154 | NZ | LYS | E | 65 | 0.325 | 10.324 | 73.336 | 1.00 | 75.60 | E | N |
| ATOM | 5155 | C | LYS | E | 65 | −2.440 | 3.666 | 71.521 | 1.00 | 58.21 | E | C |
| ATOM | 5156 | O | LYS | E | 65 | −2.912 | 3.606 | 70.383 | 1.00 | 58.41 | E | O |

APPENDIX A-continued

| Atomic coordinates of Aurora A + Inhibitory Monobody Mb60 + Danusertib | | | | | | | | | | | | |
|---|---|---|---|---|---|---|---|---|---|---|---|---|
| ATOM | 5157 | N | PRO | E | 66 | −2.971 | 3.007 | 72.561 | 1.00 | 55.77 | E | N |
| ATOM | 5158 | CA | PRO | E | 66 | −4.195 | 2.235 | 72.370 | 1.00 | 50.66 | E | C |
| ATOM | 5159 | CB | PRO | E | 66 | −4.197 | 1.289 | 73.573 | 1.00 | 57.13 | E | C |
| ATOM | 5160 | CG | PRO | E | 66 | −3.495 | 2.082 | 74.625 | 1.00 | 59.01 | E | C |
| ATOM | 5161 | CD | PRO | E | 66 | −2.396 | 2.807 | 73.904 | 1.00 | 58.32 | E | C |
| ATOM | 5162 | C | PRO | E | 66 | −5.395 | 3.161 | 72.372 | 1.00 | 47.19 | E | C |
| ATOM | 5163 | O | PRO | E | 66 | −5.411 | 4.135 | 73.109 | 1.00 | 45.10 | E | O |
| ATOM | 5164 | N | GLY | E | 67 | −6.356 | 2.893 | 71.501 | 1.00 | 47.16 | E | N |
| ATOM | 5165 | CA | GLY | E | 67 | −7.601 | 3.659 | 71.464 | 1.00 | 50.42 | E | C |
| ATOM | 5166 | C | GLY | E | 67 | −7.496 | 5.055 | 70.884 | 1.00 | 56.17 | E | C |
| ATOM | 5167 | O | GLY | E | 67 | −8.316 | 5.922 | 71.199 | 1.00 | 59.03 | E | O |
| ATOM | 5168 | N | VAL | E | 68 | −6.515 | 5.282 | 70.021 | 1.00 | 56.89 | E | N |
| ATOM | 5169 | CA | VAL | E | 68 | −6.394 | 6.561 | 69.318 | 1.00 | 60.57 | E | C |
| ATOM | 5170 | CB | VAL | E | 68 | −4.972 | 7.122 | 69.413 | 1.00 | 64.84 | E | C |
| ATOM | 5171 | CG1 | VAL | E | 68 | −4.969 | 8.608 | 69.112 | 1.00 | 68.00 | E | C |
| ATOM | 5172 | CG2 | VAL | E | 68 | −4.361 | 6.842 | 70.784 | 1.00 | 69.22 | E | C |
| ATOM | 5173 | C | VAL | E | 68 | −6.672 | 6.354 | 67.851 | 1.00 | 60.90 | E | C |
| ATOM | 5174 | O | VAL | E | 68 | −6.329 | 5.306 | 67.310 | 1.00 | 62.93 | E | O |
| ATOM | 5175 | N | ASP | E | 69 | −7.282 | 7.351 | 67.217 | 1.00 | 55.54 | E | N |
| ATOM | 5176 | CA | ASP | E | 69 | −7.327 | 7.408 | 65.768 | 1.00 | 62.62 | E | C |
| ATOM | 5177 | CB | ASP | E | 69 | −8.354 | 8.434 | 65.282 | 1.00 | 67.28 | E | C |
| ATOM | 5178 | CG | ASP | E | 69 | −9.755 | 7.850 | 65.167 | 1.00 | 72.72 | E | C |
| ATOM | 5179 | OD1 | ASP | E | 69 | −9.995 | 6.742 | 65.696 | 1.00 | 59.65 | E | O |
| ATOM | 5180 | OD2 | ASP | E | 69 | −10.613 | 8.506 | 64.525 | 1.00 | 73.91 | E | O |
| ATOM | 5181 | C | ASP | E | 69 | −5.947 | 7.736 | 65.185 | 1.00 | 57.90 | E | C |
| ATOM | 5182 | O | ASP | E | 69 | −5.241 | 8.594 | 65.718 | 1.00 | 51.71 | E | O |
| ATOM | 5183 | N | TYR | E | 70 | −5.573 | 7.009 | 64.121 | 1.00 | 56.67 | E | N |
| ATOM | 5184 | CA | TYR | E | 70 | −4.325 | 7.252 | 63.365 | 1.00 | 52.98 | E | C |
| ATOM | 5185 | CB | TYR | E | 70 | −3.322 | 6.140 | 63.634 | 1.00 | 49.02 | E | C |
| ATOM | 5186 | CG | TYR | E | 70 | −2.617 | 6.281 | 64.977 | 1.00 | 51.67 | E | C |
| ATOM | 5187 | CD1 | TYR | E | 70 | −1.459 | 7.079 | 65.117 | 1.00 | 53.33 | E | C |
| ATOM | 5188 | CE1 | TYR | E | 70 | −0.815 | 7.210 | 66.349 | 1.00 | 52.61 | E | C |
| ATOM | 5189 | CZ | TYR | E | 70 | −1.321 | 6.514 | 67.465 | 1.00 | 58.02 | E | C |
| ATOM | 5190 | OH | TYR | E | 70 | −0.722 | 6.584 | 68.706 | 1.00 | 64.69 | E | O |
| ATOM | 5191 | CE2 | TYR | E | 70 | −2.442 | 5.725 | 67.338 | 1.00 | 52.29 | E | C |
| ATOM | 5192 | CD2 | TYR | E | 70 | −3.088 | 5.609 | 66.112 | 1.00 | 53.03 | E | C |
| ATOM | 5193 | C | TYR | E | 70 | −4.579 | 7.419 | 61.852 | 1.00 | 54.49 | E | C |
| ATOM | 5194 | O | TYR | E | 70 | −5.409 | 6.712 | 61.261 | 1.00 | 57.76 | E | O |
| ATOM | 5195 | N | THR | E | 71 | −3.876 | 8.384 | 61.232 | 1.00 | 59.57 | E | N |
| ATOM | 5196 | CA | THR | E | 71 | −3.802 | 8.483 | 59.759 | 1.00 | 49.84 | E | C |
| ATOM | 5197 | CB | THR | E | 71 | −4.068 | 9.927 | 59.276 | 1.00 | 49.32 | E | C |
| ATOM | 5198 | OG1 | THR | E | 71 | −5.264 | 10.435 | 59.890 | 1.00 | 55.29 | E | O |
| ATOM | 5199 | CG2 | THR | E | 71 | −4.262 | 9.974 | 57.773 | 1.00 | 43.47 | E | C |
| ATOM | 5200 | C | THR | E | 71 | −2.414 | 7.978 | 59.287 | 1.00 | 48.81 | E | C |
| ATOM | 5201 | O | THR | E | 71 | −1.353 | 8.400 | 59.778 | 1.00 | 44.51 | E | O |
| ATOM | 5202 | N | ILE | E | 72 | −2.453 | 7.044 | 58.340 | 1.00 | 47.14 | E | N |
| ATOM | 5203 | CA | ILE | E | 72 | −1.277 | 6.405 | 57.796 | 1.00 | 38.64 | E | C |
| ATOM | 5204 | CB | ILE | E | 72 | −1.308 | 4.896 | 58.004 | 1.00 | 39.64 | E | C |
| ATOM | 5205 | CG1 | ILE | E | 72 | −1.425 | 4.561 | 59.509 | 1.00 | 42.27 | E | C |
| ATOM | 5206 | CD1 | ILE | E | 72 | −2.401 | 3.462 | 59.755 | 1.00 | 45.43 | E | C |
| ATOM | 5207 | CG2 | ILE | E | 72 | −0.090 | 4.234 | 57.390 | 1.00 | 36.55 | E | C |
| ATOM | 5208 | C | ILE | E | 72 | −1.275 | 6.640 | 56.299 | 1.00 | 41.78 | E | C |
| ATOM | 5209 | O | ILE | E | 72 | −2.304 | 6.519 | 55.617 | 1.00 | 41.07 | E | O |
| ATOM | 5210 | N | THR | E | 73 | −0.095 | 6.927 | 55.760 | 1.00 | 41.92 | E | N |
| ATOM | 5211 | CA | THR | E | 73 | −0.002 | 7.311 | 54.365 | 1.00 | 43.28 | E | C |
| ATOM | 5212 | CB | THR | E | 73 | −0.065 | 8.849 | 54.188 | 1.00 | 48.54 | E | C |
| ATOM | 5213 | OG1 | THR | E | 73 | 1.251 | 9.382 | 54.223 | 1.00 | 64.30 | E | O |
| ATOM | 5214 | CG2 | THR | E | 73 | −0.884 | 9.521 | 55.275 | 1.00 | 47.17 | E | C |
| ATOM | 5215 | C | THR | E | 73 | 1.265 | 6.708 | 53.787 | 1.00 | 37.88 | E | C |
| ATOM | 5216 | O | THR | E | 73 | 2.324 | 6.734 | 54.391 | 1.00 | 40.30 | E | O |
| ATOM | 5217 | N | VAL | E | 74 | 1.144 | 6.148 | 52.613 | 1.00 | 38.91 | E | N |
| ATOM | 5218 | CA | VAL | E | 74 | 2.249 | 5.534 | 51.932 | 1.00 | 37.78 | E | C |
| ATOM | 5219 | CB | VAL | E | 74 | 2.031 | 4.027 | 51.840 | 1.00 | 34.90 | E | C |
| ATOM | 5220 | CG1 | VAL | E | 74 | 3.242 | 3.335 | 51.244 | 1.00 | 36.65 | E | C |
| ATOM | 5221 | CG2 | VAL | E | 74 | 1.808 | 3.403 | 53.233 | 1.00 | 37.87 | E | C |
| ATOM | 5222 | C | VAL | E | 74 | 2.366 | 6.115 | 50.504 | 1.00 | 40.53 | E | C |
| ATOM | 5223 | O | VAL | E | 74 | 1.371 | 6.263 | 49.787 | 1.00 | 38.94 | E | O |
| ATOM | 5224 | N | TYR | E | 75 | 3.595 | 6.409 | 50.094 | 1.00 | 43.16 | E | N |
| ATOM | 5225 | CA | TYR | E | 75 | 3.898 | 6.688 | 48.691 | 1.00 | 40.36 | E | C |
| ATOM | 5226 | CB | TYR | E | 75 | 3.848 | 8.189 | 48.394 | 1.00 | 40.25 | E | C |
| ATOM | 5227 | CG | TYR | E | 75 | 4.895 | 9.016 | 49.076 | 1.00 | 40.40 | E | C |
| ATOM | 5228 | CD1 | TYR | E | 75 | 6.140 | 9.261 | 48.454 | 1.00 | 43.94 | E | C |
| ATOM | 5229 | CE1 | TYR | E | 75 | 7.104 | 10.071 | 49.077 | 1.00 | 46.16 | E | C |
| ATOM | 5230 | CZ | TYR | E | 75 | 6.812 | 10.616 | 50.328 | 1.00 | 48.28 | E | C |
| ATOM | 5231 | OH | TYR | E | 75 | 7.704 | 11.378 | 50.957 | 1.00 | 48.79 | E | O |
| ATOM | 5232 | CE2 | TYR | E | 75 | 5.591 | 10.389 | 50.942 | 1.00 | 45.58 | E | C |
| ATOM | 5233 | CD2 | TYR | E | 75 | 4.640 | 9.595 | 50.300 | 1.00 | 37.03 | E | C |
| ATOM | 5234 | C | TYR | E | 75 | 5.225 | 6.046 | 48.278 | 1.00 | 36.89 | E | C |

APPENDIX A-continued

| Atomic coordinates of Aurora A + Inhibitory Monobody Mb60 + Danusertib | | | | | | | | | | | |
|---|---|---|---|---|---|---|---|---|---|---|---|
| ATOM | 5235 | O | TYR | E | 75 | 6.167 | 5.951 | 49.074 | 1.00 | 37.12 | E | O |
| ATOM | 5236 | N | ALA | E | 76 | 5.238 | 5.524 | 47.055 | 1.00 | 34.04 | E | N |
| ATOM | 5237 | CA | ALA | E | 76 | 6.432 | 4.972 | 46.436 | 1.00 | 34.24 | E | C |
| ATOM | 5238 | CB | ALA | E | 76 | 6.064 | 3.968 | 45.377 | 1.00 | 37.04 | E | C |
| ATOM | 5239 | C | ALA | E | 76 | 7.367 | 6.072 | 45.835 | 1.00 | 32.36 | E | C |
| ATOM | 5240 | O | ALA | E | 76 | 6.962 | 7.224 | 45.644 | 1.00 | 33.49 | E | O |
| ATOM | 5241 | N | ILE | E | 77 | 8.608 | 5.675 | 45.601 | 1.00 | 33.46 | E | N |
| ATOM | 5242 | CA | ILE | E | 77 | 9.618 | 6.477 | 44.898 | 1.00 | 38.70 | E | C |
| ATOM | 5243 | CB | ILE | E | 77 | 10.897 | 6.715 | 45.749 | 1.00 | 41.41 | E | C |
| ATOM | 5244 | CG1 | ILE | E | 77 | 10.560 | 7.362 | 47.084 | 1.00 | 41.03 | E | C |
| ATOM | 5245 | CD1 | ILE | E | 77 | 10.094 | 8.802 | 47.030 | 1.00 | 42.56 | E | C |
| ATOM | 5246 | CG2 | ILE | E | 77 | 11.924 | 7.569 | 44.977 | 1.00 | 39.05 | E | C |
| ATOM | 5247 | C | ILE | E | 77 | 10.107 | 5.731 | 43.692 | 1.00 | 35.76 | E | C |
| ATOM | 5248 | O | ILE | E | 77 | 10.563 | 4.588 | 43.828 | 1.00 | 39.00 | E | O |
| ATOM | 5249 | N | ASP | E | 78 | 10.016 | 6.387 | 42.521 | 1.00 | 37.86 | E | N |
| ATOM | 5250 | CA | ASP | E | 78 | 10.590 | 5.910 | 41.242 | 1.00 | 36.80 | E | C |
| ATOM | 5251 | CB | ASP | E | 78 | 9.785 | 6.431 | 40.022 | 1.00 | 38.33 | E | C |
| ATOM | 5252 | CG | ASP | E | 78 | 10.297 | 5.852 | 38.696 | 1.00 | 40.80 | E | C |
| ATOM | 5253 | OD1 | ASP | E | 78 | 9.630 | 4.964 | 38.131 | 1.00 | 42.53 | E | O |
| ATOM | 5254 | OD2 | ASP | E | 78 | 11.383 | 6.272 | 38.225 | 1.00 | 38.53 | E | O |
| ATOM | 5255 | C | ASP | E | 78 | 12.030 | 6.493 | 41.174 | 1.00 | 34.12 | E | C |
| ATOM | 5256 | O | ASP | E | 78 | 12.207 | 7.667 | 41.459 | 1.00 | 32.69 | E | O |
| ATOM | 5257 | N | PHE | E | 79 | 13.009 | 5.633 | 40.849 | 1.00 | 36.60 | E | N |
| ATOM | 5258 | CA | PHE | E | 79 | 14.433 | 6.032 | 40.681 | 1.00 | 38.62 | E | C |
| ATOM | 5259 | CB | PHE | E | 79 | 15.245 | 4.868 | 40.050 | 1.00 | 42.25 | E | C |
| ATOM | 5260 | CG | PHE | E | 79 | 16.756 | 5.133 | 39.999 | 1.00 | 44.83 | E | C |
| ATOM | 5261 | CD1 | PHE | E | 79 | 17.364 | 5.691 | 38.847 | 1.00 | 43.82 | E | C |
| ATOM | 5262 | CE1 | PHE | E | 79 | 18.751 | 5.957 | 38.806 | 1.00 | 39.29 | E | C |
| ATOM | 5263 | CZ | PHE | E | 79 | 19.530 | 5.685 | 39.924 | 1.00 | 38.80 | E | C |
| ATOM | 5264 | CE2 | PHE | E | 79 | 18.945 | 5.148 | 41.081 | 1.00 | 37.55 | E | C |
| ATOM | 5265 | CD2 | PHE | E | 79 | 17.571 | 4.879 | 41.115 | 1.00 | 40.42 | E | C |
| ATOM | 5266 | C | PHE | E | 79 | 14.589 | 7.290 | 39.845 | 1.00 | 37.01 | E | C |
| ATOM | 5267 | O | PHE | E | 79 | 15.234 | 8.288 | 40.255 | 1.00 | 37.69 | E | O |
| ATOM | 5268 | N | TYR | E | 80 | 13.978 | 7.256 | 38.662 | 1.00 | 37.37 | E | N |
| ATOM | 5269 | CA | TYR | E | 80 | 14.164 | 8.325 | 37.717 | 1.00 | 33.12 | E | C |
| ATOM | 5270 | CB | TYR | E | 80 | 14.022 | 7.837 | 36.289 | 1.00 | 35.53 | E | C |
| ATOM | 5271 | CG | TYR | E | 80 | 15.051 | 6.853 | 35.884 | 1.00 | 32.99 | E | C |
| ATOM | 5272 | CD1 | TYR | E | 80 | 16.361 | 7.257 | 35.684 | 1.00 | 38.41 | E | C |
| ATOM | 5273 | CE1 | TYR | E | 80 | 17.336 | 6.345 | 35.333 | 1.00 | 36.04 | E | C |
| ATOM | 5274 | CZ | TYR | E | 80 | 16.999 | 5.029 | 35.134 | 1.00 | 42.16 | E | C |
| ATOM | 5275 | OH | TYR | E | 80 | 17.995 | 4.145 | 34.782 | 1.00 | 44.38 | E | O |
| ATOM | 5276 | CE2 | TYR | E | 80 | 15.697 | 4.589 | 35.327 | 1.00 | 39.55 | E | C |
| ATOM | 5277 | CD2 | TYR | E | 80 | 14.733 | 5.496 | 35.708 | 1.00 | 37.04 | E | C |
| ATOM | 5278 | C | TYR | E | 80 | 13.198 | 9.407 | 37.911 | 1.00 | 36.54 | E | C |
| ATOM | 5279 | O | TYR | E | 80 | 13.568 | 10.545 | 37.760 | 1.00 | 35.15 | E | O |
| ATOM | 5280 | N | TRP | E | 81 | 11.930 | 9.068 | 38.211 | 1.00 | 40.17 | E | N |
| ATOM | 5281 | CA | TRP | E | 81 | 10.847 | 10.029 | 38.053 | 1.00 | 37.29 | E | C |
| ATOM | 5282 | CB | TRP | E | 81 | 9.691 | 9.363 | 37.220 | 1.00 | 42.17 | E | C |
| ATOM | 5283 | CG | TRP | E | 81 | 10.223 | 8.906 | 35.925 | 1.00 | 36.40 | E | C |
| ATOM | 5284 | CD1 | TRP | E | 81 | 10.429 | 7.622 | 35.496 | 1.00 | 43.17 | E | C |
| ATOM | 5285 | NE1 | TRP | E | 81 | 11.038 | 7.629 | 34.251 | 1.00 | 39.58 | E | N |
| ATOM | 5286 | CE2 | TRP | E | 81 | 11.217 | 8.939 | 33.875 | 1.00 | 36.07 | E | C |
| ATOM | 5287 | CD2 | TRP | E | 81 | 10.708 | 9.758 | 34.906 | 1.00 | 34.11 | E | C |
| ATOM | 5288 | CE3 | TRP | E | 81 | 10.804 | 11.154 | 34.784 | 1.00 | 34.17 | E | C |
| ATOM | 5289 | CZ3 | TRP | E | 81 | 11.353 | 11.680 | 33.650 | 1.00 | 36.05 | E | C |
| ATOM | 5290 | CH2 | TRP | E | 81 | 11.860 | 10.838 | 32.619 | 1.00 | 34.87 | E | C |
| ATOM | 5291 | CZ2 | TRP | E | 81 | 11.830 | 9.474 | 32.728 | 1.00 | 33.30 | E | C |
| ATOM | 5292 | C | TRP | E | 81 | 10.399 | 10.579 | 39.394 | 1.00 | 37.49 | E | C |
| ATOM | 5293 | O | TRP | E | 81 | 9.561 | 11.452 | 39.423 | 1.00 | 34.02 | E | O |
| ATOM | 5294 | N | GLY | E | 82 | 10.961 | 10.098 | 40.518 | 1.00 | 38.54 | E | N |
| ATOM | 5295 | CA | GLY | E | 82 | 10.634 | 10.752 | 41.773 | 1.00 | 35.46 | E | C |
| ATOM | 5296 | C | GLY | E | 82 | 9.396 | 10.137 | 42.427 | 1.00 | 36.96 | E | C |
| ATOM | 5297 | O | GLY | E | 82 | 8.991 | 8.980 | 42.155 | 1.00 | 34.38 | E | O |
| ATOM | 5298 | N | SER | E | 83 | 8.821 | 10.914 | 43.316 | 1.00 | 34.46 | E | N |
| ATOM | 5299 | CA | SER | E | 83 | 7.799 | 10.420 | 44.214 | 1.00 | 38.96 | E | C |
| ATOM | 5300 | CB | SER | E | 83 | 7.619 | 11.433 | 45.378 | 1.00 | 39.31 | E | C |
| ATOM | 5301 | OG | SER | E | 83 | 6.790 | 12.509 | 44.934 | 1.00 | 43.51 | E | O |
| ATOM | 5302 | C | SER | E | 83 | 6.499 | 10.223 | 43.419 | 1.00 | 43.25 | E | C |
| ATOM | 5303 | O | SER | E | 83 | 6.241 | 10.916 | 42.418 | 1.00 | 39.51 | E | O |
| ATOM | 5304 | N | TYR | E | 84 | 5.673 | 9.291 | 43.855 | 1.00 | 42.25 | E | N |
| ATOM | 5305 | CA | TYR | E | 84 | 4.296 | 9.233 | 43.383 | 1.00 | 37.85 | E | C |
| ATOM | 5306 | CB | TYR | E | 84 | 3.851 | 7.778 | 43.207 | 1.00 | 39.10 | E | C |
| ATOM | 5307 | CG | TYR | E | 84 | 4.576 | 6.902 | 42.215 | 1.00 | 37.00 | E | C |
| ATOM | 5308 | CD1 | TYR | E | 84 | 4.150 | 6.822 | 40.896 | 1.00 | 35.92 | E | C |
| ATOM | 5309 | CE1 | TYR | E | 84 | 4.765 | 5.976 | 39.991 | 1.00 | 36.15 | E | C |
| ATOM | 5310 | CZ | TYR | E | 84 | 5.823 | 5.168 | 40.394 | 1.00 | 39.69 | E | C |
| ATOM | 5311 | OH | TYR | E | 84 | 6.352 | 4.331 | 39.483 | 1.00 | 37.17 | E | O |
| ATOM | 5312 | CE2 | TYR | E | 84 | 6.295 | 5.215 | 41.716 | 1.00 | 36.85 | E | C |

APPENDIX A-continued

Atomic coordinates of Aurora A + Inhibitory Monobody Mb60 + Danusertib

| | | | | | | | | | | | | |
|---|---|---|---|---|---|---|---|---|---|---|---|---|
| ATOM | 5313 | CD2 | TYR | E | 84 | 5.655 | 6.077 | 42.614 | 1.00 | 37.84 | E | C |
| ATOM | 5314 | C | TYR | E | 84 | 3.336 | 9.884 | 44.373 | 1.00 | 38.49 | E | C |
| ATOM | 5315 | O | TYR | E | 84 | 3.690 | 10.155 | 45.507 | 1.00 | 35.82 | E | O |
| ATOM | 5316 | N | SER | E | 85 | 2.096 | 10.133 | 43.953 | 1.00 | 40.59 | E | N |
| ATOM | 5317 | CA | SER | E | 85 | 1.100 | 10.693 | 44.858 | 1.00 | 43.50 | E | C |
| ATOM | 5318 | CB | SER | E | 85 | −0.070 | 11.305 | 44.066 | 1.00 | 47.85 | E | C |
| ATOM | 5319 | OG | SER | E | 85 | −0.741 | 10.250 | 43.420 | 1.00 | 48.46 | E | O |
| ATOM | 5320 | C | SER | E | 85 | 0.630 | 9.591 | 45.887 | 1.00 | 40.64 | E | C |
| ATOM | 5321 | O | SER | E | 85 | 0.625 | 8.351 | 45.590 | 1.00 | 36.15 | E | O |
| ATOM | 5322 | N | PRO | E | 86 | 0.293 | 10.039 | 47.105 | 1.00 | 45.74 | E | N |
| ATOM | 5323 | CA | PRO | E | 86 | 0.104 | 9.097 | 48.175 | 1.00 | 47.78 | E | C |
| ATOM | 5324 | CB | PRO | E | 86 | 0.426 | 9.942 | 49.417 | 1.00 | 48.65 | E | C |
| ATOM | 5325 | CG | PRO | E | 86 | −0.084 | 11.307 | 49.048 | 1.00 | 49.40 | E | C |
| ATOM | 5326 | CD | PRO | E | 86 | −0.004 | 11.425 | 47.555 | 1.00 | 48.61 | E | C |
| ATOM | 5327 | C | PRO | E | 86 | −1.320 | 8.505 | 48.256 | 1.00 | 48.59 | E | C |
| ATOM | 5328 | O | PRO | E | 86 | −2.269 | 8.909 | 47.544 | 1.00 | 39.45 | E | O |
| ATOM | 5329 | N | ILE | E | 87 | −1.410 | 7.511 | 49.133 | 1.00 | 44.69 | E | N |
| ATOM | 5330 | CA | ILE | E | 87 | −2.676 | 6.910 | 49.539 | 1.00 | 44.42 | E | C |
| ATOM | 5331 | CB | ILE | E | 87 | −2.812 | 5.514 | 48.974 | 1.00 | 42.76 | E | C |
| ATOM | 5332 | CG1 | ILE | E | 87 | −4.164 | 4.940 | 49.384 | 1.00 | 43.37 | E | C |
| ATOM | 5333 | CD1 | ILE | E | 87 | −4.524 | 3.722 | 48.619 | 1.00 | 39.81 | E | C |
| ATOM | 5334 | CG2 | ILE | E | 87 | −1.652 | 4.608 | 49.397 | 1.00 | 42.99 | E | C |
| ATOM | 5335 | C | ILE | E | 87 | −2.728 | 6.894 | 51.051 | 1.00 | 46.70 | E | C |
| ATOM | 5336 | O | ILE | E | 87 | −1.781 | 6.450 | 51.693 | 1.00 | 43.96 | E | O |
| ATOM | 5337 | N | SER | E | 88 | −3.812 | 7.434 | 51.611 | 1.00 | 52.75 | E | N |
| ATOM | 5338 | CA | SER | E | 88 | −4.024 | 7.499 | 53.059 | 1.00 | 50.76 | E | C |
| ATOM | 5339 | CB | SER | E | 88 | −4.291 | 8.943 | 53.494 | 1.00 | 54.99 | E | C |
| ATOM | 5340 | OG | SER | E | 88 | −3.084 | 9.635 | 53.736 | 1.00 | 61.98 | E | O |
| ATOM | 5341 | C | SER | E | 88 | −5.191 | 6.582 | 53.535 | 1.00 | 50.64 | E | C |
| ATOM | 5342 | O | SER | E | 88 | −6.166 | 6.377 | 52.807 | 1.00 | 50.03 | E | O |
| ATOM | 5343 | N | ILE | E | 89 | −5.063 | 6.015 | 54.743 | 1.00 | 48.43 | E | N |
| ATOM | 5344 | CA | ILE | E | 89 | −6.182 | 5.350 | 55.418 | 1.00 | 44.19 | E | C |
| ATOM | 5345 | CB | ILE | E | 89 | −6.082 | 3.797 | 55.392 | 1.00 | 40.30 | E | C |
| ATOM | 5346 | CG1 | ILE | E | 89 | −4.756 | 3.292 | 55.978 | 1.00 | 41.38 | E | C |
| ATOM | 5347 | CD1 | ILE | E | 89 | −4.789 | 1.834 | 56.374 | 1.00 | 40.56 | E | C |
| ATOM | 5348 | CG2 | ILE | E | 89 | −6.334 | 3.216 | 54.008 | 1.00 | 41.17 | E | C |
| ATOM | 5349 | C | ILE | E | 89 | −6.184 | 5.838 | 56.852 | 1.00 | 46.75 | E | C |
| ATOM | 5350 | O | ILE | E | 89 | −5.158 | 6.353 | 57.321 | 1.00 | 40.05 | E | O |
| ATOM | 5351 | N | ASN | E | 90 | −7.324 | 5.672 | 57.542 | 1.00 | 50.89 | E | N |
| ATOM | 5352 | CA | ASN | E | 90 | −7.382 | 5.779 | 59.026 | 1.00 | 53.97 | E | C |
| ATOM | 5353 | CB | ASN | E | 90 | −8.406 | 6.807 | 59.456 | 1.00 | 58.41 | E | C |
| ATOM | 5354 | CG | ASN | E | 90 | −8.081 | 8.186 | 58.937 | 1.00 | 61.08 | E | C |
| ATOM | 5355 | OD1 | ASN | E | 90 | −6.962 | 8.660 | 59.054 | 1.00 | 61.61 | E | O |
| ATOM | 5356 | ND2 | ASN | E | 90 | −9.061 | 8.822 | 58.330 | 1.00 | 69.70 | E | N |
| ATOM | 5357 | C | ASN | E | 90 | −7.650 | 4.443 | 59.751 | 1.00 | 47.45 | E | C |
| ATOM | 5358 | O | ASN | E | 90 | −8.196 | 3.507 | 59.151 | 1.00 | 42.19 | E | O |
| ATOM | 5359 | N | TYR | E | 91 | −7.217 | 4.365 | 61.013 | 1.00 | 44.83 | E | N |
| ATOM | 5360 | CA | TYR | E | 91 | −7.401 | 3.197 | 61.848 | 1.00 | 47.35 | E | C |
| ATOM | 5361 | CB | TYR | E | 91 | −6.299 | 2.159 | 61.596 | 1.00 | 47.66 | E | C |
| ATOM | 5362 | CG | TYR | E | 91 | −6.674 | 0.759 | 62.092 | 1.00 | 50.31 | E | C |
| ATOM | 5363 | CD1 | TYR | E | 91 | −6.312 | 0.329 | 63.365 | 1.00 | 47.99 | E | C |
| ATOM | 5364 | CE1 | TYR | E | 91 | −6.633 | −0.950 | 63.802 | 1.00 | 50.54 | E | C |
| ATOM | 5365 | CZ | TYR | E | 91 | −7.350 | −1.802 | 62.978 | 1.00 | 45.75 | E | C |
| ATOM | 5366 | OH | TYR | E | 91 | −7.657 | −3.066 | 63.431 | 1.00 | 54.48 | E | O |
| ATOM | 5367 | CE2 | TYR | E | 91 | −7.727 | −1.400 | 61.711 | 1.00 | 48.19 | E | C |
| ATOM | 5368 | CD2 | TYR | E | 91 | −7.406 | −0.120 | 61.280 | 1.00 | 48.29 | E | C |
| ATOM | 5369 | C | TYR | E | 91 | −7.348 | 3.578 | 63.315 | 1.00 | 54.26 | E | C |
| ATOM | 5370 | O | TYR | E | 91 | −6.412 | 4.283 | 63.722 | 1.00 | 50.78 | E | O |
| ATOM | 5371 | N | ARG | E | 92 | −8.324 | 3.100 | 64.104 | 1.00 | 52.71 | E | N |
| ATOM | 5372 | CA | ARG | E | 92 | −8.306 | 3.290 | 65.550 | 1.00 | 55.14 | E | C |
| ATOM | 5373 | CB | ARG | E | 92 | −9.723 | 3.454 | 66.115 | 1.00 | 63.18 | E | C |
| ATOM | 5374 | CG | ARG | E | 92 | −9.776 | 3.461 | 67.655 | 1.00 | 66.50 | E | C |
| ATOM | 5375 | CD | ARG | E | 92 | −9.927 | 4.836 | 68.269 | 1.00 | 70.86 | E | C |
| ATOM | 5376 | NE | ARG | E | 92 | −11.330 | 5.232 | 68.452 | 1.00 | 71.50 | E | N |
| ATOM | 5377 | CZ | ARG | E | 92 | −11.795 | 6.495 | 68.481 | 1.00 | 81.40 | E | C |
| ATOM | 5378 | NH1 | ARG | E | 92 | −10.991 | 7.559 | 68.309 | 1.00 | 73.25 | E | N |
| ATOM | 5379 | NH2 | ARG | E | 92 | −13.107 | 6.707 | 68.676 | 1.00 | 83.96 | E | N |
| ATOM | 5380 | C | ARG | E | 92 | −7.689 | 2.048 | 66.160 | 1.00 | 49.85 | E | C |
| ATOM | 5381 | O | ARG | E | 92 | −8.210 | 0.961 | 65.966 | 1.00 | 50.39 | E | O |
| ATOM | 5382 | N | THR | E | 93 | −6.627 | 2.197 | 66.941 | 1.00 | 47.59 | E | N |
| ATOM | 5383 | CA | THR | E | 93 | −6.036 | 1.015 | 67.607 | 1.00 | 52.13 | E | C |
| ATOM | 5384 | CB | THR | E | 93 | −4.732 | 1.394 | 68.295 | 1.00 | 49.75 | E | C |
| ATOM | 5385 | OG1 | THR | E | 93 | −4.925 | 2.638 | 68.988 | 1.00 | 47.84 | E | O |
| ATOM | 5386 | CG2 | THR | E | 93 | −3.680 | 1.529 | 67.257 | 1.00 | 50.09 | E | C |
| ATOM | 5387 | C | THR | E | 93 | −6.955 | 0.397 | 68.667 | 1.00 | 44.57 | E | C |
| ATOM | 5388 | O | THR | E | 93 | −7.730 | 1.141 | 69.241 | 1.00 | 48.01 | E | O |
| TER | 5389 | | THR | E | 93 | | | | | | | |

APPENDIX A-continued

| Atomic coordinates of Aurora A + Inhibitory Monobody Mb60 + Danusertib | | | | | | | | | | | | |
|---|---|---|---|---|---|---|---|---|---|---|---|---|
| HETATM | 5390 | O26 | 627 | F | 1 | 7.169 | 15.048 | 20.488 | 1.00 | 35.25 | F | O |
| HETATM | 5391 | C25 | 627 | F | 1 | 6.335 | 14.958 | 19.595 | 1.00 | 31.54 | F | C |
| HETATM | 5392 | C20 | 627 | F | 1 | 6.427 | 13.796 | 18.643 | 1.00 | 34.13 | F | C |
| HETATM | 5393 | O34 | 627 | F | 1 | 7.128 | 12.679 | 19.251 | 1.00 | 36.81 | F | O |
| HETATM | 5394 | C36 | 627 | F | 1 | 6.968 | 11.407 | 18.641 | 1.00 | 39.95 | F | C |
| HETATM | 5395 | C27 | 627 | F | 1 | 7.223 | 14.147 | 17.409 | 1.00 | 33.45 | F | C |
| HETATM | 5396 | C29 | 627 | F | 1 | 8.526 | 14.687 | 17.492 | 1.00 | 30.52 | F | C |
| HETATM | 5397 | C33 | 627 | F | 1 | 9.247 | 14.965 | 16.350 | 1.00 | 33.66 | F | C |
| HETATM | 5398 | C35 | 627 | F | 1 | 8.696 | 14.725 | 15.083 | 1.00 | 29.96 | F | C |
| HETATM | 5399 | C31 | 627 | F | 1 | 7.428 | 14.155 | 14.986 | 1.00 | 35.66 | F | C |
| HETATM | 5400 | C28 | 627 | F | 1 | 6.692 | 13.871 | 16.148 | 1.00 | 33.64 | F | C |
| HETATM | 5401 | N1 | 627 | F | 1 | 5.494 | 16.025 | 19.367 | 1.00 | 29.15 | F | N |
| HETATM | 5402 | C16 | 627 | F | 1 | 5.544 | 17.159 | 20.102 | 1.00 | 23.97 | F | C |
| HETATM | 5403 | C13 | 627 | F | 1 | 4.642 | 18.025 | 19.438 | 1.00 | 28.55 | F | C |
| HETATM | 5404 | N2 | 627 | F | 1 | 4.177 | 19.345 | 19.637 | 1.00 | 22.93 | F | N |
| HETATM | 5405 | C15 | 627 | F | 1 | 4.638 | 16.107 | 18.258 | 1.00 | 28.50 | F | C |
| HETATM | 5406 | C14 | 627 | F | 1 | 4.101 | 17.394 | 18.389 | 1.00 | 25.90 | F | C |
| HETATM | 5407 | C3 | 627 | F | 1 | 3.248 | 18.381 | 17.786 | 1.00 | 30.95 | F | C |
| HETATM | 5408 | N4 | 627 | F | 1 | 3.300 | 19.514 | 18.559 | 1.00 | 28.19 | F | N |
| HETATM | 5409 | N5 | 627 | F | 1 | 2.455 | 18.296 | 16.638 | 1.00 | 33.21 | F | N |
| HETATM | 5410 | C6 | 627 | F | 1 | 2.279 | 17.202 | 15.896 | 1.00 | 32.46 | F | C |
| HETATM | 5411 | O8 | 627 | F | 1 | 2.685 | 16.139 | 16.219 | 1.00 | 37.76 | F | O |
| HETATM | 5412 | C7 | 627 | F | 1 | 1.467 | 17.245 | 14.657 | 1.00 | 30.93 | F | C |
| HETATM | 5413 | C12 | 627 | F | 1 | 1.540 | 16.206 | 13.713 | 1.00 | 35.26 | F | C |
| HETATM | 5414 | C11 | 627 | F | 1 | 0.774 | 16.308 | 12.562 | 1.00 | 33.08 | F | C |
| HETATM | 5415 | C24 | 627 | F | 1 | −0.011 | 17.447 | 12.298 | 1.00 | 34.99 | F | C |
| HETATM | 5416 | C10 | 627 | F | 1 | −0.047 | 18.478 | 13.279 | 1.00 | 35.62 | F | C |
| HETATM | 5417 | C9 | 627 | F | 1 | 0.702 | 18.370 | 14.421 | 1.00 | 33.53 | F | C |
| HETATM | 5418 | N17 | 627 | F | 1 | −0.814 | 17.622 | 11.115 | 1.00 | 38.13 | F | N |
| HETATM | 5419 | C22 | 627 | F | 1 | −1.097 | 19.044 | 10.833 | 1.00 | 42.08 | F | C |
| HETATM | 5420 | C21 | 627 | F | 1 | −1.575 | 19.289 | 9.440 | 1.00 | 43.97 | F | C |
| HETATM | 5421 | N20 | 627 | F | 1 | −0.421 | 18.981 | 8.627 | 1.00 | 45.39 | F | N |
| HETATM | 5422 | C23 | 627 | F | 1 | −0.566 | 19.610 | 7.292 | 1.00 | 45.31 | F | C |
| HETATM | 5423 | C19 | 627 | F | 1 | −0.154 | 17.520 | 8.612 | 1.00 | 42.60 | F | C |
| HETATM | 5424 | C18 | 627 | F | 1 | −0.522 | 16.767 | 9.907 | 1.00 | 42.41 | F | C |
| HETATM | 5425 | O | HOH | H | 1 | 3.589 | 18.683 | 8.118 | 1.00 | 26.64 | | O |
| HETATM | 5426 | O | HOH | H | 2 | 37.931 | 19.650 | 5.026 | 1.00 | 26.59 | | O |
| HETATM | 5427 | O | HOH | H | 3 | 28.829 | 32.174 | 15.032 | 1.00 | 29.50 | | O |
| HETATM | 5428 | O | HOH | H | 4 | 9.732 | 29.021 | 7.885 | 1.00 | 25.95 | | O |
| HETATM | 5429 | O | HOH | H | 5 | 6.652 | 26.448 | −0.700 | 1.00 | 29.26 | | O |
| HETATM | 5430 | O | HOH | H | 6 | 24.927 | 13.175 | −4.127 | 1.00 | 33.64 | | O |
| HETATM | 5431 | O | HOH | H | 7 | 21.647 | 34.342 | 16.075 | 1.00 | 45.75 | | O |
| HETATM | 5432 | O | HOH | H | 9 | 34.770 | 17.245 | 28.725 | 1.00 | 26.04 | | O |
| HETATM | 5433 | O | HOH | H | 10 | 33.608 | 17.871 | 15.303 | 1.00 | 24.36 | | O |
| HETATM | 5434 | O | HOH | H | 11 | 9.402 | 27.561 | 20.632 | 1.00 | 27.01 | | O |
| HETATM | 5435 | O | HOH | H | 12 | 38.306 | 13.738 | 16.271 | 1.00 | 27.93 | | O |
| HETATM | 5436 | O | HOH | H | 13 | 41.403 | −0.401 | 49.373 | 1.00 | 32.44 | | O |
| HETATM | 5437 | O | HOH | H | 14 | 33.922 | 26.248 | 4.872 | 1.00 | 27.54 | | O |
| HETATM | 5438 | O | HOH | H | 15 | 4.397 | 25.804 | 18.153 | 1.00 | 30.43 | | O |
| HETATM | 5439 | O | HOH | H | 16 | 10.441 | 28.570 | 5.162 | 1.00 | 30.44 | | O |
| HETATM | 5440 | O | HOH | H | 17 | 36.176 | 14.730 | 10.317 | 1.00 | 29.61 | | O |
| HETATM | 5441 | O | HOH | H | 18 | 29.361 | 28.902 | 14.958 | 1.00 | 31.27 | | O |
| HETATM | 5442 | O | HOH | H | 19 | 7.008 | 26.131 | 6.688 | 1.00 | 26.31 | | O |
| HETATM | 5443 | O | HOH | H | 20 | 15.607 | 12.364 | 5.701 | 1.00 | 45.93 | | O |
| HETATM | 5444 | O | HOH | H | 21 | 31.871 | 14.522 | −4.675 | 1.00 | 29.81 | | O |
| HETATM | 5445 | O | HOH | H | 22 | 17.847 | 33.794 | 17.430 | 1.00 | 46.88 | | O |
| HETATM | 5446 | O | HOH | H | 23 | 20.617 | 17.314 | −12.826 | 1.00 | 35.08 | | O |
| HETATM | 5447 | O | HOH | H | 24 | 26.322 | 13.006 | 6.587 | 1.00 | 21.70 | | O |
| HETATM | 5448 | O | HOH | H | 25 | 28.561 | 28.099 | 17.364 | 1.00 | 34.07 | | O |
| HETATM | 5449 | O | HOH | H | 26 | 8.980 | 25.475 | −1.913 | 1.00 | 27.85 | | O |
| HETATM | 5450 | O | HOH | H | 27 | 12.257 | 26.691 | 23.337 | 1.00 | 26.69 | | O |
| HETATM | 5451 | O | HOH | H | 28 | 8.892 | 22.810 | −5.122 | 1.00 | 37.36 | | O |
| HETATM | 5452 | O | HOH | H | 29 | 3.518 | 24.278 | 2.209 | 1.00 | 29.41 | | O |
| HETATM | 5453 | O | HOH | H | 30 | 10.691 | 3.802 | 36.080 | 1.00 | 35.10 | | O |
| HETATM | 5454 | O | HOH | H | 31 | 15.006 | 23.427 | −4.941 | 1.00 | 29.41 | | O |
| HETATM | 5455 | O | HOH | H | 32 | 36.595 | 21.824 | 14.865 | 1.00 | 27.20 | | O |
| HETATM | 5456 | O | HOH | H | 33 | 22.858 | 31.548 | −6.905 | 1.00 | 35.33 | | O |
| HETATM | 5457 | O | HOH | H | 34 | 19.312 | 25.980 | −5.613 | 1.00 | 29.35 | | O |
| HETATM | 5458 | O | HOH | H | 35 | 37.220 | 9.678 | 6.822 | 1.00 | 30.08 | | O |
| HETATM | 5459 | O | HOH | H | 37 | 35.436 | 20.360 | 41.202 | 1.00 | 35.41 | | O |
| HETATM | 5460 | O | HOH | H | 38 | 1.464 | 24.839 | 22.812 | 1.00 | 31.44 | | O |
| HETATM | 5461 | O | HOH | H | 39 | 32.619 | 21.304 | 30.826 | 1.00 | 30.45 | | O |
| HETATM | 5462 | O | HOH | H | 40 | 36.089 | 27.811 | 9.373 | 1.00 | 35.22 | | O |
| HETATM | 5463 | O | HOH | H | 41 | 30.390 | 10.309 | 37.766 | 1.00 | 26.91 | | O |
| HETATM | 5464 | O | HOH | H | 42 | 32.752 | 20.902 | 0.504 | 1.00 | 28.49 | | O |
| HETATM | 5465 | O | HOH | H | 43 | 3.074 | 14.718 | 2.824 | 1.00 | 31.34 | | O |
| HETATM | 5466 | O | HOH | H | 44 | 37.408 | 26.563 | 13.180 | 1.00 | 37.82 | | O |
| HETATM | 5467 | O | HOH | H | 46 | 31.422 | 27.152 | 14.832 | 1.00 | 37.96 | | O |

APPENDIX A-continued

| Atomic coordinates of Aurora A + Inhibitory Monobody Mb60 + Danusertib | | | | | | | | | | | |
|---|---|---|---|---|---|---|---|---|---|---|---|
| HETATM | 5468 | O | HOH | H | 47 | 2.012 | 14.450 | 0.430 | 1.00 | 25.20 | O |
| HETATM | 5469 | O | HOH | H | 48 | 36.591 | 21.923 | 39.079 | 1.00 | 34.50 | O |
| HETATM | 5470 | O | HOH | H | 49 | 10.893 | 14.081 | 20.163 | 1.00 | 34.79 | O |
| HETATM | 5471 | O | HOH | H | 50 | 33.312 | 19.542 | 28.530 | 1.00 | 36.39 | O |
| HETATM | 5472 | O | HOH | H | 51 | 41.742 | −15.053 | 21.795 | 1.00 | 43.13 | O |
| HETATM | 5473 | O | HOH | H | 52 | 35.997 | 16.542 | 15.502 | 1.00 | 29.43 | O |
| HETATM | 5474 | O | HOH | H | 53 | 10.531 | 23.329 | −6.855 | 1.00 | 46.31 | O |
| HETATM | 5475 | O | HOH | H | 54 | 8.514 | 12.187 | 11.725 | 1.00 | 34.91 | O |
| HETATM | 5476 | O | HOH | H | 55 | 44.098 | 4.254 | 49.647 | 1.00 | 44.73 | O |
| HETATM | 5477 | O | HOH | H | 56 | 14.835 | 32.583 | 14.036 | 1.00 | 38.98 | O |
| HETATM | 5478 | O | HOH | H | 57 | 23.161 | 11.732 | 3.344 | 1.00 | 28.58 | O |
| HETATM | 5479 | O | HOH | H | 58 | 30.308 | 21.841 | 41.322 | 1.00 | 40.16 | O |
| HETATM | 5480 | O | HOH | H | 59 | 2.535 | 18.559 | 5.566 | 1.00 | 33.68 | O |
| HETATM | 5481 | O | HOH | H | 60 | 34.748 | 18.185 | 22.054 | 1.00 | 32.07 | O |
| HETATM | 5482 | O | HOH | H | 61 | 40.320 | 16.321 | 6.730 | 1.00 | 43.63 | O |
| HETATM | 5483 | O | HOH | H | 62 | 31.750 | 11.063 | 17.667 | 1.00 | 32.86 | O |
| HETATM | 5484 | O | HOH | H | 63 | 31.008 | 9.475 | 48.654 | 1.00 | 37.97 | O |
| HETATM | 5485 | O | HOH | H | 64 | 3.578 | 28.169 | 16.800 | 1.00 | 34.17 | O |
| HETATM | 5486 | O | HOH | H | 65 | 20.130 | 31.793 | −6.311 | 1.00 | 33.48 | O |
| HETATM | 5487 | O | HOH | H | 66 | 45.765 | 13.321 | 28.860 | 1.00 | 42.76 | O |
| HETATM | 5488 | O | HOH | H | 67 | 20.624 | 32.799 | 18.158 | 1.00 | 41.04 | O |
| HETATM | 5489 | O | HOH | H | 68 | 30.513 | 22.036 | 27.744 | 1.00 | 31.46 | O |
| HETATM | 5490 | O | HOH | H | 69 | 23.361 | 29.647 | −10.481 | 1.00 | 37.12 | O |
| HETATM | 5491 | O | HOH | H | 70 | 19.998 | 36.143 | 13.093 | 1.00 | 44.40 | O |
| HETATM | 5492 | O | HOH | H | 71 | 38.953 | 27.417 | 8.983 | 1.00 | 49.99 | O |
| HETATM | 5493 | O | HOH | H | 72 | 9.205 | 13.019 | 37.426 | 1.00 | 40.24 | O |
| HETATM | 5494 | O | HOH | H | 73 | 49.155 | 12.950 | 28.810 | 1.00 | 33.21 | O |
| HETATM | 5495 | O | HOH | H | 74 | 57.776 | 14.025 | 35.993 | 1.00 | 43.68 | O |
| HETATM | 5496 | O | HOH | H | 75 | 40.340 | 22.810 | 3.174 | 1.00 | 39.27 | O |
| HETATM | 5497 | O | HOH | H | 76 | 9.638 | 16.180 | 21.718 | 1.00 | 37.38 | O |
| HETATM | 5498 | O | HOH | H | 77 | 4.259 | 11.769 | 47.251 | 1.00 | 46.36 | O |
| HETATM | 5499 | O | HOH | H | 78 | 47.517 | 9.896 | 23.620 | 1.00 | 42.79 | O |
| HETATM | 5500 | O | HOH | H | 79 | 14.982 | 10.745 | 40.870 | 1.00 | 36.64 | O |
| HETATM | 5501 | O | HOH | H | 80 | 49.688 | −1.088 | 29.622 | 1.00 | 46.60 | O |
| HETATM | 5502 | O | HOH | H | 81 | 42.829 | −15.182 | 24.472 | 1.00 | 49.44 | O |
| HETATM | 5503 | O | HOH | H | 82 | 38.476 | 20.042 | 28.983 | 1.00 | 39.88 | O |
| HETATM | 5504 | O | HOH | H | 83 | 23.385 | 18.413 | 14.271 | 1.00 | 36.63 | O |
| HETATM | 5505 | O | HOH | H | 84 | 3.899 | 8.715 | 53.254 | 1.00 | 37.88 | O |
| HETATM | 5506 | O | HOH | H | 85 | 12.299 | 2.979 | 40.453 | 1.00 | 41.82 | O |
| HETATM | 5507 | O | HOH | H | 86 | 24.790 | 19.670 | −11.882 | 1.00 | 39.49 | O |
| HETATM | 5508 | O | HOH | H | 87 | 7.460 | 12.890 | 9.510 | 1.00 | 39.34 | O |
| HETATM | 5509 | O | HOH | H | 88 | 47.160 | −5.805 | 36.811 | 1.00 | 55.24 | O |
| HETATM | 5510 | O | HOH | H | 89 | 23.731 | 24.512 | 29.365 | 1.00 | 33.41 | O |
| HETATM | 5511 | O | HOH | H | 90 | 55.397 | 14.427 | 28.276 | 1.00 | 56.00 | O |
| HETATM | 5512 | O | HOH | H | 91 | 18.039 | 2.972 | 44.485 | 1.00 | 42.75 | O |
| HETATM | 5513 | O | HOH | H | 92 | 33.358 | 28.816 | 4.426 | 1.00 | 45.04 | O |
| HETATM | 5514 | O | HOH | H | 93 | 6.321 | 11.293 | 13.330 | 1.00 | 36.38 | O |
| END | | | | | | | | | | | |

APPENDIX B

| Atomic coordinates of Aurora A + Activating Monobody Mb54 + AMPPCP | | | | |
|---|---|---|---|---|
| HEADER | dePAurA+activatingMonobody+AMPPCP | | 21 Dec. 2015 | XXXX |
| COMPND | dePAurA+activatingonobody+AMPPCP | | | |
| REMARK | 3 | | | |
| REMARK | 3 | REFINEMENT. | | |
| REMARK | 3 | PROGRAM: REFMAC 5.8.0135 | | |
| REMARK | 3 | AUTHORS: MURSHUDOV, SKUBAK, LEBEDEV, PANNU, | | |
| REMARK | 3 | STEINER, NICHOLLS, WINN, LONG, VAGIN | | |
| REMARK | 3 | | | |
| REMARK | 3 | REFINEMENT TARGET: MAXIMUM LIKELIHOOD | | |
| REMARK | 3 | | | |
| REMARK | 3 | DATA USED IN REFINEMENT. | | |
| REMARK | 3 | RESOLUTION RANGE HIGH (ANGSTROMS): | 2.06 | |
| REMARK | 3 | RESOLUTION RANGE LOW (ANGSTROMS): | 77.10 | |
| REMARK | 3 | DATA CUTOFF (SIGMA(F)): | NONE | |
| REMARK | 3 | COMPLETENESS FOR RANGE (%): | 99.71 | |
| REMARK | 3 | NUMBER OF REFLECTIONS: | 29755 | |
| REMARK | 3 | | | |
| REMARK | 3 | FIT TO DATA USED IN REFINEMENT. | | |
| REMARK | 3 | CROSS-VALIDATION METHOD: | THROUGHOUT | |
| REMARK | 3 | FREE R VALUE TEST SET SELECTION: | RANDOM | |
| REMARK | 3 | R VALUE (WORKING + TEST SET): | 0.22987 | |
| REMARK | 3 | R VALUE (WORKING SET): | 0.22824 | |

APPENDIX B-continued

Atomic coordinates of Aurora A + Activating Monobody Mb54 + AMPPCP

| | | | | | |
|---|---|---|---|---|---|
| REMARK | 3 | FREE R VALUE: | 0.27442 | | |
| REMARK | 3 | FREE R VALUE TEST SET SIZE (%): | 3.4 | | |
| REMARK | 3 | FREE R VALUE TEST SET COUNT: | 1052 | | |
| REMARK | 3 | | | | |
| REMARK | 3 | FIT IN THE HIGHEST RESOLUTION BIN. | | | |
| REMARK | 3 | TOTAL NUMBER OF BINS USED: | 20 | | |
| REMARK | 3 | BIN RESOLUTION RANGE HIGH: | 2.064 | | |
| REMARK | 3 | BIN RESOLUTION RANGE LOW: | 2.118 | | |
| REMARK | 3 | REFLECTION IN BIN (WORKING SET): | 2170 | | |
| REMARK | 3 | BIN COMPLETENESS (WORKING + TEST) (%): | 99.08 | | |
| REMARK | 3 | BIN R VALUE (WORKING SET): | 0.429 | | |
| REMARK | 3 | BIN FREE R VALUE SET COUNT: | 81 | | |
| REMARK | 3 | BIN FREE R VALUE: | 0.409 | | |
| REMARK | 3 | | | | |
| REMARK | 3 | NUMBER OF NON-HYDROGEN ATOMS USED IN REFINEMENT. | | | |
| REMARK | 3 | ALL ATOMS: 3067 | | | |
| REMARK | 3 | | | | |
| REMARK | 3 | B VALUES. | | | |
| REMARK | 3 | FROM WILSON PLOT (A**2): | NULL | | |
| REMARK | 3 | MEAN B VALUE (OVERALL, A**2): | 34.118 | | |
| REMARK | 3 | OVERALL ANISOTROPIC B VALUE. | | | |
| REMARK | 3 | B11 (A**2): 0.03 | | | |
| REMARK | 3 | B22 (A**2): −0.02 | | | |
| REMARK | 3 | B33 (A**2): −0.01 | | | |
| REMARK | 3 | B12 (A**2): 0.00 | | | |
| REMARK | 3 | B13 (A**2): 0.00 | | | |
| REMARK | 3 | B23 (A**2): 0.00 | | | |
| REMARK | 3 | | | | |
| REMARK | 3 | ESTIMATED OVERALL COORDINATE ERROR. | | | |
| REMARK | 3 | ESU BASED ON R VALUE (A): | | 0.200 | |
| REMARK | 3 | ESU BASED ON FREE R VALUE (A): | | 0.184 | |
| REMARK | 3 | ESU BASED ON MAXIMUM LIKELIHOOD (A): | | 0.188 | |
| REMARK | 3 | ESU FOR B VALUES BASED ON MAXIMUM LIKELIHOOD (A**2): | | 8.096 | |
| REMARK | 3 | | | | |
| REMARK | 3 | CORRELATION COEFFICIENTS. | | | |
| REMARK | 3 | CORRELATION COEFFICIENT FO-FC: | 0.936 | | |
| REMARK | 3 | CORRELATION COEFFICIENT FO-FC FREE: | 0.912 | | |
| REMARK | 3 | | | | |
| REMARK | 3 | RMS DEVIATIONS FROM IDEAL VALUES | COUNT | RMS | WEIGHT |
| REMARK | 3 | BOND LENGTHS REFINED ATOMS (A): | 2999; | 0.016; | 0.019 |
| REMARK | 3 | BOND LENGTHS OTHERS (A): | 2788; | 0.002; | 0.020 |
| REMARK | 3 | BOND ANGLES REFINED ATOMS (DEGREES): | 4087; | 1.918; | 1.984 |
| REMARK | 3 | BOND ANGLES OTHERS (DEGREES): | 6426; | 1.035; | 3.000 |
| REMARK | 3 | TORSION ANGLES, PERIOD 1 (DEGREES): | 357; | 8.473; | 5.000 |
| REMARK | 3 | TORSION ANGLES, PERIOD 2 (DEGREES): | 138; | 35.365; | 22.899 |
| REMARK | 3 | TORSION ANGLES, PERIOD 3 (DEGREES): | 498; | 16.029; | 15.000 |
| REMARK | 3 | TORSION ANGLES, PERIOD 4 (DEGREES): | 22; | 14.764; | 15.000 |
| REMARK | 3 | CHIRAL-CENTER RESTRAINTS (A**3): | 443; | 0.104; | 0.200 |
| REMARK | 3 | GENERAL PLANES REFINED ATOMS (A): | 3312; | 0.009; | 0.021 |
| REMARK | 3 | GENERAL PLANES OTHERS (A): | 709; | 0.002; | 0.020 |
| REMARK | 3 | | | | |
| REMARK | 3 | ISOTROPIC THERMAL FACTOR RESTRAINTS. | COUNT | RMS | WEIGHT |
| REMARK | 3 | MAIN-CHAIN BOND REFINED ATOMS (A**2): | 1410; | 2.863; | 3.197 |
| REMARK | 3 | MAIN-CHAIN BOND OTHER ATOMS (A**2): | 1409; | 2.841; | 3.195 |
| REMARK | 3 | MAIN-CHAIN ANGLE REFINED ATOMS (A**2): | 1761; | 4.378; | 4.778 |
| REMARK | 3 | MAIN-CHAIN ANGLE OTHER ATOMS (A**2): | 1762; | 4.381; | 4.779 |
| REMARK | 3 | SIDE-CHAIN BOND REFINED ATOMS (A**2): | 1588; | 3.523; | 3.594 |
| REMARK | 3 | SIDE-CHAIN BOND OTHER ATOMS (A**2): | 1573; | 3.456; | 3.572 |
| REMARK | 3 | SIDE-CHAIN ANGLE OTHER ATOMS (A**2): | 2299; | 5.338; | 5.218 |
| REMARK | 3 | LONG RANGE B REFINED ATOMS (A**2): | 3478; | 7.656; | 25.890 |
| REMARK | 3 | LONG RANGE B OTHER ATOMS (A**2): | 3428; | 7.606; | 25.784 |
| REMARK | 3 | | | | |
| REMARK | 3 | NCS RESTRAINTS STATISTICS | | | |
| REMARK | 3 | NUMBER OF NCS GROUPS: NULL | | | |
| REMARK | 3 | | | | |
| REMARK | 3 | TWIN DETAILS | | | |
| REMARK | 3 | NUMBER OF TWIN DOMAINS: NULL | | | |
| REMARK | 3 | | | | |
| REMARK | 3 | | | | |
| REMARK | 3 | TLS DETAILS | | | |
| REMARK | 3 | NUMBER OF TLS GROUPS: NULL | | | |
| REMARK | 3 | | | | |
| REMARK | 3 | | | | |
| REMARK | 3 | BULK SOLVENT MODELLING. | | | |
| REMARK | 3 | METHOD USED: MASK | | | |
| REMARK | 3 | PARAMETERS FOR MASK CALCULATION | | | |
| REMARK | 3 | VDW PROBE RADIUS: 1.20 | | | |
| REMARK | 3 | ION PROBE RADIUS: 0.80 | | | |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| REMARK | 3 | SHRINKAGE RADIUS: | | | | 0.80 | | | | | | |
| REMARK | 3 | | | | | | | | | | | |
| REMARK | 3 | OTHER REFINEMENT REMARKS: | | | | | | | | | | |
| REMARK | 3 | HYDROGENS HAVE BEEN ADDED IN THE RIDING POSITIONS | | | | | | | | | | |
| REMARK | 3 | U VALUES: | | | REFINED INDIVIDUALLY | | | | | | | |
| REMARK | 3 | | | | | | | | | | | |
| CISPEP | 1 | GLN B | 31 | | MET B | 32 | | 0.00 | | | | |
| CRYST1 | 75.339 | | 91.361 | | 143.715 | 90.00 | 90.00 | 90.00 | | I 2 2 2 | | |
| SCALE1 | | 0.013273 | | | 0.000000 | 0.000000 | | 0.00000 | | | | |
| SCALE2 | | 0.000000 | | | 0.010946 | 0.000000 | | 0.00000 | | | | |
| SCALE3 | | 0.000000 | | | 0.000000 | 0.006958 | | 0.00000 | | | | |
| ATOM | 1 | N | TRP | A | 128 | −20.924 | 36.076 | −10.152 | 1.00 | 46.34 | A | N |
| ATOM | 2 | CA | TRP | A | 128 | −21.366 | 36.638 | −11.463 | 1.00 | 43.05 | A | C |
| ATOM | 3 | CB | TRP | A | 128 | −21.145 | 35.611 | −12.572 | 1.00 | 48.01 | A | C |
| ATOM | 4 | CG | TRP | A | 128 | −19.697 | 35.228 | −12.816 | 1.00 | 47.63 | A | C |
| ATOM | 5 | CD1 | TRP | A | 128 | −19.129 | 33.993 | −12.627 | 1.00 | 44.97 | A | C |
| ATOM | 6 | NE1 | TRP | A | 128 | −17.793 | 34.026 | −12.990 | 1.00 | 47.26 | A | N |
| ATOM | 7 | CE2 | TRP | A | 128 | −17.480 | 35.284 | −13.436 | 1.00 | 49.02 | A | C |
| ATOM | 8 | CD2 | TRP | A | 128 | −18.656 | 36.077 | −13.328 | 1.00 | 48.76 | A | C |
| ATOM | 9 | CE3 | TRP | A | 128 | −18.606 | 37.419 | −13.721 | 1.00 | 51.01 | A | C |
| ATOM | 10 | CZ3 | TRP | A | 128 | −17.380 | 37.940 | −14.189 | 1.00 | 58.88 | A | C |
| ATOM | 11 | CH2 | TRP | A | 128 | −16.224 | 37.128 | −14.267 | 1.00 | 57.46 | A | C |
| ATOM | 12 | CZ2 | TRP | A | 128 | −16.264 | 35.796 | −13.904 | 1.00 | 54.22 | A | C |
| ATOM | 13 | C | TRP | A | 128 | −22.854 | 36.971 | −11.440 | 1.00 | 42.45 | A | C |
| ATOM | 14 | O | TRP | A | 128 | −23.612 | 36.280 | −10.755 | 1.00 | 35.10 | A | O |
| ATOM | 15 | N | ALA | A | 129 | −23.242 | 38.056 | −12.154 | 1.00 | 40.00 | A | N |
| ATOM | 16 | CA | ALA | A | 129 | −24.660 | 38.376 | −12.519 | 1.00 | 35.63 | A | C |
| ATOM | 17 | CB | ALA | A | 129 | −25.372 | 39.186 | −11.428 | 1.00 | 33.56 | A | C |
| ATOM | 18 | C | ALA | A | 129 | −24.757 | 39.107 | −13.891 | 1.00 | 33.12 | A | C |
| ATOM | 19 | O | ALA | A | 129 | −23.747 | 39.551 | −14.446 | 1.00 | 28.04 | A | O |
| ATOM | 20 | N | LEU | A | 130 | −25.981 | 39.200 | −14.423 | 1.00 | 31.44 | A | N |
| ATOM | 21 | CA | LEU | A | 130 | −26.214 | 39.745 | −15.754 | 1.00 | 31.97 | A | C |
| ATOM | 22 | CB | LEU | A | 130 | −27.716 | 39.711 | −16.066 | 1.00 | 33.37 | A | C |
| ATOM | 23 | CG | LEU | A | 130 | −28.115 | 40.127 | −17.478 | 1.00 | 35.84 | A | C |
| ATOM | 24 | CD1 | LEU | A | 130 | −29.619 | 39.950 | −17.727 | 1.00 | 36.36 | A | C |
| ATOM | 25 | CD2 | LEU | A | 130 | −27.319 | 39.322 | −18.483 | 1.00 | 36.76 | A | C |
| ATOM | 26 | C | LEU | A | 130 | −25.603 | 41.159 | −15.928 | 1.00 | 35.19 | A | C |
| ATOM | 27 | O | LEU | A | 130 | −25.041 | 41.485 | −16.975 | 1.00 | 35.88 | A | O |
| ATOM | 28 | N | GLU | A | 131 | −25.620 | 41.943 | −14.866 | 1.00 | 36.02 | A | N |
| ATOM | 29 | CA | GLU | A | 131 | −24.961 | 43.272 | −14.819 | 1.00 | 41.48 | A | C |
| ATOM | 30 | CB | GLU | A | 131 | −25.146 | 43.965 | −13.430 | 1.00 | 46.58 | A | C |
| ATOM | 31 | CG | GLU | A | 131 | −26.574 | 44.047 | −12.899 | 1.00 | 57.70 | A | C |
| ATOM | 32 | CD | GLU | A | 131 | −26.949 | 42.930 | −11.905 | 1.00 | 63.93 | A | C |
| ATOM | 33 | OE1 | GLU | A | 131 | −27.255 | 41.818 | −12.375 | 1.00 | 67.29 | A | O |
| ATOM | 34 | OE2 | GLU | A | 131 | −26.967 | 43.150 | −10.665 | 1.00 | 70.38 | A | O |
| ATOM | 35 | C | GLU | A | 131 | −23.456 | 43.279 | −15.077 | 1.00 | 37.06 | A | C |
| ATOM | 36 | O | GLU | A | 131 | −22.890 | 44.342 | −15.231 | 1.00 | 37.36 | A | O |
| ATOM | 37 | N | ASP | A | 132 | −22.758 | 42.158 | −15.057 | 1.00 | 32.85 | A | N |
| ATOM | 38 | CA | ASP | A | 132 | −21.304 | 42.236 | −15.285 | 1.00 | 33.45 | A | C |
| ATOM | 39 | CB | ASP | A | 132 | −20.616 | 41.157 | −14.464 | 1.00 | 42.58 | A | C |
| ATOM | 40 | CG | ASP | A | 132 | −21.044 | 41.183 | −12.979 | 1.00 | 45.15 | A | C |
| ATOM | 41 | OD1 | ASP | A | 132 | −21.037 | 42.284 | −12.396 | 1.00 | 44.98 | A | O |
| ATOM | 42 | OD2 | ASP | A | 132 | −21.410 | 40.117 | −12.417 | 1.00 | 47.90 | A | O |
| ATOM | 43 | C | ASP | A | 132 | −20.912 | 42.120 | −16.764 | 1.00 | 32.57 | A | C |
| ATOM | 44 | O | ASP | A | 132 | −19.708 | 42.169 | −17.110 | 1.00 | 29.69 | A | O |
| ATOM | 45 | N | PHE | A | 133 | −21.926 | 41.967 | −17.641 | 1.00 | 31.42 | A | N |
| ATOM | 46 | CA | PHE | A | 133 | −21.694 | 41.774 | −19.077 | 1.00 | 32.90 | A | C |
| ATOM | 47 | CB | PHE | A | 133 | −22.134 | 40.350 | −19.476 | 1.00 | 33.53 | A | C |
| ATOM | 48 | CG | PHE | A | 133 | −21.434 | 39.303 | −18.686 | 1.00 | 35.58 | A | C |
| ATOM | 49 | CD1 | PHE | A | 133 | −20.106 | 38.963 | −18.990 | 1.00 | 34.07 | A | C |
| ATOM | 50 | CE1 | PHE | A | 133 | −19.424 | 38.025 | −18.233 | 1.00 | 33.40 | A | C |
| ATOM | 51 | CZ | PHE | A | 133 | −20.040 | 37.447 | −17.131 | 1.00 | 31.50 | A | C |
| ATOM | 52 | CE2 | PHE | A | 133 | −21.347 | 37.787 | −16.795 | 1.00 | 34.46 | A | C |
| ATOM | 53 | CD2 | PHE | A | 133 | −22.042 | 38.730 | −17.559 | 1.00 | 35.27 | A | C |
| ATOM | 54 | C | PHE | A | 133 | −22.429 | 42.734 | −19.965 | 1.00 | 29.70 | A | C |
| ATOM | 55 | O | PHE | A | 133 | −23.656 | 42.867 | −19.846 | 1.00 | 29.01 | A | O |
| ATOM | 56 | N | GLU | A | 134 | −21.686 | 43.338 | −20.889 | 1.00 | 27.13 | A | N |
| ATOM | 57 | CA | GLU | A | 134 | −22.303 | 43.903 | −22.100 | 1.00 | 28.70 | A | C |
| ATOM | 58 | CB | GLU | A | 134 | 21.354 | 44.819 | 22.877 | 1.00 | 30.52 | A | C |
| ATOM | 59 | CG | GLU | A | 134 | −20.898 | 46.069 | −22.119 | 1.00 | 35.53 | A | C |
| ATOM | 60 | CD | GLU | A | 134 | −20.092 | 47.060 | −22.960 | 1.00 | 39.28 | A | C |
| ATOM | 61 | OE1 | GLU | A | 134 | −19.716 | 46.779 | −24.143 | 1.00 | 40.31 | A | O |
| ATOM | 62 | OE2 | GLU | A | 134 | −19.855 | 48.152 | −22.417 | 1.00 | 45.71 | A | O |
| ATOM | 63 | C | GLU | A | 134 | −22.664 | 42.758 | −22.996 | 1.00 | 27.48 | A | C |
| ATOM | 64 | O | GLU | A | 134 | −21.875 | 41.836 | −23.185 | 1.00 | 28.94 | A | O |
| ATOM | 65 | N | ILE | A | 135 | −23.821 | 42.861 | −23.587 | 1.00 | 27.18 | A | N |
| ATOM | 66 | CA | ILE | A | 135 | −24.383 | 41.867 | −24.470 | 1.00 | 29.68 | A | C |
| ATOM | 67 | CB | ILE | A | 135 | −25.773 | 41.462 | −23.955 | 1.00 | 31.47 | A | C |

APPENDIX B-continued

| Atomic coordinates of Aurora A + Activating Monobody Mb54 + AMPPCP | | | | | | | | | | | | |
|---|---|---|---|---|---|---|---|---|---|---|---|---|
| ATOM | 68 | CG1 | ILE | A | 135 | −25.568 | 40.631 | −22.670 | 1.00 | 35.80 | A | C |
| ATOM | 69 | CD1 | ILE | A | 135 | −26.703 | 40.749 | −21.702 | 1.00 | 38.46 | A | C |
| ATOM | 70 | CG2 | ILE | A | 135 | −26.526 | 40.620 | −24.950 | 1.00 | 31.50 | A | C |
| ATOM | 71 | C | ILE | A | 135 | −24.436 | 42.413 | −25.877 | 1.00 | 29.85 | A | C |
| ATOM | 72 | O | ILE | A | 135 | −24.944 | 43.531 | −26.126 | 1.00 | 31.56 | A | O |
| ATOM | 73 | N | GLY | A | 136 | −23.877 | 41.615 | −26.783 | 1.00 | 28.68 | A | N |
| ATOM | 74 | CA | GLY | A | 136 | −23.890 | 41.851 | −28.221 | 1.00 | 27.02 | A | C |
| ATOM | 75 | C | GLY | A | 136 | −24.899 | 41.006 | −28.969 | 1.00 | 24.83 | A | C |
| ATOM | 76 | O | GLY | A | 136 | −25.922 | 40.646 | −28.453 | 1.00 | 24.19 | A | O |
| ATOM | 77 | N | ARG | A | 137 | −24.594 | 40.723 | −30.218 | 1.00 | 24.86 | A | N |
| ATOM | 78 | CA | ARG | A | 137 | −25.472 | 39.985 | −31.096 | 1.00 | 24.88 | A | C |
| ATOM | 79 | CB | ARG | A | 137 | −24.962 | 40.085 | −32.547 | 1.00 | 24.15 | A | C |
| ATOM | 80 | CG | ARG | A | 137 | −23.716 | 39.315 | −32.856 | 1.00 | 25.89 | A | C |
| ATOM | 81 | CD | ARG | A | 137 | −23.256 | 39.598 | −34.276 | 1.00 | 27.49 | A | C |
| ATOM | 82 | NE | ARG | A | 137 | −21.968 | 39.014 | −34.582 | 1.00 | 29.42 | A | N |
| ATOM | 83 | CZ | ARG | A | 137 | −21.745 | 37.714 | −34.825 | 1.00 | 30.38 | A | C |
| ATOM | 84 | NH1 | ARG | A | 137 | −22.693 | 36.809 | −34.753 | 1.00 | 30.68 | A | N |
| ATOM | 85 | NH2 | ARG | A | 137 | −20.536 | 37.298 | −35.115 | 1.00 | 29.75 | A | N |
| ATOM | 86 | C | ARG | A | 137 | −25.604 | 38.515 | −30.727 | 1.00 | 25.59 | A | C |
| ATOM | 87 | O | ARG | A | 137 | −24.698 | 37.927 | −30.133 | 1.00 | 27.63 | A | O |
| ATOM | 88 | N | PRO | A | 138 | −26.704 | 37.892 | −31.151 | 1.00 | 25.55 | A | N |
| ATOM | 89 | CA | PRO | A | 138 | −26.830 | 36.465 | −30.987 | 1.00 | 24.30 | A | C |
| ATOM | 90 | CB | PRO | A | 138 | −28.277 | 36.208 | −31.360 | 1.00 | 25.56 | A | C |
| ATOM | 91 | CG | PRO | A | 138 | −28.607 | 37.312 | −32.304 | 1.00 | 25.74 | A | C |
| ATOM | 92 | CD | PRO | A | 138 | −27.910 | 38.496 | −31.764 | 1.00 | 24.13 | A | C |
| ATOM | 93 | C | PRO | A | 138 | −25.902 | 35.711 | −31.918 | 1.00 | 29.06 | A | C |
| ATOM | 94 | O | PRO | A | 138 | −25.748 | 36.101 | −33.078 | 1.00 | 29.60 | A | O |
| ATOM | 95 | N | LEU | A | 139 | −25.225 | 34.686 | −31.373 | 1.00 | 30.85 | A | N |
| ATOM | 96 | CA | LEU | A | 139 | −24.322 | 33.797 | −32.099 | 1.00 | 28.63 | A | C |
| ATOM | 97 | CB | LEU | A | 139 | −23.194 | 33.370 | −31.190 | 1.00 | 29.83 | A | C |
| ATOM | 98 | CG | LEU | A | 139 | −22.310 | 34.516 | −30.778 | 1.00 | 30.32 | A | C |
| ATOM | 99 | CD1 | LEU | A | 139 | −21.348 | 34.052 | −29.703 | 1.00 | 32.54 | A | C |
| ATOM | 100 | CD2 | LEU | A | 139 | −21.511 | 34.968 | −31.971 | 1.00 | 33.85 | A | C |
| ATOM | 101 | C | LEU | A | 139 | −25.009 | 32.525 | −32.572 | 1.00 | 28.10 | A | C |
| ATOM | 102 | O | LEU | A | 139 | −24.584 | 31.949 | −33.544 | 1.00 | 24.92 | A | O |
| ATOM | 103 | N | GLY | A | 140 | −26.033 | 32.060 | −31.863 | 1.00 | 25.19 | A | N |
| ATOM | 104 | CA | GLY | A | 140 | −26.785 | 30.940 | −32.336 | 1.00 | 24.66 | A | C |
| ATOM | 105 | C | GLY | A | 140 | −28.020 | 30.633 | −31.536 | 1.00 | 25.38 | A | C |
| ATOM | 106 | O | GLY | A | 140 | −28.214 | 31.138 | −30.417 | 1.00 | 25.32 | A | O |
| ATOM | 107 | N | LYS | A | 141 | −28.858 | 29.795 | −32.128 | 1.00 | 28.61 | A | N |
| ATOM | 108 | CA | LYS | A | 141 | −30.103 | 29.360 | −31.516 | 1.00 | 33.29 | A | C |
| ATOM | 109 | CB | LYS | A | 141 | −31.248 | 29.402 | −32.568 | 1.00 | 34.58 | A | C |
| ATOM | 110 | CG | LYS | A | 141 | −32.519 | 28.595 | −32.311 | 1.00 | 38.76 | A | C |
| ATOM | 111 | CD | LYS | A | 141 | −33.693 | 29.317 | −31.668 | 1.00 | 44.25 | A | C |
| ATOM | 112 | CE | LYS | A | 141 | −33.793 | 29.080 | −30.148 | 1.00 | 53.96 | A | C |
| ATOM | 113 | NZ | LYS | A | 141 | −35.114 | 28.599 | −29.632 | 1.00 | 64.52 | A | N |
| ATOM | 114 | C | LYS | A | 141 | −29.829 | 27.974 | −30.921 | 1.00 | 34.00 | A | C |
| ATOM | 115 | O | LYS | A | 141 | −29.404 | 27.069 | −31.613 | 1.00 | 36.57 | A | O |
| ATOM | 116 | N | GLY | A | 142 | −30.038 | 27.826 | −29.628 | 1.00 | 33.66 | A | N |
| ATOM | 117 | CA | GLY | A | 142 | −29.878 | 26.537 | −28.990 | 1.00 | 36.63 | A | C |
| ATOM | 118 | C | GLY | A | 142 | −31.226 | 25.909 | −28.823 | 1.00 | 35.84 | A | C |
| ATOM | 119 | O | GLY | A | 142 | −32.223 | 26.519 | −29.106 | 1.00 | 41.35 | A | O |
| ATOM | 120 | N | LYS | A | 143 | −31.255 | 24.700 | −28.310 | 1.00 | 38.36 | A | N |
| ATOM | 121 | CA | LYS | A | 143 | −32.519 | 24.020 | −28.013 | 1.00 | 39.69 | A | C |
| ATOM | 122 | CB | LYS | A | 143 | −32.259 | 22.579 | −27.629 | 1.00 | 43.08 | A | C |
| ATOM | 123 | CG | LYS | A | 143 | −31.980 | 21.738 | −28.868 | 1.00 | 51.03 | A | C |
| ATOM | 124 | CD | LYS | A | 143 | −31.031 | 20.595 | −28.589 | 1.00 | 56.66 | A | C |
| ATOM | 125 | CE | LYS | A | 143 | −31.641 | 19.620 | −27.601 | 1.00 | 59.88 | A | C |
| ATOM | 126 | NZ | LYS | A | 143 | 30.568 | 19.056 | −26.758 | 1.00 | 64.75 | A | N |
| ATOM | 127 | C | LYS | A | 143 | −33.357 | 24.663 | −26.946 | 1.00 | 36.08 | A | C |
| ATOM | 128 | O | LYS | A | 143 | −34.572 | 24.665 | −27.082 | 1.00 | 37.77 | A | O |
| ATOM | 129 | N | PHE | A | 144 | −32.731 | 25.209 | −25.903 | 1.00 | 34.65 | A | N |
| ATOM | 130 | CA | PHE | A | 144 | −33.469 | 25.728 | −24.740 | 1.00 | 34.54 | A | C |
| ATOM | 131 | CB | PHE | A | 144 | −33.084 | 24.953 | −23.472 | 1.00 | 36.52 | A | C |
| ATOM | 132 | CG | PHE | A | 144 | −33.153 | 23.475 | −23.635 | 1.00 | 37.11 | A | C |
| ATOM | 133 | CD1 | PHE | A | 144 | −34.359 | 22.862 | −23.906 | 1.00 | 38.85 | A | C |
| ATOM | 134 | CE1 | PHE | A | 144 | −34.444 | 21.491 | −24.067 | 1.00 | 38.21 | A | C |
| ATOM | 135 | CZ | PHE | A | 144 | −33.318 | 20.722 | −23.967 | 1.00 | 36.90 | A | C |
| ATOM | 136 | CE2 | PHE | A | 144 | −32.099 | 21.323 | −23.720 | 1.00 | 40.42 | A | C |
| ATOM | 137 | CD2 | PHE | A | 144 | −32.014 | 22.690 | −23.549 | 1.00 | 40.19 | A | C |
| ATOM | 138 | C | PHE | A | 144 | −33.231 | 27.199 | −24.512 | 1.00 | 34.36 | A | C |
| ATOM | 139 | O | PHE | A | 144 | −33.527 | 27.749 | −23.424 | 1.00 | 30.20 | A | O |
| ATOM | 140 | N | GLY | A | 145 | −32.686 | 27.850 | −25.536 | 1.00 | 34.89 | A | N |
| ATOM | 141 | CA | GLY | A | 145 | −32.246 | 29.224 | −25.392 | 1.00 | 31.89 | A | C |
| ATOM | 142 | C | GLY | A | 145 | −31.474 | 29.707 | −26.582 | 1.00 | 30.90 | A | C |
| ATOM | 143 | O | GLY | A | 145 | −31.626 | 29.206 | −27.702 | 1.00 | 30.44 | A | O |
| ATOM | 144 | N | ASN | A | 146 | −30.636 | 30.692 | −26.330 | 1.00 | 29.02 | A | N |
| ATOM | 145 | CA | ASN | A | 146 | −29.873 | 31.356 | −27.371 | 1.00 | 29.59 | A | C |

APPENDIX B-continued

| Atomic coordinates of Aurora A + Activating Monobody Mb54 + AMPPCP | | | | | | | | | | | |
|---|---|---|---|---|---|---|---|---|---|---|---|
| ATOM | 146 | CB | ASN | A | 146 | −30.600 | 32.666 | −27.816 | 1.00 | 31.19 | A C |
| ATOM | 147 | CG | ASN | A | 146 | −31.988 | 32.391 | −28.435 | 1.00 | 31.53 | A C |
| ATOM | 148 | OD1 | ASN | A | 146 | −33.049 | 32.368 | −27.757 | 1.00 | 31.08 | A O |
| ATOM | 149 | ND2 | ASN | A | 146 | −31.968 | 32.095 | −29.717 | 1.00 | 33.41 | A N |
| ATOM | 150 | C | ASN | A | 146 | −28.510 | 31.650 | −26.793 | 1.00 | 26.19 | A C |
| ATOM | 151 | O | ASN | A | 146 | −28.392 | 31.790 | −25.590 | 1.00 | 26.89 | A O |
| ATOM | 152 | N | VAL | A | 147 | −27.486 | 31.739 | −27.643 | 1.00 | 24.61 | A N |
| ATOM | 153 | CA | VAL | A | 147 | −26.148 | 32.141 | −27.211 | 1.00 | 22.73 | A C |
| ATOM | 154 | CB | VAL | A | 147 | −25.120 | 31.106 | −27.711 | 1.00 | 25.50 | A C |
| ATOM | 155 | CG1 | VAL | A | 147 | −23.688 | 31.451 | −27.267 | 1.00 | 24.34 | A C |
| ATOM | 156 | CG2 | VAL | A | 147 | −25.512 | 29.713 | −27.215 | 1.00 | 26.07 | A C |
| ATOM | 157 | C | VAL | A | 147 | −25.837 | 33.524 | −27.757 | 1.00 | 22.82 | A C |
| ATOM | 158 | O | VAL | A | 147 | −26.072 | 33.765 | −28.929 | 1.00 | 24.50 | A O |
| ATOM | 159 | N | TYR | A | 148 | −25.308 | 34.423 | −26.935 | 1.00 | 21.59 | A N |
| ATOM | 160 | CA | TYR | A | 148 | −25.004 | 35.806 | −27.339 | 1.00 | 21.59 | A C |
| ATOM | 161 | CB | TYR | A | 148 | −25.740 | 36.794 | −26.414 | 1.00 | 22.40 | A C |
| ATOM | 162 | CG | TYR | A | 148 | −27.227 | 36.679 | −26.573 | 1.00 | 25.07 | A C |
| ATOM | 163 | CD1 | TYR | A | 148 | −27.936 | 35.758 | −25.832 | 1.00 | 26.43 | A C |
| ATOM | 164 | CE1 | TYR | A | 148 | −29.278 | 35.584 | −26.001 | 1.00 | 27.37 | A C |
| ATOM | 165 | CZ | TYR | A | 148 | −29.940 | 36.338 | −26.939 | 1.00 | 28.69 | A C |
| ATOM | 166 | OH | TYR | A | 148 | −31.280 | 36.119 | −27.125 | 1.00 | 30.79 | A O |
| ATOM | 167 | CE2 | TYR | A | 148 | −29.259 | 37.245 | −27.716 | 1.00 | 28.30 | A C |
| ATOM | 168 | CD2 | TYR | A | 148 | −27.903 | 37.418 | −27.525 | 1.00 | 25.25 | A C |
| ATOM | 169 | C | TYR | A | 148 | −23.507 | 36.077 | −27.239 | 1.00 | 20.86 | A C |
| ATOM | 170 | O | TYR | A | 148 | −22.857 | 35.578 | −26.334 | 1.00 | 19.85 | A O |
| ATOM | 171 | N | LEU | A | 149 | −22.986 | 36.925 | −28.097 | 1.00 | 20.26 | A N |
| ATOM | 172 | CA | LEU | A | 149 | −21.662 | 37.503 | −27.880 | 1.00 | 22.08 | A C |
| ATOM | 173 | CB | LEU | A | 149 | −21.199 | 38.308 | −29.079 | 1.00 | 24.65 | A C |
| ATOM | 174 | CG | LEU | A | 149 | −19.713 | 38.679 | −29.074 | 1.00 | 24.81 | A C |
| ATOM | 175 | CD1 | LEU | A | 149 | −18.833 | 37.477 | −29.326 | 1.00 | 25.70 | A C |
| ATOM | 176 | CD2 | LEU | A | 149 | −19.507 | 39.689 | −30.166 | 1.00 | 25.31 | A C |
| ATOM | 177 | C | LEU | A | 149 | −21.807 | 38.440 | −26.735 | 1.00 | 22.54 | A C |
| ATOM | 178 | O | LEU | A | 149 | −22.880 | 38.994 | −26.520 | 1.00 | 24.60 | A O |
| ATOM | 179 | N | ALA | A | 150 | −20.766 | 38.552 | −25.937 | 1.00 | 22.32 | A N |
| ATOM | 180 | CA | ALA | A | 150 | −20.851 | 39.298 | −24.716 | 1.00 | 22.71 | A C |
| ATOM | 181 | CB | ALA | A | 150 | −21.631 | 38.516 | −23.672 | 1.00 | 23.29 | A C |
| ATOM | 182 | C | ALA | A | 150 | −19.471 | 39.690 | −24.248 | 1.00 | 22.78 | A C |
| ATOM | 183 | O | ALA | A | 150 | −18.499 | 39.228 | −24.777 | 1.00 | 22.86 | A O |
| ATOM | 184 | N | ARG | A | 151 | −19.384 | 40.632 | −23.334 | 1.00 | 26.98 | A N |
| ATOM | 185 | CA | ARG | A | 151 | −18.071 | 41.200 | −22.946 | 1.00 | 30.28 | A C |
| ATOM | 186 | CB | ARG | A | 151 | −17.818 | 42.486 | −23.706 | 1.00 | 30.23 | A C |
| ATOM | 187 | CG | ARG | A | 151 | −16.455 | 43.108 | −23.563 | 1.00 | 31.23 | A C |
| ATOM | 188 | CD | ARG | A | 151 | −16.472 | 44.548 | −24.101 | 1.00 | 30.64 | A C |
| ATOM | 189 | NE | ARG | A | 151 | −16.714 | 44.622 | −25.547 | 1.00 | 29.07 | A N |
| ATOM | 190 | CZ | ARG | A | 151 | −15.761 | 44.546 | −26.494 | 1.00 | 29.58 | A C |
| ATOM | 191 | NH1 | ARG | A | 151 | −14.485 | 44.394 | −26.209 | 1.00 | 27.31 | A N |
| ATOM | 192 | NH2 | ARG | A | 151 | −16.086 | 44.603 | −27.764 | 1.00 | 29.56 | A N |
| ATOM | 193 | C | ARG | A | 151 | −18.127 | 41.513 | −21.469 | 1.00 | 31.52 | A C |
| ATOM | 194 | O | ARG | A | 151 | −19.086 | 42.102 | −20.993 | 1.00 | 28.18 | A O |
| ATOM | 195 | N | GLU | A | 152 | −17.099 | 41.080 | −20.769 | 1.00 | 36.05 | A N |
| ATOM | 196 | CA | GLU | A | 152 | −16.980 | 41.253 | −19.345 | 1.00 | 40.11 | A C |
| ATOM | 197 | CB | GLU | A | 152 | −15.998 | 40.201 | −18.814 | 1.00 | 46.68 | A C |
| ATOM | 198 | CG | GLU | A | 152 | −16.091 | 39.927 | −17.306 | 1.00 | 55.12 | A C |
| ATOM | 199 | CD | GLU | A | 152 | −15.403 | 40.992 | −16.475 | 1.00 | 60.05 | A C |
| ATOM | 200 | OE1 | GLU | A | 152 | −14.213 | 41.323 | −16.787 | 1.00 | 55.34 | A O |
| ATOM | 201 | OE2 | GLU | A | 152 | −16.065 | 41.518 | −15.533 | 1.00 | 66.45 | A O |
| ATOM | 202 | C | GLU | A | 152 | −16.483 | 42.682 | −19.102 | 1.00 | 36.44 | A C |
| ATOM | 203 | O | GLU | A | 152 | −15.367 | 43.043 | −19.548 | 1.00 | 32.14 | A O |
| ATOM | 204 | N | LYS | A | 153 | −17.276 | 43.480 | −18.378 | 1.00 | 34.51 | A N |
| ATOM | 205 | CA | LYS | A | 153 | −17.031 | 44.963 | −18.304 | 1.00 | 38.19 | A C |
| ATOM | 206 | CB | LYS | A | 153 | −18.107 | 45.660 | −17.490 | 1.00 | 35.70 | A C |
| ATOM | 207 | CG | LYS | A | 153 | −19.454 | 45.498 | −18.138 | 1.00 | 33.03 | A C |
| ATOM | 208 | CD | LYS | A | 153 | −20.525 | 46.108 | −17.292 | 1.00 | 32.16 | A C |
| ATOM | 209 | CE | LYS | A | 153 | −21.849 | 45.747 | −17.923 | 1.00 | 32.44 | A C |
| ATOM | 210 | NZ | LYS | A | 153 | −22.974 | 46.572 | −17.437 | 1.00 | 30.12 | A N |
| ATOM | 211 | C | LYS | A | 153 | −15.676 | 45.329 | −17.729 | 1.00 | 40.19 | A C |
| ATOM | 212 | O | LYS | A | 153 | −14.933 | 46.059 | −18.343 | 1.00 | 44.09 | A O |
| ATOM | 213 | N | GLN | A | 154 | −15.362 | 44.786 | −16.560 | 1.00 | 43.88 | A N |
| ATOM | 214 | CA | GLN | A | 154 | −14.053 | 44.964 | −15.929 | 1.00 | 47.04 | A C |
| ATOM | 215 | CB | GLN | A | 154 | −13.903 | 43.985 | −14.764 | 1.00 | 56.46 | A C |
| ATOM | 216 | CG | GLN | A | 154 | −14.614 | 44.397 | −13.498 | 1.00 | 62.88 | A C |
| ATOM | 217 | CD | GLN | A | 154 | −13.675 | 45.170 | −12.590 | 1.00 | 75.28 | A C |
| ATOM | 218 | OE1 | GLN | A | 154 | −13.177 | 44.634 | −11.591 | 1.00 | 80.65 | A O |
| ATOM | 219 | NE2 | GLN | A | 154 | −13.395 | 46.432 | −12.950 | 1.00 | 81.26 | A N |
| ATOM | 220 | C | GLN | A | 154 | −12.886 | 44.764 | −16.875 | 1.00 | 44.14 | A C |
| ATOM | 221 | O | GLN | A | 154 | −12.178 | 45.690 | −17.180 | 1.00 | 44.24 | A O |
| ATOM | 222 | N | SER | A | 155 | −12.717 | 43.541 | −17.356 | 1.00 | 43.29 | A N |
| ATOM | 223 | CA | SER | A | 155 | −11.610 | 43.178 | −18.210 | 1.00 | 38.19 | A C |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 224 | CB | SER | A | 155 | −11.489 | 41.646 | −18.220 | 1.00 | 44.26 | A | C |
| ATOM | 225 | OG | SER | A | 155 | −12.706 | 41.017 | −18.636 | 1.00 | 40.57 | A | O |
| ATOM | 226 | C | SER | A | 155 | −11.767 | 43.658 | −19.638 | 1.00 | 32.67 | A | C |
| ATOM | 227 | O | SER | A | 155 | −10.772 | 43.882 | −20.300 | 1.00 | 30.41 | A | O |
| ATOM | 228 | N | LYS | A | 156 | −13.012 | 43.796 | −20.101 | 1.00 | 36.04 | A | N |
| ATOM | 229 | CA | LYS | A | 156 | −13.379 | 44.071 | −21.517 | 1.00 | 37.45 | A | C |
| ATOM | 230 | CB | LYS | A | 156 | −12.665 | 45.302 | −22.080 | 1.00 | 41.55 | A | C |
| ATOM | 231 | CG | LYS | A | 156 | −13.106 | 46.583 | −21.416 | 1.00 | 45.59 | A | C |
| ATOM | 232 | CD | LYS | A | 156 | −12.301 | 47.723 | −21.973 | 1.00 | 49.18 | A | C |
| ATOM | 233 | CE | LYS | A | 156 | −12.941 | 49.024 | −21.585 | 1.00 | 54.19 | A | C |
| ATOM | 234 | NZ | LYS | A | 156 | −12.152 | 50.090 | −22.249 | 1.00 | 63.04 | A | N |
| ATOM | 235 | C | LYS | A | 156 | −13.130 | 42.890 | −22.427 | 1.00 | 38.52 | A | C |
| ATOM | 236 | O | LYS | A | 156 | −12.861 | 43.038 | −23.630 | 1.00 | 32.51 | A | O |
| ATOM | 237 | N | PHE | A | 157 | −13.260 | 41.712 | −21.839 | 1.00 | 40.11 | A | N |
| ATOM | 238 | CA | PHE | A | 157 | −12.873 | 40.486 | −22.491 | 1.00 | 39.75 | A | C |
| ATOM | 239 | CB | PHE | A | 157 | −12.309 | 39.529 | −21.433 | 1.00 | 41.98 | A | C |
| ATOM | 240 | CG | PHE | A | 157 | −11.827 | 38.219 | −21.989 | 1.00 | 41.66 | A | C |
| ATOM | 241 | CD1 | PHE | A | 157 | −10.633 | 38.147 | −22.697 | 1.00 | 42.97 | A | C |
| ATOM | 242 | CE1 | PHE | A | 157 | −10.180 | 36.932 | −23.191 | 1.00 | 45.25 | A | C |
| ATOM | 243 | CZ | PHE | A | 157 | −10.933 | 35.780 | −22.987 | 1.00 | 43.31 | A | C |
| ATOM | 244 | CE2 | PHE | A | 157 | −12.132 | 35.841 | −22.297 | 1.00 | 41.12 | A | C |
| ATOM | 245 | CD2 | PHE | A | 157 | −12.576 | 37.058 | −21.804 | 1.00 | 40.79 | A | C |
| ATOM | 246 | C | PHE | A | 157 | −14.092 | 39.877 | −23.199 | 1.00 | 32.16 | A | C |
| ATOM | 247 | O | PHE | A | 157 | −15.121 | 39.666 | −22.581 | 1.00 | 26.67 | A | O |
| ATOM | 248 | N | ILE | A | 158 | −13.947 | 39.580 | −24.482 | 1.00 | 31.96 | A | N |
| ATOM | 249 | CA | ILE | A | 158 | −15.038 | 38.991 | −25.272 | 1.00 | 31.33 | A | C |
| ATOM | 250 | CB | ILE | A | 158 | −14.763 | 39.040 | −26.795 | 1.00 | 32.37 | A | C |
| ATOM | 251 | CG1 | ILE | A | 158 | −14.764 | 40.493 | −27.299 | 1.00 | 31.82 | A | C |
| ATOM | 252 | CD1 | ILE | A | 158 | −16.113 | 41.163 | −27.178 | 1.00 | 33.97 | A | C |
| ATOM | 253 | CG2 | ILE | A | 158 | −15.807 | 38.217 | −27.576 | 1.00 | 32.85 | A | C |
| ATOM | 254 | C | ILE | A | 158 | −15.201 | 37.528 | −24.904 | 1.00 | 29.75 | A | C |
| ATOM | 255 | O | ILE | A | 158 | −14.221 | 36.770 | −24.799 | 1.00 | 26.92 | A | O |
| ATOM | 256 | N | LEU | A | 159 | −16.442 | 37.125 | −24.791 | 1.00 | 24.15 | A | N |
| ATOM | 257 | CA | LEU | A | 159 | −16.746 | 35.755 | −24.528 | 1.00 | 26.81 | A | C |
| ATOM | 258 | CB | LEU | A | 159 | −16.452 | 35.501 | −23.060 | 1.00 | 30.57 | A | C |
| ATOM | 259 | CG | LEU | A | 159 | −16.993 | 36.456 | −22.000 | 1.00 | 31.58 | A | C |
| ATOM | 260 | CD1 | LEU | A | 159 | −18.499 | 36.203 | −21.950 | 1.00 | 33.75 | A | C |
| ATOM | 261 | CD2 | LEU | A | 159 | −16.341 | 36.228 | −20.629 | 1.00 | 31.94 | A | C |
| ATOM | 262 | C | LEU | A | 159 | 18.198 | 35.468 | 24.995 | 1.00 | 25.71 | A | C |
| ATOM | 263 | O | LEU | A | 159 | −18.771 | 36.297 | −25.672 | 1.00 | 26.40 | A | O |
| ATOM | 264 | N | ALA | A | 160 | −18.749 | 34.298 | −24.753 | 1.00 | 23.73 | A | N |
| ATOM | 265 | CA | ALA | A | 160 | −20.110 | 34.007 | −25.186 | 1.00 | 24.65 | A | C |
| ATOM | 266 | CB | ALA | A | 160 | −20.165 | 32.795 | −26.081 | 1.00 | 24.57 | A | C |
| ATOM | 267 | C | ALA | A | 160 | −20.934 | 33.737 | −23.968 | 1.00 | 26.31 | A | C |
| ATOM | 268 | O | ALA | A | 160 | −20.456 | 33.176 | −23.040 | 1.00 | 28.06 | A | O |
| ATOM | 269 | N | LEU | A | 161 | −22.194 | 34.089 | −23.999 | 1.00 | 26.89 | A | N |
| ATOM | 270 | CA | LEU | A | 161 | −23.029 | 33.890 | −22.875 | 1.00 | 26.97 | A | C |
| ATOM | 271 | CB | LEU | A | 161 | −23.468 | 35.223 | −22.344 | 1.00 | 30.59 | A | C |
| ATOM | 272 | CG | LEU | A | 161 | −24.214 | 35.211 | −21.027 | 1.00 | 32.49 | A | C |
| ATOM | 273 | CD1 | LEU | A | 161 | −23.262 | 34.832 | −19.898 | 1.00 | 33.23 | A | C |
| ATOM | 274 | CD2 | LEU | A | 161 | −24.755 | 36.612 | −20.843 | 1.00 | 33.49 | A | C |
| ATOM | 275 | C | LEU | A | 161 | −24.215 | 33.127 | −23.347 | 1.00 | 27.97 | A | C |
| ATOM | 276 | O | LEU | A | 161 | −25.041 | 33.644 | −24.099 | 1.00 | 27.66 | A | O |
| ATOM | 277 | N | LYS | A | 162 | −24.300 | 31.883 | −22.883 | 1.00 | 28.28 | A | N |
| ATOM | 278 | CA | LYS | A | 162 | −25.332 | 30.987 | −23.282 | 1.00 | 27.15 | A | C |
| ATOM | 279 | CB | LYS | A | 162 | −24.797 | 29.570 | −23.331 | 1.00 | 30.32 | A | C |
| ATOM | 280 | CG | LYS | A | 162 | −25.854 | 28.501 | −23.430 | 1.00 | 30.88 | A | C |
| ATOM | 281 | CD | LYS | A | 162 | −25.202 | 27.191 | −23.829 | 1.00 | 31.20 | A | C |
| ATOM | 282 | CE | LYS | A | 162 | −26.282 | 26.153 | −23.983 | 1.00 | 29.17 | A | C |
| ATOM | 283 | NZ | LYS | A | 162 | −25.688 | 24.996 | −24.626 | 1.00 | 32.80 | A | N |
| ATOM | 284 | C | LYS | A | 162 | −26.448 | 31.102 | −22.290 | 1.00 | 27.44 | A | C |
| ATOM | 285 | O | LYS | A | 162 | −26.226 | 31.025 | −21.079 | 1.00 | 26.15 | A | O |
| ATOM | 286 | N | VAL | A | 163 | −27.647 | 31.296 | −22.813 | 1.00 | 26.03 | A | N |
| ATOM | 287 | CA | VAL | A | 163 | −28.800 | 31.539 | −21.989 | 1.00 | 26.28 | A | C |
| ATOM | 288 | CB | VAL | A | 163 | −29.464 | 32.859 | −22.377 | 1.00 | 28.10 | A | C |
| ATOM | 289 | CG1 | VAL | A | 163 | −30.746 | 33.105 | −21.586 | 1.00 | 28.38 | A | C |
| ATOM | 290 | CG2 | VAL | A | 163 | −28.474 | 33.995 | −22.158 | 1.00 | 28.80 | A | C |
| ATOM | 291 | C | VAL | A | 163 | −29.734 | 30.398 | −22.210 | 1.00 | 28.17 | A | C |
| ATOM | 292 | O | VAL | A | 163 | −30.032 | 30.012 | −23.361 | 1.00 | 30.69 | A | O |
| ATOM | 293 | N | LEU | A | 164 | −30.187 | 29.845 | −21.093 | 1.00 | 29.31 | A | N |
| ATOM | 294 | CA | LEU | A | 164 | −31.103 | 28.699 | −21.072 | 1.00 | 30.82 | A | C |
| ATOM | 295 | CB | LEU | A | 164 | −30.425 | 27.496 | −20.423 | 1.00 | 30.41 | A | C |
| ATOM | 296 | CG | LEU | A | 164 | −29.206 | 26.970 | −21.225 | 1.00 | 34.17 | A | C |
| ATOM | 297 | CD1 | LEU | A | 164 | −28.120 | 26.370 | −20.360 | 1.00 | 35.43 | A | C |
| ATOM | 298 | CD2 | LEU | A | 164 | −29.634 | 25.934 | −22.233 | 1.00 | 37.49 | A | C |
| ATOM | 299 | C | LEU | A | 164 | −32.351 | 29.076 | −20.273 | 1.00 | 31.69 | A | C |
| ATOM | 300 | O | LEU | A | 164 | −32.240 | 29.608 | −19.156 | 1.00 | 32.10 | A | O |
| ATOM | 301 | N | PHE | A | 165 | −33.520 | 28.756 | −20.827 | 1.00 | 28.55 | A | N |

APPENDIX B-continued

Atomic coordinates of Aurora A + Activating Monobody Mb54 + AMPPCP

| | | | | | | | | | | | |
|---|---|---|---|---|---|---|---|---|---|---|---|
| ATOM | 302 | CA | PHE | A | 165 | −34.796 | 29.045 | −20.143 | 1.00 | 30.09 | A | C |
| ATOM | 303 | CB | PHE | A | 165 | −35.914 | 29.487 | −21.154 | 1.00 | 31.07 | A | C |
| ATOM | 304 | CG | PHE | A | 165 | −35.677 | 30.866 | −21.706 | 1.00 | 33.40 | A | C |
| ATOM | 305 | CD1 | PHE | A | 165 | −36.128 | 31.997 | −21.020 | 1.00 | 35.43 | A | C |
| ATOM | 306 | CE1 | PHE | A | 165 | −35.824 | 33.279 | −21.490 | 1.00 | 36.16 | A | C |
| ATOM | 307 | CZ | PHE | A | 165 | −35.060 | 33.454 | −22.642 | 1.00 | 33.74 | A | C |
| ATOM | 308 | CE2 | PHE | A | 165 | −34.606 | 32.345 | −23.331 | 1.00 | 35.80 | A | C |
| ATOM | 309 | CD2 | PHE | A | 165 | −34.889 | 31.056 | −22.856 | 1.00 | 34.03 | A | C |
| ATOM | 310 | C | PHE | A | 165 | −35.216 | 27.847 | −19.303 | 1.00 | 28.07 | A | C |
| ATOM | 311 | O | PHE | A | 165 | −35.476 | 26.749 | −19.829 | 1.00 | 24.70 | A | O |
| ATOM | 312 | N | LYS | A | 166 | −35.295 | 28.085 | −17.989 | 1.00 | 31.49 | A | N |
| ATOM | 313 | CA | LYS | A | 166 | −35.694 | 27.054 | −17.004 | 1.00 | 30.40 | A | C |
| ATOM | 314 | CB | LYS | A | 166 | −35.874 | 27.676 | −15.663 | 1.00 | 28.24 | A | C |
| ATOM | 315 | CG | LYS | A | 166 | −34.563 | 28.128 | −15.085 | 1.00 | 29.76 | A | C |
| ATOM | 316 | CD | LYS | A | 166 | −34.766 | 28.757 | −13.715 | 1.00 | 30.76 | A | C |
| ATOM | 317 | CE | LYS | A | 166 | −33.399 | 29.136 | −13.138 | 1.00 | 32.71 | A | C |
| ATOM | 318 | NZ | LYS | A | 166 | −33.541 | 29.760 | −11.817 | 1.00 | 31.62 | A | N |
| ATOM | 319 | C | LYS | A | 166 | −36.984 | 26.342 | −17.420 | 1.00 | 33.68 | A | C |
| ATOM | 320 | O | LYS | A | 166 | −37.083 | 25.112 | −17.326 | 1.00 | 32.09 | A | O |
| ATOM | 321 | N | ALA | A | 167 | −37.949 | 27.121 | −17.918 | 1.00 | 34.50 | A | N |
| ATOM | 322 | CA | ALA | A | 167 | −39.212 | 26.558 | −18.364 | 1.00 | 34.79 | A | C |
| ATOM | 323 | CB | ALA | A | 167 | −40.147 | 27.661 | −18.890 | 1.00 | 34.01 | A | C |
| ATOM | 324 | C | ALA | A | 167 | −38.945 | 25.491 | −19.432 | 1.00 | 35.51 | A | C |
| ATOM | 325 | O | ALA | A | 167 | −39.547 | 24.424 | −19.415 | 1.00 | 32.45 | A | O |
| ATOM | 326 | N | GLN | A | 168 | −38.018 | 25.760 | −20.343 | 1.00 | 35.47 | A | N |
| ATOM | 327 | CA | GLN | A | 168 | −37.767 | 24.819 | −21.451 | 1.00 | 35.68 | A | C |
| ATOM | 328 | CB | GLN | A | 168 | −37.106 | 25.548 | −22.594 | 1.00 | 36.11 | A | C |
| ATOM | 329 | CG | GLN | A | 168 | −37.947 | 26.693 | −23.123 | 1.00 | 37.09 | A | C |
| ATOM | 330 | CD | GLN | A | 168 | −37.246 | 27.417 | −24.243 | 1.00 | 37.56 | A | C |
| ATOM | 331 | OE1 | GLN | A | 168 | −37.039 | 28.616 | −24.182 | 1.00 | 44.75 | A | O |
| ATOM | 332 | NE2 | GLN | A | 168 | −36.862 | 26.686 | −25.264 | 1.00 | 37.34 | A | N |
| ATOM | 333 | C | GLN | A | 168 | −36.901 | 23.626 | −21.024 | 1.00 | 36.14 | A | C |
| ATOM | 334 | O | GLN | A | 168 | −37.031 | 22.523 | −21.556 | 1.00 | 35.72 | A | O |
| ATOM | 335 | N | LEU | A | 169 | −35.983 | 23.884 | −20.099 | 1.00 | 34.86 | A | N |
| ATOM | 336 | CA | LEU | A | 169 | −35.173 | 22.835 | −19.491 | 1.00 | 35.00 | A | C |
| ATOM | 337 | CB | LEU | A | 169 | −34.202 | 23.416 | −18.450 | 1.00 | 34.63 | A | C |
| ATOM | 338 | CG | LEU | A | 169 | −33.068 | 24.273 | −19.003 | 1.00 | 34.00 | A | C |
| ATOM | 339 | CD1 | LEU | A | 169 | −32.277 | 24.873 | −17.871 | 1.00 | 33.07 | A | C |
| ATOM | 340 | CD2 | LEU | A | 169 | −32.172 | 23.429 | −19.917 | 1.00 | 34.68 | A | C |
| ATOM | 341 | C | LEU | A | 169 | −36.063 | 21.862 | −18.758 | 1.00 | 36.94 | A | C |
| ATOM | 342 | O | LEU | A | 169 | −35.933 | 20.641 | −18.913 | 1.00 | 39.22 | A | O |
| ATOM | 343 | N | GLU | A | 170 | −36.967 | 22.402 | −17.946 | 1.00 | 37.97 | A | N |
| ATOM | 344 | CA | GLU | A | 170 | −37.763 | 21.559 | −17.069 | 1.00 | 39.51 | A | C |
| ATOM | 345 | CB | GLU | A | 170 | −38.428 | 22.384 | −15.983 | 1.00 | 41.66 | A | C |
| ATOM | 346 | CG | GLU | A | 170 | −37.381 | 22.958 | −15.018 | 1.00 | 40.94 | A | C |
| ATOM | 347 | CD | GLU | A | 170 | −37.905 | 24.137 | −14.213 | 1.00 | 46.52 | A | C |
| ATOM | 348 | OE1 | GLU | A | 170 | −39.147 | 24.339 | −14.220 | 1.00 | 48.62 | A | O |
| ATOM | 349 | OE2 | GLU | A | 170 | −37.102 | 24.862 | −13.563 | 1.00 | 40.79 | A | O |
| ATOM | 350 | C | GLU | A | 170 | −38.712 | 20.756 | −17.914 | 1.00 | 36.09 | A | C |
| ATOM | 351 | O | GLU | A | 170 | −38.869 | 19.567 | −17.690 | 1.00 | 33.54 | A | O |
| ATOM | 352 | N | LYS | A | 171 | −39.233 | 21.373 | −18.965 | 1.00 | 39.09 | A | N |
| ATOM | 353 | CA | LYS | A | 171 | −40.082 | 20.659 | −19.925 | 1.00 | 42.47 | A | C |
| ATOM | 354 | CB | LYS | A | 171 | −40.596 | 21.627 | −21.000 | 1.00 | 46.39 | A | C |
| ATOM | 355 | CG | LYS | A | 171 | −41.485 | 21.044 | −22.097 | 1.00 | 49.66 | A | C |
| ATOM | 356 | CD | LYS | A | 171 | −42.756 | 20.399 | −21.542 | 1.00 | 56.56 | A | C |
| ATOM | 357 | CE | LYS | A | 171 | −43.500 | 19.624 | −22.621 | 1.00 | 58.28 | A | C |
| ATOM | 358 | NZ | LYS | A | 171 | −43.915 | 20.517 | −23.752 | 1.00 | 62.53 | A | N |
| ATOM | 359 | C | LYS | A | 171 | −39.351 | 19.459 | −20.542 | 1.00 | 41.07 | A | C |
| ATOM | 360 | O | LYS | A | 171 | −39.887 | 18.354 | −20.571 | 1.00 | 39.07 | A | O |
| ATOM | 361 | N | ALA | A | 172 | −38.118 | 19.664 | −20.988 | 1.00 | 40.02 | A | N |
| ATOM | 362 | CA | ALA | A | 172 | −37.331 | 18.587 | −21.617 | 1.00 | 42.12 | A | C |
| ATOM | 363 | CB | ALA | A | 172 | −36.233 | 19.227 | −22.443 | 1.00 | 45.72 | A | C |
| ATOM | 364 | C | ALA | A | 172 | −36.714 | 17.504 | −20.669 | 1.00 | 39.85 | A | C |
| ATOM | 365 | O | ALA | A | 172 | −36.219 | 16.470 | −21.128 | 1.00 | 37.82 | A | O |
| ATOM | 366 | N | GLY | A | 173 | −36.706 | 17.770 | −19.371 | 1.00 | 35.80 | A | N |
| ATOM | 367 | CA | GLY | A | 173 | −36.184 | 16.829 | −18.394 | 1.00 | 34.95 | A | C |
| ATOM | 368 | C | GLY | A | 173 | −34.687 | 16.849 | −18.175 | 1.00 | 34.19 | A | C |
| ATOM | 369 | O | GLY | A | 173 | −34.167 | 15.932 | −17.568 | 1.00 | 35.89 | A | O |
| ATOM | 370 | N | VAL | A | 174 | −33.985 | 17.895 | −18.591 | 1.00 | 31.61 | A | N |
| ATOM | 371 | CA | VAL | A | 174 | −32.541 | 17.807 | −18.727 | 1.00 | 33.16 | A | C |
| ATOM | 372 | CB | VAL | A | 174 | −32.053 | 18.205 | −20.170 | 1.00 | 36.72 | A | C |
| ATOM | 373 | CG1 | VAL | A | 174 | −32.688 | 17.347 | −21.284 | 1.00 | 36.40 | A | C |
| ATOM | 374 | CG2 | VAL | A | 174 | −32.280 | 19.683 | −20.457 | 1.00 | 38.38 | A | C |
| ATOM | 375 | C | VAL | A | 174 | −31.711 | 18.568 | −17.695 | 1.00 | 33.22 | A | C |
| ATOM | 376 | O | VAL | A | 174 | −30.483 | 18.740 | −17.919 | 1.00 | 35.31 | A | O |
| ATOM | 377 | N | GLU | A | 175 | −32.298 | 18.999 | −16.573 | 1.00 | 34.82 | A | N |
| ATOM | 378 | CA | GLU | A | 175 | −31.531 | 19.801 | −15.589 | 1.00 | 36.69 | A | C |
| ATOM | 379 | CB | GLU | A | 175 | −32.425 | 20.410 | −14.487 | 1.00 | 41.46 | A | C |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 380 | CG | GLU | A | 175 | −31.715 | 21.416 | −13.508 | 1.00 | 47.14 | A | C |
| ATOM | 381 | CD | GLU | A | 175 | −31.069 | 20.820 | −12.221 | 1.00 | 46.87 | A | C |
| ATOM | 382 | OE1 | GLU | A | 175 | −30.302 | 21.545 | −11.554 | 1.00 | 50.88 | A | O |
| ATOM | 383 | OE2 | GLU | A | 175 | −31.314 | 19.647 | −11.837 | 1.00 | 50.86 | A | O |
| ATOM | 384 | C | GLU | A | 175 | −30.336 | 19.039 | −14.982 | 1.00 | 36.38 | A | C |
| ATOM | 385 | O | GLU | A | 175 | −29.285 | 19.642 | −14.691 | 1.00 | 38.04 | A | O |
| ATOM | 386 | N | HIS | A | 176 | −30.473 | 17.726 | −14.812 | 1.00 | 38.29 | A | N |
| ATOM | 387 | CA | HIS | A | 176 | −29.381 | 16.909 | −14.255 | 1.00 | 39.56 | A | C |
| ATOM | 388 | CB | HIS | A | 176 | −29.827 | 15.450 | −14.014 | 1.00 | 42.18 | A | C |
| ATOM | 389 | CG | HIS | A | 176 | −30.857 | 15.307 | −12.925 | 1.00 | 53.70 | A | C |
| ATOM | 390 | ND1 | HIS | A | 176 | −31.233 | 16.349 | −12.089 | 1.00 | 61.11 | A | N |
| ATOM | 391 | CE1 | HIS | A | 176 | −32.171 | 15.936 | −11.256 | 1.00 | 56.27 | A | C |
| ATOM | 392 | NE2 | HIS | A | 176 | −32.408 | 14.661 | −11.503 | 1.00 | 57.30 | A | N |
| ATOM | 393 | CD2 | HIS | A | 176 | −31.599 | 14.240 | −12.536 | 1.00 | 58.56 | A | C |
| ATOM | 394 | C | HIS | A | 176 | −28.140 | 16.972 | −15.125 | 1.00 | 33.86 | A | C |
| ATOM | 395 | O | HIS | A | 176 | −27.027 | 17.055 | −14.582 | 1.00 | 33.88 | A | O |
| ATOM | 396 | N | GLN | A | 177 | −28.341 | 16.998 | −16.458 | 1.00 | 30.54 | A | N |
| ATOM | 397 | CA | AGLN | A | 177 | −27.254 | 17.135 | −17.460 | 0.50 | 29.78 | A | C |
| ATOM | 398 | CA | BGLN | A | 177 | −27.212 | 17.108 | −17.388 | 0.50 | 28.21 | A | C |
| ATOM | 399 | CB | AGLN | A | 177 | −27.769 | 16.990 | −18.908 | 0.50 | 29.34 | A | C |
| ATOM | 400 | CB | BGLN | A | 177 | −27.613 | 16.690 | −18.802 | 0.50 | 25.75 | A | C |
| ATOM | 401 | CG | AGLN | A | 177 | −28.496 | 15.706 | −19.302 | 0.50 | 30.35 | A | C |
| ATOM | 402 | CG | BGLN | A | 177 | −27.839 | 15.190 | −18.924 | 0.50 | 24.71 | A | C |
| ATOM | 403 | CD | AGLN | A | 177 | −29.247 | 15.852 | −20.647 | 0.50 | 30.44 | A | C |
| ATOM | 404 | CD | BGLN | A | 177 | −29.211 | 14.777 | −18.466 | 0.50 | 23.01 | A | C |
| ATOM | 405 | OE1 | AGLN | A | 177 | −30.381 | 15.418 | −20.772 | 0.50 | 33.15 | A | O |
| ATOM | 406 | OE1 | BGLN | A | 177 | −30.205 | 15.089 | −19.092 | 0.50 | 23.25 | A | O |
| ATOM | 407 | NE2 | AGLN | A | 177 | −28.629 | 16.484 | −21.627 | 0.50 | 27.53 | A | N |
| ATOM | 408 | NE2 | BGLN | A | 177 | −29.271 | 14.100 | −17.347 | 0.50 | 23.86 | A | N |
| ATOM | 409 | C | GLN | A | 177 | −26.566 | 18.515 | −17.320 | 1.00 | 29.11 | A | C |
| ATOM | 410 | O | GLN | A | 177 | −25.349 | 18.657 | −17.448 | 1.00 | 29.79 | A | O |
| ATOM | 411 | N | LEU | A | 178 | −27.361 | 19.546 | −17.068 | 1.00 | 26.85 | A | N |
| ATOM | 412 | CA | LEU | A | 178 | −26.820 | 20.879 | −16.864 | 1.00 | 26.91 | A | C |
| ATOM | 413 | CB | LEU | A | 178 | −27.971 | 21.911 | −16.824 | 1.00 | 27.01 | A | C |
| ATOM | 414 | CG | LEU | A | 178 | −27.626 | 23.408 | −16.813 | 1.00 | 28.31 | A | C |
| ATOM | 415 | CD1 | LEU | A | 178 | −26.709 | 23.796 | −17.964 | 1.00 | 30.75 | A | C |
| ATOM | 416 | CD2 | LEU | A | 178 | −28.881 | 24.262 | −16.845 | 1.00 | 28.84 | A | C |
| ATOM | 417 | C | LEU | A | 178 | −25.937 | 20.938 | −15.603 | 1.00 | 27.56 | A | C |
| ATOM | 418 | O | LEU | A | 178 | −24.812 | 21.425 | −15.690 | 1.00 | 26.41 | A | O |
| ATOM | 419 | N | ARG | A | 179 | −26.416 | 20.373 | −14.476 | 1.00 | 27.03 | A | N |
| ATOM | 420 | CA | ARG | A | 179 | −25.635 | 20.247 | −13.241 | 1.00 | 26.58 | A | C |
| ATOM | 421 | CB | ARG | A | 179 | −26.401 | 19.420 | −12.165 | 1.00 | 27.34 | A | C |
| ATOM | 422 | CG | ARG | A | 179 | −25.614 | 19.156 | −10.880 | 1.00 | 27.75 | A | C |
| ATOM | 423 | CD | ARG | A | 179 | −26.447 | 18.430 | −9.821 | 1.00 | 29.48 | A | C |
| ATOM | 424 | NE | ARG | A | 179 | −27.508 | 19.284 | −9.283 | 1.00 | 30.84 | A | N |
| ATOM | 425 | CZ | ARG | A | 179 | −27.346 | 20.262 | −8.372 | 1.00 | 31.44 | A | C |
| ATOM | 426 | NH1 | ARG | A | 179 | −26.174 | 20.550 | −7.805 | 1.00 | 29.44 | A | N |
| ATOM | 427 | NH2 | ARG | A | 179 | −28.399 | 20.984 | −8.027 | 1.00 | 34.07 | A | N |
| ATOM | 428 | C | ARG | A | 179 | −24.281 | 19.605 | −13.535 | 1.00 | 26.35 | A | C |
| ATOM | 429 | O | ARG | A | 179 | −23.176 | 20.131 | −13.147 | 1.00 | 24.29 | A | O |
| ATOM | 430 | N | ARG | A | 180 | −24.374 | 18.488 | −14.249 | 1.00 | 25.90 | A | N |
| ATOM | 431 | CA | ARG | A | 180 | −23.193 | 17.723 | −14.568 | 1.00 | 28.81 | A | C |
| ATOM | 432 | CB | ARG | A | 180 | −23.569 | 16.421 | −15.307 | 1.00 | 32.62 | A | C |
| ATOM | 433 | CG | ARG | A | 180 | −22.434 | 15.397 | −15.439 | 1.00 | 34.00 | A | C |
| ATOM | 434 | CD | ARG | A | 180 | −21.914 | 14.819 | −14.107 | 1.00 | 34.18 | A | C |
| ATOM | 435 | NE | ARG | A | 180 | −22.860 | 13.901 | −13.453 | 1.00 | 31.42 | A | N |
| ATOM | 436 | CZ | ARG | A | 180 | −23.080 | 12.634 | −13.801 | 1.00 | 33.65 | A | C |
| ATOM | 437 | NH1 | ARG | A | 180 | −23.980 | 11.901 | −13.151 | 1.00 | 34.73 | A | N |
| ATOM | 438 | NH2 | ARG | A | 180 | −22.446 | 12.076 | −14.814 | 1.00 | 33.22 | A | N |
| ATOM | 439 | C | ARG | A | 180 | −22.228 | 18.563 | −15.399 | 1.00 | 28.30 | A | C |
| ATOM | 440 | O | ARG | A | 180 | −21.006 | 18.639 | −15.099 | 1.00 | 25.46 | A | O |
| ATOM | 441 | N | GLU | A | 181 | −22.765 | 19.200 | −16.440 | 1.00 | 25.71 | A | N |
| ATOM | 442 | CA | GLU | A | 181 | −21.955 | 20.088 | −17.281 | 1.00 | 26.11 | A | C |
| ATOM | 443 | CB | GLU | A | 181 | −22.790 | 20.761 | −18.410 | 1.00 | 26.85 | A | C |
| ATOM | 444 | CG | GLU | A | 181 | −21.931 | 21.652 | −19.313 | 1.00 | 29.31 | A | C |
| ATOM | 445 | CD | GLU | A | 181 | −22.636 | 22.146 | −20.578 | 1.00 | 31.50 | A | C |
| ATOM | 446 | OE1 | GLU | A | 181 | −21.959 | 22.296 | −21.613 | 1.00 | 36.47 | A | O |
| ATOM | 447 | OE2 | GLU | A | 181 | −23.839 | 22.401 | −20.551 | 1.00 | 31.66 | A | O |
| ATOM | 448 | C | GLU | A | 181 | −21.218 | 21.154 | −16.451 | 1.00 | 25.81 | A | C |
| ATOM | 449 | O | GLU | A | 181 | −20.008 | 21.364 | −16.626 | 1.00 | 23.45 | A | O |
| ATOM | 450 | N | VAL | A | 182 | −21.937 | 21.845 | −15.561 | 1.00 | 24.67 | A | N |
| ATOM | 451 | CA | VAL | A | 182 | −21.304 | 22.948 | −14.804 | 1.00 | 24.21 | A | C |
| ATOM | 452 | CB | VAL | A | 182 | −22.346 | 23.842 | −14.042 | 1.00 | 24.66 | A | C |
| ATOM | 453 | CG1 | VAL | A | 182 | −21.650 | 24.953 | −13.262 | 1.00 | 23.71 | A | C |
| ATOM | 454 | CG2 | VAL | A | 182 | −23.345 | 24.482 | −14.997 | 1.00 | 24.77 | A | C |
| ATOM | 455 | C | VAL | A | 182 | −20.249 | 22.437 | −13.831 | 1.00 | 22.96 | A | C |
| ATOM | 456 | O | VAL | A | 182 | −19.117 | 22.981 | −13.731 | 1.00 | 22.00 | A | O |
| ATOM | 457 | N | GLU | A | 183 | −20.628 | 21.391 | −13.106 | 1.00 | 25.33 | A | N |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 458 | CA | GLU | A | 183 | −19.783 | 20.907 | −11.983 | 1.00 | 25.40 | A | C |
| ATOM | 459 | CB | GLU | A | 183 | −20.623 | 19.954 | −11.071 | 1.00 | 27.43 | A | C |
| ATOM | 460 | CG | GLU | A | 183 | −21.651 | 20.762 | −10.234 | 1.00 | 29.88 | A | C |
| ATOM | 461 | CD | GLU | A | 183 | −22.549 | 19.941 | −9.316 | 1.00 | 30.59 | A | C |
| ATOM | 462 | OE1 | GLU | A | 183 | −22.501 | 18.736 | −9.452 | 1.00 | 32.29 | A | O |
| ATOM | 463 | OE2 | GLU | A | 183 | −23.351 | 20.487 | −8.495 | 1.00 | 32.34 | A | O |
| ATOM | 464 | C | GLU | A | 183 | −18.445 | 20.315 | −12.472 | 1.00 | 23.77 | A | C |
| ATOM | 465 | O | GLU | A | 183 | −17.407 | 20.480 | −11.849 | 1.00 | 21.80 | A | O |
| ATOM | 466 | N | ILE | A | 184 | −18.477 | 19.640 | −13.618 | 1.00 | 23.95 | A | N |
| ATOM | 467 | CA | ILE | A | 184 | −17.286 | 19.089 | −14.237 | 1.00 | 23.65 | A | C |
| ATOM | 468 | CB | ILE | A | 184 | −17.686 | 17.886 | −15.118 | 1.00 | 23.93 | A | C |
| ATOM | 469 | CG1 | ILE | A | 184 | −18.316 | 16.852 | −14.191 | 1.00 | 26.65 | A | C |
| ATOM | 470 | CD1 | ILE | A | 184 | −18.262 | 15.412 | −14.681 | 1.00 | 27.91 | A | C |
| ATOM | 471 | CG2 | ILE | A | 184 | −16.512 | 17.304 | −15.907 | 1.00 | 23.28 | A | C |
| ATOM | 472 | C | ILE | A | 184 | −16.546 | 20.146 | −15.019 | 1.00 | 22.64 | A | C |
| ATOM | 473 | O | ILE | A | 184 | −15.329 | 20.358 | −14.800 | 1.00 | 23.43 | A | O |
| ATOM | 474 | N | GLN | A | 185 | −17.249 | 20.796 | −15.945 | 1.00 | 21.71 | A | N |
| ATOM | 475 | CA | GLN | A | 185 | −16.564 | 21.608 | −16.975 | 1.00 | 23.22 | A | C |
| ATOM | 476 | CB | GLN | A | 185 | −17.486 | 21.955 | −18.159 | 1.00 | 24.17 | A | C |
| ATOM | 477 | CG | GLN | A | 185 | −16.761 | 22.274 | −19.458 | 1.00 | 24.87 | A | C |
| ATOM | 478 | CD | GLN | A | 185 | −17.701 | 22.703 | −20.576 | 1.00 | 26.41 | A | C |
| ATOM | 479 | OE1 | GLN | A | 185 | −18.916 | 22.478 | −20.517 | 1.00 | 25.15 | A | O |
| ATOM | 480 | NE2 | GLN | A | 185 | −17.139 | 23.370 | −21.590 | 1.00 | 27.36 | A | N |
| ATOM | 481 | C | GLN | A | 185 | −15.944 | 22.835 | −16.387 | 1.00 | 20.79 | A | C |
| ATOM | 482 | O | GLN | A | 185 | −14.956 | 23.270 | −16.885 | 1.00 | 22.19 | A | O |
| ATOM | 483 | N | SER | A | 186 | −16.474 | 23.359 | −15.281 | 1.00 | 23.16 | A | N |
| ATOM | 484 | CA | SER | A | 186 | −15.813 | 24.501 | −14.557 | 1.00 | 23.12 | A | C |
| ATOM | 485 | CB | SER | A | 186 | −16.528 | 24.789 | −13.280 | 1.00 | 23.70 | A | C |
| ATOM | 486 | OG | SER | A | 186 | −17.850 | 25.118 | −13.590 | 1.00 | 26.73 | A | O |
| ATOM | 487 | C | SER | A | 186 | −14.415 | 24.265 | −14.144 | 1.00 | 23.88 | A | C |
| ATOM | 488 | O | SER | A | 186 | −13.661 | 25.213 | −13.936 | 1.00 | 23.37 | A | O |
| ATOM | 489 | N | HIS | A | 187 | −14.083 | 22.985 | −13.947 | 1.00 | 23.30 | A | N |
| ATOM | 490 | CA | HIS | A | 187 | −12.774 | 22.609 | −13.489 | 1.00 | 22.36 | A | C |
| ATOM | 491 | CB | HIS | A | 187 | −12.908 | 21.426 | −12.536 | 1.00 | 22.81 | A | C |
| ATOM | 492 | CG | HIS | A | 187 | −13.581 | 21.782 | −11.263 | 1.00 | 22.51 | A | C |
| ATOM | 493 | ND1 | HIS | A | 187 | −12.902 | 22.290 | −10.170 | 1.00 | 23.32 | A | N |
| ATOM | 494 | CE1 | HIS | A | 187 | −13.775 | 22.533 | −9.209 | 1.00 | 24.26 | A | C |
| ATOM | 495 | NE2 | HIS | A | 187 | −14.995 | 22.254 | −9.654 | 1.00 | 22.28 | A | N |
| ATOM | 496 | CD2 | HIS | A | 187 | −14.894 | 21.768 | −10.931 | 1.00 | 23.38 | A | C |
| ATOM | 497 | C | HIS | A | 187 | −11.795 | 22.324 | −14.614 | 1.00 | 23.09 | A | C |
| ATOM | 498 | O | HIS | A | 187 | −10.598 | 22.150 | −14.360 | 1.00 | 24.38 | A | O |
| ATOM | 499 | N | LEU | A | 188 | −12.240 | 22.351 | −15.862 | 1.00 | 22.60 | A | N |
| ATOM | 500 | CA | LEU | A | 188 | −11.352 | 21.929 | −16.944 | 1.00 | 25.38 | A | C |
| ATOM | 501 | CB | LEU | A | 188 | −12.124 | 20.995 | −17.888 | 1.00 | 27.27 | A | C |
| ATOM | 502 | CG | LEU | A | 188 | −12.839 | 19.799 | −17.262 | 1.00 | 27.33 | A | C |
| ATOM | 503 | CD1 | LEU | A | 188 | −13.708 | 19.095 | −18.287 | 1.00 | 27.08 | A | C |
| ATOM | 504 | CD2 | LEU | A | 188 | −11.840 | 18.797 | −16.661 | 1.00 | 28.02 | A | C |
| ATOM | 505 | C | LEU | A | 188 | −10.655 | 23.045 | −17.745 | 1.00 | 26.16 | A | C |
| ATOM | 506 | O | LEU | A | 188 | −11.305 | 23.803 | −18.469 | 1.00 | 26.77 | A | O |
| ATOM | 507 | N | ARG | A | 189 | −9.329 | 23.106 | −17.640 | 1.00 | 25.15 | A | N |
| ATOM | 508 | CA | ARG | A | 189 | −8.533 | 24.168 | −18.178 | 1.00 | 26.60 | A | C |
| ATOM | 509 | CB | ARG | A | 189 | −7.821 | 24.922 | −17.056 | 1.00 | 30.06 | A | C |
| ATOM | 510 | CG | ARG | A | 189 | −8.808 | 25.732 | −16.255 | 1.00 | 37.19 | A | C |
| ATOM | 511 | CD | ARG | A | 189 | −8.268 | 26.523 | −15.054 | 1.00 | 47.96 | A | C |
| ATOM | 512 | NE | ARG | A | 189 | −9.439 | 26.845 | −14.199 | 1.00 | 56.94 | A | N |
| ATOM | 513 | CZ | ARG | A | 189 | −9.878 | 26.127 | −13.149 | 1.00 | 60.94 | A | C |
| ATOM | 514 | NH1 | ARG | A | 189 | −9.212 | 25.056 | −12.694 | 1.00 | 66.83 | A | N |
| ATOM | 515 | NH2 | ARG | A | 189 | −10.991 | 26.495 | −12.514 | 1.00 | 60.04 | A | N |
| ATOM | 516 | C | ARG | A | 189 | −7.524 | 23.583 | −19.089 | 1.00 | 26.76 | A | C |
| ATOM | 517 | O | ARG | A | 189 | −6.483 | 23.103 | −18.644 | 1.00 | 24.20 | A | O |
| ATOM | 518 | N | HIS | A | 190 | −7.822 | 23.618 | −20.385 | 1.00 | 26.08 | A | N |
| ATOM | 519 | CA | HIS | A | 190 | −6.890 | 23.080 | −21.371 | 1.00 | 24.74 | A | C |
| ATOM | 520 | CB | HIS | A | 190 | −7.187 | 21.580 | −21.531 | 1.00 | 24.19 | A | C |
| ATOM | 521 | CG | HIS | A | 190 | −6.181 | 20.887 | −22.377 | 1.00 | 24.91 | A | C |
| ATOM | 522 | ND1 | HIS | A | 190 | −6.341 | 20.749 | −23.743 | 1.00 | 23.88 | A | N |
| ATOM | 523 | CE1 | HIS | A | 190 | −5.273 | 20.160 | −24.245 | 1.00 | 25.94 | A | C |
| ATOM | 524 | NE2 | HIS | A | 190 | −4.415 | 19.934 | −23.255 | 1.00 | 26.02 | A | N |
| ATOM | 525 | CD2 | HIS | A | 190 | −4.952 | 20.396 | −22.079 | 1.00 | 23.61 | A | C |
| ATOM | 526 | C | HIS | A | 190 | −7.070 | 23.803 | −22.705 | 1.00 | 22.42 | A | C |
| ATOM | 527 | O | HIS | A | 190 | −8.189 | 24.112 | −23.037 | 1.00 | 22.94 | A | O |
| ATOM | 528 | N | PRO | A | 191 | −6.005 | 24.034 | −23.492 | 1.00 | 22.06 | A | N |
| ATOM | 529 | CA | PRO | A | 191 | −6.201 | 24.757 | −24.803 | 1.00 | 22.36 | A | C |
| ATOM | 530 | CB | PRO | A | 191 | −4.841 | 24.618 | −25.513 | 1.00 | 20.27 | A | C |
| ATOM | 531 | CG | PRO | A | 191 | −3.858 | 24.355 | −24.430 | 1.00 | 21.04 | A | C |
| ATOM | 532 | CD | PRO | A | 191 | −4.579 | 23.689 | −23.285 | 1.00 | 21.65 | A | C |
| ATOM | 533 | C | PRO | A | 191 | −7.279 | 24.238 | −25.745 | 1.00 | 21.93 | A | C |
| ATOM | 534 | O | PRO | A | 191 | −7.856 | 25.016 | −26.464 | 1.00 | 20.09 | A | O |
| ATOM | 535 | N | ASN | A | 192 | −7.521 | 22.925 | −25.714 | 1.00 | 21.51 | A | N |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 536 | CA | ASN | A | 192 | −8.499 | 22.252 | −26.562 | 1.00 | 20.04 | A | C |
| ATOM | 537 | CB | ASN | A | 192 | −7.805 | 21.055 | −27.239 | 1.00 | 20.93 | A | C |
| ATOM | 538 | CG | ASN | A | 192 | −6.609 | 21.482 | −28.010 | 1.00 | 19.92 | A | C |
| ATOM | 539 | OD1 | ASN | A | 192 | −5.486 | 21.209 | −27.654 | 1.00 | 22.19 | A | O |
| ATOM | 540 | ND2 | ASN | A | 192 | −6.846 | 22.216 | −29.043 | 1.00 | 21.65 | A | N |
| ATOM | 541 | C | ASN | A | 192 | −9.803 | 21.838 | −25.878 | 1.00 | 19.01 | A | C |
| ATOM | 542 | O | ASN | A | 192 | −10.509 | 20.974 | −26.379 | 1.00 | 17.67 | A | O |
| ATOM | 543 | N | ILE | A | 193 | −10.110 | 22.450 | −24.744 | 1.00 | 18.49 | A | N |
| ATOM | 544 | CA | ILE | A | 193 | −11.393 | 22.254 | −24.086 | 1.00 | 19.39 | A | C |
| ATOM | 545 | CB | ILE | A | 193 | −11.259 | 21.624 | −22.669 | 1.00 | 20.64 | A | C |
| ATOM | 546 | CG1 | ILE | A | 193 | −10.657 | 20.201 | −22.738 | 1.00 | 22.35 | A | C |
| ATOM | 547 | CD1 | ILE | A | 193 | −10.448 | 19.511 | −21.379 | 1.00 | 22.11 | A | C |
| ATOM | 548 | CG2 | ILE | A | 193 | −12.629 | 21.526 | −21.978 | 1.00 | 20.43 | A | C |
| ATOM | 549 | C | ILE | A | 193 | −11.997 | 23.632 | −23.979 | 1.00 | 19.22 | A | C |
| ATOM | 550 | O | ILE | A | 193 | −11.344 | 24.560 | −23.513 | 1.00 | 18.32 | A | O |
| ATOM | 551 | N | LEU | A | 194 | −13.258 | 23.760 | −24.364 | 1.00 | 20.97 | A | N |
| ATOM | 552 | CA | LEU | A | 194 | −13.951 | 25.017 | −24.227 | 1.00 | 21.46 | A | C |
| ATOM | 553 | CB | LEU | A | 194 | −15.339 | 24.937 | −24.859 | 1.00 | 22.29 | A | C |
| ATOM | 554 | CG | LEU | A | 194 | −15.957 | 26.342 | −25.084 | 1.00 | 22.46 | A | C |
| ATOM | 555 | CD1 | LEU | A | 194 | −15.401 | 26.962 | −26.374 | 1.00 | 23.33 | A | C |
| ATOM | 556 | CD2 | LEU | A | 194 | −17.495 | 26.308 | −25.145 | 1.00 | 22.36 | A | C |
| ATOM | 557 | C | LEU | A | 194 | −14.075 | 25.406 | −22.760 | 1.00 | 20.35 | A | C |
| ATOM | 558 | O | LEU | A | 194 | −14.728 | 24.687 | −22.004 | 1.00 | 21.23 | A | O |
| ATOM | 559 | N | ARG | A | 195 | −13.526 | 26.568 | −22.379 | 1.00 | 21.18 | A | N |
| ATOM | 560 | CA | ARG | A | 195 | −13.628 | 27.055 | −20.991 | 1.00 | 25.15 | A | C |
| ATOM | 561 | CB | ARG | A | 195 | −12.959 | 28.397 | −20.803 | 1.00 | 30.14 | A | C |
| ATOM | 562 | CG | ARG | A | 195 | −11.465 | 28.440 | −20.976 | 1.00 | 35.79 | A | C |
| ATOM | 563 | CD | ARG | A | 195 | −10.670 | 27.981 | −19.735 | 1.00 | 44.03 | A | C |
| ATOM | 564 | NE | ARG | A | 195 | −11.467 | 27.963 | −18.506 | 1.00 | 46.35 | A | N |
| ATOM | 565 | CZ | ARG | A | 195 | −11.316 | 28.755 | −17.448 | 1.00 | 47.20 | A | C |
| ATOM | 566 | NH1 | ARG | A | 195 | −12.153 | 28.571 | −16.416 | 1.00 | 44.34 | A | N |
| ATOM | 567 | NH2 | ARG | A | 195 | −10.362 | 29.703 | −17.406 | 1.00 | 48.23 | A | N |
| ATOM | 568 | C | ARG | A | 195 | −15.063 | 27.278 | −20.647 | 1.00 | 24.74 | A | C |
| ATOM | 569 | O | ARG | A | 195 | −15.778 | 27.879 | −21.429 | 1.00 | 23.59 | A | O |
| ATOM | 570 | N | LEU | A | 196 | −15.490 | 26.794 | −19.493 | 1.00 | 25.11 | A | N |
| ATOM | 571 | CA | LEU | A | 196 | −16.705 | 27.290 | −18.841 | 1.00 | 26.41 | A | C |
| ATOM | 572 | CB | LEU | A | 196 | −17.603 | 26.166 | −18.370 | 1.00 | 26.53 | A | C |
| ATOM | 573 | CG | LEU | A | 196 | −18.751 | 26.589 | −17.452 | 1.00 | 29.48 | A | C |
| ATOM | 574 | CD1 | LEU | A | 196 | −19.671 | 27.597 | −18.091 | 1.00 | 32.41 | A | C |
| ATOM | 575 | CD2 | LEU | A | 196 | −19.606 | 25.389 | −17.139 | 1.00 | 30.74 | A | C |
| ATOM | 576 | C | LEU | A | 196 | −16.157 | 28.093 | −17.649 | 1.00 | 28.20 | A | C |
| ATOM | 577 | O | LEU | A | 196 | −15.694 | 27.507 | −16.660 | 1.00 | 25.67 | A | O |
| ATOM | 578 | N | TYR | A | 197 | −16.147 | 29.417 | −17.801 | 1.00 | 27.37 | A | N |
| ATOM | 579 | CA | TYR | A | 197 | −15.687 | 30.338 | −16.771 | 1.00 | 26.78 | A | C |
| ATOM | 580 | CB | TYR | A | 197 | −15.558 | 31.771 | −17.325 | 1.00 | 25.40 | A | C |
| ATOM | 581 | CG | TYR | A | 197 | −14.500 | 31.920 | −18.367 | 1.00 | 26.30 | A | C |
| ATOM | 582 | CD1 | TYR | A | 197 | −13.193 | 32.092 | −18.011 | 1.00 | 33.05 | A | C |
| ATOM | 583 | CE1 | TYR | A | 197 | −12.188 | 32.219 | −18.964 | 1.00 | 32.27 | A | C |
| ATOM | 584 | CZ | TYR | A | 197 | −12.523 | 32.201 | −20.278 | 1.00 | 32.26 | A | C |
| ATOM | 585 | OH | TYR | A | 197 | −11.546 | 32.352 | −21.212 | 1.00 | 34.75 | A | O |
| ATOM | 586 | CE2 | TYR | A | 197 | −13.837 | 32.053 | −20.664 | 1.00 | 29.89 | A | C |
| ATOM | 587 | CD2 | TYR | A | 197 | −14.808 | 31.918 | −19.704 | 1.00 | 27.12 | A | C |
| ATOM | 588 | C | TYR | A | 197 | −16.603 | 30.336 | −15.529 | 1.00 | 24.11 | A | C |
| ATOM | 589 | O | TYR | A | 197 | −16.147 | 30.622 | −14.485 | 1.00 | 24.74 | A | O |
| ATOM | 590 | N | GLY | A | 198 | −17.868 | 30.027 | −15.626 | 1.00 | 21.36 | A | N |
| ATOM | 591 | CA | GLY | A | 198 | −18.744 | 30.189 | −14.463 | 1.00 | 21.07 | A | C |
| ATOM | 592 | C | GLY | A | 198 | −20.169 | 30.173 | −14.968 | 1.00 | 23.40 | A | C |
| ATOM | 593 | O | GLY | A | 198 | −20.374 | 30.129 | −16.171 | 1.00 | 22.09 | A | O |
| ATOM | 594 | N | TYR | A | 199 | −21.136 | 30.222 | −14.056 | 1.00 | 24.35 | A | N |
| ATOM | 595 | CA | TYR | A | 199 | −22.531 | 30.371 | −14.408 | 1.00 | 25.84 | A | C |
| ATOM | 596 | CB | TYR | A | 199 | −23.176 | 28.991 | −14.430 | 1.00 | 26.27 | A | C |
| ATOM | 597 | CG | TYR | A | 199 | −23.785 | 28.556 | −13.121 | 1.00 | 27.64 | A | C |
| ATOM | 598 | CD1 | TYR | A | 199 | −25.182 | 28.461 | −12.980 | 1.00 | 29.80 | A | C |
| ATOM | 599 | CE1 | TYR | A | 199 | −25.763 | 28.078 | −11.776 | 1.00 | 30.80 | A | C |
| ATOM | 600 | CZ | TYR | A | 199 | −24.953 | 27.768 | −10.701 | 1.00 | 29.26 | A | C |
| ATOM | 601 | OH | TYR | A | 199 | −25.548 | 27.361 | −9.529 | 1.00 | 28.16 | A | O |
| ATOM | 602 | CE2 | TYR | A | 199 | −23.570 | 27.840 | −10.821 | 1.00 | 30.14 | A | C |
| ATOM | 603 | CD2 | TYR | A | 199 | −22.986 | 28.247 | −12.019 | 1.00 | 27.26 | A | C |
| ATOM | 604 | C | TYR | A | 199 | −23.248 | 31.296 | −13.385 | 1.00 | 28.34 | A | C |
| ATOM | 605 | O | TYR | A | 199 | −22.640 | 31.739 | −12.398 | 1.00 | 26.92 | A | O |
| ATOM | 606 | N | PHE | A | 200 | −24.534 | 31.569 | −13.612 | 1.00 | 27.98 | A | N |
| ATOM | 607 | CA | PHE | A | 200 | −25.373 | 32.174 | −12.583 | 1.00 | 29.41 | A | C |
| ATOM | 608 | CB | PHE | A | 200 | −25.116 | 33.659 | −12.419 | 1.00 | 33.18 | A | C |
| ATOM | 609 | CG | PHE | A | 200 | −25.063 | 34.453 | −13.732 | 1.00 | 37.34 | A | C |
| ATOM | 610 | CD1 | PHE | A | 200 | −23.880 | 34.551 | −14.470 | 1.00 | 37.22 | A | C |
| ATOM | 611 | CE1 | PHE | A | 200 | −23.818 | 35.305 | −15.641 | 1.00 | 38.10 | A | C |
| ATOM | 612 | CZ | PHE | A | 200 | −24.939 | 35.990 | −16.098 | 1.00 | 37.86 | A | C |
| ATOM | 613 | CE2 | PHE | A | 200 | −26.125 | 35.922 | −15.364 | 1.00 | 40.72 | A | C |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 614 | CD2 | PHE | A | 200 | −26.180 | 35.158 | −14.185 | 1.00 | 41.69 | A | C |
| ATOM | 615 | C | PHE | A | 200 | −26.760 | 31.931 | −13.063 | 1.00 | 29.08 | A | C |
| ATOM | 616 | O | PHE | A | 200 | −26.920 | 31.335 | −14.111 | 1.00 | 30.23 | A | O |
| ATOM | 617 | N | HIS | A | 201 | −27.768 | 32.351 | −12.318 | 1.00 | 29.81 | A | N |
| ATOM | 618 | CA | HIS | A | 201 | −29.156 | 32.182 | −12.784 | 1.00 | 30.42 | A | C |
| ATOM | 619 | CB | HIS | A | 201 | −29.667 | 30.764 | −12.535 | 1.00 | 30.60 | A | C |
| ATOM | 620 | CG | HIS | A | 201 | −29.717 | 30.366 | −11.078 | 1.00 | 32.84 | A | C |
| ATOM | 621 | ND1 | HIS | A | 201 | −30.881 | 29.975 | −10.453 | 1.00 | 32.68 | A | N |
| ATOM | 622 | CE1 | HIS | A | 201 | −30.631 | 29.673 | −9.197 | 1.00 | 33.59 | A | C |
| ATOM | 623 | NE2 | HIS | A | 201 | −29.338 | 29.845 | −8.982 | 1.00 | 34.70 | A | N |
| ATOM | 624 | CD2 | HIS | A | 201 | −28.744 | 30.280 | −10.139 | 1.00 | 32.98 | A | C |
| ATOM | 625 | C | HIS | A | 201 | −30.105 | 33.173 | −12.151 | 1.00 | 31.79 | A | C |
| ATOM | 626 | O | HIS | A | 201 | −29.777 | 33.832 | −11.170 | 1.00 | 32.67 | A | O |
| ATOM | 627 | N | ASP | A | 202 | −31.306 | 33.247 | −12.709 | 1.00 | 33.30 | A | N |
| ATOM | 628 | CA | ASP | A | 202 | −32.318 | 34.133 | −12.179 | 1.00 | 34.23 | A | C |
| ATOM | 629 | CB | ASP | A | 202 | −32.232 | 35.524 | −12.852 | 1.00 | 33.68 | A | C |
| ATOM | 630 | CG | ASP | A | 202 | −32.694 | 35.551 | −14.336 | 1.00 | 35.38 | A | C |
| ATOM | 631 | OD1 | ASP | A | 202 | −33.564 | 34.752 | −14.821 | 1.00 | 36.84 | A | O |
| ATOM | 632 | OD2 | ASP | A | 202 | −32.165 | 36.442 | −15.034 | 1.00 | 35.49 | A | O |
| ATOM | 633 | C | ASP | A | 202 | −33.652 | 33.461 | −12.272 | 1.00 | 35.98 | A | C |
| ATOM | 634 | O | ASP | A | 202 | −33.722 | 32.279 | −12.567 | 1.00 | 37.71 | A | O |
| ATOM | 635 | N | ALA | A | 203 | −34.729 | 34.190 | −12.026 | 1.00 | 38.75 | A | N |
| ATOM | 636 | CA | ALA | A | 203 | −36.022 | 33.537 | −11.899 | 1.00 | 37.88 | A | C |
| ATOM | 637 | CB | ALA | A | 203 | −37.094 | 34.559 | −11.581 | 1.00 | 38.49 | A | C |
| ATOM | 638 | C | ALA | A | 203 | −36.417 | 32.747 | −13.126 | 1.00 | 39.78 | A | C |
| ATOM | 639 | O | ALA | A | 203 | −37.219 | 31.833 | −13.033 | 1.00 | 45.26 | A | O |
| ATOM | 640 | N | THR | A | 204 | −35.907 | 33.114 | −14.291 | 1.00 | 39.25 | A | N |
| ATOM | 641 | CA | THR | A | 204 | −36.356 | 32.460 | −15.515 | 1.00 | 38.56 | A | C |
| ATOM | 642 | CB | THR | A | 204 | −37.014 | 33.523 | −16.397 | 1.00 | 39.09 | A | C |
| ATOM | 643 | OG1 | THR | A | 204 | −36.052 | 34.545 | −16.703 | 1.00 | 35.66 | A | O |
| ATOM | 644 | CG2 | THR | A | 204 | −38.172 | 34.146 | −15.629 | 1.00 | 36.35 | A | C |
| ATOM | 645 | C | THR | A | 204 | −35.254 | 31.767 | −16.299 | 1.00 | 37.64 | A | C |
| ATOM | 646 | O | THR | A | 204 | −35.536 | 30.895 | −17.165 | 1.00 | 35.72 | A | O |
| ATOM | 647 | N | ARG | A | 205 | −34.010 | 32.158 | −16.029 | 1.00 | 34.91 | A | N |
| ATOM | 648 | CA | ARG | A | 205 | −32.920 | 31.787 | −16.912 | 1.00 | 36.54 | A | C |
| ATOM | 649 | CB | ARG | A | 205 | −32.497 | 32.994 | −17.756 | 1.00 | 38.09 | A | C |
| ATOM | 650 | CG | ARG | A | 205 | −33.602 | 33.427 | −18.736 | 1.00 | 42.62 | A | C |
| ATOM | 651 | CD | ARG | A | 205 | −33.537 | 34.884 | −19.157 | 1.00 | 44.26 | A | C |
| ATOM | 652 | NE | ARG | A | 205 | −33.802 | 35.823 | −18.059 | 1.00 | 48.87 | A | N |
| ATOM | 653 | CZ | ARG | A | 205 | −34.088 | 37.113 | −18.212 | 1.00 | 48.19 | A | C |
| ATOM | 654 | NH1 | ARG | A | 205 | −34.179 | 37.648 | −19.414 | 1.00 | 50.54 | A | N |
| ATOM | 655 | NH2 | ARG | A | 205 | −34.291 | 37.878 | −17.148 | 1.00 | 50.77 | A | N |
| ATOM | 656 | C | ARG | A | 205 | −31.746 | 31.253 | −16.154 | 1.00 | 33.76 | A | C |
| ATOM | 657 | O | ARG | A | 205 | −31.487 | 31.666 | −15.027 | 1.00 | 32.36 | A | O |
| ATOM | 658 | N | VAL | A | 206 | −31.038 | 30.329 | −16.802 | 1.00 | 33.87 | A | N |
| ATOM | 659 | CA | VAL | A | 206 | −29.657 | 29.995 | −16.428 | 1.00 | 32.35 | A | C |
| ATOM | 660 | CB | VAL | A | 206 | −29.442 | 28.442 | −16.240 | 1.00 | 34.15 | A | C |
| ATOM | 661 | CG1 | VAL | A | 206 | −30.483 | 27.812 | −15.310 | 1.00 | 32.59 | A | C |
| ATOM | 662 | CG2 | VAL | A | 206 | −28.035 | 28.143 | −15.709 | 1.00 | 36.33 | A | C |
| ATOM | 663 | C | VAL | A | 206 | −28.699 | 30.534 | −17.500 | 1.00 | 31.64 | A | C |
| ATOM | 664 | O | VAL | A | 206 | −28.956 | 30.450 | −18.704 | 1.00 | 32.14 | A | O |
| ATOM | 665 | N | TYR | A | 207 | −27.550 | 31.017 | −17.048 | 1.00 | 31.80 | A | N |
| ATOM | 666 | CA | TYR | A | 207 | −26.541 | 31.614 | −17.905 | 1.00 | 30.18 | A | C |
| ATOM | 667 | CB | TYR | A | 207 | −26.260 | 33.077 | −17.465 | 1.00 | 32.47 | A | C |
| ATOM | 668 | CG | TYR | A | 207 | −27.480 | 33.992 | −17.483 | 1.00 | 33.67 | A | C |
| ATOM | 669 | CD1 | TYR | A | 207 | −28.396 | 33.998 | −16.411 | 1.00 | 36.55 | A | C |
| ATOM | 670 | CE1 | TYR | A | 207 | −29.531 | 34.843 | −16.428 | 1.00 | 38.08 | A | C |
| ATOM | 671 | CZ | TYR | A | 207 | −29.758 | 35.700 | −17.513 | 1.00 | 35.54 | A | C |
| ATOM | 672 | OH | TYR | A | 207 | −30.879 | 36.500 | −17.512 | 1.00 | 34.61 | A | O |
| ATOM | 673 | CE2 | TYR | A | 207 | −28.866 | 35.705 | −18.586 | 1.00 | 33.65 | A | C |
| ATOM | 674 | CD2 | TYR | A | 207 | −27.732 | 34.861 | −18.563 | 1.00 | 34.47 | A | C |
| ATOM | 675 | C | TYR | A | 207 | −25.259 | 30.838 | −17.744 | 1.00 | 29.48 | A | C |
| ATOM | 676 | O | TYR | A | 207 | −24.833 | 30.649 | −16.626 | 1.00 | 26.78 | A | O |
| ATOM | 677 | N | LEU | A | 208 | −24.617 | 30.438 | −18.846 | 1.00 | 29.14 | A | N |
| ATOM | 678 | CA | LEU | A | 208 | −23.264 | 29.882 | −18.802 | 1.00 | 28.27 | A | C |
| ATOM | 679 | CB | LEU | A | 208 | −23.209 | 28.587 | −19.592 | 1.00 | 30.76 | A | C |
| ATOM | 680 | CG | LEU | A | 208 | −24.068 | 27.405 | −19.121 | 1.00 | 33.72 | A | C |
| ATOM | 681 | CD1 | LEU | A | 208 | −23.735 | 26.163 | −19.927 | 1.00 | 34.68 | A | C |
| ATOM | 682 | CD2 | LEU | A | 208 | −23.805 | 27.165 | −17.650 | 1.00 | 34.55 | A | C |
| ATOM | 683 | C | LEU | A | 208 | −22.321 | 30.809 | −19.457 | 1.00 | 26.70 | A | C |
| ATOM | 684 | O | LEU | A | 208 | −22.543 | 31.230 | −20.599 | 1.00 | 27.06 | A | O |
| ATOM | 685 | N | ILE | A | 209 | −21.255 | 31.111 | −18.758 | 1.00 | 24.59 | A | N |
| ATOM | 686 | CA | ILE | A | 209 | −20.243 | 31.998 | −19.256 | 1.00 | 25.36 | A | C |
| ATOM | 687 | CB | ILE | A | 209 | −19.575 | 32.791 | −18.099 | 1.00 | 25.18 | A | C |
| ATOM | 688 | CG1 | ILE | A | 209 | −20.597 | 33.626 | −17.333 | 1.00 | 26.71 | A | C |
| ATOM | 689 | CD1 | ILE | A | 209 | −20.175 | 33.965 | −15.910 | 1.00 | 25.52 | A | C |
| ATOM | 690 | CG2 | ILE | A | 209 | −18.497 | 33.761 | −18.607 | 1.00 | 24.88 | A | C |
| ATOM | 691 | C | ILE | A | 209 | −19.169 | 31.162 | −19.932 | 1.00 | 25.84 | A | C |

APPENDIX B-continued

Atomic coordinates of Aurora A + Activating Monobody Mb54 + AMPPCP

| | | | | | | | | | | | |
|---|---|---|---|---|---|---|---|---|---|---|---|
| ATOM | 692 | O | ILE | A | 209 | −18.325 | 30.620 | −19.241 | 1.00 | 29.94 | A O |
| ATOM | 693 | N | LEU | A | 210 | −19.108 | 31.195 | −21.254 | 1.00 | 24.13 | A N |
| ATOM | 694 | CA | LEU | A | 210 | −18.225 | 30.351 | −22.058 | 1.00 | 22.81 | A C |
| ATOM | 695 | CB | LEU | A | 210 | −19.062 | 29.587 | −23.061 | 1.00 | 22.27 | A C |
| ATOM | 696 | CG | LEU | A | 210 | −20.236 | 28.757 | −22.534 | 1.00 | 22.91 | A C |
| ATOM | 697 | CD1 | LEU | A | 210 | −21.080 | 28.207 | −23.653 | 1.00 | 22.73 | A C |
| ATOM | 698 | CD2 | LEU | A | 210 | −19.641 | 27.584 | −21.782 | 1.00 | 25.54 | A C |
| ATOM | 699 | C | LEU | A | 210 | −17.198 | 31.119 | −22.847 | 1.00 | 23.88 | A C |
| ATOM | 700 | O | LEU | A | 210 | −17.448 | 32.253 | −23.217 | 1.00 | 24.72 | A O |
| ATOM | 701 | N | GLU | A | 211 | −16.050 | 30.483 | −23.117 | 1.00 | 22.84 | A N |
| ATOM | 702 | CA | GLU | A | 211 | −15.120 | 30.954 | −24.123 | 1.00 | 22.18 | A C |
| ATOM | 703 | CB | GLU | A | 211 | −13.979 | 29.969 | −24.239 | 1.00 | 22.41 | A C |
| ATOM | 704 | CG | GLU | A | 211 | −12.931 | 30.233 | −25.329 | 1.00 | 22.47 | A C |
| ATOM | 705 | CD | GLU | A | 211 | −11.859 | 29.141 | −25.303 | 1.00 | 23.94 | A C |
| ATOM | 706 | OE1 | GLU | A | 211 | −12.023 | 28.239 | −24.472 | 1.00 | 24.93 | A O |
| ATOM | 707 | OE2 | GLU | A | 211 | −10.877 | 29.104 | −26.128 | 1.00 | 26.84 | A O |
| ATOM | 708 | C | GLU | A | 211 | −15.821 | 31.069 | −25.481 | 1.00 | 22.86 | A C |
| ATOM | 709 | O | GLU | A | 211 | −16.565 | 30.176 | −25.875 | 1.00 | 22.22 | A O |
| ATOM | 710 | N | TYR | A | 212 | −15.523 | 32.151 | −26.196 | 1.00 | 23.68 | A N |
| ATOM | 711 | CA | TYR | A | 212 | −16.025 | 32.412 | −27.545 | 1.00 | 23.66 | A C |
| ATOM | 712 | CB | TYR | A | 212 | −16.100 | 33.935 | −27.785 | 1.00 | 25.22 | A C |
| ATOM | 713 | CG | TYR | A | 212 | −16.279 | 34.435 | −29.217 | 1.00 | 24.20 | A C |
| ATOM | 714 | CD1 | TYR | A | 212 | −17.336 | 34.059 | −30.001 | 1.00 | 27.11 | A C |
| ATOM | 715 | CE1 | TYR | A | 212 | −17.497 | 34.553 | −31.304 | 1.00 | 26.27 | A C |
| ATOM | 716 | CZ | TYR | A | 212 | −16.575 | 35.428 | −31.791 | 1.00 | 25.74 | A C |
| ATOM | 717 | OH | TYR | A | 212 | −16.616 | 35.960 | −33.045 | 1.00 | 27.39 | A O |
| ATOM | 718 | CE2 | TYR | A | 212 | −15.536 | 35.806 | −31.017 | 1.00 | 26.43 | A C |
| ATOM | 719 | CD2 | TYR | A | 212 | −15.405 | 35.315 | −29.739 | 1.00 | 25.26 | A C |
| ATOM | 720 | C | TYR | A | 212 | −15.164 | 31.700 | −28.596 | 1.00 | 23.04 | A C |
| ATOM | 721 | O | TYR | A | 212 | −13.941 | 31.846 | −28.663 | 1.00 | 22.27 | A O |
| ATOM | 722 | N | ALA | A | 213 | −15.831 | 30.903 | −29.412 | 1.00 | 23.26 | A N |
| ATOM | 723 | CA | ALA | A | 213 | −15.180 | 30.218 | −30.464 | 1.00 | 22.62 | A C |
| ATOM | 724 | CB | ALA | A | 213 | −15.572 | 28.749 | −30.470 | 1.00 | 22.43 | A C |
| ATOM | 725 | C | ALA | A | 213 | −15.623 | 30.916 | −31.739 | 1.00 | 23.65 | A C |
| ATOM | 726 | O | ALA | A | 213 | −16.702 | 30.594 | −32.290 | 1.00 | 24.75 | A O |
| ATOM | 727 | N | PRO | A | 214 | −14.776 | 31.819 | −32.246 | 1.00 | 22.13 | A N |
| ATOM | 728 | CA | PRO | A | 214 | −15.159 | 32.598 | −33.423 | 1.00 | 24.35 | A C |
| ATOM | 729 | CB | PRO | A | 214 | −14.006 | 33.606 | −33.587 | 1.00 | 22.27 | A C |
| ATOM | 730 | CG | PRO | A | 214 | −12.902 | 33.063 | −32.807 | 1.00 | 22.01 | A C |
| ATOM | 731 | CD | PRO | A | 214 | −13.439 | 32.167 | −31.769 | 1.00 | 21.63 | A C |
| ATOM | 732 | C | PRO | A | 214 | −15.347 | 31.822 | −34.698 | 1.00 | 25.28 | A C |
| ATOM | 733 | O | PRO | A | 214 | −16.101 | 32.253 | −35.510 | 1.00 | 25.51 | A O |
| ATOM | 734 | N | LEU | A | 215 | −14.702 | 30.668 | −34.873 | 1.00 | 26.30 | A N |
| ATOM | 735 | CA | LEU | A | 215 | −14.845 | 29.897 | −36.135 | 1.00 | 22.53 | A C |
| ATOM | 736 | CB | LEU | A | 215 | −13.492 | 29.311 | −36.561 | 1.00 | 22.20 | A C |
| ATOM | 737 | CG | LEU | A | 215 | −12.737 | 30.215 | −37.551 | 1.00 | 23.94 | A C |
| ATOM | 738 | CD1 | LEU | A | 215 | −12.762 | 31.651 | −37.120 | 1.00 | 26.78 | A C |
| ATOM | 739 | CD2 | LEU | A | 215 | −11.268 | 29.820 | −37.702 | 1.00 | 25.18 | A C |
| ATOM | 740 | C | LEU | A | 215 | −15.943 | 28.865 | −36.125 | 1.00 | 21.28 | A C |
| ATOM | 741 | O | LEU | A | 215 | −16.079 | 28.097 | −37.068 | 1.00 | 22.46 | A O |
| ATOM | 742 | N | GLY | A | 216 | −16.783 | 28.865 | −35.108 | 1.00 | 21.39 | A N |
| ATOM | 743 | CA | GLY | A | 216 | −17.962 | 28.005 | −35.082 | 1.00 | 21.04 | A C |
| ATOM | 744 | C | GLY | A | 216 | −17.675 | 26.513 | −34.841 | 1.00 | 21.85 | A C |
| ATOM | 745 | O | GLY | A | 216 | −16.606 | 26.131 | −34.406 | 1.00 | 21.66 | A O |
| ATOM | 746 | N | THR | A | 217 | −18.668 | 25.692 | −35.171 | 1.00 | 22.04 | A N |
| ATOM | 747 | CA | THR | A | 217 | −18.639 | 24.233 | −34.980 | 1.00 | 21.15 | A C |
| ATOM | 748 | CB | THR | A | 217 | −20.036 | 23.651 | −34.843 | 1.00 | 20.76 | A C |
| ATOM | 749 | OG1 | THR | A | 217 | −20.746 | 23.787 | −36.075 | 1.00 | 21.63 | A O |
| ATOM | 750 | CG2 | THR | A | 217 | −20.784 | 24.378 | −33.696 | 1.00 | 21.08 | A C |
| ATOM | 751 | C | THR | A | 217 | −17.985 | 23.459 | −36.083 | 1.00 | 21.09 | A C |
| ATOM | 752 | O | THR | A | 217 | −18.041 | 23.848 | −37.228 | 1.00 | 22.87 | A O |
| ATOM | 753 | N | VAL | A | 218 | −17.371 | 22.342 | −35.721 | 1.00 | 20.68 | A N |
| ATOM | 754 | CA | VAL | A | 218 | −16.752 | 21.459 | −36.694 | 1.00 | 21.06 | A C |
| ATOM | 755 | CB | VAL | A | 218 | −15.959 | 20.389 | −35.970 | 1.00 | 21.08 | A C |
| ATOM | 756 | CG1 | VAL | A | 218 | −15.382 | 19.410 | −36.934 | 1.00 | 20.76 | A C |
| ATOM | 757 | CG2 | VAL | A | 218 | −14.852 | 21.064 | −35.120 | 1.00 | 21.60 | A C |
| ATOM | 758 | C | VAL | A | 218 | −17.861 | 20.830 | −37.535 | 1.00 | 22.36 | A C |
| ATOM | 759 | O | VAL | A | 218 | −17.698 | 20.563 | −38.698 | 1.00 | 21.37 | A O |
| ATOM | 760 | N | TYR | A | 219 | −19.001 | 20.588 | −36.911 | 1.00 | 25.49 | A N |
| ATOM | 761 | CA | TYR | A | 219 | −20.170 | 20.159 | −37.612 | 1.00 | 24.15 | A C |
| ATOM | 762 | CB | TYR | A | 219 | −21.313 | 20.113 | −36.640 | 1.00 | 25.68 | A C |
| ATOM | 763 | CG | TYR | A | 219 | −22.616 | 19.766 | −37.297 | 1.00 | 30.82 | A C |
| ATOM | 764 | CD1 | TYR | A | 219 | −22.967 | 18.458 | −37.558 | 1.00 | 30.01 | A C |
| ATOM | 765 | CE1 | TYR | A | 219 | −24.160 | 18.158 | −38.167 | 1.00 | 33.62 | A C |
| ATOM | 766 | CZ | TYR | A | 219 | −25.006 | 19.196 | −38.546 | 1.00 | 39.33 | A C |
| ATOM | 767 | OH | TYR | A | 219 | −26.237 | 19.022 | −39.160 | 1.00 | 42.57 | A O |
| ATOM | 768 | CE2 | TYR | A | 219 | −24.663 | 20.492 | −38.285 | 1.00 | 37.72 | A C |
| ATOM | 769 | CD2 | TYR | A | 219 | −23.483 | 20.772 | −37.671 | 1.00 | 33.97 | A C |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 770 | C | TYR | A | 219 | −20.447 | 21.050 | −38.860 | 1.00 | 26.57 | A | C |
| ATOM | 771 | O | TYR | A | 219 | −20.518 | 20.538 | −39.972 | 1.00 | 24.49 | A | O |
| ATOM | 772 | N | ARG | A | 220 | −20.495 | 22.374 | −38.699 | 1.00 | 28.64 | A | N |
| ATOM | 773 | CA | ARG | A | 220 | −20.771 | 23.259 | −39.836 | 1.00 | 29.90 | A | C |
| ATOM | 774 | CB | ARG | A | 220 | −21.133 | 24.690 | −39.385 | 1.00 | 35.43 | A | C |
| ATOM | 775 | CG | ARG | A | 220 | −21.377 | 25.689 | −40.525 | 1.00 | 47.82 | A | C |
| ATOM | 776 | CD | ARG | A | 220 | −22.821 | 26.220 | −40.684 | 1.00 | 60.80 | A | C |
| ATOM | 777 | NE | ARG | A | 220 | −23.016 | 27.090 | −41.892 | 1.00 | 74.55 | A | N |
| ATOM | 778 | CZ | ARG | A | 220 | −22.687 | 28.399 | −42.034 | 1.00 | 70.04 | A | C |
| ATOM | 779 | NH1 | ARG | A | 220 | −22.111 | 29.103 | −41.061 | 1.00 | 63.56 | A | N |
| ATOM | 780 | NH2 | ARG | A | 220 | −22.935 | 29.023 | −43.187 | 1.00 | 69.59 | A | N |
| ATOM | 781 | C | ARG | A | 220 | −19.609 | 23.210 | −40.846 | 1.00 | 27.45 | A | C |
| ATOM | 782 | O | ARG | A | 220 | −19.847 | 23.143 | −42.032 | 1.00 | 25.42 | A | O |
| ATOM | 783 | N | GLU | A | 221 | −18.359 | 23.177 | −40.384 | 1.00 | 26.84 | A | N |
| ATOM | 784 | CA | GLU | A | 221 | −17.237 | 23.016 | −41.301 | 1.00 | 27.36 | A | C |
| ATOM | 785 | CB | GLU | A | 221 | −15.898 | 23.129 | −40.574 | 1.00 | 28.77 | A | C |
| ATOM | 786 | CG | GLU | A | 221 | −14.704 | 23.460 | −41.502 | 1.00 | 36.81 | A | C |
| ATOM | 787 | CD | GLU | A | 221 | −13.295 | 23.183 | −40.899 | 1.00 | 40.18 | A | C |
| ATOM | 788 | OE1 | GLU | A | 221 | −13.195 | 22.570 | −39.821 | 1.00 | 46.08 | A | O |
| ATOM | 789 | OE2 | GLU | A | 221 | −12.246 | 23.532 | −41.495 | 1.00 | 40.91 | A | O |
| ATOM | 790 | C | GLU | A | 221 | −17.348 | 21.729 | −42.139 | 1.00 | 25.37 | A | C |
| ATOM | 791 | O | GLU | A | 221 | −17.034 | 21.752 | −43.293 | 1.00 | 24.37 | A | O |
| ATOM | 792 | N | LEU | A | 222 | −17.815 | 20.625 | −41.556 | 1.00 | 26.00 | A | N |
| ATOM | 793 | CA | LEU | A | 222 | −17.936 | 19.368 | −42.276 | 1.00 | 27.52 | A | C |
| ATOM | 794 | CB | LEU | A | 222 | −18.086 | 18.158 | −41.335 | 1.00 | 27.66 | A | C |
| ATOM | 795 | CG | LEU | A | 222 | −17.950 | 16.754 | −41.958 | 1.00 | 27.82 | A | C |
| ATOM | 796 | CD1 | LEU | A | 222 | −18.147 | 15.715 | −40.875 | 1.00 | 29.49 | A | C |
| ATOM | 797 | CD2 | LEU | A | 222 | −16.625 | 16.506 | −42.644 | 1.00 | 25.91 | A | C |
| ATOM | 798 | C | LEU | A | 222 | −19.100 | 19.374 | −43.251 | 1.00 | 27.57 | A | C |
| ATOM | 799 | O | LEU | A | 222 | −18.956 | 18.849 | −44.303 | 1.00 | 25.01 | A | O |
| ATOM | 800 | N | GLN | A | 223 | −20.241 | 19.936 | −42.868 | 1.00 | 29.01 | A | N |
| ATOM | 801 | CA | GLN | A | 223 | −21.311 | 20.272 | −43.795 | 1.00 | 32.12 | A | C |
| ATOM | 802 | CB | GLN | A | 223 | −22.425 | 21.094 | −43.128 | 1.00 | 36.84 | A | C |
| ATOM | 803 | CG | GLN | A | 223 | −23.478 | 20.305 | −42.357 | 1.00 | 43.82 | A | C |
| ATOM | 804 | CD | GLN | A | 223 | −24.760 | 21.133 | −42.068 | 1.00 | 58.20 | A | C |
| ATOM | 805 | OE1 | GLN | A | 223 | −24.715 | 22.303 | −41.633 | 1.00 | 61.81 | A | O |
| ATOM | 806 | NE2 | GLN | A | 223 | −25.912 | 20.515 | −42.299 | 1.00 | 64.35 | A | N |
| ATOM | 807 | C | GLN | A | 223 | −20.797 | 21.055 | −44.998 | 1.00 | 32.88 | A | C |
| ATOM | 808 | O | GLN | A | 223 | −21.162 | 20.726 | −46.098 | 1.00 | 32.42 | A | O |
| ATOM | 809 | N | LYS | A | 224 | −19.933 | 22.052 | −44.812 | 1.00 | 32.90 | A | N |
| ATOM | 810 | CA | LYS | A | 224 | −19.490 | 22.860 | −45.945 | 1.00 | 33.74 | A | C |
| ATOM | 811 | CB | LYS | A | 224 | −18.900 | 24.199 | −45.509 | 1.00 | 38.76 | A | C |
| ATOM | 812 | CG | LYS | A | 224 | −20.019 | 25.218 | −45.322 | 1.00 | 47.54 | A | C |
| ATOM | 813 | CD | LYS | A | 224 | −19.760 | 26.318 | −44.294 | 1.00 | 58.11 | A | C |
| ATOM | 814 | CE | LYS | A | 224 | −18.771 | 27.377 | −44.776 | 1.00 | 61.39 | A | C |
| ATOM | 815 | NZ | LYS | A | 224 | −18.962 | 28.598 | −43.943 | 1.00 | 67.93 | A | N |
| ATOM | 816 | C | LYS | A | 224 | −18.538 | 22.121 | −46.827 | 1.00 | 33.65 | A | C |
| ATOM | 817 | O | LYS | A | 224 | −18.737 | 22.076 | −48.047 | 1.00 | 34.50 | A | O |
| ATOM | 818 | N | LEU | A | 225 | −17.523 | 21.517 | −46.229 | 1.00 | 29.65 | A | N |
| ATOM | 819 | CA | LEU | A | 225 | −16.476 | 20.858 | −46.999 | 1.00 | 29.77 | A | C |
| ATOM | 820 | CB | LEU | A | 225 | −15.158 | 20.805 | −46.194 | 1.00 | 27.97 | A | C |
| ATOM | 821 | CG | LEU | A | 225 | −14.609 | 22.181 | −45.814 | 1.00 | 29.73 | A | C |
| ATOM | 822 | CD1 | LEU | A | 225 | −13.301 | 22.042 | −45.052 | 1.00 | 28.47 | A | C |
| ATOM | 823 | CD2 | LEU | A | 225 | −14.398 | 23.098 | −47.014 | 1.00 | 29.25 | A | C |
| ATOM | 824 | C | LEU | A | 225 | −16.869 | 19.437 | −47.451 | 1.00 | 30.17 | A | C |
| ATOM | 825 | O | LEU | A | 225 | −16.177 | 18.866 | −48.293 | 1.00 | 27.26 | A | O |
| ATOM | 826 | N | SER | A | 226 | −17.960 | 18.903 | −46.889 | 1.00 | 27.61 | A | N |
| ATOM | 827 | CA | SER | A | 226 | −18.369 | 17.490 | −46.971 | 1.00 | 30.17 | A | C |
| ATOM | 828 | CB | SER | A | 226 | −18.906 | 17.194 | −48.365 | 1.00 | 33.53 | A | C |
| ATOM | 829 | OG | SER | A | 226 | −17.856 | 16.928 | −49.196 | 1.00 | 35.86 | A | O |
| ATOM | 830 | C | SER | A | 226 | −17.411 | 16.392 | −46.421 | 1.00 | 26.86 | A | C |
| ATOM | 831 | O | SER | A | 226 | −17.879 | 15.487 | −45.733 | 1.00 | 25.50 | A | O |
| ATOM | 832 | N | LYS | A | 227 | −16.113 | 16.484 | −46.655 | 1.00 | 25.54 | A | N |
| ATOM | 833 | CA | LYS | A | 227 | −15.112 | 15.595 | −46.025 | 1.00 | 28.92 | A | C |
| ATOM | 834 | CB | LYS | A | 227 | −14.606 | 14.545 | −47.014 | 1.00 | 32.94 | A | C |
| ATOM | 835 | CG | LYS | A | 227 | −15.675 | 13.725 | −47.712 | 1.00 | 40.93 | A | C |
| ATOM | 836 | CD | LYS | A | 227 | −15.070 | 12.611 | −48.572 | 1.00 | 45.68 | A | C |
| ATOM | 837 | CE | LYS | A | 227 | −14.670 | 13.052 | −49.972 | 1.00 | 49.00 | A | C |
| ATOM | 838 | NZ | LYS | A | 227 | −14.046 | 11.919 | −50.746 | 1.00 | 50.79 | A | N |
| ATOM | 839 | C | LYS | A | 227 | −13.903 | 16.439 | −45.684 | 1.00 | 26.56 | A | C |
| ATOM | 840 | O | LYS | A | 227 | −13.688 | 17.407 | −46.345 | 1.00 | 27.42 | A | O |
| ATOM | 841 | N | PHE | A | 228 | −13.074 | 16.038 | −44.734 | 1.00 | 22.48 | A | N |
| ATOM | 842 | CA | PHE | A | 228 | −11.823 | 16.739 | −44.477 | 1.00 | 20.70 | A | C |
| ATOM | 843 | CB | PHE | A | 228 | −11.528 | 16.903 | −42.986 | 1.00 | 19.43 | A | C |
| ATOM | 844 | CG | PHE | A | 228 | −12.562 | 17.662 | −42.196 | 1.00 | 19.79 | A | C |
| ATOM | 845 | CD1 | PHE | A | 228 | −13.237 | 18.769 | −42.719 | 1.00 | 21.05 | A | C |
| ATOM | 846 | CE1 | PHE | A | 228 | −14.154 | 19.458 | −41.941 | 1.00 | 21.48 | A | C |
| ATOM | 847 | CZ | PHE | A | 228 | −14.371 | 19.062 | −40.616 | 1.00 | 21.48 | A | C |

APPENDIX B-continued

Atomic coordinates of Aurora A + Activating Monobody Mb54 + AMPPCP

| | | | | | | | | | | | |
|---|---|---|---|---|---|---|---|---|---|---|---|
| ATOM | 848 | CE2 | PHE | A | 228 | −13.686 | 17.989 | −40.092 | 1.00 | 18.07 | A C |
| ATOM | 849 | CD2 | PHE | A | 228 | −12.795 | 17.318 | −40.871 | 1.00 | 18.57 | A C |
| ATOM | 850 | C | PHE | A | 228 | −10.677 | 15.953 | −45.055 | 1.00 | 21.60 | A C |
| ATOM | 851 | O | PHE | A | 228 | −10.722 | 14.741 | −45.093 | 1.00 | 26.75 | A O |
| ATOM | 852 | N | ASP | A | 229 | −9.637 | 16.633 | −45.485 | 1.00 | 20.56 | A N |
| ATOM | 853 | CA | ASP | A | 229 | −8.434 | 15.951 | −45.883 | 1.00 | 22.49 | A C |
| ATOM | 854 | CB | ASP | A | 229 | −7.570 | 16.887 | −46.767 | 1.00 | 23.22 | A C |
| ATOM | 855 | CG | ASP | A | 229 | −6.742 | 17.931 | −45.994 | 1.00 | 26.90 | A C |
| ATOM | 856 | OD1 | ASP | A | 229 | −6.369 | 17.836 | −44.791 | 1.00 | 26.31 | A O |
| ATOM | 857 | OD2 | ASP | A | 229 | −6.359 | 18.892 | −46.686 | 1.00 | 35.29 | A O |
| ATOM | 858 | C | ASP | A | 229 | −7.661 | 15.352 | −44.709 | 1.00 | 20.68 | A C |
| ATOM | 859 | O | ASP | A | 229 | −7.939 | 15.582 | −43.530 | 1.00 | 23.27 | A O |
| ATOM | 860 | N | GLU | A | 230 | −6.654 | 14.601 | −45.023 | 1.00 | 21.18 | A N |
| ATOM | 861 | CA | GLU | A | 230 | −5.897 | 13.912 | −43.966 | 1.00 | 22.76 | A C |
| ATOM | 862 | CB | GLU | A | 230 | −4.883 | 12.917 | −44.549 | 1.00 | 22.37 | A C |
| ATOM | 863 | CG | GLU | A | 230 | −5.569 | 11.836 | −45.390 | 1.00 | 25.75 | A C |
| ATOM | 864 | CD | GLU | A | 230 | −4.729 | 10.588 | −45.588 | 1.00 | 26.62 | A C |
| ATOM | 865 | OE1 | GLU | A | 230 | −3.616 | 10.631 | −46.165 | 1.00 | 27.51 | A O |
| ATOM | 866 | OE2 | GLU | A | 230 | −5.209 | 9.534 | −45.148 | 1.00 | 28.28 | A O |
| ATOM | 867 | C | GLU | A | 230 | −5.200 | 14.819 | −42.971 | 1.00 | 21.11 | A C |
| ATOM | 868 | O | GLU | A | 230 | −5.095 | 14.461 | −41.798 | 1.00 | 20.12 | A O |
| ATOM | 869 | N | GLN | A | 231 | −4.781 | 16.004 | −43.397 | 1.00 | 22.22 | A N |
| ATOM | 870 | CA | GLN | A | 231 | −3.980 | 16.895 | −42.538 | 1.00 | 24.92 | A C |
| ATOM | 871 | CB | GLN | A | 231 | −3.210 | 17.950 | −43.339 | 1.00 | 26.02 | A C |
| ATOM | 872 | CG | GLN | A | 231 | −2.024 | 17.356 | −44.106 | 1.00 | 28.20 | A C |
| ATOM | 873 | CD | GLN | A | 231 | −2.463 | 16.575 | −45.364 | 1.00 | 32.05 | A C |
| ATOM | 874 | OE1 | GLN | A | 231 | −3.297 | 17.039 | 46.193 | 1.00 | 38.08 | A O |
| ATOM | 875 | NE2 | GLN | A | 231 | −1.930 | 15.368 | −45.498 | 1.00 | 30.17 | A N |
| ATOM | 876 | C | GLN | A | 231 | −4.877 | 17.541 | −41.519 | 1.00 | 23.96 | A C |
| ATOM | 877 | O | GLN | A | 231 | −4.569 | 17.595 | −40.327 | 1.00 | 25.69 | A O |
| ATOM | 878 | N | ARG | A | 232 | −6.005 | 18.026 | −41.999 | 1.00 | 23.72 | A N |
| ATOM | 879 | CA | ARG | A | 232 | −6.959 | 18.606 | −41.132 | 1.00 | 23.55 | A C |
| ATOM | 880 | CB | ARG | A | 232 | −8.117 | 19.182 | −41.938 | 1.00 | 26.14 | A C |
| ATOM | 881 | CG | ARG | A | 232 | −8.995 | 20.029 | −41.025 | 1.00 | 32.74 | A C |
| ATOM | 882 | CD | ARG | A | 232 | −10.339 | 20.336 | −41.600 | 1.00 | 38.21 | A C |
| ATOM | 883 | NE | ARG | A | 232 | −10.171 | 21.140 | −42.787 | 1.00 | 47.16 | A N |
| ATOM | 884 | CZ | ARG | A | 232 | −9.986 | 22.452 | −42.798 | 1.00 | 50.61 | A C |
| ATOM | 885 | NH1 | ARG | A | 232 | −9.942 | 23.151 | −41.674 | 1.00 | 56.51 | A N |
| ATOM | 886 | NH2 | ARG | A | 232 | −9.837 | 23.056 | −43.958 | 1.00 | 55.74 | A N |
| ATOM | 887 | C | ARG | A | 232 | −7.466 | 17.569 | −40.129 | 1.00 | 22.51 | A C |
| ATOM | 888 | O | ARG | A | 232 | −7.548 | 17.838 | −38.944 | 1.00 | 20.18 | A O |
| ATOM | 889 | N | THR | A | 233 | −7.816 | 16.379 | −40.629 | 1.00 | 22.59 | A N |
| ATOM | 890 | CA | THR | A | 233 | −8.300 | 15.303 | −39.795 | 1.00 | 20.45 | A C |
| ATOM | 891 | CB | THR | A | 233 | −8.689 | 14.124 | −40.654 | 1.00 | 20.06 | A C |
| ATOM | 892 | OG1 | THR | A | 233 | −9.753 | 14.523 | −41.558 | 1.00 | 19.90 | A O |
| ATOM | 893 | CG2 | THR | A | 233 | −9.207 | 12.978 | −39.766 | 1.00 | 20.60 | A C |
| ATOM | 894 | C | THR | A | 233 | −7.311 | 14.902 | −38.693 | 1.00 | 21.56 | A C |
| ATOM | 895 | O | THR | A | 233 | −7.663 | 14.914 | −37.500 | 1.00 | 22.27 | A O |
| ATOM | 896 | N | ALA | A | 234 | −6.069 | 14.640 | −39.083 | 1.00 | 20.74 | A N |
| ATOM | 897 | CA | ALA | A | 234 | −5.007 | 14.257 | −38.154 | 1.00 | 21.19 | A C |
| ATOM | 898 | CB | ALA | A | 234 | −3.748 | 13.927 | −38.957 | 1.00 | 22.14 | A C |
| ATOM | 899 | C | ALA | A | 234 | −4.698 | 15.308 | −37.081 | 1.00 | 21.24 | A C |
| ATOM | 900 | O | ALA | A | 234 | −4.494 | 14.995 | −35.887 | 1.00 | 19.51 | A O |
| ATOM | 901 | N | THR | A | 235 | −4.713 | 16.569 | −37.509 | 1.00 | 21.13 | A N |
| ATOM | 902 | CA | THR | A | 235 | −4.467 | 17.650 | −36.628 | 1.00 | 19.49 | A C |
| ATOM | 903 | CB | THR | A | 235 | −4.271 | 18.974 | −37.416 | 1.00 | 20.11 | A C |
| ATOM | 904 | OG1 | THR | A | 235 | −3.190 | 18.827 | −38.360 | 1.00 | 18.53 | A O |
| ATOM | 905 | CG2 | THR | A | 235 | −3.920 | 20.061 | −36.447 | 1.00 | 18.85 | A C |
| ATOM | 906 | C | THR | A | 235 | −5.586 | 17.750 | −35.620 | 1.00 | 18.38 | A C |
| ATOM | 907 | O | THR | A | 235 | −5.356 | 17.942 | −34.424 | 1.00 | 17.83 | A O |
| ATOM | 908 | N | TYR | A | 236 | −6.821 | 17.650 | −36.062 | 1.00 | 18.27 | A N |
| ATOM | 909 | CA | TYR | A | 236 | −7.930 | 17.666 | −35.092 | 1.00 | 17.93 | A C |
| ATOM | 910 | CB | TYR | A | 236 | −9.264 | 17.612 | −35.790 | 1.00 | 19.25 | A C |
| ATOM | 911 | CG | TYR | A | 236 | −9.775 | 18.855 | −36.509 | 1.00 | 21.76 | A C |
| ATOM | 912 | CD1 | TYR | A | 236 | −9.413 | 20.149 | −36.110 | 1.00 | 22.33 | A C |
| ATOM | 913 | CE1 | TYR | A | 236 | −9.935 | 21.258 | −36.751 | 1.00 | 21.34 | A C |
| ATOM | 914 | CZ | TYR | A | 236 | −10.817 | 21.121 | −37.751 | 1.00 | 20.01 | A C |
| ATOM | 915 | OH | TYR | A | 236 | −11.268 | 22.237 | −38.363 | 1.00 | 19.87 | A O |
| ATOM | 916 | CE2 | TYR | A | 236 | −11.208 | 19.863 | −38.175 | 1.00 | 21.77 | A C |
| ATOM | 917 | CD2 | TYR | A | 236 | −10.717 | 18.739 | −37.534 | 1.00 | 20.33 | A C |
| ATOM | 918 | C | TYR | A | 236 | −7.910 | 16.443 | −34.143 | 1.00 | 19.09 | A C |
| ATOM | 919 | O | TYR | A | 236 | −8.211 | 16.577 | −32.970 | 1.00 | 18.55 | A O |
| ATOM | 920 | N | ILE | A | 237 | −7.605 | 15.236 | −34.653 | 1.00 | 19.19 | A N |
| ATOM | 921 | CA | ILE | A | 237 | −7.539 | 14.065 | −33.790 | 1.00 | 19.27 | A C |
| ATOM | 922 | CB | ILE | A | 237 | −7.272 | 12.724 | −34.573 | 1.00 | 20.75 | A C |
| ATOM | 923 | CG1 | ILE | A | 237 | −8.404 | 12.390 | −35.525 | 1.00 | 20.29 | A C |
| ATOM | 924 | CD1 | ILE | A | 237 | −9.778 | 12.414 | −34.891 | 1.00 | 21.58 | A C |
| ATOM | 925 | CG2 | ILE | A | 237 | −7.089 | 11.532 | −33.621 | 1.00 | 20.61 | A C |

APPENDIX B-continued

| Atomic coordinates of Aurora A + Activating Monobody Mb54 + AMPPCP | | | | | | | | | | | |
|---|---|---|---|---|---|---|---|---|---|---|---|
| ATOM | 926 | C | ILE | A | 237 | −6.448 | 14.263 | −32.717 | 1.00 | 18.94 | A C |
| ATOM | 927 | O | ILE | A | 237 | −6.658 | 13.852 | −31.559 | 1.00 | 17.41 | A O |
| ATOM | 928 | N | THR | A | 238 | −5.292 | 14.832 | −33.090 | 1.00 | 17.16 | A N |
| ATOM | 929 | CA | THR | A | 238 | −4.265 | 15.207 | −32.110 | 1.00 | 16.25 | A C |
| ATOM | 930 | CB | THR | A | 238 | −3.119 | 15.884 | −32.847 | 1.00 | 17.98 | A C |
| ATOM | 931 | OG1 | THR | A | 238 | −2.528 | 14.937 | −33.708 | 1.00 | 17.23 | A O |
| ATOM | 932 | CG2 | THR | A | 238 | −1.989 | 16.493 | −31.930 | 1.00 | 19.23 | A C |
| ATOM | 933 | C | THR | A | 238 | −4.760 | 16.172 | −31.025 | 1.00 | 17.02 | A C |
| ATOM | 934 | O | THR | A | 238 | −4.496 | 16.016 | −29.859 | 1.00 | 17.09 | A O |
| ATOM | 935 | N | GLU | A | 239 | −5.495 | 17.186 | −31.407 | 1.00 | 19.25 | A N |
| ATOM | 936 | CA | GLU | A | 239 | −6.011 | 18.133 | −30.435 | 1.00 | 20.37 | A C |
| ATOM | 937 | CB | GLU | A | 239 | −6.611 | 19.349 | −31.175 | 1.00 | 23.28 | A C |
| ATOM | 938 | CG | GLU | A | 239 | −5.494 | 20.162 | −31.868 | 1.00 | 26.72 | A C |
| ATOM | 939 | CD | GLU | A | 239 | −5.940 | 21.221 | −32.872 | 1.00 | 29.07 | A C |
| ATOM | 940 | OE1 | GLU | A | 239 | −7.101 | 21.233 | −33.307 | 1.00 | 33.26 | A O |
| ATOM | 941 | OE2 | GLU | A | 239 | −5.098 | 22.053 | −33.265 | 1.00 | 36.18 | A O |
| ATOM | 942 | C | GLU | A | 239 | −7.018 | 17.487 | −29.513 | 1.00 | 18.58 | A C |
| ATOM | 943 | O | GLU | A | 239 | −7.023 | 17.705 | −28.290 | 1.00 | 16.10 | A O |
| ATOM | 944 | N | LEU | A | 240 | −7.891 | 16.691 | −30.099 | 1.00 | 18.69 | A N |
| ATOM | 945 | CA | LEU | A | 240 | −8.911 | 16.045 | −29.318 | 1.00 | 18.98 | A C |
| ATOM | 946 | CB | LEU | A | 240 | −9.932 | 15.394 | −30.228 | 1.00 | 20.00 | A C |
| ATOM | 947 | CG | LEU | A | 240 | −11.192 | 14.897 | −29.539 | 1.00 | 21.37 | A C |
| ATOM | 948 | CD1 | LEU | A | 240 | −11.780 | 15.863 | −28.504 | 1.00 | 21.91 | A C |
| ATOM | 949 | CD2 | LEU | A | 240 | −12.227 | 14.544 | −30.591 | 1.00 | 23.26 | A C |
| ATOM | 950 | C | LEU | A | 240 | −8.277 | 15.029 | −28.360 | 1.00 | 20.55 | A C |
| ATOM | 951 | O | LEU | A | 240 | −8.662 | 14.914 | −27.205 | 1.00 | 20.40 | A O |
| ATOM | 952 | N | ALA | A | 241 | −7.241 | 14.344 | −28.811 | 1.00 | 21.93 | A N |
| ATOM | 953 | CA | ALA | A | 241 | −6.548 | 13.378 | −27.946 | 1.00 | 21.59 | A C |
| ATOM | 954 | CB | ALA | A | 241 | −5.538 | 12.550 | −28.749 | 1.00 | 21.68 | A C |
| ATOM | 955 | C | ALA | A | 241 | −5.865 | 14.064 | −26.818 | 1.00 | 20.37 | A C |
| ATOM | 956 | O | ALA | A | 241 | −5.799 | 13.554 | −25.753 | 1.00 | 22.70 | A O |
| ATOM | 957 | N | ASN | A | 242 | −5.334 | 15.228 | −27.027 | 1.00 | 21.91 | A N |
| ATOM | 958 | CA | ASN | A | 242 | −4.709 | 15.919 | −25.891 | 1.00 | 23.36 | A C |
| ATOM | 959 | CB | ASN | A | 242 | −3.933 | 17.106 | −26.383 | 1.00 | 23.78 | A C |
| ATOM | 960 | CG | ASN | A | 242 | −2.650 | 16.685 | −27.081 | 1.00 | 26.74 | A C |
| ATOM | 961 | OD1 | ASN | A | 242 | −2.019 | 15.770 | −26.659 | 1.00 | 30.61 | A O |
| ATOM | 962 | ND2 | ASN | A | 242 | −2.272 | 17.366 | −28.138 | 1.00 | 27.60 | A N |
| ATOM | 963 | C | ASN | A | 242 | −5.699 | 16.321 | −24.819 | 1.00 | 23.10 | A C |
| ATOM | 964 | O | ASN | A | 242 | −5.471 | 16.138 | −23.639 | 1.00 | 23.84 | A O |
| ATOM | 965 | N | ALA | A | 243 | −6.808 | 16.865 | −25.263 | 1.00 | 22.67 | A N |
| ATOM | 966 | CA | ALA | A | 243 | −7.880 | 17.218 | −24.387 | 1.00 | 22.59 | A C |
| ATOM | 967 | CB | ALA | A | 243 | −8.952 | 17.878 | −25.219 | 1.00 | 23.41 | A C |
| ATOM | 968 | C | ALA | A | 243 | −8.491 | 16.039 | −23.581 | 1.00 | 20.53 | A C |
| ATOM | 969 | O | ALA | A | 243 | −8.826 | 16.177 | −22.404 | 1.00 | 19.49 | A O |
| ATOM | 970 | N | LEU | A | 244 | −8.697 | 14.912 | −24.254 | 1.00 | 19.70 | A N |
| ATOM | 971 | CA | LEU | A | 244 | −9.206 | 13.734 | −23.601 | 1.00 | 18.01 | A C |
| ATOM | 972 | CB | LEU | A | 244 | −9.681 | 12.667 | −24.603 | 1.00 | 17.92 | A C |
| ATOM | 973 | CG | LEU | A | 244 | −10.818 | 13.043 | −25.565 | 1.00 | 18.18 | A C |
| ATOM | 974 | CD1 | LEU | A | 244 | −10.867 | 12.055 | −26.722 | 1.00 | 17.46 | A C |
| ATOM | 975 | CD2 | LEU | A | 244 | −12.159 | 13.117 | −24.846 | 1.00 | 17.60 | A C |
| ATOM | 976 | C | LEU | A | 244 | −8.120 | 13.180 | −22.710 | 1.00 | 16.94 | A C |
| ATOM | 977 | O | LEU | A | 244 | −8.450 | 12.605 | −21.729 | 1.00 | 16.11 | A O |
| ATOM | 978 | N | SER | A | 245 | −6.839 | 13.343 | −23.014 | 1.00 | 17.59 | A N |
| ATOM | 979 | CA | ASER | A | 245 | −5.783 | 12.876 | −22.090 | 0.50 | 19.21 | A C |
| ATOM | 980 | CA | BSER | A | 245 | −5.808 | 12.856 | −22.090 | 0.50 | 18.24 | A C |
| ATOM | 981 | CB | ASER | A | 245 | −4.365 | 13.118 | −22.606 | 0.50 | 20.73 | A C |
| ATOM | 982 | CB | BSER | A | 245 | −4.412 | 13.006 | −22.672 | 0.50 | 18.57 | A C |
| ATOM | 983 | OG | ASER | A | 245 | −4.225 | 12.873 | −23.993 | 0.50 | 22.01 | A O |
| ATOM | 984 | OG | BSER | A | 245 | −3.427 | 12.387 | −21.867 | 0.50 | 17.20 | A O |
| ATOM | 985 | C | SER | A | 245 | −5.939 | 13.624 | −20.790 | 1.00 | 20.52 | A C |
| ATOM | 986 | O | SER | A | 245 | −5.914 | 13.026 | −19.699 | 1.00 | 23.61 | A O |
| ATOM | 987 | N | TYR | A | 246 | −6.107 | 14.953 | −20.910 | 1.00 | 20.79 | A N |
| ATOM | 988 | CA | TYR | A | 246 | −6.309 | 15.825 | −19.787 | 1.00 | 19.36 | A C |
| ATOM | 989 | CB | TYR | A | 246 | −6.356 | 17.294 | −20.263 | 1.00 | 19.46 | A C |
| ATOM | 990 | CG | TYR | A | 246 | −6.773 | 18.298 | −19.203 | 1.00 | 20.48 | A C |
| ATOM | 991 | CD1 | TYR | A | 246 | −8.133 | 18.557 | −18.947 | 1.00 | 20.86 | A C |
| ATOM | 992 | CE1 | TYR | A | 246 | −8.511 | 19.466 | −17.948 | 1.00 | 21.97 | A C |
| ATOM | 993 | CZ | TYR | A | 246 | −7.518 | 20.158 | −17.226 | 1.00 | 23.02 | A C |
| ATOM | 994 | OH | TYR | A | 246 | −7.911 | 21.070 | −16.234 | 1.00 | 23.17 | A O |
| ATOM | 995 | CE2 | TYR | A | 246 | −6.167 | 19.912 | −17.474 | 1.00 | 19.60 | A C |
| ATOM | 996 | CD2 | TYR | A | 246 | −5.806 | 19.001 | −18.444 | 1.00 | 20.05 | A C |
| ATOM | 997 | C | TYR | A | 246 | −7.599 | 15.383 | −19.054 | 1.00 | 19.60 | A C |
| ATOM | 998 | O | TYR | A | 246 | −7.550 | 15.162 | −17.856 | 1.00 | 20.90 | A O |
| ATOM | 999 | N | CYS | A | 247 | −8.728 | 15.204 | −19.737 | 1.00 | 19.37 | A N |
| ATOM | 1000 | CA | CYS | A | 247 | −9.898 | 14.647 | −19.020 | 1.00 | 21.26 | A C |
| ATOM | 1001 | CB | CYS | A | 247 | −11.098 | 14.482 | −19.930 | 1.00 | 23.09 | A C |
| ATOM | 1002 | SG | CYS | A | 247 | −11.536 | 16.108 | −20.606 | 1.00 | 26.01 | A S |
| ATOM | 1003 | C | CYS | A | 247 | −9.645 | 13.343 | −18.246 | 1.00 | 22.09 | A C |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 1004 | O | CYS | A | 247 | −10.016 | 13.212 | −17.079 | 1.00 | 23.47 | A | O |
| ATOM | 1005 | N | HIS | A | 248 | −9.037 | 12.379 | −18.900 | 1.00 | 23.53 | A | N |
| ATOM | 1006 | CA | HIS | A | 248 | −8.897 | 11.031 | −18.349 | 1.00 | 24.49 | A | C |
| ATOM | 1007 | CB | HIS | A | 248 | −8.430 | 10.053 | −19.440 | 1.00 | 21.89 | A | C |
| ATOM | 1008 | CG | HIS | A | 248 | −9.457 | 9.820 | −20.500 | 1.00 | 20.05 | A | C |
| ATOM | 1009 | ND1 | HIS | A | 248 | −9.276 | 8.947 | −21.543 | 1.00 | 18.52 | A | N |
| ATOM | 1010 | CE1 | HIS | A | 248 | −10.371 | 8.920 | 22.286 | 1.00 | 19.21 | A | C |
| ATOM | 1011 | NE2 | HIS | A | 248 | −11.235 | 9.784 | −21.792 | 1.00 | 18.68 | A | N |
| ATOM | 1012 | CD2 | HIS | A | 248 | −10.690 | 10.359 | −20.672 | 1.00 | 19.66 | A | C |
| ATOM | 1013 | C | HIS | A | 248 | −7.938 | 11.049 | −17.138 | 1.00 | 28.22 | A | C |
| ATOM | 1014 | O | HIS | A | 248 | −8.156 | 10.357 | −16.175 | 1.00 | 29.44 | A | O |
| ATOM | 1015 | N | SER | A | 249 | −6.926 | 11.888 | −17.136 | 1.00 | 28.12 | A | N |
| ATOM | 1016 | CA | SER | A | 249 | −6.124 | 12.008 | −15.909 | 1.00 | 28.34 | A | C |
| ATOM | 1017 | CB | SER | A | 249 | −4.983 | 12.934 | −16.135 | 1.00 | 27.01 | A | C |
| ATOM | 1018 | OG | SER | A | 249 | −4.437 | 12.488 | −17.322 | 1.00 | 27.97 | A | O |
| ATOM | 1019 | C | SER | A | 249 | −6.909 | 12.509 | −14.719 | 1.00 | 27.28 | A | C |
| ATOM | 1020 | O | SER | A | 249 | −6.560 | 12.174 | −13.629 | 1.00 | 27.16 | A | O |
| ATOM | 1021 | N | LYS | A | 250 | −7.938 | 13.323 | −14.910 | 1.00 | 24.78 | A | N |
| ATOM | 1022 | CA | LYS | A | 250 | −8.820 | 13.667 | −13.789 | 1.00 | 27.24 | A | C |
| ATOM | 1023 | CB | LYS | A | 250 | −9.423 | 15.046 | −14.013 | 1.00 | 28.92 | A | C |
| ATOM | 1024 | CG | LYS | A | 250 | −8.322 | 16.081 | −14.149 | 1.00 | 30.06 | A | C |
| ATOM | 1025 | CD | LYS | A | 250 | −8.842 | 17.501 | −14.253 | 1.00 | 31.13 | A | C |
| ATOM | 1026 | CE | LYS | A | 250 | −7.684 | 18.432 | −13.987 | 1.00 | 33.98 | A | C |
| ATOM | 1027 | NZ | LYS | A | 250 | −8.217 | 19.669 | −13.426 | 1.00 | 36.80 | A | N |
| ATOM | 1028 | C | LYS | A | 250 | −9.922 | 12.651 | −13.604 | 1.00 | 27.26 | A | C |
| ATOM | 1029 | O | LYS | A | 250 | −10.883 | 12.867 | −12.841 | 1.00 | 24.99 | A | O |
| ATOM | 1030 | N | ARG | A | 251 | −9.813 | 11.567 | −14.369 | 1.00 | 29.69 | A | N |
| ATOM | 1031 | CA | ARG | A | 251 | −10.755 | 10.466 | −14.331 | 1.00 | 33.12 | A | C |
| ATOM | 1032 | CB | ARG | A | 251 | −10.756 | 9.840 | −12.936 | 1.00 | 40.77 | A | C |
| ATOM | 1033 | CG | ARG | A | 251 | −9.322 | 9.637 | −12.359 | 1.00 | 48.46 | A | C |
| ATOM | 1034 | CD | ARG | A | 251 | −8.738 | 8.254 | −12.531 | 1.00 | 57.00 | A | C |
| ATOM | 1035 | NE | ARG | A | 251 | −9.647 | 7.287 | −11.884 | 1.00 | 72.48 | A | N |
| ATOM | 1036 | CZ | ARG | A | 251 | −10.620 | 6.577 | −12.496 | 1.00 | 80.34 | A | C |
| ATOM | 1037 | NH1 | ARG | A | 251 | −10.837 | 6.670 | −13.820 | 1.00 | 82.24 | A | N |
| ATOM | 1038 | NH2 | ARG | A | 251 | −11.405 | 5.759 | −11.780 | 1.00 | 80.55 | A | N |
| ATOM | 1039 | C | ARG | A | 251 | −12.119 | 10.923 | −14.750 | 1.00 | 29.24 | A | C |
| ATOM | 1040 | O | ARG | A | 251 | −13.126 | 10.400 | −14.291 | 1.00 | 27.44 | A | O |
| ATOM | 1041 | N | VAL | A | 252 | −12.126 | 11.863 | −15.690 | 1.00 | 29.44 | A | N |
| ATOM | 1042 | CA | VAL | A | 252 | −13.353 | 12.377 | −16.325 | 1.00 | 25.70 | A | C |
| ATOM | 1043 | CB | VAL | A | 252 | −13.319 | 13.904 | −16.381 | 1.00 | 25.65 | A | C |
| ATOM | 1044 | CG1 | VAL | A | 252 | −14.447 | 14.449 | −17.225 | 1.00 | 26.43 | A | C |
| ATOM | 1045 | CG2 | VAL | A | 252 | −13.474 | 14.434 | −14.969 | 1.00 | 29.57 | A | C |
| ATOM | 1046 | C | VAL | A | 252 | −13.446 | 11.824 | −17.716 | 1.00 | 22.37 | A | C |
| ATOM | 1047 | O | VAL | A | 252 | −12.461 | 11.850 | −18.467 | 1.00 | 21.66 | A | O |
| ATOM | 1048 | N | ILE | A | 253 | −14.633 | 11.355 | −18.062 | 1.00 | 20.75 | A | N |
| ATOM | 1049 | CA | ILE | A | 253 | −14.936 | 10.783 | −19.400 | 1.00 | 21.38 | A | C |
| ATOM | 1050 | CB | ILE | A | 253 | −15.481 | 9.317 | −19.295 | 1.00 | 22.16 | A | C |
| ATOM | 1051 | CG1 | ILE | A | 253 | −14.664 | 8.478 | −18.285 | 1.00 | 23.45 | A | C |
| ATOM | 1052 | CD1 | ILE | A | 253 | −15.236 | 7.098 | −17.972 | 1.00 | 23.83 | A | C |
| ATOM | 1053 | CG2 | ILE | A | 253 | −15.545 | 8.639 | −20.671 | 1.00 | 23.18 | A | C |
| ATOM | 1054 | C | ILE | A | 253 | −16.021 | 11.617 | −20.073 | 1.00 | 19.42 | A | C |
| ATOM | 1055 | O | ILE | A | 253 | −17.041 | 11.862 | −19.443 | 1.00 | 18.50 | A | O |
| ATOM | 1056 | N | HIS | A | 254 | −15.844 | 11.997 | −21.345 | 1.00 | 18.24 | A | N |
| ATOM | 1057 | CA | HIS | A | 254 | −16.806 | 12.911 | −22.006 | 1.00 | 19.04 | A | C |
| ATOM | 1058 | CB | HIS | A | 254 | −16.139 | 13.564 | −23.247 | 1.00 | 21.52 | A | C |
| ATOM | 1059 | CG | HIS | A | 254 | −16.943 | 14.676 | −23.837 | 1.00 | 22.96 | A | C |
| ATOM | 1060 | ND1 | HIS | A | 254 | −18.007 | 14.454 | −24.679 | 1.00 | 23.80 | A | N |
| ATOM | 1061 | CE1 | HIS | A | 254 | −18.577 | 15.600 | −24.992 | 1.00 | 24.61 | A | C |
| ATOM | 1062 | NE2 | HIS | A | 254 | −17.883 | 16.567 | −24.419 | 1.00 | 24.54 | A | N |
| ATOM | 1063 | CD2 | HIS | A | 254 | −16.868 | 16.012 | −23.677 | 1.00 | 22.78 | A | C |
| ATOM | 1064 | C | HIS | A | 254 | −18.129 | 12.265 | −22.366 | 1.00 | 17.53 | A | C |
| ATOM | 1065 | O | HIS | A | 254 | −19.200 | 12.770 | −22.030 | 1.00 | 20.37 | A | O |
| ATOM | 1066 | N | ARG | A | 255 | −18.011 | 11.148 | −23.059 | 1.00 | 18.16 | A | N |
| ATOM | 1067 | CA | ARG | A | 255 | −19.082 | 10.237 | −23.438 | 1.00 | 21.11 | A | C |
| ATOM | 1068 | CB | ARG | A | 255 | −19.861 | 9.677 | −22.233 | 1.00 | 21.58 | A | C |
| ATOM | 1069 | CG | ARG | A | 255 | −18.941 | 9.165 | −21.132 | 1.00 | 23.39 | A | C |
| ATOM | 1070 | CD | ARG | A | 255 | −19.736 | 8.438 | −20.058 | 1.00 | 25.92 | A | C |
| ATOM | 1071 | NE | ARG | A | 255 | −20.733 | 9.304 | −19.438 | 1.00 | 26.53 | A | N |
| ATOM | 1072 | CZ | ARG | A | 255 | −21.594 | 8.909 | −18.504 | 1.00 | 27.86 | A | C |
| ATOM | 1073 | NH1 | ARG | A | 255 | −21.596 | 7.669 | −18.066 | 1.00 | 28.50 | A | N |
| ATOM | 1074 | NH2 | ARG | A | 255 | −22.461 | 9.766 | −18.011 | 1.00 | 28.70 | A | N |
| ATOM | 1075 | C | ARG | A | 255 | −20.051 | 10.772 | −24.483 | 1.00 | 23.27 | A | C |
| ATOM | 1076 | O | ARG | A | 255 | −21.106 | 10.172 | −24.742 | 1.00 | 25.01 | A | O |
| ATOM | 1077 | N | ASP | A | 256 | −19.676 | 11.836 | −25.159 | 1.00 | 22.40 | A | N |
| ATOM | 1078 | CA | ASP | A | 256 | −20.539 | 12.335 | −26.211 | 1.00 | 22.49 | A | C |
| ATOM | 1079 | CB | ASP | A | 256 | −21.650 | 13.229 | −25.635 | 1.00 | 21.15 | A | C |
| ATOM | 1080 | CG | ASP | A | 256 | −22.763 | 13.513 | −26.670 | 1.00 | 22.35 | A | C |
| ATOM | 1081 | OD1 | ASP | A | 256 | −22.979 | 12.727 | −27.655 | 1.00 | 21.08 | A | O |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 1082 | OD2 | ASP | A | 256 | −23.439 | 14.550 | −26.506 | 1.00 | 28.04 | A | O |
| ATOM | 1083 | C | ASP | A | 256 | −19.757 | 13.049 | −27.268 | 1.00 | 20.68 | A | C |
| ATOM | 1084 | O | ASP | A | 256 | −20.148 | 14.126 | −27.653 | 1.00 | 21.04 | A | O |
| ATOM | 1085 | N | ILE | A | 257 | −18.610 | 12.495 | −27.649 | 1.00 | 20.61 | A | N |
| ATOM | 1086 | CA | ILE | A | 257 | −17.759 | 13.031 | −28.690 | 1.00 | 19.72 | A | C |
| ATOM | 1087 | CB | ILE | A | 257 | −16.470 | 12.228 | −28.839 | 1.00 | 20.22 | A | C |
| ATOM | 1088 | CG1 | ILE | A | 257 | −15.477 | 12.525 | −27.730 | 1.00 | 22.70 | A | C |
| ATOM | 1089 | CD1 | ILE | A | 257 | −14.344 | 11.463 | −27.585 | 1.00 | 21.44 | A | C |
| ATOM | 1090 | CG2 | ILE | A | 257 | −15.797 | 12.499 | −30.152 | 1.00 | 21.92 | A | C |
| ATOM | 1091 | C | ILE | A | 257 | −18.531 | 12.900 | −29.999 | 1.00 | 20.85 | A | C |
| ATOM | 1092 | O | ILE | A | 257 | −19.024 | 11.795 | −30.369 | 1.00 | 22.82 | A | O |
| ATOM | 1093 | N | LYS | A | 258 | −18.635 | 14.017 | −30.685 | 1.00 | 19.53 | A | N |
| ATOM | 1094 | CA | LYS | A | 258 | −19.288 | 14.091 | −32.014 | 1.00 | 23.13 | A | C |
| ATOM | 1095 | CB | LYS | A | 258 | −20.821 | 13.819 | −31.947 | 1.00 | 21.47 | A | C |
| ATOM | 1096 | CG | LYS | A | 258 | −21.596 | 14.777 | −31.069 | 1.00 | 21.70 | A | C |
| ATOM | 1097 | CD | LYS | A | 258 | −23.090 | 14.476 | −31.159 | 1.00 | 21.35 | A | C |
| ATOM | 1098 | CE | LYS | A | 258 | −23.850 | 15.289 | −30.135 | 1.00 | 21.51 | A | C |
| ATOM | 1099 | NZ | LYS | A | 258 | −25.295 | 15.016 | −30.232 | 1.00 | 22.63 | A | N |
| ATOM | 1100 | C | LYS | A | 258 | −19.047 | 15.483 | −32.607 | 1.00 | 21.46 | A | C |
| ATOM | 1101 | O | LYS | A | 258 | −18.654 | 16.404 | −31.859 | 1.00 | 21.74 | A | O |
| ATOM | 1102 | N | PRO | A | 259 | −19.321 | 15.659 | −33.920 | 1.00 | 22.59 | A | N |
| ATOM | 1103 | CA | PRO | A | 259 | −18.908 | 16.931 | −34.538 | 1.00 | 21.86 | A | C |
| ATOM | 1104 | CB | PRO | A | 259 | −19.208 | 16.702 | −36.013 | 1.00 | 22.34 | A | C |
| ATOM | 1105 | CG | PRO | A | 259 | −19.054 | 15.240 | −36.202 | 1.00 | 20.73 | A | C |
| ATOM | 1106 | CD | PRO | A | 259 | −19.703 | 14.684 | −34.955 | 1.00 | 21.31 | A | C |
| ATOM | 1107 | C | PRO | A | 259 | −19.618 | 18.164 | −33.985 | 1.00 | 21.08 | A | C |
| ATOM | 1108 | O | PRO | A | 259 | −19.028 | 19.218 | −33.978 | 1.00 | 17.23 | A | O |
| ATOM | 1109 | N | GLU | A | 260 | −20.855 | 18.015 | −33.513 | 1.00 | 21.06 | A | N |
| ATOM | 1110 | CA | GLU | A | 260 | −21.621 | 19.145 | −32.953 | 1.00 | 23.49 | A | C |
| ATOM | 1111 | CB | GLU | A | 260 | −23.053 | 18.738 | −32.614 | 1.00 | 26.98 | A | C |
| ATOM | 1112 | CG | GLU | A | 260 | −23.864 | 18.421 | −33.835 | 1.00 | 30.85 | A | C |
| ATOM | 1113 | CD | GLU | A | 260 | −23.798 | 16.976 | −34.267 | 1.00 | 33.80 | A | C |
| ATOM | 1114 | OE1 | GLU | A | 260 | −22.718 | 16.279 | −34.228 | 1.00 | 34.27 | A | O |
| ATOM | 1115 | OE2 | GLU | A | 260 | −24.883 | 16.551 | −34.672 | 1.00 | 40.35 | A | O |
| ATOM | 1116 | C | GLU | A | 260 | −21.075 | 19.695 | −31.662 | 1.00 | 22.64 | A | C |
| ATOM | 1117 | O | GLU | A | 260 | −21.401 | 20.809 | −31.295 | 1.00 | 21.89 | A | O |
| ATOM | 1118 | N | ASN | A | 261 | −20.310 | 18.880 | −30.942 | 1.00 | 21.19 | A | N |
| ATOM | 1119 | CA | ASN | A | 261 | −19.729 | 19.249 | −29.679 | 1.00 | 19.82 | A | C |
| ATOM | 1120 | CB | ASN | A | 261 | −19.832 | 18.062 | −28.736 | 1.00 | 20.52 | A | C |
| ATOM | 1121 | CG | ASN | A | 261 | −21.272 | 17.716 | −28.407 | 1.00 | 22.19 | A | C |
| ATOM | 1122 | OD1 | ASN | A | 261 | −22.160 | 18.548 | −28.571 | 1.00 | 23.38 | A | O |
| ATOM | 1123 | ND2 | ASN | A | 261 | −21.511 | 16.498 | −27.939 | 1.00 | 21.28 | A | N |
| ATOM | 1124 | C | ASN | A | 261 | −18.281 | 19.712 | −29.805 | 1.00 | 19.21 | A | C |
| ATOM | 1125 | O | ASN | A | 261 | −17.578 | 19.822 | −28.824 | 1.00 | 18.48 | A | O |
| ATOM | 1126 | N | LEU | A | 262 | −17.863 | 20.047 | −31.006 | 1.00 | 18.81 | A | N |
| ATOM | 1127 | CA | LEU | A | 262 | −16.522 | 20.543 | −31.204 | 1.00 | 19.71 | A | C |
| ATOM | 1128 | CB | LEU | A | 262 | −15.785 | 19.618 | −32.146 | 1.00 | 19.91 | A | C |
| ATOM | 1129 | CG | LEU | A | 262 | −15.709 | 18.141 | −31.744 | 1.00 | 19.85 | A | C |
| ATOM | 1130 | CD1 | LEU | A | 262 | −15.069 | 17.297 | −32.818 | 1.00 | 19.34 | A | C |
| ATOM | 1131 | CD2 | LEU | A | 262 | −14.942 | 17.972 | −30.437 | 1.00 | 21.25 | A | C |
| ATOM | 1132 | C | LEU | A | 262 | −16.654 | 21.930 | −31.804 | 1.00 | 20.64 | A | C |
| ATOM | 1133 | O | LEU | A | 262 | −17.418 | 22.122 | −32.746 | 1.00 | 23.83 | A | O |
| ATOM | 1134 | N | LEU | A | 263 | −15.922 | 22.885 | −31.250 | 1.00 | 19.17 | A | N |
| ATOM | 1135 | CA | LEU | A | 263 | −15.906 | 24.249 | −31.722 | 1.00 | 19.05 | A | C |
| ATOM | 1136 | CB | LEU | A | 263 | −16.442 | 25.160 | −30.652 | 1.00 | 19.31 | A | C |
| ATOM | 1137 | CG | LEU | A | 263 | −17.912 | 24.938 | −30.308 | 1.00 | 19.85 | A | C |
| ATOM | 1138 | CD1 | LEU | A | 263 | −18.164 | 25.398 | −28.917 | 1.00 | 22.37 | A | C |
| ATOM | 1139 | CD2 | LEU | A | 263 | −18.789 | 25.806 | −31.145 | 1.00 | 21.15 | A | C |
| ATOM | 1140 | C | LEU | A | 263 | −14.476 | 24.639 | −32.092 | 1.00 | 19.92 | A | C |
| ATOM | 1141 | O | LEU | A | 263 | −13.532 | 23.873 | −31.878 | 1.00 | 20.03 | A | O |
| ATOM | 1142 | N | LEU | A | 264 | −14.331 | 25.803 | −32.692 | 1.00 | 19.09 | A | N |
| ATOM | 1143 | CA | LEU | A | 264 | −13.070 | 26.188 | −33.317 | 1.00 | 19.34 | A | C |
| ATOM | 1144 | CB | LEU | A | 264 | −13.281 | 26.118 | −34.823 | 1.00 | 19.60 | A | C |
| ATOM | 1145 | CG | LEU | A | 264 | −13.363 | 24.714 | −35.434 | 1.00 | 21.19 | A | C |
| ATOM | 1146 | CD1 | LEU | A | 264 | −13.848 | 24.753 | −36.887 | 1.00 | 21.49 | A | C |
| ATOM | 1147 | CD2 | LEU | A | 264 | −12.009 | 24.017 | −35.362 | 1.00 | 21.70 | A | C |
| ATOM | 1148 | C | LEU | A | 264 | −12.652 | 27.599 | −32.871 | 1.00 | 19.28 | A | C |
| ATOM | 1149 | O | LEU | A | 264 | −13.405 | 28.605 | −32.997 | 1.00 | 18.51 | A | O |
| ATOM | 1150 | N | GLY | A | 265 | −11.456 | 27.681 | −32.348 | 1.00 | 20.94 | A | N |
| ATOM | 1151 | CA | GLY | A | 265 | −10.864 | 28.938 | −31.960 | 1.00 | 24.42 | A | C |
| ATOM | 1152 | C | GLY | A | 265 | −10.454 | 29.773 | −33.145 | 1.00 | 27.40 | A | C |
| ATOM | 1153 | O | GLY | A | 265 | −10.671 | 29.397 | −34.294 | 1.00 | 28.97 | A | O |
| ATOM | 1154 | N | SER | A | 266 | −9.834 | 30.908 | −32.852 | 1.00 | 28.25 | A | N |
| ATOM | 1155 | CA | SER | A | 266 | −9.534 | 31.904 | −33.886 | 1.00 | 31.54 | A | C |
| ATOM | 1156 | CB | SER | A | 266 | −9.167 | 33.255 | −33.250 | 1.00 | 33.21 | A | C |
| ATOM | 1157 | OG | SER | A | 266 | −7.847 | 33.201 | −32.743 | 1.00 | 33.86 | A | O |
| ATOM | 1158 | C | SER | A | 266 | −8.414 | 31.453 | −34.810 | 1.00 | 29.10 | A | C |
| ATOM | 1159 | O | SER | A | 266 | −8.405 | 31.786 | −35.957 | 1.00 | 31.62 | A | O |

APPENDIX B-continued

| Atomic coordinates of Aurora A + Activating Monobody Mb54 + AMPPCP | | | | | | | | | | | | |
|---|---|---|---|---|---|---|---|---|---|---|---|---|
| ATOM | 1160 | N | ALA | A | 267 | −7.484 | 30.680 | −34.303 | 1.00 | 28.92 | A | N |
| ATOM | 1161 | CA | ALA | A | 267 | −6.512 | 30.003 | −35.142 | 1.00 | 27.94 | A | C |
| ATOM | 1162 | CB | ALA | A | 267 | −5.216 | 29.809 | −34.343 | 1.00 | 27.56 | A | C |
| ATOM | 1163 | C | ALA | A | 267 | −7.021 | 28.661 | −35.697 | 1.00 | 26.45 | A | C |
| ATOM | 1164 | O | ALA | A | 267 | −6.236 | 27.895 | −36.153 | 1.00 | 27.50 | A | O |
| ATOM | 1165 | N | GLY | A | 268 | −8.320 | 28.363 | −35.665 | 1.00 | 27.62 | A | N |
| ATOM | 1166 | CA | GLY | A | 268 | −8.849 | 27.086 | −36.209 | 1.00 | 27.33 | A | C |
| ATOM | 1167 | C | GLY | A | 268 | −8.580 | 25.820 | −35.371 | 1.00 | 25.56 | A | C |
| ATOM | 1168 | O | GLY | A | 268 | −8.649 | 24.707 | −35.869 | 1.00 | 25.24 | A | O |
| ATOM | 1169 | N | GLU | A | 269 | −8.308 | 25.999 | −34.103 | 1.00 | 24.17 | A | N |
| ATOM | 1170 | CA | GLU | A | 269 | −7.897 | 24.929 | −33.226 | 1.00 | 26.10 | A | C |
| ATOM | 1171 | CB | GLU | A | 269 | −6.867 | 25.429 | −32.224 | 1.00 | 27.77 | A | C |
| ATOM | 1172 | CG | GLU | A | 269 | −7.374 | 26.417 | −31.201 | 1.00 | 32.96 | A | C |
| ATOM | 1173 | CD | GLU | A | 269 | −7.262 | 27.898 | −31.583 | 1.00 | 35.81 | A | C |
| ATOM | 1174 | OE1 | GLU | A | 269 | −7.367 | 28.271 | −32.759 | 1.00 | 34.60 | A | O |
| ATOM | 1175 | OE2 | GLU | A | 269 | −7.133 | 28.713 | −30.644 | 1.00 | 46.04 | A | O |
| ATOM | 1176 | C | GLU | A | 269 | −9.125 | 24.327 | −32.525 | 1.00 | 24.66 | A | C |
| ATOM | 1177 | O | GLU | A | 269 | −10.033 | 25.045 | −32.131 | 1.00 | 25.67 | A | O |
| ATOM | 1178 | N | LEU | A | 270 | −9.170 | 23.010 | −32.379 | 1.00 | 20.80 | A | N |
| ATOM | 1179 | CA | LEU | A | 270 | −10.388 | 22.363 | −31.925 | 1.00 | 20.24 | A | C |
| ATOM | 1180 | CB | LEU | A | 270 | −10.271 | 20.872 | −32.219 | 1.00 | 20.43 | A | C |
| ATOM | 1181 | CG | LEU | A | 270 | −11.284 | 19.891 | −31.636 | 1.00 | 20.23 | A | C |
| ATOM | 1182 | CD1 | LEU | A | 270 | −11.312 | 18.649 | −32.519 | 1.00 | 19.70 | A | C |
| ATOM | 1183 | CD2 | LEU | A | 270 | −10.901 | 19.508 | −30.215 | 1.00 | 21.89 | A | C |
| ATOM | 1184 | C | LEU | A | 270 | −10.651 | 22.626 | −30.442 | 1.00 | 19.35 | A | C |
| ATOM | 1185 | O | LEU | A | 270 | −9.711 | 22.759 | −29.638 | 1.00 | 17.25 | A | O |
| ATOM | 1186 | N | LYS | A | 271 | −11.920 | 22.688 | −30.050 | 1.00 | 19.78 | A | N |
| ATOM | 1187 | CA | LYS | A | 271 | −12.274 | 22.891 | −28.639 | 1.00 | 21.66 | A | C |
| ATOM | 1188 | CB | LYS | A | 271 | −12.784 | 24.318 | −28.372 | 1.00 | 24.94 | A | C |
| ATOM | 1189 | CG | LYS | A | 271 | −11.861 | 25.486 | −28.740 | 1.00 | 27.55 | A | C |
| ATOM | 1190 | CD | LYS | A | 271 | −10.891 | 25.887 | −27.642 | 1.00 | 27.88 | A | C |
| ATOM | 1191 | CE | LYS | A | 271 | −9.988 | 26.990 | −28.171 | 1.00 | 27.66 | A | C |
| ATOM | 1192 | NZ | LYS | A | 271 | −9.021 | 27.459 | −27.148 | 1.00 | 27.61 | A | N |
| ATOM | 1193 | C | LYS | A | 271 | −13.415 | 21.955 | −28.301 | 1.00 | 22.14 | A | C |
| ATOM | 1194 | O | LYS | A | 271 | −14.464 | 22.163 | −28.840 | 1.00 | 20.73 | A | O |
| ATOM | 1195 | N | ILE | A | 272 | −13.256 | 20.967 | −27.417 | 1.00 | 20.29 | A | N |
| ATOM | 1196 | CA | ILE | A | 272 | −14.396 | 20.110 | −27.124 | 1.00 | 19.44 | A | C |
| ATOM | 1197 | CB | ILE | A | 272 | −14.023 | 18.662 | −26.733 | 1.00 | 21.12 | A | C |
| ATOM | 1198 | CG1 | ILE | A | 272 | −15.276 | 17.875 | −26.390 | 1.00 | 21.97 | A | C |
| ATOM | 1199 | CD1 | ILE | A | 272 | −15.149 | 16.403 | −26.641 | 1.00 | 26.03 | A | C |
| ATOM | 1200 | CG2 | ILE | A | 272 | −13.108 | 18.585 | −25.522 | 1.00 | 22.78 | A | C |
| ATOM | 1201 | C | ILE | A | 272 | −15.270 | 20.777 | −26.093 | 1.00 | 18.24 | A | C |
| ATOM | 1202 | O | ILE | A | 272 | −14.771 | 21.391 | −25.192 | 1.00 | 18.89 | A | O |
| ATOM | 1203 | N | ALA | A | 273 | −16.575 | 20.662 | −26.230 | 1.00 | 17.98 | A | N |
| ATOM | 1204 | CA | ALA | A | 273 | −17.516 | 21.287 | −25.294 | 1.00 | 20.19 | A | C |
| ATOM | 1205 | CB | ALA | A | 273 | −18.064 | 22.553 | −25.924 | 1.00 | 21.21 | A | C |
| ATOM | 1206 | C | ALA | A | 273 | −18.667 | 20.347 | −24.991 | 1.00 | 21.40 | A | C |
| ATOM | 1207 | O | ALA | A | 273 | −18.608 | 19.181 | −25.317 | 1.00 | 24.64 | A | O |
| ATOM | 1208 | N | ASP | A | 274 | −19.708 | 20.849 | −24.358 | 1.00 | 21.08 | A | N |
| ATOM | 1209 | CA | ASP | A | 274 | −20.880 | 20.051 | −24.090 | 1.00 | 23.43 | A | C |
| ATOM | 1210 | CB | ASP | A | 274 | −21.622 | 19.656 | −25.389 | 1.00 | 27.42 | A | C |
| ATOM | 1211 | CG | ASP | A | 274 | −21.914 | 20.880 | −26.301 | 1.00 | 32.02 | A | C |
| ATOM | 1212 | OD1 | ASP | A | 274 | −22.615 | 21.815 | −25.844 | 1.00 | 30.94 | A | O |
| ATOM | 1213 | OD2 | ASP | A | 274 | −21.395 | 20.923 | −27.441 | 1.00 | 36.92 | A | O |
| ATOM | 1214 | C | ASP | A | 274 | −20.596 | 18.835 | −23.255 | 1.00 | 21.16 | A | C |
| ATOM | 1215 | O | ASP | A | 274 | −20.780 | 17.723 | −23.701 | 1.00 | 20.94 | A | O |
| ATOM | 1216 | N | PHE | A | 275 | −20.235 | 19.084 | −22.004 | 1.00 | 22.08 | A | N |
| ATOM | 1217 | CA | PHE | A | 275 | −19.987 | 18.058 | −20.996 | 1.00 | 22.48 | A | C |
| ATOM | 1218 | CB | PHE | A | 275 | −18.861 | 18.528 | −20.043 | 1.00 | 21.34 | A | C |
| ATOM | 1219 | CG | PHE | A | 275 | −17.474 | 18.464 | −20.656 | 1.00 | 21.07 | A | C |
| ATOM | 1220 | CD1 | PHE | A | 275 | −17.087 | 19.345 | −21.651 | 1.00 | 20.92 | A | C |
| ATOM | 1221 | CE1 | PHE | A | 275 | −15.810 | 19.313 | −22.211 | 1.00 | 17.83 | A | C |
| ATOM | 1222 | CZ | PHE | A | 275 | −14.931 | 18.390 | −21.779 | 1.00 | 19.73 | A | C |
| ATOM | 1223 | CE2 | PHE | A | 275 | −15.283 | 17.504 | −20.762 | 1.00 | 20.75 | A | C |
| ATOM | 1224 | CD2 | PHE | A | 275 | −16.542 | 17.564 | −20.198 | 1.00 | 21.63 | A | C |
| ATOM | 1225 | C | PHE | A | 275 | −21.272 | 17.593 | −20.235 | 1.00 | 21.09 | A | C |
| ATOM | 1226 | O | PHE | A | 275 | −21.191 | 16.965 | −19.193 | 1.00 | 20.40 | A | O |
| ATOM | 1227 | N | GLY | A | 276 | −22.443 | 17.844 | −20.795 | 1.00 | 21.62 | A | N |
| ATOM | 1228 | CA | GLY | A | 276 | −23.718 | 17.328 | −20.269 | 1.00 | 23.14 | A | C |
| ATOM | 1229 | C | GLY | A | 276 | −23.741 | 15.841 | −19.933 | 1.00 | 25.18 | A | C |
| ATOM | 1230 | O | GLY | A | 276 | −24.340 | 15.451 | −18.956 | 1.00 | 26.25 | A | O |
| ATOM | 1231 | N | TRP | A | 277 | −23.095 | 14.994 | −20.733 | 1.00 | 24.92 | A | N |
| ATOM | 1232 | CA | TRP | A | 277 | −23.173 | 13.569 | −20.530 | 1.00 | 23.84 | A | C |
| ATOM | 1233 | CB | TRP | A | 277 | −23.514 | 12.884 | −21.843 | 1.00 | 25.27 | A | C |
| ATOM | 1234 | CG | TRP | A | 277 | −24.908 | 13.137 | −22.311 | 1.00 | 26.44 | A | C |
| ATOM | 1235 | CD1 | TRP | A | 277 | −25.312 | 13.797 | −23.465 | 1.00 | 27.81 | A | C |
| ATOM | 1236 | NE1 | TRP | A | 277 | −26.706 | 13.804 | −23.549 | 1.00 | 28.09 | A | N |
| ATOM | 1237 | CE2 | TRP | A | 277 | −27.207 | 13.126 | −22.465 | 1.00 | 29.78 | A | C |

APPENDIX B-continued

Atomic coordinates of Aurora A + Activating Monobody Mb54 + AMPPCP

| | | | | | | | | | | | |
|---|---|---|---|---|---|---|---|---|---|---|---|
| ATOM | 1238 | CD2 | TRP | A | 277 | −26.094 | 12.675 | −21.678 | 1.00 | 28.38 | A | C |
| ATOM | 1239 | CE3 | TRP | A | 277 | −26.345 | 11.955 | −20.503 | 1.00 | 27.25 | A | C |
| ATOM | 1240 | CZ3 | TRP | A | 277 | −27.680 | 11.706 | −20.138 | 1.00 | 27.97 | A | C |
| ATOM | 1241 | CH2 | TRP | A | 277 | −28.744 | 12.137 | −20.956 | 1.00 | 28.96 | A | C |
| ATOM | 1242 | CZ2 | TRP | A | 277 | −28.524 | 12.876 | −22.095 | 1.00 | 28.09 | A | C |
| ATOM | 1243 | C | TRP | A | 277 | −21.880 | 13.039 | −19.964 | 1.00 | 23.15 | A | C |
| ATOM | 1244 | O | TRP | A | 277 | −21.737 | 11.849 | −19.831 | 1.00 | 21.63 | A | O |
| ATOM | 1245 | N | SER | A | 278 | −20.955 | 13.910 | −19.582 | 1.00 | 23.58 | A | N |
| ATOM | 1246 | CA | SER | A | 278 | −19.709 | 13.443 | −18.997 | 1.00 | 24.79 | A | C |
| ATOM | 1247 | CB | SER | A | 278 | −18.655 | 14.539 | −18.977 | 1.00 | 25.66 | A | C |
| ATOM | 1248 | OG | SER | A | 278 | −18.999 | 15.594 | −18.102 | 1.00 | 27.05 | A | O |
| ATOM | 1249 | C | SER | A | 278 | −19.928 | 12.895 | −17.566 | 1.00 | 26.18 | A | C |
| ATOM | 1250 | O | SER | A | 278 | −20.989 | 13.067 | −16.957 | 1.00 | 21.79 | A | O |
| ATOM | 1251 | N | VAL | A | 279 | −18.904 | 12.242 | −17.049 | 1.00 | 24.73 | A | N |
| ATOM | 1252 | CA | VAL | A | 279 | −18.998 | 11.551 | −15.766 | 1.00 | 26.02 | A | C |
| ATOM | 1253 | CB | VAL | A | 279 | −19.580 | 10.121 | −15.966 | 1.00 | 25.46 | A | C |
| ATOM | 1254 | CG1 | VAL | A | 279 | −18.569 | 9.237 | −16.679 | 1.00 | 26.05 | A | C |
| ATOM | 1255 | CG2 | VAL | A | 279 | −20.015 | 9.481 | −14.671 | 1.00 | 25.05 | A | C |
| ATOM | 1256 | C | VAL | A | 279 | −17.614 | 11.506 | −15.154 | 1.00 | 24.76 | A | C |
| ATOM | 1257 | O | VAL | A | 279 | −16.601 | 11.423 | −15.876 | 1.00 | 24.86 | A | O |
| ATOM | 1258 | N | HIS | A | 280 | −17.557 | 11.619 | −13.836 | 1.00 | 25.77 | A | N |
| ATOM | 1259 | CA | HIS | A | 280 | −16.301 | 11.335 | −13.095 | 1.00 | 26.52 | A | C |
| ATOM | 1260 | CB | HIS | A | 280 | −16.260 | 12.181 | −11.843 | 1.00 | 27.86 | A | C |
| ATOM | 1261 | CG | HIS | A | 280 | −15.083 | 11.931 | −10.949 | 1.00 | 27.80 | A | C |
| ATOM | 1262 | ND1 | HIS | A | 280 | −15.230 | 11.673 | −9.600 | 1.00 | 26.11 | A | N |
| ATOM | 1263 | CE1 | HIS | A | 280 | −14.029 | 11.551 | −9.056 | 1.00 | 28.36 | A | C |
| ATOM | 1264 | NE2 | HIS | A | 280 | −13.113 | 11.734 | −9.994 | 1.00 | 26.33 | A | N |
| ATOM | 1265 | CD2 | HIS | A | 280 | −13.744 | 11.971 | −11.188 | 1.00 | 28.18 | A | C |
| ATOM | 1266 | C | HIS | A | 280 | −16.352 | 9.857 | −12.736 | 1.00 | 24.70 | A | C |
| ATOM | 1267 | O | HIS | A | 280 | −17.284 | 9.422 | −12.072 | 1.00 | 21.65 | A | O |
| ATOM | 1268 | N | ALA | A | 281 | −15.370 | 9.087 | −13.206 | 1.00 | 26.01 | A | N |
| ATOM | 1269 | CA | ALA | A | 281 | −15.447 | 7.586 | −13.108 | 1.00 | 27.56 | A | C |
| ATOM | 1270 | CB | ALA | A | 281 | −14.321 | 6.922 | −13.909 | 1.00 | 25.29 | A | C |
| ATOM | 1271 | C | ALA | A | 281 | −15.584 | 7.002 | −11.665 | 1.00 | 25.81 | A | C |
| ATOM | 1272 | O | ALA | A | 281 | −16.505 | 6.210 | −11.412 | 1.00 | 27.31 | A | O |
| ATOM | 1273 | N | PRO | A | 282 | −14.755 | 7.458 | −10.706 | 1.00 | 26.97 | A | N |
| ATOM | 1274 | CA | PRO | A | 282 | −14.890 | 7.041 | −9.298 | 1.00 | 28.70 | A | C |
| ATOM | 1275 | CB | PRO | A | 282 | −13.843 | 7.859 | −8.576 | 1.00 | 28.23 | A | C |
| ATOM | 1276 | CG | PRO | A | 282 | −12.810 | 8.144 | −9.623 | 1.00 | 29.79 | A | C |
| ATOM | 1277 | CD | PRO | A | 282 | −13.621 | 8.373 | −10.867 | 1.00 | 29.37 | A | C |
| ATOM | 1278 | C | PRO | A | 282 | −16.233 | 7.373 | −8.682 | 1.00 | 32.84 | A | C |
| ATOM | 1279 | O | PRO | A | 282 | −16.594 | 6.758 | −7.693 | 1.00 | 34.78 | A | O |
| ATOM | 1280 | N | SER | A | 283 | −16.968 | 8.337 | −9.231 | 1.00 | 30.36 | A | N |
| ATOM | 1281 | CA | SER | A | 283 | −18.198 | 8.744 | −8.621 | 1.00 | 29.28 | A | C |
| ATOM | 1282 | CB | SER | A | 283 | −18.292 | 10.265 | −8.585 | 1.00 | 28.09 | A | C |
| ATOM | 1283 | OG | SER | A | 283 | −17.168 | 10.872 | −7.963 | 1.00 | 28.01 | A | O |
| ATOM | 1284 | C | SER | A | 283 | −19.370 | 8.127 | −9.349 | 1.00 | 31.42 | A | C |
| ATOM | 1285 | O | SER | A | 283 | −20.497 | 8.523 | −9.112 | 1.00 | 37.30 | A | O |
| ATOM | 1286 | N | SER | A | 284 | −19.164 | 7.124 | −10.180 | 1.00 | 34.18 | A | N |
| ATOM | 1287 | CA | SER | A | 284 | −20.329 | 6.557 | −10.876 | 1.00 | 35.82 | A | C |
| ATOM | 1288 | CB | SER | A | 284 | −20.563 | 7.324 | −12.182 | 1.00 | 38.37 | A | C |
| ATOM | 1289 | OG | SER | A | 284 | −21.358 | 6.579 | −13.102 | 1.00 | 41.94 | A | O |
| ATOM | 1290 | C | SER | A | 284 | −20.156 | 5.099 | −11.194 | 1.00 | 34.23 | A | C |
| ATOM | 1291 | O | SER | A | 284 | −19.065 | 4.647 | −11.378 | 1.00 | 31.91 | A | O |
| ATOM | 1292 | N | ARG | A | 285 | −21.274 | 4.396 | −11.298 | 1.00 | 38.18 | A | N |
| ATOM | 1293 | CA | ARG | A | 285 | −21.309 | 2.949 | −11.574 | 1.00 | 44.61 | A | C |
| ATOM | 1294 | CB | ARG | A | 285 | −22.666 | 2.383 | −11.121 | 1.00 | 53.85 | A | C |
| ATOM | 1295 | CG | ARG | A | 285 | −23.864 | 2.815 | −11.991 | 1.00 | 66.07 | A | C |
| ATOM | 1296 | CD | ARG | A | 285 | −25.257 | 2.488 | −11.410 | 1.00 | 76.96 | A | C |
| ATOM | 1297 | NE | ARG | A | 285 | −25.557 | 3.224 | −10.173 | 1.00 | 80.40 | A | N |
| ATOM | 1298 | CZ | ARG | A | 285 | −25.258 | 2.823 | −8.929 | 1.00 | 79.26 | A | C |
| ATOM | 1299 | NH1 | ARG | A | 285 | −24.629 | 1.665 | −8.695 | 1.00 | 77.37 | A | N |
| ATOM | 1300 | NH2 | ARG | A | 285 | −25.580 | 3.604 | −7.896 | 1.00 | 76.21 | A | N |
| ATOM | 1301 | C | ARG | A | 285 | −21.075 | 2.590 | −13.043 | 1.00 | 41.86 | A | C |
| ATOM | 1302 | O | ARG | A | 285 | −20.600 | 1.479 | −13.353 | 1.00 | 41.30 | A | O |
| ATOM | 1303 | N | ARG | A | 286 | −21.465 | 3.526 | −13.922 | 1.00 | 37.62 | A | N |
| ATOM | 1304 | CA | ARG | A | 286 | −21.233 | 3.487 | −15.374 | 1.00 | 35.02 | A | C |
| ATOM | 1305 | CB | ARG | A | 286 | −19.739 | 3.652 | −15.707 | 1.00 | 32.04 | A | C |
| ATOM | 1306 | CG | ARG | A | 286 | −19.221 | 5.082 | −15.549 | 1.00 | 32.94 | A | C |
| ATOM | 1307 | CD | ARG | A | 286 | −18.146 | 5.141 | −14.504 | 1.00 | 35.89 | A | C |
| ATOM | 1308 | NE | ARG | A | 286 | −17.196 | 4.120 | −14.817 | 1.00 | 38.61 | A | N |
| ATOM | 1309 | CZ | ARG | A | 286 | −16.386 | 3.495 | −13.985 | 1.00 | 34.02 | A | C |
| ATOM | 1310 | NH1 | ARG | A | 286 | −16.284 | 3.802 | −12.720 | 1.00 | 33.38 | A | N |
| ATOM | 1311 | NH2 | ARG | A | 286 | −15.608 | 2.579 | −14.498 | 1.00 | 35.38 | A | N |
| ATOM | 1312 | C | ARG | A | 286 | −21.802 | 2.261 | −16.057 | 1.00 | 32.35 | A | C |
| ATOM | 1313 | O | ARG | A | 286 | −21.076 | 1.490 | −16.758 | 1.00 | 30.56 | A | O |
| ATOM | 1314 | N | THR | A | 287 | −23.096 | 2.094 | −15.841 | 1.00 | 28.81 | A | N |
| ATOM | 1315 | CA | THR | A | 287 | −23.856 | 1.026 | −16.428 | 1.00 | 31.94 | A | C |

APPENDIX B-continued

Atomic coordinates of Aurora A + Activating Monobody Mb54 + AMPPCP

| | | | | | | | | | | | |
|---|---|---|---|---|---|---|---|---|---|---|---|
| ATOM | 1316 | CB | THR | A | 287 | −24.384 | 0.054 | −15.328 | 1.00 | 36.32 | A | C |
| ATOM | 1317 | OG1 | THR | A | 287 | −25.195 | 0.785 | −14.399 | 1.00 | 39.40 | A | O |
| ATOM | 1318 | CG2 | THR | A | 287 | −23.210 | −0.675 | −14.571 | 1.00 | 34.96 | A | C |
| ATOM | 1319 | C | THR | A | 287 | −25.011 | 1.508 | −17.269 | 1.00 | 32.15 | A | C |
| ATOM | 1320 | O | THR | A | 287 | −25.666 | 0.713 | −17.876 | 1.00 | 34.34 | A | O |
| ATOM | 1321 | N | THR | A | 288 | −25.256 | 2.803 | −17.339 | 1.00 | 35.13 | A | N |
| ATOM | 1322 | CA | THR | A | 288 | −26.313 | 3.349 | −18.172 | 1.00 | 37.26 | A | C |
| ATOM | 1323 | CB | THR | A | 288 | −26.996 | 4.507 | −17.436 | 1.00 | 37.90 | A | C |
| ATOM | 1324 | OG1 | THR | A | 288 | −27.185 | 4.098 | −16.089 | 1.00 | 39.08 | A | O |
| ATOM | 1325 | CG2 | THR | A | 288 | −28.343 | 4.915 | −18.068 | 1.00 | 37.36 | A | C |
| ATOM | 1326 | C | THR | A | 288 | −25.719 | 3.884 | −19.470 | 1.00 | 37.71 | A | C |
| ATOM | 1327 | O | THR | A | 288 | −24.620 | 4.441 | −19.500 | 1.00 | 33.43 | A | O |
| ATOM | 1328 | N | LEU | A | 289 | −26.501 | 3.728 | −20.519 | 1.00 | 35.32 | A | N |
| ATOM | 1329 | CA | LEU | A | 289 | −26.148 | 4.138 | −21.833 | 1.00 | 35.73 | A | C |
| ATOM | 1330 | CB | LEU | A | 289 | −26.966 | 3.342 | −22.867 | 1.00 | 34.38 | A | C |
| ATOM | 1331 | CG | LEU | A | 289 | −26.787 | 3.667 | −24.353 | 1.00 | 33.97 | A | C |
| ATOM | 1332 | CD1 | LEU | A | 289 | −27.046 | 2.464 | −25.228 | 1.00 | 38.36 | A | C |
| ATOM | 1333 | CD2 | LEU | A | 289 | −27.708 | 4.773 | −24.801 | 1.00 | 33.47 | A | C |
| ATOM | 1334 | C | LEU | A | 289 | −26.485 | 5.604 | −21.947 | 1.00 | 37.47 | A | C |
| ATOM | 1335 | O | LEU | A | 289 | −27.610 | 6.020 | −21.603 | 1.00 | 40.41 | A | O |
| ATOM | 1336 | N | CYS | A | 290 | −25.508 | 6.360 | −22.462 | 1.00 | 35.92 | A | N |
| ATOM | 1337 | CA | CYS | A | 290 | −25.706 | 7.720 | −22.922 | 1.00 | 33.45 | A | C |
| ATOM | 1338 | CB | CYS | A | 290 | −25.536 | 8.662 | −21.742 | 1.00 | 33.34 | A | C |
| ATOM | 1339 | SG | CYS | A | 290 | −23.869 | 8.604 | −21.074 | 1.00 | 42.34 | A | S |
| ATOM | 1340 | C | CYS | A | 290 | −24.755 | 8.120 | −24.081 | 1.00 | 32.02 | A | C |
| ATOM | 1341 | O | CYS | A | 290 | −23.764 | 7.481 | −24.406 | 1.00 | 27.49 | A | O |
| ATOM | 1342 | N | GLY | A | 291 | −25.083 | 9.228 | −24.714 | 1.00 | 37.46 | A | N |
| ATOM | 1343 | CA | GLY | A | 291 | −24.335 | 9.700 | −25.894 | 1.00 | 34.40 | A | C |
| ATOM | 1344 | C | GLY | A | 291 | −25.270 | 9.861 | −27.040 | 1.00 | 30.48 | A | C |
| ATOM | 1345 | O | GLY | A | 291 | −26.447 | 10.097 | −26.849 | 1.00 | 29.93 | A | O |
| ATOM | 1346 | N | THR | A | 292 | −24.755 | 9.665 | −28.247 | 1.00 | 31.28 | A | N |
| ATOM | 1347 | CA | THR | A | 292 | −25.499 | 9.994 | −29.450 | 1.00 | 26.97 | A | C |
| ATOM | 1348 | CB | THR | A | 292 | −24.899 | 11.259 | −30.076 | 1.00 | 25.56 | A | C |
| ATOM | 1349 | OG1 | THR | A | 292 | −25.125 | 12.352 | −29.191 | 1.00 | 24.10 | A | O |
| ATOM | 1350 | CG2 | THR | A | 292 | −25.508 | 11.557 | −31.468 | 1.00 | 25.66 | A | C |
| ATOM | 1351 | C | THR | A | 292 | −25.366 | 8.810 | −30.390 | 1.00 | 27.39 | A | C |
| ATOM | 1352 | O | THR | A | 292 | −24.255 | 8.300 | −30.573 | 1.00 | 28.24 | A | O |
| ATOM | 1353 | N | LEU | A | 293 | −26.498 | 8.413 | −30.983 | 1.00 | 27.08 | A | N |
| ATOM | 1354 | CA | LEU | A | 293 | −26.666 | 7.157 | −31.717 | 1.00 | 26.08 | A | C |
| ATOM | 1355 | CB | LEU | A | 293 | −27.862 | 7.319 | −32.658 | 1.00 | 25.65 | A | C |
| ATOM | 1356 | CG | LEU | A | 293 | −28.126 | 6.088 | −33.539 | 1.00 | 28.51 | A | C |
| ATOM | 1357 | CD1 | LEU | A | 293 | −29.313 | 6.260 | −34.444 | 1.00 | 30.17 | A | C |
| ATOM | 1358 | CD2 | LEU | A | 293 | −28.284 | 4.820 | −32.695 | 1.00 | 28.53 | A | C |
| ATOM | 1359 | C | LEU | A | 293 | −25.442 | 6.603 | −32.510 | 1.00 | 27.62 | A | C |
| ATOM | 1360 | O | LEU | A | 293 | −24.951 | 5.489 | −32.257 | 1.00 | 25.44 | A | O |
| ATOM | 1361 | N | ASP | A | 294 | −24.957 | 7.394 | −33.466 | 1.00 | 26.33 | A | N |
| ATOM | 1362 | CA | ASP | A | 294 | −23.948 | 6.932 | −34.372 | 1.00 | 25.87 | A | C |
| ATOM | 1363 | CB | ASP | A | 294 | −23.865 | 7.871 | −35.565 | 1.00 | 28.50 | A | C |
| ATOM | 1364 | CG | ASP | A | 294 | −24.986 | 7.648 | −36.542 | 1.00 | 30.44 | A | C |
| ATOM | 1365 | OD1 | ASP | A | 294 | −24.973 | 6.619 | −37.250 | 1.00 | 34.11 | A | O |
| ATOM | 1366 | OD2 | ASP | A | 294 | −25.891 | 8.480 | −36.559 | 1.00 | 30.81 | A | O |
| ATOM | 1367 | C | ASP | A | 294 | −22.594 | 6.798 | −33.741 | 1.00 | 24.20 | A | C |
| ATOM | 1368 | O | ASP | A | 294 | −21.712 | 6.156 | −34.309 | 1.00 | 24.04 | A | O |
| ATOM | 1369 | N | TYR | A | 295 | −22.454 | 7.384 | −32.561 | 1.00 | 23.51 | A | N |
| ATOM | 1370 | CA | TYR | A | 295 | −21.203 | 7.415 | −31.804 | 1.00 | 25.11 | A | C |
| ATOM | 1371 | CB | TYR | A | 295 | −21.017 | 8.875 | −31.351 | 1.00 | 24.98 | A | C |
| ATOM | 1372 | CG | TYR | A | 295 | −20.538 | 9.651 | −32.502 | 1.00 | 27.00 | A | C |
| ATOM | 1373 | CD1 | TYR | A | 295 | −19.182 | 9.660 | −32.780 | 1.00 | 30.04 | A | C |
| ATOM | 1374 | CE1 | TYR | A | 295 | −18.689 | 10.329 | −33.875 | 1.00 | 30.09 | A | C |
| ATOM | 1375 | CZ | TYR | A | 295 | −19.549 | 10.953 | −34.737 | 1.00 | 27.14 | A | C |
| ATOM | 1376 | OH | TYR | A | 295 | −18.901 | 11.593 | −35.797 | 1.00 | 34.84 | A | O |
| ATOM | 1377 | CE2 | TYR | A | 295 | −20.920 | 10.974 | −34.509 | 1.00 | 26.60 | A | C |
| ATOM | 1378 | CD2 | TYR | A | 295 | −21.419 | 10.332 | −33.377 | 1.00 | 26.65 | A | C |
| ATOM | 1379 | C | TYR | A | 295 | −21.081 | 6.455 | −30.585 | 1.00 | 23.93 | A | C |
| ATOM | 1380 | O | TYR | A | 295 | −19.960 | 6.319 | −29.971 | 1.00 | 22.64 | A | O |
| ATOM | 1381 | N | LEU | A | 296 | −22.203 | 5.830 | −30.230 | 1.00 | 23.68 | A | N |
| ATOM | 1382 | CA | LEU | A | 296 | −22.279 | 4.932 | −29.071 | 1.00 | 25.49 | A | C |
| ATOM | 1383 | CB | LEU | A | 296 | −23.693 | 4.417 | −28.878 | 1.00 | 27.27 | A | C |
| ATOM | 1384 | CG | LEU | A | 296 | −24.748 | 5.451 | −28.545 | 1.00 | 29.02 | A | C |
| ATOM | 1385 | CD1 | LEU | A | 296 | −26.144 | 4.843 | −28.740 | 1.00 | 30.71 | A | C |
| ATOM | 1386 | CD2 | LEU | A | 296 | −24.542 | 5.976 | −27.139 | 1.00 | 30.42 | A | C |
| ATOM | 1387 | C | LEU | A | 296 | −21.366 | 3.731 | −29.235 | 1.00 | 24.61 | A | C |
| ATOM | 1388 | O | LEU | A | 296 | −21.371 | 3.106 | −30.290 | 1.00 | 26.32 | A | O |
| ATOM | 1389 | N | PRO | A | 297 | −20.554 | 3.415 | −28.189 | 1.00 | 25.61 | A | N |
| ATOM | 1390 | CA | PRO | A | 297 | −19.722 | 2.207 | −28.222 | 1.00 | 25.27 | A | C |
| ATOM | 1391 | CB | PRO | A | 297 | −18.724 | 2.458 | −27.091 | 1.00 | 25.32 | A | C |
| ATOM | 1392 | CG | PRO | A | 297 | −19.528 | 3.217 | −26.095 | 1.00 | 25.36 | A | C |
| ATOM | 1393 | CD | PRO | A | 297 | −20.386 | 4.145 | −26.908 | 1.00 | 23.83 | A | C |

APPENDIX B-continued

Atomic coordinates of Aurora A + Activating Monobody Mb54 + AMPPCP

| | | | | | | | | | | | |
|---|---|---|---|---|---|---|---|---|---|---|---|
| ATOM | 1394 | C | PRO | A | 297 | −20.519 | 0.916 | −27.980 | 1.00 | 25.43 | A | C |
| ATOM | 1395 | O | PRO | A | 297 | −21.674 | 0.970 | −27.488 | 1.00 | 24.45 | A | O |
| ATOM | 1396 | N | PRO | A | 298 | −19.933 | −0.233 | −28.354 | 1.00 | 27.30 | A | N |
| ATOM | 1397 | CA | PRO | A | 298 | −20.670 | −1.493 | −28.238 | 1.00 | 28.89 | A | C |
| ATOM | 1398 | CB | PRO | A | 298 | −19.754 | −2.534 | −28.909 | 1.00 | 28.81 | A | C |
| ATOM | 1399 | CG | PRO | A | 298 | −18.395 | −1.906 | −29.074 | 1.00 | 29.11 | A | C |
| ATOM | 1400 | CD | PRO | A | 298 | −18.578 | −0.408 | −28.921 | 1.00 | 29.38 | A | C |
| ATOM | 1401 | C | PRO | A | 298 | −20.944 | −1.838 | −26.791 | 1.00 | 26.98 | A | C |
| ATOM | 1402 | O | PRO | A | 298 | −22.081 | −2.192 | −26.441 | 1.00 | 26.01 | A | O |
| ATOM | 1403 | N | GLU | A | 299 | −19.950 | −1.634 | −25.947 | 1.00 | 26.80 | A | N |
| ATOM | 1404 | CA | GLU | A | 299 | −20.130 | −1.925 | −24.530 | 1.00 | 28.17 | A | C |
| ATOM | 1405 | CB | GLU | A | 299 | −18.944 | −1.507 | −23.648 | 1.00 | 28.85 | A | C |
| ATOM | 1406 | CG | GLU | A | 299 | −18.494 | −0.065 | −23.702 | 1.00 | 25.83 | A | C |
| ATOM | 1407 | CD | GLU | A | 299 | −17.308 | 0.068 | −24.637 | 1.00 | 27.82 | A | C |
| ATOM | 1408 | OE1 | GLU | A | 299 | −17.423 | −0.489 | −25.760 | 1.00 | 31.01 | A | O |
| ATOM | 1409 | OE2 | GLU | A | 299 | −16.266 | 0.684 | −24.280 | 1.00 | 26.70 | A | O |
| ATOM | 1410 | C | GLU | A | 299 | −21.412 | −1.377 | −23.917 | 1.00 | 29.63 | A | C |
| ATOM | 1411 | O | GLU | A | 299 | −22.014 | −2.048 | −23.061 | 1.00 | 29.13 | A | O |
| ATOM | 1412 | N | MET | A | 300 | −21.824 | −0.185 | −24.335 | 1.00 | 28.88 | A | N |
| ATOM | 1413 | CA | MET | A | 300 | −22.981 | 0.455 | −23.728 | 1.00 | 28.66 | A | C |
| ATOM | 1414 | CB | MET | A | 300 | −23.034 | 1.958 | −24.041 | 1.00 | 29.91 | A | C |
| ATOM | 1415 | CG | MET | A | 300 | −22.321 | 2.875 | −23.073 | 1.00 | 29.92 | A | C |
| ATOM | 1416 | SD | MET | A | 300 | −22.512 | 4.629 | −23.554 | 1.00 | 29.15 | A | S |
| ATOM | 1417 | CE | MET | A | 300 | −21.391 | 5.470 | −22.446 | 1.00 | 29.00 | A | C |
| ATOM | 1418 | C | MET | A | 300 | −24.216 | −0.152 | −24.270 | 1.00 | 31.12 | A | C |
| ATOM | 1419 | O | MET | A | 300 | −25.225 | −0.194 | −23.575 | 1.00 | 32.48 | A | O |
| ATOM | 1420 | N | ILE | A | 301 | −24.151 | −0.560 | −25.537 | 1.00 | 32.48 | A | N |
| ATOM | 1421 | CA | ILE | A | 301 | −25.287 | −1.192 | −26.223 | 1.00 | 35.67 | A | C |
| ATOM | 1422 | CB | ILE | A | 301 | −25.015 | −1.383 | −27.747 | 1.00 | 38.22 | A | C |
| ATOM | 1423 | CG1 | ILE | A | 301 | −24.624 | −0.055 | −28.453 | 1.00 | 40.46 | A | C |
| ATOM | 1424 | CD1 | ILE | A | 301 | −25.738 | 0.790 | −29.004 | 1.00 | 40.02 | A | C |
| ATOM | 1425 | CG2 | ILE | A | 301 | −26.203 | −2.022 | −28.457 | 1.00 | 38.28 | A | C |
| ATOM | 1426 | C | ILE | A | 301 | −25.520 | −2.589 | −25.592 | 1.00 | 34.49 | A | C |
| ATOM | 1427 | O | ILE | A | 301 | −26.641 | −3.027 | −25.391 | 1.00 | 32.01 | A | O |
| ATOM | 1428 | N | GLU | A | 302 | −24.425 | −3.256 | −25.272 | 1.00 | 34.26 | A | N |
| ATOM | 1429 | CA | GLU | A | 302 | −24.453 | −4.592 | −24.753 | 1.00 | 36.03 | A | C |
| ATOM | 1430 | CB | GLU | A | 302 | −23.174 | −5.324 | −25.130 | 1.00 | 34.25 | A | C |
| ATOM | 1431 | CG | GLU | A | 302 | −23.016 | −5.425 | −26.644 | 1.00 | 33.50 | A | C |
| ATOM | 1432 | CD | GLU | A | 302 | −21.597 | −5.736 | −27.072 | 1.00 | 35.73 | A | C |
| ATOM | 1433 | OE1 | GLU | A | 302 | −20.666 | −5.813 | −26.209 | 1.00 | 38.84 | A | O |
| ATOM | 1434 | OE2 | GLU | A | 302 | −21.410 | −5.894 | −28.302 | 1.00 | 33.05 | A | O |
| ATOM | 1435 | C | GLU | A | 302 | −24.652 | −4.580 | −23.266 | 1.00 | 39.00 | A | C |
| ATOM | 1436 | O | GLU | A | 302 | −24.689 | −5.641 | −22.664 | 1.00 | 40.10 | A | O |
| ATOM | 1437 | N | GLY | A | 303 | −24.776 | −3.398 | −22.656 | 1.00 | 41.20 | A | N |
| ATOM | 1438 | CA | GLY | A | 303 | −25.262 | −3.289 | −21.274 | 1.00 | 40.25 | A | C |
| ATOM | 1439 | C | GLY | A | 303 | −24.185 | −3.353 | −20.217 | 1.00 | 38.93 | A | C |
| ATOM | 1440 | O | GLY | A | 303 | −24.518 | −3.185 | −19.073 | 1.00 | 46.45 | A | O |
| ATOM | 1441 | N | ARG | A | 304 | −22.910 | −3.520 | −20.596 | 1.00 | 35.12 | A | N |
| ATOM | 1442 | CA | ARG | A | 304 | −21.790 | −3.612 | −19.655 | 1.00 | 37.49 | A | C |
| ATOM | 1443 | CB | ARG | A | 304 | −20.577 | −4.240 | −20.312 | 1.00 | 42.12 | A | C |
| ATOM | 1444 | CG | ARG | A | 304 | −20.809 | −5.563 | −21.005 | 1.00 | 52.90 | A | C |
| ATOM | 1445 | CD | ARG | A | 304 | −20.088 | −5.480 | −22.323 | 1.00 | 59.43 | A | C |
| ATOM | 1446 | NE | ARG | A | 304 | −19.890 | −6.754 | −22.970 | 1.00 | 69.23 | A | N |
| ATOM | 1447 | CZ | ARG | A | 304 | −18.882 | −7.013 | −23.806 | 1.00 | 79.03 | A | C |
| ATOM | 1448 | NH1 | ARG | A | 304 | −17.946 | −6.077 | −24.101 | 1.00 | 77.57 | A | N |
| ATOM | 1449 | NH2 | ARG | A | 304 | −18.794 | −8.229 | −24.347 | 1.00 | 71.67 | A | N |
| ATOM | 1450 | C | ARG | A | 304 | −21.252 | −2.309 | −19.037 | 1.00 | 37.46 | A | C |
| ATOM | 1451 | O | ARG | A | 304 | −21.414 | −1.207 | −19.534 | 1.00 | 42.29 | A | O |
| ATOM | 1452 | N | MET | A | 305 | −20.534 | −2.494 | −17.950 | 1.00 | 34.61 | A | N |
| ATOM | 1453 | CA | MET | A | 305 | −19.894 | −1.428 | −17.287 | 1.00 | 33.12 | A | C |
| ATOM | 1454 | CB | MET | A | 305 | −19.257 | −1.936 | −15.996 | 1.00 | 33.40 | A | C |
| ATOM | 1455 | CG | MET | A | 305 | −18.616 | −0.856 | −15.138 | 1.00 | 34.42 | A | C |
| ATOM | 1456 | SD | MET | A | 305 | −17.936 | −1.557 | −13.635 | 1.00 | 36.17 | A | S |
| ATOM | 1457 | CE | MET | A | 305 | −16.994 | −0.155 | −13.036 | 1.00 | 35.04 | A | C |
| ATOM | 1458 | C | MET | A | 305 | −18.813 | −0.860 | −18.224 | 1.00 | 33.41 | A | C |
| ATOM | 1459 | O | MET | A | 305 | −17.933 | −1.608 | −18.758 | 1.00 | 29.21 | A | O |
| ATOM | 1460 | N | HIS | A | 306 | −18.848 | 0.465 | −18.372 | 1.00 | 31.32 | A | N |
| ATOM | 1461 | CA | HIS | A | 306 | −17.873 | 1.185 | −19.235 | 1.00 | 29.04 | A | C |
| ATOM | 1462 | CB | HIS | A | 306 | −18.592 | 2.027 | −20.275 | 1.00 | 26.44 | A | C |
| ATOM | 1463 | CG | HIS | A | 306 | −19.478 | 3.080 | −19.703 | 1.00 | 24.94 | A | C |
| ATOM | 1464 | ND1 | HIS | A | 306 | −20.843 | 2.933 | −19.632 | 1.00 | 25.34 | A | N |
| ATOM | 1465 | CE1 | HIS | A | 306 | −21.378 | 4.031 | −19.122 | 1.00 | 24.84 | A | C |
| ATOM | 1466 | NE2 | HIS | A | 306 | −20.403 | 4.886 | −18.878 | 1.00 | 24.96 | A | N |
| ATOM | 1467 | CD2 | HIS | A | 306 | −19.208 | 4.324 | −19.248 | 1.00 | 24.14 | A | C |
| ATOM | 1468 | C | HIS | A | 306 | −16.847 | 2.041 | −18.516 | 1.00 | 25.79 | A | C |
| ATOM | 1469 | O | HIS | A | 306 | −16.994 | 2.355 | −17.324 | 1.00 | 26.47 | A | O |
| ATOM | 1470 | N | ASP | A | 307 | −15.819 | 2.436 | −19.269 | 1.00 | 23.57 | A | N |
| ATOM | 1471 | CA | ASP | A | 307 | −14.806 | 3.276 | −18.719 | 1.00 | 24.33 | A | C |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 1472 | CB | ASP | A | 307 | −13.736 | 2.372 | −18.083 | 1.00 | 22.37 | A | C |
| ATOM | 1473 | CG | ASP | A | 307 | −12.932 | 1.578 | −19.125 | 1.00 | 25.05 | A | C |
| ATOM | 1474 | OD1 | ASP | A | 307 | −13.225 | 1.641 | −20.356 | 1.00 | 25.12 | A | O |
| ATOM | 1475 | OD2 | ASP | A | 307 | −11.988 | 0.864 | −18.716 | 1.00 | 26.63 | A | O |
| ATOM | 1476 | C | ASP | A | 307 | −14.276 | 4.282 | −19.776 | 1.00 | 23.96 | A | C |
| ATOM | 1477 | O | ASP | A | 307 | −14.897 | 4.490 | −20.822 | 1.00 | 20.49 | A | O |
| ATOM | 1478 | N | GLU | A | 308 | −13.109 | 4.871 | −19.501 | 1.00 | 26.36 | A | N |
| ATOM | 1479 | CA | GLU | A | 308 | −12.550 | 5.876 | −20.370 | 1.00 | 27.09 | A | C |
| ATOM | 1480 | CB | GLU | A | 308 | −11.283 | 6.522 | −19.771 | 1.00 | 32.43 | A | C |
| ATOM | 1481 | CG | GLU | A | 308 | −9.912 | 5.909 | −20.045 | 1.00 | 38.68 | A | C |
| ATOM | 1482 | CD | GLU | A | 308 | −9.759 | 4.514 | −19.474 | 1.00 | 42.95 | A | C |
| ATOM | 1483 | OE1 | GLU | A | 308 | −8.997 | 3.683 | −20.054 | 1.00 | 44.49 | A | O |
| ATOM | 1484 | OE2 | GLU | A | 308 | −10.439 | 4.254 | −18.461 | 1.00 | 49.84 | A | O |
| ATOM | 1485 | C | GLU | A | 308 | −12.402 | 5.434 | −21.843 | 1.00 | 25.29 | A | C |
| ATOM | 1486 | O | GLU | A | 308 | −12.377 | 6.284 | −22.753 | 1.00 | 22.81 | A | O |
| ATOM | 1487 | N | LYS | A | 309 | −12.415 | 4.124 | −22.092 | 1.00 | 23.09 | A | N |
| ATOM | 1488 | CA | LYS | A | 309 | −12.260 | 3.601 | −23.464 | 1.00 | 21.48 | A | C |
| ATOM | 1489 | CB | LYS | A | 309 | −12.060 | 2.070 | −23.462 | 1.00 | 23.02 | A | C |
| ATOM | 1490 | CG | LYS | A | 309 | −10.783 | 1.542 | −22.814 | 1.00 | 23.06 | A | C |
| ATOM | 1491 | CD | LYS | A | 309 | −9.564 | 2.058 | −23.526 | 1.00 | 25.99 | A | C |
| ATOM | 1492 | CE | LYS | A | 309 | −8.305 | 1.375 | −23.011 | 1.00 | 27.90 | A | C |
| ATOM | 1493 | NZ | LYS | A | 309 | −7.071 | 1.810 | −23.749 | 1.00 | 28.49 | A | N |
| ATOM | 1494 | C | LYS | A | 309 | −13.438 | 3.904 | −24.367 | 1.00 | 20.05 | A | C |
| ATOM | 1495 | O | LYS | A | 309 | −13.335 | 3.702 | −25.552 | 1.00 | 18.84 | A | O |
| ATOM | 1496 | N | VAL | A | 310 | −14.573 | 4.334 | −23.833 | 1.00 | 19.14 | A | N |
| ATOM | 1497 | CA | VAL | A | 310 | −15.701 | 4.665 | −24.694 | 1.00 | 19.52 | A | C |
| ATOM | 1498 | CB | VAL | A | 310 | −17.016 | 4.924 | −23.914 | 1.00 | 18.82 | A | C |
| ATOM | 1499 | CG1 | VAL | A | 310 | −17.382 | 3.726 | −23.051 | 1.00 | 18.34 | A | C |
| ATOM | 1500 | CG2 | VAL | A | 310 | −16.942 | 6.183 | −23.081 | 1.00 | 20.29 | A | C |
| ATOM | 1501 | C | VAL | A | 310 | −15.359 | 5.928 | −25.498 | 1.00 | 20.42 | A | C |
| ATOM | 1502 | O | VAL | A | 310 | −15.780 | 6.079 | −26.619 | 1.00 | 22.16 | A | O |
| ATOM | 1503 | N | ASP | A | 311 | −14.580 | 6.826 | −24.898 | 1.00 | 21.06 | A | N |
| ATOM | 1504 | CA | ASP | A | 311 | −14.089 | 8.003 | −25.617 | 1.00 | 20.75 | A | C |
| ATOM | 1505 | CB | ASP | A | 311 | −13.324 | 8.976 | −24.686 | 1.00 | 19.36 | A | C |
| ATOM | 1506 | CG | ASP | A | 311 | −14.231 | 9.832 | −23.782 | 1.00 | 19.34 | A | C |
| ATOM | 1507 | OD1 | ASP | A | 311 | −15.494 | 9.909 | −23.958 | 1.00 | 17.47 | A | O |
| ATOM | 1508 | OD2 | ASP | A | 311 | −13.629 | 10.473 | −22.865 | 1.00 | 19.08 | A | O |
| ATOM | 1509 | C | ASP | A | 311 | −13.183 | 7.580 | −26.773 | 1.00 | 20.30 | A | C |
| ATOM | 1510 | O | ASP | A | 311 | −13.183 | 8.195 | −27.850 | 1.00 | 20.76 | A | O |
| ATOM | 1511 | N | LEU | A | 312 | −12.388 | 6.547 | −26.542 | 1.00 | 20.70 | A | N |
| ATOM | 1512 | CA | LEU | A | 312 | −11.492 | 6.002 | −27.587 | 1.00 | 20.49 | A | C |
| ATOM | 1513 | CB | LEU | A | 312 | −10.533 | 4.955 | −27.015 | 1.00 | 18.91 | A | C |
| ATOM | 1514 | CG | LEU | A | 312 | −9.252 | 5.468 | −26.360 | 1.00 | 19.21 | A | C |
| ATOM | 1515 | CD1 | LEU | A | 312 | −8.296 | 6.072 | −27.360 | 1.00 | 19.57 | A | C |
| ATOM | 1516 | CD2 | LEU | A | 312 | −9.504 | 6.476 | −25.242 | 1.00 | 20.04 | A | C |
| ATOM | 1517 | C | LEU | A | 312 | −12.290 | 5.436 | −28.809 | 1.00 | 20.18 | A | C |
| ATOM | 1518 | O | LEU | A | 312 | −11.982 | 5.729 | −29.963 | 1.00 | 18.40 | A | O |
| ATOM | 1519 | N | TRP | A | 313 | −13.314 | 4.654 | −28.539 | 1.00 | 18.68 | A | N |
| ATOM | 1520 | CA | TRP | A | 313 | −14.209 | 4.232 | −29.586 | 1.00 | 19.44 | A | C |
| ATOM | 1521 | CB | TRP | A | 313 | −15.374 | 3.487 | −28.990 | 1.00 | 17.87 | A | C |
| ATOM | 1522 | CG | TRP | A | 313 | −16.405 | 3.137 | −29.952 | 1.00 | 19.32 | A | C |
| ATOM | 1523 | CD1 | TRP | A | 313 | −17.501 | 3.897 | −30.312 | 1.00 | 19.92 | A | C |
| ATOM | 1524 | NE1 | TRP | A | 313 | −18.221 | 3.243 | −31.286 | 1.00 | 21.10 | A | N |
| ATOM | 1525 | CE2 | TRP | A | 313 | −17.631 | 2.015 | −31.530 | 1.00 | 21.23 | A | C |
| ATOM | 1526 | CD2 | TRP | A | 313 | −16.499 | 1.911 | −30.702 | 1.00 | 19.22 | A | C |
| ATOM | 1527 | CE3 | TRP | A | 313 | −15.744 | 0.744 | −30.744 | 1.00 | 18.70 | A | C |
| ATOM | 1528 | CZ3 | TRP | A | 313 | −16.114 | −0.278 | −31.621 | 1.00 | 20.17 | A | C |
| ATOM | 1529 | CH2 | TRP | A | 313 | −17.255 | −0.173 | −32.408 | 1.00 | 20.96 | A | C |
| ATOM | 1530 | CZ2 | TRP | A | 313 | −18.025 | 0.964 | −32.398 | 1.00 | 21.63 | A | C |
| ATOM | 1531 | C | TRP | A | 313 | −14.744 | 5.444 | −30.346 | 1.00 | 20.19 | A | C |
| ATOM | 1532 | O | TRP | A | 313 | −14.681 | 5.502 | −31.571 | 1.00 | 20.27 | A | O |
| ATOM | 1533 | N | SER | A | 314 | −15.300 | 6.403 | −29.622 | 1.00 | 21.64 | A | N |
| ATOM | 1534 | CA | SER | A | 314 | −15.997 | 7.532 | −30.295 | 1.00 | 21.48 | A | C |
| ATOM | 1535 | CB | SER | A | 314 | −16.818 | 8.364 | −29.301 | 1.00 | 22.63 | A | C |
| ATOM | 1536 | OG | SER | A | 314 | −17.847 | 7.508 | −28.700 | 1.00 | 24.09 | A | O |
| ATOM | 1537 | C | SER | A | 314 | −15.040 | 8.396 | −31.092 | 1.00 | 20.73 | A | C |
| ATOM | 1538 | O | SER | A | 314 | −15.414 | 8.911 | −32.116 | 1.00 | 16.97 | A | O |
| ATOM | 1539 | N | LEU | A | 315 | −13.788 | 8.485 | −30.639 | 1.00 | 19.58 | A | N |
| ATOM | 1540 | CA | LEU | A | 315 | −12.738 | 9.120 | −31.406 | 1.00 | 19.30 | A | C |
| ATOM | 1541 | CB | LEU | A | 315 | −11.404 | 9.046 | −30.620 | 1.00 | 19.43 | A | C |
| ATOM | 1542 | CG | LEU | A | 315 | −10.191 | 9.817 | −31.146 | 1.00 | 19.71 | A | C |
| ATOM | 1543 | CD1 | LEU | A | 315 | −10.564 | 11.292 | −31.240 | 1.00 | 19.59 | A | C |
| ATOM | 1544 | CD2 | LEU | A | 315 | −8.975 | 9.667 | −30.235 | 1.00 | 19.36 | A | C |
| ATOM | 1545 | C | LEU | A | 315 | −12.564 | 8.481 | −32.775 | 1.00 | 20.37 | A | C |
| ATOM | 1546 | O | LEU | A | 315 | −12.232 | 9.176 | −33.762 | 1.00 | 19.50 | A | O |
| ATOM | 1547 | N | GLY | A | 316 | −12.716 | 7.152 | −32.845 | 1.00 | 19.16 | A | N |
| ATOM | 1548 | CA | GLY | A | 316 | −12.465 | 6.442 | −34.097 | 1.00 | 18.54 | A | C |
| ATOM | 1549 | C | GLY | A | 316 | −13.597 | 6.661 | −35.078 | 1.00 | 18.07 | A | C |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 1550 | O | GLY | A | 316 | −13.370 | 6.782 | −36.275 | 1.00 | 17.66 | A | O |
| ATOM | 1551 | N | VAL | A | 317 | −14.810 | 6.708 | −34.553 | 1.00 | 16.71 | A | N |
| ATOM | 1552 | CA | VAL | A | 317 | −16.000 | 7.007 | −35.342 | 1.00 | 18.95 | A | C |
| ATOM | 1553 | CB | VAL | A | 317 | −17.262 | 6.981 | −34.451 | 1.00 | 19.42 | A | C |
| ATOM | 1554 | CG1 | VAL | A | 317 | −18.499 | 7.367 | −35.227 | 1.00 | 19.94 | A | C |
| ATOM | 1555 | CG2 | VAL | A | 317 | −17.469 | 5.593 | −33.873 | 1.00 | 20.36 | A | C |
| ATOM | 1556 | C | VAL | A | 317 | −15.855 | 8.396 | −35.959 | 1.00 | 18.77 | A | C |
| ATOM | 1557 | O | VAL | A | 317 | −16.155 | 8.640 | −37.116 | 1.00 | 17.47 | A | O |
| ATOM | 1558 | N | LEU | A | 318 | −15.355 | 9.292 | −35.128 | 1.00 | 19.96 | A | N |
| ATOM | 1559 | CA | LEU | A | 318 | −15.155 | 10.671 | −35.513 | 1.00 | 21.14 | A | C |
| ATOM | 1560 | CB | LEU | A | 318 | −14.726 | 11.477 | −34.307 | 1.00 | 21.18 | A | C |
| ATOM | 1561 | CG | LEU | A | 318 | −15.081 | 12.939 | −33.930 | 1.00 | 22.84 | A | C |
| ATOM | 1562 | CD1 | LEU | A | 318 | −16.232 | 13.538 | −34.664 | 1.00 | 22.09 | A | C |
| ATOM | 1563 | CD2 | LEU | A | 318 | −13.861 | 13.832 | −33.891 | 1.00 | 22.15 | A | C |
| ATOM | 1564 | C | LEU | A | 318 | −14.138 | 10.787 | −36.612 | 1.00 | 20.24 | A | C |
| ATOM | 1565 | O | LEU | A | 318 | −14.347 | 11.518 | −37.564 | 1.00 | 20.35 | A | O |
| ATOM | 1566 | N | CYS | A | 319 | −13.039 | 10.068 | −36.484 | 1.00 | 20.24 | A | N |
| ATOM | 1567 | CA | CYS | A | 319 | −11.972 | 10.102 | −37.480 | 1.00 | 18.70 | A | C |
| ATOM | 1568 | CB | CYS | A | 319 | −10.807 | 9.280 | −37.007 | 1.00 | 19.16 | A | C |
| ATOM | 1569 | SG | CYS | A | 319 | −9.279 | 9.416 | −37.969 | 1.00 | 24.22 | A | S |
| ATOM | 1570 | C | CYS | A | 319 | −12.535 | 9.594 | −38.769 | 1.00 | 19.38 | A | C |
| ATOM | 1571 | O | CYS | A | 319 | −12.301 | 10.178 | −39.811 | 1.00 | 21.88 | A | O |
| ATOM | 1572 | N | TYR | A | 320 | −13.370 | 8.568 | −38.712 | 1.00 | 19.50 | A | N |
| ATOM | 1573 | CA | TYR | A | 320 | −13.947 | 8.014 | −39.911 | 1.00 | 19.69 | A | C |
| ATOM | 1574 | CB | TYR | A | 320 | −14.723 | 6.725 | −39.585 | 1.00 | 19.63 | A | C |
| ATOM | 1575 | CG | TYR | A | 320 | −15.400 | 6.044 | −40.762 | 1.00 | 19.38 | A | C |
| ATOM | 1576 | CD1 | TYR | A | 320 | −16.582 | 6.532 | −41.268 | 1.00 | 21.24 | A | C |
| ATOM | 1577 | CE1 | TYR | A | 320 | −17.246 | 5.892 | −42.322 | 1.00 | 23.46 | A | C |
| ATOM | 1578 | CZ | TYR | A | 320 | −16.737 | 4.709 | −42.845 | 1.00 | 23.52 | A | C |
| ATOM | 1579 | OH | TYR | A | 320 | −17.408 | 4.133 | −43.890 | 1.00 | 22.38 | A | O |
| ATOM | 1580 | CE2 | TYR | A | 320 | −15.560 | 4.171 | −42.329 | 1.00 | 22.51 | A | C |
| ATOM | 1581 | CD2 | TYR | A | 320 | −14.904 | 4.847 | −41.289 | 1.00 | 21.23 | A | C |
| ATOM | 1582 | C | TYR | A | 320 | −14.862 | 9.042 | −40.558 | 1.00 | 19.94 | A | C |
| ATOM | 1583 | O | TYR | A | 320 | −14.783 | 9.279 | −41.776 | 1.00 | 20.91 | A | O |
| ATOM | 1584 | N | GLU | A | 321 | −15.740 | 9.622 | −39.761 | 1.00 | 20.41 | A | N |
| ATOM | 1585 | CA | GLU | A | 321 | −16.682 | 10.598 | −40.282 | 1.00 | 20.32 | A | C |
| ATOM | 1586 | CB | GLU | A | 321 | −17.662 | 11.053 | −39.216 | 1.00 | 22.35 | A | C |
| ATOM | 1587 | CG | GLU | A | 321 | −18.755 | 11.915 | −39.847 | 1.00 | 24.55 | A | C |
| ATOM | 1588 | CD | GLU | A | 321 | −19.922 | 12.276 | −38.982 | 1.00 | 26.32 | A | C |
| ATOM | 1589 | OE1 | GLU | A | 321 | −19.968 | 11.941 | −37.792 | 1.00 | 27.48 | A | O |
| ATOM | 1590 | OE2 | GLU | A | 321 | −20.811 | 12.959 | −39.529 | 1.00 | 32.22 | A | O |
| ATOM | 1591 | C | GLU | A | 321 | −16.010 | 11.821 | −40.877 | 1.00 | 19.30 | A | C |
| ATOM | 1592 | O | GLU | A | 321 | −16.450 | 12.362 | −41.890 | 1.00 | 16.50 | A | O |
| ATOM | 1593 | N | PHE | A | 322 | −14.943 | 12.269 | −40.249 | 1.00 | 19.08 | A | N |
| ATOM | 1594 | CA | PHE | A | 322 | −14.130 | 13.327 | −40.828 | 1.00 | 19.61 | A | C |
| ATOM | 1595 | CB | PHE | A | 322 | −12.913 | 13.632 | −39.911 | 1.00 | 18.96 | A | C |
| ATOM | 1596 | CG | PHE | A | 322 | −13.242 | 14.400 | −38.648 | 1.00 | 18.85 | A | C |
| ATOM | 1597 | CD1 | PHE | A | 322 | −14.477 | 14.956 | −38.425 | 1.00 | 18.38 | A | C |
| ATOM | 1598 | CE1 | PHE | A | 322 | −14.732 | 15.681 | −37.279 | 1.00 | 18.82 | A | C |
| ATOM | 1599 | CZ | PHE | A | 322 | −13.739 | 15.913 | −36.385 | 1.00 | 19.02 | A | C |
| ATOM | 1600 | CE2 | PHE | A | 322 | −12.468 | 15.372 | −36.587 | 1.00 | 19.69 | A | C |
| ATOM | 1601 | CD2 | PHE | A | 322 | −12.236 | 14.627 | −37.711 | 1.00 | 19.73 | A | C |
| ATOM | 1602 | C | PHE | A | 322 | −13.617 | 12.962 | −42.244 | 1.00 | 20.76 | A | C |
| ATOM | 1603 | O | PHE | A | 322 | −13.698 | 13.777 | −43.172 | 1.00 | 22.18 | A | O |
| ATOM | 1604 | N | LEU | A | 323 | −13.078 | 11.754 | −42.401 | 1.00 | 20.88 | A | N |
| ATOM | 1605 | CA | LEU | A | 323 | −12.450 | 11.351 | −43.633 | 1.00 | 20.35 | A | C |
| ATOM | 1606 | CB | LEU | A | 323 | −11.532 | 10.150 | −43.413 | 1.00 | 20.80 | A | C |
| ATOM | 1607 | CG | LEU | A | 323 | −10.222 | 10.519 | −42.703 | 1.00 | 21.40 | A | C |
| ATOM | 1608 | CD1 | LEU | A | 323 | −9.330 | 9.301 | −42.539 | 1.00 | 21.62 | A | C |
| ATOM | 1609 | CD2 | LEU | A | 323 | −9.440 | 11.591 | −43.461 | 1.00 | 21.24 | A | C |
| ATOM | 1610 | C | LEU | A | 323 | −13.441 | 11.014 | −44.725 | 1.00 | 22.04 | A | C |
| ATOM | 1611 | O | LEU | A | 323 | −13.132 | 11.212 | −45.919 | 1.00 | 22.24 | A | O |
| ATOM | 1612 | N | VAL | A | 324 | −14.595 | 10.487 | −44.337 | 1.00 | 20.82 | A | N |
| ATOM | 1613 | CA | VAL | A | 324 | −15.544 | 9.928 | −45.283 | 1.00 | 22.17 | A | C |
| ATOM | 1614 | CB | VAL | A | 324 | −15.938 | 8.504 | −44.835 | 1.00 | 25.29 | A | C |
| ATOM | 1615 | CG1 | VAL | A | 324 | −17.076 | 7.906 | −45.660 | 1.00 | 28.11 | A | C |
| ATOM | 1616 | CG2 | VAL | A | 324 | −14.738 | 7.558 | −44.883 | 1.00 | 26.83 | A | C |
| ATOM | 1617 | C | VAL | A | 324 | −16.780 | 10.824 | −45.385 | 1.00 | 23.64 | A | C |
| ATOM | 1618 | O | VAL | A | 324 | −17.475 | 10.821 | −46.396 | 1.00 | 22.79 | A | O |
| ATOM | 1619 | N | GLY | A | 325 | −17.087 | 11.584 | −44.354 | 1.00 | 21.11 | A | N |
| ATOM | 1620 | CA | GLY | A | 325 | −18.200 | 12.485 | −44.448 | 1.00 | 22.79 | A | C |
| ATOM | 1621 | C | GLY | A | 325 | −19.495 | 11.920 | −43.961 | 1.00 | 25.84 | A | C |
| ATOM | 1622 | O | GLY | A | 325 | −20.510 | 12.607 | −44.037 | 1.00 | 27.36 | A | O |
| ATOM | 1623 | N | LYS | A | 326 | −19.481 | 10.691 | −43.434 | 1.00 | 29.10 | A | N |
| ATOM | 1624 | CA | LYS | A | 326 | −20.630 | 10.131 | −42.733 | 1.00 | 30.48 | A | C |
| ATOM | 1625 | CB | LYS | A | 326 | −21.621 | 9.520 | −43.739 | 1.00 | 37.82 | A | C |
| ATOM | 1626 | CG | LYS | A | 326 | −21.059 | 8.297 | −44.485 | 1.00 | 45.74 | A | C |
| ATOM | 1627 | CD | LYS | A | 326 | −22.110 | 7.510 | −45.279 | 1.00 | 55.09 | A | C |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 1628 | CE | LYS | A | 326 | −22.339 | 8.119 | −46.657 | 1.00 | 58.81 | A | C |
| ATOM | 1629 | NZ | LYS | A | 326 | −23.570 | 7.592 | −47.305 | 1.00 | 64.30 | A | N |
| ATOM | 1630 | C | LYS | A | 326 | −20.118 | 9.079 | −41.757 | 1.00 | 26.07 | A | C |
| ATOM | 1631 | O | LYS | A | 326 | −19.053 | 8.486 | −41.987 | 1.00 | 22.40 | A | O |
| ATOM | 1632 | N | PRO | A | 327 | −20.889 | 8.800 | −40.691 | 1.00 | 24.73 | A | N |
| ATOM | 1633 | CA | PRO | A | 327 | −20.336 | 7.870 | −39.712 | 1.00 | 26.82 | A | C |
| ATOM | 1634 | CB | PRO | A | 327 | −21.148 | 8.189 | −38.428 | 1.00 | 25.97 | A | C |
| ATOM | 1635 | CG | PRO | A | 327 | −22.383 | 8.930 | −38.903 | 1.00 | 25.51 | A | C |
| ATOM | 1636 | CD | PRO | A | 327 | −22.280 | 9.167 | −40.362 | 1.00 | 25.29 | A | C |
| ATOM | 1637 | C | PRO | A | 327 | −20.437 | 6.408 | −40.196 | 1.00 | 25.00 | A | C |
| ATOM | 1638 | O | PRO | A | 327 | −21.299 | 6.096 | −41.010 | 1.00 | 23.68 | A | O |
| ATOM | 1639 | N | PRO | A | 328 | −19.534 | 5.535 | −39.732 | 1.00 | 23.58 | A | N |
| ATOM | 1640 | CA | PRO | A | 328 | −19.439 | 4.166 | −40.247 | 1.00 | 24.74 | A | C |
| ATOM | 1641 | CB | PRO | A | 328 | −18.218 | 3.592 | −39.526 | 1.00 | 24.83 | A | C |
| ATOM | 1642 | CG | PRO | A | 328 | −17.981 | 4.456 | −38.353 | 1.00 | 24.15 | A | C |
| ATOM | 1643 | CD | PRO | A | 328 | −18.643 | 5.773 | −38.597 | 1.00 | 24.49 | A | C |
| ATOM | 1644 | C | PRO | A | 328 | −20.667 | 3.238 | −40.042 | 1.00 | 25.20 | A | C |
| ATOM | 1645 | O | PRO | A | 328 | −20.856 | 2.337 | −40.844 | 1.00 | 25.48 | A | O |
| ATOM | 1646 | N | PHE | A | 329 | −21.469 | 3.443 | −38.997 | 1.00 | 25.32 | A | N |
| ATOM | 1647 | CA | PHE | A | 329 | −22.581 | 2.516 | −38.659 | 1.00 | 25.92 | A | C |
| ATOM | 1648 | CB | PHE | A | 329 | −22.522 | 2.130 | −37.176 | 1.00 | 23.21 | A | C |
| ATOM | 1649 | CG | PHE | A | 329 | −21.181 | 1.570 | −36.764 | 1.00 | 21.42 | A | C |
| ATOM | 1650 | CD1 | PHE | A | 329 | −20.791 | 0.344 | −37.209 | 1.00 | 20.04 | A | C |
| ATOM | 1651 | CE1 | PHE | A | 329 | −19.554 | −0.176 | −36.852 | 1.00 | 21.28 | A | C |
| ATOM | 1652 | CZ | PHE | A | 329 | −18.678 | 0.577 | −36.030 | 1.00 | 20.11 | A | C |
| ATOM | 1653 | CE2 | PHE | A | 329 | −19.082 | 1.806 | −35.577 | 1.00 | 20.57 | A | C |
| ATOM | 1654 | CD2 | PHE | A | 329 | −20.308 | 2.314 | −35.975 | 1.00 | 19.99 | A | C |
| ATOM | 1655 | C | PHE | A | 329 | −23.947 | 3.065 | −39.002 | 1.00 | 28.15 | A | C |
| ATOM | 1656 | O | PHE | A | 329 | −24.967 | 2.571 | −38.530 | 1.00 | 31.64 | A | O |
| ATOM | 1657 | N | GLU | A | 330 | −23.960 | 4.075 | −39.855 | 1.00 | 31.75 | A | N |
| ATOM | 1658 | CA | GLU | A | 330 | −25.167 | 4.763 | −40.239 | 1.00 | 35.12 | A | C |
| ATOM | 1659 | CB | GLU | A | 330 | −24.821 | 5.804 | −41.284 | 1.00 | 38.78 | A | C |
| ATOM | 1660 | CG | GLU | A | 330 | −25.967 | 6.764 | −41.541 | 1.00 | 44.64 | A | C |
| ATOM | 1661 | CD | GLU | A | 330 | −25.475 | 8.095 | −42.045 | 1.00 | 50.10 | A | C |
| ATOM | 1662 | OE1 | GLU | A | 330 | −24.876 | 8.124 | −43.155 | 1.00 | 50.26 | A | O |
| ATOM | 1663 | OE2 | GLU | A | 330 | −25.663 | 9.086 | −41.298 | 1.00 | 58.26 | A | O |
| ATOM | 1664 | C | GLU | A | 330 | −26.223 | 3.806 | −40.818 | 1.00 | 35.18 | A | C |
| ATOM | 1665 | O | GLU | A | 330 | −25.894 | 2.968 | −41.625 | 1.00 | 35.04 | A | O |
| ATOM | 1666 | N | ALA | A | 331 | −27.472 | 3.944 | −40.403 | 1.00 | 36.89 | A | N |
| ATOM | 1667 | CA | ALA | A | 331 | −28.551 | 3.085 | −40.876 | 1.00 | 40.41 | A | C |
| ATOM | 1668 | CB | ALA | A | 331 | −28.507 | 1.752 | −40.136 | 1.00 | 38.55 | A | C |
| ATOM | 1669 | C | ALA | A | 331 | −29.925 | 3.771 | −40.714 | 1.00 | 43.51 | A | C |
| ATOM | 1670 | O | ALA | A | 331 | −30.041 | 4.768 | −40.040 | 1.00 | 41.06 | A | O |
| ATOM | 1671 | N | ASN | A | 332 | −30.974 | 3.219 | −41.302 | 1.00 | 47.88 | A | N |
| ATOM | 1672 | CA | ASN | A | 332 | −32.275 | 3.926 | −41.331 | 1.00 | 52.36 | A | C |
| ATOM | 1673 | CB | ASN | A | 332 | −33.206 | 3.345 | −42.408 | 1.00 | 56.78 | A | C |
| ATOM | 1674 | CG | ASN | A | 332 | −32.465 | 3.001 | −43.674 | 1.00 | 57.74 | A | C |
| ATOM | 1675 | OD1 | ASN | A | 332 | −31.997 | 1.855 | −43.861 | 1.00 | 59.70 | A | O |
| ATOM | 1676 | ND2 | ASN | A | 332 | −32.269 | 4.007 | −44.514 | 1.00 | 59.05 | A | N |
| ATOM | 1677 | C | ASN | A | 332 | −33.006 | 3.899 | −40.011 | 1.00 | 50.02 | A | C |
| ATOM | 1678 | O | ASN | A | 332 | −33.949 | 4.650 | −39.856 | 1.00 | 60.70 | A | O |
| ATOM | 1679 | N | THR | A | 333 | −32.632 | 3.009 | −39.091 | 1.00 | 47.19 | A | N |
| ATOM | 1680 | CA | THR | A | 333 | −33.239 | 2.974 | −37.745 | 1.00 | 48.28 | A | C |
| ATOM | 1681 | CB | THR | A | 333 | −34.279 | 1.819 | −37.548 | 1.00 | 52.24 | A | C |
| ATOM | 1682 | OG1 | THR | A | 333 | −33.622 | 0.538 | −37.642 | 1.00 | 52.38 | A | O |
| ATOM | 1683 | CG2 | THR | A | 333 | −35.469 | 1.900 | −38.537 | 1.00 | 49.15 | A | C |
| ATOM | 1684 | C | THR | A | 333 | −32.196 | 2.744 | −36.667 | 1.00 | 44.76 | A | C |
| ATOM | 1685 | O | THR | A | 333 | −31.138 | 2.130 | −36.898 | 1.00 | 39.40 | A | O |
| ATOM | 1686 | N | TYR | A | 334 | −32.538 | 3.138 | −35.456 | 1.00 | 43.15 | A | N |
| ATOM | 1687 | CA | TYR | A | 334 | −31.581 | 2.978 | −34.389 | 1.00 | 50.55 | A | C |
| ATOM | 1688 | CB | TYR | A | 334 | −31.960 | 3.831 | −33.185 | 1.00 | 55.54 | A | C |
| ATOM | 1689 | CG | TYR | A | 334 | −32.897 | 3.211 | −32.222 | 1.00 | 64.30 | A | C |
| ATOM | 1690 | CD1 | TYR | A | 334 | −32.457 | 2.216 | −31.341 | 1.00 | 72.74 | A | C |
| ATOM | 1691 | CE1 | TYR | A | 334 | −33.321 | 1.648 | −30.422 | 1.00 | 78.93 | A | C |
| ATOM | 1692 | CZ | TYR | A | 334 | −34.635 | 2.093 | −30.365 | 1.00 | 79.55 | A | C |
| ATOM | 1693 | OH | TYR | A | 334 | −35.490 | 1.532 | −29.457 | 1.00 | 91.49 | A | O |
| ATOM | 1694 | CE2 | TYR | A | 334 | −35.094 | 3.090 | −31.219 | 1.00 | 74.87 | A | C |
| ATOM | 1695 | CD2 | TYR | A | 334 | −34.225 | 3.641 | −32.143 | 1.00 | 71.27 | A | C |
| ATOM | 1696 | C | TYR | A | 334 | −31.307 | 1.508 | −34.059 | 1.00 | 47.33 | A | C |
| ATOM | 1697 | O | TYR | A | 334 | −30.193 | 1.142 | −33.667 | 1.00 | 45.78 | A | O |
| ATOM | 1698 | N | GLN | A | 335 | −32.296 | 0.656 | −34.311 | 1.00 | 50.00 | A | N |
| ATOM | 1699 | CA | GLN | A | 335 | −32.153 | −0.794 | −34.131 | 1.00 | 47.23 | A | C |
| ATOM | 1700 | CB | GLN | A | 335 | −33.441 | −1.550 | −34.451 | 1.00 | 51.24 | A | C |
| ATOM | 1701 | CG | GLN | A | 335 | −34.565 | −1.239 | −33.476 | 1.00 | 53.00 | A | C |
| ATOM | 1702 | CD | GLN | A | 335 | −35.352 | 0.020 | −33.833 | 1.00 | 56.97 | A | C |
| ATOM | 1703 | OE1 | GLN | A | 335 | −35.464 | 0.417 | −34.998 | 1.00 | 61.92 | A | O |
| ATOM | 1704 | NE2 | GLN | A | 335 | −35.912 | 0.643 | −32.830 | 1.00 | 60.75 | A | N |
| ATOM | 1705 | C | GLN | A | 335 | −31.059 | −1.343 | −34.980 | 1.00 | 41.42 | A | C |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 1706 | O | GLN | A | 335 | −30.193 | −2.004 | −34.439 | 1.00 | 42.58 | A | O |
| ATOM | 1707 | N | GLU | A | 336 | −31.070 | −1.059 | −36.289 | 1.00 | 41.06 | A | N |
| ATOM | 1708 | CA | GLU | A | 336 | −30.035 | −1.620 | −37.189 | 1.00 | 43.76 | A | C |
| ATOM | 1709 | CB | GLU | A | 336 | −30.258 | −1.251 | −38.656 | 1.00 | 51.53 | A | C |
| ATOM | 1710 | CG | GLU | A | 336 | −31.573 | −1.664 | −39.325 | 1.00 | 61.60 | A | C |
| ATOM | 1711 | CD | GLU | A | 336 | −31.835 | −0.830 | −40.594 | 1.00 | 71.96 | A | C |
| ATOM | 1712 | OE1 | GLU | A | 336 | −31.164 | −1.070 | −41.638 | 1.00 | 73.74 | A | O |
| ATOM | 1713 | OE2 | GLU | A | 336 | −32.683 | 0.107 | −40.546 | 1.00 | 74.23 | A | O |
| ATOM | 1714 | C | GLU | A | 336 | −28.632 | −1.108 | −36.795 | 1.00 | 41.87 | A | C |
| ATOM | 1715 | O | GLU | A | 336 | −27.636 | −1.862 | −36.799 | 1.00 | 38.37 | A | O |
| ATOM | 1716 | N | THR | A | 337 | −28.585 | 0.195 | −36.506 | 1.00 | 37.47 | A | N |
| ATOM | 1717 | CA | THR | A | 337 | −27.398 | 0.892 | −36.068 | 1.00 | 36.30 | A | C |
| ATOM | 1718 | CB | THR | A | 337 | −27.720 | 2.406 | −35.879 | 1.00 | 38.27 | A | C |
| ATOM | 1719 | OG1 | THR | A | 337 | −28.039 | 2.949 | −37.149 | 1.00 | 38.48 | A | O |
| ATOM | 1720 | CG2 | THR | A | 337 | −26.548 | 3.201 | −35.336 | 1.00 | 37.85 | A | C |
| ATOM | 1721 | C | THR | A | 337 | −26.813 | 0.225 | −34.809 | 1.00 | 35.37 | A | C |
| ATOM | 1722 | O | THR | A | 337 | −25.594 | −0.036 | −34.745 | 1.00 | 31.83 | A | O |
| ATOM | 1723 | N | TYR | A | 338 | −27.671 | −0.103 | −33.842 | 1.00 | 35.24 | A | N |
| ATOM | 1724 | CA | TYR | A | 338 | −27.203 | −0.829 | −32.644 | 1.00 | 35.23 | A | C |
| ATOM | 1725 | CB | TYR | A | 338 | −28.338 | −1.095 | −31.667 | 1.00 | 36.76 | A | C |
| ATOM | 1726 | CG | TYR | A | 338 | −28.695 | 0.026 | −30.717 | 1.00 | 36.88 | A | C |
| ATOM | 1727 | CD1 | TYR | A | 338 | −28.604 | 1.374 | −31.084 | 1.00 | 42.31 | A | C |
| ATOM | 1728 | CE1 | TYR | A | 338 | −28.986 | 2.401 | −30.194 | 1.00 | 39.71 | A | C |
| ATOM | 1729 | CZ | TYR | A | 338 | −29.447 | 2.081 | −28.937 | 1.00 | 37.49 | A | C |
| ATOM | 1730 | OH | TYR | A | 338 | −29.788 | 3.058 | −28.074 | 1.00 | 38.17 | A | O |
| ATOM | 1731 | CE2 | TYR | A | 338 | −29.533 | 0.761 | −28.548 | 1.00 | 38.42 | A | C |
| ATOM | 1732 | CD2 | TYR | A | 338 | −29.171 | −0.257 | −29.442 | 1.00 | 37.07 | A | C |
| ATOM | 1733 | C | TYR | A | 338 | −26.586 | −2.162 | −32.986 | 1.00 | 34.02 | A | C |
| ATOM | 1734 | O | TYR | A | 338 | −25.460 | −2.487 | −32.559 | 1.00 | 30.71 | A | O |
| ATOM | 1735 | N | LYS | A | 339 | −27.316 | −2.945 | −33.777 | 1.00 | 36.06 | A | N |
| ATOM | 1736 | CA | LYS | A | 339 | −26.797 | −4.262 | −34.208 | 1.00 | 36.71 | A | C |
| ATOM | 1737 | CB | LYS | A | 339 | −27.778 | −4.958 | −35.147 | 1.00 | 42.19 | A | C |
| ATOM | 1738 | CG | LYS | A | 339 | −29.068 | −5.382 | −34.456 | 1.00 | 52.02 | A | C |
| ATOM | 1739 | CD | LYS | A | 339 | −30.258 | −5.480 | −35.408 | 1.00 | 59.71 | A | C |
| ATOM | 1740 | CE | LYS | A | 339 | −31.558 | −5.837 | −34.686 | 1.00 | 57.34 | A | C |
| ATOM | 1741 | NZ | LYS | A | 339 | −32.306 | −6.806 | −35.529 | 1.00 | 63.08 | A | N |
| ATOM | 1742 | C | LYS | A | 339 | −25.432 | −4.108 | −34.887 | 1.00 | 34.51 | A | C |
| ATOM | 1743 | O | LYS | A | 339 | −24.466 | −4.818 | −34.583 | 1.00 | 28.23 | A | O |
| ATOM | 1744 | N | ARG | A | 340 | −25.352 | −3.144 | −35.787 | 1.00 | 34.90 | A | N |
| ATOM | 1745 | CA | ARG | A | 340 | −24.125 | −2.945 | −36.546 | 1.00 | 36.41 | A | C |
| ATOM | 1746 | CB | ARG | A | 340 | −24.431 | −2.003 | −37.686 | 1.00 | 42.33 | A | C |
| ATOM | 1747 | CG | ARG | A | 340 | −25.267 | −2.745 | −38.745 | 1.00 | 49.38 | A | C |
| ATOM | 1748 | CD | ARG | A | 340 | −25.497 | −1.890 | −39.956 | 1.00 | 57.91 | A | C |
| ATOM | 1749 | NE | ARG | A | 340 | −24.206 | −1.324 | −40.370 | 1.00 | 70.32 | A | N |
| ATOM | 1750 | CZ | ARG | A | 340 | −24.019 | −0.369 | −41.286 | 1.00 | 69.05 | A | C |
| ATOM | 1751 | NH1 | ARG | A | 340 | −25.056 | 0.128 | −41.990 | 1.00 | 71.37 | A | N |
| ATOM | 1752 | NH2 | ARG | A | 340 | −22.763 | 0.062 | −41.500 | 1.00 | 58.26 | A | N |
| ATOM | 1753 | C | ARG | A | 340 | −22.922 | −2.513 | −35.692 | 1.00 | 30.69 | A | C |
| ATOM | 1754 | O | ARG | A | 340 | −21.800 | −3.000 | −35.900 | 1.00 | 28.53 | A | O |
| ATOM | 1755 | N | ILE | A | 341 | −23.180 | −1.687 | −34.683 | 1.00 | 26.21 | A | N |
| ATOM | 1756 | CA | ILE | A | 341 | −22.148 | −1.269 | −33.730 | 1.00 | 25.81 | A | C |
| ATOM | 1757 | CB | ILE | A | 341 | −22.674 | −0.154 | −32.789 | 1.00 | 24.11 | A | C |
| ATOM | 1758 | CG1 | ILE | A | 341 | −22.847 | 1.166 | −33.535 | 1.00 | 25.51 | A | C |
| ATOM | 1759 | CD1 | ILE | A | 341 | −23.801 | 2.156 | −32.831 | 1.00 | 26.18 | A | C |
| ATOM | 1760 | CG2 | ILE | A | 341 | −21.745 | 0.065 | −31.604 | 1.00 | 23.77 | A | C |
| ATOM | 1761 | C | ILE | A | 341 | −21.707 | −2.478 | −32.899 | 1.00 | 26.91 | A | C |
| ATOM | 1762 | O | ILE | A | 341 | −20.513 | −2.837 | −32.800 | 1.00 | 27.09 | A | O |
| ATOM | 1763 | N | SER | A | 342 | −22.705 | −3.128 | −32.326 | 1.00 | 29.31 | A | N |
| ATOM | 1764 | CA | SER | A | 342 | −22.508 | −4.339 | −31.509 | 1.00 | 32.69 | A | C |
| ATOM | 1765 | CB | SER | A | 342 | −23.867 | −4.928 | −31.109 | 1.00 | 34.13 | A | C |
| ATOM | 1766 | OG | SER | A | 342 | −23.678 | −5.730 | −29.993 | 1.00 | 40.58 | A | O |
| ATOM | 1767 | C | SER | A | 342 | −21.678 | −5.401 | −32.204 | 1.00 | 29.85 | A | C |
| ATOM | 1768 | O | SER | A | 342 | −20.829 | −5.976 | −31.610 | 1.00 | 26.75 | A | O |
| ATOM | 1769 | N | ARG | A | 343 | −21.912 | −5.595 | −33.497 | 1.00 | 32.67 | A | N |
| ATOM | 1770 | CA | ARG | A | 343 | −21.101 | −6.484 | −34.311 | 1.00 | 33.97 | A | C |
| ATOM | 1771 | CB | ARG | A | 343 | −21.974 | −7.134 | −35.369 | 1.00 | 42.98 | A | C |
| ATOM | 1772 | CG | ARG | A | 343 | −23.270 | −7.797 | −34.867 | 1.00 | 49.05 | A | C |
| ATOM | 1773 | CD | ARG | A | 343 | −23.406 | −9.174 | −35.501 | 1.00 | 57.03 | A | C |
| ATOM | 1774 | NE | ARG | A | 343 | −24.792 | −9.628 | −35.663 | 1.00 | 61.52 | A | N |
| ATOM | 1775 | CZ | ARG | A | 343 | −25.442 | −10.442 | −34.825 | 1.00 | 55.79 | A | C |
| ATOM | 1776 | NH1 | ARG | A | 343 | −24.852 | −10.898 | −33.708 | 1.00 | 55.98 | A | N |
| ATOM | 1777 | NH2 | ARG | A | 343 | −26.701 | −10.801 | −35.103 | 1.00 | 54.23 | A | N |
| ATOM | 1778 | C | ARG | A | 343 | −19.937 | −5.817 | −35.050 | 1.00 | 32.98 | A | C |
| ATOM | 1779 | O | ARG | A | 343 | −19.272 | −6.501 | −35.849 | 1.00 | 27.89 | A | O |
| ATOM | 1780 | N | VAL | A | 344 | −19.688 | −4.510 | −34.817 | 1.00 | 28.24 | A | N |
| ATOM | 1781 | CA | VAL | A | 344 | −18.643 | −3.798 | −35.530 | 1.00 | 25.47 | A | C |
| ATOM | 1782 | CB | VAL | A | 344 | −17.257 | −4.098 | −34.916 | 1.00 | 25.69 | A | C |
| ATOM | 1783 | CG1 | VAL | A | 344 | −16.216 | −3.094 | −35.373 | 1.00 | 26.33 | A | C |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 1784 | CG2 | VAL | A | 344 | −17.329 | −4.011 | −33.416 | 1.00 | 26.58 | A | C |
| ATOM | 1785 | C | VAL | A | 344 | −18.732 | −4.169 | −37.033 | 1.00 | 25.95 | A | C |
| ATOM | 1786 | O | VAL | A | 344 | −17.780 | −4.705 | −37.636 | 1.00 | 25.80 | A | O |
| ATOM | 1787 | N | GLU | A | 345 | −19.914 | −3.934 | −37.603 | 1.00 | 24.61 | A | N |
| ATOM | 1788 | CA | GLU | A | 345 | −20.163 | −4.136 | −39.017 | 1.00 | 27.12 | A | C |
| ATOM | 1789 | CB | GLU | A | 345 | −21.558 | −4.746 | −39.256 | 1.00 | 32.00 | A | C |
| ATOM | 1790 | CG | GLU | A | 345 | −21.650 | −6.227 | −38.896 | 1.00 | 33.40 | A | C |
| ATOM | 1791 | CD | GLU | A | 345 | −23.082 | −6.734 | −38.755 | 1.00 | 35.77 | A | C |
| ATOM | 1792 | OE1 | GLU | A | 345 | −24.044 | −5.979 | −38.993 | 1.00 | 39.05 | A | O |
| ATOM | 1793 | OE2 | GLU | A | 345 | −23.247 | −7.934 | −38.436 | 1.00 | 40.49 | A | O |
| ATOM | 1794 | C | GLU | A | 345 | −20.032 | −2.815 | −39.774 | 1.00 | 25.80 | A | C |
| ATOM | 1795 | O | GLU | A | 345 | −20.962 | −2.023 | −39.824 | 1.00 | 21.60 | A | O |
| ATOM | 1796 | N | PHE | A | 346 | −18.854 | −2.599 | −40.365 | 1.00 | 23.99 | A | N |
| ATOM | 1797 | CA | PHE | A | 346 | −18.621 | −1.418 | −41.192 | 1.00 | 25.28 | A | C |
| ATOM | 1798 | CB | PHE | A | 346 | −18.362 | −0.149 | −40.311 | 1.00 | 24.09 | A | C |
| ATOM | 1799 | CG | PHE | A | 346 | −16.930 | −0.027 | −39.873 | 1.00 | 24.15 | A | C |
| ATOM | 1800 | CD1 | PHE | A | 346 | −16.446 | −0.765 | −38.797 | 1.00 | 23.16 | A | C |
| ATOM | 1801 | CE1 | PHE | A | 346 | −15.123 | −0.713 | −38.430 | 1.00 | 24.96 | A | C |
| ATOM | 1802 | CZ | PHE | A | 346 | −14.233 | 0.055 | −39.154 | 1.00 | 24.90 | A | C |
| ATOM | 1803 | CE2 | PHE | A | 346 | −14.679 | 0.735 | −40.261 | 1.00 | 26.05 | A | C |
| ATOM | 1804 | CD2 | PHE | A | 346 | −16.041 | 0.708 | −40.610 | 1.00 | 25.27 | A | C |
| ATOM | 1805 | C | PHE | A | 346 | −17.427 | −1.676 | −42.154 | 1.00 | 24.18 | A | C |
| ATOM | 1806 | O | PHE | A | 346 | −16.534 | −2.487 | −41.880 | 1.00 | 27.08 | A | O |
| ATOM | 1807 | N | THR | A | 347 | −17.421 | −0.923 | −43.244 | 1.00 | 22.23 | A | N |
| ATOM | 1808 | CA | THR | A | 347 | −16.417 | −0.989 | −44.289 | 1.00 | 22.18 | A | C |
| ATOM | 1809 | CB | THR | A | 347 | −17.015 | −1.672 | −45.554 | 1.00 | 21.06 | A | C |
| ATOM | 1810 | OG1 | THR | A | 347 | −18.249 | −1.044 | −45.968 | 1.00 | 22.02 | A | O |
| ATOM | 1811 | CG2 | THR | A | 347 | −17.313 | −3.106 | −45.234 | 1.00 | 21.62 | A | C |
| ATOM | 1812 | C | THR | A | 347 | −15.912 | 0.466 | −44.613 | 1.00 | 23.25 | A | C |
| ATOM | 1813 | O | THR | A | 347 | −16.607 | 1.479 | −44.356 | 1.00 | 22.00 | A | O |
| ATOM | 1814 | N | PHE | A | 348 | −14.715 | 0.545 | −45.164 | 1.00 | 21.57 | A | N |
| ATOM | 1815 | CA | PHE | A | 348 | −14.156 | 1.780 | −45.572 | 1.00 | 23.32 | A | C |
| ATOM | 1816 | CB | PHE | A | 348 | −12.664 | 1.784 | −45.311 | 1.00 | 23.98 | A | C |
| ATOM | 1817 | CG | PHE | A | 348 | −12.280 | 1.584 | −43.901 | 1.00 | 22.56 | A | C |
| ATOM | 1818 | CD1 | PHE | A | 348 | −12.000 | 0.329 | −43.434 | 1.00 | 22.63 | A | C |
| ATOM | 1819 | CE1 | PHE | A | 348 | −11.533 | 0.151 | −42.128 | 1.00 | 24.46 | A | C |
| ATOM | 1820 | CZ | PHE | A | 348 | −11.375 | 1.258 | −41.277 | 1.00 | 25.03 | A | C |
| ATOM | 1821 | CE2 | PHE | A | 348 | −11.656 | 2.535 | −41.751 | 1.00 | 22.24 | A | C |
| ATOM | 1822 | CD2 | PHE | A | 348 | −12.085 | 2.699 | −43.048 | 1.00 | 22.47 | A | C |
| ATOM | 1823 | C | PHE | A | 348 | −14.245 | 1.913 | −47.069 | 1.00 | 26.14 | A | C |
| ATOM | 1824 | O | PHE | A | 348 | −14.039 | 0.901 | −47.784 | 1.00 | 24.67 | A | O |
| ATOM | 1825 | N | PRO | A | 349 | −14.428 | 3.162 | −47.573 | 1.00 | 27.35 | A | N |
| ATOM | 1026 | CA | PRO | A | 349 | −14.240 | 3.359 | −49.017 | 1.00 | 27.11 | A | C |
| ATOM | 1827 | CB | PRO | A | 349 | −14.670 | 4.796 | −49.257 | 1.00 | 28.28 | A | C |
| ATOM | 1828 | CG | PRO | A | 349 | −15.331 | 5.291 | −47.988 | 1.00 | 27.36 | A | C |
| ATOM | 1829 | CD | PRO | A | 349 | −15.269 | 4.207 | −46.967 | 1.00 | 28.64 | A | C |
| ATOM | 1830 | C | PRO | A | 349 | −12.782 | 3.138 | −49.391 | 1.00 | 27.66 | A | C |
| ATOM | 1831 | O | PRO | A | 349 | −11.923 | 3.073 | −48.486 | 1.00 | 26.57 | A | O |
| ATOM | 1832 | N | ASP | A | 350 | −12.510 | 2.945 | −50.691 | 1.00 | 27.64 | A | N |
| ATOM | 1833 | CA | ASP | A | 350 | −11.135 | 2.685 | −51.159 | 1.00 | 28.77 | A | C |
| ATOM | 1834 | CB | ASP | A | 350 | −11.108 | 2.170 | −52.619 | 1.00 | 32.72 | A | C |
| ATOM | 1835 | CG | ASP | A | 350 | −11.701 | 0.738 | −52.770 | 1.00 | 38.76 | A | C |
| ATOM | 1836 | OD1 | ASP | A | 350 | −11.686 | −0.071 | −51.792 | 1.00 | 40.86 | A | O |
| ATOM | 1837 | OD2 | ASP | A | 350 | −12.194 | 0.422 | −53.876 | 1.00 | 40.24 | A | O |
| ATOM | 1838 | C | ASP | A | 350 | −10.241 | 3.914 | −51.007 | 1.00 | 27.93 | A | C |
| ATOM | 1839 | O | ASP | A | 350 | −9.034 | 3.764 | −50.787 | 1.00 | 32.45 | A | O |
| ATOM | 1840 | N | PHE | A | 351 | −10.798 | 5.129 | −51.079 | 1.00 | 26.28 | A | N |
| ATOM | 1841 | CA | PHE | A | 351 | −9.945 | 6.319 | −50.885 | 1.00 | 26.23 | A | C |
| ATOM | 1842 | CB | PHE | A | 351 | −10.620 | 7.645 | −51.317 | 1.00 | 23.24 | A | C |
| ATOM | 1843 | CG | PHE | A | 351 | −11.785 | 8.027 | −50.501 | 1.00 | 24.99 | A | C |
| ATOM | 1844 | CD1 | PHE | A | 351 | −11.605 | 8.683 | −49.272 | 1.00 | 25.73 | A | C |
| ATOM | 1845 | CE1 | PHE | A | 351 | −12.711 | 9.035 | −48.523 | 1.00 | 25.79 | A | C |
| ATOM | 1846 | CZ | PHE | A | 351 | −13.996 | 8.746 | −48.981 | 1.00 | 24.13 | A | C |
| ATOM | 1847 | CE2 | PHE | A | 351 | −14.182 | 8.130 | −50.191 | 1.00 | 23.49 | A | C |
| ATOM | 1848 | CD2 | PHE | A | 351 | −13.078 | 7.762 | −50.943 | 1.00 | 24.40 | A | C |
| ATOM | 1849 | C | PHE | A | 351 | −9.240 | 6.404 | −49.498 | 1.00 | 24.76 | A | C |
| ATOM | 1850 | O | PHE | A | 351 | −8.139 | 6.885 | −49.440 | 1.00 | 24.00 | A | O |
| ATOM | 1851 | N | VAL | A | 352 | −9.816 | 5.832 | −48.435 | 1.00 | 26.18 | A | N |
| ATOM | 1852 | CA | VAL | A | 352 | −9.227 | 5.934 | −47.083 | 1.00 | 24.49 | A | C |
| ATOM | 1853 | CB | VAL | A | 352 | −10.125 | 5.299 | −46.021 | 1.00 | 23.36 | A | C |
| ATOM | 1854 | CG1 | VAL | A | 352 | −9.424 | 5.325 | −44.647 | 1.00 | 23.84 | A | C |
| ATOM | 1855 | CG2 | VAL | A | 352 | −11.496 | 5.983 | −46.007 | 1.00 | 20.92 | A | C |
| ATOM | 1856 | C | VAL | A | 352 | −7.878 | 5.258 | −47.081 | 1.00 | 23.69 | A | C |
| ATOM | 1857 | O | VAL | A | 352 | −7.789 | 4.115 | −47.408 | 1.00 | 23.15 | A | O |
| ATOM | 1858 | N | THR | A | 353 | −6.822 | 5.948 | −46.710 | 1.00 | 22.49 | A | N |
| ATOM | 1859 | CA | THR | A | 353 | −5.505 | 5.339 | −46.873 | 1.00 | 23.11 | A | C |
| ATOM | 1860 | CB | THR | A | 353 | −4.382 | 6.385 | −46.666 | 1.00 | 21.79 | A | C |
| ATOM | 1861 | OG1 | THR | A | 353 | −4.467 | 6.896 | −45.331 | 1.00 | 20.42 | A | O |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 1862 | CG2 | THR | A | 353 | −4.520 | 7.542 | −47.642 | 1.00 | 21.88 | A | C |
| ATOM | 1863 | C | THR | A | 353 | −5.250 | 4.207 | −45.866 | 1.00 | 23.15 | A | C |
| ATOM | 1864 | O | THR | A | 353 | −5.893 | 4.076 | −44.862 | 1.00 | 22.02 | A | O |
| ATOM | 1865 | N | GLU | A | 354 | −4.201 | 3.468 | −46.124 | 1.00 | 26.57 | A | N |
| ATOM | 1866 | CA | GLU | A | 354 | −3.752 | 2.428 | −45.263 | 1.00 | 29.80 | A | C |
| ATOM | 1867 | CB | GLU | A | 354 | −2.441 | 1.884 | −45.837 | 1.00 | 36.56 | A | C |
| ATOM | 1868 | CG | GLU | A | 354 | −2.187 | 0.419 | −45.549 | 1.00 | 51.67 | A | C |
| ATOM | 1869 | CD | GLU | A | 354 | −3.294 | −0.544 | −46.058 | 1.00 | 58.30 | A | C |
| ATOM | 1870 | OE1 | GLU | A | 354 | −4.298 | −0.122 | −46.738 | 1.00 | 56.91 | A | O |
| ATOM | 1871 | OE2 | GLU | A | 354 | −3.144 | −1.757 | −45.751 | 1.00 | 59.35 | A | O |
| ATOM | 1872 | C | GLU | A | 354 | −3.588 | 2.844 | −43.797 | 1.00 | 27.07 | A | C |
| ATOM | 1873 | O | GLU | A | 354 | −4.122 | 2.204 | −42.860 | 1.00 | 25.40 | A | O |
| ATOM | 1874 | N | GLY | A | 355 | −2.862 | 3.924 | −43.595 | 1.00 | 22.73 | A | N |
| ATOM | 1875 | CA | GLY | A | 355 | −2.602 | 4.400 | −42.260 | 1.00 | 21.34 | A | C |
| ATOM | 1876 | C | GLY | A | 355 | −3.806 | 4.857 | −41.465 | 1.00 | 20.02 | A | C |
| ATOM | 1877 | O | GLY | A | 355 | −3.854 | 4.636 | −40.280 | 1.00 | 18.86 | A | O |
| ATOM | 1878 | N | ALA | A | 356 | −4.771 | 5.479 | −42.129 | 1.00 | 21.19 | A | N |
| ATOM | 1879 | CA | ALA | A | 356 | −6.061 | 5.913 | −41.503 | 1.00 | 21.14 | A | C |
| ATOM | 1880 | CB | ALA | A | 356 | −6.837 | 6.807 | −42.484 | 1.00 | 20.91 | A | C |
| ATOM | 1881 | C | ALA | A | 356 | −6.927 | 4.734 | −41.141 | 1.00 | 22.13 | A | C |
| ATOM | 1882 | O | ALA | A | 356 | −7.625 | 4.683 | −40.093 | 1.00 | 18.70 | A | O |
| ATOM | 1883 | N | ARG | A | 357 | −6.946 | 3.805 | −42.081 | 1.00 | 23.64 | A | N |
| ATOM | 1884 | CA | ARG | A | 357 | −7.612 | 2.534 | −41.872 | 1.00 | 25.21 | A | C |
| ATOM | 1885 | CB | ARG | A | 357 | −7.406 | 1.772 | −43.167 | 1.00 | 30.06 | A | C |
| ATOM | 1886 | CG | ARG | A | 357 | −7.907 | 0.385 | −43.253 | 1.00 | 38.35 | A | C |
| ATOM | 1887 | CD | ARG | A | 357 | −7.576 | −0.210 | −44.616 | 1.00 | 41.10 | A | C |
| ATOM | 1888 | NE | ARG | A | 357 | −8.715 | −0.039 | −45.519 | 1.00 | 44.78 | A | N |
| ATOM | 1889 | CZ | ARG | A | 357 | −9.699 | −0.924 | −45.709 | 1.00 | 40.82 | A | C |
| ATOM | 1890 | NH1 | ARG | A | 357 | −9.729 | −2.108 | −45.063 | 1.00 | 41.20 | A | N |
| ATOM | 1891 | NH2 | ARG | A | 357 | −10.674 | −0.616 | −46.562 | 1.00 | 38.24 | A | N |
| ATOM | 1892 | C | ARG | A | 357 | −7.068 | 1.836 | −40.605 | 1.00 | 22.79 | A | C |
| ATOM | 1893 | O | ARG | A | 357 | −7.824 | 1.422 | −39.748 | 1.00 | 20.95 | A | O |
| ATOM | 1894 | N | ASP | A | 358 | −5.737 | 1.763 | −40.453 | 1.00 | 23.81 | A | N |
| ATOM | 1895 | CA | ASP | A | 358 | −5.120 | 1.123 | −39.302 | 1.00 | 22.65 | A | C |
| ATOM | 1896 | CB | ASP | A | 358 | −3.601 | 1.152 | −39.408 | 1.00 | 25.70 | A | C |
| ATOM | 1897 | CG | ASP | A | 358 | −2.900 | 0.376 | −38.294 | 1.00 | 29.07 | A | C |
| ATOM | 1898 | OD1 | ASP | A | 358 | −3.062 | −0.884 | −38.227 | 1.00 | 31.89 | A | O |
| ATOM | 1899 | OD2 | ASP | A | 358 | −2.104 | 0.991 | −37.528 | 1.00 | 28.06 | A | O |
| ATOM | 1900 | C | ASP | A | 358 | −5.547 | 1.840 | −38.047 | 1.00 | 24.08 | A | C |
| ATOM | 1901 | O | ASP | A | 358 | −6.003 | 1.181 | −37.106 | 1.00 | 22.35 | A | O |
| ATOM | 1902 | N | LEU | A | 359 | −5.403 | 3.183 | −38.021 | 1.00 | 20.30 | A | N |
| ATOM | 1903 | CA | LEU | A | 359 | −5.757 | 3.911 | −36.817 | 1.00 | 20.07 | A | C |
| ATOM | 1904 | CB | LEU | A | 359 | −5.491 | 5.436 | −36.913 | 1.00 | 21.16 | A | C |
| ATOM | 1905 | CG | LEU | A | 359 | −5.980 | 6.271 | −35.702 | 1.00 | 19.30 | A | C |
| ATOM | 1906 | CD1 | LEU | A | 359 | −5.727 | 7.756 | −35.873 | 1.00 | 20.08 | A | C |
| ATOM | 1907 | CD2 | LEU | A | 359 | −5.290 | 5.784 | −34.471 | 1.00 | 18.65 | A | C |
| ATOM | 1908 | C | LEU | A | 359 | −7.193 | 3.700 | −36.425 | 1.00 | 18.35 | A | C |
| ATOM | 1909 | O | LEU | A | 359 | −7.480 | 3.415 | −35.267 | 1.00 | 17.37 | A | O |
| ATOM | 1910 | N | ILE | A | 360 | −8.089 | 3.845 | −37.371 | 1.00 | 17.43 | A | N |
| ATOM | 1911 | CA | ILE | A | 360 | −9.513 | 3.685 | −37.072 | 1.00 | 17.95 | A | C |
| ATOM | 1912 | CB | ILE | A | 360 | −10.332 | 4.058 | −38.325 | 1.00 | 18.56 | A | C |
| ATOM | 1913 | CG1 | ILE | A | 360 | −10.275 | 5.569 | −38.525 | 1.00 | 21.02 | A | C |
| ATOM | 1914 | CD1 | ILE | A | 360 | −10.645 | 6.033 | −39.938 | 1.00 | 24.42 | A | C |
| ATOM | 1915 | CG2 | ILE | A | 360 | −11.809 | 3.693 | −38.178 | 1.00 | 19.56 | A | C |
| ATOM | 1916 | C | ILE | A | 360 | −9.832 | 2.274 | −36.590 | 1.00 | 19.66 | A | C |
| ATOM | 1917 | O | ILE | A | 360 | −10.669 | 2.072 | −35.694 | 1.00 | 20.27 | A | O |
| ATOM | 1918 | N | SER | A | 361 | −9.219 | 1.272 | −37.244 | 1.00 | 20.59 | A | N |
| ATOM | 1919 | CA | SER | A | 361 | −9.504 | −0.140 | −36.931 | 1.00 | 19.44 | A | C |
| ATOM | 1920 | CB | SER | A | 361 | −8.834 | −1.076 | −37.951 | 1.00 | 17.78 | A | C |
| ATOM | 1921 | OG | SER | A | 361 | −9.403 | −0.817 | −39.240 | 1.00 | 17.73 | A | O |
| ATOM | 1922 | C | SER | A | 361 | −9.015 | −0.413 | −35.509 | 1.00 | 21.28 | A | C |
| ATOM | 1923 | O | SER | A | 361 | −9.693 | −1.127 | −34.774 | 1.00 | 24.58 | A | O |
| ATOM | 1924 | N | ARG | A | 362 | −7.873 | 0.154 | −35.109 | 1.00 | 19.92 | A | N |
| ATOM | 1925 | CA | ARG | A | 362 | −7.440 | 0.048 | −33.713 | 1.00 | 21.60 | A | C |
| ATOM | 1926 | CB | ARG | A | 362 | −6.056 | 0.623 | −33.580 | 1.00 | 21.19 | A | C |
| ATOM | 1927 | CG | ARG | A | 362 | −4.983 | −0.143 | −34.331 | 1.00 | 23.25 | A | C |
| ATOM | 1928 | CD | ARG | A | 362 | −3.651 | 0.649 | −34.315 | 1.00 | 24.03 | A | C |
| ATOM | 1929 | NE | ARG | A | 362 | −2.526 | −0.130 | −34.833 | 1.00 | 26.50 | A | N |
| ATOM | 1930 | CZ | ARG | A | 362 | −1.794 | −0.996 | −34.121 | 1.00 | 28.92 | A | C |
| ATOM | 1931 | NH1 | ARG | A | 362 | −2.029 | −1.192 | −32.835 | 1.00 | 29.14 | A | N |
| ATOM | 1932 | NH2 | ARG | A | 362 | −0.764 | −1.627 | −34.678 | 1.00 | 29.50 | A | N |
| ATOM | 1933 | C | ARG | A | 362 | −8.425 | 0.713 | −32.686 | 1.00 | 22.47 | A | C |
| ATOM | 1934 | O | ARG | A | 362 | −8.704 | 0.165 | −31.625 | 1.00 | 24.17 | A | O |
| ATOM | 1935 | N | LEU | A | 363 | −8.959 | 1.886 | −33.012 | 1.00 | 21.45 | A | N |
| ATOM | 1936 | CA | LEU | A | 363 | −9.971 | 2.531 | −32.168 | 1.00 | 20.62 | A | C |
| ATOM | 1937 | CB | LEU | A | 363 | −10.209 | 3.967 | −32.625 | 1.00 | 21.45 | A | C |
| ATOM | 1938 | CG | LEU | A | 363 | −9.316 | 5.091 | −32.062 | 1.00 | 26.53 | A | C |
| ATOM | 1939 | CD1 | LEU | A | 363 | −8.923 | 6.123 | −33.122 | 1.00 | 26.54 | A | C |

APPENDIX B-continued

| Atomic coordinates of Aurora A + Activating Monobody Mb54 + AMPPCP | | | | | | | | | | | |
|---|---|---|---|---|---|---|---|---|---|---|---|
| ATOM | 1940 | CD2 | LEU | A | 363 | −8.066 | 4.621 | −31.366 | 1.00 | 30.68 | A C |
| ATOM | 1941 | C | LEU | A | 363 | −11.295 | 1.768 | −32.125 | 1.00 | 19.60 | A C |
| ATOM | 1942 | O | LEU | A | 363 | −11.926 | 1.707 | −31.051 | 1.00 | 18.05 | A O |
| ATOM | 1943 | N | LEU | A | 364 | −11.737 | 1.217 | −33.260 | 1.00 | 18.80 | A N |
| ATOM | 1944 | CA | LEU | A | 364 | −13.051 | 0.563 | −33.339 | 1.00 | 20.85 | A C |
| ATOM | 1945 | CB | LEU | A | 364 | −13.757 | 0.927 | −34.655 | 1.00 | 20.28 | A C |
| ATOM | 1946 | CG | LEU | A | 364 | −13.877 | 2.412 | −34.962 | 1.00 | 21.49 | A C |
| ATOM | 1947 | CD1 | LEU | A | 364 | −14.746 | 2.588 | −36.203 | 1.00 | 21.72 | A C |
| ATOM | 1948 | CD2 | LEU | A | 364 | −14.521 | 3.143 | −33.808 | 1.00 | 19.84 | A C |
| ATOM | 1949 | C | LEU | A | 364 | −13.009 | −0.974 | −33.139 | 1.00 | 22.13 | A C |
| ATOM | 1950 | O | LEU | A | 364 | −13.570 | −1.736 | −33.899 | 1.00 | 25.28 | A O |
| ATOM | 1951 | N | LYS | A | 365 | −12.391 | −1.375 | −32.051 | 1.00 | 25.50 | A N |
| ATOM | 1952 | CA | LYS | A | 365 | −12.404 | −2.747 | −31.565 | 1.00 | 29.46 | A C |
| ATOM | 1953 | CB | LYS | A | 365 | −11.156 | −3.055 | −30.781 | 1.00 | 29.35 | A C |
| ATOM | 1954 | CG | LYS | A | 365 | −9.883 | −2.647 | −31.493 | 1.00 | 32.73 | A C |
| ATOM | 1955 | CD | LYS | A | 365 | −9.051 | −3.802 | −31.953 | 1.00 | 34.45 | A C |
| ATOM | 1956 | CE | LYS | A | 365 | −9.713 | −4.594 | −33.018 | 1.00 | 35.01 | A C |
| ATOM | 1957 | NZ | LYS | A | 365 | −8.625 | −5.265 | −33.788 | 1.00 | 36.67 | A N |
| ATOM | 1958 | C | LYS | A | 365 | −13.521 | −2.945 | −30.613 | 1.00 | 27.89 | A C |
| ATOM | 1959 | O | LYS | A | 365 | −13.730 | −2.151 | −29.678 | 1.00 | 26.30 | A O |
| ATOM | 1960 | N | HIS | A | 366 | −14.191 | −4.062 | −30.811 | 1.00 | 29.99 | A N |
| ATOM | 1961 | CA | HIS | A | 366 | −15.288 | −4.470 | −29.933 | 1.00 | 28.57 | A C |
| ATOM | 1962 | CB | HIS | A | 366 | −15.804 | −5.860 | −30.342 | 1.00 | 27.29 | A C |
| ATOM | 1963 | CG | HIS | A | 366 | −17.077 | −6.217 | −29.663 | 1.00 | 29.01 | A C |
| ATOM | 1964 | ND1 | HIS | A | 366 | −17.126 | −6.984 | −28.515 | 1.00 | 29.74 | A N |
| ATOM | 1965 | CE1 | HIS | A | 366 | −18.386 | −7.077 | −28.118 | 1.00 | 28.73 | A C |
| ATOM | 1966 | NE2 | HIS | A | 366 | −19.139 | −6.381 | −28.953 | 1.00 | 26.88 | A N |
| ATOM | 1967 | CD2 | HIS | A | 366 | −18.348 | −5.835 | −29.925 | 1.00 | 25.60 | A C |
| ATOM | 1968 | C | HIS | A | 366 | −14.846 | −4.496 | −28.463 | 1.00 | 28.54 | A C |
| ATOM | 1969 | O | HIS | A | 366 | −15.575 | −4.060 | −27.565 | 1.00 | 29.19 | A O |
| ATOM | 1970 | N | ASN | A | 367 | −13.643 | −5.017 | −28.234 | 1.00 | 28.60 | A N |
| ATOM | 1971 | CA | ASN | A | 367 | −13.138 | −5.171 | −26.896 | 1.00 | 28.45 | A C |
| ATOM | 1972 | CB | ASN | A | 367 | −12.189 | −6.356 | −26.822 | 1.00 | 29.34 | A C |
| ATOM | 1973 | CG | ASN | A | 367 | −11.638 | −6.599 | −25.414 | 1.00 | 30.66 | A C |
| ATOM | 1974 | OD1 | ASN | A | 367 | −11.740 | −5.788 | −24.495 | 1.00 | 28.74 | A O |
| ATOM | 1975 | ND2 | ASN | A | 367 | −11.006 | −7.727 | −25.265 | 1.00 | 32.92 | A N |
| ATOM | 1976 | C | ASN | A | 367 | −12.443 | −3.892 | −26.450 | 1.00 | 27.11 | A C |
| ATOM | 1977 | O | ASN | A | 367 | −11.317 | −3.572 | −26.906 | 1.00 | 27.91 | A O |
| ATOM | 1978 | N | PRO | A | 368 | −13.041 | −3.209 | −25.485 | 1.00 | 24.90 | A N |
| ATOM | 1979 | CA | PRO | A | 368 | −12.500 | −1.924 | −25.046 | 1.00 | 26.03 | A C |
| ATOM | 1980 | CB | PRO | A | 368 | −13.360 | −1.549 | −23.832 | 1.00 | 26.06 | A C |
| ATOM | 1981 | CG | PRO | A | 368 | −14.578 | −2.384 | −23.949 | 1.00 | 28.47 | A C |
| ATOM | 1982 | CD | PRO | A | 368 | −14.224 | −3.630 | −24.716 | 1.00 | 27.11 | A C |
| ATOM | 1983 | C | PRO | A | 368 | −11.026 | −1.992 | −24.645 | 1.00 | 28.81 | A C |
| ATOM | 1984 | O | PRO | A | 368 | −10.251 | −1.079 | −24.974 | 1.00 | 27.98 | A O |
| ATOM | 1985 | N | SER | A | 369 | −10.645 | −3.068 | −23.952 | 1.00 | 26.05 | A N |
| ATOM | 1986 | CA | SER | A | 369 | −9.301 | −3.193 | −23.459 | 1.00 | 26.64 | A C |
| ATOM | 1987 | CB | SER | A | 369 | −9.191 | −4.417 | −22.538 | 1.00 | 27.63 | A C |
| ATOM | 1988 | OG | SER | A | 369 | −10.195 | −4.325 | −21.513 | 1.00 | 31.03 | A O |
| ATOM | 1989 | C | SER | A | 369 | −8.317 | −3.282 | −24.583 | 1.00 | 25.20 | A C |
| ATOM | 1990 | O | SER | A | 369 | −7.156 | −2.972 | −24.373 | 1.00 | 25.92 | A O |
| ATOM | 1991 | N | GLN | A | 370 | −8.750 | −3.677 | −25.780 | 1.00 | 25.35 | A N |
| ATOM | 1992 | CA | GLN | A | 370 | −7.812 | −3.713 | −26.938 | 1.00 | 30.12 | A C |
| ATOM | 1993 | CB | GLN | A | 370 | −8.245 | −4.699 | −28.009 | 1.00 | 33.59 | A C |
| ATOM | 1994 | CG | GLN | A | 370 | −8.022 | −6.129 | −27.618 | 1.00 | 40.71 | A C |
| ATOM | 1995 | CD | GLN | A | 370 | −8.737 | −7.105 | −28.533 | 1.00 | 48.28 | A C |
| ATOM | 1996 | OE1 | GLN | A | 370 | −9.138 | −6.790 | −29.663 | 1.00 | 49.25 | A O |
| ATOM | 1997 | NE2 | GLN | A | 370 | −8.882 | −8.313 | −28.048 | 1.00 | 55.10 | A N |
| ATOM | 1998 | C | GLN | A | 370 | −7.551 | −2.369 | −27.623 | 1.00 | 28.54 | A C |
| ATOM | 1999 | O | GLN | A | 370 | −6.572 | −2.267 | −28.338 | 1.00 | 30.61 | A O |
| ATOM | 2000 | N | ARG | A | 371 | −8.413 | −1.382 | −27.413 | 1.00 | 23.31 | A N |
| ATOM | 2001 | CA | ARG | A | 371 | −8.225 | −0.013 | −27.913 | 1.00 | 23.05 | A C |
| ATOM | 2002 | CB | ARG | A | 371 | −9.416 | 0.850 | −27.562 | 1.00 | 22.19 | A C |
| ATOM | 2003 | CG | ARG | A | 371 | −10.683 | 0.322 | −28.246 | 1.00 | 22.45 | A C |
| ATOM | 2004 | CD | ARG | A | 371 | −11.957 | 1.010 | −27.750 | 1.00 | 23.22 | A C |
| ATOM | 2005 | NE | ARG | A | 371 | −13.138 | 0.182 | −27.948 | 1.00 | 22.28 | A N |
| ATOM | 2006 | CZ | ARG | A | 371 | −14.236 | 0.236 | −27.195 | 1.00 | 22.89 | A C |
| ATOM | 2007 | NH1 | ARG | A | 371 | −14.315 | 1.096 | −26.238 | 1.00 | 22.44 | A N |
| ATOM | 2008 | NH2 | ARG | A | 371 | −15.256 | −0.597 | −27.397 | 1.00 | 23.06 | A N |
| ATOM | 2009 | C | ARG | A | 371 | −6.975 | 0.613 | −27.327 | 1.00 | 23.64 | A C |
| ATOM | 2010 | O | ARG | A | 371 | −6.618 | 0.352 | −26.190 | 1.00 | 22.29 | A O |
| ATOM | 2011 | N | PRO | A | 372 | −6.282 | 1.441 | −28.124 | 1.00 | 25.90 | A N |
| ATOM | 2012 | CA | PRO | A | 372 | −5.061 | 2.032 | −27.621 | 1.00 | 24.56 | A C |
| ATOM | 2013 | CB | PRO | A | 372 | −4.463 | 2.691 | −28.858 | 1.00 | 23.86 | A C |
| ATOM | 2014 | CG | PRO | A | 372 | −5.610 | 3.009 | −29.687 | 1.00 | 23.59 | A C |
| ATOM | 2015 | CD | PRO | A | 372 | −6.531 | 1.845 | −29.520 | 1.00 | 25.10 | A C |
| ATOM | 2016 | C | PRO | A | 372 | −5.311 | 3.085 | −26.575 | 1.00 | 26.15 | A C |
| ATOM | 2017 | O | PRO | A | 372 | −6.411 | 3.598 | −26.427 | 1.00 | 22.44 | A O |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 2018 | N | MET | A | 373 | −4.255 | 3.397 | −25.848 | 1.00 | 28.57 | A | N |
| ATOM | 2019 | CA | MET | A | 373 | −4.242 | 4.584 | −25.028 | 1.00 | 29.95 | A | C |
| ATOM | 2020 | CB | MET | A | 373 | −3.086 | 4.520 | −24.015 | 1.00 | 32.65 | A | C |
| ATOM | 2021 | CG | MET | A | 373 | −3.338 | 3.552 | −22.860 | 1.00 | 38.51 | A | C |
| ATOM | 2022 | SD | MET | A | 373 | −1.800 | 3.343 | −21.908 | 1.00 | 48.32 | A | S |
| ATOM | 2023 | CE | MET | A | 373 | −2.257 | 2.018 | −20.749 | 1.00 | 55.26 | A | C |
| ATOM | 2024 | C | MET | A | 373 | −4.106 | 5.805 | −25.940 | 1.00 | 25.80 | A | C |
| ATOM | 2025 | O | MET | A | 373 | −3.635 | 5.707 | −27.074 | 1.00 | 24.82 | A | O |
| ATOM | 2026 | N | LEU | A | 374 | −4.490 | 6.960 | −25.420 | 1.00 | 23.63 | A | N |
| ATOM | 2027 | CA | LEU | A | 374 | −4.419 | 8.177 | −26.160 | 1.00 | 23.99 | A | C |
| ATOM | 2028 | CB | LEU | A | 374 | −4.991 | 9.283 | −25.338 | 1.00 | 24.44 | A | C |
| ATOM | 2029 | CG | LEU | A | 374 | −6.446 | 9.744 | −25.368 | 1.00 | 24.98 | A | C |
| ATOM | 2030 | CD1 | LEU | A | 374 | −7.239 | 9.430 | −24.125 | 1.00 | 26.65 | A | C |
| ATOM | 2031 | CD2 | LEU | A | 374 | −7.205 | 9.412 | −26.636 | 1.00 | 25.91 | A | C |
| ATOM | 2032 | C | LEU | A | 374 | −2.965 | 8.476 | −26.527 | 1.00 | 24.38 | A | C |
| ATOM | 2033 | O | LEU | A | 374 | −2.692 | 9.002 | −27.603 | 1.00 | 24.46 | A | O |
| ATOM | 2034 | N | ARG | A | 375 | −2.032 | 8.109 | −25.660 | 1.00 | 26.04 | A | N |
| ATOM | 2035 | CA | ARG | A | 375 | −0.597 | 8.233 | −25.948 | 1.00 | 27.39 | A | C |
| ATOM | 2036 | CB | ARG | A | 375 | 0.188 | 7.639 | −24.769 | 1.00 | 33.47 | A | C |
| ATOM | 2037 | CG | ARG | A | 375 | 1.725 | 7.621 | −24.907 | 1.00 | 42.11 | A | C |
| ATOM | 2038 | CD | ARG | A | 375 | 2.350 | 8.970 | −25.328 | 1.00 | 50.34 | A | C |
| ATOM | 2039 | NE | ARG | A | 375 | 1.729 | 10.105 | −24.611 | 1.00 | 63.62 | A | N |
| ATOM | 2040 | CZ | ARG | A | 375 | 1.614 | 11.372 | −25.043 | 1.00 | 58.68 | A | C |
| ATOM | 2041 | NH1 | ARG | A | 375 | 2.109 | 11.783 | −26.214 | 1.00 | 57.42 | A | N |
| ATOM | 2042 | NH2 | ARG | A | 375 | 0.963 | 12.238 | −24.276 | 1.00 | 60.53 | A | N |
| ATOM | 2043 | C | ARG | A | 375 | −0.220 | 7.561 | −27.265 | 1.00 | 27.35 | A | C |
| ATOM | 2044 | O | ARG | A | 375 | 0.575 | 8.097 | −28.079 | 1.00 | 24.41 | A | O |
| ATOM | 2045 | N | GLU | A | 376 | −0.801 | 6.379 | −27.479 | 1.00 | 24.47 | A | N |
| ATOM | 2046 | CA | GLU | A | 376 | −0.467 | 5.598 | −28.641 | 1.00 | 25.88 | A | C |
| ATOM | 2047 | CB | GLU | A | 376 | −0.873 | 4.125 | −28.444 | 1.00 | 28.96 | A | C |
| ATOM | 2048 | CG | GLU | A | 376 | −0.168 | 3.408 | −27.278 | 1.00 | 35.39 | A | C |
| ATOM | 2049 | CD | GLU | A | 376 | −0.833 | 2.046 | −26.934 | 1.00 | 39.56 | A | C |
| ATOM | 2050 | OE1 | GLU | A | 376 | −0.177 | 1.001 | −27.168 | 1.00 | 47.23 | A | O |
| ATOM | 2051 | OE2 | GLU | A | 376 | −2.023 | 2.016 | −26.491 | 1.00 | 36.91 | A | O |
| ATOM | 2052 | C | GLU | A | 376 | −1.147 | 6.156 | −29.853 | 1.00 | 22.91 | A | C |
| ATOM | 2053 | O | GLU | A | 376 | −0.649 | 6.010 | −30.984 | 1.00 | 21.29 | A | O |
| ATOM | 2054 | N | VAL | A | 377 | −2.338 | 6.724 | −29.656 | 1.00 | 23.43 | A | N |
| ATOM | 2055 | CA | VAL | A | 377 | −2.985 | 7.449 | −30.742 | 1.00 | 23.25 | A | C |
| ATOM | 2056 | CB | VAL | A | 377 | −4.384 | 7.919 | −30.359 | 1.00 | 24.46 | A | C |
| ATOM | 2057 | CG1 | VAL | A | 377 | −4.927 | 8.907 | −31.399 | 1.00 | 22.16 | A | C |
| ATOM | 2058 | CG2 | VAL | A | 377 | −5.299 | 6.705 | −30.197 | 1.00 | 24.32 | A | C |
| ATOM | 2059 | C | VAL | A | 377 | −2.125 | 8.629 | −31.194 | 1.00 | 22.62 | A | C |
| ATOM | 2060 | O | VAL | A | 377 | −1.885 | 8.785 | −32.370 | 1.00 | 25.01 | A | O |
| ATOM | 2061 | N | LEU | A | 378 | −1.620 | 9.407 | −30.247 | 1.00 | 22.83 | A | N |
| ATOM | 2062 | CA | LEU | A | 378 | −0.750 | 10.554 | −30.548 | 1.00 | 24.90 | A | C |
| ATOM | 2063 | CB | LEU | A | 378 | −0.449 | 11.408 | −29.287 | 1.00 | 24.22 | A | C |
| ATOM | 2064 | CG | LEU | A | 378 | −1.679 | 12.182 | −28.772 | 1.00 | 25.36 | A | C |
| ATOM | 2065 | CD1 | LEU | A | 378 | −1.545 | 12.600 | −27.320 | 1.00 | 24.60 | A | C |
| ATOM | 2066 | CD2 | LEU | A | 378 | −1.965 | 13.388 | −29.667 | 1.00 | 23.89 | A | C |
| ATOM | 2067 | C | LEU | A | 378 | 0.535 | 10.140 | −31.219 | 1.00 | 25.37 | A | C |
| ATOM | 2068 | O | LEU | A | 378 | 1.064 | 10.881 | −32.006 | 1.00 | 26.98 | A | O |
| ATOM | 2069 | N | GLU | A | 379 | 1.012 | 8.940 | −30.939 | 1.00 | 27.84 | A | N |
| ATOM | 2070 | CA | GLU | A | 379 | 2.229 | 8.425 | −31.560 | 1.00 | 27.63 | A | C |
| ATOM | 2071 | CB | GLU | A | 379 | 2.995 | 7.592 | −30.535 | 1.00 | 33.77 | A | C |
| ATOM | 2072 | CG | GLU | A | 379 | 3.602 | 8.433 | −29.422 | 1.00 | 39.59 | A | C |
| ATOM | 2073 | CD | GLU | A | 379 | 4.148 | 7.584 | −28.264 | 1.00 | 50.88 | A | C |
| ATOM | 2074 | OE1 | GLU | A | 379 | 4.999 | 8.121 | −27.502 | 1.00 | 59.56 | A | O |
| ATOM | 2075 | OE2 | GLU | A | 379 | 3.733 | 6.391 | −28.097 | 1.00 | 48.74 | A | O |
| ATOM | 2076 | C | GLU | A | 379 | 1.983 | 7.595 | −32.809 | 1.00 | 23.91 | A | C |
| ATOM | 2077 | O | GLU | A | 379 | 2.929 | 7.183 | −33.454 | 1.00 | 24.51 | A | O |
| ATOM | 2078 | N | HIS | A | 380 | 0.751 | 7.355 | −33.184 | 1.00 | 20.49 | A | N |
| ATOM | 2079 | CA | HIS | A | 380 | 0.490 | 6.531 | −34.363 | 1.00 | 21.70 | A | C |
| ATOM | 2080 | CB | HIS | A | 380 | −0.997 | 6.455 | −34.580 | 1.00 | 21.75 | A | C |
| ATOM | 2081 | CG | HIS | A | 380 | −1.398 | 5.430 | −35.563 | 1.00 | 23.89 | A | C |
| ATOM | 2082 | ND1 | HIS | A | 380 | −1.315 | 5.649 | −36.915 | 1.00 | 23.29 | A | N |
| ATOM | 2083 | CE1 | HIS | A | 380 | −1.685 | 4.555 | −37.548 | 1.00 | 22.96 | A | C |
| ATOM | 2084 | NE2 | HIS | A | 380 | −2.016 | 3.646 | −36.651 | 1.00 | 22.19 | A | N |
| ATOM | 2085 | CD2 | HIS | A | 380 | −1.847 | 4.157 | −35.402 | 1.00 | 22.39 | A | C |
| ATOM | 2086 | C | HIS | A | 380 | 1.203 | 7.119 | −35.621 | 1.00 | 23.57 | A | C |
| ATOM | 2087 | O | HIS | A | 380 | 1.266 | 8.343 | −35.795 | 1.00 | 23.31 | A | O |
| ATOM | 2088 | N | PRO | A | 381 | 1.722 | 6.254 | −36.520 | 1.00 | 26.16 | A | N |
| ATOM | 2089 | CA | PRO | A | 381 | 2.522 | 6.847 | −37.595 | 1.00 | 25.75 | A | C |
| ATOM | 2090 | CB | PRO | A | 381 | 3.206 | 5.628 | −38.265 | 1.00 | 25.96 | A | C |
| ATOM | 2091 | CG | PRO | A | 381 | 2.368 | 4.486 | −37.920 | 1.00 | 26.25 | A | C |
| ATOM | 2092 | CD | PRO | A | 381 | 1.734 | 4.770 | −36.586 | 1.00 | 26.53 | A | C |
| ATOM | 2093 | C | PRO | A | 381 | 1.712 | 7.691 | −38.589 | 1.00 | 24.16 | A | C |
| ATOM | 2094 | O | PRO | A | 381 | 2.240 | 8.657 | −39.123 | 1.00 | 24.11 | A | O |
| ATOM | 2095 | N | TRP | A | 382 | 0.459 | 7.335 | −38.833 | 1.00 | 21.68 | A | N |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 2096 | CA | TRP | A | 382 | −0.401 | 8.154 | −39.667 | 1.00 | 21.30 | A | C |
| ATOM | 2097 | CB | TRP | A | 382 | −1.749 | 7.496 | −39.841 | 1.00 | 21.52 | A | C |
| ATOM | 2098 | CG | TRP | A | 382 | −2.619 | 8.213 | −40.742 | 1.00 | 21.15 | A | C |
| ATOM | 2099 | CD1 | TRP | A | 382 | −2.513 | 8.278 | −42.105 | 1.00 | 20.36 | A | C |
| ATOM | 2100 | NE1 | TRP | A | 382 | −3.539 | 9.028 | −42.620 | 1.00 | 20.61 | A | N |
| ATOM | 2101 | CE2 | TRP | A | 382 | −4.331 | 9.452 | −41.578 | 1.00 | 21.05 | A | C |
| ATOM | 2102 | CD2 | TRP | A | 382 | −3.757 | 8.979 | −40.382 | 1.00 | 20.35 | A | C |
| ATOM | 2103 | CE3 | TRP | A | 382 | −4.391 | 9.246 | −39.173 | 1.00 | 21.07 | A | C |
| ATOM | 2104 | CZ3 | TRP | A | 382 | −5.513 | 10.022 | −39.161 | 1.00 | 21.90 | A | C |
| ATOM | 2105 | CH2 | TRP | A | 382 | −6.051 | 10.515 | −40.369 | 1.00 | 22.41 | A | C |
| ATOM | 2106 | CZ2 | TRP | A | 382 | −5.457 | 10.246 | −41.584 | 1.00 | 21.26 | A | C |
| ATOM | 2107 | C | TRP | A | 382 | −0.621 | 9.555 | −39.123 | 1.00 | 22.37 | A | C |
| ATOM | 2108 | O | TRP | A | 382 | −0.605 | 10.549 | −39.914 | 1.00 | 20.74 | A | O |
| ATOM | 2109 | N | ILE | A | 383 | −0.817 | 9.625 | −37.797 | 1.00 | 22.14 | A | N |
| ATOM | 2110 | CA | ILE | A | 383 | −0.969 | 10.879 | −37.064 | 1.00 | 22.35 | A | C |
| ATOM | 2111 | CB | ILE | A | 383 | −1.365 | 10.609 | −35.607 | 1.00 | 24.60 | A | C |
| ATOM | 2112 | CG1 | ILE | A | 383 | −2.806 | 10.107 | −35.556 | 1.00 | 24.43 | A | C |
| ATOM | 2113 | CD1 | ILE | A | 383 | −3.860 | 11.157 | −35.753 | 1.00 | 23.59 | A | C |
| ATOM | 2114 | CG2 | ILE | A | 383 | −1.143 | 11.818 | −34.688 | 1.00 | 24.92 | A | C |
| ATOM | 2115 | C | ILE | A | 383 | 0.311 | 11.713 | −37.158 | 1.00 | 23.21 | A | C |
| ATOM | 2116 | O | ILE | A | 383 | 0.267 | 12.875 | −37.537 | 1.00 | 21.64 | A | O |
| ATOM | 2117 | N | THR | A | 384 | 1.438 | 11.115 | −36.807 | 1.00 | 23.15 | A | N |
| ATOM | 2118 | CA | THR | A | 384 | 2.757 | 11.724 | −36.989 | 1.00 | 24.26 | A | C |
| ATOM | 2119 | CB | THR | A | 384 | 3.803 | 10.641 | −36.697 | 1.00 | 25.31 | A | C |
| ATOM | 2120 | OG1 | THR | A | 384 | 3.670 | 10.280 | −35.323 | 1.00 | 27.88 | A | O |
| ATOM | 2121 | CG2 | THR | A | 384 | 5.211 | 11.121 | −36.952 | 1.00 | 26.12 | A | C |
| ATOM | 2122 | C | THR | A | 384 | 3.007 | 12.314 | −38.397 | 1.00 | 26.88 | A | C |
| ATOM | 2123 | O | THR | A | 384 | 3.622 | 13.367 | −38.560 | 1.00 | 28.45 | A | O |
| ATOM | 2124 | N | ALA | A | 385 | 2.536 | 11.615 | −39.419 | 1.00 | 26.36 | A | N |
| ATOM | 2125 | CA | ALA | A | 385 | 2.855 | 11.970 | −40.764 | 1.00 | 24.99 | A | C |
| ATOM | 2126 | CB | ALA | A | 385 | 2.763 | 10.735 | −41.648 | 1.00 | 24.80 | A | C |
| ATOM | 2127 | C | ALA | A | 385 | 1.976 | 13.082 | −41.317 | 1.00 | 25.18 | A | C |
| ATOM | 2128 | O | ALA | A | 385 | 2.270 | 13.599 | −42.380 | 1.00 | 24.20 | A | O |
| ATOM | 2129 | N | ASN | A | 386 | 0.871 | 13.371 | −40.646 | 1.00 | 25.51 | A | N |
| ATOM | 2130 | CA | ASN | A | 386 | −0.170 | 14.243 | −41.198 | 1.00 | 26.94 | A | C |
| ATOM | 2131 | CB | ASN | A | 386 | −1.393 | 13.408 | −41.541 | 1.00 | 26.11 | A | C |
| ATOM | 2132 | CG | ASN | A | 386 | −1.155 | 12.493 | −42.743 | 1.00 | 28.79 | A | C |
| ATOM | 2133 | OD1 | ASN | A | 386 | −0.925 | 12.995 | −43.842 | 1.00 | 32.38 | A | O |
| ATOM | 2134 | ND2 | ASN | A | 386 | −1.224 | 11.155 | −42.552 | 1.00 | 25.11 | A | N |
| ATOM | 2135 | C | ASN | A | 386 | −0.591 | 15.428 | −40.325 | 1.00 | 26.05 | A | C |
| ATOM | 2136 | O | ASN | A | 386 | −1.211 | 16.371 | −40.851 | 1.00 | 26.99 | A | O |
| ATOM | 2137 | N | SER | A | 387 | −0.292 | 15.370 | −39.034 | 1.00 | 24.16 | A | N |
| ATOM | 2138 | CA | SER | A | 387 | −0.634 | 16.429 | −38.118 | 1.00 | 29.06 | A | C |
| ATOM | 2139 | CB | SER | A | 387 | −0.414 | 16.033 | −36.678 | 1.00 | 28.02 | A | C |
| ATOM | 2140 | OG | SER | A | 387 | −1.499 | 15.288 | −36.312 | 1.00 | 33.91 | A | O |
| ATOM | 2141 | C | SER | A | 387 | 0.217 | 17.647 | −38.321 | 1.00 | 30.19 | A | C |
| ATOM | 2142 | O | SER | A | 387 | 1.419 | 17.508 | −38.364 | 1.00 | 24.64 | A | O |
| ATOM | 2143 | N | SER | A | 388 | −0.434 | 18.819 | −38.344 | 1.00 | 36.20 | A | N |
| ATOM | 2144 | CA | SER | A | 388 | 0.240 | 20.144 | −38.405 | 1.00 | 40.84 | A | C |
| ATOM | 2145 | CB | SER | A | 388 | −0.760 | 21.275 | −38.536 | 1.00 | 38.33 | A | C |
| ATOM | 2146 | OG | SER | A | 388 | −1.732 | 20.968 | −39.500 | 1.00 | 45.27 | A | O |
| ATOM | 2147 | C | SER | A | 388 | 1.090 | 20.433 | −37.188 | 1.00 | 45.32 | A | C |
| ATOM | 2148 | O | SER | A | 388 | 0.804 | 19.980 | −36.102 | 1.00 | 46.83 | A | O |
| ATOM | 2149 | N | LYS | A | 389 | 2.047 | 21.320 | −37.388 | 1.00 | 60.82 | A | N |
| ATOM | 2150 | CA | LYS | A | 389 | 3.176 | 21.558 | −36.496 | 1.00 | 73.94 | A | C |
| ATOM | 2151 | CB | LYS | A | 389 | 4.496 | 21.685 | −37.318 | 1.00 | 74.39 | A | C |
| ATOM | 2152 | CG | LYS | A | 389 | 4.570 | 20.896 | −38.656 | 1.00 | 76.42 | A | C |
| ATOM | 2153 | CD | LYS | A | 389 | 3.923 | 21.625 | −39.871 | 1.00 | 74.93 | A | C |
| ATOM | 2154 | CE | LYS | A | 389 | 3.047 | 20.783 | −40.824 | 1.00 | 73.30 | A | C |
| ATOM | 2155 | NZ | LYS | A | 389 | 2.829 | 19.352 | −40.464 | 1.00 | 76.49 | A | N |
| ATOM | 2156 | C | LYS | A | 389 | 2.827 | 22.881 | −35.754 | 1.00 | 83.33 | A | C |
| ATOM | 2157 | O | LYS | A | 389 | 2.708 | 23.918 | −36.411 | 1.00 | 101.15 | A | O |
| ATOM | 2158 | N | PRO | A | 390 | 2.643 | 22.856 | −34.405 | 1.00 | 93.22 | A | N |
| ATOM | 2159 | CA | PRO | A | 390 | 2.001 | 23.982 | −33.664 | 1.00 | 97.20 | A | C |
| ATOM | 2160 | CB | PRO | A | 390 | 2.359 | 23.684 | −32.192 | 1.00 | 98.32 | A | C |
| ATOM | 2161 | CG | PRO | A | 390 | 3.456 | 22.656 | −32.233 | 1.00 | 96.33 | A | C |
| ATOM | 2162 | CD | PRO | A | 390 | 3.169 | 21.845 | −33.463 | 1.00 | 95.95 | A | C |
| ATOM | 2163 | C | PRO | A | 390 | 2.433 | 25.420 | −34.039 | 1.00 | 97.78 | A | C |
| ATOM | 2164 | O | PRO | A | 390 | 3.616 | 25.770 | −33.939 | 1.00 | 103.98 | A | O |
| TER | 2165 | | PRO | A | 390 | | | | | | | |
| ATOM | 2166 | N | LYS | B | 9 | −27.640 | 12.134 | 3.291 | 1.00 | 75.11 | B | N |
| ATOM | 2167 | CA | LYS | B | 9 | −26.818 | 11.411 | 4.331 | 1.00 | 77.38 | B | C |
| ATOM | 2168 | CB | LYS | B | 9 | −27.582 | 10.183 | 4.867 | 1.00 | 77.62 | B | C |
| ATOM | 2169 | CG | LYS | B | 9 | −27.010 | 9.642 | 6.157 | 1.00 | 76.50 | B | C |
| ATOM | 2170 | CD | LYS | B | 9 | −27.985 | 8.752 | 6.879 | 1.00 | 77.06 | B | C |
| ATOM | 2171 | CE | LYS | B | 9 | −27.334 | 8.220 | 8.146 | 1.00 | 72.63 | B | C |
| ATOM | 2172 | NZ | LYS | B | 9 | −28.363 | 7.998 | 9.195 | 1.00 | 68.63 | B | N |
| ATOM | 2173 | C | LYS | B | 9 | −25.368 | 11.010 | 3.893 | 1.00 | 67.96 | B | C |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 2174 | O | LYS | B | 9 | −25.053 | 10.858 | 2.691 | 1.00 | 56.98 | B | O |
| ATOM | 2175 | N | LEU | B | 10 | −24.489 | 10.901 | 4.901 | 1.00 | 60.45 | B | N |
| ATOM | 2176 | CA | LEU | B | 10 | −23.065 | 10.577 | 4.721 | 1.00 | 52.08 | B | C |
| ATOM | 2177 | CB | LEU | B | 10 | −22.195 | 11.481 | 5.584 | 1.00 | 47.80 | B | C |
| ATOM | 2178 | CG | LEU | B | 10 | −20.677 | 11.361 | 5.556 | 1.00 | 49.57 | B | C |
| ATOM | 2179 | CD1 | LEU | B | 10 | −20.080 | 11.402 | 4.166 | 1.00 | 52.07 | B | C |
| ATOM | 2180 | CD2 | LEU | B | 10 | −20.084 | 12.498 | 6.371 | 1.00 | 49.64 | B | C |
| ATOM | 2181 | C | LEU | B | 10 | −22.900 | 9.150 | 5.144 | 1.00 | 49.78 | B | C |
| ATOM | 2182 | O | LEU | B | 10 | −23.537 | 8.738 | 6.138 | 1.00 | 50.87 | B | O |
| ATOM | 2183 | N | GLU | B | 11 | −22.108 | 8.386 | 4.378 | 1.00 | 45.19 | B | N |
| ATOM | 2184 | CA | GLU | B | 11 | −21.868 | 6.973 | 4.692 | 1.00 | 45.56 | B | C |
| ATOM | 2185 | CB | GLU | B | 11 | −22.839 | 6.078 | 3.916 | 1.00 | 50.52 | B | C |
| ATOM | 2186 | CG | GLU | B | 11 | −22.338 | 5.475 | 2.611 | 1.00 | 57.25 | B | C |
| ATOM | 2187 | CD | GLU | B | 11 | −23.437 | 4.717 | 1.870 | 1.00 | 63.10 | B | C |
| ATOM | 2188 | OE1 | GLU | B | 11 | −24.590 | 4.638 | 2.377 | 1.00 | 60.51 | B | O |
| ATOM | 2189 | OE2 | GLU | B | 11 | −23.144 | 4.197 | 0.770 | 1.00 | 64.07 | B | O |
| ATOM | 2190 | C | GLU | B | 11 | −20.422 | 6.552 | 4.489 | 1.00 | 41.35 | B | C |
| ATOM | 2191 | O | GLU | B | 11 | −19.743 | 7.087 | 3.615 | 1.00 | 33.93 | B | O |
| ATOM | 2192 | N | VAL | B | 12 | −19.949 | 5.631 | 5.342 | 1.00 | 41.43 | B | N |
| ATOM | 2193 | CA | VAL | B | 12 | −18.600 | 5.027 | 5.212 | 1.00 | 46.45 | B | C |
| ATOM | 2194 | CB | VAL | B | 12 | −17.883 | 4.873 | 6.582 | 1.00 | 52.81 | B | C |
| ATOM | 2195 | CG1 | VAL | B | 12 | −16.457 | 4.341 | 6.418 | 1.00 | 53.29 | B | C |
| ATOM | 2196 | CG2 | VAL | B | 12 | −17.841 | 6.215 | 7.301 | 1.00 | 52.52 | B | C |
| ATOM | 2197 | C | VAL | B | 12 | −18.726 | 3.679 | 4.467 | 1.00 | 44.25 | B | C |
| ATOM | 2198 | O | VAL | B | 12 | −19.393 | 2.784 | 4.909 | 1.00 | 35.57 | B | O |
| ATOM | 2199 | N | VAL | B | 13 | −18.087 | 3.595 | 3.312 | 1.00 | 45.62 | B | N |
| ATOM | 2200 | CA | VAL | B | 13 | −18.311 | 2.541 | 2.337 | 1.00 | 53.08 | B | C |
| ATOM | 2201 | CB | VAL | B | 13 | −18.059 | 3.094 | 0.880 | 1.00 | 62.14 | B | C |
| ATOM | 2202 | CG1 | VAL | B | 13 | −17.808 | 1.994 | −0.152 | 1.00 | 63.87 | B | C |
| ATOM | 2203 | CG2 | VAL | B | 13 | −19.223 | 3.993 | 0.431 | 1.00 | 62.10 | B | C |
| ATOM | 2204 | C | VAL | B | 13 | −17.394 | 1.386 | 2.680 | 1.00 | 48.70 | B | C |
| ATOM | 2205 | O | VAL | B | 13 | −17.725 | 0.233 | 2.465 | 1.00 | 52.25 | B | O |
| ATOM | 2206 | N | ALA | B | 14 | −16.242 | 1.712 | 3.229 | 1.00 | 47.10 | B | N |
| ATOM | 2207 | CA | ALA | B | 14 | −15.164 | 0.772 | 3.363 | 1.00 | 46.97 | B | C |
| ATOM | 2208 | CB | ALA | B | 14 | −14.496 | 0.515 | 2.019 | 1.00 | 49.54 | B | C |
| ATOM | 2209 | C | ALA | B | 14 | −14.191 | 1.430 | 4.258 | 1.00 | 47.57 | B | C |
| ATOM | 2210 | O | ALA | B | 14 | −14.035 | 2.638 | 4.216 | 1.00 | 51.68 | B | O |
| ATOM | 2211 | N | ALA | B | 15 | −13.523 | 0.634 | 5.060 | 1.00 | 53.27 | B | N |
| ATOM | 2212 | CA | ALA | B | 15 | −12.620 | 1.142 | 6.083 | 1.00 | 57.61 | B | C |
| ATOM | 2213 | CB | ALA | B | 15 | −13.320 | 1.170 | 7.442 | 1.00 | 56.09 | B | C |
| ATOM | 2214 | C | ALA | B | 15 | −11.438 | 0.210 | 6.125 | 1.00 | 58.11 | B | C |
| ATOM | 2215 | O | ALA | B | 15 | −11.594 | −0.967 | 5.863 | 1.00 | 68.89 | B | O |
| ATOM | 2216 | N | THR | B | 16 | −10.255 | 0.738 | 6.410 | 1.00 | 58.78 | B | N |
| ATOM | 2217 | CA | THR | B | 16 | −9.098 | −0.072 | 6.793 | 1.00 | 56.74 | B | C |
| ATOM | 2218 | CB | THR | B | 16 | −7.931 | −0.079 | 5.733 | 1.00 | 54.25 | B | C |
| ATOM | 2219 | OG1 | THR | B | 16 | −7.094 | 1.066 | 5.926 | 1.00 | 53.79 | B | O |
| ATOM | 2220 | CG2 | THR | B | 16 | −8.452 | −0.171 | 4.226 | 1.00 | 48.31 | B | C |
| ATOM | 2221 | C | THR | B | 16 | −8.699 | 0.448 | 8.195 | 1.00 | 56.88 | B | C |
| ATOM | 2222 | O | THR | B | 16 | −9.435 | 1.248 | 8.805 | 1.00 | 46.55 | B | O |
| ATOM | 2223 | N | PRO | B | 17 | −7.610 | −0.085 | 8.760 | 1.00 | 61.73 | B | N |
| ATOM | 2224 | CA | PRO | B | 17 | −7.204 | 0.492 | 10.060 | 1.00 | 64.68 | B | C |
| ATOM | 2225 | CB | PRO | B | 17 | −6.076 | −0.452 | 10.516 | 1.00 | 66.94 | B | C |
| ATOM | 2226 | CG | PRO | B | 17 | −6.457 | −1.778 | 9.896 | 1.00 | 64.67 | B | C |
| ATOM | 2227 | CD | PRO | B | 17 | −7.108 | −1.466 | 8.577 | 1.00 | 59.33 | B | C |
| ATOM | 2228 | C | PRO | B | 17 | −6.744 | 1.960 | 9.990 | 1.00 | 59.45 | B | C |
| ATOM | 2229 | O | PRO | B | 17 | −6.949 | 2.716 | 10.953 | 1.00 | 57.09 | B | O |
| ATOM | 2230 | N | THR | B | 18 | −6.156 | 2.355 | 8.855 | 1.00 | 61.86 | B | N |
| ATOM | 2231 | CA | THR | B | 18 | −5.676 | 3.734 | 8.631 | 1.00 | 57.04 | B | C |
| ATOM | 2232 | CB | THR | B | 18 | −4.211 | 3.726 | 8.122 | 1.00 | 58.70 | B | C |
| ATOM | 2233 | OG1 | THR | B | 18 | −4.077 | 2.753 | 7.073 | 1.00 | 59.24 | B | O |
| ATOM | 2234 | CG2 | THR | B | 18 | −3.249 | 3.402 | 9.263 | 1.00 | 62.13 | B | C |
| ATOM | 2235 | C | THR | B | 18 | −6.521 | 4.607 | 7.670 | 1.00 | 53.10 | B | C |
| ATOM | 2236 | O | THR | B | 18 | −6.255 | 5.808 | 7.576 | 1.00 | 54.42 | B | O |
| ATOM | 2237 | N | SER | B | 19 | −7.524 | 4.048 | 6.985 | 1.00 | 46.54 | B | N |
| ATOM | 2238 | CA | SER | B | 19 | −8.258 | 4.774 | 5.919 | 1.00 | 46.75 | B | C |
| ATOM | 2239 | CB | SER | B | 19 | −7.663 | 4.415 | 4.555 | 1.00 | 42.06 | B | C |
| ATOM | 2240 | OG | SER | B | 19 | −8.290 | 3.251 | 4.053 | 1.00 | 39.57 | B | O |
| ATOM | 2241 | C | SER | B | 19 | −9.792 | 4.518 | 5.859 | 1.00 | 47.30 | B | C |
| ATOM | 2242 | O | SER | B | 19 | −10.234 | 3.397 | 6.098 | 1.00 | 46.02 | B | O |
| ATOM | 2243 | N | LEU | B | 20 | −10.575 | 5.545 | 5.490 | 1.00 | 43.49 | B | N |
| ATOM | 2244 | CA | LEU | B | 20 | −12.017 | 5.403 | 5.214 | 1.00 | 42.84 | B | C |
| ATOM | 2245 | CB | LEU | B | 20 | −12.851 | 6.194 | 6.219 | 1.00 | 42.43 | B | C |
| ATOM | 2246 | CG | LEU | B | 20 | −12.612 | 5.900 | 7.700 | 1.00 | 47.78 | B | C |
| ATOM | 2247 | CD1 | LEU | B | 20 | −13.387 | 6.870 | 8.582 | 1.00 | 51.15 | B | C |
| ATOM | 2248 | CD2 | LEU | B | 20 | −12.993 | 4.464 | 8.045 | 1.00 | 52.49 | B | C |
| ATOM | 2249 | C | LEU | B | 20 | −12.379 | 5.883 | 3.807 | 1.00 | 42.83 | B | C |
| ATOM | 2250 | O | LEU | B | 20 | −11.919 | 6.919 | 3.367 | 1.00 | 49.84 | B | O |
| ATOM | 2251 | N | LEU | B | 21 | −13.213 | 5.122 | 3.125 | 1.00 | 40.09 | B | N |

APPENDIX B-continued

| Atomic coordinates of Aurora A + Activating Monobody Mb54 + AMPPCP | | | | | | | | | | | |
|---|---|---|---|---|---|---|---|---|---|---|---|
| ATOM | 2252 | CA | LEU | B | 21 | −13.803 | 5.528 | 1.889 | 1.00 | 38.80 | B | C |
| ATOM | 2253 | CB | LEU | B | 21 | −13.890 | 4.345 | 0.924 | 1.00 | 37.49 | B | C |
| ATOM | 2254 | CG | LEU | B | 21 | −14.662 | 4.591 | −0.380 | 1.00 | 39.18 | B | C |
| ATOM | 2255 | CD1 | LEU | B | 21 | −14.029 | 5.748 | −1.143 | 1.00 | 39.69 | B | C |
| ATOM | 2256 | CD2 | LEU | B | 21 | −14.757 | 3.339 | −1.254 | 1.00 | 37.63 | B | C |
| ATOM | 2257 | C | LEU | B | 21 | −15.184 | 6.011 | 2.279 | 1.00 | 39.17 | B | C |
| ATOM | 2258 | O | LEU | B | 21 | −15.973 | 5.235 | 2.787 | 1.00 | 45.15 | B | O |
| ATOM | 2259 | N | ILE | B | 22 | −15.457 | 7.296 | 2.078 | 1.00 | 40.48 | B | N |
| ATOM | 2260 | CA | ILE | B | 22 | −16.772 | 7.897 | 2.375 | 1.00 | 38.37 | B | C |
| ATOM | 2261 | CB | ILE | B | 22 | −16.642 | 9.131 | 3.270 | 1.00 | 40.15 | B | C |
| ATOM | 2262 | CG1 | ILE | B | 22 | −15.827 | 10.223 | 2.579 | 1.00 | 39.36 | B | C |
| ATOM | 2263 | CD1 | ILE | B | 22 | −15.896 | 11.537 | 3.309 | 1.00 | 40.61 | B | C |
| ATOM | 2264 | CG2 | ILE | B | 22 | −15.982 | 8.763 | 4.603 | 1.00 | 42.66 | B | C |
| ATOM | 2265 | C | ILE | B | 22 | −17.532 | 8.322 | 1.104 | 1.00 | 37.12 | B | C |
| ATOM | 2266 | O | ILE | B | 22 | −16.953 | 8.493 | 0.055 | 1.00 | 30.64 | B | O |
| ATOM | 2267 | N | SER | B | 23 | −18.830 | 8.524 | 1.246 | 1.00 | 37.19 | B | N |
| ATOM | 2268 | CA | SER | B | 23 | −19.705 | 8.726 | 0.110 | 1.00 | 38.64 | B | C |
| ATOM | 2269 | CB | SER | B | 23 | −20.256 | 7.414 | −0.423 | 1.00 | 37.18 | B | C |
| ATOM | 2270 | OG | SER | B | 23 | −21.330 | 7.712 | −1.321 | 1.00 | 42.30 | B | O |
| ATOM | 2271 | C | SER | B | 23 | −20.876 | 9.571 | 0.554 | 1.00 | 39.62 | B | C |
| ATOM | 2272 | O | SER | B | 23 | −21.500 | 9.290 | 1.606 | 1.00 | 34.42 | B | O |
| ATOM | 2273 | N | TRP | B | 24 | −21.167 | 10.580 | −0.270 | 1.00 | 37.60 | B | N |
| ATOM | 2274 | CA | TRP | B | 24 | −22.256 | 11.504 | −0.033 | 1.00 | 36.00 | B | C |
| ATOM | 2275 | CB | TRP | B | 24 | −21.687 | 12.864 | 0.336 | 1.00 | 33.97 | B | C |
| ATOM | 2276 | CG | TRP | B | 24 | −20.775 | 13.415 | −0.667 | 1.00 | 33.15 | B | C |
| ATOM | 2277 | CD1 | TRP | B | 24 | −21.143 | 14.039 | −1.826 | 1.00 | 33.62 | B | C |
| ATOM | 2278 | NE1 | TRP | B | 24 | −20.022 | 14.391 | −2.545 | 1.00 | 33.86 | B | N |
| ATOM | 2279 | CE2 | TRP | B | 24 | −18.905 | 13.998 | −1.865 | 1.00 | 29.90 | B | C |
| ATOM | 2280 | CD2 | TRP | B | 24 | −19.338 | 13.378 | −0.668 | 1.00 | 29.17 | B | C |
| ATOM | 2281 | CE3 | TRP | B | 24 | −18.388 | 12.889 | 0.207 | 1.00 | 27.57 | B | C |
| ATOM | 2282 | CZ3 | TRP | B | 24 | −17.061 | 13.041 | −0.109 | 1.00 | 26.85 | B | C |
| ATOM | 2283 | CH2 | TRP | B | 24 | −16.661 | 13.660 | −1.300 | 1.00 | 29.46 | B | C |
| ATOM | 2284 | CZ2 | TRP | B | 24 | −17.577 | 14.159 | −2.182 | 1.00 | 29.19 | B | C |
| ATOM | 2285 | C | TRP | B | 24 | −23.266 | 11.556 | −1.181 | 1.00 | 39.03 | B | C |
| ATOM | 2286 | O | TRP | B | 24 | −24.071 | 12.458 | −1.231 | 1.00 | 44.05 | B | O |
| ATOM | 2287 | N | ASP | B | 25 | −23.238 | 10.533 | −2.040 | 1.00 | 45.75 | B | N |
| ATOM | 2288 | CA | AASP | B | 25 | −24.260 | 10.287 | −3.089 | 0.50 | 49.38 | B | C |
| ATOM | 2289 | CA | BASP | B | 25 | −24.246 | 10.301 | −3.103 | 0.50 | 47.55 | B | C |
| ATOM | 2290 | CB | AASP | B | 25 | −24.253 | 8.809 | −3.566 | 0.50 | 49.18 | B | C |
| ATOM | 2291 | CB | BASP | B | 25 | −24.122 | 8.838 | −3.654 | 0.50 | 44.99 | B | C |
| ATOM | 2292 | CG | AASP | B | 25 | −22.944 | 8.395 | −4.190 | 0.50 | 48.91 | B | C |
| ATOM | 2293 | CG | BASP | B | 25 | −25.130 | 8.510 | −4.773 | 0.50 | 42.76 | B | C |
| ATOM | 2294 | OD1 | AASP | B | 25 | −22.029 | 9.231 | −4.221 | 0.50 | 49.35 | B | O |
| ATOM | 2295 | OD1 | BASP | B | 25 | −26.327 | 8.324 | −4.480 | 0.50 | 39.98 | B | O |
| ATOM | 2296 | OD2 | AASP | B | 25 | −22.826 | 7.230 | −4.626 | 0.50 | 50.82 | B | O |
| ATOM | 2297 | OD2 | BASP | B | 25 | −24.719 | 8.405 | −5.948 | 0.50 | 42.88 | B | O |
| ATOM | 2298 | C | ASP | B | 25 | −25.679 | 10.597 | −2.633 | 1.00 | 47.29 | B | C |
| ATOM | 2299 | O | ASP | B | 25 | −26.493 | 11.102 | −3.417 | 1.00 | 53.33 | B | O |
| ATOM | 2300 | N | ALA | B | 26 | −25.981 | 10.269 | −1.376 | 1.00 | 50.36 | B | N |
| ATOM | 2301 | CA | ALA | B | 26 | −27.332 | 10.503 | −0.779 | 1.00 | 54.04 | B | C |
| ATOM | 2302 | CB | ALA | B | 26 | 27.438 | 9.820 | 0.581 | 1.00 | 52.98 | B | C |
| ATOM | 2303 | C | ALA | B | 26 | −27.760 | 11.977 | −0.649 | 1.00 | 53.07 | B | C |
| ATOM | 2304 | O | ALA | B | 26 | −28.947 | 12.265 | −0.748 | 1.00 | 56.80 | B | O |
| ATOM | 2305 | N | GLN | B | 27 | −26.794 | 12.878 | −0.412 | 1.00 | 50.06 | B | N |
| ATOM | 2306 | CA | GLN | B | 27 | −27.037 | 14.314 | −0.266 | 1.00 | 47.50 | B | C |
| ATOM | 2307 | CB | GLN | B | 27 | −25.744 | 15.032 | 0.133 | 1.00 | 44.06 | B | C |
| ATOM | 2308 | CG | GLN | B | 27 | −25.868 | 16.527 | 0.365 | 1.00 | 40.98 | B | C |
| ATOM | 2309 | CD | GLN | B | 27 | −24.549 | 17.149 | 0.847 | 1.00 | 42.48 | B | C |
| ATOM | 2310 | OE1 | GLN | B | 27 | −23.445 | 16.790 | 0.412 | 1.00 | 44.22 | B | O |
| ATOM | 2311 | NE2 | GLN | B | 27 | −24.661 | 18.068 | 1.763 | 1.00 | 38.92 | B | N |
| ATOM | 2312 | C | GLN | B | 27 | −27.569 | 14.879 | −1.572 | 1.00 | 48.61 | B | C |
| ATOM | 2313 | O | GLN | B | 27 | −27.063 | 14.548 | −2.665 | 1.00 | 57.53 | B | O |
| ATOM | 2314 | N | THR | B | 28 | −28.590 | 15.721 | −1.439 | 1.00 | 45.95 | B | N |
| ATOM | 2315 | CA | THR | B | 28 | −29.312 | 16.339 | −2.572 | 1.00 | 49.27 | B | C |
| ATOM | 2316 | CB | THR | B | 28 | −30.806 | 15.923 | −2.565 | 1.00 | 47.06 | B | C |
| ATOM | 2317 | OG1 | THR | B | 28 | −31.427 | 16.395 | −1.374 | 1.00 | 46.12 | B | O |
| ATOM | 2318 | CG2 | THR | B | 28 | −30.953 | 14.386 | −2.608 | 1.00 | 46.20 | B | C |
| ATOM | 2319 | C | THR | B | 28 | −29.180 | 17.865 | −2.501 | 1.00 | 47.44 | B | C |
| ATOM | 2320 | O | THR | B | 28 | −28.896 | 18.401 | −1.454 | 1.00 | 51.18 | B | O |
| ATOM | 2321 | N | TYR | B | 29 | −29.356 | 18.570 | −3.612 | 1.00 | 48.28 | B | N |
| ATOM | 2322 | CA | TYR | B | 29 | −29.107 | 20.029 | −3.644 | 1.00 | 44.79 | B | C |
| ATOM | 2323 | CB | TYR | B | 29 | −27.865 | 20.306 | −4.501 | 1.00 | 46.00 | B | C |
| ATOM | 2324 | CG | TYR | B | 29 | −26.702 | 19.462 | −4.055 | 1.00 | 46.58 | B | C |
| ATOM | 2325 | CD1 | TYR | B | 29 | −25.934 | 19.847 | −2.944 | 1.00 | 45.87 | B | C |
| ATOM | 2326 | CE1 | TYR | B | 29 | −24.878 | 19.056 | −2.490 | 1.00 | 46.11 | B | C |
| ATOM | 2327 | CZ | TYR | B | 29 | −24.581 | 17.829 | −3.134 | 1.00 | 45.38 | B | C |
| ATOM | 2328 | OH | TYR | B | 29 | −23.533 | 17.070 | −2.627 | 1.00 | 36.82 | B | O |
| ATOM | 2329 | CE2 | TYR | B | 29 | −25.353 | 17.407 | −4.236 | 1.00 | 45.14 | B | C |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 2330 | CD2 | TYR | B | 29 | −26.409 | 18.217 | −4.682 | 1.00 | 46.69 | B | C |
| ATOM | 2331 | C | TYR | B | 29 | −30.354 | 20.689 | −4.190 | 1.00 | 42.85 | B | C |
| ATOM | 2332 | O | TYR | B | 29 | −31.229 | 19.984 | −4.667 | 1.00 | 42.34 | B | O |
| ATOM | 2333 | N | GLN | B | 30 | −30.491 | 22.009 | −4.066 | 1.00 | 44.63 | B | N |
| ATOM | 2334 | CA | GLN | B | 30 | −31.511 | 22.751 | −4.865 | 1.00 | 50.72 | B | C |
| ATOM | 2335 | CB | GLN | B | 30 | −31.697 | 24.159 | −4.303 | 1.00 | 53.06 | B | C |
| ATOM | 2336 | CG | GLN | B | 30 | −33.161 | 24.567 | −4.200 | 1.00 | 61.71 | B | C |
| ATOM | 2337 | CD | GLN | B | 30 | −33.342 | 25.925 | −3.550 | 1.00 | 67.22 | B | C |
| ATOM | 2338 | OE1 | GLN | B | 30 | −32.468 | 26.421 | −2.826 | 1.00 | 77.20 | B | O |
| ATOM | 2339 | NE2 | GLN | B | 30 | −34.477 | 26.541 | −3.812 | 1.00 | 73.21 | B | N |
| ATOM | 2340 | C | GLN | B | 30 | −30.851 | 22.734 | −6.241 | 1.00 | 46.33 | B | C |
| ATOM | 2341 | O | GLN | B | 30 | −29.757 | 23.252 | −6.346 | 1.00 | 50.99 | B | O |
| ATOM | 2342 | N | MET | B | 31 | −31.448 | 22.243 | −7.330 | 1.00 | 51.45 | B | N |
| ATOM | 2343 | CA | MET | B | 31 | −32.377 | 22.933 | −8.264 | 1.00 | 49.00 | B | C |
| ATOM | 2344 | CB | MET | B | 31 | −33.807 | 23.140 | −7.766 | 1.00 | 55.04 | B | C |
| ATOM | 2345 | CG | MET | B | 31 | −34.832 | 23.206 | −8.930 | 1.00 | 63.87 | B | C |
| ATOM | 2346 | SD | MET | B | 31 | −34.674 | 22.062 | −10.368 | 1.00 | 69.01 | B | S |
| ATOM | 2347 | CE | MET | B | 31 | −36.042 | 22.557 | −11.391 | 1.00 | 61.70 | B | C |
| ATOM | 2348 | C | MET | B | 31 | −31.658 | 24.217 | −8.752 | 1.00 | 40.71 | B | C |
| ATOM | 2349 | O | MET | B | 31 | −31.776 | 25.277 | −8.160 | 1.00 | 34.39 | B | O |
| ATOM | 2350 | N | TYR | B | 32 | −30.799 | 24.058 | −9.766 | 1.00 | 35.20 | B | N |
| ATOM | 2351 | CA | TYR | B | 32 | −29.947 | 25.159 | −10.295 | 1.00 | 31.72 | B | C |
| ATOM | 2352 | CB | TYR | B | 32 | −30.777 | 26.355 | −10.783 | 1.00 | 28.72 | B | C |
| ATOM | 2353 | CG | TYR | B | 32 | −31.856 | 25.915 | −11.753 | 1.00 | 28.31 | B | C |
| ATOM | 2354 | CD1 | TYR | B | 32 | −31.515 | 25.306 | −12.926 | 1.00 | 26.22 | B | C |
| ATOM | 2355 | CE1 | TYR | B | 32 | −32.474 | 24.882 | −13.816 | 1.00 | 28.85 | B | C |
| ATOM | 2356 | CZ | TYR | B | 32 | −33.821 | 25.068 | −13.543 | 1.00 | 28.83 | B | C |
| ATOM | 2357 | OH | TYR | B | 32 | −34.728 | 24.621 | −14.487 | 1.00 | 29.89 | B | O |
| ATOM | 2358 | CE2 | TYR | B | 32 | −34.205 | 25.662 | −12.354 | 1.00 | 26.90 | B | C |
| ATOM | 2359 | CD2 | TYR | B | 32 | −33.223 | 26.065 | −11.459 | 1.00 | 27.79 | B | C |
| ATOM | 2360 | C | TYR | B | 32 | −28.844 | 25.643 | −9.362 | 1.00 | 31.21 | B | C |
| ATOM | 2361 | O | TYR | B | 32 | −28.173 | 26.640 | −9.685 | 1.00 | 28.87 | B | O |
| ATOM | 2362 | N | ASP | B | 33 | −28.628 | 24.965 | −8.225 | 1.00 | 31.86 | B | N |
| ATOM | 2363 | CA | ASP | B | 33 | −27.581 | 25.400 | −7.263 | 1.00 | 34.25 | B | C |
| ATOM | 2364 | CB | ASP | B | 33 | −28.149 | 25.665 | −5.844 | 1.00 | 37.33 | B | C |
| ATOM | 2365 | CG | ASP | B | 33 | −27.101 | 26.251 | −4.901 | 1.00 | 40.23 | B | C |
| ATOM | 2366 | OD1 | ASP | B | 33 | −26.728 | 27.436 | −5.045 | 1.00 | 41.78 | B | O |
| ATOM | 2367 | OD2 | ASP | B | 33 | −26.618 | 25.515 | −4.022 | 1.00 | 42.40 | B | O |
| ATOM | 2368 | C | ASP | B | 33 | −26.458 | 24.340 | −7.271 | 1.00 | 32.97 | B | C |
| ATOM | 2369 | O | ASP | B | 33 | −26.615 | 23.226 | −6.791 | 1.00 | 32.60 | B | O |
| ATOM | 2370 | N | TYR | B | 34 | −25.326 | 24.716 | −7.840 | 1.00 | 32.19 | B | N |
| ATOM | 2371 | CA | TYR | B | 34 | −24.317 | 23.758 | −8.242 | 1.00 | 30.39 | B | C |
| ATOM | 2372 | CB | TYR | B | 34 | −23.978 | 23.956 | −9.718 | 1.00 | 28.13 | B | C |
| ATOM | 2373 | CG | TYR | B | 34 | −25.177 | 23.787 | −10.648 | 1.00 | 29.00 | B | C |
| ATOM | 2374 | CD1 | TYR | B | 34 | −26.199 | 22.880 | −10.368 | 1.00 | 32.42 | B | C |
| ATOM | 2375 | CE1 | TYR | B | 34 | −27.290 | 22.715 | −11.239 | 1.00 | 32.11 | B | C |
| ATOM | 2376 | CZ | TYR | B | 34 | −27.360 | 23.458 | −12.397 | 1.00 | 31.43 | B | C |
| ATOM | 2377 | OH | TYR | B | 34 | −28.451 | 23.322 | −13.247 | 1.00 | 30.51 | B | O |
| ATOM | 2378 | CE2 | TYR | B | 34 | −26.355 | 24.357 | −12.697 | 1.00 | 29.46 | B | C |
| ATOM | 2379 | CD2 | TYR | B | 34 | −25.277 | 24.516 | −11.838 | 1.00 | 29.49 | B | C |
| ATOM | 2380 | C | TYR | B | 34 | −23.112 | 23.912 | −7.362 | 1.00 | 28.69 | B | C |
| ATOM | 2381 | O | TYR | B | 34 | −22.807 | 25.003 | −6.935 | 1.00 | 30.34 | B | O |
| ATOM | 2382 | N | VAL | B | 35 | −22.426 | 22.797 | −7.139 | 1.00 | 27.12 | B | N |
| ATOM | 2383 | CA | VAL | B | 35 | −21.430 | 22.662 | −6.128 | 1.00 | 26.59 | B | C |
| ATOM | 2384 | CB | VAL | B | 35 | −21.383 | 21.224 | −5.536 | 1.00 | 27.91 | B | C |
| ATOM | 2385 | CG1 | VAL | B | 35 | −20.320 | 21.129 | −4.462 | 1.00 | 25.66 | B | C |
| ATOM | 2386 | CG2 | VAL | B | 35 | −22.751 | 20.754 | −5.048 | 1.00 | 26.85 | B | C |
| ATOM | 2387 | C | VAL | B | 35 | −20.112 | 22.865 | −6.777 | 1.00 | 27.69 | B | C |
| ATOM | 2388 | O | VAL | B | 35 | −19.765 | 22.180 | −7.754 | 1.00 | 29.29 | B | O |
| ATOM | 2389 | N | SER | B | 36 | −19.360 | 23.771 | −6.194 | 1.00 | 28.08 | B | N |
| ATOM | 2390 | CA | SER | B | 36 | −18.018 | 24.046 | −6.637 | 1.00 | 29.97 | B | C |
| ATOM | 2391 | CB | SER | B | 36 | −17.619 | 25.447 | −6.170 | 1.00 | 30.50 | B | C |
| ATOM | 2392 | OG | SER | B | 36 | −16.260 | 25.675 | −6.457 | 1.00 | 32.94 | B | O |
| ATOM | 2393 | C | SER | B | 36 | −17.028 | 23.043 | −6.115 | 1.00 | 30.27 | B | C |
| ATOM | 2394 | O | SER | B | 36 | −16.148 | 22.625 | −6.843 | 1.00 | 32.83 | B | O |
| ATOM | 2395 | N | TYR | B | 37 | −17.135 | 22.725 | −4.825 | 1.00 | 32.94 | B | N |
| ATOM | 2396 | CA | TYR | B | 37 | −16.198 | 21.812 | −4.145 | 1.00 | 36.70 | B | C |
| ATOM | 2397 | CB | TYR | B | 37 | −14.800 | 22.440 | −3.944 | 1.00 | 37.40 | B | C |
| ATOM | 2398 | CG | TYR | B | 37 | −14.800 | 23.581 | −2.977 | 1.00 | 42.33 | B | C |
| ATOM | 2399 | CD1 | TYR | B | 37 | −15.372 | 24.798 | −3.321 | 1.00 | 47.28 | B | C |
| ATOM | 2400 | CE1 | TYR | B | 37 | −15.423 | 25.862 | −2.433 | 1.00 | 47.98 | B | C |
| ATOM | 2401 | CZ | TYR | B | 37 | −14.895 | 25.715 | −1.180 | 1.00 | 49.23 | B | C |
| ATOM | 2402 | OH | TYR | B | 37 | −14.951 | 26.778 | −0.338 | 1.00 | 42.88 | B | O |
| ATOM | 2403 | CE2 | TYR | B | 37 | −14.332 | 24.508 | −0.789 | 1.00 | 52.15 | B | C |
| ATOM | 2404 | CD2 | TYR | B | 37 | −14.281 | 23.446 | −1.699 | 1.00 | 50.15 | B | C |
| ATOM | 2405 | C | TYR | B | 37 | −16.766 | 21.381 | −2.801 | 1.00 | 35.71 | B | C |
| ATOM | 2406 | O | TYR | B | 37 | −17.768 | 21.927 | −2.355 | 1.00 | 35.25 | B | O |
| ATOM | 2407 | N | TYR | B | 38 | −16.106 | 20.407 | −2.169 | 1.00 | 36.05 | B | N |

APPENDIX B-continued

Atomic coordinates of Aurora A + Activating Monobody Mb54 + AMPPCP

| | | | | | | | | | | | |
|---|---|---|---|---|---|---|---|---|---|---|---|
| ATOM | 2408 | CA | TYR | B | 38 | −16.483 | 19.887 | −0.845 | 1.00 | 30.17 | B | C |
| ATOM | 2409 | CB | TYR | B | 38 | −16.741 | 18.408 | −0.903 | 1.00 | 27.63 | B | C |
| ATOM | 2410 | CG | TYR | B | 38 | −17.969 | 18.057 | −1.677 | 1.00 | 28.30 | B | C |
| ATOM | 2411 | CD1 | TYR | B | 38 | −17.905 | 17.827 | −3.049 | 1.00 | 26.76 | B | C |
| ATOM | 2412 | CE1 | TYR | B | 38 | −19.039 | 17.513 | −3.768 | 1.00 | 26.98 | B | C |
| ATOM | 2413 | CZ | TYR | B | 38 | −20.281 | 17.432 | −3.117 | 1.00 | 29.35 | B | C |
| ATOM | 2414 | OH | TYR | B | 38 | −21.406 | 17.110 | −3.844 | 1.00 | 28.78 | B | O |
| ATOM | 2415 | CE2 | TYR | B | 38 | −20.366 | 17.663 | −1.760 | 1.00 | 27.79 | B | C |
| ATOM | 2416 | CD2 | TYR | B | 38 | −19.209 | 17.987 | −1.053 | 1.00 | 26.32 | B | C |
| ATOM | 2417 | C | TYR | B | 38 | −15.316 | 20.149 | 0.062 | 1.00 | 31.58 | B | C |
| ATOM | 2418 | O | TYR | B | 38 | −14.133 | 19.957 | −0.340 | 1.00 | 28.44 | B | O |
| ATOM | 2419 | N | ARG | B | 39 | −15.632 | 20.651 | 1.262 | 1.00 | 33.48 | B | N |
| ATOM | 2420 | CA | ARG | B | 39 | −14.655 | 20.690 | 2.357 | 1.00 | 35.82 | B | C |
| ATOM | 2421 | CB | ARG | B | 39 | −14.749 | 21.951 | 3.201 | 1.00 | 41.64 | B | C |
| ATOM | 2422 | CG | ARG | B | 39 | −13.476 | 22.182 | 4.025 | 1.00 | 48.19 | B | C |
| ATOM | 2423 | CD | ARG | B | 39 | −13.427 | 23.583 | 4.599 | 1.00 | 53.23 | B | C |
| ATOM | 2424 | NE | ARG | B | 39 | −14.562 | 23.786 | 5.520 | 1.00 | 57.64 | B | N |
| ATOM | 2425 | CZ | ARG | B | 39 | −15.724 | 24.405 | 5.230 | 1.00 | 62.89 | B | C |
| ATOM | 2426 | NH1 | ARG | B | 39 | −15.994 | 24.932 | 4.005 | 1.00 | 58.37 | B | N |
| ATOM | 2427 | NH2 | ARG | B | 39 | −16.649 | 24.494 | 6.190 | 1.00 | 61.38 | B | N |
| ATOM | 2428 | C | ARG | B | 39 | −14.869 | 19.469 | 3.252 | 1.00 | 35.77 | B | C |
| ATOM | 2429 | O | ARG | B | 39 | −16.008 | 19.241 | 3.813 | 1.00 | 27.17 | B | O |
| ATOM | 2430 | N | ILE | B | 40 | −13.792 | 18.676 | 3.366 | 1.00 | 30.36 | B | N |
| ATOM | 2431 | CA | ILE | B | 40 | −13.893 | 17.432 | 4.101 | 1.00 | 35.43 | B | C |
| ATOM | 2432 | CB | ILE | B | 40 | −13.553 | 16.168 | 3.286 | 1.00 | 36.98 | B | C |
| ATOM | 2433 | CG1 | ILE | B | 40 | −14.401 | 16.116 | 2.012 | 1.00 | 40.12 | B | C |
| ATOM | 2434 | CD1 | ILE | B | 40 | −14.061 | 14.985 | 1.069 | 1.00 | 40.75 | B | C |
| ATOM | 2435 | CG2 | ILE | B | 40 | −13.914 | 14.925 | 4.105 | 1.00 | 36.03 | B | C |
| ATOM | 2436 | C | ILE | B | 40 | −13.049 | 17.511 | 5.347 | 1.00 | 36.09 | B | C |
| ATOM | 2437 | O | ILE | B | 40 | −11.768 | 17.713 | 5.301 | 1.00 | 31.10 | B | O |
| ATOM | 2438 | N | THR | B | 41 | −13.775 | 17.313 | 6.444 | 1.00 | 35.08 | B | N |
| ATOM | 2439 | CA | THR | B | 41 | −13.145 | 17.331 | 7.745 | 1.00 | 43.95 | B | C |
| ATOM | 2440 | CB | THR | B | 41 | −13.501 | 18.606 | 8.475 | 1.00 | 43.22 | B | C |
| ATOM | 2441 | OG1 | THR | B | 41 | −12.426 | 18.838 | 9.364 | 1.00 | 53.83 | B | O |
| ATOM | 2442 | CG2 | THR | B | 41 | −14.822 | 18.477 | 9.232 | 1.00 | 40.27 | B | C |
| ATOM | 2443 | C | THR | B | 41 | −13.320 | 16.115 | 8.689 | 1.00 | 42.94 | B | C |
| ATOM | 2444 | O | THR | B | 41 | −14.369 | 15.453 | 8.734 | 1.00 | 36.44 | B | O |
| ATOM | 2445 | N | TYR | B | 42 | −12.256 | 15.864 | 9.449 | 1.00 | 46.71 | B | N |
| ATOM | 2446 | CA | TYR | B | 42 | −12.111 | 14.646 | 10.250 | 1.00 | 47.48 | B | C |
| ATOM | 2447 | CB | TYR | B | 42 | −11.663 | 13.489 | 9.384 | 1.00 | 43.34 | B | C |
| ATOM | 2448 | CG | TYR | B | 42 | −10.260 | 13.634 | 8.794 | 1.00 | 41.77 | B | C |
| ATOM | 2449 | CD1 | TYR | B | 42 | −10.021 | 14.465 | 7.730 | 1.00 | 42.35 | B | C |
| ATOM | 2450 | CE1 | TYR | B | 42 | −8.766 | 14.564 | 7.163 | 1.00 | 45.43 | B | C |
| ATOM | 2451 | CZ | TYR | B | 42 | −7.727 | 13.835 | 7.655 | 1.00 | 43.78 | B | C |
| ATOM | 2452 | OH | TYR | B | 42 | −6.495 | 13.941 | 7.059 | 1.00 | 39.63 | B | O |
| ATOM | 2453 | CE2 | TYR | B | 42 | −7.937 | 12.999 | 8.722 | 1.00 | 42.53 | B | C |
| ATOM | 2454 | CD2 | TYR | B | 42 | −9.196 | 12.912 | 9.287 | 1.00 | 41.34 | B | C |
| ATOM | 2455 | C | TYR | B | 42 | −11.115 | 14.792 | 11.398 | 1.00 | 51.26 | B | C |
| ATOM | 2456 | O | TYR | B | 42 | −10.008 | 15.313 | 11.218 | 1.00 | 47.06 | B | O |
| ATOM | 2457 | N | GLY | B | 43 | −11.529 | 14.282 | 12.559 | 1.00 | 58.18 | B | N |
| ATOM | 2458 | CA | GLY | B | 43 | −10.716 | 14.270 | 13.777 | 1.00 | 58.77 | B | C |
| ATOM | 2459 | C | GLY | B | 43 | −11.346 | 13.419 | 14.866 | 1.00 | 53.89 | B | C |
| ATOM | 2460 | O | GLY | B | 43 | −12.491 | 12.965 | 14.728 | 1.00 | 50.63 | B | O |
| ATOM | 2461 | N | GLU | B | 44 | −10.599 | 13.264 | 15.958 | 1.00 | 56.20 | B | N |
| ATOM | 2462 | CA | GLU | B | 44 | −10.902 | 12.301 | 17.028 | 1.00 | 56.59 | B | C |
| ATOM | 2463 | CB | GLU | B | 44 | −9.681 | 12.075 | 17.931 | 1.00 | 56.76 | B | C |
| ATOM | 2464 | CG | GLU | B | 44 | −8.428 | 11.582 | 17.220 | 1.00 | 66.43 | B | C |
| ATOM | 2465 | CD | GLU | B | 44 | −7.277 | 11.248 | 18.184 | 1.00 | 69.74 | B | C |
| ATOM | 2466 | OE1 | GLU | B | 44 | −6.184 | 11.838 | 18.008 | 1.00 | 63.66 | B | O |
| ATOM | 2467 | OE2 | GLU | B | 44 | −7.455 | 10.412 | 19.114 | 1.00 | 61.93 | B | O |
| ATOM | 2468 | C | GLU | B | 44 | −12.031 | 12.785 | 17.894 | 1.00 | 48.55 | B | C |
| ATOM | 2469 | O | GLU | B | 44 | −11.793 | 13.613 | 18.745 | 1.00 | 54.81 | B | O |
| ATOM | 2470 | N | THR | B | 45 | −13.235 | 12.245 | 17.709 | 1.00 | 47.09 | B | N |
| ATOM | 2471 | CA | THR | B | 45 | −14.450 | 12.655 | 18.476 | 1.00 | 53.39 | B | C |
| ATOM | 2472 | CB | THR | B | 45 | −15.529 | 11.509 | 18.505 | 1.00 | 51.63 | B | C |
| ATOM | 2473 | OG1 | THR | B | 45 | −15.752 | 10.972 | 17.178 | 1.00 | 50.67 | B | O |
| ATOM | 2474 | CG2 | THR | B | 45 | −16.875 | 11.994 | 19.102 | 1.00 | 46.00 | B | C |
| ATOM | 2475 | C | THR | B | 45 | −14.125 | 13.110 | 19.939 | 1.00 | 55.89 | B | C |
| ATOM | 2476 | O | THR | B | 45 | −13.533 | 12.348 | 20.691 | 1.00 | 53.74 | B | O |
| ATOM | 2477 | N | GLY | B | 46 | −14.469 | 14.349 | 20.317 | 1.00 | 63.93 | B | N |
| ATOM | 2478 | CA | GLY | B | 46 | −14.154 | 14.883 | 21.658 | 1.00 | 68.87 | B | C |
| ATOM | 2479 | C | GLY | B | 46 | −12.685 | 15.241 | 21.934 | 1.00 | 78.79 | B | C |
| ATOM | 2480 | O | GLY | B | 46 | −12.345 | 16.420 | 21.922 | 1.00 | 80.80 | B | O |
| ATOM | 2481 | N | GLY | B | 47 | −11.816 | 14.240 | 22.167 | 1.00 | 84.02 | B | N |
| ATOM | 2482 | CA | GLY | B | 47 | −10.420 | 14.444 | 22.659 | 1.00 | 83.16 | B | C |
| ATOM | 2483 | C | GLY | B | 47 | −9.363 | 14.890 | 21.642 | 1.00 | 90.53 | B | C |
| ATOM | 2484 | O | GLY | B | 47 | −9.107 | 14.179 | 20.669 | 1.00 | 77.09 | B | O |
| ATOM | 2485 | N | ASN | B | 48 | −8.666 | 15.999 | 21.955 | 1.00 | 99.26 | B | N |

APPENDIX B-continued

| Atomic coordinates of Aurora A + Activating Monobody Mb54 + AMPPCP | | | | | | | | | | | | |
|---|---|---|---|---|---|---|---|---|---|---|---|---|
| ATOM | 2486 | CA | ASN | B | 48 | −8.205 | 17.012 | 20.954 | 1.00 | 101.75 | B | C |
| ATOM | 2487 | CB | ASN | B | 48 | −8.448 | 18.420 | 21.522 | 1.00 | 95.13 | B | C |
| ATOM | 2488 | CG | ASN | B | 48 | −9.878 | 18.632 | 21.963 | 1.00 | 93.20 | B | C |
| ATOM | 2489 | OD1 | ASN | B | 48 | −10.131 | 19.115 | 23.065 | 1.00 | 94.12 | B | O |
| ATOM | 2490 | ND2 | ASN | B | 48 | −10.823 | 18.263 | 21.109 | 1.00 | 84.54 | B | N |
| ATOM | 2491 | C | ASN | B | 48 | −6.776 | 17.040 | 20.350 | 1.00 | 108.41 | B | C |
| ATOM | 2492 | O | ASN | B | 48 | −5.773 | 17.138 | 21.066 | 1.00 | 108.80 | B | O |
| ATOM | 2493 | N | SER | B | 49 | −6.740 | 16.979 | 19.011 | 1.00 | 113.12 | B | N |
| ATOM | 2494 | CA | SER | B | 49 | −5.691 | 17.560 | 18.144 | 1.00 | 105.70 | B | C |
| ATOM | 2495 | CB | SER | B | 49 | −4.929 | 16.469 | 17.365 | 1.00 | 103.20 | B | C |
| ATOM | 2496 | OG | SER | B | 49 | −4.599 | 15.359 | 18.181 | 1.00 | 97.09 | B | O |
| ATOM | 2497 | C | SER | B | 49 | −6.446 | 18.500 | 17.181 | 1.00 | 102.32 | B | C |
| ATOM | 2498 | O | SER | B | 49 | −7.671 | 18.638 | 17.304 | 1.00 | 92.17 | B | O |
| ATOM | 2499 | N | PRO | B | 50 | −5.743 | 19.166 | 16.231 | 1.00 | 109.04 | B | N |
| ATOM | 2500 | CA | PRO | B | 50 | −6.556 | 20.009 | 15.336 | 1.00 | 108.06 | B | C |
| ATOM | 2501 | CB | PRO | B | 50 | −5.512 | 20.929 | 14.656 | 1.00 | 110.20 | B | C |
| ATOM | 2502 | CG | PRO | B | 50 | −4.155 | 20.336 | 14.941 | 1.00 | 109.66 | B | C |
| ATOM | 2503 | CD | PRO | B | 50 | −4.328 | 19.109 | 15.800 | 1.00 | 110.36 | B | C |
| ATOM | 2504 | C | PRO | B | 50 | −7.299 | 19.119 | 14.317 | 1.00 | 102.10 | B | C |
| ATOM | 2505 | O | PRO | B | 50 | −6.632 | 18.347 | 13.612 | 1.00 | 109.28 | B | O |
| ATOM | 2506 | N | VAL | B | 51 | −8.643 | 19.182 | 14.264 | 1.00 | 80.31 | B | N |
| ATOM | 2507 | CA | VAL | B | 51 | −9.400 | 18.420 | 13.243 | 1.00 | 69.28 | B | C |
| ATOM | 2508 | CB | VAL | B | 51 | −10.951 | 18.616 | 13.249 | 1.00 | 70.55 | B | C |
| ATOM | 2509 | CG1 | VAL | B | 51 | −11.559 | 18.094 | 14.542 | 1.00 | 73.42 | B | C |
| ATOM | 2510 | CG2 | VAL | B | 51 | −11.373 | 20.055 | 13.001 | 1.00 | 71.39 | B | C |
| ATOM | 2511 | C | VAL | B | 51 | −8.853 | 18.788 | 11.886 | 1.00 | 55.52 | B | C |
| ATOM | 2512 | O | VAL | B | 51 | −8.726 | 19.943 | 11.593 | 1.00 | 58.92 | B | O |
| ATOM | 2513 | N | GLN | B | 52 | −8.459 | 17.798 | 11.099 | 1.00 | 52.97 | B | N |
| ATOM | 2514 | CA | GLN | B | 52 | −7.871 | 18.030 | 9.777 | 1.00 | 52.58 | B | C |
| ATOM | 2515 | CB | GLN | B | 52 | −6.914 | 16.917 | 9.429 | 1.00 | 53.52 | B | C |
| ATOM | 2516 | CG | GLN | B | 52 | −5.661 | 16.969 | 10.249 | 1.00 | 52.51 | B | C |
| ATOM | 2517 | CD | GLN | B | 52 | −5.011 | 15.617 | 10.281 | 1.00 | 53.88 | B | C |
| ATOM | 2518 | OE1 | GLN | B | 52 | −5.536 | 14.685 | 10.897 | 1.00 | 57.47 | B | O |
| ATOM | 2519 | NE2 | GLN | B | 52 | −3.887 | 15.481 | 9.599 | 1.00 | 54.71 | B | N |
| ATOM | 2520 | C | GLN | B | 52 | −8.900 | 18.150 | 8.654 | 1.00 | 48.48 | B | C |
| ATOM | 2521 | O | GLN | B | 52 | −10.045 | 17.713 | 8.790 | 1.00 | 42.54 | B | O |
| ATOM | 2522 | N | GLU | B | 53 | −8.462 | 18.756 | 7.545 | 1.00 | 50.20 | B | N |
| ATOM | 2523 | CA | GLU | B | 53 | −9.333 | 19.000 | 6.385 | 1.00 | 48.46 | B | C |
| ATOM | 2524 | CB | GLU | B | 53 | −10.108 | 20.295 | 6.526 | 1.00 | 47.62 | B | C |
| ATOM | 2525 | CG | GLU | B | 53 | −9.246 | 21.524 | 6.572 | 1.00 | 47.80 | B | C |
| ATOM | 2526 | CD | GLU | B | 53 | −10.068 | 22.793 | 6.671 | 1.00 | 53.34 | B | C |
| ATOM | 2527 | OE1 | GLU | B | 53 | −11.321 | 22.755 | 6.823 | 1.00 | 48.45 | B | O |
| ATOM | 2528 | OE2 | GLU | B | 53 | −9.430 | 23.857 | 6.593 | 1.00 | 63.07 | B | O |
| ATOM | 2529 | C | GLU | B | 53 | −8.646 | 18.999 | 5.046 | 1.00 | 44.09 | B | C |
| ATOM | 2530 | O | GLU | B | 53 | −7.439 | 19.180 | 4.954 | 1.00 | 46.46 | B | O |
| ATOM | 2531 | N | PHE | B | 54 | −9.451 | 18.773 | 4.011 | 1.00 | 45.77 | B | N |
| ATOM | 2532 | CA | PHE | B | 54 | −9.022 | 18.944 | 2.623 | 1.00 | 38.87 | B | C |
| ATOM | 2533 | CB | PHE | B | 54 | −8.210 | 17.739 | 2.142 | 1.00 | 36.41 | B | C |
| ATOM | 2534 | CG | PHE | B | 54 | −9.020 | 16.472 | 2.091 | 1.00 | 44.73 | B | C |
| ATOM | 2535 | CD1 | PHE | B | 54 | −9.416 | 15.825 | 3.273 | 1.00 | 47.78 | B | C |
| ATOM | 2536 | CE1 | PHE | B | 54 | −10.170 | 14.660 | 3.238 | 1.00 | 47.27 | B | C |
| ATOM | 2537 | CZ | PHE | B | 54 | −10.583 | 14.141 | 2.012 | 1.00 | 50.39 | B | C |
| ATOM | 2538 | CE2 | PHE | B | 54 | −10.227 | 14.777 | 0.830 | 1.00 | 45.07 | B | C |
| ATOM | 2539 | CD2 | PHE | B | 54 | −9.461 | 15.942 | 0.869 | 1.00 | 45.95 | B | C |
| ATOM | 2540 | C | PHE | B | 54 | −10.320 | 19.185 | 1.807 | 1.00 | 39.06 | B | C |
| ATOM | 2541 | O | PHE | B | 54 | −11.453 | 19.182 | 2.364 | 1.00 | 33.87 | B | O |
| ATOM | 2542 | N | THR | B | 55 | −10.146 | 19.464 | 0.510 | 1.00 | 37.96 | B | N |
| ATOM | 2543 | CA | THR | B | 55 | −11.264 | 19.763 | −0.387 | 1.00 | 36.63 | B | C |
| ATOM | 2544 | CB | THR | B | 55 | −11.273 | 21.247 | −0.857 | 1.00 | 40.34 | B | C |
| ATOM | 2545 | OG1 | THR | B | 55 | −9.958 | 21.632 | −1.291 | 1.00 | 38.77 | B | O |
| ATOM | 2546 | CG2 | THR | B | 55 | −11.686 | 22.162 | 0.262 | 1.00 | 40.67 | B | C |
| ATOM | 2547 | C | THR | B | 55 | −11.145 | 18.926 | −1.612 | 1.00 | 31.86 | B | C |
| ATOM | 2548 | O | THR | B | 55 | −10.048 | 18.598 | −2.045 | 1.00 | 31.26 | B | O |
| ATOM | 2549 | N | VAL | B | 56 | −12.285 | 18.599 | −2.182 | 1.00 | 30.95 | B | N |
| ATOM | 2550 | CA | VAL | B | 56 | −12.328 | 17.912 | −3.461 | 1.00 | 31.51 | B | C |
| ATOM | 2551 | CB | VAL | B | 56 | −12.845 | 16.474 | −3.357 | 1.00 | 29.18 | B | C |
| ATOM | 2552 | CG1 | VAL | B | 56 | −11.814 | 15.598 | −2.647 | 1.00 | 28.56 | B | C |
| ATOM | 2553 | CG2 | VAL | B | 56 | −14.239 | 16.426 | −2.697 | 1.00 | 28.05 | B | C |
| ATOM | 2554 | C | VAL | B | 56 | −13.271 | 18.677 | −4.382 | 1.00 | 30.91 | B | C |
| ATOM | 2555 | O | VAL | B | 56 | −14.144 | 19.381 | −3.890 | 1.00 | 25.04 | B | O |
| ATOM | 2556 | N | PRO | B | 57 | −13.123 | 18.487 | −5.704 | 1.00 | 30.32 | B | N |
| ATOM | 2557 | CA | PRO | B | 57 | −14.033 | 19.167 | −6.598 | 1.00 | 31.07 | B | C |
| ATOM | 2558 | CB | PRO | B | 57 | −13.463 | 18.834 | −7.985 | 1.00 | 31.31 | B | C |
| ATOM | 2559 | CG | PRO | B | 57 | −12.004 | 18.641 | −7.739 | 1.00 | 30.04 | B | C |
| ATOM | 2560 | CD | PRO | B | 57 | −11.974 | 17.924 | −6.434 | 1.00 | 31.09 | B | C |
| ATOM | 2561 | C | PRO | B | 57 | −15.459 | 18.714 | −6.462 | 1.00 | 29.19 | B | C |
| ATOM | 2562 | O | PRO | B | 57 | −15.734 | 17.579 | −6.084 | 1.00 | 29.67 | B | O |
| ATOM | 2563 | N | GLY | B | 58 | −16.368 | 19.625 | −6.790 | 1.00 | 29.82 | B | N |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 2564 | CA | GLY | B | 58 | −17.807 | 19.427 | −6.618 | 1.00 | 27.98 | B | C |
| ATOM | 2565 | C | GLY | B | 58 | −18.387 | 18.252 | −7.372 | 1.00 | 28.24 | B | C |
| ATOM | 2566 | O | GLY | B | 58 | −19.451 | 17.739 | −7.036 | 1.00 | 29.51 | B | O |
| ATOM | 2567 | N | TYR | B | 59 | −17.714 | 17.833 | −8.429 | 1.00 | 27.51 | B | N |
| ATOM | 2568 | CA | TYR | B | 59 | −18.182 | 16.668 | −9.186 | 1.00 | 26.10 | B | C |
| ATOM | 2569 | CB | TYR | B | 59 | −17.628 | 16.729 | −10.628 | 1.00 | 23.36 | B | C |
| ATOM | 2570 | CG | TYR | B | 59 | −16.104 | 16.787 | −10.796 | 1.00 | 19.98 | B | C |
| ATOM | 2571 | CD1 | TYR | B | 59 | −15.352 | 15.648 | −10.790 | 1.00 | 20.21 | B | C |
| ATOM | 2572 | CE1 | TYR | B | 59 | −13.975 | 15.688 | −10.951 | 1.00 | 20.54 | B | C |
| ATOM | 2573 | CZ | TYR | B | 59 | −13.338 | 16.860 | −11.190 | 1.00 | 18.65 | B | C |
| ATOM | 2574 | OH | TYR | B | 59 | −11.997 | 16.848 | −11.375 | 1.00 | 23.35 | B | O |
| ATOM | 2575 | CE2 | TYR | B | 59 | −14.040 | 18.009 | −11.226 | 1.00 | 20.18 | B | C |
| ATOM | 2576 | CD2 | TYR | B | 59 | −15.454 | 17.956 | −11.038 | 1.00 | 20.50 | B | C |
| ATOM | 2577 | C | TYR | B | 59 | −17.828 | 15.294 | −8.509 | 1.00 | 27.16 | B | C |
| ATOM | 2578 | O | TYR | B | 59 | −18.251 | 14.261 | −8.996 | 1.00 | 25.95 | B | O |
| ATOM | 2579 | N | TYR | B | 60 | −17.003 | 15.286 | −7.454 | 1.00 | 28.00 | B | N |
| ATOM | 2580 | CA | TYR | B | 60 | −16.810 | 14.074 | −6.653 | 1.00 | 27.24 | B | C |
| ATOM | 2581 | CB | TYR | B | 60 | −15.707 | 14.251 | −5.669 | 1.00 | 25.21 | B | C |
| ATOM | 2582 | CG | TYR | B | 60 | −14.317 | 14.077 | −6.208 | 1.00 | 24.73 | B | C |
| ATOM | 2583 | CD1 | TYR | B | 60 | −13.925 | 14.634 | −7.392 | 1.00 | 27.09 | B | C |
| ATOM | 2584 | CE1 | TYR | B | 60 | −12.613 | 14.518 | −7.870 | 1.00 | 26.81 | B | C |
| ATOM | 2585 | CZ | TYR | B | 60 | −11.673 | 13.848 | −7.116 | 1.00 | 28.33 | B | C |
| ATOM | 2586 | OH | TYR | B | 60 | −10.396 | 13.714 | −7.566 | 1.00 | 27.53 | B | O |
| ATOM | 2587 | CE2 | TYR | B | 60 | −12.036 | 13.313 | −5.902 | 1.00 | 26.65 | B | C |
| ATOM | 2588 | CD2 | TYR | B | 60 | −13.360 | 13.429 | −5.464 | 1.00 | 26.35 | B | C |
| ATOM | 2589 | C | TYR | B | 60 | −18.104 | 13.715 | −5.905 | 1.00 | 29.73 | B | C |
| ATOM | 2590 | O | TYR | B | 60 | −18.842 | 14.596 | −5.484 | 1.00 | 31.24 | B | O |
| ATOM | 2591 | N | SER | B | 61 | −18.398 | 12.422 | −5.794 | 1.00 | 29.50 | B | N |
| ATOM | 2592 | CA | SER | B | 61 | −19.443 | 11.961 | −4.902 | 1.00 | 30.81 | B | C |
| ATOM | 2593 | CB | SER | B | 61 | −20.603 | 11.343 | −5.693 | 1.00 | 29.86 | B | C |
| ATOM | 2594 | OG | SER | B | 61 | −20.278 | 10.028 | −6.121 | 1.00 | 33.78 | B | O |
| ATOM | 2595 | C | SER | B | 61 | −18.894 | 11.060 | −3.755 | 1.00 | 30.67 | B | C |
| ATOM | 2596 | O | SER | B | 61 | −19.641 | 10.738 | −2.814 | 1.00 | 30.16 | B | O |
| ATOM | 2597 | N | THR | B | 62 | −17.603 | 10.720 | −3.793 | 1.00 | 30.69 | B | N |
| ATOM | 2598 | CA | THR | B | 62 | −16.926 | 9.960 | −2.736 | 1.00 | 31.84 | B | C |
| ATOM | 2599 | CB | THR | B | 62 | −16.832 | 8.418 | −2.990 | 1.00 | 33.65 | B | C |
| ATOM | 2600 | OG1 | THR | B | 62 | −16.013 | 8.152 | −4.129 | 1.00 | 39.47 | B | O |
| ATOM | 2601 | CG2 | THR | B | 62 | −18.158 | 7.806 | −3.239 | 1.00 | 35.29 | B | C |
| ATOM | 2602 | C | THR | B | 62 | −15.495 | 10.442 | −2.651 | 1.00 | 34.64 | B | C |
| ATOM | 2603 | O | THR | B | 62 | −14.995 | 11.113 | −3.560 | 1.00 | 35.40 | B | O |
| ATOM | 2604 | N | ALA | B | 63 | −14.836 | 10.064 | −1.562 | 1.00 | 33.70 | B | N |
| ATOM | 2605 | CA | ALA | B | 63 | −13.440 | 10.377 | −1.322 | 1.00 | 34.17 | B | C |
| ATOM | 2606 | CB | ALA | B | 63 | −13.319 | 11.803 | −0.820 | 1.00 | 35.17 | B | C |
| ATOM | 2607 | C | ALA | B | 63 | −12.875 | 9.432 | −0.270 | 1.00 | 36.74 | B | C |
| ATOM | 2608 | O | ALA | B | 63 | −13.610 | 8.927 | 0.596 | 1.00 | 39.38 | B | O |
| ATOM | 2609 | N | THR | B | 64 | −11.568 | 9.231 | −0.341 | 1.00 | 37.96 | B | N |
| ATOM | 2610 | CA | THR | B | 64 | −10.807 | 8.464 | 0.633 | 1.00 | 40.46 | B | C |
| ATOM | 2611 | CB | THR | B | 64 | −9.693 | 7.675 | −0.059 | 1.00 | 39.49 | B | C |
| ATOM | 2612 | OG1 | THR | B | 64 | −10.291 | 6.810 | −1.015 | 1.00 | 40.96 | B | O |
| ATOM | 2613 | CG2 | THR | B | 64 | −8.853 | 6.846 | 0.973 | 1.00 | 41.76 | B | C |
| ATOM | 2614 | C | THR | B | 64 | −10.115 | 9.351 | 1.651 | 1.00 | 40.20 | B | C |
| ATOM | 2615 | O | THR | B | 64 | −9.467 | 10.278 | 1.272 | 1.00 | 48.03 | B | O |
| ATOM | 2616 | N | ILE | B | 65 | −10.213 | 9.039 | 2.938 | 1.00 | 43.48 | B | N |
| ATOM | 2617 | CA | ILE | B | 65 | −9.377 | 9.689 | 3.973 | 1.00 | 39.06 | B | C |
| ATOM | 2618 | CB | ILE | B | 65 | −10.206 | 10.156 | 5.183 | 1.00 | 36.08 | B | C |
| ATOM | 2619 | CG1 | ILE | B | 65 | −11.429 | 10.969 | 4.711 | 1.00 | 37.76 | B | C |
| ATOM | 2620 | CD1 | ILE | B | 65 | −12.493 | 11.321 | 5.736 | 1.00 | 36.76 | B | C |
| ATOM | 2621 | CG2 | ILE | B | 65 | −9.324 | 10.947 | 6.130 | 1.00 | 37.78 | B | C |
| ATOM | 2622 | C | ILE | B | 65 | −8.375 | 8.615 | 4.387 | 1.00 | 42.34 | B | C |
| ATOM | 2623 | O | ILE | B | 65 | −8.782 | 7.489 | 4.725 | 1.00 | 40.57 | B | O |
| ATOM | 2624 | N | SER | B | 66 | −7.086 | 8.937 | 4.315 | 1.00 | 40.79 | B | N |
| ATOM | 2625 | CA | SER | B | 66 | −6.026 | 7.984 | 4.648 | 1.00 | 41.00 | B | C |
| ATOM | 2626 | CB | SER | B | 66 | −5.213 | 7.625 | 3.411 | 1.00 | 39.84 | B | C |
| ATOM | 2627 | OG | SER | B | 66 | −4.757 | 8.789 | 2.805 | 1.00 | 41.86 | B | O |
| ATOM | 2628 | C | SER | B | 66 | −5.139 | 8.507 | 5.786 | 1.00 | 41.25 | B | C |
| ATOM | 2629 | O | SER | B | 66 | −5.303 | 9.642 | 6.215 | 1.00 | 35.77 | B | O |
| ATOM | 2630 | N | GLY | B | 67 | −4.273 | 7.632 | 6.322 | 1.00 | 46.04 | B | N |
| ATOM | 2631 | CA | GLY | B | 67 | −3.397 | 7.947 | 7.481 | 1.00 | 45.74 | B | C |
| ATOM | 2632 | C | GLY | B | 67 | −4.082 | 8.271 | 8.793 | 1.00 | 44.03 | B | C |
| ATOM | 2633 | O | GLY | B | 67 | −3.690 | 9.188 | 9.513 | 1.00 | 45.24 | B | O |
| ATOM | 2634 | N | LEU | B | 68 | −5.137 | 7.539 | 9.089 | 1.00 | 46.67 | B | N |
| ATOM | 2635 | CA | LEU | B | 68 | −5.827 | 7.629 | 10.380 | 1.00 | 49.37 | B | C |
| ATOM | 2636 | CB | LEU | B | 68 | −7.297 | 7.247 | 10.195 | 1.00 | 52.05 | B | C |
| ATOM | 2637 | CG | LEU | B | 68 | −8.137 | 8.020 | 9.164 | 1.00 | 49.45 | B | C |
| ATOM | 2638 | CD1 | LEU | B | 68 | −9.286 | 7.217 | 8.558 | 1.00 | 47.97 | B | C |
| ATOM | 2639 | CD2 | LEU | B | 68 | −8.676 | 9.277 | 9.821 | 1.00 | 50.97 | B | C |
| ATOM | 2640 | C | LEU | B | 68 | −5.181 | 6.646 | 11.381 | 1.00 | 49.21 | B | C |
| ATOM | 2641 | O | LEU | B | 68 | −4.544 | 5.641 | 10.990 | 1.00 | 50.54 | B | O |

APPENDIX B-continued

Atomic coordinates of Aurora A + Activating Monobody Mb54 + AMPPCP

| | | | | | | | | | | | |
|---|---|---|---|---|---|---|---|---|---|---|---|
| ATOM | 2642 | N | LYS | B | 69 | −5.361 | 6.909 | 12.667 | 1.00 | 51.39 | B | N |
| ATOM | 2643 | CA | LYS | B | 69 | −4.836 | 5.978 | 13.691 | 1.00 | 58.07 | B | C |
| ATOM | 2644 | CB | LYS | B | 69 | −4.363 | 6.717 | 14.948 | 1.00 | 63.49 | B | C |
| ATOM | 2645 | CG | LYS | B | 69 | −3.003 | 7.371 | 14.724 | 1.00 | 68.80 | B | C |
| ATOM | 2646 | CD | LYS | B | 69 | −2.581 | 8.315 | 15.849 | 1.00 | 76.46 | B | C |
| ATOM | 2647 | CE | LYS | B | 69 | −1.478 | 9.262 | 15.379 | 1.00 | 78.48 | B | C |
| ATOM | 2648 | NZ | LYS | B | 69 | −0.457 | 9.532 | 16.428 | 1.00 | 80.10 | B | N |
| ATOM | 2649 | C | LYS | B | 69 | −5.907 | 4.921 | 13.993 | 1.00 | 51.34 | B | C |
| ATOM | 2650 | O | LYS | B | 69 | −7.096 | 5.276 | 14.113 | 1.00 | 47.35 | B | O |
| ATOM | 2651 | N | PRO | B | 70 | −5.507 | 3.622 | 14.047 | 1.00 | 49.27 | B | N |
| ATOM | 2652 | CA | PRO | B | 70 | −6.462 | 2.522 | 14.368 | 1.00 | 43.17 | B | C |
| ATOM | 2653 | CB | PRO | B | 70 | −5.580 | 1.268 | 14.334 | 1.00 | 45.05 | B | C |
| ATOM | 2654 | CG | PRO | B | 70 | −4.340 | 1.649 | 13.581 | 1.00 | 46.51 | B | C |
| ATOM | 2655 | CD | PRO | B | 70 | −4.131 | 3.106 | 13.856 | 1.00 | 46.96 | B | C |
| ATOM | 2656 | C | PRO | B | 70 | −7.155 | 2.646 | 15.748 | 1.00 | 40.40 | B | C |
| ATOM | 2657 | O | PRO | B | 70 | −6.674 | 3.350 | 16.622 | 1.00 | 39.95 | B | O |
| ATOM | 2658 | N | GLY | B | 71 | −8.284 | 1.962 | 15.932 | 1.00 | 37.09 | B | N |
| ATOM | 2659 | CA | GLY | B | 71 | −8.996 | 1.943 | 17.203 | 1.00 | 34.94 | B | C |
| ATOM | 2660 | C | GLY | B | 71 | −9.362 | 3.308 | 17.754 | 1.00 | 39.11 | B | C |
| ATOM | 2661 | O | GLY | B | 71 | −9.382 | 3.483 | 18.993 | 1.00 | 39.50 | B | O |
| ATOM | 2662 | N | VAL | B | 72 | −9.633 | 4.275 | 16.852 | 1.00 | 39.42 | B | N |
| ATOM | 2663 | CA | VAL | B | 72 | −10.004 | 5.636 | 17.242 | 1.00 | 39.25 | B | C |
| ATOM | 2664 | CB | VAL | B | 72 | −9.024 | 6.702 | 16.721 | 1.00 | 41.74 | B | C |
| ATOM | 2665 | CG1 | VAL | B | 72 | −9.295 | 8.030 | 17.421 | 1.00 | 43.71 | B | C |
| ATOM | 2666 | CG2 | VAL | B | 72 | −7.577 | 6.304 | 16.972 | 1.00 | 42.93 | B | C |
| ATOM | 2667 | C | VAL | B | 72 | −11.400 | 6.005 | 16.770 | 1.00 | 39.11 | B | C |
| ATOM | 2668 | O | VAL | B | 72 | −11.797 | 5.716 | 15.648 | 1.00 | 40.60 | B | O |
| ATOM | 2669 | N | ASP | B | 73 | −12.149 | 6.645 | 17.647 | 1.00 | 40.13 | B | N |
| ATOM | 2670 | CA | ASP | B | 73 | −13.392 | 7.287 | 17.247 | 1.00 | 43.50 | B | C |
| ATOM | 2671 | CB | ASP | B | 73 | −14.215 | 7.707 | 18.482 | 1.00 | 43.00 | B | C |
| ATOM | 2672 | CG | ASP | B | 73 | −14.797 | 6.513 | 19.251 | 1.00 | 52.06 | B | C |
| ATOM | 2673 | OD1 | ASP | B | 73 | −14.720 | 5.327 | 18.793 | 1.00 | 48.94 | B | O |
| ATOM | 2674 | OD2 | ASP | B | 73 | −15.355 | 6.783 | 20.341 | 1.00 | 61.23 | B | O |
| ATOM | 2675 | C | ASP | B | 73 | −13.086 | 8.522 | 16.359 | 1.00 | 44.23 | B | C |
| ATOM | 2676 | O | ASP | B | 73 | −12.406 | 9.471 | 16.788 | 1.00 | 42.21 | B | O |
| ATOM | 2677 | N | TYR | B | 74 | −13.567 | 8.513 | 15.118 | 1.00 | 44.54 | B | N |
| ATOM | 2678 | CA | TYR | B | 74 | −13.559 | 9.733 | 14.298 | 1.00 | 39.87 | B | C |
| ATOM | 2679 | CB | TYR | B | 74 | −12.894 | 9.458 | 12.954 | 1.00 | 39.46 | B | C |
| ATOM | 2680 | CG | TYR | B | 74 | −11.411 | 9.328 | 13.057 | 1.00 | 39.14 | B | C |
| ATOM | 2681 | CD1 | TYR | B | 74 | −10.608 | 10.454 | 13.177 | 1.00 | 44.96 | B | C |
| ATOM | 2682 | CE1 | TYR | B | 74 | −9.220 | 10.351 | 13.279 | 1.00 | 45.90 | B | C |
| ATOM | 2683 | CZ | TYR | B | 74 | −8.638 | 9.098 | 13.290 | 1.00 | 46.73 | B | C |
| ATOM | 2684 | OH | TYR | B | 74 | −7.275 | 8.967 | 13.381 | 1.00 | 50.22 | B | O |
| ATOM | 2685 | CE2 | TYR | B | 74 | −9.424 | 7.960 | 13.178 | 1.00 | 47.47 | B | C |
| ATOM | 2686 | CD2 | TYR | B | 74 | −10.802 | 8.080 | 13.075 | 1.00 | 43.51 | B | C |
| ATOM | 2687 | C | TYR | B | 74 | −14.973 | 10.325 | 14.145 | 1.00 | 41.44 | B | C |
| ATOM | 2688 | O | TYR | B | 74 | −15.992 | 9.612 | 14.234 | 1.00 | 37.58 | B | O |
| ATOM | 2689 | N | THR | B | 75 | −15.002 | 11.651 | 14.010 | 1.00 | 40.63 | B | N |
| ATOM | 2690 | CA | THR | B | 75 | −16.133 | 12.375 | 13.453 | 1.00 | 41.28 | B | C |
| ATOM | 2691 | CB | THR | B | 75 | −16.596 | 13.503 | 14.396 | 1.00 | 43.52 | B | C |
| ATOM | 2692 | OG1 | THR | B | 75 | −16.984 | 12.947 | 15.675 | 1.00 | 45.93 | B | O |
| ATOM | 2693 | CG2 | THR | B | 75 | −17.780 | 14.275 | 13.786 | 1.00 | 43.38 | B | C |
| ATOM | 2694 | C | THR | B | 75 | −15.682 | 12.943 | 12.075 | 1.00 | 40.46 | B | C |
| ATOM | 2695 | O | THR | B | 75 | −14.613 | 13.610 | 11.967 | 1.00 | 33.05 | B | O |
| ATOM | 2696 | N | ILE | B | 76 | −16.462 | 12.591 | 11.038 | 1.00 | 40.48 | B | N |
| ATOM | 2697 | CA | ILE | B | 76 | −16.232 | 12.989 | 9.635 | 1.00 | 38.50 | B | C |
| ATOM | 2698 | CB | ILE | B | 76 | −16.175 | 11.763 | 8.671 | 1.00 | 43.30 | B | C |
| ATOM | 2699 | CG1 | ILE | B | 76 | −14.944 | 10.875 | 8.971 | 1.00 | 43.31 | B | C |
| ATOM | 2700 | CD1 | ILE | B | 76 | −15.347 | 9.561 | 9.595 | 1.00 | 48.30 | B | C |
| ATOM | 2701 | CG2 | ILE | B | 76 | −16.129 | 12.160 | 7.192 | 1.00 | 44.15 | B | C |
| ATOM | 2702 | C | ILE | B | 76 | −17.381 | 13.916 | 9.291 | 1.00 | 36.17 | B | C |
| ATOM | 2703 | O | ILE | B | 76 | −18.560 | 13.566 | 9.458 | 1.00 | 31.49 | B | O |
| ATOM | 2704 | N | THR | B | 77 | −17.021 | 15.111 | 8.840 | 1.00 | 37.62 | B | N |
| ATOM | 2705 | CA | THR | B | 77 | −17.978 | 16.091 | 8.387 | 1.00 | 39.47 | B | C |
| ATOM | 2706 | CB | THR | B | 77 | −18.048 | 17.241 | 9.405 | 1.00 | 39.98 | B | C |
| ATOM | 2707 | OG1 | THR | B | 77 | −18.201 | 16.675 | 10.719 | 1.00 | 39.29 | B | O |
| ATOM | 2708 | CG2 | THR | B | 77 | −19.220 | 18.201 | 9.071 | 1.00 | 38.31 | B | C |
| ATOM | 2709 | C | THR | B | 77 | −17.633 | 16.589 | 6.965 | 1.00 | 41.39 | B | C |
| ATOM | 2710 | O | THR | B | 77 | −16.442 | 16.850 | 6.595 | 1.00 | 37.46 | B | O |
| ATOM | 2711 | N | VAL | B | 78 | −18.699 | 16.714 | 6.170 | 1.00 | 43.09 | B | N |
| ATOM | 2712 | CA | VAL | B | 78 | −18.606 | 17.213 | 4.775 | 1.00 | 39.45 | B | C |
| ATOM | 2713 | CB | VAL | B | 78 | −18.965 | 16.093 | 3.767 | 1.00 | 39.32 | B | C |
| ATOM | 2714 | CG1 | VAL | B | 78 | −19.132 | 16.633 | 2.341 | 1.00 | 37.41 | B | C |
| ATOM | 2715 | CG2 | VAL | B | 78 | −17.879 | 15.021 | 3.806 | 1.00 | 37.86 | B | C |
| ATOM | 2716 | C | VAL | B | 78 | −19.469 | 18.467 | 4.542 | 1.00 | 35.90 | B | C |
| ATOM | 2717 | O | VAL | B | 78 | −20.688 | 18.423 | 4.769 | 1.00 | 31.94 | B | O |
| ATOM | 2718 | N | TYR | B | 79 | −18.830 | 19.552 | 4.072 | 1.00 | 33.21 | B | N |
| ATOM | 2719 | CA | TYR | B | 79 | −19.525 | 20.794 | 3.713 | 1.00 | 37.49 | B | C |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 2720 | CB | TYR | B | 79 | −18.852 | 22.032 | 4.345 | 1.00 | 46.24 | B | C |
| ATOM | 2721 | CG | TYR | B | 79 | −18.663 | 21.965 | 5.854 | 1.00 | 51.55 | B | C |
| ATOM | 2722 | CD1 | TYR | B | 79 | −17.532 | 21.322 | 6.411 | 1.00 | 52.27 | B | C |
| ATOM | 2723 | CE1 | TYR | B | 79 | −17.357 | 21.243 | 7.783 | 1.00 | 49.09 | B | C |
| ATOM | 2724 | CZ | TYR | B | 79 | −18.293 | 21.815 | 8.601 | 1.00 | 50.72 | B | C |
| ATOM | 2725 | OH | TYR | B | 79 | −18.104 | 21.751 | 9.935 | 1.00 | 55.70 | B | O |
| ATOM | 2726 | CE2 | TYR | B | 79 | −19.415 | 22.461 | 8.099 | 1.00 | 52.94 | B | C |
| ATOM | 2727 | CD2 | TYR | B | 79 | −19.596 | 22.536 | 6.724 | 1.00 | 52.50 | B | C |
| ATOM | 2728 | C | TYR | B | 79 | −19.513 | 20.940 | 2.201 | 1.00 | 33.33 | B | C |
| ATOM | 2729 | O | TYR | B | 79 | −18.439 | 21.148 | 1.580 | 1.00 | 28.56 | B | O |
| ATOM | 2730 | N | ALA | B | 80 | −20.710 | 20.803 | 1.624 | 1.00 | 30.16 | B | N |
| ATOM | 2731 | CA | ALA | B | 80 | −20.962 | 21.109 | 0.219 | 1.00 | 29.59 | B | C |
| ATOM | 2732 | CB | ALA | B | 80 | −22.272 | 20.493 | −0.230 | 1.00 | 30.55 | B | C |
| ATOM | 2733 | C | ALA | B | 80 | −20.979 | 22.641 | 0.024 | 1.00 | 32.77 | B | C |
| ATOM | 2734 | O | ALA | B | 80 | −21.876 | 23.331 | 0.563 | 1.00 | 32.41 | B | O |
| ATOM | 2735 | N | GLU | B | 81 | −19.936 | 23.138 | −0.665 | 1.00 | 34.68 | B | N |
| ATOM | 2736 | CA | GLU | B | 81 | −19.775 | 24.536 | −1.083 | 1.00 | 38.10 | B | C |
| ATOM | 2737 | CB | GLU | B | 81 | −18.295 | 24.978 | −0.980 | 1.00 | 39.48 | B | C |
| ATOM | 2738 | CG | GLU | B | 81 | −17.714 | 25.037 | 0.432 | 1.00 | 44.19 | B | C |
| ATOM | 2739 | CD | GLU | B | 81 | −18.611 | 25.683 | 1.493 | 1.00 | 46.57 | B | C |
| ATOM | 2740 | OE1 | GLU | B | 81 | −19.426 | 26.589 | 1.215 | 1.00 | 50.03 | B | O |
| ATOM | 2741 | OE2 | GLU | B | 81 | −18.497 | 25.268 | 2.659 | 1.00 | 58.85 | B | O |
| ATOM | 2742 | C | GLU | B | 81 | −20.275 | 24.784 | −2.518 | 1.00 | 36.08 | B | C |
| ATOM | 2743 | O | GLU | B | 81 | −19.560 | 24.519 | −3.509 | 1.00 | 34.68 | B | O |
| ATOM | 2744 | N | GLY | B | 82 | −21.515 | 25.264 | −2.605 | 1.00 | 39.36 | B | N |
| ATOM | 2745 | CA | GLY | B | 82 | −22.100 | 25.781 | −3.856 | 1.00 | 39.91 | B | C |
| ATOM | 2746 | C | GLY | B | 82 | −21.321 | 26.990 | −4.383 | 1.00 | 42.22 | B | C |
| ATOM | 2747 | O | GLY | B | 82 | −20.564 | 27.652 | −3.654 | 1.00 | 43.89 | B | O |
| ATOM | 2748 | N | TYR | B | 83 | −21.457 | 27.244 | −5.675 | 1.00 | 41.21 | B | N |
| ATOM | 2749 | CA | TYR | B | 83 | −20.957 | 28.468 | −6.268 | 1.00 | 37.27 | B | C |
| ATOM | 2750 | CB | TYR | B | 83 | −21.125 | 28.417 | −7.802 | 1.00 | 37.24 | B | C |
| ATOM | 2751 | CG | TYR | B | 83 | −20.084 | 27.524 | −8.487 | 1.00 | 34.46 | B | C |
| ATOM | 2752 | CD1 | TYR | B | 83 | −18.767 | 27.974 | −8.642 | 1.00 | 34.34 | B | C |
| ATOM | 2753 | CE1 | TYR | B | 83 | −17.786 | 27.184 | −9.229 | 1.00 | 34.82 | B | C |
| ATOM | 2754 | CZ | TYR | B | 83 | −18.095 | 25.893 | −9.680 | 1.00 | 34.50 | B | C |
| ATOM | 2755 | OH | TYR | B | 83 | −17.048 | 25.152 | −10.249 | 1.00 | 38.31 | B | O |
| ATOM | 2756 | CE2 | TYR | B | 83 | −19.400 | 25.405 | −9.536 | 1.00 | 32.58 | B | C |
| ATOM | 2757 | CD2 | TYR | B | 83 | −20.390 | 26.217 | −8.929 | 1.00 | 32.21 | B | C |
| ATOM | 2758 | C | TYR | B | 83 | −21.668 | 29.671 | −5.604 | 1.00 | 37.83 | B | C |
| ATOM | 2759 | O | TYR | B | 83 | −21.029 | 30.666 | −5.330 | 1.00 | 36.30 | B | O |
| ATOM | 2760 | N | TYR | B | 84 | −22.956 | 29.524 | −5.267 | 1.00 | 40.24 | B | N |
| ATOM | 2761 | CA | TYR | B | 84 | −23.775 | 30.591 | −4.680 | 1.00 | 43.03 | B | C |
| ATOM | 2762 | CB | TYR | B | 84 | −24.952 | 30.930 | −5.661 | 1.00 | 48.39 | B | C |
| ATOM | 2763 | CG | TYR | B | 84 | −24.363 | 31.558 | −6.913 | 1.00 | 46.33 | B | C |
| ATOM | 2764 | CD1 | TYR | B | 84 | −23.989 | 32.917 | −6.935 | 1.00 | 43.72 | B | C |
| ATOM | 2765 | CE1 | TYR | B | 84 | −23.368 | 33.480 | −8.044 | 1.00 | 43.00 | B | C |
| ATOM | 2766 | CZ | TYR | B | 84 | −23.065 | 32.674 | −9.138 | 1.00 | 42.96 | B | C |
| ATOM | 2767 | OH | TYR | B | 84 | −22.418 | 33.175 | −10.238 | 1.00 | 42.02 | B | O |
| ATOM | 2768 | CE2 | TYR | B | 84 | −23.383 | 31.326 | −9.122 | 1.00 | 48.26 | B | C |
| ATOM | 2769 | CD2 | TYR | B | 84 | −24.029 | 30.770 | −8.011 | 1.00 | 46.19 | B | C |
| ATOM | 2770 | C | TYR | B | 84 | −24.287 | 30.271 | −3.264 | 1.00 | 48.57 | B | C |
| ATOM | 2771 | O | TYR | B | 84 | −25.136 | 30.992 | −2.746 | 1.00 | 50.31 | B | O |
| ATOM | 2772 | N | SER | B | 85 | −23.740 | 29.238 | −2.615 | 1.00 | 46.76 | B | N |
| ATOM | 2773 | CA | ASER | B | 85 | −24.333 | 28.712 | −1.397 | 0.50 | 46.73 | B | C |
| ATOM | 2774 | CA | BSER | B | 85 | −24.337 | 28.700 | −1.404 | 0.50 | 46.71 | B | C |
| ATOM | 2775 | CB | ASER | B | 85 | −25.554 | 27.845 | −1.747 | 0.50 | 47.73 | B | C |
| ATOM | 2776 | CB | BSER | B | 85 | −25.536 | 27.810 | −1.772 | 0.50 | 47.75 | B | C |
| ATOM | 2777 | OG | ASER | B | 85 | −25.152 | 26.698 | −2.491 | 0.50 | 48.09 | B | O |
| ATOM | 2778 | OG | BSER | B | 85 | −25.103 | 26.665 | −2.503 | 0.50 | 47.68 | B | O |
| ATOM | 2779 | C | SER | B | 85 | −23.340 | 27.900 | −0.563 | 1.00 | 46.74 | B | C |
| ATOM | 2780 | O | SER | B | 85 | −22.269 | 27.482 | −1.054 | 1.00 | 45.77 | B | O |
| ATOM | 2781 | N | SER | B | 86 | −23.711 | 27.709 | 0.706 | 1.00 | 44.71 | B | N |
| ATOM | 2782 | CA | SER | B | 86 | −23.041 | 26.789 | 1.634 | 1.00 | 43.27 | B | C |
| ATOM | 2783 | CB | SER | B | 86 | −22.352 | 27.525 | 2.758 | 1.00 | 42.03 | B | C |
| ATOM | 2784 | OG | SER | B | 86 | −21.165 | 28.079 | 2.288 | 1.00 | 43.68 | B | O |
| ATOM | 2785 | C | SER | B | 86 | −24.144 | 25.934 | 2.196 | 1.00 | 41.59 | B | C |
| ATOM | 2786 | O | SER | B | 86 | −25.088 | 26.460 | 2.745 | 1.00 | 38.38 | B | O |
| ATOM | 2787 | N | TYR | B | 87 | −24.051 | 24.622 | 2.001 | 1.00 | 45.02 | B | N |
| ATOM | 2788 | CA | TYR | B | 87 | −25.028 | 23.689 | 2.549 | 1.00 | 45.96 | B | C |
| ATOM | 2789 | CB | TYR | B | 87 | −25.159 | 22.433 | 1.681 | 1.00 | 47.35 | B | C |
| ATOM | 2790 | CG | TYR | B | 87 | −25.900 | 22.646 | 0.370 | 1.00 | 48.32 | B | C |
| ATOM | 2791 | CD1 | TYR | B | 87 | −25.260 | 23.234 | −0.755 | 1.00 | 47.20 | B | C |
| ATOM | 2792 | CE1 | TYR | B | 87 | −25.956 | 23.450 | −1.949 | 1.00 | 46.08 | B | C |
| ATOM | 2793 | CZ | TYR | B | 87 | −27.321 | 23.060 | −2.054 | 1.00 | 48.68 | B | C |
| ATOM | 2794 | OH | TYR | B | 87 | −28.064 | 23.211 | −3.226 | 1.00 | 47.04 | B | O |
| ATOM | 2795 | CE2 | TYR | B | 87 | −27.950 | 22.451 | −0.962 | 1.00 | 50.21 | B | C |
| ATOM | 2796 | CD2 | TYR | B | 87 | −27.249 | 22.256 | 0.238 | 1.00 | 47.54 | B | C |
| ATOM | 2797 | C | TYR | B | 87 | −24.556 | 23.354 | 3.969 | 1.00 | 45.11 | B | C |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| ATOM | 2798 | O | TYR | B | 87 | −23.333 | 23.394 | 4.309 | 1.00 | 38.73 | B | O |
| ATOM | 2799 | N | SER | B | 88 | −25.528 | 23.092 | 4.825 | 1.00 | 48.54 | B | N |
| ATOM | 2800 | CA | SER | B | 88 | −25.182 | 22.830 | 6.210 | 1.00 | 58.14 | B | C |
| ATOM | 2801 | CB | SER | B | 88 | −26.366 | 23.059 | 7.159 | 1.00 | 58.66 | B | C |
| ATOM | 2802 | OG | SER | B | 88 | −27.406 | 22.141 | 6.925 | 1.00 | 60.70 | B | O |
| ATOM | 2803 | C | SER | B | 88 | −24.590 | 21.398 | 6.278 | 1.00 | 57.53 | B | C |
| ATOM | 2804 | O | SER | B | 88 | −25.100 | 20.478 | 5.608 | 1.00 | 49.11 | B | O |
| ATOM | 2805 | N | PRO | B | 89 | −23.490 | 21.226 | 7.052 | 1.00 | 58.35 | B | N |
| ATOM | 2806 | CA | PRO | B | 89 | −22.740 | 19.967 | 7.112 | 1.00 | 54.29 | B | C |
| ATOM | 2807 | CB | PRO | B | 89 | −21.860 | 20.131 | 8.352 | 1.00 | 57.58 | B | C |
| ATOM | 2808 | CG | PRO | B | 89 | −22.477 | 21.248 | 9.121 | 1.00 | 56.57 | B | C |
| ATOM | 2809 | CD | PRO | B | 89 | −22.997 | 22.172 | 8.072 | 1.00 | 58.10 | B | C |
| ATOM | 2810 | C | PRO | B | 89 | −23.584 | 18.714 | 7.283 | 1.00 | 49.35 | B | C |
| ATOM | 2811 | O | PRO | B | 89 | −24.640 | 18.749 | 7.918 | 1.00 | 46.65 | B | O |
| ATOM | 2812 | N | ILE | B | 90 | −23.131 | 17.637 | 6.655 | 1.00 | 42.55 | B | N |
| ATOM | 2813 | CA | ILE | B | 90 | −23.537 | 16.317 | 7.038 | 1.00 | 43.03 | B | C |
| ATOM | 2814 | CB | ILE | B | 90 | −24.201 | 15.523 | 5.892 | 1.00 | 46.55 | B | C |
| ATOM | 2815 | CG1 | ILE | B | 90 | −23.258 | 15.394 | 4.687 | 1.00 | 54.48 | B | C |
| ATOM | 2816 | CD1 | ILE | B | 90 | −23.740 | 14.394 | 3.640 | 1.00 | 59.41 | B | C |
| ATOM | 2817 | CG2 | ILE | B | 90 | −25.535 | 16.169 | 5.493 | 1.00 | 42.42 | B | C |
| ATOM | 2818 | C | ILE | B | 90 | −22.273 | 15.656 | 7.629 | 1.00 | 46.77 | B | C |
| ATOM | 2819 | O | ILE | B | 90 | −21.111 | 15.973 | 7.245 | 1.00 | 48.79 | B | O |
| ATOM | 2820 | N | SER | B | 91 | −22.503 | 14.798 | 8.621 | 1.00 | 45.28 | B | N |
| ATOM | 2821 | CA | SER | B | 91 | −21.421 | 14.180 | 9.372 | 1.00 | 46.63 | B | C |
| ATOM | 2822 | CB | SER | B | 91 | −21.033 | 15.042 | 10.568 | 1.00 | 45.49 | B | C |
| ATOM | 2823 | OG | SER | B | 91 | −22.111 | 15.016 | 11.441 | 1.00 | 46.03 | B | O |
| ATOM | 2824 | C | SER | B | 91 | −21.768 | 12.771 | 9.850 | 1.00 | 44.19 | B | C |
| ATOM | 2825 | O | SER | B | 91 | −22.921 | 12.304 | 9.790 | 1.00 | 38.25 | B | O |
| ATOM | 2826 | N | ILE | B | 92 | −20.728 | 12.093 | 10.298 | 1.00 | 41.20 | B | N |
| ATOM | 2827 | CA | ILE | B | 92 | −20.856 | 10.719 | 10.717 | 1.00 | 42.74 | B | C |
| ATOM | 2828 | CB | ILE | B | 92 | −20.976 | 9.768 | 9.484 | 1.00 | 44.70 | B | C |
| ATOM | 2829 | CG1 | ILE | B | 92 | −21.549 | 8.392 | 9.909 | 1.00 | 47.27 | B | C |
| ATOM | 2830 | CD1 | ILE | B | 92 | −22.161 | 7.575 | 8.769 | 1.00 | 45.64 | B | C |
| ATOM | 2831 | CG2 | ILE | B | 92 | −19.643 | 9.659 | 8.732 | 1.00 | 43.03 | B | C |
| ATOM | 2832 | C | ILE | B | 92 | −19.650 | 10.397 | 11.597 | 1.00 | 42.90 | B | C |
| ATOM | 2833 | O | ILE | B | 92 | −18.542 | 10.905 | 11.373 | 1.00 | 42.16 | B | O |
| ATOM | 2834 | N | ASN | B | 93 | −19.894 | 9.564 | 12.598 | 1.00 | 41.17 | B | N |
| ATOM | 2835 | CA | ASN | B | 93 | −18.851 | 9.041 | 13.473 | 1.00 | 41.71 | B | C |
| ATOM | 2836 | CB | ASN | B | 93 | −19.298 | 9.121 | 14.934 | 1.00 | 44.41 | B | C |
| ATOM | 2837 | CG | ASN | B | 93 | −19.649 | 10.533 | 15.353 | 1.00 | 45.39 | B | C |
| ATOM | 2838 | OD1 | ASN | B | 93 | −18.897 | 11.493 | 15.131 | 1.00 | 45.94 | B | O |
| ATOM | 2839 | ND2 | ASN | B | 93 | −20.818 | 10.672 | 15.908 | 1.00 | 47.17 | B | N |
| ATOM | 2840 | C | ASN | B | 93 | −18.537 | 7.604 | 13.117 | 1.00 | 38.20 | B | C |
| ATOM | 2841 | O | ASN | B | 93 | −19.450 | 6.812 | 12.833 | 1.00 | 36.07 | B | O |
| ATOM | 2842 | N | TYR | B | 94 | −17.259 | 7.267 | 13.128 | 1.00 | 35.02 | B | N |
| ATOM | 2843 | CA | TYR | B | 94 | −16.840 | 5.923 | 12.786 | 1.00 | 39.32 | B | C |
| ATOM | 2844 | CB | TYR | B | 94 | −16.532 | 5.803 | 11.295 | 1.00 | 39.17 | B | C |
| ATOM | 2845 | CG | TYR | B | 94 | −16.467 | 4.379 | 10.784 | 1.00 | 37.42 | B | C |
| ATOM | 2846 | CD1 | TYR | B | 94 | 17.660 | 3.711 | 10.423 | 1.00 | 38.77 | B | C |
| ATOM | 2847 | CE1 | TYR | B | 94 | −17.636 | 2.421 | 9.927 | 1.00 | 37.72 | B | C |
| ATOM | 2848 | CZ | TYR | B | 94 | −16.417 | 1.794 | 9.782 | 1.00 | 37.64 | B | C |
| ATOM | 2849 | OH | TYR | B | 94 | −16.487 | 0.521 | 9.316 | 1.00 | 48.47 | B | O |
| ATOM | 2850 | CE2 | TYR | B | 94 | −15.214 | 2.408 | 10.136 | 1.00 | 36.14 | B | C |
| ATOM | 2851 | CD2 | TYR | B | 94 | −15.242 | 3.707 | 10.629 | 1.00 | 34.80 | B | C |
| ATOM | 2852 | C | TYR | B | 94 | −15.601 | 5.605 | 13.560 | 1.00 | 42.10 | B | C |
| ATOM | 2853 | O | TYR | B | 94 | −14.817 | 6.520 | 13.839 | 1.00 | 44.65 | B | O |
| ATOM | 2854 | N | ARG | B | 95 | −15.434 | 4.316 | 13.888 | 1.00 | 41.64 | B | N |
| ATOM | 2855 | CA | ARG | B | 95 | −14.316 | 3.850 | 14.697 | 1.00 | 42.13 | B | C |
| ATOM | 2856 | CB | ARG | B | 95 | −14.784 | 3.135 | 15.992 | 1.00 | 43.74 | B | C |
| ATOM | 2857 | CG | ARG | B | 95 | −13.625 | 2.562 | 16.832 | 1.00 | 46.98 | B | C |
| ATOM | 2858 | CD | ARG | B | 95 | −14.064 | 1.878 | 18.130 | 1.00 | 52.02 | B | C |
| ATOM | 2859 | NE | ARG | B | 95 | −13.890 | 2.795 | 19.246 | 1.00 | 58.27 | B | N |
| ATOM | 2860 | CZ | ARG | B | 95 | −12.839 | 2.859 | 20.052 | 1.00 | 58.65 | B | C |
| ATOM | 2861 | NH1 | ARG | B | 95 | −12.823 | 3.804 | 20.973 | 1.00 | 71.03 | B | N |
| ATOM | 2862 | NH2 | ARG | B | 95 | −11.826 | 2.003 | 19.981 | 1.00 | 57.79 | B | N |
| ATOM | 2863 | C | ARG | B | 95 | −13.451 | 2.944 | 13.837 | 1.00 | 40.45 | B | C |
| ATOM | 2864 | O | ARG | B | 95 | −13.873 | 1.854 | 13.412 | 1.00 | 33.80 | B | O |
| ATOM | 2865 | N | THR | B | 96 | −12.228 | 3.400 | 13.604 | 1.00 | 40.13 | B | N |
| ATOM | 2866 | CA | THR | B | 96 | −11.249 | 2.570 | 12.935 | 1.00 | 47.05 | B | C |
| ATOM | 2867 | CB | THR | B | 96 | −9.983 | 3.370 | 12.662 | 1.00 | 44.02 | B | C |
| ATOM | 2868 | OG1 | THR | B | 96 | −9.589 | 4.030 | 13.872 | 1.00 | 42.34 | B | O |
| ATOM | 2869 | CG2 | THR | B | 96 | −10.269 | 4.424 | 11.600 | 1.00 | 45.99 | B | C |
| ATOM | 2870 | C | THR | B | 96 | −10.912 | 1.356 | 13.805 | 1.00 | 54.12 | B | C |
| ATOM | 2871 | O | THR | B | 96 | −10.172 | 0.477 | 13.363 | 1.00 | 66.00 | B | O |
| TER | 2872 | | THR | B | 96 | | | | | | | |
| HETATM | 2873 | O2A | ACP | C | 1 | −24.933 | 25.110 | −27.162 | 1.00 | 41.11 | C | O |
| HETATM | 2874 | PA | ACP | C | 1 | −25.998 | 25.656 | −28.083 | 1.00 | 41.26 | C | P |
| HETATM | 2875 | O1A | ACP | C | 1 | −27.072 | 26.577 | −27.496 | 1.00 | 37.59 | C | O |

APPENDIX B-continued

Atomic coordinates of Aurora A + Activating Monobody Mb54 + AMPPCP

| | | | | | | | | | | | | |
|---|---|---|---|---|---|---|---|---|---|---|---|---|
| HETATM | 2876 | O3A | ACP | C | 1 | −26.535 | 24.427 | −28.970 | 1.00 | 41.29 | C | O |
| HETATM | 2877 | PB | ACP | C | 1 | −27.557 | 23.279 | −28.499 | 1.00 | 47.60 | C | P |
| HETATM | 2878 | O1B | ACP | C | 1 | −28.250 | 22.662 | −29.672 | 1.00 | 45.22 | C | O |
| HETATM | 2879 | O2B | ACP | C | 1 | −28.634 | 23.745 | −27.386 | 1.00 | 40.54 | C | O |
| HETATM | 2880 | C3B | ACP | C | 1 | −26.440 | 22.064 | −27.788 | 1.00 | 57.98 | C | C |
| HETATM | 2881 | PG | ACP | C | 1 | −27.155 | 21.543 | −26.211 | 1.00 | 79.33 | C | P |
| HETATM | 2882 | O2G | ACP | C | 1 | −27.763 | 22.745 | −25.230 | 1.00 | 66.62 | C | O |
| HETATM | 2883 | O3G | ACP | C | 1 | −28.346 | 20.506 | −26.528 | 1.00 | 59.91 | C | O |
| HETATM | 2884 | O1G | ACP | C | 1 | −25.962 | 20.857 | −25.663 | 1.00 | 63.47 | C | O |
| HETATM | 2885 | O5' | ACP | C | 1 | −25.282 | 26.425 | −29.290 | 1.00 | 38.03 | C | O |
| HETATM | 2886 | C5' | ACP | C | 1 | −26.107 | 26.972 | −30.315 | 1.00 | 35.27 | C | C |
| HETATM | 2887 | C4' | ACP | C | 1 | −25.260 | 27.522 | −31.432 | 1.00 | 32.78 | C | C |
| HETATM | 2888 | C3' | ACP | C | 1 | −24.179 | 26.561 | −31.841 | 1.00 | 36.33 | C | C |
| HETATM | 2889 | O3' | ACP | C | 1 | −24.626 | 25.683 | −32.832 | 1.00 | 36.68 | C | O |
| HETATM | 2890 | C2' | ACP | C | 1 | −23.084 | 27.495 | −32.327 | 1.00 | 38.14 | C | C |
| HETATM | 2891 | O2' | ACP | C | 1 | −23.315 | 27.936 | −33.674 | 1.00 | 44.70 | C | O |
| HETATM | 2892 | C1' | ACP | C | 1 | −23.206 | 28.682 | −31.388 | 1.00 | 31.45 | C | C |
| HETATM | 2893 | O4' | ACP | C | 1 | −24.576 | 28.696 | −30.969 | 1.00 | 29.73 | C | O |
| HETATM | 2894 | N9 | ACP | C | 1 | −22.306 | 28.592 | −30.203 | 1.00 | 28.85 | C | N |
| HETATM | 2895 | C4 | ACP | C | 1 | −21.153 | 29.266 | −30.098 | 1.00 | 27.99 | C | C |
| HETATM | 2896 | C5 | ACP | C | 1 | −20.616 | 28.939 | −28.772 | 1.00 | 25.04 | C | C |
| HETATM | 2897 | N7 | ACP | C | 1 | −21.458 | 28.095 | −28.146 | 1.00 | 26.65 | C | N |
| HETATM | 2898 | C8 | ACP | C | 1 | −22.484 | 27.889 | −29.027 | 1.00 | 27.79 | C | C |
| HETATM | 2899 | N3 | ACP | C | 1 | −20.445 | 30.124 | −30.881 | 1.00 | 27.95 | C | N |
| HETATM | 2900 | C2 | ACP | C | 1 | −19.253 | 30.652 | −30.473 | 1.00 | 27.22 | C | C |
| HETATM | 2901 | N1 | ACP | C | 1 | −18.711 | 30.375 | −29.283 | 1.00 | 24.37 | C | N |
| HETATM | 2902 | C6 | ACP | C | 1 | −19.365 | 29.564 | −28.452 | 1.00 | 24.44 | C | C |
| HETATM | 2903 | N6 | ACP | C | 1 | −18.878 | 29.265 | −27.276 | 1.00 | 29.61 | C | N |
| HETATM | 2904 | MG | MG | C | 2 | −24.415 | 21.621 | −24.007 | 1.00 | 45.79 | C | MG |
| HETATM | 2905 | O4 | SO4 | C | 3 | −15.467 | 5.389 | −52.813 | 1.00 | 38.51 | C | O |
| HETATM | 2906 | S | SO4 | C | 3 | −14.457 | 4.405 | −53.268 | 1.00 | 38.79 | C | S |
| HETATM | 2907 | O1 | SO4 | C | 3 | −13.063 | 4.918 | −53.129 | 1.00 | 36.55 | C | O |
| HETATM | 2908 | O2 | SO4 | C | 3 | −14.741 | 4.173 | −54.714 | 1.00 | 37.37 | C | O |
| HETATM | 2909 | O3 | SO4 | C | 3 | −14.605 | 3.181 | −52.387 | 1.00 | 34.12 | C | O |
| HETATM | 2910 | O4 | SO4 | C | 4 | −23.398 | 8.287 | −13.228 | 1.00 | 46.01 | C | O |
| HETATM | 2911 | S | SO4 | C | 4 | −24.025 | 8.149 | −14.576 | 1.00 | 48.55 | C | S |
| HETATM | 2912 | O1 | SO4 | C | 4 | −23.315 | 7.129 | −15.410 | 1.00 | 54.72 | C | O |
| HETATM | 2913 | O2 | SO4 | C | 4 | −24.018 | 9.457 | −15.201 | 1.00 | 49.03 | C | O |
| HETATM | 2914 | O3 | SO4 | C | 4 | −25.432 | 7.716 | −14.407 | 1.00 | 54.10 | C | O |
| HETATM | 2915 | O4 | SO4 | C | 5 | −7.079 | 7.351 | −21.498 | 1.00 | 37.76 | C | O |
| HETATM | 2916 | S | SO4 | C | 5 | −5.578 | 7.372 | −21.695 | 1.00 | 49.39 | C | S |
| HETATM | 2917 | O1 | SO4 | C | 5 | −4.909 | 8.708 | −21.781 | 1.00 | 47.14 | C | O |
| HETATM | 2918 | O2 | SO4 | C | 5 | −5.288 | 6.634 | −22.907 | 1.00 | 53.58 | C | O |
| HETATM | 2919 | O3 | SO4 | C | 5 | −4.915 | 6.592 | −20.639 | 1.00 | 62.85 | C | O |
| HETATM | 2920 | O4 | SO4 | C | 6 | −4.944 | 13.213 | 1.993 | 1.00 | 78.62 | C | O |
| HETATM | 2921 | S | SO4 | C | 6 | −6.202 | 13.034 | 2.789 | 1.00 | 95.25 | C | S |
| HETATM | 2922 | O1 | SO4 | C | 6 | −7.237 | 13.888 | 2.169 | 1.00 | 102.73 | C | O |
| HETATM | 2923 | O2 | SO4 | C | 6 | −5.992 | 13.418 | 4.206 | 1.00 | 89.58 | C | O |
| HETATM | 2924 | O3 | SO4 | C | 6 | −6.705 | 11.634 | 2.812 | 1.00 | 84.72 | C | O |
| HETATM | 2925 | O | HOH | D | 1 | −20.695 | 15.137 | −22.438 | 1.00 | 18.17 | | O |
| HETATM | 2926 | O | HOH | D | 2 | −17.930 | 26.416 | −38.182 | 1.00 | 21.00 | | O |
| HETATM | 2927 | O | HOH | D | 3 | −10.765 | 14.583 | −10.848 | 1.00 | 20.73 | | O |
| HETATM | 2928 | O | HOH | D | 4 | −10.062 | 24.376 | −38.246 | 1.00 | 16.82 | | O |
| HETATM | 2929 | O | HOH | D | 5 | −20.522 | 3.954 | −32.756 | 1.00 | 17.75 | | O |
| HETATM | 2930 | O | HOH | D | 6 | −17.840 | −4.293 | −26.045 | 1.00 | 30.31 | | O |
| HETATM | 2931 | O | HOH | D | 7 | −7.464 | 8.466 | −45.568 | 1.00 | 19.00 | | O |
| HETATM | 2932 | O | HOH | D | 8 | −17.242 | 9.946 | −26.308 | 1.00 | 21.92 | | O |
| HETATM | 2933 | O | HOH | D | 9 | −11.026 | 12.301 | −46.759 | 1.00 | 25.09 | | O |
| HETATM | 2934 | O | HOH | D | 10 | −0.571 | −1.276 | −37.569 | 1.00 | 21.18 | | O |
| HETATM | 2935 | O | HOH | D | 11 | −4.523 | −1.468 | −25.895 | 1.00 | 31.21 | | O |
| HETATM | 2936 | O | HOH | D | 12 | −20.026 | 12.083 | −12.498 | 1.00 | 22.98 | | O |
| HETATM | 2937 | O | HOH | D | 13 | −29.081 | 27.795 | −25.762 | 1.00 | 26.43 | | O |
| HETATM | 2938 | O | HOH | D | 14 | −19.639 | 23.621 | −23.004 | 1.00 | 18.71 | | O |
| HETATM | 2939 | O | HOH | D | 15 | −10.603 | 24.795 | −20.899 | 1.00 | 24.48 | | O |
| HETATM | 2940 | O | HOH | D | 16 | −4.103 | −0.229 | −30.823 | 1.00 | 22.10 | | O |
| HETATM | 2941 | O | HOH | D | 17 | −1.443 | 5.749 | −44.954 | 1.00 | 28.58 | | O |
| HETATM | 2942 | O | HOH | D | 18 | −25.470 | 45.336 | −22.790 | 1.00 | 32.88 | | O |
| HETATM | 2943 | O | HOH | D | 19 | −9.813 | 26.706 | −24.275 | 1.00 | 24.49 | | O |
| HETATM | 2944 | O | HOH | D | 20 | −28.283 | 41.214 | −28.740 | 1.00 | 27.94 | | O |
| HETATM | 2945 | O | HOH | O | 21 | −29.788 | 25.327 | −25.418 | 1.00 | 25.76 | | O |
| HETATM | 2946 | O | HOH | D | 22 | −21.615 | 11.116 | −29.106 | 1.00 | 30.28 | | O |
| HETATM | 2947 | O | HOH | D | 23 | −22.103 | 8.433 | −28.261 | 1.00 | 27.57 | | O |
| HETATM | 2948 | O | HOH | D | 24 | −3.095 | 20.006 | −28.808 | 1.00 | 29.32 | | O |
| HETATM | 2949 | O | HOH | D | 25 | −4.554 | 10.472 | −19.676 | 1.00 | 35.18 | | O |
| HETATM | 2950 | O | HOH | D | 26 | −17.239 | 3.124 | −51.950 | 1.00 | 27.15 | | O |
| HETATM | 2951 | O | HOH | D | 27 | −6.978 | 22.437 | −35.978 | 1.00 | 30.62 | | O |
| HETATM | 2952 | O | HOH | D | 28 | −4.002 | −0.650 | −43.241 | 1.00 | 31.85 | | O |
| HETATM | 2953 | O | HOH | D | 29 | −15.207 | −8.487 | −27.521 | 1.00 | 29.20 | | O |

APPENDIX B-continued

Atomic coordinates of Aurora A + Activating Monobody Mb54 + AMPPCP

| | | | | | | | | | | | |
|---|---|---|---|---|---|---|---|---|---|---|---|
| HETATM | 2954 | O | HOH | D | 30 | −15.437 | 0.862 | −21.743 | 1.00 | 26.12 | O |
| HETATM | 2955 | O | HOH | D | 31 | −13.653 | 34.097 | −24.980 | 1.00 | 26.56 | O |
| HETATM | 2956 | O | HOH | D | 32 | −11.831 | 30.209 | −28.626 | 1.00 | 23.53 | O |
| HETATM | 2957 | O | HOH | D | 33 | −11.868 | −2.860 | −35.842 | 1.00 | 33.59 | O |
| HETATM | 2958 | O | HOH | D | 34 | −21.870 | 10.314 | −11.242 | 1.00 | 41.02 | O |
| HETATM | 2959 | O | HOH | D | 35 | −19.412 | 0.887 | −43.338 | 1.00 | 28.62 | O |
| HETATM | 2960 | O | HOH | D | 36 | −9.847 | 31.360 | −30.093 | 1.00 | 32.28 | O |
| HETATM | 2961 | O | HOH | D | 37 | −26.010 | 43.188 | −18.944 | 1.00 | 28.40 | O |
| HETATM | 2962 | O | HOH | D | 38 | −5.828 | 14.002 | −48.087 | 1.00 | 32.32 | O |
| HETATM | 2963 | O | HOH | D | 39 | −11.791 | 36.953 | −26.010 | 1.00 | 33.47 | O |
| HETATM | 2964 | O | HOH | D | 40 | −4.364 | 21.220 | −40.266 | 1.00 | 34.52 | O |
| HETATM | 2965 | O | HOH | D | 41 | −23.524 | 19.464 | −22.718 | 1.00 | 29.68 | O |
| HETATM | 2966 | O | HOH | D | 42 | −17.400 | −4.414 | −18.737 | 1.00 | 31.14 | O |
| HETATM | 2967 | O | HOH | D | 43 | −6.664 | −1.520 | −30.991 | 1.00 | 29.39 | O |
| HETATM | 2968 | O | HOH | D | 44 | −17.322 | 3.433 | −9.601 | 1.00 | 45.69 | O |
| HETATM | 2969 | O | HOH | D | 45 | −2.659 | 3.714 | −48.713 | 1.00 | 30.53 | O |
| HETATM | 2970 | O | HOH | D | 46 | −5.482 | 22.492 | −15.181 | 1.00 | 38.93 | O |
| HETATM | 2971 | O | HOH | D | 47 | −19.508 | 2.154 | −45.879 | 1.00 | 24.14 | O |
| HETATM | 2972 | O | HOH | D | 48 | −8.777 | −1.180 | −20.598 | 1.00 | 24.83 | O |
| HETATM | 2973 | O | HOH | D | 49 | −28.577 | 26.573 | −0.665 | 1.00 | 43.97 | O |
| HETATM | 2974 | O | HOH | D | 50 | 0.414 | −2.341 | −39.973 | 1.00 | 28.90 | O |
| HETATM | 2975 | O | HOH | D | 51 | 0.353 | 13.984 | −32.404 | 1.00 | 35.30 | O |
| HETATM | 2976 | O | HOH | D | 52 | −13.861 | 47.490 | −25.942 | 1.00 | 29.11 | O |
| HETATM | 2977 | O | HOH | D | 53 | −19.565 | 30.343 | −11.425 | 1.00 | 28.01 | O |
| HETATM | 2978 | O | HOH | D | 54 | 0.373 | 6.251 | −42.778 | 1.00 | 33.45 | O |
| HETATM | 2979 | O | HOH | D | 55 | −5.522 | 21.456 | −13.354 | 1.00 | 37.40 | O |
| HETATM | 2980 | O | HOH | D | 56 | −13.365 | 9.836 | −5.770 | 1.00 | 37.96 | O |
| HETATM | 2981 | O | HOH | D | 57 | −16.328 | −4.588 | −21.865 | 1.00 | 30.18 | O |
| HETATM | 2982 | O | HOH | D | 58 | −6.960 | 21.092 | −38.425 | 1.00 | 32.78 | O |
| HETATM | 2983 | O | HOH | D | 59 | −28.972 | 19.058 | −21.973 | 1.00 | 41.12 | O |
| HETATM | 2984 | O | HOH | D | 60 | −12.729 | 35.911 | −17.991 | 1.00 | 33.10 | O |
| HETATM | 2985 | O | HOH | D | 61 | −8.115 | 28.398 | −39.485 | 1.00 | 31.39 | O |
| HETATM | 2986 | O | HOH | D | 62 | −9.849 | 36.019 | −18.824 | 1.00 | 47.70 | O |
| HETATM | 2987 | O | HOH | D | 63 | −30.402 | 38.614 | −23.960 | 1.00 | 39.06 | O |
| HETATM | 2988 | O | HOH | D | 64 | −39.120 | 31.464 | −20.000 | 1.00 | 33.99 | O |
| HETATM | 2989 | O | HOH | D | 65 | −11.835 | −6.530 | −30.169 | 1.00 | 23.77 | O |
| HETATM | 2990 | O | HOH | D | 66 | −22.441 | 0.896 | −20.106 | 1.00 | 28.79 | O |
| HETATM | 2991 | O | HOH | D | 67 | −17.090 | −8.419 | −16.693 | 1.00 | 33.62 | O |
| HETATM | 2992 | O | HOH | D | 68 | −9.697 | 1.747 | −47.682 | 1.00 | 22.95 | O |
| HETATM | 2993 | O | HOH | D | 69 | −13.415 | 25.420 | −17.809 | 1.00 | 31.52 | O |
| HETATM | 2994 | O | HOH | D | 70 | −26.133 | 9.926 | −34.561 | 1.00 | 29.47 | O |
| HETATM | 2995 | O | HOH | D | 71 | −22.035 | 16.450 | −10.989 | 1.00 | 29.91 | O |
| HETATM | 2996 | O | HOH | D | 72 | −19.983 | 15.395 | −45.041 | 1.00 | 33.17 | O |
| HETATM | 2997 | O | HOH | D | 73 | −4.919 | 0.784 | −22.409 | 1.00 | 33.22 | O |
| HETATM | 2998 | O | HOH | D | 74 | 1.759 | 10.368 | −21.196 | 1.00 | 40.65 | O |
| HETATM | 2999 | O | HOH | D | 75 | −37.816 | 30.160 | −17.817 | 1.00 | 31.46 | O |
| HETATM | 3000 | O | HOH | D | 76 | −24.195 | 13.193 | −9.305 | 1.00 | 37.97 | O |
| HETATM | 3001 | O | HOH | D | 77 | −4.564 | 23.511 | −30.621 | 1.00 | 28.24 | O |
| HETATM | 3002 | O | HOH | D | 78 | −18.508 | 7.486 | −25.827 | 1.00 | 26.94 | O |
| HETATM | 3003 | O | HOH | D | 79 | −23.326 | 17.576 | −6.609 | 1.00 | 41.53 | O |
| HETATM | 3004 | O | HOH | D | 80 | −13.889 | 23.494 | 7.686 | 1.00 | 40.58 | O |
| HETATM | 3005 | O | HOH | D | 81 | −3.341 | −1.150 | −28.306 | 1.00 | 30.25 | O |
| HETATM | 3006 | O | HOH | D | 82 | −28.300 | 20.893 | −40.075 | 1.00 | 44.41 | O |
| HETATM | 3007 | O | HOH | D | 83 | −21.273 | 7.571 | −25.580 | 1.00 | 27.96 | O |
| HETATM | 3008 | O | HOH | D | 84 | −21.161 | 27.318 | −36.032 | 1.00 | 36.93 | O |
| HETATM | 3009 | O | HOH | D | 85 | 0.824 | 12.463 | −45.786 | 1.00 | 35.36 | O |
| HETATM | 3010 | O | HOH | D | 86 | −9.249 | 7.476 | −16.814 | 1.00 | 36.61 | O |
| HETATM | 3011 | O | HOH | D | 87 | −17.491 | 21.431 | −9.206 | 1.00 | 30.05 | O |
| HETATM | 3012 | O | HOH | D | 88 | −13.320 | −6.154 | −32.971 | 1.00 | 27.83 | O |
| HETATM | 3013 | O | HOH | D | 89 | −21.564 | 18.090 | −47.211 | 1.00 | 35.24 | O |
| HETATM | 3014 | O | HOH | D | 90 | −6.870 | 8.887 | −9.716 | 1.00 | 46.87 | O |
| HETATM | 3015 | O | HOH | D | 91 | −10.977 | −6.894 | −20.120 | 1.00 | 36.97 | O |
| HETATM | 3016 | O | HOH | D | 92 | −24.942 | 36.188 | −38.178 | 1.00 | 41.89 | O |
| HETATM | 3017 | O | HOH | D | 93 | −25.677 | 23.222 | −22.095 | 1.00 | 38.56 | O |
| HETATM | 3018 | O | HOH | D | 94 | −19.671 | 4.767 | −44.964 | 1.00 | 28.41 | O |
| HETATM | 3019 | O | HOH | D | 95 | −9.926 | 22.342 | −9.125 | 1.00 | 46.64 | O |
| HETATM | 3020 | O | HOH | D | 96 | −0.742 | 1.085 | −30.268 | 1.00 | 33.35 | O |
| HETATM | 3021 | O | HOH | D | 97 | −30.272 | 33.433 | −8.222 | 1.00 | 36.14 | O |
| HETATM | 3022 | O | HOH | D | 98 | −24.187 | 27.099 | −5.847 | 1.00 | 32.54 | O |
| HETATM | 3023 | O | HOH | D | 99 | −24.730 | 33.683 | 0.100 | 1.00 | 43.67 | O |
| HETATM | 3024 | O | HOH | D | 100 | −24.410 | 15.543 | −10.926 | 1.00 | 34.74 | O |
| HETATM | 3025 | O | HOH | D | 101 | 0.124 | 18.456 | −41.751 | 1.00 | 35.51 | O |
| HETATM | 3026 | O | HOH | D | 102 | 4.904 | 8.482 | −39.542 | 1.00 | 33.89 | O |
| HETATM | 3027 | O | HOH | D | 103 | −11.475 | 39.895 | −25.221 | 1.00 | 40.19 | O |
| HETATM | 3028 | O | HOH | D | 104 | −17.432 | 6.346 | −51.816 | 1.00 | 37.32 | O |
| HETATM | 3029 | O | HOH | D | 105 | −35.655 | 30.535 | −26.597 | 1.00 | 34.09 | O |
| HETATM | 3030 | O | HOH | D | 106 | −5.334 | 16.430 | −15.997 | 1.00 | 47.01 | O |
| HETATM | 3031 | O | HOH | D | 107 | −9.688 | 19.440 | −45.504 | 1.00 | 38.80 | O |

APPENDIX B-continued

Atomic coordinates of Aurora A + Activating Monobody Mb54 + AMPPCP

| | | | | | | | | | | | |
|---|---|---|---|---|---|---|---|---|---|---|---|
| HETATM | 3032 | O | HOH | D | 108 | −21.174 | 16.331 | −6.214 | 1.00 | 43.42 | O |
| HETATM | 3033 | O | HOH | D | 109 | −12.129 | 36.418 | −33.377 | 1.00 | 38.60 | O |
| HETATM | 3034 | O | HOH | D | 110 | −3.578 | −4.678 | −25.837 | 1.00 | 35.17 | O |
| HETATM | 3035 | O | HOH | D | 111 | −17.833 | −5.758 | −16.246 | 1.00 | 36.95 | O |
| HETATM | 3036 | O | HOH | D | 112 | −16.427 | −1.791 | −20.867 | 1.00 | 34.20 | O |
| HETATM | 3037 | O | HOH | D | 113 | −21.851 | 4.903 | −43.393 | 1.00 | 31.86 | O |
| HETATM | 3038 | O | HOH | D | 114 | −22.466 | 5.454 | −37.137 | 1.00 | 32.70 | O |
| HETATM | 3039 | O | HOH | D | 115 | −2.634 | 8.115 | −22.546 | 1.00 | 26.27 | O |
| HETATM | 3040 | O | HOH | D | 116 | −4.466 | 17.164 | −0.500 | 1.00 | 40.19 | O |
| HETATM | 3041 | O | HOH | D | 117 | −28.066 | 22.710 | −22.271 | 1.00 | 39.94 | O |
| HETATM | 3042 | O | HOH | D | 118 | −5.458 | −1.774 | −37.428 | 1.00 | 36.70 | O |
| HETATM | 3043 | O | HOH | D | 119 | −23.427 | 2.426 | −43.077 | 1.00 | 28.74 | O |
| HETATM | 3044 | O | HOH | D | 120 | −29.398 | 42.589 | −14.283 | 1.00 | 40.14 | O |
| HETATM | 3045 | O | HOH | D | 121 | −13.978 | 27.875 | −14.472 | 1.00 | 29.88 | O |
| HETATM | 3046 | O | HOH | D | 122 | −7.455 | 4.763 | −22.676 | 1.00 | 40.46 | O |
| HETATM | 3047 | O | HOH | D | 123 | −28.769 | 14.995 | −25.141 | 1.00 | 38.25 | O |
| HETATM | 3048 | O | HOH | D | 124 | −1.549 | 10.657 | −22.853 | 1.00 | 34.88 | O |
| HETATM | 3049 | O | HOH | D | 125 | −19.625 | 28.202 | −0.826 | 1.00 | 38.62 | O |
| HETATM | 3050 | O | HOH | D | 126 | 23.625 | 24.268 | −35.950 | 1.00 | 50.51 | O |
| HETATM | 3051 | O | HOH | D | 127 | −31.074 | 38.538 | −14.092 | 1.00 | 36.49 | O |
| HETATM | 3052 | O | HOH | D | 128 | −12.081 | 22.251 | −6.414 | 1.00 | 41.09 | O |
| HETATM | 3053 | O | HOH | D | 129 | −10.403 | 26.482 | −39.743 | 1.00 | 31.80 | O |
| HETATM | 3054 | O | HOH | D | 130 | −8.730 | 10.456 | −47.162 | 1.00 | 40.04 | O |
| HETATM | 3055 | O | HOH | D | 131 | −25.463 | 15.993 | −7.142 | 1.00 | 39.48 | O |
| HETATM | 3056 | O | HOH | D | 132 | −10.898 | 5.494 | −54.513 | 1.00 | 40.37 | O |
| HETATM | 3057 | O | HOH | D | 133 | 0.000 | 0.000 | −41.715 | 1.00 | 68.48 | O |
| HETATM | 3058 | O | HOH | D | 134 | −8.933 | −7.962 | −32.603 | 1.00 | 37.56 | O |
| HETATM | 3059 | O | HOH | D | 135 | −19.329 | 3.388 | −53.629 | 1.00 | 32.51 | O |
| HETATM | 3060 | O | HOH | D | 136 | −16.870 | 47.112 | −22.022 | 1.00 | 38.73 | O |
| HETATM | 3061 | O | HOH | D | 137 | −28.490 | 21.100 | −20.924 | 1.00 | 31.23 | O |
| HETATM | 3062 | O | HOH | D | 138 | −10.595 | 11.724 | −9.496 | 1.00 | 35.20 | O |
| HETATM | 3063 | O | HOH | D | 139 | −25.928 | 35.836 | −9.915 | 1.00 | 27.53 | O |
| HETATM | 3064 | O | HOH | D | 140 | −2.791 | 16.559 | −22.557 | 1.00 | 35.55 | O |
| HETATM | 3065 | O | HOH | D | 141 | −27.720 | 28.633 | −34.606 | 1.00 | 44.56 | O |
| HETATM | 3066 | O | HOH | D | 142 | −24.271 | 8.926 | 0.861 | 1.00 | 39.76 | O |
| HETATM | 3067 | O | HOH | D | 143 | −36.027 | 27.988 | −27.533 | 1.00 | 39.61 | O |
| HETATM | 3068 | O | HOH | D | 144 | −31.876 | 6.659 | −30.352 | 1.00 | 45.10 | O |
| HETATM | 3069 | O | HOH | D | 145 | 2.805 | 10.761 | −45.562 | 1.00 | 36.62 | O |
| END | | | | | | | | | | | |

What is claimed is:

1. A pharmaceutical composition comprising an effective amount of an agent that specifically binds a PIF pocket on a kinase, an effective amount of an agent that specifically binds an ATP-binding site on the kinase, and a pharmaceutically acceptable carrier, wherein the agent that specifically binds a PIF pocket on a kinase is a monobody comprising any one of the following sequences:

AuroraA_44 (Mb44)
(SEQ ID NO: 1)
GSVSSVPTKL EVVAATPTSL LISWDAPAVT VDFYVITYGE

TGGYSYPWQE FEVPGSKSTA TISGLKPGVD YTITVYADYG

QYFYSPISIN YRT

AuroraA_51 (Mb51)
(SEQ ID NO: 2)
GSVSSVPTKL EVVAATPTSL LISWDAKPMS YEPVYYYRIT

YGETGGNSPV QEFTVPGYYS TATISGLKPG VDYTITVYAD

SMSSYYYSPI SINYRT

AuroraA_56 (Mb56)
(SEQ ID NO: 3)
GSVSSVPTKL EVVAATPTSL LISWDAMSDW YYWVDYYRIT

YGETGGNSPV QEFTVPGSYS TATISGLKPG VDYTITVYAS

DDVWGDYSPI SINYRT

-continued

AuroraA_60 (Mb60)
(SEQ ID NO: 4)
GSVSSVPTKL EVVAATPTSL LISWDAPAVT VVHYVITYGE

TGGNSPVQEF TVPGSKSTAT ISGLKPGVDY TITVYAIDFY

WGSYSPISIN YRT and, wherein the agent that specifically binds the ATP-binding site is Danusertib.

2. The pharmaceutical composition of claim 1, wherein the kinase is Aurora A kinase.

3. A method of decreasing activity of a kinase, the method comprising contacting a kinase with an effective amount of the pharmaceutical composition of claim 1.

4. A method of inhibiting development of resistance to kinase inhibition in a subject, inhibiting growth and/or proliferation of a cancer cell, or treating cancer associated with kinase activity, the method comprising administering to the subject an effective amount of the pharmaceutical composition of claim 1, thereby preventing or inhibiting development of resistance to kinase inhibition in a subject.

5. A method of increasing affinity of binding of a kinase inhibitor to an ATP-binding site of a kinase, the method comprising contacting the kinase with an effective amount of the pharmaceutical composition of claim 1, thereby increasing affinity of binding of the kinase inhibitor to the ATP-binding site of the kinase.

* * * * *

SEQUENCE LISTING

```
<160> NUMBER OF SEQ ID NOS: 14

<210> SEQ ID NO 1
<211> LENGTH: 93
<212> TYPE: PRT
<213> ORGANISM: Homo sapiens

<400> SEQUENCE: 1

Gly Ser Val Ser Ser Val Pro Thr Lys Leu Glu Val Val Ala Ala Thr
1               5                   10                  15

Pro Thr Ser Leu Leu Ile Ser Trp Asp Ala Pro Ala Val Thr Val Asp
            20                  25                  30

Phe Tyr Val Ile Thr Tyr Gly Glu Thr Gly Gly Tyr Ser Tyr Pro Trp
        35                  40                  45

Gln Glu Phe Glu Val Pro Gly Ser Lys Ser Thr Ala Thr Ile Ser Gly
    50                  55                  60

Leu Lys Pro Gly Val Asp Tyr Thr Ile Thr Val Tyr Ala Asp Tyr Gly
65                  70                  75                  80

Gln Tyr Phe Tyr Ser Pro Ile Ser Ile Asn Tyr Arg Thr
                85                  90


<210> SEQ ID NO 2
<211> LENGTH: 96
<212> TYPE: PRT
```

<213> ORGANISM: Homo sapiens

<400> SEQUENCE: 2

Gly Ser Val Ser Ser Val Pro Thr Lys Leu Glu Val Val Ala Ala Thr
1 5 10 15

Pro Thr Ser Leu Leu Ile Ser Trp Asp Ala Lys Pro Met Ser Tyr Glu
20 25 30

Pro Val Tyr Tyr Tyr Arg Ile Thr Tyr Gly Glu Thr Gly Gly Asn Ser
35 40 45

Pro Val Gln Glu Phe Thr Val Pro Gly Tyr Tyr Ser Thr Ala Thr Ile
50 55 60

Ser Gly Leu Lys Pro Gly Val Asp Tyr Thr Ile Thr Val Tyr Ala Asp
65 70 75 80

Ser Met Ser Ser Tyr Tyr Tyr Ser Pro Ile Ser Ile Asn Tyr Arg Thr
85 90 95

<210> SEQ ID NO 3
<211> LENGTH: 96
<212> TYPE: PRT
<213> ORGANISM: Homo sapiens

<400> SEQUENCE: 3

Gly Ser Val Ser Ser Val Pro Thr Lys Leu Glu Val Val Ala Ala Thr
1 5 10 15

Pro Thr Ser Leu Leu Ile Ser Trp Asp Ala Met Ser Asp Trp Tyr Tyr
20 25 30

Trp Val Asp Tyr Tyr Arg Ile Thr Tyr Gly Glu Thr Gly Gly Asn Ser
35 40 45

Pro Val Gln Glu Phe Thr Val Pro Gly Ser Tyr Ser Thr Ala Thr Ile
50 55 60

Ser Gly Leu Lys Pro Gly Val Asp Tyr Thr Ile Thr Val Tyr Ala Ser
65 70 75 80

Asp Asp Val Trp Gly Asp Tyr Ser Pro Ile Ser Ile Asn Tyr Arg Thr
85 90 95

<210> SEQ ID NO 4
<211> LENGTH: 93
<212> TYPE: PRT
<213> ORGANISM: Homo sapiens

<400> SEQUENCE: 4

Gly Ser Val Ser Ser Val Pro Thr Lys Leu Glu Val Val Ala Ala Thr
1 5 10 15

Pro Thr Ser Leu Leu Ile Ser Trp Asp Ala Pro Ala Val Thr Val Val
20 25 30

His Tyr Val Ile Thr Tyr Gly Glu Thr Gly Gly Asn Ser Pro Val Gln
35 40 45

Glu Phe Thr Val Pro Gly Ser Lys Ser Thr Ala Thr Ile Ser Gly Leu
50 55 60

Lys Pro Gly Val Asp Tyr Thr Ile Thr Val Tyr Ala Ile Asp Phe Tyr
65 70 75 80

Trp Gly Ser Tyr Ser Pro Ile Ser Ile Asn Tyr Arg Thr
85 90

<210> SEQ ID NO 5
<211> LENGTH: 13
<212> TYPE: PRT
<213> ORGANISM: Homo sapiens

<400> SEQUENCE: 5

```
Ala Pro Ser Ser Arg Arg Thr Thr Leu Cys Gly Thr Leu
1               5                   10
```

<210> SEQ ID NO 6
<211> LENGTH: 7
<212> TYPE: PRT
<213> ORGANISM: Homo sapiens

<400> SEQUENCE: 6

```
Leu Arg Arg Ala Ser Leu Gly
1               5
```

<210> SEQ ID NO 7
<211> LENGTH: 15
<212> TYPE: PRT
<213> ORGANISM: Homo sapiens

<400> SEQUENCE: 7

```
Ala Thr Leu Ala Arg Arg Asp Ser Leu Gln Lys Pro Gly Leu Glu
1               5                   10                  15
```

<210> SEQ ID NO 8
<211> LENGTH: 403
<212> TYPE: PRT
<213> ORGANISM: Homo sapiens

<400> SEQUENCE: 8

```
Met Asp Arg Ser Lys Glu Asn Cys Ile Ser Gly Pro Val Lys Ala Thr
1               5                   10                  15

Ala Pro Val Gly Gly Pro Lys Arg Val Leu Val Thr Gln Gln Phe Pro
            20                  25                  30

Cys Gln Asn Pro Leu Pro Val Asn Ser Gly Gln Ala Gln Arg Val Leu
        35                  40                  45

Cys Pro Ser Asn Ser Ser Gln Arg Ile Pro Leu Gln Ala Gln Lys Leu
    50                  55                  60

Val Ser Ser His Lys Pro Val Gln Asn Gln Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
            100                 105                 110

Glu Leu Ala Ser Lys Gln Lys Asn Glu Glu Ser Lys Lys Arg Gln Trp
        115                 120                 125

Ala Leu Glu Asp Phe Glu Ile Gly Arg Pro Leu Gly Lys Gly Lys Phe
    130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175

Gln Leu Arg Arg Glu Val Glu Ile Gln Ser His Leu Arg His Pro Asn
            180                 185                 190

Ile Leu Arg Leu Tyr Gly Tyr Phe His Asp Ala Thr Arg Val Tyr Leu
        195                 200                 205

Ile Leu Glu Tyr Ala Pro Leu Gly Thr Val Tyr Arg Glu Leu Gln Lys
    210                 215                 220

Leu Ser Lys Phe Asp Glu Gln Arg Thr Ala Thr Tyr Ile Thr Glu Leu
```

-continued

```
225                 230                 235                 240

Ala Asn Ala Leu Ser Tyr Cys His Ser Lys Arg Val Ile His Arg Asp
                245                 250                 255

Ile Lys Pro Glu Asn Leu Leu Leu Gly Ser Ala Gly Glu Leu Lys Ile
            260                 265                 270

Ala Asp Phe Gly Trp Ser Val His Ala Pro Ser Ser Arg Arg Thr Thr
        275                 280                 285

Leu Cys Gly Thr Leu Asp Tyr Leu Pro Pro Glu Met Ile Glu Gly Arg
    290                 295                 300

Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                325                 330                 335

Thr Tyr Lys Arg Ile Ser Arg Val Glu Phe Thr Phe Pro Asp Phe Val
            340                 345                 350

Thr Glu Gly Ala Arg Asp Leu Ile Ser Arg Leu Leu Lys His Asn Pro
        355                 360                 365

Ser Gln Arg Pro Met Leu Arg Glu Val Leu Glu His Pro Trp Ile Thr
    370                 375                 380

Ala Asn Ser Ser Lys Pro Ser Asn Cys Gln Asn Lys Glu Ser Ala Ser
385                 390                 395                 400

Lys Gln Ser


<210> SEQ ID NO 9
<211> LENGTH: 2121
<212> TYPE: DNA
<213> ORGANISM: Homo sapiens

<400> SEQUENCE: 9

acaaggcagc ctcgctcgag cgcaggccaa tcggctttct agctagaggg tttaactcct      60

atttaaaaag aagaaccttt gaattctaac ggctgagctc ttggaagact tgggtccttg     120

ggtcgcaggc atcatggacc gatctaaaga aaactgcatt tcaggacctg ttaaggctac     180

agctccagtt ggaggtccaa aacgtgttct cgtgactcag caatttcctt gtcagaatcc     240

attacctgta aatagtggcc aggctcagcg ggtcttgtgt ccttcaaatt cttcccagcg     300

cattcctttg caagcacaaa agcttgtctc cagtcacaag ccggttcaga atcagaagca     360

gaagcaattg caggcaacca gtgtacctca tcctgtctcc aggccactga ataacaccca     420

aaagagcaag cagcccctgc catcggcacc tgaaaataat cctgaggagg aactggcatc     480

aaaacagaaa aatgaagaat caaaaaagag gcagtgggct ttggaagact ttgaaattgg     540

tcgccctctg ggtaaaggaa agtttggtaa tgtttatttg gcaagagaaa agcaaagcaa     600

gtttattctg gctcttaaag tgttatttaa agctcagctg gagaaagccg gagtggagca     660

tcagctcaga agagaagtag aaatacagtc ccaccttcgg catcctaata ttcttagact     720

gtatggttat ttccatgatg ctaccagagt ctacctaatt ctggaatatg caccacttgg     780

aacagtttat agagaacttc agaaactttc aaagtttgat gagcagagaa ctgctactta     840

tataacagaa ttggcaaatg ccctgtctta ctgtcattcg aagagagtta ttcatagaga     900

cattaagcca gagaacttac ttcttggatc agctggagag cttaaaattg cagattttgg     960

gtggtcagta catgctccat cttccaggag gaccactctc tgtggcaccc tggactacct    1020

gccccctgaa atgattgaag gtcggatgca tgatgagaag gtggatctct ggagccttgg    1080

agttctttgc tatgaatttt tagttgggaa gcctcctttt gaggcaaaca cataccaaga    1140
```

```
gacctacaaa agaatatcac gggttgaatt cacattccct gactttgtaa cagagggagc   1200

cagggacctc atttcaagac tgttgaagca taatcccagc cagaggccaa tgctcagaga   1260

agtacttgaa cacccctgga tcacagcaaa ttcatcaaaa ccatcaaatt gccaaaacaa   1320

agaatcagct agcaaacagt cttaggaatc gtgcaggggg agaaatcctt gagccagggc   1380

tgccatataa cctgacagga acatgctact gaagtttatt ttaccattga ctgctgccct   1440

caatctagaa cgctacacaa gaaatatttg ttttactcag caggtgtgcc ttaacctccc   1500

tattcagaaa gctccacatc aataaacatg acactctgaa gtgaaagtag ccacgagaat   1560

tgtgctactt atactggttc ataatctgga ggcaaggttc gactgcagcc gccccgtcag   1620

cctgtgctag gcatggtgtc ttcacaggag gcaaatccag agcctggctg tggggaaagt   1680

gaccactctg ccctgacccc gatcagttaa ggagctgtgc aataaccttc ctagtacctg   1740

agtgagtgtg taacttattg ggttggcgaa gcctggtaaa gctgttggaa tgagtatgtg   1800

attcttttta agtatgaaaa taaagatata tgtacagact tgtatttttt ctctggtggc   1860

attcctttag gaatgctgtg tgtctgtccg gcaccccggt aggcctgatt gggtttctag   1920

tcctccttaa ccacttatct cccatatgag agtgtgaaaa ataggaacac gtgctctacc   1980

tccatttagg gatttgcttg ggatacagaa gaggccatgt gtctcagagc tgttaagggc   2040

ttattttttt aaaacattgg agtcatagca tgtgtgtaaa ctttaaatat gcaaataaat   2100

aagtatctat gtctaaaaaa a                                             2121
```

```
<210> SEQ ID NO 10
<211> LENGTH: 96
<212> TYPE: PRT
<213> ORGANISM: Homo sapiens

<400> SEQUENCE: 10

Gly Ser Val Ser Ser Val Pro Thr Lys Leu Glu Val Val Ala Ala Thr
1               5                   10                  15

Pro Thr Ser Leu Leu Ile Ser Trp Asp Ala Phe Gly His Gln Tyr Glu
            20                  25                  30

Pro Val Tyr Tyr Tyr Arg Ile Thr Tyr Gly Glu Thr Gly Gly Asn Ser
        35                  40                  45

Pro Val Gln Glu Phe Thr Val Pro Gly Tyr Tyr Ser Thr Ala Thr Ile
    50                  55                  60

Ser Gly Leu Lys Pro Gly Val Asp Tyr Thr Ile Thr Val Tyr Ala Trp
65                  70                  75                  80

Tyr Val Asp Gly Ser Tyr Ser Ser Pro Ile Ser Ile Asn Tyr Arg Thr
                85                  90                  95


<210> SEQ ID NO 11
<211> LENGTH: 96
<212> TYPE: PRT
<213> ORGANISM: Homo sapiens

<400> SEQUENCE: 11

Gly Ser Val Ser Ser Val Pro Thr Lys Leu Glu Val Val Ala Ala Thr
1               5                   10                  15

Pro Thr Ser Leu Leu Ile Ser Trp Asp Ala Gln Thr Tyr Gln Met Tyr
            20                  25                  30

Asp Tyr Val Ser Tyr Tyr Arg Ile Thr Tyr Gly Glu Thr Gly Gly Asn
        35                  40                  45

Ser Pro Val Gln Glu Phe Thr Val Pro Gly Tyr Tyr Ser Thr Ala Thr
```

50 55 60

Ile Ser Gly Leu Lys Pro Gly Val Asp Tyr Thr Ile Thr Val Tyr Ala
65 70 75 80

Glu Gly Tyr Tyr Ser Ser Tyr Ser Pro Ile Ser Ile Asn Tyr Arg Thr
85 90 95

<210> SEQ ID NO 12
<211> LENGTH: 783
<212> TYPE: PRT
<213> ORGANISM: Homo sapiens

<400> SEQUENCE: 12

Met Ser Gln Val Lys Ser Ser Tyr Ser Tyr Asp Ala Pro Ser Asp Phe
1 5 10 15

Ile Asn Phe Ser Ser Leu Asp Asp Glu Gly Asp Thr Gln Asn Ile Asp
20 25 30

Ser Trp Phe Glu Glu Lys Ala Asn Leu Glu Asn Lys Leu Leu Gly Lys
35 40 45

Asn Gly Thr Gly Gly Leu Phe Gln Gly Lys Thr Pro Leu Arg Lys Ala
50 55 60

Asn Leu Gln Gln Ala Ile Val Thr Pro Leu Lys Pro Val Asp Asn Thr
65 70 75 80

Tyr Tyr Lys Glu Ala Glu Lys Glu Asn Leu Val Glu Gln Ser Ile Pro
85 90 95

Ser Asn Ala Cys Ser Ser Leu Glu Val Glu Ala Ala Ile Ser Arg Lys
100 105 110

Thr Pro Ala Gln Pro Gln Arg Arg Ser Leu Arg Leu Ser Ala Gln Lys
115 120 125

Asp Leu Glu Gln Lys Glu Lys His His Val Lys Met Lys Ala Lys Arg
130 135 140

Cys Ala Thr Pro Val Ile Ile Asp Glu Ile Leu Pro Ser Lys Lys Met
145 150 155 160

Lys Val Ser Asn Asn Lys Lys Lys Pro Glu Glu Glu Gly Ser Ala His
165 170 175

Gln Asp Thr Ala Glu Lys Asn Ala Ser Ser Pro Glu Lys Ala Lys Gly
180 185 190

Arg His Thr Val Pro Cys Met Pro Pro Ala Lys Gln Lys Phe Leu Lys
195 200 205

Ser Thr Glu Glu Gln Glu Leu Glu Lys Ser Met Lys Met Gln Gln Glu
210 215 220

Val Val Glu Met Arg Lys Lys Asn Glu Glu Phe Lys Lys Leu Ala Leu
225 230 235 240

Ala Gly Ile Gly Gln Pro Val Lys Lys Ser Val Ser Gln Val Thr Lys
245 250 255

Ser Val Asp Phe His Phe Arg Thr Asp Glu Arg Ile Lys Gln His Pro
260 265 270

Lys Asn Gln Glu Glu Tyr Lys Glu Val Asn Phe Thr Ser Glu Leu Arg
275 280 285

Lys His Pro Ser Ser Pro Ala Arg Val Thr Lys Gly Cys Thr Ile Val
290 295 300

Lys Pro Phe Asn Leu Ser Gln Gly Lys Lys Arg Thr Phe Asp Glu Thr
305 310 315 320

Val Ser Thr Tyr Val Pro Leu Ala Gln Gln Val Glu Asp Phe His Lys
325 330 335

-continued

```
Arg Thr Pro Asn Arg Tyr His Leu Arg Ser Lys Lys Asp Asp Ile Lys
            340                 345                 350

Thr Gly Ser Cys Ser Val Thr Gln Ala Gly Val Gln Trp Arg Asp His
        355                 360                 365

Gly Ser Leu Gln Cys Pro Thr Pro Gly Leu Lys Gln Ser Ser Cys Leu
    370                 375                 380

Ser Leu Pro Asn Leu Leu Pro Ser Lys Ser Ser Val Thr Lys Ile Cys
385                 390                 395                 400

Arg Asp Pro Gln Thr Pro Val Leu Gln Thr Lys His Arg Ala Arg Ala
                405                 410                 415

Val Thr Cys Lys Ser Thr Ala Glu Leu Glu Ala Glu Glu Leu Glu Lys
            420                 425                 430

Leu Gln Gln Tyr Lys Phe Lys Ala Arg Glu Leu Asp Pro Arg Ile Leu
        435                 440                 445

Glu Gly Gly Pro Ile Leu Pro Lys Lys Pro Pro Val Lys Pro Pro Thr
    450                 455                 460

Glu Pro Ile Gly Phe Asp Leu Glu Ile Glu Lys Arg Ile Gln Glu Arg
465                 470                 475                 480

Glu Ser Lys Lys Lys Thr Glu Asp Glu His Phe Glu Phe His Ser Arg
                485                 490                 495

Pro Cys Pro Thr Lys Ile Leu Glu Asp Val Val Gly Val Pro Glu Lys
            500                 505                 510

Lys Val Leu Pro Ile Thr Val Pro Lys Ser Pro Ala Phe Ala Leu Lys
        515                 520                 525

Asn Arg Ile Arg Met Pro Thr Lys Glu Asp Glu Glu Glu Asp Glu Pro
    530                 535                 540

Val Val Ile Lys Ala Gln Pro Val Pro His Tyr Gly Val Pro Phe Lys
545                 550                 555                 560

Pro Gln Ile Pro Glu Ala Arg Thr Val Glu Ile Cys Pro Phe Ser Phe
                565                 570                 575

Asp Ser Arg Asp Lys Glu Arg Gln Leu Gln Lys Glu Lys Lys Ile Lys
            580                 585                 590

Glu Leu Gln Lys Gly Glu Val Pro Lys Phe Lys Ala Leu Pro Leu Pro
        595                 600                 605

His Phe Asp Thr Ile Asn Leu Pro Glu Lys Lys Val Lys Asn Val Thr
    610                 615                 620

Gln Ile Glu Pro Phe Cys Leu Glu Thr Asp Arg Arg Gly Ala Leu Lys
625                 630                 635                 640

Ala Gln Thr Trp Lys His Gln Leu Glu Glu Glu Leu Arg Gln Gln Lys
                645                 650                 655

Glu Ala Ala Cys Phe Lys Ala Arg Pro Asn Thr Val Ile Ser Gln Glu
            660                 665                 670

Pro Phe Val Pro Lys Lys Glu Lys Lys Ser Val Ala Glu Gly Leu Ser
        675                 680                 685

Gly Ser Leu Val Gln Glu Pro Phe Gln Leu Ala Thr Glu Lys Arg Ala
    690                 695                 700

Lys Glu Arg Gln Glu Leu Glu Lys Arg Met Ala Glu Val Glu Ala Gln
705                 710                 715                 720

Lys Ala Gln Gln Leu Glu Glu Ala Arg Leu Gln Glu Glu Glu Gln Lys
                725                 730                 735

Lys Glu Glu Leu Ala Arg Leu Arg Arg Glu Leu Val His Lys Ala Asn
            740                 745                 750

Pro Ile Arg Lys Tyr Gln Gly Leu Glu Ile Lys Ser Ser Asp Gln Pro
```

755 760 765

Leu Thr Val Pro Val Ser Pro Lys Phe Ser Thr Arg Phe His Cys
770 775 780

<210> SEQ ID NO 13
<211> LENGTH: 3685
<212> TYPE: DNA
<213> ORGANISM: Homo sapiens

<400> SEQUENCE: 13
agtggactca cgcaggcgca ggagactaca cttcccagga actccgggcc gcgttgttcg 60
ctggtacctc cttctgactt ccggtattgc tgcggtctgt agggccaatc gggagcctgg 120
aattgctttc ccggcgctct gattggtgca ttcgactagg ctgcctgggt tcaaaatttc 180
aacgatactg aatgagtccc gcggcgggtt ggctcgcgct tcgttgtcag atctgaggcg 240
aggctaggtg agccgtggga agaaaagagg gagcagctag ggcgcgggtc tccctcctcc 300
cggagtttgg aacggctgaa gttcaccttc cagcccctag cgccgttcgc gccgctaggc 360
ctggcttctg aggcggttgc ggtgctcggt cgccgcctag gcggggcagg gtgcgagcag 420
gggcttcggg ccacgcttct cttggcgaca ggattttgct gtgaagtccg tccgggaaac 480
ggaggaaaaa aagagttgcg ggaggctgtc ggctaataac ggttcttgat acatatttgc 540
cagacttcaa gatttcagaa aaggggtgaa agagaagatt gcaactttga gtcagacctg 600
taggcctgat agactgatta aaccacagaa ggtgacctgc tgagaaaagt ggtacaaata 660
ctgggaaaaa cctgctcttc tgcgttaagt gggagacaat gtcacaagtt aaaagctctt 720
attcctatga tgccccctcg gatttcatca atttttcatc cttggatgat gaaggagata 780
ctcaaaacat agattcatgg tttgaggaga aggccaattt ggagaataag ttactgggga 840
agaatggaac tggagggctt tttcagggca aaactccttt gagaaaggct aatcttcagc 900
aagctattgt cacacctttg aaaccagttg acaacactta ctacaaagag gcagaaaaag 960
aaaatcttgt ggaacaatcc attccgtcaa atgcttgttc ttccctggaa gttgaggcag 1020
ccatatcaag aaaaactcca gcccagcctc agagaagatc tcttaggctt tctgctcaga 1080
aggatttgga acagaaagaa aagcatcatg taaaaatgaa agccaagaga tgtgccactc 1140
ctgtaatcat cgatgaaatt ctaccctcta agaaaatgaa agtttctaac aacaaaaaga 1200
agccagagga agaaggcagt gctcatcaag atactgctga aaagaatgca tcttccccag 1260
agaaagccaa gggtagacat actgtgcctt gtatgccacc tgcaaagcag aagtttctaa 1320
aaagtactga ggagcaagag ctggagaaga gtatgaaaat gcagcaagag gtggtggaga 1380
tgcggaaaaa gaatgaagaa ttcaagaaac ttgctctggc tggaataggg caacctgtga 1440
agaaatcagt gagccaggtc accaaatcag ttgacttcca cttccgcaca gatgagcgaa 1500
tcaaacaaca tcctaagaac caggaggaat ataaggaagt gaactttaca tctgaactac 1560
gaaagcatcc ttcatctcct gcccgagtga ctaagggatg taccattgtt aagcctttca 1620
acctgtccca aggaaagaaa agaacatttg atgaaacagt ttctacatat gtgccccttg 1680
cacagcaagt tgaagacttc cataaacgaa cccctaacag atatcatttg aggagcaaga 1740
aggatgatat taacctgtta ccctccaaat cttctgtgac caagatttgc agagacccac 1800
agactcctgt actgcaaacc aaacaccgtg cacgggctgt gacctgcaaa agtacagcag 1860
agctggaggc tgaggagctc gagaaattgc aacaatacaa attcaaagca cgtgaacttg 1920
atcccagaat acttgaaggt gggcccatct tgcccaagaa accacctgtg aaaccaccca 1980

-continued

```
ccgagcctat tggctttgat ttggaaattg agaaaagaat ccaggagcga gaatcaaaga   2040

agaaaacaga ggatgaacac tttgaatttc attccagacc ttgccctact aagattttgg   2100

aagatgttgt gggtgttcct gaaaagaagg tacttccaat caccgtcccc aagtcaccag   2160

cctttgcatt gaagaacaga attcgaatgc ccaccaaaga agatgaggaa gaggacgaac   2220

cggtagtgat aaaagctcaa cctgtgccac attatggggt gccttttaag ccccaaatcc   2280

cagaggcaag aactgtggaa atatgccctt tctcgtttga ttctcgagac aaagaacgtc   2340

agttacagaa ggagaagaaa ataaaagaac tgcagaaagg ggaggtgccc aagttcaagg   2400

cacttccctt gcctcatttt gacaccatta acctgccaga gaagaaggta aagaatgtga   2460

cccagattga acctttctgc ttggagactg acagaagagg tgctctgaag gcacagactt   2520

ggaagcacca gctggaagaa gaactgagac agcagaaaga agcagcttgt ttcaaggctc   2580

gtccaaacac cgtcatctct caggagccct ttgttcccaa gaaagagaag aaatcagttg   2640

ctgagggcct ttctggttct ctagttcagg aacctttttca gctggctact gagaagagag   2700

ccaaagagcg gcaggagctg gagaagagaa tggctgaggt agaagcccag aaagcccagc   2760

agttggagga ggccagacta caggaggaag agcagaaaaa agaggagctg gccaggctac   2820

ggagagaact ggtgcataag gcaaatccaa tacgcaagta ccagggtctg gagataaagt   2880

caagtgacca gcctctgact gtgcctgtat ctcccaaatt ctccactcga ttccactgct   2940

aaactcagct gtgagctgcg gataccgccc ggcaatggga cctgctctta acctcaaacc   3000

taggaccgtc ttgctttgtc attgggcatg gagagaaccc atttctccag acttttacct   3060

acccgtgcct gagaaagcat acttgacaac tgtggactcc agttttgttg agaattgttt   3120

tcttacatta ctaaggctaa taatgagatg taactcatga atgtctcgat tagactccat   3180

gtagttactt cctttaaacc atcagccggc cttttatatg ggtcttcact ctgactagaa   3240

tttagtctct gtgtcagcac agtgtaatct ctattgctat tgccccttac gactctcacc   3300

ctctccccac tttttttaaa aattttaacc agaaaataaa gatagttaaa tcctaagata   3360

gagattaagt catggtttaa atgaggaaca atcagtaaat cagattctgt cctcttctct   3420

gcataccgtg aatttatagt taaggatccc tttgctgtga gggtagaaaa cctcaccaac   3480

tgcaccagtg aggaagaaga ctgcgtggat tcatggggag cctcacagca gccacgcagc   3540

aggctctggg tggggctgcc gttaaggcac gttctttcct tactggtgct gataacaaca   3600

gggaaccgtg cagtgtgcat tttaagacct ggcctggaat aaatacgttt tgtctttccc   3660

tcaaaaaaaa aaaaaaaaaa aaaaa                                          3685
```

```
<210> SEQ ID NO 14
<211> LENGTH: 127
<212> TYPE: PRT
<213> ORGANISM: Homo sapiens

<400> SEQUENCE: 14

Met Lys His His His His His His Ser Ser Gly Leu Asn Asp Ile Phe
1               5                   10                  15

Glu Ala Gln Lys Ile Glu Trp His Glu Glu Asn Leu Tyr Phe Gln Gly
            20                  25                  30

Ser Val Ser Ser Val Pro Thr Lys Leu Glu Val Val Ala Ala Thr Pro
        35                  40                  45

Thr Ser Leu Leu Ile Ser Trp Asp Ala Phe Gly His Gln Tyr Glu Pro
    50                  55                  60

Val Tyr Tyr Tyr Arg Ile Thr Tyr Gly Glu Thr Gly Gly Asn Ser Pro
```

-continued

| | | | | | | | | | | | | | | | |
|---|---|---|---|---|---|---|---|---|---|---|---|---|---|---|---|
| 65 | | | | | 70 | | | | | 75 | | | | | 80 |
| Val | Gln | Glu | Phe | Thr | Val | Pro | Gly | Tyr | Tyr | Ser | Thr | Ala | Thr | Ile | Ser |
| | | | | 85 | | | | | 90 | | | | | 95 | |
| Gly | Leu | Lys | Pro | Gly | Val | Asp | Tyr | Thr | Ile | Thr | Val | Tyr | Ala | Trp | Tyr |
| | | | 100 | | | | | 105 | | | | | 110 | | |
| Val | Asp | Gly | Ser | Tyr | Ser | Ser | Pro | Ile | Ser | Ile | Asn | Tyr | Arg | Thr | |
| | | 115 | | | | | 120 | | | | | 125 | | | |